United States Patent
Achab et al.

(10) Patent No.: US 9,938,281 B2
(45) Date of Patent: Apr. 10, 2018

(54) PURINE INHIBITORS OF HUMAN PHOSPHATIDYLINOSITOL 3-KINASE DELTA

(71) Applicant: Merck Sharp & Dohme Corp., Rahway, NJ (US)

(72) Inventors: Abdelghani Abe Achab, Melrose, MA (US); Michael D. Altman, Needham, MA (US); Yongqi Deng, Newton, MA (US); Solomon Kattar, Wakefield, MA (US); Jason D. Katz, Newton, MA (US); Joey L. Methot, Westwood, MA (US); Hua Zhou, Acton, MA (US); Meredeth McGowan, Boston, MA (US); Matthew P. Christopher, Brookline, MA (US); Yudith Garcia, Brookline, MA (US); Neville John Anthony, Northborough, MA (US); Francesc Xavier Fradera Llinas, Brookline, MA (US); Liping Yang, Arlington, MA (US); Changwei Mu, Beijing (CN); Xiaona Wang, Beijing (CN); Feng Shi, Beijing (CN); Baijun Ye, Beijing (CN); Sixing Zhang, Beijing (CN); Xiaoli Zhao, Beijing (CN); Rong Zhang, Beijing (CN); Kin Chiu Fong, Beijing (CN); Xiansheng Leng, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/443,314

(22) PCT Filed: Nov. 15, 2013

(86) PCT No.: PCT/CN2013/001395
§ 371 (c)(1),
(2) Date: May 15, 2015

(87) PCT Pub. No.: WO2014/075393
PCT Pub. Date: May 22, 2014

(65) Prior Publication Data
US 2016/0207926 A1    Jul. 21, 2016

Related U.S. Application Data

(60) Provisional application No. 61/727,392, filed on Nov. 16, 2012.

(51) Int. Cl.
| | | |
|---|---|---|
| *A61K 31/52* | (2006.01) |
| *A61K 31/535* | (2006.01) |
| *C07D 473/00* | (2006.01) |
| *C07D 403/00* | (2006.01) |
| *C07D 487/04* | (2006.01) |
| *C07D 473/34* | (2006.01) |
| *A61K 45/06* | (2006.01) |
| *A61K 31/5377* | (2006.01) |
| *A61K 31/55* | (2006.01) |
| *C07D 519/00* | (2006.01) |

(52) U.S. Cl.
CPC .......... *C07D 487/04* (2013.01); *A61K 31/52* (2013.01); *A61K 31/5377* (2013.01); *A61K 31/55* (2013.01); *A61K 45/06* (2013.01); *C07D 473/34* (2013.01); *C07D 519/00* (2013.01)

(58) Field of Classification Search
CPC .............................. A61K 31/52; C07D 473/34
USPC ................. 514/263.1, 263.2, 263.21, 234.2; 544/277, 264; 540/600
See application file for complete search history.

(56) References Cited

U.S. PATENT DOCUMENTS

| 5,117,830 A | 6/1992 | McAfee et al. |
| 5,670,501 A * | 9/1997 | Peck .................... C07D 473/34 514/234.2 |
| 7,517,888 B2 * | 4/2009 | Cristalli ............... C07D 473/34 514/263.4 |
| 2007/0191279 A1 * | 8/2007 | Cronstein ............ A61K 31/522 514/11.8 |

FOREIGN PATENT DOCUMENTS

| CN | 101031569 | 9/2007 |
| CN | 102838600 A | 12/2012 |
| WO | 9606845 A1 | 3/1996 |
| WO | WO0058305 | 10/2000 |
| WO | 2005105803 A1 | 11/2005 |

(Continued)

OTHER PUBLICATIONS

EP Search Report and Written Opinion issued in Application No. 13855780.6 dated Apr. 21, 2016, 11 pages.

(Continued)

*Primary Examiner* — Shengjun Wang
(74) *Attorney, Agent, or Firm* — Patricia A. Shatynski; John C. Todaro

(57) ABSTRACT

The instant invention provides compounds of formula I which are PI3K-delta inhibitors, and as such are useful for the treatment of PI3K-delta-mediated diseases such as inflammation, asthma, COPD and cancer.

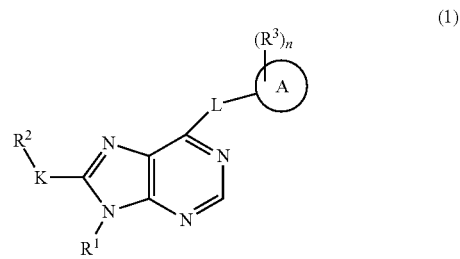

18 Claims, No Drawings

(56) References Cited

FOREIGN PATENT DOCUMENTS

| WO | 2005113556 | 12/2005 |
|---|---|---|
| WO | WO2006099204 | 9/2006 |
| WO | WO2011075630 A1 | 6/2011 |
| WO | WO2011075643 A1 | 6/2011 |
| WO | WO2011113802 | 9/2011 |
| WO | WO2012003264 A1 | 1/2012 |
| WO | WO2012004299 A1 | 1/2012 |
| WO | WO2012037226 A1 | 3/2012 |
| WO | WO2012058645 | 5/2012 |
| WO | WO2012146666 | 11/2012 |

OTHER PUBLICATIONS

Skinner et al., Synthesis and Biological Activity of Some 6-(Substituted)-aminopurines, Journal of the American Chemical Society, 1957, 2843-2846, 79(11).

Temple et al., Synthesis of Potential Antimalarial Agents. I. 6- and 6,9-Disubstituted purines, Journal of Medicinal Chemistry, American Chemical Society, 1968, 1213-1215, 11(6).

Borrmann, et al., Structure-Activity Relatiohnships of Adenine and Deazaadenine Derivatives as Ligands for Adenine Receptors, A New Purinergic Receptor Family, Journal of Medicinal Chemistry, Sep. 4, 2009, pp. 5974-5989, vol. 52.

CAS RN 109292-91-3, STN Entry Date Jul. 18, 1987.

CAS RN-1347497-11-3, STN Entry Date Dec. 2, 2011.

CAS RN-1348555-71-4, STN Entry Date Dec. 4, 2011.

CAS RN-1349793-28-7, STN Entry Date Dec. 6, 2011.

De Ligt et al., Synthesis & biological evaluation of disubstituted N6-cyclopentyladenine analogues: the search for a neutral antagonist with high affinity for the adenosine A1 receptor, Bioorganic & Medicinal Chemistry, 2004, pp. 139-149, vol. 12.

Jorda et al., Anti-leishmanial activity of disubstituted purines and related pyrazolo[4,3-d]pyrimidines, Bioorganic & Medicinal Chemistry Letters, 2011, pp. 4233-4237, vol. 21.

Fossa, et al, New pyrazolo[3,4,-b]pyridones as selective A1, adenosine receptor antagonists: synthesis, biological evaluation and molecular mode !ling studies, Org. Biomol. Chem., 2005, pp. 2262-2270, 3.

Japanese Patent Application No. 2015-542135 Office Action dated Sep. 28, 2017.

* cited by examiner

PURINE INHIBITORS OF HUMAN PHOSPHATIDYLINOSITOL 3-KINASE DELTA

CROSS REFERENCE TO RELATED APPLICATIONS

This application is a U.S. National Phase application under 35 U.S. C. §371 of PCT Application No. PCT/CN2013/001395, filed Nov. 15, 2013 which claims priority under 35 U.S.C. § 119(e) from U.S. Provisional Application Ser. No. 61/727,392, filed on Nov. 16, 2012.

BACKGROUND OF THE INVENTION

Compounds are provided that inhibit phosphatidylinositol 3-kinase delta isoform (PI3K-delta) activity, including compounds that selectively inhibit PI3K-delta activity. The invention provides methods of using PI3K-delta inhibitory compounds to inhibit PI3K-delta mediated processes in vitro and in vivo.

Methods of inhibiting PI3K-delta activity, and methods of treating diseases, such as disorders of immunity and inflammation, in which PI3K-delta plays a role in leukocyte function are disclosed. Methods of using PI3K-delta inhibitory compounds to inhibit cancer cell growth or proliferation are also provided. Preferably, the methods employ active agents that selectively inhibit PI3K-delta, while not significantly inhibiting activity of other PI3K isoforms.

SUMMARY OF THE INVENTION

The present invention provides novel compounds which are inhibitors of phosphoinositide 3-kinases delta (PI3K-delta). The invention also provides a method for the treatment and prevention of PI3K-delta-mediated diseases and disorders using the novel compounds, as well as pharmaceutical compositions containing the compounds.

DETAILED DESCRIPTION OF THE INVENTION

The present invention provides compounds of formula I or pharmaceutically acceptable salts or stereoisomers thereof:

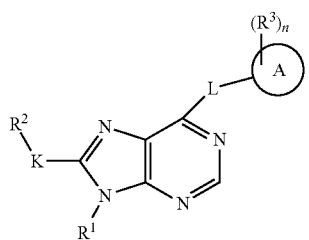

I $R^1$ is selected from hydrogen, $C_{1-5}$alkyl, $C_{3-5}$cycloalkyl, $C_{1-5}$heteroalkyl, and $C_{3-5}$heterocycloalkyl, wherein $R^1$ is optionally substituted by 0, 1, 2, 3, or 4 groups independently selected from hydrogen, fluoro, chloro, methyl, amino, $OR^a$, $O(C=O)R^a$, $O(C=O)OR^a$ and $NH(C=O)R^a$;
$R^a$ is independently selected from hydrogen, $C_{1-10}$alkyl, $C_{1-10}$heteroalkyl, aryl, $C_{3-12}$ cycloalkyl, $C_{3-12}$ heterocycloalkyl, and heteroaryl;

$R^2$ is selected from hydrogen, $C_{1-10}$alkyl, $C_{3-12}$ cycloalkyl, $C_{3-12}$heterocycloalkyl, $C_{1-10}$ heteroalkyl, $C_{2-10}$alkynyl, aryl, and heteroaryl, wherein $R^2$ is substituted with 0, 1, 2, 3, or 4 $R^3$ substituents;
n is 0, 1, 2, 3, or 4;
A is $C_{3-12}$ cycloalkyl$C_{0-8}$ alkyl, $C_{3-12}$heterocycloalkyl$C_{0-8}$ alkyl, and $C_{6-12}$spirocyclyl;
L is selected from NH, and $N(C_{1-10}$alkyl);
K is selected from a bond, NH, O, C(O), $CH_2$, $N(C_{1-5})$alkyl, —C(O)N($R^b$)—$(CH_2)_m$—, N, S, $SO_2$, and $C_{2-10}$ alkynylene;
$R^b$ is H or $C_{1-10}$ alkyl,
m is 0, 1, 2, or 3;
$R^3$ is independently selected from:
halogen,
$C_{1-10}$ alkyl(oxy)$_{0-1}$(carbonyl)$_{0-1}$$C_{0-10}$ alkyl,
$C_{2-10}$ alkenyl(oxy)$_{0-1}$(carbonyl)$_{0-1}$$C_{0-10}$ alkyl,
$C_{1-10}$ heteroalkyl(oxy)$_{0-1}$(carbonyl)$_{0-1}$$C_{0-10}$ alkyl,
aryl $C_{0-10}$ alkyl(oxy)$_{0-1}$(carbonyl)$_{0-1}$$C_{0-10}$ alkyl,
aryl $C_{2-10}$ alkynyl(oxy)$_{0-1}$(carbonyl)$_{0-1}$$C_{0-10}$ alkyl,
$C_{3-12}$ cycloalkyl$C_{0-10}$alkyl(oxy)$_{0-1}$(carbonyl)$_{0-1}$$C_{0-10}$ alkyl,
heteroaryl $C_{0-10}$ alkyl(oxy)$_{0-1}$(carbonyl)$_{0-1}$$C_{0-10}$ alkyl,
$(C_{3-12})$heterocycloalkyl $C_{0-10}$ alkyl(oxy)$_{0-1}$(carbonyl)$_{0-1}$$C_{0-10}$ alkyl,
$C_{1-10}$ alkyl(carbonyl)$_{0-1}$oxy$C_{0-10}$ alkyl,
$C_{1-10}$ heteroalkyl(carbonyl)$_{0-1}$oxy$C_{0-10}$ alkyl,
$C_{1-10}$ heteroalkyl(carbonyl)$_{0-1}$oxy$C_{0-10}$ alkyl,
aryl $C_{0-10}$ alkyl (carbonyl)$_{0-1}$oxy$C_{0-10}$ alkyl,
$(C_{3-12})$cycloalkyl $C_{0-10}$ alkyl(carbonyl)$_{0-1}$oxy$C_{0-10}$ alkyl,
heteroaryl$C_{0-10}$ alkyl(carbonyl)$_{0-1}$oxy$C_{0-10}$ alkyl,
$(C_{3-12})$heterocycloalkyl $C_{0-10}$ alkyl(carbonyl)$_{0-1}$oxy$C_{0-10}$ alkyl,
$((C_{0-10})$alkyl$)_{1-2}$aminocarbonyloxy,
$(C_{0-10})$heteroalkylaminocarbonyloxy,
aryl$(C_{0-10})$alkylaminocarbonyloxy,
$(C_{3-12})$cycloalkyl$(C_{0-10})$alkylaminocarbonyloxy,
heteroaryl$(C_{0-10})$alkylaminocarbonyloxy,
$(C_{3-12})$heterocycloalkyl$(C_{0-10})$alkylaminocarbonyloxy,
$C_{0-10}$ alkylamino(carbonyl)$_{0-1}$$C_{0-10}$ alkyl,
$(C_{1-10})$heteroalkylamino(carbonyl)$_{0-1}$$C_{0-10}$ alkyl,
$C_{3-12}$ cycloalkyl $C_{0-10}$ alkylamino(carbonyl)$_{0-1}$$C_{0-10}$ alkyl,
aryl $C_{0-10}$alkylamino(carbonyl)$_{0-1}$$C_{0-10}$ alkyl,
heteroaryl$C_{0-10}$alkylamino(carbonyl)$_{0-1}$$C_{0-10}$ alkyl,
$(C_{3-12})$heterocycloalkyl$C_{0-10}$ alkylamino(carbonyl)$_{0-1}$$C_{0-10}$ alkyl,
$C_{1-10}$ alkyl(oxy)$_{0-1}$(carbonyl)$_{0-1}$amino$C_{0-10}$ alkyl,
$C_{1-10}$ heteroalkyl (oxy)$_{0-1}$(carbonyl)$_{0-1}$amino$C_{0-10}$ alkyl,
$C_{3-12}$ cycloalkyl $C_{0-10}$ alkyl (oxy)$_{0-1}$(carbonyl)$_{0-1}$amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino$C_{0-10}$ alkyl,
$(C_{3-12})$heterocycloalkyl $C_{0-10}$ alkyl(oxy)$_{0-1}$(carbonyl)$_{0-1}$amino$C_{0-10}$ alkyl,
—$CO_2(C_{0-10}$ alkyl),
—$(C_{0-10}$ alkyl)$CO_2H$,
Oxo (=O);
$C_{1-10}$ alkylS(O)$_{1-2}$,
$C_{1-10}$ heteroalkyl S(O)$_{1-2}$,
$(C_{3-12})$ cycloalkylS(O)$_{1-2}$,
$(C_{3-12})$ cycloheteroalkylS(O)$_{1-2}$,
heteroarylS(O)$_{1-2}$,
arylS(O)$_{1-2}$,
—$SO_2N(C_{0-6}$ alkyl)$_{0-2}$,
$C_{0-6}$ alkyl(amino)$_{0-1}$S(O)$_{1-2}$amino,
$C_{1-10}$ heteroalkyl(amino)$_{0-1}$S(O)$_{1-2}$amino, ($C_{3-12}$)cycloalkyl(amino)$_{0-1}$S(O)$_{1-2}$amino,
($C_{3-12}$)cycloheteroalkyl(amino)$_{0-1}$S(O)$_{1-2}$amino,
heteroaryl(amino)$_{0-1}$S(O)$_{1-2}$amino,
aryl(amino)$_{0-1}$S(O)$_{1-2}$amino,
—SO$_2$CF$_3$,
—SO$_2$CF$_2$H,
—Si(C$_{0-6}$ alkyl)$_3$,
amino,
(C$_{0-10}$ alkyl)$_{1-2}$ amino,
C$_{1-4}$acylamino C$_{0-10}$ alkyl,
hydroxyl,
(C$_{1-10}$ alkyl)OH,
C$_{0-10}$ alkylalkoxyl,
cyano,
C$_{1-6}$alkylcyano, and
C$_{1-6}$haloalkyl;
wherein R$^3$ is each substituted with 0, 1, 2, 3, or 4 R$^4$ substituents and each R$^4$ is independently selected from:
halogen,
C$_{1-10}$ alkyl(oxy)$_{0-1}$(carbonyl)$_{0-1}$C$_{0-10}$ alkyl,
C$_{1-10}$ heteroalkyl(oxy)$_{0-1}$(carbonyl)$_{0-1}$C$_{0-10}$ alkyl,
aryl C$_{0-10}$ alkyl(oxy)$_{0-1}$(carbonyl)$_{0-1}$C$_{0-10}$ alkyl,
aryl C$_{2-10}$ alkynyl(oxy)$_{0-1}$(carbonyl)$_{0-1}$C$_{0-10}$ alkyl,
C$_{3-12}$ cycloalkyl C$_{0-10}$ alkyl(oxy)$_{0-1}$(carbonyl)$_{0-1}$C$_{0-10}$ alkyl,
heteroaryl C$_{0-10}$ alkyl(oxy)$_{0-1}$(carbonyl)$_{0-1}$C$_{0-10}$ alkyl,
(C$_{3-12}$)heterocycloalkyl C$_{0-10}$ alkyl(oxy)$_{0-1}$(carbonyl)$_{0-1}$ C$_{0-10}$ alkyl,
C$_{1-10}$ alkyl(carbonyl)$_{0-1}$oxyC$_{0-10}$ alkyl,
C$_{1-10}$ heteroalkyl(carbonyl)$_{0-1}$oxyC$_{0-10}$ alkyl,
aryl C$_{0-10}$ alkyl (carbonyl)$_{0-1}$oxyC$_{0-10}$ alkyl,
(C$_{3-12}$)cycloalkyl C$_{0-10}$ alkyl(carbonyl)$_{0-1}$oxyC$_{0-10}$ alkyl,
heteroarylC$_{0-10}$ alkyl(carbonyl)$_{0-1}$oxyC$_{0-10}$ alkyl,
(C$_{3-12}$)heterocycloalkyl C$_{0-10}$ alkyl(carbonyl)$_{0-1}$oxyC$_{0-10}$ alkyl,
((C$_{0-10}$)alkyl)$_{1-2}$aminocarbonyloxy,
aryl (C$_{0-10}$)alkylaminocarbonyloxy,
(C$_{3-12}$)cycloalkyl(C$_{0-10}$)alkylaminocarbonyloxy,
heteroaryl(C$_{0-10}$)alkylaminocarbonyloxy,
(C$_{3-12}$)heterocycloalkyl(C$_{0-10}$)alkylaminocarbonyloxy,
C$_{1-10}$ alkylaminocarbonylC$_{0-10}$ alkyl,
C$_{3-12}$ cycloalkyl C$_{0-10}$ alkylaminocarbonylC$_{0-10}$ alkyl,
aryl C$_{0-10}$ alkylaminocarbonylC$_{0-10}$ alkyl,
heteroaryl C$_{0-10}$ alkylaminocarbonylC$_{0-10}$ alkyl,
(C$_{3-12}$)heterocycloalkyl C$_{0-10}$ alkylaminocarbonylC$_{0-10}$ alkyl,
C$_{1-10}$ alkyl (oxy)$_{0-1}$(carbonyl)$_{0-1}$aminoC$_{0-10}$ alkyl,
C$_{3-12}$ cycloalkyl C$_{0-10}$ alkyl (oxy)$_{0-1}$(carbonyl)$_{0-1}$ aminoC$_{0-10}$ alkyl,
aryl C$_{0-10}$ alkyl(oxy)$_{0-1}$(carbonyl)$_{0-1}$aminoC$_{0-10}$ alkyl,
heteroaryl C$_{0-10}$ alkyl(oxy)$_{0-1}$(carbonyl)$_{0-1}$aminoC$_{0-10}$ alkyl,
(C$_{3-12}$)heterocycloalkyl C$_{0-10}$ alkyl(oxy)$_{0-1}$(carbonyl)$_{0-1}$ aminoC$_{0-10}$ alkyl,
—CO$_2$(C$_{0-10}$ alkyl),
—(C$_{0-10}$ alkyl)CO$_2$H,
Oxo (=O),
C$_{1-10}$ alkylS(O)$_{1-2}$,
C$_{1-10}$ heteroalkyl S(O)$_{1-2}$,
(C$_{3-12}$)cycloalkylS(O)$_{1-2}$,
(C$_{3-12}$)cycloheteroalkylS(O)$_{1-2}$,
heteroarylS(O)$_{1-2}$,
arylS(O)$_{1-2}$,
C$_{0-6}$ alkyl(amino)$_{0-1}$S(O)$_{1-2}$amino,
C$_{1-10}$ heteroalkyl(amino)$_{0-1}$S(O)$_{1-2}$amino,
(C$_{3-12}$)cycloalkyl(amino)$_{0-1}$S(O)$_{1-2}$amino,
(C$_{3-12}$)cycloheteroalkyl(amino)$_{0-1}$S(O)$_{1-2}$amino,
heteroaryl(amino)$_{0-1}$S(O)$_{1-2}$amino,
aryl(amino)$_{0-1}$S(O)$_{1-2}$amino,
—SO$_2$N(C$_{1-6}$alkyl)$_{1-2}$,
—SO$_2$C$_{1-6}$alkyl,
—SO$_2$CF$_3$,
—SO$_2$CF$_2$H,
amino,
(C$_{0-10}$ alkyl)$_{1-2}$ amino,
-(oxy)$_{0-1}$(carbonyl)$_{0-1}$N(C$_{0-10}$ alkyl)$_{1-2}$,
hydroxy,
(C$_{1-10}$ alkyl)OH,
C$_{1-10}$ alkoxy,
cyano, and
C$_{1-6}$haloalkyl;
R$^4$ is substituted with 0, 1, 2, or 3 R$^5$ substituents and each R$^5$ substituent is independently selected from hydroxy, (C$_{1-6}$)alkyl, (C$_{1-6}$)alkoxy, (C$_{1-10}$ alkyl)OH, halogen, CO$_2$H, —(C$_{0-6}$)alkylCN, —O(C=O)C$_1$-C$_6$ alkyl, —(C=O)OC$_1$-C$_6$ alkyl, NO$_2$, trifluoromethoxy, trifluoroethoxy, trifluoromethyl, trifluoroethyl, —N—C(O)O(C$_{0-6}$)alkyl, C$_{1-10}$ alkylsulfonyl, C$_{1-10}$ heteroalkyl, aryl, (C$_{3-12}$)cycloalkyl, heteroaryl, (C$_{3-12}$)heterocycloalkyl, C$_{1-10}$ heteroalkylsulfonyl, oxo (O=), (C$_{3-12}$)cycloalkylsulfonyl, (C$_{3-12}$)cycloheteroalkylsulfonyl, heteroarylsulfonyl, arylsulfonyl, aminosulfonyl, —SO$_2$N(C$_{1-6}$alkyl)$_{1-2}$, —SO$_2$C$_{1-6}$alkyl, —SO$_2$CF$_3$, —SO$_2$CF$_2$H, —C$_{1-10}$ alkylsulfinyl, —O$_{(0-1)}$(C$_{1-10}$)haloalkyl, amino(C$_{1-6}$alkyl)$_{0-2}$ and NH$_2$; and
R$^5$ is substituted with 0, 1, or 2 R$^6$ substituents and each R$^6$ substituent is independently selected from hydroxy, (C$_{1-6}$) alkyl, (C$_{1-6}$)alkoxy, (C$_{1-10}$ alkyl)OH, halogen, CO$_2$H, —(C$_{0-6}$)alkylCN, —O(C=O)C$_1$-C$_6$ alkyl, —(C=O)OC$_1$-C$_6$ alkyl, NO$_2$, trifluoromethoxy, trifluoroethoxy, trifluoromethyl, trifluoroethyl, —N—C(O)O(C$_{0-6}$)alkyl, C$_{1-10}$ alkylsulfonyl, C$_{1-10}$ heteroalkylsulfonyl, oxo (O=), (C$_{3-12}$) cycloalkylsulfonyl, (C$_{3-12}$)cycloheteroalkylsulfonyl, heteroarylsulfonyl, arylsulfonyl, aminosulfonyl, —SO$_2$N (C$_{1-6}$alkyl)$_{1-2}$, —SO$_2$C$_{1-6}$alkyl, —SO$_2$CF$_3$, —SO$_2$CF$_2$H, —O$_{(0-1)}$(C$_{1-10}$)haloalkyl, amino(C$_{1-6}$alkyl)$_{0-2}$ and NH$_2$.

Representative compounds of the instant invention include, but are not limited to, the following compounds and their pharmaceutically acceptable salts and their stereoisomers thereof:

tert-butyl-3-{[8-(1-ethyl-5-methyl-1H-pyrazol-4-yl)-9-methyl-9H-purin-6-yl]amino}pyrrolidine-1-carboxylate;
tert-butyl 3-((8-(1-ethyl-5-methyl-1H-pyrazol-4-yl)-9-methyl-9H-purin-6-yl)(methyl)amino)pyrrolidine-1-carboxylate;
tert-butyl 3-((9-ethyl-8-(6-methoxy-5-methylpyridin-3-yl)-9H-purin-6-yl)(methyl)amino)pyrrolidine-1-carboxylate;
tert-butyl 3-((9-ethyl-8-(6-methoxy-5-methylpyridin-3-yl)-9H-purin-6-yl)amino)pyrrolidine-1-carboxylate;
tert-butyl 3-((8-(2-(tert-butyl)thiazol-5-yl)-9-ethyl-9H-purin-6-yl)amino)pyrrolidine-1-carboxylate;
tert-butyl 3-((8-(2-(tert-butyl)thiazol-5-yl)-9-ethyl-9H-purin-6-yl)(methyl)amino)pyrrolidine-1-carboxylate;
tert-butyl 3-((8-(6-methoxy-5-methylpyridin-3-yl)-9-methyl-9H-purin-6-yl)amino)pyrrolidine-1-carboxylate;
tert-butyl 3-((8-(2-(tert-butyl)thiazol-5-yl)-9-methyl-9H-purin-6-yl)amino)pyrrolidine-1-carboxylate;
tert-butyl 3-((8-(1-ethyl-5-methyl-1H-pyrazol-4-yl)-9-methyl-9H-purin-6-yl)amino)azetidine-1-carboxylate;
tert-butyl 3-((8-(1-ethyl-5-methyl-1H-pyrazol-4-yl)-9-methyl-9H-purin-6-yl)amino)piperidine-1-carboxylate;
tert-butyl 3-((9-ethyl-8-(2-methylpyrimidin-5-yl)-9H-purin-6-yl)amino)pyrrolidine-1-carboxylate;
8-(1-ethyl-5-methyl-1H-pyrazol-4-yl)-9-methyl-N-[1-propanoylpyrrolidin-3-yl]-9H-purin-6-amine;

N-{1-[(2,5-dimethyl-1,3-oxazol-4-yl)carbonyl]pyrrolidin-3-yl}-8-(1-ethyl-5-methyl-1H-pyrazol-4-yl)-9-methyl-9H-purin-6-amine;

8-(1-ethyl-5-methyl-1H-pyrazol-4-yl)-9-methyl-N-[1-propanoylpyrrolidin-3-yl]-9H-purin-6-amine;

8-(1-ethyl-5-methyl-1H-pyrazol-4-yl)-9-methyl-N-[1-(tetrahydro-2H-pyran-4-ylcarbonyl)pyrrolidin-3-yl]-9H-purin-6-amine;

N-{1-[(2,5-dimethyl-1,3-oxazol-4-yl)carbonyl]pyrrolidin-3-yl}-8-[(1-ethyl-5-methyl-1H-pyrazol-4-yl)-9-methyl-9H-purin-6-amine;

N-{1-[(2,2-dimethyltetrahydro-2H-pyran-4-yl)carbonyl]pyrrolidin-3-yl}-8-(1-ethyl-5-methyl-1H-pyrazol-4-yl)-9-methyl-9H-purin-6-amine;

N-[1-(cyclopropylcarbonyl)pyrrolidin-3-yl]-8-(1-ethyl-5-methyl-1H-pyrazol-4-yl)-9-methyl-9H-purin-6-amine;

1-(3-((9-ethyl-8-(6-methoxy-5-methylpyridin-3-yl)-9H-purin-6-yl)(methyl)amino)pyrrolidin-1-yl)propan-1-one;

1-(3-((9-ethyl-8-(6-methoxy-5-methylpyridin-3-yl)-9H-purin-6-yl)amino)pyrrolidin-1-yl)propan-1-one;

1-(3-((8-(2-(tert-butyl)thiazol-5-yl)-9-ethyl-9H-purin-6-yl)amino)pyrrolidin-1-yl)propan-1-one;

1-(3-((8-(2-(tert-butyl)thiazol-5-yl)-9-ethyl-9H-purin-6-yl)(methyl)amino)pyrrolidin-1-yl)propan-1-one;

1-(3-((8-(6-methoxy-5-methylpyridin-3-yl)-9-methyl-9H-purin-6-yl)amino)pyrrolidin-1-yl)propan-1-one;

1-(3-((8-(6-methoxy-5-methylpyridin-3-yl)-9-methyl-9H-purin-6-yl)(methyl)amino)pyrrolidin-1-yl)propan-1-one;

1-(3-((8-(2-(tert-butyl)thiazol-5-yl)-9-methyl-9H-purin-6-yl)amino)pyrrolidin-1-yl)propan-1-one;

1-(3-((9-ethyl-8-(1-ethyl-5-methyl-1H-pyrazol-4-yl)-9H-purin-6-yl)amino)pyrrolidin-1-yl)propan-1-one;

1-(3-((9-cyclopropyl-8-(1-ethyl-5-methyl-1H-pyrazol-4-yl)-9H-purin-6-yl)amino)pyrrolidin-1-yl)propan-1-one;

1-(3-((9-ethyl-8-(2-methylpyrimidin-5-yl)-9H-purin-6-yl)amino)pyrrolidin-1-yl)propan-1-one;

(3-((9-ethyl-8-(2-methylpyrimidin-5-yl)-9H-purin-6-yl)amino)pyrrolidin-1-yl)(tetrahydro-2H-pyran-4-yl)methanone;

(2,5-dimethyloxazol-4-yl)(3-((9-ethyl-8-(2-methylpyrimidin-5-yl)-9H-purin-6-yl)amino)pyrrolidin-1-yl)methanone;

(2,2-dimethyltetrahydro-2H-pyran-4-yl)(3-((9-ethyl-8-(2-methylpyrimidin-5-yl)-9H-purin-6-yl)amino)pyrrolidin-1-yl)methanone;

cyclopropyl(3-((9-ethyl-8-(2-methylpyrimidin-5-yl)-9H-purin-6-yl)amino)pyrrolidin-1-yl)methanone;

cyclobutyl(3-((9-ethyl-8-(2-methylpyrimidin-5-yl)-9H-purin-6-yl)amino)pyrrolidin-1-yl)methanone;

cyclopentyl(3-((9-ethyl-8-(2-methylpyrimidin-5-yl)-9H-purin-6-yl)amino)pyrrolidin-1-yl)methanone;

(3,3-difluorocyclobutyl)(3-((9-ethyl-8-(2-methylpyrimidin-5-yl)-9H-purin-6-yl)amino)pyrrolidin-1-yl)methanone;

1-(3-((9-methyl-8-(6-(trifluoromethyl)pyridin-3-yl)-9H-purin-6-yl)amino)pyrrolidin-1-yl)propan-1-one;

1-(3-((9-methyl-8-(1H-pyrrolo[2,3-b]pyridin-5-yl)-9H-purin-6-yl)amino)pyrrolidin-1-yl)propan-1-one;

1-(3-((8-(1H-indazol-5-yl)-9-methyl-9H-purin-6-yl)amino)pyrrolidin-1-yl)propan-1-one;

1-(3-((8-(1H-indol-6-yl)-9-methyl-9H-purin-6-yl)amino)pyrrolidin-1-yl)propan-1-one;

1-(3-((9-methyl-8-(6-methylpyridin-3-yl)-9H-purin-6-yl)amino)pyrrolidin-1-yl)propan-1-one;

1-(3-((8-(1H-indazol-6-yl)-9-methyl-9H-purin-6-yl)amino)pyrrolidin-1-yl)propan-1-one;

1-(3-((8-(6-methoxy-5-(trifluoromethyl)pyridin-3-yl)-9-methyl-9H-purin-6-yl)amino)pyrrolidin-1-yl)propan-1-one;

1-(3-((8-(1H-indol-5-yl)-9-methyl-9H-purin-6-yl)amino)pyrrolidin-1-yl)propan-1-one;

tert-butyl-3-{[9-ethyl-8-(1-ethyl-5-methyl-1H-pyrazol-4-yl)-9H-purin-6-yl]amino}pyrrolidine-1-carboxylate;

tert-butyl-3-{[9-ethyl-8-(2-methylpyrimidin-5-yl)-9H-purin-6-yl]amino}-4-hydroxypyrrolidine-1-carboxylate;

tert-butyl-3-{[9-ethyl-8-(2-methylpyrimidin-5-yl)-9H-purin-6-yl]amino}piperidine-1-carboxylate;

1-tert-butyl 2-methyl-4-{[9-ethyl-8-(2-methylpyrimidin-5-yl)-9H-purin-6-yl]amino}pyrrolidine-1,2-dicarboxylate;

1-(tert-butoxycarbonyl)-4-{[9-ethyl-8-(2-methylpyrimidin-5-yl)-9H-purin-6-yl]amino}-D-proline;

1-tert-butyl 2-methyl-4-{[9-ethyl-8-(2-methylpyrimidin-5-yl)-9H-purin-6-yl]amino}pyrrolidine-1,2-dicarboxylate;

tert-butyl-4-{[9-ethyl-8-(2-methylpyrimidin-5-yl)-9H-purin-6-yl]amino}-2-(hydroxymethyl)pyrrolidine-1-carboxylate;

tert-butyl4-{[9-ethyl-8-(2-methylpyrimidin-5-yl)-9H-purin-6-yl]amino}-3,3-difluoropyrrolidine-1-carboxylate;

tert-butyl-3-({9-ethyl-8-[6-(trifluoromethyl)pyridin-3-yl]-9H-purin-6-yl}amino)pyrrolidine-1-carboxylate;

tert-butyl-3-{[9-ethyl-8-(6-methoxypyridin-3-yl)-9H-purin-6-yl]amino}pyrrolidine-1-carboxylate;

tert-butyl-3-({9-ethyl-8-[4-(trifluoromethyl)phenyl]-9H-purin-6-yl}amino)pyrrolidine-1-carboxylate;

N-[1-(cyclopropylcarbonyl)-4,4-difluoropyrrolidin-3-yl]-9-ethyl-8-(2-methylpyrimidin-5-yl)-9H-purin-6-amine;

N-[-1-(cyclopropylcarbonyl)-4,4-difluoropyrrolidin-3-yl]-9-ethyl-8-(2-methylpyrimidin-5-yl)-9H-purin-6-amine;

9-ethyl-8-(2-methylpyrimidin-5-yl)-N-[-1-propanoylpiperidin-3-yl]-9H-purin-6-amine;

N-[-1-(cyclopropylcarbonyl)piperidin-3-yl]-9-ethyl-8-(2-methylpyrimidin-5-yl)-9H-purin-6-amine;

8-(1-ethyl-5-methyl-1H-pyrazol-4-yl)-9-methyl-N-[-1-(tetrahydro-2H-pyran-4-ylcarbonyl)piperidin-3-yl]-9H-purin-6-amine;

4-[-3-{[9-ethyl-8-(2-methylpyrimidin-5-yl)-9H-purin-6-yl]amino}pyrrolidin-1-yl]-2-methyl-4-oxobutan-2-ol;

N-{-1-[(dimethylamino)acetyl]pyrrolidin-3-yl}-9-ethyl-8-(2-methylpyrimidin-5-yl)-9H-purin-6-amine;

9-ethyl-8-(2-methylpyrimidin-5-yl)-N-[-1-(tetrahydrofuran-2-ylcarbonyl)pyrrolidin-3-yl]-9H-purin-6-amine;

9-ethyl-8-(2-methylpyrimidin-5-yl)-N-[(1-(spiro[2.4]hept-1-ylcarbonyl)pyrrolidin-3-yl]-9H-purin-6-amine;

9-ethyl-8-(2-methylpyrimidin-5-yl)-N-[-1-(phenylacetyl)pyrrolidin-3-yl]-9H-purin-6-amine;

3-((9-ethyl-8-(2-methylpyrimidin-5-yl)-9H-purin-6-yl)amino)pyrrolidin-1-yl)((-2-(fluoromethyl)cyclopropyl)methanone;

9-ethyl-N-{-1-[(trans-3-methoxycyclobutyl)carbonyl]pyrrolidin-3-yl}-8-(2-methylpyrimidin-5-yl)-9H-purin-6-amine;

9-ethyl-8-(2-methylpyrimidin-5-yl)-N-{(-1-[-tetrahydrofuran-3-ylcarbonyl]pyrrolidin-3-yl}-9H-purin-6-amine;

9-ethyl-N-[-1-(1-methyl-D-prolyl)pyrrolidin-3-yl]-8-(2-methylpyrimidin-5-yl)-9H-purin-6-amine;

9-ethyl-N-[-1-(2-methylpropanoyl)piperidin-3-yl]-8-(2-methylpyrimidin-5-yl)-9H-purin-6-amine;

8-(1-ethyl-5-methyl-1H-pyrazol-4-yl)-9-methyl-N-(1-propanoylazetidin-3-yl)-9H-purin-6-amine;

8-(1-ethyl-5-methyl-1H-pyrazol-4-yl)-9-methyl-N-[-1-propanoylpiperidin-3-yl]-9H-purin-6-amine;

9-ethyl-N-{-1-[(1-methylcyclopropyl)carbonyl]pyrrolidin-3-yl}-8-(2-methylpyrimidin-5-yl)-9H-purin-6-amine;

8-(1-ethyl-5-methyl-1H-pyrazol-4-yl)-9-methyl-N-[1-(tetrahydro-2H-pyran-4-ylcarbonyl)azetidin-3-yl]-9H-purin-6-amine;

N-[-1-(cyclopropylcarbonyl)pyrrolidin-3-yl]-9-ethyl-8-[6-(trifluoromethyl)pyridin-3-yl]-9H-purin-6-amine;

N-[-1-(cyclopropylcarbonyl)pyrrolidin-3-yl]-9-ethyl-8-(6-methoxypyridin-3-yl)-9H-purin-6-amine;

N-[1-{[-2,2-dimethylcyclopropyl]carbonyl}pyrrolidin-3-yl]-9-ethyl-8-[6-(trifluoromethyl)pyridin-3-yl]-9H-purin-6-amine;

[1-(cyclopropylcarbonyl)-4-{[9-ethyl-8-(2-methylpyrimidin-5-yl)-9H-purin-6-yl]amino}pyrrolidin-2-yl]methanol;

methyl-1-(cyclopropylcarbonyl)-4-{[9-ethyl-8-(2-methylpyrimidin-5-yl)-9H-purin-6-yl]amino}-D-prolinate;

N-{-1-[(-2,2-difluorocyclopropyl)carbonyl]pyrrolidin-3-yl}-9-ethyl-8-(2-methylpyrimidin-5-yl)-9H-purin-6-amine;

N-{-1-[(-2,2-dimethylcyclopropyl)carbonyl]pyrrolidin-3-yl}-9-ethyl-8-(2-methylpyrimidin-5-yl)-9H-purin-6-amine;

9-ethyl-N-[-1-{[1-(methoxymethyl)cyclobutyl]carbonyl}pyrrolidin-3-yl]-8-(2-methylpyrimidin-5-yl)-9H-purin-6-amine;

1-{[-3-{[9-ethyl-8-(2-methylpyrimidin-5-yl)-9H-purin-6-yl]amino}pyrrolidin-1-yl]carbonyl}cyclopentanol;

N-{-1-[(3,3-dimethylcyclobutyl)carbonyl]pyrrolidin-3-yl}-9-ethyl-8-(2-methylpyrimidin-5-yl)-9H-purin-6-amine;

9-ethyl-8-(2-methylpyrimidin-5-yl)-N-{-1-[(2,2,3,3-tetramethylcyclopropyl)carbonyl]pyrrolidin-3-yl}-9H-purin-6-amine;

9-ethyl-N-[-1-{[1-(methoxymethyl)cyclopropyl]carbonyl}pyrrolidin-3-yl]-8-(2-methylpyrimidin-5-yl)-9H-purin-6-amine;

1-{[-3-{[9-ethyl-8-(2-methylpyrimidin-5-yl)-9H-purin-6-yl]amino}pyrrolidin-1-yl]carbonyl}cyclopentanecarbonitrile;

3-{[-3-{[9-ethyl-8-(2-methylpyrimidin-5-yl)-9H-purin-6-yl]amino}pyrrolidin-1-yl]carbonyl}cyclobutanol;

5-{[-3-{[9-ethyl-8-(2-methylpyrimidin-5-yl)-9H-purin-6-yl]amino}pyrrolidin-1-yl]carbonyl}pyrrolidin-2-one;

1-{[-3-{[9-ethyl-8-(2-methylpyrimidin-5-yl)-9H-purin-6-yl]amino}pyrrolidin-1-yl]carbonyl}cyclopropanecarbonitrile;

1-{[-3-{[9-ethyl-8-(2-methylpyrimidin-5-yl)-9H-purin-6-yl]amino}pyrrolidin-1-yl]carbonyl}cyclopropanol;

4-{[-3-{[9-ethyl-8-(2-methylpyrimidin-5-yl)-9H-purin-6-yl]amino}pyrrolidin-1-yl]carbonyl}-3,3-dimethylazetidin-2-one;

9-ethyl-8-(2-methylpyrimidin-5-yl)-N-{-1-[(-2-methyltetrahydrofuran-2-yl)carbonyl]pyrrolidin-3-yl}-9H-purin-6-amine;

[3-{9-ethyl-8-(2-methylpyrimidin-5-yl)-9H-purin-6-yl]amino}pyrrolidin-1-yl](1-methyl-1H-imidazol-5-yl)methanone;

9-ethyl-N-{-1-[(5-methylisoxazol-3-yl)carbonyl]pyrrolidin-3-yl}-8-(2-methylpyrimidin-5-yl)-9H-purin-6-amine;

9-ethyl-8-(2-methylpyrimidin-5-yl)-N-{-1-[(5-methyl-1,2,3-thiadiazol-4-yl)carbonyl]pyrrolidin-3-yl}-9H-purin-6-amine;

9-ethyl-8-(2-methylpyrimidin-5-yl)-N-[-1-(1,3-oxazol-4-yl-carbonyl)pyrrolidin-3-yl]-9H-purin-6-amine;

9-ethyl-N-{-1-[(1-methyl-1H-pyrazol-4-yl)carbonyl]pyrrolidin-3-yl}-8-(2-methylpyrimidin-5-yl)-9H-purin-6-amine;

9-ethyl-N-{-1-[(4-methyl-1,3-oxazol-5-yl)carbonyl]pyrrolidin-3-yl}-8-(2-methylpyrimidin-5-yl)-9H-purin-6-amine;

9-ethyl-8-(2-methylpyrimidin-5-yl)-N-{-1-[(1-methyl-1H-1,2,3-triazol-4-yl)carbonyl]pyrrolidin-3-yl}-9H-purin-6-amine;

9-ethyl-8-(2-methylpyrimidin-5-yl)-N-[-1-(1,3-oxazol-5-yl-carbonyl)pyrrolidin-3-yl]-9H-purin-6-amine;

N-[-1-(bicyclo[1.1.1]pent-1-ylcarbonyl)pyrrolidin-3-yl]-9-ethyl-8-(2-methylpyrimidin-5-yl)-9H-purin-6-amine;

9-ethyl-8-(2-methylpyrimidin-5-yl)-N-[-1-(piperidin-4-yl-carbonyl)pyrrolidin-3-yl]-9H-purin-6-amine;

9-ethyl-N-[-1-{[1-(1-methylethyl)azetidin-3-yl]carbonyl}pyrrolidin-3-yl]-8-(2-methylpyrimidin-5-yl)-9H-purin-6-amine;

N-[-1-(2-amino-2-methylpropanoyl)pyrrolidin-3-yl]-9-ethyl-8-(2-methylpyrimidin-5-yl)-9H-purin-6-amine;

4-{[(3    S)-3-{[9-ethyl-8-(2-methylpyrimidin-5-yl)-9H-purin-6-yl]amino}pyrrolidin-1-yl]carbonyl}-1-(1-methylethyl)pyrrolidin-2-one;

9-ethyl-N-[-1-{[1-(methylamino)cyclopropyl]carbonyl}pyrrolidin-3-yl]-8-(2-methylpyrimidin-5-yl)-9H-purin-6-amine;

9-ethyl-8-(2-methylpyrimidin-5-yl)-N-[-1-(piperidin-2-yl-carbonyl)pyrrolidin-3-yl]-9H-purin-6-amine;

N-{-1-[(1-aminocyclopropyl)carbonyl]pyrrolidin-3-yl}-9-ethyl-8-(2-methylpyrimidin-5-yl)-9H-purin-6-amine;

N-[(-1-2-azabicyclo[3.1.0]hex-6-ylcarbonyl)pyrrolidin-3-yl]-9-ethyl-8-(2-methylpyrimidin-5-yl)-9H-purin-6-amine;

9-ethyl-N-{-1-[3-(methylamino)propanoyl]pyrrolidin-3-yl}-8-(2-methylpyrimidin-5-yl)-9H-purin-6-amine;

N-[-1-(cyclopropylcarbonyl)-4-methylpyrrolidin-3-yl]-9-ethyl-8-(2-methylpyrimidin-5-yl)-9H-purin-6-amine;

9-ethyl-8-(2-methylpyrimidin-5-yl)-N-[-4-methyl-1-(-spiro[2.5]oct-1-ylcarbonyl)pyrrolidin-3-yl]-9H-purin-6-amine;

9-ethyl-N-[-{-4-methyl-1-(1,3-oxazol-4-ylcarbonyl)pyrrolidin-3-yl]-8-(2-methylpyrimidin-5-yl)-9H-purin-6-amine;

9-ethyl-N-[-1-{[-2-methylcyclopropyl]carbonyl}pyrrolidin-3-yl]-8-(2-methylpyrimidin-5-yl)-9H-purin-6-amine;

N-[-1-(cyclopropylcarbonyl)-2-methylpyrrolidin-3-yl]-9-ethyl-8-(2-methylpyrimidin-5-yl)-9H-purin-6-amine;

N-[1-(cyclopropylcarbonyl)-4,4-dimethylpyrrolidin-3-yl]-9-ethyl-8-(2-methylpyrimidin-5-yl)-9H-purin-6-amine;

1-(cyclopropylcarbonyl)-4-{-[9-ethyl-8-(2-methylpyrimidin-5-yl)-9H-purin-6-yl]amino}pyrrolidin-3-ol;

4-{[-3-{[9-ethyl-8-(2-methylpyrimidin-5-yl)-9H-purin-6-yl]amino}pyrrolidin-1-yl]carbonyl}cyclohexanol;

4-{[-3-{[9-ethyl-8-(2-methylpyrimidin-5-yl)-9H-purin-6-yl](methyl)amino}pyrrolidin-1-yl]carbonyl}cyclohexanol;

9-ethyl-N-{-1-[-tetrahydrofuran-3-ylcarbonyl]pyrrolidin-3-yl}-8-[6-(trifluoromethyl)pyridin-3-yl]-9H-purin-6-amine;

9-ethyl-N-{-1-[(3-methoxycyclobutyl)carbonyl]pyrrolidin-3-yl}-8-[6-(trifluoromethyl)pyridin-3-yl]-9H-purin-6-amine;

3-fluoro-5-(9-methyl-6-{[-1-propanoylpyrrolidin-3-yl]amino}-9H-purin-8-yl)phenol;

8-(3-fluoro-4-methoxyphenyl)-9-methyl-N-[-1-propanoylpyrrolidin-3-yl]-9H-purin-6-amine;

9-methyl-8-(5-methyl-1-phenyl-1H-pyrazol-4-yl)-N-[-1-propanoylpyrrolidin-3-yl]-9H-purin-6-amine;

8-(1-ethyl-5-methyl-1H-imidazol-4-yl)-9-methyl-N-[-1-propanoylpyrrolidin-3-yl]-9H-purin-6-amine;

8-(5-aminopyridin-3-yl)-9-methyl-N-[-1-propanoylpyrrolidin-3-yl]-9H-purin-6-amine;

8-(6-chloropyridin-3-yl)-9-methyl-N-[-1-propanoylpyrrolidin-3-yl]-9H-purin-6-amine;

9-methyl-8-(2-methylpyrimidin-5-yl)-N-[-1-propanoylpyrrolidin-3-yl]-9H-purin-6-amine;
N-[-1-(cyclopropylcarbonyl)-4-methylpyrrolidin-3-yl]-9-ethyl-8-(2-methylpyrimidin-5-yl)-9H-purin-6-amine;
N-[5-(cyclopropylcarbonyl)-5-azaspiro[2.4]hept-7-yl]-9-ethyl-8-(2-methylpyrimidin-5-yl)-9H-purin-6-amine;
N-[-1-(cyclopropylcarbonyl)-3-methylpyrrolidin-3-yl]-9-ethyl-8-(2-methylpyrimidin-5-yl)-9H-purin-6-amine;
N-[-1-(cyclopropylcarbonyl)-4-ethylpyrrolidin-3-yl]-9-ethyl-8-(2-methylpyrimidin-5-yl)-9H-purin-6-amine;
N-[-1-(cyclopropylcarbonyl)-4-fluoropyrrolidin-3-yl]-9-ethyl-8-(2-methylpyrimidin-5-yl)-9H-purin-6-amine;
N-[-1-(cyclopropylcarbonyl)-4-(trifluoromethyl)pyrrolidin-3-yl]-9-ethyl-8-(2-methylpyrimidin-5-yl)-9H-purin-6-amine;
N-[-1-(cyclopropylcarbonyl)pyrrolidin-3-yl]-9-methyl-8-(2-methylpyrimidin-5-yl)-9H-purin-6-amine;
N-[-1-(cyclopropylcarbonyl)pyrrolidin-3-yl]-9-ethyl-8-(1H-pyrrolo[2,3-b]pyridin-5-yl)-9H-purin-6-amine;
8-(5-chloro-6-methoxypyridin-3-yl)-N-[-1-(cyclopropylcarbonyl)pyrrolidin-3-yl]-9-ethyl-9H-purin-6-amine;
N-[-1-(cyclopropylcarbonyl)-4-fluoropyrrolidin-3-yl]-9-ethyl-8-(2-methylpyrimidin-5-yl)-9H-purin-6-amine;
9-methyl-8-[4-(methylsulfonyl)phenyl]-N-[-1-propanoylpyrrolidin-3-yl]-9H-purin-6-amine;
N-[-1-(cyclopropylcarbonyl)pyrrolidin-3-yl]-N,9-diethyl-8-(2-methylpyrimidin-5-yl)-9H-purin-6-amine;
N-[-1-(cyclopropylcarbonyl)pyrrolidin-3-yl]-9-ethyl-N-methyl-8-(2-methylpyrimidin-5-yl)-9H-purin-6-amine;
N-[-1-(cyclopropylcarbonyl)pyrrolidin-3-yl]-9-ethyl-8-[4-(trifluoromethyl)phenyl]-9H-purin-6-amine;
8-(6-methoxypyridin-3-yl)-9-methyl-N-[-1-propanoylpyrrolidin-3-yl]-9H-purin-6-amine;
8-(4-methoxy-3-methylphenyl)-9-methyl-N-[-1-propanoylpyrrolidin-3-yl]-9H-purin-6-amine;
2-methoxy-5-(9-methyl-6-{[-1-propanoylpyrrolidin-3-yl]amino}-9H-purin-8-yl)pyridine-3-carbonitrile;
2-[5-(9-methyl-6-{[-1-propanoylpyrrolidin-3-yl]amino}-9H-purin-8-yl)pyridin-3-yl]propan-2-ol;
N-[-1-(cyclopropylcarbonyl)pyrrolidin-3-yl]-9-ethyl-8-(1-methyl-1H-pyrazolo[3,4-b]pyridin-5-yl)-9H-purin-6-amine;
N-[-1-(cyclopropylcarbonyl)pyrrolidin-3-yl]-9-ethyl-8-[1-(2,2,2-trifluoroethyl)-1H-pyrazol-4-yl]-9H-purin-6-amine;
N-[-1-(cyclopropylcarbonyl)pyrrolidin-3-yl]-9-ethyl-8-(5-phenylpyridin-3-yl)-9H-purin-6-amine;
8-(5-chloropyridin-3-yl)-N-[-1-(cyclopropylcarbonyl)pyrrolidin-3-yl]-9-ethyl-9H-purin-6-amine;
[5-(6-{[-1-(cyclopropylcarbonyl)pyrrolidin-3-yl]amino}-9-ethyl-9H-purin-8-yl)pyrimidin-2-yl]methanol;
9-ethyl-8-(2-methylpyrimidin-5-yl)-N-[-1-pyridin-2-ylpyrrolidin-3-yl]-9H-purin-6-amine;
9-ethyl-8-(2-methylpyrimidin-5-yl)-N-[-1-pyrimidin-2-ylpyrrolidin-3-yl]-9H-purin-6-amine;
9-ethyl-N-[-1-(5-methylpyridin-2-yl)pyrrolidin-3-yl]-8-(2-methylpyrimidin-5-yl)-9H-purin-6-amine;
9-ethyl-N-[-1-pyridin-2-ylpyrrolidin-3-yl]-8-[6-(trifluoromethyl)pyridin-3-yl]-9H-purin-6-amine;
9-ethyl-8-(2-methylpyrimidin-5-yl)-N-[-1-pyridin-2-ylpiperidin-3-yl]-9H-purin-6-amine;
9-ethyl-N-[-1-(4-ethylpyridin-2-yl)pyrrolidin-3-yl]-8-(2-methylpyrimidin-5-yl)-9H-purin-6-amine;
9-ethyl-N-[-1-(6-methoxypyridin-2-yl)pyrrolidin-3-yl]-8-(2-methylpyrimidin-5-yl)-9H-purin-6-amine;
9-ethyl-N-{-1-[6-(methylamino)pyridin-2-yl]pyrrolidin-3-yl}-8-(2-methylpyrimidin-5-yl)-9H-purin-6-amine;
9-ethyl-N-[-1-isoquinolin-1-ylpyrrolidin-3-yl]-8-(2-methylpyrimidin-5-yl)-9H-purin-6-amine;
9-ethyl-N-[-1-(3-methylpyridin-2-yl)pyrrolidin-3-yl]-8-(2-methylpyrimidin-5-yl)-9H-purin-6-amine;
6-[-3-{[9-ethyl-8-(2-methylpyrimidin-5-yl)-9H-purin-6-yl]amino}pyrrolidin-1-yl]pyridine-3-carbonitrile;
methyl-4-{[9-ethyl-8-(2-methylpyrimidin-5-yl)-9H-purin-6-yl]amino}-1-pyridin-2-yl-D-prolinate;
9-ethyl-8-(2-methylpyrimidin-5-yl)-N-[-1-thieno[3,2-c]pyridin-4-ylpyrrolidin-3-yl]-9H-purin-6-amine;
N-cyclopropyl-3-{[9-ethyl-8-(2-methylpyrimidin-5-yl)-9H-purin-6-yl]amino}-N-methylcyclopentanecarboxamide;
N-[-3-(azetidin-1-ylcarbonyl)cyclopentyl]-9-ethyl-8-(2-methylpyrimidin-5-yl)-9H-purin-6-amine;
methyl-3-{[9-ethyl-8-(2-methylpyrimidin-5-yl)-9H-purin-6-yl]amino}cyclopentanecarboxylate;
3-{[9-ethyl-8-(2-methylpyrimidin-5-yl)-9H-purin-6-yl]amino}-N,N-dimethylcyclopentanecarboxamide;
N-cyclopropyl-3-{[9-ethyl-8-(2-methylpyrimidin-5-yl)-9H-purin-6-yl]amino}-N-methylcyclopentanecarboxamide;
N-[-3-(azetidin-1-ylcarbonyl)cyclopentyl]-9-ethyl-8-(2-methylpyrimidin-5-yl)-9H-purin-6-amine;
3-{[9-ethyl-8-(2-methylpyrimidin-5-yl)-9H-purin-6-yl]amino}-N-methylcyclopentanecarboxamide;
N-(3-{[9-ethyl-8-(2-methylpyrimidin-5-yl)-9H-purin-6-yl]amino}cyclohexyl)-1,3-oxazole-4-carboxamide;
6-{[1-(cyclopropylcarbonyl)pyrrolidin-3-yl]amino}-N-(cyclopropylmethyl)-9-ethyl-9H-purine-8-carboxamide;
6-{[-1-(cyclopropylcarbonyl)pyrrolidin-3-yl]amino}-9-ethyl-N-(2-methoxyethyl)-9H-purine-8-carboxamide;
6-{[-1-(cyclopropylcarbonyl)pyrrolidin-3-yl]amino}-9-ethyl-N-(2,2,2-trifluoroethyl)-9H-purine-8-carboxamide;
N-[-1-(cyclopropylcarbonyl)pyrrolidin-3-yl]-9-ethyl-8-(morpholin-4-ylcarbonyl)-9H-purin-6-amine;
6-{[-1-(cyclopropylcarbonyl)pyrrolidin-3-yl]amino}-9-ethyl-N,N-dimethyl-9H-purine-8-carboxamide;
6-{[-1-(cyclopropylcarbonyl)pyrrolidin-3-yl]amino}-9-ethyl-N-oxetan-3-yl-9H-purine-8-carboxamide;
6-{[-1-(cyclopropylcarbonyl)pyrrolidin-3-yl]amino}-9-ethyl-N-(trans-4-hydroxycyclohexyl)-9H-purine-8-carboxamide;
N-[-1-(cyclopropylcarbonyl)pyrrolidin-3-yl]-9-ethyl-8-(pyrrolidin-1-ylcarbonyl)-9H-purin-6-amine;
6-{[-1-(cyclobutylcarbonyl)pyrrolidin-3-yl]amino}-9-ethyl-N-(2,2,2-trifluoroethyl)-9H-purine-8-carboxamide;
9-ethyl-6-{[-1-pyridin-2-ylpyrrolidin-3-yl]amino}-N-(2,2,2-trifluoroethyl)-9H-purine-8-carboxamide;
6-{[-1-(cyclopropylcarbonyl)pyrrolidin-3-yl]amino}-9-ethyl-9H-purine-8-carboxamide;
6-{[-1-(cyclopropylcarbonyl)pyrrolidin-3-yl]amino}-N-[(1S)-1-cyclopropylethyl]-9-ethyl-9H-purine-8-carboxamide;
N-cyclohexyl-6-{[-1-(cyclopropylcarbonyl)pyrrolidin-3-yl]amino}-9-ethyl-9H-purine-8-carboxamide;
6-{[-1-(cyclopropylcarbonyl)pyrrolidin-3-yl]amino}-9-ethyl-N-methyl-N-(2,2,2-trifluoroethyl)-9H-purine-8-carboxamide;
N-tert-butyl-6-{[-1-(cyclopropylcarbonyl)pyrrolidin-3-yl]amino}-9-ethyl-9H-purine-8-carboxamide;
6-{[-1-(cyclopropylcarbonyl)pyrrolidin-3-yl]amino}-9-ethyl-N-(3,3,3-trifluoropropyl)-9H-purine-8-carboxamide;
6-{[-1-(cyclopropylcarbonyl)pyrrolidin-3-yl]amino}-9-ethyl-N-phenyl-9H-purine-8-carboxamide;
6-{[-1-(cyclopropylcarbonyl)pyrrolidin-3-yl]amino}-N,9-diethyl-9H-purine-8-carboxamide;

6-{[-1-(cyclopropylcarbonyl)pyrrolidin-3-yl]amino}-9-ethyl-N-pyridin-2-yl-9H-purine-8-carboxamide;
6-{[-1-(cyclopropylcarbonyl)pyrrolidin-3-yl]amino}-9-ethyl-N-pyridin-3-yl-9H-purine-8-carboxamide;
N-[-1-(cyclopropylcarbonyl)pyrrolidin-3-yl]-8-(cyclopropylmethyl)-9-ethyl-9H-purin-6-amine;
9-ethyl-8-(2-methylpropyl)-N-[-1-propanoylpyrrolidin-3-yl]-9H-purin-6-amine;
9-methyl-8-(2-methylpropyl)-N-[-1-propanoylpyrrolidin-3-yl]-9H-purin-6-amine;
9-ethyl-8-methyl-N-[-1-propanoylpyrrolidin-3-yl]-9H-purin-6-amine;
N-[-1-(cyclopropylcarbonyl)pyrrolidin-3-yl]-9-ethyl-8-(1-methylethyl)-9H-purin-6-amine;
3-(6-{[-1-(cyclopropylcarbonyl)pyrrolidin-3-yl]amino}-9-ethyl-9H-purin-8-yl)propan-1-ol;
N-[-1-(cyclopropylcarbonyl)pyrrolidin-3-yl]-9-ethyl-8-(2,2,2-trifluoroethyl)-9H-purin-6-amine;
N-[-1-(cyclopropylcarbonyl)pyrrolidin-3-yl]-9-ethyl-8-(methoxymethyl)-9H-purin-6-amine;
8-cyclopropyl-9-methyl-N-[-1-propanoylpyrrolidin-3-yl]-9H-purin-6-amine;
8-cyclopropyl-N-[-1-(cyclopropylcarbonyl)pyrrolidin-3-yl]-9-ethyl-9H-purin-6-amine;
9-ethyl-N-[-1-propanoylpyrrolidin-3-yl]-8-(trifluoromethyl)-9H-purin-6-amine;
8-(difluoromethyl)-9-ethyl-N-{-1-[(1-methyl-1H-pyrazol-3-yl)carbonyl]pyrrolidin-3-yl}-9H-purin-6-amine;
8-(difluoromethyl)-9-ethyl-N-[-1-propanoylpyrrolidin-3-yl]-9H-purin-6-amine;
N-[-1-(cyclopropylcarbonyl)pyrrolidin-3-yl]-8-(difluoromethyl)-9-ethyl-9H-purin-6-amine;
N-[-1-(cyclobutylcarbonyl)pyrrolidin-3-yl]-8-(difluoromethyl)-9-ethyl-9H-purin-6-amine;
8-(difluoromethyl)-9-ethyl-N-[-1-(1,3-oxazol-4-ylcarbonyl)pyrrolidin-3-yl]-9H-purin-6-amine;
8-(difluoromethyl)-9-ethyl-N-{-1-[(trans-3-methoxycyclobutyl)carbonyl]pyrrolidin-3-yl}-9H-purin-6-amine;
8-(difluoromethyl)-9-ethyl-N-[-1-(1-methyl-D-prolyl)pyrrolidin-3-yl]-9H-purin-6-amine;
8-(difluoromethyl)-9-ethyl-N-[-1-(spiro[2.4]hept-1-ylcarbonyl)pyrrolidin-3-yl]-9H-purin-6-amine;
N-[-1-(cyclopropylcarbonyl)pyrrolidin-3-yl]-9-ethyl-8-(2-methoxyethyl)-9H-purin-6-amine;
N-[-1-(cyclopropylcarbonyl)pyrrolidin-3-yl]-8,9-diethyl-9H-purin-6-amine;
8-tert-butyl-N-[-1-(cyclopropylcarbonyl)pyrrolidin-3-yl]-9-ethyl-9H-purin-6-amine;
N-[-1-(cyclopropylcarbonyl)pyrrolidin-3-yl]-9-ethyl-8-{[1-(methylsulfonyl)azetidin-3-yl]methyl}-9H-purin-6-amine;
8-(difluoromethyl)-9-ethyl-N-[-1-pyridin-2-ylpyrrolidin-3-yl]-9H-purin-6-amine;
N-[-1-(azetidin-1-ylcarbonyl)pyrrolidin-3-yl]-8-(difluoromethyl)-9-ethyl-9H-purin-6-amine;
8-(difluoromethyl)-9-ethyl-N-{-1-[(3-methoxyazetidin-1-yl)carbonyl]pyrrolidin-3-yl}-9H-purin-6-amine;
1-(6-{[-1-(cyclopropylcarbonyl)pyrrolidin-3-yl]amino}-9-ethyl-9H-purin-8-yl)pyrrolidin-3-ol;
8-(1H-benzimidazol-1-yl)-N-[-1-(cyclopropylcarbonyl)pyrrolidin-3-yl]-9-ethyl-9H-purin-6-amine;
N-[-1-(cyclopropylcarbonyl)pyrrolidin-3-yl]-9-ethyl-8-[4-(trifluoromethyl)-1H-imidazol-1-yl]-9H-purin-6-amine;
cyclopropyl[-3-({9-ethyl-8-[methyl(2-methylpropyl)amino]-9H-purin-6-yl}amino)pyrrolidin-1-yl]methanone;
N-[-1-(cyclopropylcarbonyl)pyrrolidin-3-yl]-9-ethyl-8-phenoxy-9H-purin-6-amine;
N-[-1-(cyclopropylcarbonyl)pyrrolidin-3-yl]-9-ethyl-8-(3-fluoro-4-methoxyphenoxy)-9H-purin-6-amine;
N-[-1-(cyclopropylcarbonyl)pyrrolidin-3-yl]-9-ethyl-8-(1-methylethoxy)-9H-purin-6-amine;
N-[-1-(cyclopropylcarbonyl)pyrrolidin-3-yl]-9-ethyl-8-(4,5,6,7-tetrahydro-1H-benzimidazol-1-yl)-9H-purin-6-amine;
8-(1-ethyl-5-methyl-1H-pyrazol-4-yl)-N-[-1-propanoylpyrrolidin-3-yl]-9-propyl-9H-purin-6-amine;
8-(2-methylpyrimidin-5-yl)-N-[-1-propanoylpyrrolidin-3-yl]-9-propyl-9H-purin-6-amine;
9-(cyclopropylmethyl)-8-(1-ethyl-5-methyl-1H-pyrazol-4-yl)-N-[-1-propanoylpyrrolidin-3-yl]-9H-purin-6-amine;
9-(2,2-difluoroethyl)-8-(1-ethyl-5-methyl-1H-pyrazol-4-yl)-N-[-1-propanoylpyrrolidin-3-yl]-9H-purin-6-amine;
N-[-1-(cyclopropylcarbonyl)pyrrolidin-3-yl]-8-(2-methylpyrimidin-5-yl)-9-(2,2,2-trifluoroethyl)-9H-purin-6-amine;
8-(1-ethyl-5-methyl-1H-pyrazol-4-yl)-9-methyl-N-[-1-propylpyrrolidin-3-yl]-9H-purin-6-amine;
N-[-5-(1-cyclopropylethyl)-5-azaspiro[2.4]hept-7-yl]-9-ethyl-8-(2-methylpyrimidin-5-yl)-9H-purin-6-amine;
9-ethyl-N-[-5-(1-methylethyl)-5-azaspiro[2.4]hept-7-yl]-8-(2-methylpyrimidin-5-yl)-9H-purin-6-amine;
8-(1-ethyl-5-methyl-1H-pyrazol-4-yl)-N-[-1-(ethylsulfonyl)piperidin-3-yl]-9-methyl-9H-purin-6-amine;
N-ethyl-3-{[8-(1-ethyl-5-methyl-1H-pyrazol-4-yl)-9-methyl-9H-purin-6-yl]amino}piperidine-1-carboxamide;
3-{[9-ethyl-8-(2-methylpyrimidin-5-yl)-9H-purin-6-yl]amino}-N-(2-methoxyethyl)pyrrolidine-1-carboxamide;
9-ethyl-N-{-1-[(2-methylazetidin-1-yl)carbonyl]pyrrolidin-3-yl}-8-(2-methylpyrimidin-5-yl)-9H-purin-6-amine;
9-ethyl-8-(2-methylpyrimidin-5-yl)-N-[-1-(morpholin-4-ylcarbonyl)pyrrolidin-3-yl]-9H-purin-6-amine;
9-ethyl-8-(2-methylpyrimidin-5-yl)-N-[-1-(piperidin-1-ylcarbonyl)pyrrolidin-3-yl]-9H-purin-6-amine;
N-cyclopropyl-3-{[9-ethyl-8-(2-methylpyrimidin-5-yl)-9H-purin-6-yl]amino}pyrrolidine-1-carboxamide;
N-(cyclopropylmethyl)-3-{[9-ethyl-8-(2-methylpyrimidin-5-yl)-9H-purin-6-yl]amino}pyrrolidine-1-carboxamide;
3-{[9-ethyl-8-(2-methylpyrimidin-5-yl)-9H-purin-6-yl]amino}-N-(2,2,2-trifluoroethyl)pyrrolidine-1-carboxamide;
N-[-1-(azetidin-1-ylcarbonyl)pyrrolidin-3-yl]-9-ethyl-8-(2-methylpyrimidin-5-yl)-9H-purin-6-amine;
9-ethyl-N-{-1-[(3-methoxyazetidin-1-yl)carbonyl]pyrrolidin-3-yl}-8-(2-methylpyrimidin-5-yl)-9H-purin-6-amine;
N-{-1-[(3,3-dimethylpyrrolidin-1-yl)carbonyl]pyrrolidin-3-yl}-9-ethyl-8-(2-methylpyrimidin-5-yl)-9H-purin-6-amine;
9-ethyl-N-[-1-{[-3-fluoropyrrolidin-1-yl]carbonyl}pyrrolidin-3-yl]-8-(2-methylpyrimidin-5-yl)-9H-purin-6-amine;
9-ethyl-N-[-1-{[-3-methoxypyrrolidin-1-yl]carbonyl}pyrrolidin-3-yl]-8-(2-methylpyrimidin-5-yl)-9H-purin-6-amine;
N-cyclohexyl-3-{[9-ethyl-8-(2-methylpyrimidin-5-yl)-9H-purin-6-yl]amino}pyrrolidine-1-carboxamide;
ethyl N-{[-3-{[9-ethyl-8-(2-methylpyrimidin-5-yl)-9H-purin-6-yl]amino}pyrrolidin-1-yl]carbonyl}-beta-alaninate;
ethyl N-{[-3-{[9-ethyl-8-(2-methylpyrimidin-5-yl)-9H-purin-6-yl]amino}pyrrolidin-1-yl]carbonyl}(D and L)-alaninate;
3-{[9-ethyl-8-(2-methylpyrimidin-5-yl)-9H-purin-6-yl]amino}-N-(1-methylethyl)pyrrolidine-1-carboxamide;

N-[(-1,1-dioxidotetrahydrothiophen-3-yl)methyl]-3-{[9-ethyl-8-(2-methylpyrimidin-5-yl)-9H-purin-6-yl]amino}pyrrolidine-1-carboxamide;
3-{[9-ethyl-8-(2-methylpyrimidin-5-yl)-9H-purin-6-yl]amino}-N-(furan-2-ylmethyl)pyrrolidine-1-carboxamide;
N-cyclobutyl-3-{[9-ethyl-8-(2-methylpyrimidin-5-yl)-9H-purin-6-yl]amino}pyrrolidine-1-carboxamide;
N-butyl-3-{[9-ethyl-8-(2-methylpyrimidin-5-yl)-9H-purin-6-yl]amino}pyrrolidine-1-carboxamide;
methyl N-{[-3-{[9-ethyl-8-(2-methylpyrimidin-5-yl)-9H-purin-6-yl]amino}pyrrolidin-1-yl]carbonyl}-2-methylalaninate;
3-{[9-ethyl-8-(2-methylpyrimidin-5-yl)-9H-purin-6-yl]amino}-N-(1,1,3,3-tetramethylbutyl)pyrrolidine-1-carboxamide;
N-[-1-(azetidin-1-ylcarbonyl)pyrrolidin-3-yl]-9-ethyl-8-[6-(trifluoromethyl)pyridin-3-yl]-9H-purin-6-amine;
9-ethyl-6-({-1-[(3-methoxyazetidin-1-yl)carbonyl]pyrrolidin-3-yl}amino)-N-(2,2,2-trifluoroethyl)-9H-purine-8-carboxamide;
2,2,2-trifluoroethyl-3-{[9-ethyl-8-(2-methylpyrimidin-5-yl)-9H-purin-6-yl]amino}pyrrolidine-1-carboxylate;
methyl-3-{[9-ethyl-8-(2-methylpyrimidin-5-yl)-9H-purin-6-yl]amino}pyrrolidine-1-carboxylate;
2-fluoroethyl-3-{[9-ethyl-8-(2-methylpyrimidin-5-yl)-9H-purin-6-yl]amino}pyrrolidine-1-carboxylate;
2,2-dimethylpropyl-3-{[9-ethyl-8-(2-methylpyrimidin-5-yl)-9H-purin-6-yl]amino}pyrrolidine-1-carboxylate;
1-methylethyl-3-{[9-ethyl-8-(2-methylpyrimidin-5-yl)-9H-purin-6-yl]amino}pyrrolidine-1-carboxylate;
1,1-dioxidotetrahydrothiophen-3-yl-3-{[9-ethyl-8-(2-methylpyrimidin-5-yl)-9H-purin-6-yl]amino}pyrrolidine-1-carboxylate;
2-methoxyethyl-3-{[9-ethyl-8-(2-methylpyrimidin-5-yl)-9H-purin-6-yl]amino}pyrrolidine-1-carboxylate;
cyclohexyl-3-{[9-ethyl-8-(2-methylpyrimidin-5-yl)-9H-purin-6-yl]amino}pyrrolidine-1-carboxylate;
1-methylpropyl-3-{[9-ethyl-8-(2-methylpyrimidin-5-yl)-9H-purin-6-yl]amino}pyrrolidine-1-carboxylate;
benzyl-3-{[9-ethyl-8-(2-methylpyrimidin-5-yl)-9H-purin-6-yl]amino}pyrrolidine-1-carboxylate;
3-(dimethylamino)propyl-3-{[9-ethyl-8-(2-methylpyrimidin-5-yl)-9H-purin-6-yl]amino}pyrrolidine-1-carboxylate;
4-{[8-(1-ethyl-5-methyl-1H-pyrazol-4-yl)-9-methyl-9H-purin-6-yl]amino}-1-propylpyrrolidin-2-one;
4-{[8-(1-ethyl-5-methyl-1H-pyrazol-4-yl)-9-methyl-9H-purin-6-yl]amino}-1-(2-methylprop-2-en-1-yl)pyrrolidin-2-one;
4-{[8-(1-ethyl-5-methyl-1H-pyrazol-4-yl)-9-methyl-9H-purin-6-yl]amino}-1-(2-methylpropyl)pyrrolidin-2-one;
4-{[9-ethyl-8-(2-methylpyrimidin-5-yl)-9H-purin-6-yl]amino}-1-propylpyrrolidin-2-one;
5-{[9-ethyl-8-(2-methylpyrimidin-5-yl)-9H-purin-6-yl]amino}-1-propylpiperidin-2-one;
5-1-(cyclopropylmethyl)-5-{[9-ethyl-8-(2-methylpyrimidin-5-yl)-9H-purin-6-yl]amino}piperidin-2-one;
1-(cyclopropylmethyl)-6-{[9-ethyl-8-(2-methylpyrimidin-5-yl)-9H-purin-6-yl]amino}azepan-2-one;
1-(cyclopropylcarbonyl)-4-{[9-ethyl-8-(2-methylpyrimidin-5-yl)-9H-purin-6-yl]amino}-D-proline;
1-(cyclopropylcarbonyl)-4-{[9-ethyl-8-(2-methylpyrimidin-5-yl)-9H-purin-6-yl]amino}-N,N-dimethyl-D-prolinamide;
1-(cyclopropylcarbonyl)-4-{[9-ethyl-8-(2-methylpyrimidin-5-yl)-9H-purin-6-yl]amino}-N-methyl-D-prolinamide;
1-(cyclopropylcarbonyl)-4-{[9-ethyl-8-(2-methylpyrimidin-5-yl)-9H-purin-6-yl]amino}-N-(1-methylethyl)-D-prolinamide;
1-(cyclopropylcarbonyl)-4-{[9-ethyl-8-(2-methylpyrimidin-5-yl)-9H-purin-6-yl]amino}-D-prolinamide;
1-(cyclopropylcarbonyl)-N-[-1,2-dimethylpropyl]-4-{[9-ethyl-8-(2-methylpyrimidin-5-yl)-9H-purin-6-yl]amino}-D-prolinamide;
1-(cyclopropylcarbonyl)-4-{[9-ethyl-8-(2-methylpyrimidin-5-yl)-9H-purin-6-yl]amino}-N-(2-hydroxyethyl)-D-prolinamide;
1-(cyclopropylcarbonyl)-N-[2-(dimethylamino)ethyl]-4-{[9-ethyl-8-(2-methylpyrimidin-5-yl)-9H-purin-6-yl]amino}-D-prolinamide;
1-(cyclopropylcarbonyl)-4-{[9-ethyl-8-(2-methylpyrimidin-5-yl)-9H-purin-6-yl]amino}-N-methyl-L-prolinamide;
1-(cyclopropylcarbonyl)-4-{[9-ethyl-8-(2-methylpyrimidin-5-yl)-9H-purin-6-yl]amino}-L-prolinamide;
4-{[9-ethyl-8-(2-methylpyrimidin-5-yl)-9H-purin-6-yl]amino}-1-pyridin-2-yl-D-prolinamide;
4-{[9-ethyl-8-(2-methylpyrimidin-5-yl)-9H-purin-6-yl]amino}-N-(2-hydroxyethyl)-1-pyridin-2-yl-D-prolinamide;
N-cyclopropyl-4-{[9-ethyl-8-(2-methylpyrimidin-5-yl)-9H-purin-6-yl]amino}-N-methyl-D-prolinamide;
N-[-1-(cyclopropylcarbonyl)-5-(5-methyl-1,3,4-oxadiazol-2-yl)pyrrolidin-3-yl]-9-ethyl-8-(2-methylpyrimidin-5-yl)-9H-purin-6-amine;
N-[-1-(cyclopropylcarbonyl)pyrrolidin-3-yl]-9-ethyl-8-(phenylethynyl)-9H-purin-6-amine;
N-[-1-(cyclopropylcarbonyl)pyrrolidin-3-yl]-9-ethyl-8-(pyrimidin-5-ylethynyl)-9H-purin-6-amine;
N-[-1-(cyclopropylcarbonyl)pyrrolidin-3-yl]-9-ethyl-8-(3-methoxyprop-1-yn-1-yl)-9H-purin-6-amine; and
3-(6-{[-1-(cyclopropylcarbonyl)pyrrolidin-3-yl]amino}-9-ethyl-9H-purin-8-yl)prop-2-yn-1-ol.

The invention also encompasses pharmaceutical compositions containing a compound of formula I, and methods for treatment or prevention of PI3K-delta mediated diseases using compounds of formula I.

One aspect of the present invention is to provide compounds that can inhibit the biological activity of human PI3K-delta. Another aspect of the invention is to provide methods of selectively modulating human PI3K-delta activity and thereby promoting medical treatment of diseases mediated by PI3K-delta dysfunction.

In one embodiment of the invention, the compounds of formula I inhibit PI3K-delta activity in biochemical and cell-based assays and to exhibit therapeutic activity in medical conditions in which PI3K-delta activity is excessive or undesirable.

The invention is described using the following definitions unless otherwise indicated.

"Acyl" means a —C(O)R radical Where R is optionally substituted alkyl, alkenyl, cycloalkyl, heterocycloalkyl, aryl heteroaryl, etc.

"Acylamino" means a —NRR' radical where R is H, OH, or alkoxy and R' is acyl, as defined herein.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

The term "alkyl" refers to an aliphatic hydrocarbon group which may be straight or branched and having the indicated number of carbon atoms. Non-limiting examples of alkyl groups include methyl, ethyl, propyl, isopropyl, butyl, s- and t-butyl, pentyl, hexyl, and the like.

The term "heteroalkyl" refers to an alkyl group where 1, 2, or 3 of the carbon atoms are each independently replaced by a heteroatom independently selected from N, O, or S.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkynyl" refers to an aliphatic hydrocarbon group containing at least one carbon-carbon triple bond and which may be straight or branched and having the indicated number of carbon atoms. Non-limiting examples of suitable alkynyl groups include ethynyl, propynyl, 2-butynyl and 3-methylbutynyl.

"Alkoxy" refers to an alkyl-O— group in which the alkyl group is as described above. $C_{1-6}$alkoxy, for example, includes methoxy, ethoxy, propoxy, isopropoxy, and the like.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "$C_0$" as employed in expressions such as "$C_{0-6}$ alkyl" means a direct covalent bond; or when the term appears at the terminus of a substituent, $C_{0-6}$ alkyl means hydrogen or C1-6alkyl. Similarly, when an integer defining the presence of a certain number of atoms in a group is equal to zero, it means that the atoms adjacent thereto are connected directly by a bond. For example, in the structure

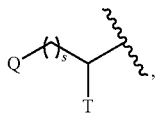

wherein s is an integer equal to zero, 1 or 2, the structure is

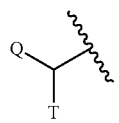

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and polycarbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

"Carboxy" refers to the functional group —C(O)OR, for example: ethylcarboxy is

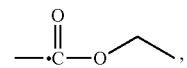

phenylcarboxy is

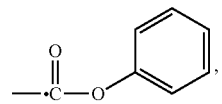

and cyclopropycarboxy is

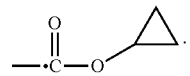

"Carboxyalkyl" refers to an alkyl group substituted with at least one, specifically one or two, —C(O)OH group(s).

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other is saturated or unsaturated, with attachment via any carbon atom that results in a stable compound. Representative examples of this subset include the following:

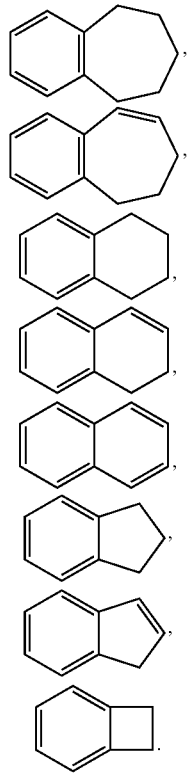

"Cyanoalkyl" refers to an alkyl group as described above in which one hydrogen atom has been replaced by a cyano group. Examples include $CH_2CN$, $CH_2CH_2CN$ and $CH(CN)CH_3$.

"Cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro [2.2]pentane), or are bridged groups (e.g., norbornane). Additional examples within the above meaning include, but are not limited to, cyclopropane, cyclobutane, cyclopentane, cyclohexane, perhydroindan, decalin, spiro[4.5]decane, spiro[2.5]oxtyl, bicyclo[2.2.2]octane, and the like.

"Heterocycloalkyl" refers to a "cycloalkyl" wherein one or more of the carbon atoms are replaced by at least one heteroatom, such as, for example, 1 to 4 heteroatoms selected from nitrogen, oxygen, and sulfur.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$haloalkyl, for example, includes —$CF_3$, —$CF_2CF_3$, $CHFCH_3$, and the like.

"Heterocycle", "heterocyclic" or "heterocyclyl" represents a monocyclic or bicyclic 3-12 membered ring system in which at least one ring is non-aromatic (saturated or partially unsaturated) and containing at least one heteroatom selected from O, S and N. In a bicyclic ring system, the second ring may be a heteroaryl, heterocycle or a saturated, partially unsaturated or aromatic carbocycle, and the point(s) of attachment to the rest of the molecule may be on either ring. "Heterocyclyl" therefore includes heteroaryls, as well as dihydro and tetrahydro analogs thereof. Attachment of a heterocyclyl substituent can occur via a carbon atom or via a heteroatom.

Examples of heterocycles (heterocyclyl) include, but are not limited to, azetidinyl, pyrrolidinyl, piperidinyl, piperazinyl, morpholinyl, thiamorpholinyl, tetrahydrofuranyl, dihydrofuranyl, tetrahydrothienyl, tetrahydropyranyl, dihydropyranyl, dihydroimidazolyl, dihydroindolyl, 1,2,3,4-tetrahydroisoquinolinyl, 5,6,7,8-tetrahydroimidazo[1,2-a]pyrazine, 2,3-dihydrobenzofuranyl, benzo-1,4-dioxanyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

Saturated heterocyclics form a subset of the heterocycles; i.e., the terms "saturated heterocyclic and heterocycloalkyl" generally refers to a heterocycle as defined above in which the entire ring system (whether mono- or poly-cyclic) is saturated. The term "saturated heterocyclic ring" refers to a 3- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, azetidinyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. For a bicyclic heteroaryl only one of the rings need to be heteroaromatic, the second ring may be a heteroaromatic or an aromatic, saturated, or partially unsaturated carbocycle, and the point(s) of attachment to the rest of the molecule may be on either ring. In the case of substituted heteroaryl rings containing at least one nitrogen atom (e.g., pyridine), such substitutions can be those resulting in N-oxide formation. Examples of heteroaryl include, but are not limited to, furanyl, thienyl (or thiophenyl), pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzopyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]-pyrimidinyl, 5,6-dihydropyrrolo[1,2-b]pyrazolyl, pyrrolo[3,2-c]pyridinyl, pyrrolo[2,3-b]pyridinyl, pyrazolo[3,4-b]pyridinyl, 4,5,6,7-tetrahydro-1H-benzimidazolyl, thieno[2,3-b]pyrrolyl, furopyridine and thienopyridine.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl

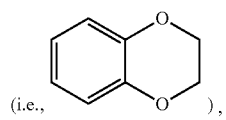

(i.e., ), imidazo(2,1-b)(1,3)thiazole,

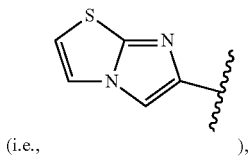 [SMILES: *c1cn2ccsc2n1]

(i.e., ), and benzo-1,3-dioxolyl

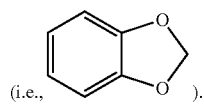

(i.e., ).

In certain contexts herein,

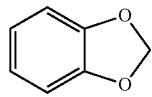

is alternatively referred to as phenyl having as a substituent methylenedioxy attached to two adjacent carbon atoms.

"Heteroalicyclic" group refers to a monocyclic or fused ring of 3 to 12 ring atoms containing one, or more heteroatoms in the ring.

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

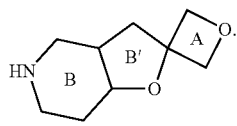

In one embodiment, all rings of the spirocyclyl system are saturated, such as spiro[2.5]octyl. In another embodiment, the individual rings of the spirocyclyl system are selected from both saturated and unsaturated rings.

For example a heteroalicyclic spirocyclyl or "spiroheterocyclic ring," as used herein, refers to a bicyclic heterocyclic ring as defined above wherein the two rings are joined through a common ring carbon atom. In one embodiment, a spiroheterocyclic ring is a 3- to 12-membered ring system containing one to three heteroatoms, e.g., one to two heteroatoms, selected from the group consisting of N and O. Non-limiting examples of spiroheterocyclic rings include azaspiro[2.4]heptyl, 1,9-diazaspiro[5.5]undecane; 2,8-diazaspiro[5.5]undecane; 2,8-diazaspiro[4.5]decane; 1,7-diazaspiro[4.4]nonane; 1,7-diazaspiro[4.5]decane; 2,7-diazaspiro[4.5]decane, 1-oxa-8-azaspiro[5.5]undecane; 2-oxa-7-azaspiro[4.5]decane; 1-oxa-7-azaspiro[4.5]decane; 1,4-dioxa-7-azaspiro[4.5]decane; 1,4-dioxa-8-azaspiro[4.5]decane, and 1,4-dioxaspiro[4.5]decane.

Non-limiting examples of a carbocyclic spirocyclyl systems comprising include: spiro[2.2]pentane, spiro[cylclobutane-1,2'-indene], spiro[4.4]nonane, and spiro[4.5]decane.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

Structural representations of compounds having substituents terminating with a methyl group may display the terminal methyl group either using the characters "$CH_3$", e.g. "—$CH_3$" or using a straight line representing the presence of the methyl group, e.g. "-", i.e.,

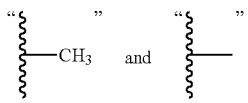

have equivalent meanings.

For variable definitions containing terms having repeated terms, e.g., $(CR_iR_j)_r$, where r is the integer 2, $R_i$ is a defined variable, and $R_j$ is a defined variable, the value of $R_i$ may differ in each instance in which it occurs, and the value of $R_j$ may differ in each instance in which it occurs. For example, if $R_i$ and $R_j$ are independently selected from the group consisting of methyl, ethyl, propyl and butyl, then $(CR_iR_j)_2$ can be

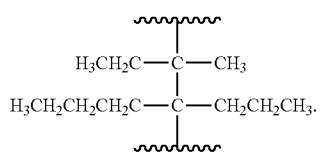

In one embodiment of the invention, $R^1$ is selected from hydrogen, $C_{1-5}$alkyl, and $C_{3-5}$ cycloalkyl$C_{0-4}$alkyl, wherein $R^1$ is optionally substituted by 0, 1, 2, 3, or 4 groups independently selected from hydrogen, fluoro, chloro, methyl, amino, $OR^a$, $O(C=O)R^a$, $O(C=O)OR^a$ and $NH(C=O)R^a$. In a variant of this invention, $R^1$ is selected from $C_{1-5}$alkyl and $C_{3-5}$ cycloalkyl$C_{0-4}$alkyl.

In a further embodiment of the invention, $R^1$ is selected from methyl, ethyl, propyl, butyl, pentyl, cyclopropyl, cyclobutyl, cyclopentyl, cyclopropyl$C_{0-4}$alkyl, cyclobutyl $C_{0-4}$alkyl, and cyclopentyl $C_{0-4}$alkyl. In a variant of this embodiment, $R^1$ is methyl, ethyl, propyl, methylcyclopropyl, or cyclopropyl, optionally substituted by 0, 1, 2, 3, or 4 groups independently selected from hydrogen, fluoro, chloro, methyl, amino, $OR^a$, $O(C=O)R^a$, $O(C=O)OR^a$ and $NH(C=O)R^a$. In another variant of this embodiment, $R^1$ is selected from methyl, ethyl, propyl, cyclopropyl and cyclopropylmethyl.

In another embodiment, $R^1$ is $C_{1-5}$heteroalkyl$C_{0-4}$alkyl or $C_{3-5}$heterocycloalkyl$C_{0-4}$alkyl. In a variant of this embodiment, $R^1$ is difluoroethyl, 2-2-difluoroethyl, trifluoroethyl, and 2-2-2-trifluoroethyl.

In another embodiment of the invention, $R^1$ is selected from methyl, ethyl, propyl, cyclopropyl, cyclopropylmethyl, 2-2-difluoroethyl, and 2-2-2-trifluoroethyl.

In one embodiment of the invention, $R^a$ is selected from hydrogen, $C_{1-10}$alkyl, $C_{1-10}$ heteroalkyl, aryl, cycloalkyl, heterocycloalkyl, and heteroaryl. In a variant of this embodiment, $R^a$ is selected from hydrogen, $C_{1-10}$alkyl, and $C_{1-10}$ heteroalkyl. In another variant, $R^a$ is hydrogen or $C_{1-10}$alkyl. In a variant of this embodiment, $R^a$ is hydrogen, methyl, ethyl, or propyl.

In one embodiment of the invention, $R^2$ is selected from hydrogen, $C_{1-10}$alkyl, $C_{3-12}$ cycloalkyl, $(C_{3-12})$ heterocycloalkyl, $C_{1-10}$ heteroalkyl, $C_{2-10}$ alkynyl, aryl, and heteroaryl, wherein $R^2$ is substituted with 0, 1, 2, 3, or 4 independently selected $R^3$.

In another embodiment of the invention, $R^2$ is selected from $C_{1-10}$alkyl, $C_{3-12}$ cycloalkyl, $(C_{3-12})$ heterocycloalkyl, $C_{1-10}$ heteroalkyl, $C_{2-10}$ alkynyl, aryl, and heteroaryl, optionally substituted with one or more $R^3$.

$R^2$ is selected from $C_{1-10}$alkyl, $C_{3-12}$ cycloalkyl, $(C_{3-12})$ heterocycloalkyl, $C_{1-10}$ heteroalkyl, aryl, and heteroaryl, optionally substituted with one or more $R^3$.

In another embodiment, $R^2$ is selected from $C_{3-12}$ cycloalkyl, $(C_{3-12})$ heterocycloalkyl, aryl, and heteroaryl, optionally substituted with one or more $R^3$.

In another embodiment of the invention, $R^2$ is selected from hydrogen, $C_{1-10}$alkyl, $C_{3-12}$ cycloalkyl, $(C_{3-12})$ heterocycloalkyl, and $C_{1-10}$ heteroalkyl, optionally substituted with one or more $R^3$.

In one embodiment, $R^2$ is selected from pyridazinyl, pyrimidinyl, pyrazinyl, pyridinyl, pyrrolo[2,3-b]pyridinyl, pyrrolidinyl, oxetanyl, cyclohexyl, azetidinyl, phenyl, quinazolinyl, isoquinolinyl, pyrazolyl, imidazolyl, indolyl, indazolyl, thiazolyl, cyclobutyl, hydrogen, 1H-pyrazolo[3,4-b]pyridinyl], benzimidazolyl, cyclopropyl, cyclohexyl, tert-butyl, ethyl, methyl, methylethyl, 4,5,6,7-tetrahydro-1H-benzimidazolyl, methylpropyl, and morpholinyl, wherein $R^2$ is substituted with 0, 1, 2, 3, or 4 independently selected $R^3$.

In one variant of this embodiment, $R^2$ is selected from: pyrimidinyl, pyridinyl, pyrrolo[2,3-b]pyridinyl, pyrrolidinyl, oxetanyl, cyclohexyl, azetidinyl, phenyl, pyrazolyl, imidazolyl, indolyl, indazolyl, thiazolyl, hydrogen, 1H-pyrazolo[3,4-b]pyridinyl], benzimidazolyl, cyclopropyl, cyclohexyl, tert-butyl, ethyl, methyl, methylpropyl, 4,5,6,7-tetrahydro-1H-benzimidazolyl, and morpholinyl, wherein $R^2$ is substituted with 0, 1, 2, 3, or 4 independently selected $R^3$.

In one embodiment, A is selected from $C_{3-12}$ cycloalkyl, and $(C_{3-12})$heterocycloalkyl.

In one embodiment, A is $(C_{6-12})$spirocyclic. In a variant of this embodiment the rings of the spirocyclyl system are saturated.

In one embodiment, A is selected from pyrrolidinyl, piperidinyl, azetidinyl, azaspiro[2.4]hept-7-yl, cyclohexyl, azepanyl, and cyclopentyl.

In one embodiment of the invention, L is selected from L is selected from NH and N($C_{1-6}$alkyl).

In another embodiment, L is selected from —NH—, —N(ethyl)- and —N(methyl)-.

In yet another embodiment, L is —NH—.

In one embodiment of the invention, K is selected from a bond. In another embodiment of the invention, K is selected from NH, O, C(O), $CH_2$, N($C_{1-5}$)alkyl, S, $SO_2$, and $C_{2-10}$ alkynylene.

In yet another embodiment, K is selected from a bond, NH, O, C(O), $CH_2$, N($C_{1-5}$)alkyl, —C(O)N($R^b$)—$(CH_2)_m$—, N, S, $SO_2$, and $C_{2-10}$ alkynylene, wherein $R^b$ is H or $C_{1-10}$ alkyl.

In a variant of this embodiment, K is selected from: a bond, —C(O)—NH—, —C(O)—, —C(O)—N($CH_3$)—, —C(O)—N($CH_3$)—$CH_2$—, —$CH_2$—, —O—, —C≡C—, and —C(O)—NH—$CH_2$—.

In one embodiment of the invention, $R^3$ is independently selected from: halogen, $C_{1-10}$ alkyl(oxy)$_{0-1}$(carbonyl)$_{0-1}$ $C_{0-10}$ alkyl, $C_{2-10}$ alkenyl(oxy)$_{0-1}$(carbonyl)$_{0-1}$$C_{0-10}$ alkyl, $C_{1-10}$ heteroalkyl(oxy)$_{0-1}$(carbonyl)$_{0-1}$$C_{0-10}$ alkyl, aryl $C_{0-10}$ alkyl(oxy)$_{0-10}$(carbonyl)$_{0-1}$$C_{0-10}$ alkyl, aryl $C_{2-10}$ alkynyl (oxy)$_{0-1}$(carbonyl)$_{0-1}$$C_{0-10}$ alkyl, $C_{3-12}$ cycloalkyl$C_{0-10}$ alkyl (oxy)$_{0-1}$(carbonyl)$_{0-1}$$C_{0-10}$ alkyl, heteroaryl $C_{0-10}$ alkyl (oxy)$_{0-1}$(carbonyl)$_{0-1}$$C_{0-10}$ alkyl, $(C_{3-12})$heterocycloalkyl $C_{0-10}$ alkyl(oxy)$_{0-1}$(carbonyl)$_{0-1}$$C_{0-10}$ alkyl, $C_{0-10}$ alkylamino(carbonyl)$_{0-1}$$C_{0-10}$ alkyl, $(C_{1-10})$heteroalkylamino (carbonyl)$_{0-1}$$C_{0-10}$ alkyl, $C_{3-12}$ cycloalkyl $C_{0-10}$ alkylamino (carbonyl)$_{0-1}$$C_{0-10}$ alkyl, aryl $C_{0-10}$alkylamino(carbonyl)$_{0-1}$ $C_{0-10}$ alkyl, heteroaryl$C_{0-10}$alkylamino(carbonyl)$_{0-1}$$C_{0-10}$ alkyl, (C$_{3-12}$)heterocycloalkylC$_{0-10}$alkylamino(carbonyl)$_{0-1}$ C$_{0-10}$ alkyl, C$_{1-10}$ alkyl(oxy)$_{0-1}$(carbonyl)$_{0-1}$aminoC$_{0-10}$ alkyl, C$_{1-10}$ heteroalkyl (oxy)$_{0-1}$(carbonyl)$_{0-1}$aminoC$_{0-10}$ alkyl, C$_{3-12}$ cycloalkyl C$_{0-10}$ alkyl (oxy)$_{0-1}$(carbonyl)$_{0-1}$ aminoC$_{0-10}$ alkyl, aryl C$_{0-10}$ alkyl(oxy)$_{0-1}$(carbonyl)$_{0-1}$ aminoC$_{0-10}$ alkyl, heteroaryl C$_{0-10}$ alkyl(oxy)$_{0-1}$(carbonyl)$_{0-1}$aminoC$_{0-10}$ alkyl, (C$_{3-12}$)heterocycloalkyl C$_{0-10}$ alkyl(oxy)$_{0-1}$(carbonyl)$_{0-1}$aminoC$_{0-10}$ alkyl, —CO$_2$(C$_{0-10}$ alkyl), Oxo (═O), C$_{1-10}$ alkylS(O)$_{1-2}$, C$_{1-10}$ heteroalkyl S(O)$_{1-2}$, (C$_{3-12}$) cycloalkylS(O)$_{1-2}$, (C$_{3-12}$) cycloheteroalkylS(O)$_{1-2}$, heteroarylS(O)$_{1-2}$, arylS(O)$_{1-2}$, C$_{0-6}$ alkyl (amino)$_{0-1}$S(O)$_{1-2}$amino, C$_{1-10}$ heteroalkyl(amino)$_{0-1}$ S(O)$_{1-2}$amino, (C$_{3-12}$)cycloalkyl(amino)$_{0-1}$S(O)$_{1-2}$amino, (C$_{3-12}$)cycloheteroalkyl(amino)$_{0-1}$S(O)$_{1-2}$amino, heteroaryl (amino)$_{0-1}$S(O)$_{1-2}$amino, aryl(amino)$_{0-1}$S(O)$_{1-2}$amino, amino, (C$_{0-10}$ alkyl)$_{1-2}$ amino, hydroxy, (C$_{1-10}$ alkyl)OH, C$_{0-10}$ alkylalkoxyl, cyano, and C$_{1-6}$haloalkyl; wherein R$^3$ is each substituted with 0, 1, 2, 3, or 4 R$^4$ substituents.

In another embodiment of the invention, R$^3$ is independently selected from: halogen, C$_{1-10}$ alkyl(oxy)$_{0-1}$(carbonyl)$_{0-1}$C$_{0-10}$ alkyl, C$_{2-10}$ alkenyl(oxy)$_{0-1}$(carbonyl)$_{0-1}$ C$_{0-10}$ alkyl, C$_{1-10}$ heteroalkyl(oxy)$_{0-1}$(carbonyl)$_{0-1}$C$_{0-10}$ alkyl, aryl C$_{0-10}$ alkyl(oxy)$_{0-1}$(carbonyl)$_{0-1}$C$_{0-10}$ alkyl, C$_{3-12}$ cycloalkylC$_{0-10}$ alkyl(oxy)$_{0-1}$(carbonyl)$_{0-1}$C$_{0-10}$ alkyl, heteroaryl C$_{0-10}$ alkyl(oxy)$_{0-1}$(carbonyl)$_{0-1}$C$_{0-10}$ alkyl, (C$_{3-12}$) heterocycloalkyl C$_{0-10}$ alkyl(oxy)$_{0-1}$(carbonyl)$_{0-1}$C$_{0-10}$ alkyl, C$_{0-10}$ alkylamino(carbonyl)$_{0-1}$C$_{0-10}$ alkyl, (C$_{1-10}$)heteroalkylamino(carbonyl)$_{0-1}$C$_{0-10}$ alkyl, C$_{3-12}$ cycloalkyl C$_{0-10}$ alkylamino(carbonyl)$_{0-1}$C$_{0-10}$ alkyl, aryl C$_{0-10}$alkylamino(carbonyl)$_{0-1}$C$_{0-10}$ alkyl, heteroarylC$_{0-10}$alkylamino (carbonyl)$_{0-1}$C$_{0-10}$ alkyl, (C$_{3-12}$)heterocycloalkylC$_{0-1}$alkylamino(carbonyl)$_{0-1}$C$_{0-10}$ alkyl, C$_{1-10}$ alkyl(oxy$_{0-1}$) (carbonyl)$_{0-1}$aminoC$_{0-10}$ alkyl, C$_{3-12}$ cycloalkyl C$_{0-10}$ alkyl (oxy)$_{0-1}$(carbonyl)$_{0-1}$aminoC$_{0-10}$ alkyl, heteroaryl C$_{0-10}$ alkyl(oxy)$_{0-1}$(carbonyl)$_{0-1}$aminoC$_{0-10}$ alkyl, (C$_{3-12}$)heterocycloalkylC$_{0-10}$ alkyl(oxy)$_{0-1}$(carbonyl)$_{0-1}$aminoC$_{0-10}$ alkyl, —CO$_2$(C$_{0-10}$ alkyl), Oxo (═O), C$_{1-10}$ alkylS(O)$_{1-2}$, arylS (O)$_{1-2}$, C$_{0-6}$ alkyl(amino)$_{0-1}$S(O)$_{1-2}$amino, amino, (C$_{0-10}$ alkyl)$_{1-2}$ amino, hydroxy, (C$_{1-10}$ alkyl)OH, C$_{0-10}$ alkylalkoxyl, cyano, and C$_{1-6}$haloalkyl; wherein R$^3$ is each substituted with 0, 1, 2, 3, or 4 R$^4$ substituents.

In yet an another embodiment of the invention R$^3$ is selected from: halogen, C$_{1-10}$ alkyl(oxy)$_{0-1}$(carbonyl)$_{0-1}$ C$_{0-10}$ alkyl, C$_{2-10}$ alkenyl(oxy)$_{0-1}$(carbonyl)$_{0-1}$C$_{0-10}$ alkyl, C$_{1-10}$ heteroalkyl(oxy)$_{0-1}$(carbonyl)$_{0-1}$C$_{0-10}$ alkyl, aryl C$_{0-10}$ alkyl(oxy)$_{0-1}$(carbonyl)$_{0-1}$C$_{0-10}$ alkyl, C$_{3-12}$ cycloalkylC$_{0-10}$ alkyl(oxy)$_{0-1}$(carbonyl)$_{0-1}$C$_{0-10}$ alkyl, heteroaryl C$_{0-10}$ alkyl (oxy)$_{0-1}$(carbonyl)$_{0-1}$C$_{0-10}$ alkyl, (C$_{3-12}$)heterocycloalkyl C$_{0-10}$ alkyl(oxy)$_{0-1}$(carbonyl)$_{0-1}$C$_{0-10}$ alkyl, C$_{0-10}$ alkylamino(carbonyl)$_{0-1}$C$_{0-10}$ alkyl, (C$_{1-10}$)heteroalkylamino (carbonyl)$_{0-1}$C$_{0-10}$ alkyl, C$_{3-12}$ cycloalkyl C$_{0-10}$ alkylamino (carbonyl)$_{0-1}$C$_{0-10}$ alkyl, aryl C$_{0-10}$alkylamino(carbonyl)$_{0-1}$C$_{0-10}$ alkyl, heteroarylC$_{0-10}$alkylamino(carbonyl)$_{0-1}$C$_{0-10}$ alkyl, (C$_{3-12}$)heterocycloalkylC$_{0-1}$alkylamino (carbonyl)$_{0-1}$C$_{0-10}$ alkyl, C$_{1-10}$ alkyl(oxy$_{0-1}$ (carbonyl)$_{0-1}$ aminoC$_{0-10}$ alkyl, C$_{3-12}$ cycloalkyl C$_{0-10}$ alkyl (oxy)$_{0-1}$(carbonyl)$_{0-1}$aminoC$_{0-10}$ alkyl, heteroaryl C$_{0-10}$ alkyl(oxy)$_{0-1}$ (carbonyl)$_{0-1}$aminoC$_{0-10}$ alkyl, (C$_{3-12}$)heterocycloalkyl C$_{0-10}$ alkyl(oxy)$_{0-1}$(carbonyl)$_{0-1}$aminoC$_{0-10}$ alkyl, —CO$_2$ (C$_{0-10}$ alkyl), Oxo (═O); C$_{1-10}$ alkylS(O)$_{1-2}$, arylS(O)$_{1-2}$, C$_{0-6}$ alkyl(amino)$_{0-1}$S(O)$_{1-2}$amino, amino, (C$_{0-10}$ alkyl)$_{1-2}$ amino, hydroxy, (C$_{1-10}$ alkyl)OH, C$_{0-10}$ alkylalkoxy, cyano, and C$_{1-6}$haloalkyl; wherein R$^3$ is each substituted with 0, 1, 2, 3, or 4 substituents, R$^4$.

In one embodiment, R$^3$ is independently selected from: fluoro, chloro, methyl, ethyl, propyl, methoxy, methoxymethyl, methylethyl, 2-methylbuten-4-yl, 2-methylpropyl, 1,3,4-oxadiazolyl, pyridinyl, isoquinolinyl, cyclopropylmethyl, hydroxy, oxo(═O), dimethylamino, tert-butyl, trifluoromethyl, trifluoroethyl, carboxy, tert-butylcarboxy, fluoroethylcarboxy, tetrahydrothiophenylcarboxy, methylpropylcarboxy, propylcarboxy, ethoxycarbonyl, benzylcarboxy, 2,2-dimethylpropylcarboxy, methylcarboxy, ethylcarboxy, methylethylcarboxy, cyclopentylcarbonyl, cyclohexylcarboxy, cyclobutylcarbonyl, 2,2,2-trifluoroethylcarboxy, spiro[2.4]hept-1-ylcarbonyl, spiro[2.5]oct-1-ylcarbonyl, benzylcarbonyl, imidazolylcarbonyl, ethylcarbonyl, methylethylcarbonyl, piperidinylcarbonyl, pyrrolidinylcarbonyl, cyclohexylcarbonyl, isopropylcarbonyl, methylcarbonyl, tetrahydro-2H-pyran-4-ylcarbonyl, oxazolylcarbonyl, cyclopropylcarbonyl, azetidinylcarbonyl, tetrahydropyranylcarbonylamino, cyclopropylaminocarbonyl, tetrahydrofuranylcarbonyl, isoxazolylcarbonyl, triazolylcarbonyl, thiadiazolylcarbonyl, cyclobutylaminocarbonyl, furanylmethylaminocarbonyl, aminocarbonyl, pyrazolylcarbonyl, hydroxymethyl, fluoromethyl, oxadiazolylcarbonyl, ethylsulfonyl, methylsulfonyl, ethylsulfonylamino, methylsulfonylamino, (methylethyl)sulfonyl, phenylsulfonyl, (cyclopropylmethyl)aminocarbonyl, azabicyclo[3.1.0]hex-6-ylcarbonyl, trifluoroethylaminocarbonyl, (tetrahydrothiophenylmethyl)aminocarbonyl, methylethylaminocarbonyl, cyclohexylaminocarbonyl, ethylaminocarbonyl, (1,1,3,3-tetramethylbutyl)aminocarbonyl, oxazolylcarbonylamino, dimethylpropylaminocarbonyl, methylcarbonylamino, bicyclo[1.1.1]pent-1-ylcarbonyl, methylaminocarbonyl, propylaminocarbonyl, isopropylaminocarbonyl, phenyl, pyrimidinyl, thieno[3,2-c]pyridinyl, difluoromethyl, morpholinylcarbonyl, butylaminocarbonyl, tert-butylaminocarbonyl, tert-, 2-methylpropylcarbonyl, (2-methylprop-1-ene)carbonyl, ethylcarbonylamino, cyclopropylcarbonylamino, cyano, (methylamino)methyl, tetrahydro-2H-pyranylcarbonylamino, pyranylcarbonylamino, amino, hydroxyisopropyl, 2-hydroxypropyl, and isobutylcarbonyl; wherein R$^3$ is each substituted with 0, 1, 2, 3, or 4 substituents, R$^4$.

In one embodiment, R$^3$ is independently selected from: fluoro, chloro, methyl, ethyl, propyl, methoxy, methoxymethyl, methylethyl, 2-methylbuten-4-yl, 2-methylpropyl, 1,3,4-oxadiazolyl, pyridinyl, isoquinolinyl, cyclopropylmethyl, hydroxy, oxo (═O), dimethylamino, tert-butyl, trifluoromethyl, trifluoroethyl, carboxy, tert-butylcarboxy, fluoroethylcarboxy, tetrahydrothiophenylcarboxy, methylpropylcarboxy, propylcarboxy, ethoxycarbonyl, benzylcarboxy, 2,2-dimethylpropylcarboxy, methylcarboxy, ethylcarboxy, methylethylcarboxy, cyclopentylcarbonyl, cyclohexylcarboxy, cyclobutylcarbonyl, 2,2,2-trifluoroethylcarboxy, spiro[2.4]hept-1-ylcarbonyl, spiro[2.5]oct-1-ylcarbonyl, benzylcarbonyl, imidazolylcarbonyl, ethylcarbonyl, methylethylcarbonyl, piperidinylcarbonyl, pyrrolidinylcarbonyl, cyclohexylcarbonyl, isopropylcarbonyl, methylcarbonyl, tetrahydro-2H-pyran-4-ylcarbonyl, oxazolylcarbonyl, cyclopropylcarbonyl, azetidinylcarbonyl, cyclopropylaminocarbonyl, tetrahydrofuranylcarbonyl, isoxazolylcarbonyl, triazolylcarbonyl, thiadiazolylcarbonyl, cyclobutylaminocarbonyl, furanylmethylaminocarbonyl, aminocarbonyl, pyrazolylcarbonyl, hydroxymethyl, ethylsulfonyl, methylsulfonyl, (cyclopropylmethyl)aminocarbonyl, azabicyclo[3.1.0]hex-6-ylcarbonyl, trifluoroethylaminocarbonyl, (tetrahydrothiophenylmethyl)aminocarbonyl, methylethylaminocarbonyl, cyclohexylaminocarbonyl, ethylaminocarbonyl, (1,1,3,3-tetramethylbutyl)aminocarbonyl, oxazolylcarbonylamino, bicyclo[1.1.1]pent-1-ylcarbonyl, methylaminocarbonyl, phenyl, pyrimidinyl, thieno[3,2-c] pyridinyl, morpholinylcarbonyl, butylaminocarbonyl, cyano, amino, and hydroxyisopropyl; wherein $R^3$ is each substituted with 0, 1, 2, 3, or 4 substituents, $R^4$.

In one embodiment, $R^3$ is independently selected from: halogen, methyl, ethyl, methoxy, pyrazolyl, hydroxy, dimethylamino, morpholinyl, imidazolyl, pyrrolidinyl, tert-butyl, trifluoromethyl, tert-butylcarboxy, phenylcarboxy, hydrogen, methylpropylcarboxy, napthalen-2ylcarboxy, benzylcarboxy, 2,2-dimethylpropylcarboxy, methylcarboxy, ethylcarboxy, methylethylcarboxy, cyclopentylcarbonyl, imidazolylcarbonyl, oxazolylcarbonyl, ethylcarbonyl, phenylcarbonyl, napthalenylcarbonyl, cyclohexylcarbonyl, methylcarbonyl, tetrahydro-2H-pyran-4-ylcarbonyl, oxazolylcarbonyl, pyridinylcarbonyl, cyclopropylcarbonyl, tetrahydrofuranylcarbonyl, isoxazolylcarbonyl, pyrrolindinylmethylcarbonyl, pyridinylcarbonyl, oxadiazolylcarbonyl, pyrazolo[1,5-a]pyridinylcarbonyl, imidazolylcarbonyl, triazolylcarbonyl, imidazo[1,2-a]pyrimidinylcarbonyl, thiadiazolylcarbonyl, furo[3,2-b]pyrrolylcarbonyl, pyrazolylcarbonyl, pyrrolindinylcarbonyl, pyrrolylcarbonyl, imidazo[1,2-b]pyrazolylcarbonyl, pyrrolo[3,2-b]pyridinylcarbonyl, pyrrolo[1,2-d]tetrazolylcarbonyl, oxadiazolylcarbonyl, pyrrolo[1,2-b]pyrazolylcarbonyl, ethylcarbonyl, tert-butylcarbonyl, trifluoromethylsulfonyl, ethylsulfonyl, methylethylsulfonyl, phenylsulfonyl, imidazolylsulfonyl, napthylsulfonyl, 5,6,7,8-tetrahydro[1,2,4]triazolo[4,3-a]pyridinylcarbonyl, [1,2,4]triazolo-[1,5-a]pyridinylcarbonyl, acetylamino, methylethylaminocarbonyl, cyclohexylaminocarbonyl, phenylaminocarbonyl, dimethylethylaminocarbonyl, tetramethylbutylaminocarbonyl, benzylaminocarbonyl, ethylaminocarbonyl, benzyl, phenylethyl, cyclohexylmethyl, phenylmethyl, pyrrolylmethyl, pyrimidinyl, thieno[2,3-d]pyrimidinyl, thieno[3,2-c]pyridinyl, pyridinyl, [1,2,4]triazolo[4.3-a]pyrazinyl, phthalazinyl, pyrizanyl, pyrazolo[3,4-d]pyrimidinyl, morpholinylcarbonyl, tert-butyloxycarbonylamino, tetrahydro-2H-pyranylcarbonylamino, imidazo[4,5-b]pyridinyl, pyranylcarbonylamino, pyranylcarbonyl, cyclopentylcarbonyl, ethyloxycarbonyl, and isobutylcarbonyl; wherein $R^3$ is each substituted with 0, 1, 2, 3, or 4 substituents, $R^4$.

In one embodiment of the invention, $R^4$ is independently selected from: halogen, $C_{1-10}$ alkyl(oxy)$_{0-1}$(carbonyl)$_{0-1}$ $C_{0-10}$ alkyl, $C_{1-10}$ heteroalkyl(oxy)$_{0-1}$-(carbonyl)$_{0-1}$$C_{0-10}$ alkyl, aryl $C_{0-10}$ alkyl(oxy)$_{0-1}$(carbonyl)$_{0-1}$$C_{0-10}$ alkyl, $C_{3-8}$ cycloalkyl $C_{0-10}$ alkyl(oxy)$_{0-1}$(carbonyl)$_{0-1}$$C_{0-10}$ alkyl, heteroaryl $C_{0-10}$ alkyl(oxy)$_{0-1}$(carbonyl)$_{0-1}$$C_{0-10}$ alkyl, $C_{3-8}$heterocycloalkyl $C_{0-10}$ alkyl(oxy)$_{0-1}$(carbonyl)$_{0-1}$$C_{0-10}$ alkyl, $C_{1-10}$ alkyl(carbonyl)$_{0-1}$oxy$C_{0-10}$ alkyl, $C_{1-10}$ heteroalkyl(carbonyl)$_{0-1}$oxy$C_{0-10}$ alkyl, aryl $C_{0-10}$ alkyl (carbonyl)$_{0-1}$oxy$C_{0-10}$ alkyl, $C_{3-8}$cycloalkyl $C_{0-10}$ alkyl(carbonyl)$_{0-1}$oxy$C_{0-10}$ alkyl, heteroaryl$C_{0-10}$ alkyl(carbonyl)$_{0-1}$oxy$C_{0-10}$ alkyl, $C_{3-8}$heterocycloalkyl $C_{0-10}$ alkyl(carbonyl)$_{0-1}$oxy $C_{0-10}$ alkyl, $C_{1-10}$ alkylaminocarbonyl$C_{0-10}$ alkyl, $C_{3-8}$ cycloalkyl $C_{0-10}$ alkylaminocarbonyl$C_{0-10}$ alkyl, aryl $C_{0-10}$ alkylaminocarbonyl$C_{0-10}$ alkyl, heteroaryl $C_{0-10}$ alkylaminocarbonyl$C_{0-10}$ alkyl, $C_{3-8}$heterocycloalkyl $C_{0-10}$ alkylaminocarbonyl$C_{0-10}$ alkyl, —$CO_2$($C_{0-10}$ alkyl), —($C_{0-10}$ alkyl)$CO_2H$, Oxo (=O), $C_{1-10}$ alkylS(O)$_{1-2}$, $C_{1-10}$ heteroalkyl S(O)$_{1-2}$, $C_{3-8}$cycloalkylS(O)$_{1-2}$, $C_{3-8}$cycloheteroalkylS(O)$_{1-2}$, heteroarylS(O)$_{1-2}$, arylS(O)$_{1-2}$, —$SO_2N(C_{1-6}$ alkyl)$_{1-2}$, —$SO_2C_{1-6}$alkyl, —$SO_2CF_3$, amino, ($C_{0-10}$ alkyl)$_{1-2}$ amino, ($C_{1-10}$ alkyl)OH, $C_{1-10}$ alkoxy, cyano, and $C_{1-6}$haloalkyl; wherein $R_4$ is substituted with 0, 1, 2, or 3 $R_5$.

In another embodiment of the invention $R^4$, independently selected from: halogen, $C_{1-10}$ alkyl(oxy)$_{0-1}$(carbonyl)$_{0-1}$$C_{0-10}$ alkyl, aryl $C_{0-10}$ alkyl(oxy)$_{0-1}$(carbonyl)$_{0-1}$ $C_{0-10}$ alkyl, $C_{3-8}$ cycloalkyl $C_{0-10}$ alkyl(oxy)$_{0-1}$(carbonyl)$_{0-1}$ $C_{0-10}$ alkyl, heteroaryl $C_{0-10}$ alkyl(oxy)$_{0-1}$(carbonyl)$_{0-1}$$C_{0-10}$ alkyl, $C_{3-8}$heterocycloalkyl $C_{0-10}$ alkyl(oxy)$_{0-1}$(carbonyl)$_{0-1}$ $C_{0-10}$ alkyl, $C_{1-10}$ alkylaminocarbonyl$C_{0-10}$ alkyl, Oxo (=O), ($C_{0-10}$ alkyl)$_{1-2}$ amino, hydroxy, ($C_{1-10}$ alkyl)OH, $C_{1-10}$ alkoxy, cyano, and $C_{1-6}$haloalkyl; wherein $R_4$ is substituted with 0, 1, 2, or 3 $R_5$.

In another embodiment of the invention, $R_4$ is halogen, and methyl.

In one embodiment, $R_5$ is independently selected from hydroxy, $(C_{1-6})$alkyl, $(C_{1-6})$alkoxy, $(C_{1-10}$ alkyl)OH, halogen, $CO_2H$, —$(C_{0-6})$alkylCN, $NO_2$, trifluoromethyl, trifluoroethyl, $C_{1-10}$ alkylsulfonyl, $C_{1-10}$ heteroalkyl, aryl, $C_{3-8}$ cycloalkyl, heteroaryl, $(C_{3-8})$heterocycloalkyl, oxo (O=), —$O_{(0-1)}(C_{1-10})$haloalkyl, and amino$(C_{1-6}$alkyl)$_{0-2}$.

In another embodiment of the invention, $R_5$ is selected from —O(C=O)$C_1$-$C_6$ alkyl, —(C=O)O$C_1$-$C_6$ alkyl, trifluoromethoxy, trifluoroethoxy, —N—C(O)O($C_{0-6}$)alkyl, $C_{1-10}$ heteroalkylsulfonyl, $(C_{3-8})$ cycloalkylsulfonyl, $(C_{3-8})$ cycloheteroalkylsulfonyl, heteroarylsulfonyl, arylsulfonyl, aminosulfonyl, —$SO_2N(C_{1-6}$alkyl)$_{1-2}$, —$SO_2C_{1-6}$alkyl, —$SO_2CF_3$, —$SO_2CF_2H$, —$C_{1-10}$alkylsulfinyl, and $NH_2$.

In one embodiment, $R_5$ is selected from hydroxy, $(C_{1-6})$ alkyl, $(C_{1-6})$alkoxy, $(C_{1-10}$ alkyl)OH, halogen, $CO_2H$, —$(C_{0-6})$alkylCN, $NO_2$, trifluoromethyl, trifluoroethyl, oxo (O=), —$O_{(0-1)}(C_{1-10})$haloalkyl, and amino$(C_{1-6}$alkyl)$_{0-2}$. In one variant of the invention, $R_5$ is selected from hydroxy, $(C_{1-6})$alkyl, $(C_{1-6})$alkoxy, $(C_{1-10}$ alkyl)OH, halogen, and $CO_2H$.

In one embodiment of the invention, $R_6$ is selected from hydroxy, $(C_{1-6})$alkyl, $(C_{1-6})$alkoxy, $(C_{1-10}$ alkyl)OH, halogen, $CO_2H$, trifluoromethyl, trifluoroethyl, oxo (O=), —$SO_2N(C_{1-6}$alkyl)$_{1-2}$, —$SO_2C_{1-6}$alkyl, —$SO_2CF_3$, —$O_{(0-1)}(C_{1-10})$haloalkyl, amino$(C_{1-6}$alkyl)$_{0-2}$ and amino.

One embodiment of the invention provides compounds of formula I or pharmaceutically acceptable salts or stereoisomers thereof:

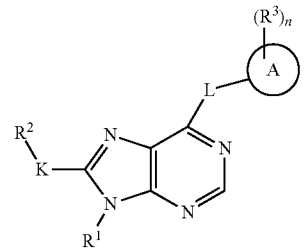

I wherein:

$R^1$ is selected from hydrogen, $C_{1-5}$alkyl, $C_{3-5}$cycloalkyl, $C_{1-5}$heteroalkyl, and $C_{3-5}$heterocycloalkyl, wherein $R^1$ is optionally substituted by 0, 1, 2, 3, or 4 groups independently selected from hydrogen, fluoro, chloro, methyl, amino, $OR^a$, $O(C=O)R^a$, $O(C=O)OR^a$ and $NH(C=O)R^a$;

$R^a$ is independently selected from hydrogen, $C_{1-10}$alkyl, $C_{1-10}$heteroalkyl, aryl, cycloalkyl, heterocycloalkyl, and heteroaryl;

$R^2$ is selected from hydrogen, $C_{1-10}$alkyl, $C_{3-8}$ cycloalkyl, $C_{3-8}$heterocycloalkyl, $C_{1-10}$ heteroalkyl, $C_{2-10}$alkynyl, aryl, and heteroaryl, wherein $R^2$ is substituted with 0, 1, 2, or 4 $R^3$ substituents;

n is 0, 1, 2, 3, or 4;

A is $C_{3-12}$ cycloalkyl, $C_{3-12}$heterocycloalkyl, and $C_{6-12}$spirocyclyl;

L is selected from NH, and N($C_{1-10}$alkyl);

K is selected from a bond, NH, O, C(O), CH$_2$, N(C$_{1-5}$)alkyl, S, SO$_2$, and C$_{2-10}$ alkynylene;

R$^3$ is independently selected from:
- halogen,
- C$_{1-10}$ alkyl(oxy)$_{0-1}$(carbonyl)$_{0-1}$C$_{0-10}$ alkyl,
- C$_{1-10}$ heteroalkyl(oxy)$_{0-1}$(carbonyl)$_{0-1}$C$_{0-10}$ alkyl,
- aryl C$_{0-10}$ alkyl(oxy)$_{0-1}$(carbonyl)$_{0-1}$C$_{0-10}$ alkyl,
- aryl C$_{2-10}$ alkynyl(oxy)$_{0-1}$(carbonyl)$_{0-1}$C$_{0-10}$ alkyl,
- C$_{3-8}$ cycloalkylC$_{0-10}$ alkyl(oxy)$_{0-1}$(carbonyl)$_{0-1}$C$_{0-10}$ alkyl,
- heteroaryl C$_{0-10}$ alkyl(oxy)$_{0-1}$(carbonyl)$_{0-1}$C$_{0-10}$ alkyl,
- (C$_{3-8}$)heterocycloalkyl C$_{0-10}$ alkyl(oxy)$_{0-1}$(carbonyl)$_{0-1}$C$_{0-10}$ alkyl,
- C$_{1-10}$ alkyl(carbonyl)$_{0-1}$oxyC$_{0-10}$ alkyl,
- C$_{1-10}$ heteroalkyl(carbonyl)$_{0-1}$oxyC$_{0-10}$ alkyl,
- C$_{1-10}$ heteroalkyl(carbonyl)$_{0-1}$oxyC$_{0-10}$ alkyl,
- aryl C$_{0-10}$ alkyl (carbonyl)$_{0-1}$oxyC$_{0-10}$ alkyl,
- (C$_{3-8}$)cycloalkyl C$_{0-10}$ alkyl(carbonyl)$_{0-1}$oxyC$_{0-10}$ alkyl,
- heteroarylC$_{0-10}$ alkyl(carbonyl)$_{0-1}$oxyC$_{0-10}$ alkyl,
- (C$_{3-8}$)heterocycloalkyl C$_{0-10}$ alkyl(carbonyl)$_{0-1}$oxyC$_{0-10}$ alkyl,
- ((C$_{0-10}$)alkyl)$_{1-2}$aminocarbonyloxy,
- (C$_{0-10}$)heteroalkylaminocarbonyloxy,
- aryl(C$_{0-10}$)alkylaminocarbonyloxy,
- (C$_{3-8}$)cycloalkyl(C$_{0-10}$)alkylaminocarbonyloxy,
- heteroaryl(C$_{0-10}$)alkylaminocarbonyloxy,
- (C$_{3-8}$)heterocycloalkyl(C$_{0-10}$)alkylaminocarbonyloxy,
- C$_{1-10}$ alkylamino(carbonyl)$_{0-1}$C$_{0-10}$ alkyl,
- (C$_{1-10}$)heteroalkylamino(carbonyl)$_{0-1}$C$_{0-10}$ alkyl,
- C$_{3-8}$ cycloalkyl C$_{0-10}$ alkylamino(carbonyl)$_{0-1}$C$_{0-10}$ alkyl,
- aryl C$_{0-10}$alkylamino(carbonyl)$_{0-1}$C$_{0-10}$ alkyl,
- heteroarylC$_{0-10}$alkylamino(carbonyl)$_{0-1}$C$_{0-10}$ alkyl,
- (C$_{3-8}$)heterocycloalkylC$_{0-10}$alkylamino(carbonyl)$_{0-1}$C$_{0-10}$ alkyl,
- C$_{1-10}$ alkyl(oxy)$_{0-1}$(carbonyl)$_{0-1}$aminoC$_{0-10}$ alkyl,
- C$_{1-10}$ heteroalkyl (oxy)$_{0-1}$(carbonyl)$_{0-1}$aminoC$_{0-10}$ alkyl,
- C$_{3-8}$ cycloalkyl C$_{0-10}$ alkyl (oxy)$_{0-1}$(carbonyl)$_{0-1}$amino C$_{0-10}$ alkyl,
- aryl C$_{0-10}$ alkyl(oxy)$_{0-1}$(carbonyl)$_{0-1}$aminoC$_{0-10}$ alkyl,
- heteroaryl C$_{0-10}$ alkyl(oxy)$_{0-1}$(carbonyl)$_{0-1}$aminoC$_{0-10}$ alkyl,
- (C$_{3-8}$)heterocycloalkyl C$_{0-10}$ alkyl(oxy)$_{0-1}$(carbonyl)$_{0-1}$aminoC$_{0-10}$ alkyl,
- —CO$_2$(C$_{0-10}$ alkyl),
- —(C$_{0-10}$ alkyl)CO$_2$H,
- Oxo (=O);
- C$_{1-10}$ alkylS(O)$_{1-2}$,
- C$_{1-10}$ heteroalkyl S(O)$_{1-2}$,
- (C$_{3-8}$) cycloalkylS(O)$_{1-2}$,
- (C$_{3-8}$) cycloheteroalkylS(O)$_{1-2}$,
- heteroarylS(O)$_{1-2}$,
- arylS(O)$_{1-2}$,
- —SO$_2$N(C$_{0-6}$ alkyl)$_{0-2}$,
- C$_{0-6}$alkyl(amino)$_{0-1}$S(O)$_{1-2}$amino,
- C$_{1-10}$ heteroalkyl(amino)$_{0-1}$S(O)$_{1-2}$amino,
- (C$_{3-8}$) cycloalkyl(amino)$_{0-1}$S(O)$_{1-2}$amino,
- (C$_{3-8}$) cycloheteroalkyl(amino)$_{0-1}$S(O)$_{1-2}$amino,
- heteroaryl(amino)$_{0-1}$S(O)$_{1-2}$amino,
- aryl(amino)$_{0-1}$S(O)$_{1-2}$amino,
- —SO$_2$CF$_3$,
- —SO$_2$CF$_2$H,
- —Si(C$_{0-6}$ alkyl)$_3$,
- amino,
- (C$_{0-10}$ alkyl)$_{1-2}$ amino,
- C$_{1-4}$acylamino C$_{0-10}$ alkyl,
- hydroxyl,
- (C$_{1-10}$ alkyl)OH,
- C$_{0-10}$ alkylalkoxyl,
- cyano,
- C$_{1-6}$alkylcyano, and
- C$_{1-6}$haloalkyl;

wherein R$^3$ is each substituted with 0, 1, 2, 3, or 4 R$^4$ substituents and each R$^4$ is independently selected from:
- halogen,
- C$_{1-10}$ alkyl(oxy)$_{0-1}$(carbonyl)$_{0-1}$C$_{0-10}$ alkyl,
- C$_{1-10}$ heteroalkyl(oxy)$_{0-1}$(carbonyl)$_{0-1}$C$_{0-10}$ alkyl,
- aryl C$_{0-10}$ alkyl(oxy)$_{0-1}$(carbonyl)$_{0-1}$C$_{0-10}$ alkyl,
- aryl C$_{2-10}$ alkynyl(oxy)$_{0-1}$(carbonyl)$_{0-1}$C$_{0-10}$ alkyl,
- C$_{3-8}$ cycloalkyl C$_{0-10}$ alkyl(oxy)$_{0-1}$(carbonyl)$_{0-1}$C$_{0-10}$ alkyl,
- heteroaryl C$_{0-10}$ alkyl(oxy)$_{0-1}$(carbonyl)$_{0-1}$C$_{0-10}$ alkyl,
- (C$_{3-8}$)heterocycloalkyl C$_{0-10}$ alkyl(oxy)$_{0-1}$(carbonyl)$_{0-1}$C$_{0-10}$ alkyl,
- C$_{1-10}$ alkyl(carbonyl)$_{0-1}$oxyC$_{0-10}$ alkyl,
- C$_{1-10}$ heteroalkyl(carbonyl)$_{0-1}$oxyC$_{0-10}$ alkyl,
- aryl C$_{0-10}$ alkyl (carbonyl)$_{0-1}$oxyC$_{0-10}$ alkyl,
- (C$_{3-8}$)cycloalkyl C$_{0-10}$ alkyl(carbonyl)$_{0-1}$oxyC$_{0-10}$ alkyl,
- heteroarylC$_{0-10}$ alkyl(carbonyl)$_{0-1}$oxyC$_{0-10}$ alkyl,
- (C$_{3-8}$)heterocycloalkyl C$_{0-10}$ alkyl(carbonyl)$_{0-1}$oxyC$_{0-10}$ alkyl,
- ((C$_{0-10}$)alkyl)$_{1-2}$aminocarbonyloxy,
- aryl (C$_{0-10}$)alkylaminocarbonyloxy,
- (C$_{3-8}$)cycloalkyl(C$_{0-10}$)alkylaminocarbonyloxy,
- heteroaryl(C$_{0-10}$)alkylaminocarbonyloxy,
- (C$_{3-8}$)heterocycloalkyl(C$_{0-10}$)alkylaminocarbonyloxy,
- C$_{1-10}$ alkylaminocarbonylC$_{0-10}$ alkyl,
- C$_{3-8}$ cycloalkyl C$_{0-10}$ alkylaminocarbonylC$_{0-10}$ alkyl,
- aryl C$_{0-10}$ alkylaminocarbonylC$_{0-10}$ alkyl,
- heteroaryl C$_{0-10}$ alkylaminocarbonylC$_{0-10}$ alkyl,
- (C$_{3-8}$)heterocycloalkyl C$_{0-10}$ alkylaminocarbonylC$_{0-10}$ alkyl,
- C$_{1-10}$ alkyl (oxy)$_{0-1}$(carbonyl)$_{0-1}$aminoC$_{0-10}$ alkyl,
- C$_{3-8}$ cycloalkyl C$_{0-10}$ alkyl (oxy)$_{0-1}$(carbonyl)$_{0-1}$amino C$_{0-10}$ alkyl,
- aryl C$_{0-10}$ alkyl(oxy)$_{0-1}$(carbonyl)$_{0-1}$aminoC$_{0-10}$ alkyl,
- heteroaryl C$_{0-10}$ alkyl(oxy)$_{0-1}$(carbonyl)$_{0-1}$aminoC$_{0-10}$ alkyl,
- (C$_{3-8}$)heterocycloalkyl C$_{0-10}$ alkyl(oxy)$_{0-1}$(carbonyl)$_{0-1}$aminoC$_{0-10}$ alkyl,
- —CO$_2$(C$_{0-10}$ alkyl),
- —(C$_{0-10}$ alkyl)CO$_2$H,
- Oxo (=O),
- C$_{1-10}$ alkylS(O)$_{1-2}$,
- C$_{1-10}$ heteroalkyl S(O)$_{1-2}$,
- (C$_{3-8}$) cycloalkylS(O)$_{1-2}$,
- (C$_{3-8}$) cycloheteroalkylS(O)$_{1-2}$,
- heteroarylS(O)$_{1-2}$,
- arylS(O)$_{1-2}$,
- C$_{0-6}$ alkyl(amino)$_{0-1}$S(O)$_{1-2}$amino,
- C$_{1-10}$ heteroalkyl(amino)$_{0-1}$S(O)$_{1-2}$amino,
- (C$_{3-8}$) cycloalkyl(amino)$_{0-1}$S(O)$_{1-2}$amino,
- (C$_{3-8}$) cycloheteroalkyl(amino)$_{0-1}$S(O)$_{1-2}$amino,
- heteroaryl(amino)$_{0-1}$S(O)$_{1-2}$amino,
- aryl(amino)$_{0-1}$S(O)$_{1-2}$amino,
- —SO$_2$N(C$_{1-6}$alkyl)$_{1-2}$,
- —SO$_2$C$_{1-6}$alkyl,
- —SO$_2$CF$_3$,
- —SO$_2$CF$_2$H,
- amino,
- (C$_{0-10}$ alkyl)$_{1-2}$ amino,
- -(oxy)$_{0-1}$(carbonyl)$_{0-1}$N(C$_{0-10}$ alkyl)$_{1-2}$,
- hydroxy,
- (C$_{1-10}$ alkyl)OH,
- C$_{1-10}$ alkoxy,
- cyano, and
- C$_{1-6}$haloalkyl;

$R_4$ is substituted with 0, 1, 2, or 3 $R_5$ substituents and each $R_5$ substituent is independently selected from hydroxy, $(C_{1-6})$alkyl, $(C_{1-6})$alkoxy, $(C_{1-10}$ alkyl)OH, halogen, $CO_2H$, —$(C_{0-6})$alkylCN, —O(C=O)$C_1$-$C_6$ alkyl, —(C=O)O$C_1$-$C_6$ alkyl, $NO_2$, trifluoromethoxy, trifluoroethoxy, trifluoromethyl, trifluoroethyl, —N—C(O)O$(C_{0-6})$alkyl, $C_{1-10}$ alkylsulfonyl, $C_{1-10}$ heteroalkyl, aryl, $C_{3-8}$ cycloalkyl, heteroaryl, $(C_{3-8})$heterocycloalkyl, $C_{0-10}$heteroalkylsulfonyl, oxo (O=), $(C_{3-8})$ cycloalkylsulfonyl, $(C_{3-8})$ cycloheteroalkylsulfonyl, heteroarylsulfonyl, arylsulfonyl, aminosulfonyl, —$SO_2N(C_{1-6}$alkyl$)_{1-2}$, —$SO_2C_{1-6}$alkyl, —$SO_2CF_3$, —$SO_2CF_2H$, —$CO_{1-10}$ alkylsulfinyl, —$O_{(0-1)}(C_{1-10})$haloalkyl, amino($C_{1-6}$alkyl$)_{0-2}$ and $NH_2$; and $R_5$ is substituted with 0, 1, or 2 $R_6$ substituents and each $R_6$ substituent is independently selected from hydroxy, $(C_{1-6})$ alkyl, $(C_{1-6})$alkoxy, $(C_{1-10}$ alkyl)OH, halogen, $CO_2H$, —$(C_{0-6})$alkylCN, —O(C=O)$C_1$-$C_6$ alkyl, —(C=O)O$C_1$-$C_6$ alkyl, $NO_2$, trifluoromethoxy, trifluoroethoxy, trifluoromethyl, trifluoroethyl, —N—C(O)O$(C_{0-6})$alkyl, $C_{1-10}$ alkylsulfonyl, $C_{1-10}$ heteroalkylsulfonyl, oxo (O=), $(C_{3-8})$ cycloalkylsulfonyl, $(C_{3-8})$ cycloheteroalkylsulfonyl, heteroarylsulfonyl, arylsulfonyl, aminosulfonyl, —$SO_2N(C_{1-6}$alkyl$)_{1-2}$, —$SO_2C_{1-6}$alkyl, —$SO_2CF_3$, —$SO_2CF_2H$, —$O_{(0-1)}(C_{1-10})$haloalkyl, amino($C_{1-6}$alkyl$)_{0-2}$ and $NH_2$.

Another embodiment of the invention includes compounds of formula II or pharmaceutically acceptable salts or stereoisomers thereof:

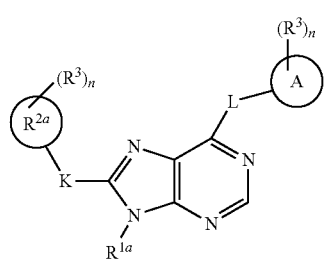

II $R^{1a}$ is selected from difluoroethyl, 2-2-difluoroethyl, trifluoroethyl, and 2-2-2-trifluoroethyl.

$R^{2a}$ is independently selected from pyrimidinyl, pyridinyl, pyrrolo[2,3-b]pyridinyl, pyrrolidinyl, oxetanyl, cyclohexyl, azetidinyl, phenyl, pyrazolyl, imidazolyl, indolyl, indazolyl, thiazolyl, hydrogen, 1H-pyrazolo[3,4-b]pyridinyl], benzimidazolyl, cyclopropyl, cyclohexyl, tert-butyl, ethyl, methyl, methylpropyl, 4,5,6,7-tetrahydro-1H-benzimidazolyl, and morpholinyl;

n is 0, 1, 2, 3, or 4;

A is $C_{3-12}$ cycloalkyl$C_{0-8}$ alkyl, $C_{3-12}$heterocycloalkyl$C_{0-8}$ alkyl, and $C_{6-12}$spirocyclyl;

L is selected from NH, and N($C_{1-10}$alkyl);

K is selected from: a bond, —C(O)—NH—, —C(O)—, —C(O)—N(CH$_3$)—, —C(O)—N(CH$_3$)—CH$_2$—, —CH$_2$—, —O—, —C≡C—, and —C(O)—NH—CH$_2$—;

$R^{3a}$ is independently selected from: methyl, ethyl, methoxy, tert-butyl, trifluoromethyl, dimethylamino, phenyl, amino, chloro, methylsulfonyl, cyano, hydroxyisopropyl, hydroxymethyl, fluoro, cyclopropyl, methoxymethyl, trifluoroethyl, and methylsulfonyl, wherein $R^{3a}$ is each substituted with 0, 1, 2, 3, or 4 $R^4$ substituents;

$R^3$ is independently selected from:
$C_{1-10}$ alkyl(oxy)$_{0-1}$(carbonyl)$_{0-1}$$C_{0-10}$ alkyl,
$C_{2-10}$ alkenyl(oxy)$_{0-1}$(carbonyl)$_{0-1}$$C_{0-10}$ alkyl,
$C_{1-10}$ heteroalkyl(oxy)$_{0-1}$(carbonyl)$_{0-1}$$C_{0-10}$ alkyl,
aryl $C_{0-10}$ alkyl(oxy)$_{0-1}$(carbonyl)$_{0-1}$$C_{0-10}$ alkyl,
$C_{3-12}$ cycloalkyl$C_{0-10}$ alkyl(oxy)$_{0-1}$(carbonyl)$_{0-1}$$C_{0-10}$ alkyl,
heteroaryl $C_{0-10}$ alkyl(oxy)$_{0-1}$(carbonyl)$_{0-1}$$C_{0-10}$ alkyl,
$(C_{3-12})$heterocycloalkyl $C_{0-10}$ alkyl(oxy)$_{0-1}$(carbonyl)$_{0-1}$$C_{0-10}$ alkyl,
$C_{0-10}$ alkylamino(carbonyl)$_{0-1}$$C_{0-10}$ alkyl,
$(C_{1-10})$heteroalkylamino(carbonyl)$_{0-1}$$C_{0-10}$ alkyl,
$C_{3-12}$ cycloalkyl $C_{0-10}$ alkylamino(carbonyl)$_{0-1}$$C_{0-10}$ alkyl,
aryl $C_{0-10}$alkylamino(carbonyl)$_{0-1}$$C_{0-10}$ alkyl,
heteroaryl$C_{0-10}$alkylamino(carbonyl)$_{0-1}$$C_{0-10}$ alkyl,
$(C_{3-12})$heterocycloalkyl$C_{0-10}$alkylamino(carbonyl)$_{0-1}$$C_{0-10}$ alkyl,
$C_{1-10}$ alkyl(oxy)$_{0-1}$(carbonyl)$_{0-1}$amino$C_{0-10}$ alkyl,
$C_{3-12}$ cycloalkyl $C_{0-10}$ alkyl (oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino$C_{0-10}$ alkyl,
$(C_{3-12})$heterocycloalkyl $C_{0-10}$ alkyl(oxy)$_{0-1}$(carbonyl)$_{0-1}$amino$C_{0-10}$ alkyl,
—$CO_2$($C_{0-10}$ alkyl),
Oxo (=O);
$C_{1-10}$ alkylS(O)$_{1-2}$,
arylS(O)$_{1-2}$,
$C_{0-6}$ alkyl(amino)$_{0-1}$S(O)$_{1-2}$amino,
amino,
$(C_{0-10}$ alkyl)$_{1-2}$ amino,
hydroxy,
$(C_{1-10}$ alkyl)OH,
$C_{0-10}$ alkylalkoxy,
cyano, and
$C_{1-6}$haloalkyl;

wherein $R^3$ is each substituted with 0, 1, 2, 3, or 4 $R^4$ substituents and each $R^4$ is independently selected from:
halogen,
$C_{1-10}$ alkyl(oxy)$_{0-1}$(carbonyl)$_{0-1}$$C_{0-10}$ alkyl,
aryl $C_{0-10}$ alkyl(oxy)$_{0-1}$(carbonyl)$_{0-1}$$C_{0-10}$ alkyl,
$C_{3-8}$ cycloalkyl $C_{0-10}$ alkyl(oxy)$_{0-1}$(carbonyl)$_{0-1}$$C_{0-10}$ alkyl,
heteroaryl $C_{0-10}$ alkyl(oxy)$_{0-1}$(carbonyl)$_{0-1}$$C_{0-10}$ alkyl,
$C_{3-8}$heterocycloalkyl $C_{0-10}$ alkyl(oxy)$_{0-1}$(carbonyl)$_{0-1}$$C_{0-10}$ alkyl,
$C_{1-10}$ alkylaminocarbonyl$C_{0-10}$ alkyl,
Oxo (=O),
$(C_{0-10}$ alkyl)$_{1-2}$ amino,
hydroxy,
$(C_{1-10}$ alkyl)OH,
$C_{1-10}$ alkoxy,
cyano, and
$C_{1-6}$haloalkyl;

wherein $R^4$ is substituted with 0, 1, 2, or 3 $R^5$ substituents and each $R^5$ substituent is selected from hydroxy, $(C_{1-6})$ alkyl, $(C_{1-6})$alkoxy, $(C_{1-10}$ alkyl)OH, halogen, $CO_2H$, —$(C_{0-6})$alkylCN, $NO_2$, trifluoromethyl, trifluoroethyl, oxo (O=), —$O_{(0-1)}(C_{1-10})$haloalkyl, and amino($C_{1-6}$alkyl)$_{0-2}$.

In one embodiment of the invention, A is selected from pyrrolidinyl, piperidinyl, azetidinyl, azaspiro[2.4]hept-7-yl, cyclohexyl, azepanyl, and cyclopentyl. In a variant of this embodiment, A is selected from pyrrolidinyl and piperidinyl. In yet another embodiment of the invention A is selected from azetidinyl, azaspiro[2.4]hept-7-yl, cyclohexyl, azepanyl, and cyclopentyl.

In one embodiment of the invention, $R^3$ is independently selected from: In one embodiment, $R^3$ is independently selected from: fluoro, chloro, methyl, ethyl, propyl, methoxy, methoxymethyl, methylethyl, 2-methylbuten-4-yl, 2-methylpropyl, 1,3,4-oxadiazolyl, pyridinyl, isoquinolinyl, cyclopropylmethyl, hydroxy, oxo(=O), dimethylamino, tert-butyl, trifluoromethyl, trifluoroethyl, carboxy, tert-butylcarboxy, fluoroethylcarboxy, tetrahydrothiophenylcarboxy, methylpropylcarboxy, propylcarboxy, ethoxycarbonyl, benzylcarboxy, 2,2-dimethylpropylcarboxy, methylcarboxy, ethylcarboxy, methylethylcarboxy, cyclopentylcarbonyl, cyclohexylcarboxy, cyclobutylcarbonyl, 2,2,2-trifluoroethylcarboxy, spiro[2.4]hept-1-ylcarbonyl, spiro[2.5]oct-1-ylcarbonyl, benzylcarbonyl, imidazolylcarbonyl, ethylcarbonyl, methylethylcarbonyl, piperidinylcarbonyl, pyrrolidinylcarbonyl, cyclohexylcarbonyl, isopropylcarbonyl, methylcarbonyl, tetrahydro-2H-pyran-4-ylcarbonyl, oxazolylcarbonyl, cyclopropylcarbonyl, azetidinylcarbonyl, cyclopropylaminocarbonyl, tetrahydrofuranylcarbonyl, isoxazolylcarbonyl, triazolylcarbonyl, thiadiazolylcarbonyl, cyclobutylaminocarbonyl, furanylmethylaminocarbonyl, aminocarbonyl, pyrazolylcarbonyl, hydroxymethyl, ethylsulfonyl, methylsulfonyl, (cyclopropylmethyl)aminocarbonyl, azabicyclo[3.1.0]hex-6-ylcarbonyl, trifluoroethylaminocarbonyl, (tetrahydrothiophenylmethyl) aminocarbonyl, methylethylaminocarbonyl, cyclohexylaminocarbonyl, ethylaminocarbonyl, (1,1,3,3-tetramethylbutyl)aminocarbonyl, oxazolylcarbonylamino, bicyclo[1.1.1] pent-1-ylcarbonyl, methylaminocarbonyl, phenyl, pyrimidinyl, thieno[3,2-c]pyridinyl, morpholinylcarbonyl, butylaminocarbonyl, cyano, amino, and hydroxyisopropyl; wherein $R^3$ is each substituted with 0, 1, 2, 3, or 4 substituents, $R^4$ In another embodiment of the invention, $R_4$ is halogen, and methyl.

In one embodiment, $R_5$ is independently selected from hydroxy, $(C_{1-6})$alkyl, $(C_{1-6})$alkoxy, $(C_{1-10}$ alkyl)OH, halogen, $CO_2H$, $—(C_{0-6})$alkylCN, $NO_2$, trifluoromethyl, trifluoroethyl, $C_{1-10}$ alkylsulfonyl, $C_{1-10}$ heteroalkyl, aryl, $C_{3-8}$ cycloalkyl, heteroaryl, $(C_{3-8})$heterocycloalkyl, oxo (O=), $—O_{(0-1)}(C_{1-10})$haloalkyl, and amino$(C_{1-6}$alkyl)$_{0-2}$.

In another embodiment of the invention, $R_5$ is selected from methyl, ethyl, and halogen.

One embodiment of the invention include the following compounds and their pharmaceutically acceptable salts and their stereoisomers thereof:
cyclopropyl(3-((9-ethyl-8-(2-methylpyrimidin-5-yl)-9H-purin-6-yl)amino)pyrrolidin-1-yl)methanone;
N-[1-(cyclopropylcarbonyl)-4,4-difluoropyrrolidin-3-yl]-9-ethyl-8-(2-methylpyrimidin-5-yl)-9H-purin-6-amine
N-[1-(cyclopropylcarbonyl)piperidin-3-yl]-9-ethyl-8-(2-methylpyrimidin-5-yl)-9H-purin-6-amine;
9-ethyl-8-(2-methylpyrimidin-5-yl)-N-[1-(tetrahydrofuran-2-ylcarbonyl)pyrrolidin-3-yl]-9H-purin-6-amine;
9-ethyl-8-(2-methylpyrimidin-5-yl)-N-[1-(tetrahydrofuran-2-ylcarbonyl)pyrrolidin-3-yl]-9H-purin-6-amine;
(3-((9-ethyl-8-(2-methylpyrimidin-5-yl)-9H-purin-6-yl) amino)pyrrolidin-1-yl)(2-(fluoromethyl)cyclopropyl) methanone;
9-ethyl-8-(2-methylpyrimidin-5-yl)-N-{1-[tetrahydrofuran-3-ylcarbonyl]pyrrolidin-3-yl}-9H-purin-6-amine;
9-ethyl-N-[-(1-methyl-L-prolyl)pyrrolidin-3-yl]-8-(2-methylpyrimidin-5-yl)-9H-purin-6-amine;
N-[1-(cyclopropylcarbonyl)pyrrolidin-3-yl]-9-ethyl-8-[6-(trifluoromethyl)pyridin-3-yl]-9H-purin-6-amine;
9-ethyl-8-(2-methylpyrimidin-5-yl)-N-[1-(1,3-oxazol-4-ylcarbonyl)pyrrolidin-3-yl]-9H-purin-6-amine;
N-[1-(cyclopropylcarbonyl)-4-methylpyrrolidin-3-yl]-9-ethyl-8-(2-methylpyrimidin-5-yl)-9H-purin-6-amine;
9-ethyl-8-(2-methylpyrimidin-5-yl)-N-[4-methyl-1-(spiro [2.5]oct-1-ylcarbonyl)pyrrolidin-3-yl]-9H-purin-6-amine;
9-ethyl-N-[1-{[2-methylcyclopropyl]carbonyl}pyrrolidin-3-yl]-8-(2-methylpyrimidin-5-yl)-9H-purin-6-amine;
N-[1-(cyclopropylcarbonyl)-2-methylpyrrolidin-3-yl]-9-ethyl-8-(2-methylpyrimidin-5-yl)-9H-purin-6-amine;
4-{[3-{[9-ethyl-8-(2-methylpyrimidin-5-yl)-9H-purin-6-yl] amino}pyrrolidin-1-yl]carbonyl}cyclohexanol;
9-ethyl-N-{1-[tetrahydrofuran-3-ylcarbonyl]pyrrolidin-3-yl}-8-[6-(trifluoromethyl)pyridin-3-yl]-9H-purin-6-amine;
9-ethyl-N-{1-[(3-methoxycyclobutyl)carbonyl]pyrrolidin-3-yl}-8-[6-(trifluoromethyl)pyridin-3-yl]-9H-purin-6-amine;
9-ethyl-8-(5-fluoro-6-methoxypyridin-3-yl)-N-{1-[(1-methyl-1H-imidazol-5-yl)carbonyl]pyrrolidin-3-yl}-9H-purin-6-amine;
N-{1-[(3,3-difluorocyclobutyl)carbonyl]pyrrolidin-3-yl}-9-ethyl-8-(5-fluoro-6-methoxypyridin-3-yl)-9H-purin-6-amine;
9-ethyl-8-(2-methylpyrimidin-5-yl)-N-[1-pyridin-2-ylpyrrolidin-3-yl]-9H-purin-6-amine;
6-{[1-(cyclopropylcarbonyl)pyrrolidin-3-yl]amino}-9-ethyl-N-(2,2,2-trifluoroethyl)-9H-purine-8-carboxamide;
6-{[1-(cyclopropylcarbonyl)pyrrolidin-3-yl]amino}-N-[1-cyclopropylethyl]-9-ethyl-9H-purine-8-carboxamide;
8-(difluoromethyl)-9-ethyl-N-{1-[(3-methoxycyclobutyl) carbonyl]pyrrolidin-3-yl}-9H-purin-6-amine;
8-(difluoromethyl)-9-ethyl-N-[1-(spiro[2.4]hept-1-ylcarbonyl)pyrrolidin-3-yl]-9H-purin-6-amine;
8-(difluoromethyl)-9-ethyl-N-{1-[(3-methoxyazetidin-1-yl) carbonyl]pyrrolidin-3-yl}-9H-purin-6-amine;
8-(1H-benzimidazol-1-yl)-N-[1-(cyclopropylcarbonyl)pyrrolidin-3-yl]-9-ethyl-9H-purin-6-amine;
N-[1-(cyclopropylcarbonyl)pyrrolidin-3-yl]-9-ethyl-8-[4-(trifluoromethyl)-1H-imidazol-1-yl]-9H-purin-6-amine;
N-[1-(cyclopropylcarbonyl)pyrrolidin-3-yl]-9-ethyl-8-(3-fluoro-4-methoxyphenoxy)-9H-purin-6-amine;
9-ethyl-N-[1-{[3-fluoropyrrolidin-1-yl] carbonyl}pyrrolidin-3-yl]-8-(2-methylpyrimidin-5-yl)-9H-purin-6-amine;
N-butyl-3-{[9-ethyl-8-(2-methylpyrimidin-5-yl)-9H-purin-6-yl]amino}pyrrolidine-1-carboxamide;
methyl N-{[3-{[9-ethyl-8-(2-methylpyrimidin-5-yl)-9H-purin-6-yl]amino}pyrrolidin-1-yl]carbonyl}-2-methylalaninate;
9-ethyl-6-({1-[(3-methoxyazetidin-1-yl)carbonyl]pyrrolidin-3-yl}amino)-N-(2,2,2-trifluoroethyl)-9H-purine-8-carboxamide;
5-1-(cyclopropylmethyl)-5-{[9-ethyl-8-(2-methylpyrimidin-5-yl)-9H-purin-6-yl]amino}piperidin-2-one; and
N-[1-(cyclopropylcarbonyl)pyrrolidin-3-yl]-9-ethyl-8-(phenylethynyl)-9H-purin-6-amine.

In a variant of this embodiment, include the following compounds and their pharmaceutically acceptable salts and their stereoisomers thereof:
cyclopropyl(3-((9-ethyl-8-(2-methylpyrimidin-5-yl)-9H-purin-6-yl)amino)pyrrolidin-1-yl)methanone;
N-[1-(cyclopropylcarbonyl)-4,4-difluoropyrrolidin-3-yl]-9-ethyl-8-(2-methylpyrimidin-5-yl)-9H-purin-6-amine;
(3-((9-ethyl-8-(2-methylpyrimidin-5-yl)-9H-purin-6-yl) amino)pyrrolidin-1-yl)(-2-(fluoromethyl)cyclopropyl) methanone;
N-[1-(cyclopropylcarbonyl)pyrrolidin-3-yl]-9-ethyl-8-[6-(trifluoromethyl)pyridin-3-yl]-9H-purin-6-amine;

N-[1-(cyclopropylcarbonyl)-4-methylpyrrolidin-3-yl]-9-ethyl-8-(2-methylpyrimidin-5-yl)-9H-purin-6-amine;
9-ethyl-N-[1-{[2-methylcyclopropyl]carbonyl}pyrrolidin-3-yl]-8-(2-methylpyrimidin-5-yl)-9H-purin-6-amine;
N-[1-(cyclopropylcarbonyl)-2-methylpyrrolidin-3-yl]-9-ethyl-8-(2-methylpyrimidin-5-yl)-9H-purin-6-amine;
9-ethyl-N-{1-[tetrahydrofuran-3-ylcarbonyl]pyrrolidin-3-yl}-8-[6-(trifluoromethyl)pyridin-3-yl]-9H-purin-6-amine;
9-ethyl-8-(2-methylpyrimidin-5-yl)-N-[-pyridin-2-ylpyrrolidin-3-yl]-9H-purin-6-amine;
6-{[1-(cyclopropylcarbonyl)pyrrolidin-3-yl]amino}-9-ethyl-N-(2,2,2-trifluoroethyl)-9H-purine-8-carboxamide;
8-(difluoromethyl)-9-ethyl-N-{1-[(3-methoxycyclobutyl)carbonyl]pyrrolidin-3-yl}-9H-purin-6-amine;
N-[1-(cyclopropylcarbonyl)pyrrolidin-3-yl]-9-ethyl-8-[4-(trifluoromethyl)-1H-imidazol-1-yl]-9H-purin-6-amine;
N-butyl-3-{[9-ethyl-8-(2-methylpyrimidin-5-yl)-9H-purin-6-yl]amino}pyrrolidine-1-carboxamide; and
methyl N-{[3-{[9-ethyl-8-(2-methylpyrimidin-5-yl)-9H-purin-6-yl]amino}pyrrolidin-1-yl]carbonyl}-2-methylalaninate.

In yet another embodiment of the invention includes the following compounds and their pharmaceutically acceptable salts and their stereoisomers thereof:
N-[1-(cyclopropylcarbonyl)-4,4-difluoropyrrolidin-3-yl]-9-ethyl-8-(2-methylpyrimidin-5-yl)-9H-purin-6-amine;
N-[1-(cyclopropylcarbonyl)piperidin-3-yl]-9-ethyl-8-(2-methylpyrimidin-5-yl)-9H-purin-6-amine;
9-ethyl-8-(2-methylpyrimidin-5-yl)-N-[1-(tetrahydrofuran-2-ylcarbonyl)pyrrolidin-3-yl]-9H-purin-6-amine;
9-ethyl-8-(2-methylpyrimidin-5-yl)-N-{1-[tetrahydrofuran-3-ylcarbonyl]pyrrolidin-3-yl}-9H-purin-6-amine;
9-ethyl-N-[-(1-methyl-L-prolyl)pyrrolidin-3-yl]-8-(2-methylpyrimidin-5-yl)-9H-purin-6-amine;
9-ethyl-8-(2-methylpyrimidin-5-yl)-N-[1-(1,3-oxazol-4-ylcarbonyl)pyrrolidin-3-yl]-9H-purin-6-amine;
9-ethyl-8-(2-methylpyrimidin-5-yl)-N-[4-methyl-1-(spiro[2.5]oct-1-ylcarbonyl)pyrrolidin-3-yl]-9H-purin-6-amine;
4-{[3-{[9-ethyl-8-(2-methylpyrimidin-5-yl)-9H-purin-6-yl]amino}pyrrolidin-1-yl]carbonyl}cyclohexanol;
9-ethyl-N-{1-[(3-methoxycyclobutyl)carbonyl]pyrrolidin-3-yl}-8-[6-(trifluoromethyl)pyridin-3-yl]-9H-purin-6-amine;
9-ethyl-8-(5-fluoro-6-methoxypyridin-3-yl)-N-{1-[(1-methyl-1H-imidazol-5-yl)carbonyl]pyrrolidin-3-yl}-9H-purin-6-amine;
N-{1-[(3,3-difluorocyclobutyl)carbonyl]pyrrolidin-3-yl}-9-ethyl-8-(5-fluoro-6-methoxypyridin-3-yl)-9H-purin-6-amine;
9-ethyl-8-(2-methylpyrimidin-5-yl)-N-[1-pyridin-2-ylpyrrolidin-3-yl]-9H-purin-6-amine;
6-{[1-(cyclopropylcarbonyl)pyrrolidin-3-yl]amino}-9-ethyl-N-(2,2,2-trifluoroethyl)-9H-purine-8-carboxamide;
6-{[1-(cyclopropylcarbonyl)pyrrolidin-3-yl]amino}-N-[1-cyclopropylethyl]-9-ethyl-9H-purine-8-carboxamide;
8-(difluoromethyl)-9-ethyl-N-{1-[(3-methoxycyclobutyl)carbonyl]pyrrolidin-3-yl}-9H-purin-6-amine;
8-(difluoromethyl)-9-ethyl-N-[1-(spiro[2.4]hept-1-ylcarbonyl)pyrrolidin-3-yl]-9H-purin-6-amine;
8-(difluoromethyl)-9-ethyl-N-{1-[(3-methoxyazetidin-1-yl)carbonyl]pyrrolidin-3-yl}-9H-purin-6-amine;
8-(1H-benzimidazol-1-yl)-N-[1-(cyclopropylcarbonyl)pyrrolidin-3-yl]-9-ethyl-9H-purin-6-amine;
N-[1-(cyclopropylcarbonyl)pyrrolidin-3-yl]-9-ethyl-8-(3-fluoro-4-methoxyphenoxy)-9H-purin-6-amine;
9-ethyl-N-[1-{[3-fluoropyrrolidin-1-yl]carbonyl}pyrrolidin-3-yl]-8-(2-methylpyrimidin-5-yl)-9H-purin-6-amine;
9-ethyl-6-({1-[(3-methoxyazetidin-1-yl)carbonyl]pyrrolidin-3-yl}amino)-N-(2,2,2-trifluoroethyl)-9H-purine-8-carboxamide;
5-1-(cyclopropylmethyl)-5-{[9-ethyl-8-(2-methylpyrimidin-5-yl)-9H-purin-6-yl]amino}piperidin-2-one; and
N-[1-(cyclopropylcarbonyl)pyrrolidin-3-yl]-9-ethyl-8-(phenylethynyl)-9H-purin-6-amine.

"Patient" for the purposes of the present invention includes humans and other animals, particularly mammals and other organisms. Thus the methods are applicable to both human therapy and beterinary applications.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —($CR_3R_3$)$_2$—, each occurrence of the two $R_3$ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

Optical Isomers—Diastereomers—Geometric Isomers—Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the class of compounds without specific stereochemistry. When the compounds of the present invention contain one chiral center, the term "stereoisomer" includes both enantiomers and mixtures of enantiomers, such as the specific 50:50 mixture referred to as racemic mixtures.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereomeric compound is named using an "and" in the stereomeric designation, for example, (S and R)-tert-butyl 3-((8-(1-ethyl-5-methyl-1H-pyrazol-4-yl)-9-methyl-9H-purin-6-yl)oxy)piperidine-1-carboxylate, the "and" indicates a racemic mixture of the enantiomers. That is, the individual enantiomers were not individually isolated.

When the stereomeric nomenclature includes "or", for example, (S or R)-tert-butyl 3-((8-(1-ethyl-5-methyl-1H-pyrazol-4-yl)-9-methyl-9H-purin-6-yl)oxy)piperidine-1-carboxylate, the "or" indicates that chiral resolution of racemate into individual enantiomers was accomplished but the actual optical activity of the specific enantiomer was not determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I, subsets thereof, embodiments thereof, as well as specific compounds are meant to also include the pharmaceutically acceptable salts.

Furthermore, some of the crystalline forms for compounds of the present invention may exist as polymorphs and as such all forms are intended to be included in the present invention.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$ alkyl, $(C_3-C_7)$ cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy $(C_1-C_6)$alkyl, amino$(C_1-C_4)$alkyl or mono-N— or di-N,N— $(C_1-C_6)$alkylaminoalkyl, —$C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Additionally, the present invention is meant to include in compounds of generic Formula I, all suitable replacements of sp3 orbital carbons to sp3 Si as can readily be invisoned by one of ordinary skill in the art.

Utilities

Compounds of the Invention have activity for PI3K-delta. Compounds of this invention have been tested using the assays described in the Biological Examples and have been determined to be inhibitors of PI3K-delta. Suitable in vitro assays for measuring PI3K-delta activity and the inhibition thereof by compounds are known in the art. For further details of an in vitro assay for measuring PI3K-delta see the Biological Examples herein. Cell-based assays for measurement of in vitro efficacy in treatment of cancer are known in the art. In addition, assays are described in the Biological Examples provided herein.

Suitable in vivo models for cancer are known to those of ordinary skill in the art. See for example, international patent application published as WO 2012/037226 for further details of in vivo models for prostate adenocarcinoma, glioblastoma, lung carcinoma, and melanoma. Following the examples disclosed herein, as well as that disclosed in the art, a person of ordinary skill in the art can determine the activity of a compound of this invention.

Compounds of Formula I are useful for treating diseases, including autoimmune disorders, inflammatory diseases, and cancers, which are listed below.

Cancers: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplasia syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

Autoimmune diseases: Hashimoto's thyroiditis, systemic lupus erythematosus (SLE), Goodpasture's syndrome, pemphigus, receptor autoimmune diseases, Basedow's disease (Graves' disease), myasthernia gravis, insulin resistant diseases, autoimmune hemolytic anemia, autoimmune thrombocytopenic purpura, autoimmune encephalomyelitis, rheumatism, rheumatoid arthritis, scleroderma, mixed connective tissue disease, polymyositis, pernicious anemia, idiopathic Addison's disease, some types of infertility, glomerulonephritis, bullous pemphigus, Sjogren's syndrome, some types of diabetes, adrenergic agent resistance, chronic active hepatitis, primary biliary cirrhosis, endocrine failure, vitiligo, angiitis, post-cardiac surgery syndrome, urticaria, atopic dermatiti and multiple sclerosis, autoimmune polyglandular disease (also known as autoimmune polyglandular syndrome), autoimmune alopecia; pernicious anemia; vitiligo; autoimmune hypopituatarism, and Guillain-Barre syndrome.

Inflammatory Diseases: asthma, allergic rhinitis, psoriasis, inflammatory arthritis, rheumatoid arthritis, psoriatic arthritis or osteoarthritis, irritable bowel syndrome, ulcerative colitis, Crohn's disease, respiratory allergies (asthma, hay fever, allergic rhinitis) or skin allergies, scleracierma, mycosis fungoides, acute inflammatory responses (such as acute respiratory distress syndrome and ishchemia/reperfusion injury), dermatomyositis, alopecia greata, chronic actinic dermatitis, eczema, Behcet's disease, Pustulosis palmoplanteris, Pyoderma gangrenum, Sezary's syndrome, atopic dermatitis, systemic sclerosis, and morphea.

Central Nervous System Disorders: multiple sclerosis, schizophrenia

Thus, in one embodiment, the invention provides a method of inhibiting PI3K-delta comprising contacting the PI3K-delta with an effective amount of a compound as disclosed herein.

In one embodiment, the compounds of the instant invention are selective PI3K-delta inhibitors relative to PI3K-alpha. The determination of relative selectivity for a given compound of PI3K-delta inhibition is defined as the relative ratio of the (PI3K-alpha $IC_{50}$ value/PI3K-delta $IC_{50}$ value) is at least 2. In yet another embodiment, for a given compound, the relative ratios of the (PI3K-alpha $IC_{50}$ value/PI3K-delta $IC_{50}$ value) is at least 4.

In another embodiment, the invention provides a method of treating a PI3K-delta modulated disease comprising administering to a mammal in need of such treatment a therapeutically effective amount of a compound as disclosed herein.

In another embodiment, the invention provides a method of treating cancer disease mediated by PI3K-delta comprising administering to a mammal in need of such treatment a therapeutically effective amount of a compound as disclosed herein.

Compounds of the invention are also useful as inhibitors of PI3K-delta in vivo for studying the in vivo role of PI3K-delta in biological processes, including the diseases described herein. Accordingly, the invention also comprises a method of inhibiting PI3K-delta in vivo comprising administering a compound or composition of the invention to a mammal.

Accordingly, another aspect of the present invention provides a method for the treatment or prevention of a PI3K-delta mediated disease or disorder comprising administering to a mammal in need thereof a therapeutically effective amount of a compound of formula I. In one embodiment such diseases include asthma and rheumatoid arthritis.

Another aspect of the present invention provides for the use of a compound of formula I in the manufacture of a medicament for the treatment or prevention of a PI3K-delta mediated diseases or disorder.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 milligram of active agent per kilogram body weight of a mammal (mg/kg) to about 100 mg/kg, typically, between 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.01 mg to 10 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, 400 mg, or 500 mg.

If formulated as a fixed dose, such combination products employ the compounds of this invention within the dosage range described above and the other pharmaceutically acceptable agent(s) when a combination formulation is inappropriate.

The final dosage regimen will be determined by the attending physician in view of good medical practice, considering various factors that modify the action of drugs, e.g., the agent's specific activity, the identity and severity of the disease state, the responsiveness of the patient, the age, condition, body weight, sex, and diet of the patient, and the severity of any infection. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, can be preferred for continuous infusion.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 m to about 10 m; however, for effective delivery to the distal lung, at least 95 percent of the active agent particles are 5 m or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

In certain embodiments, a compound of Formula I is combined in a pharmaceutical combination formulation, or dosing regimen as combination therapy, with one or more other therapeutic agent that has anti-inflammatory or anti-hyperproliferative properties or that is useful for treating an inflammation, immune-response disorder, or hyperproliferative disorder (e.g., cancer). The other therapeutic agent of the pharmaceutical combination formulation or dosing regimen preferably has complementary activities to the compound of Formula I such that they do not adversely affect each other. Such agents are suitably present in combination in amounts that are effective for the purpose intended.

In one embodiment of the invention, the compound of Formula I, or a stereoisomer, tautomer, or pharmaceutically acceptable salt or prodrug thereof, may be co-administered with one or more other therapeutic agents for the treatment and prevention of PI3Kdelta mediated diseases. Thus in another aspect the present invention provides pharmaceutical compositions for treating PI3Kdelta mediated diseases comprising a therapeutically effective amount of a compound of formula I and one or more other therapeutic agents.

In one embodiment for example, for the treatment of the inflammatory diseases rheumatoid arthritis, psoriasis, inflammatory bowel disease, COPD, asthma and allergic rhinitis a compound of formula I may be combined with other therapeutic agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclidinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

In another embodiment of the invention, the compounds of Formula I, or a stereoisomer, tautomer, or pharmaceutically acceptable salt or prodrug thereof, may be employed alone or in combination with other therapeutic agents for the treatment of hyperproliferative disorders (e.g., cancer) including standard chemotherapy regimens, and anti-CD20 monoclonal antibodies, rituximab, bendamustine, ofatumumab, fludarabine, lenalidomide, and/or bortezomib.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active therapeutic agents simultaneously exert their biological activities.

SCHEMES AND EXAMPLES

The abbreviations used herein have the following tabulated meanings. Abbreviations not tabulated below have their meanings as commonly used unless specifically stated otherwise.

Abbreviations Used in the Description of Compound Preparation

| | |
|---|---|
| BAST | bis(2-methoxyethyl)aminosulfur trifluoride |
| Boc | tert-butoxycarbamate |
| BSA | N-(trimethylsilyl)acetimidate |
| DBU | 1,8-diazabicyclo[5.4.0]undec-7-ene |
| DCM | dichloromethane |
| DIEA | N,N-diisopropylethylamine |
| DMF | dimethylformamide |
| DMSO | dimethyl sulfoxide |
| EDC•HCl | N-(3-dimethylaminopropyl)-N'-ethylcarbodiimide hydrochloride |
| EI | electron ionization |
| EtOAc | ethyl acetate |
| HATU | 1-[bis(dimethylamino)methylene]-1H-1,2,3-triazolo[4,5-b]pyridinium 3-oxid hexafluorophosphate |
| HOBT | 1-hydroxybenzotriazole hydrate |
| HPLC | high performance liquid chromatography |
| i-PrOH | isopropanol |
| LC/MS | liquid chromatography coupled to mass spectrometer |
| LDA | lithium diisopropylamide |
| MeCN | acetonitrile |
| MeOH | methanol |
| MS | mass spectrum (data) |
| NMP | N-methylpyrrolidone |
| NMR | nuclear magnetic resonance (data) |
| Pd(dppf) | [1,1'-bis(diphenylphosphino)ferrocene]dichloropalladium(II) |
| PE | petroleum ether |
| RT | room temperature |
| SFC | supercritical fluidic chromatography |
| t-BuOH | tert-butanol |
| TEA | triethylamine |
| TFA | trifluoroacetic acid |
| THF | tetrahydrofuran |
| TLC | thin-layer chromatography |

General Synthetic Schemes

Several synthetic routes were employed in the syntheses of the compounds described herein. In one approach, 4,6-dichloropyrimidine-5-amine was elaborated to a common intermediate Gen-1 by addition of an amine (e.g. $R^1$—$NH_2$) followed by cyclization. For example, oxidative cyclization with an aldehyde would yield the corresponding purine. Next, Gen-1 was elaborated to Gen-2 by addition of the appropriate amine nucleophile. For example, reaction with a substituted aminopyrrolidine would yield the corresponding compound where the A ring is a pyrrolidine.

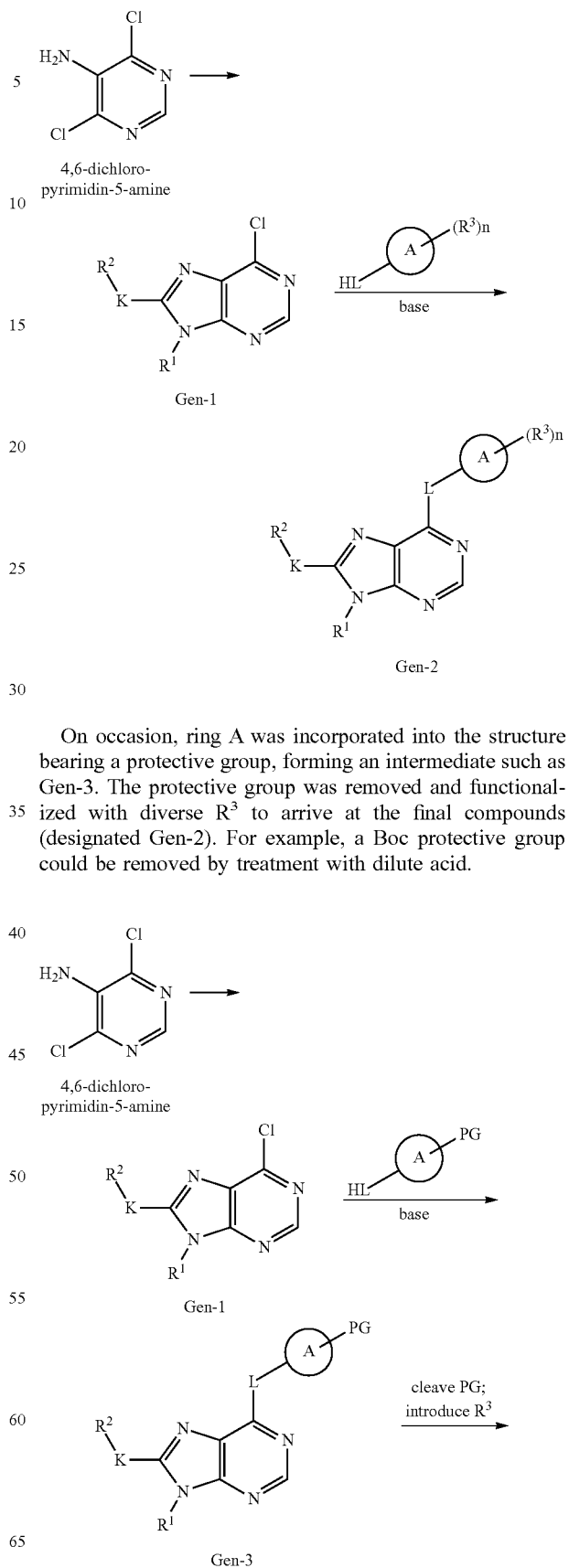

On occasion, ring A was incorporated into the structure bearing a protective group, forming an intermediate such as Gen-3. The protective group was removed and functionalized with diverse $R^3$ to arrive at the final compounds (designated Gen-2). For example, a Boc protective group could be removed by treatment with dilute acid.

-continued

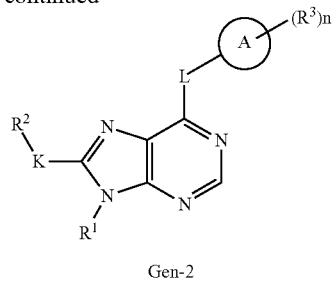
Gen-2

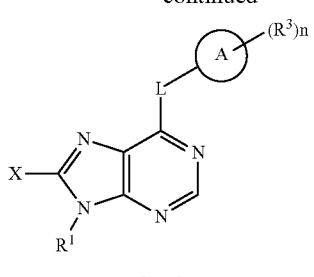
Gen-5

In another approach, 6-chloro-9H-purine was elaborated to Gen-4 via alkylation with an alkyl halide, followed by halogenation of the 2-position of the purine (X=Cl, I). Gen-4 was then elaborated to Gen-1 via cross-coupling, for example Suzuki coupling with a boronic ester. On occasion, Gen-4 was then elaborated to Gen-1 via addition of a nucleophile, for example an amine to form the corresponding 2-aminopurine. Next, Gen-1 was elaborated to Gen-2 by either of the two approaches described above.

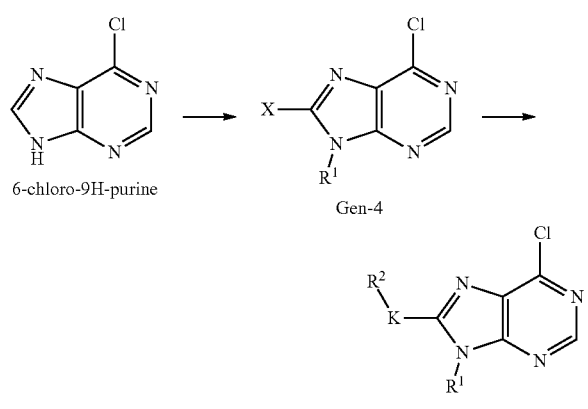

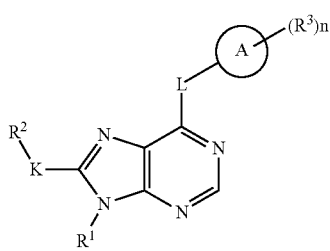
Gen-2

In a similar approach, ring A was incorporated into the structure bearing a protective group, forming an intermediate such as Gen-6. Gen-6 was then elaborated to an intermediate Gen-7 via cross-coupling, for example Suzuki coupling with a boronic ester. On occasion, Gen-6 was elaborated to Gen-7 via addition of a nucleophile, for example an amine to form the corresponding 2-aminopurine. The protective group was removed and functionalized with diverse $R^3$ to arrive at Gen-2 in a manner analogous to that described above.

In another approach, Gen-4 was elaborated to Gen-5 by addition of the appropriate amine nucleophile. Gen-5 was then elaborated to Gen-2 via cross-coupling, for example Suzuki coupling with a boronic ester. On occasion, Gen-4 was elaborated to Gen-2 via addition of a nucleophile. For example the addition of an amine would form the corresponding 2-aminopurine.

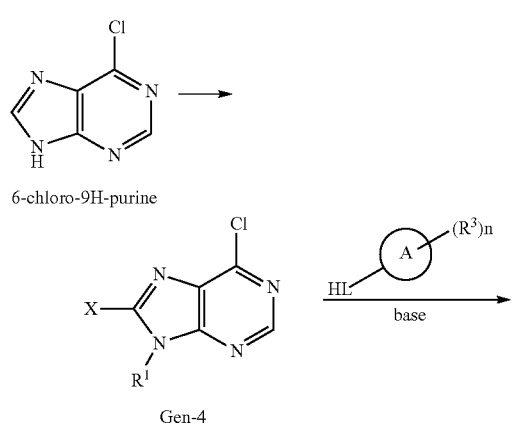

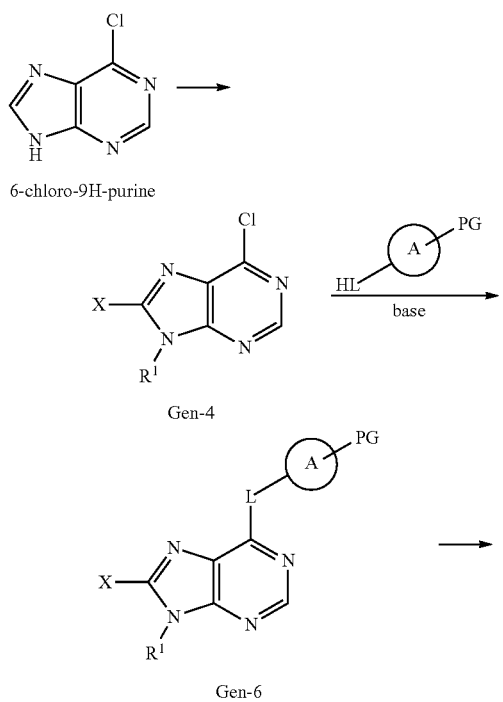

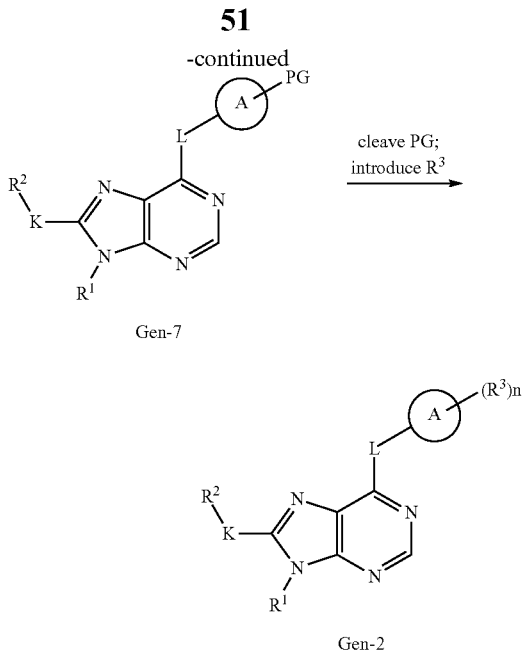

Gen-7

Gen-2

Examples of these general synthetic approaches can be found in the descriptions of the syntheses of several examples enclosed herein.

Compound Examples of Table 1

Example 1: Preparation of Compound 1-2 temperature for 2 hours, then at 60° C. for 18 hours. LC/MS analysis indicated incomplete conversion to the desired product. To this mixture were added another 0.2 mL of (S)-tert-butyl 3-aminopyrrolidine-1-carboxylate and 0.40 ml of i-Pr$_2$NEt. The mixture was heated at 80° C. for another 2 days, then cooled and diluted with EtOAc and washed with water, then brine, dried over sodium sulfate, filtered, and concentrated in vacuo. Purification by chromatography on SiO$_2$ (0-10% MeOH in DCM) afforded (S)-tert-butyl 3-((8-(1-ethyl-5-methyl-1H-pyrazol-4-yl)-9-methyl-9H-purin-6-yl)amino)pyrrolidine-1-carboxylate (1-2). $^1$H NMR (600 MHz, DMSO-d$_6$) δ 8.19 (s, 1H), 7.89 (s, 1H), 7.73 (s, 1H), 4.13 (q, J=7.2 Hz, 2H), 3.72 (s, 3H), 3.65-3.54 (m, 1H), 3.50-3.40 (m, 1H), 3.35-3.18 (m, 3H), 2.52 (s, 3H), 2.20-2.05 (m, 1H), 2.04-1.90 (m, 1H), 1.38-1.33 (m, 9H), 1.32 (t, J=7.3 Hz, 3H);[2] MS (EI) Calc'd for C$_{21}$H$_{31}$N$_8$O$_2$ [M+H]$^+$, 427. found 427.

[1] For the preparation of intermediate I; 6-chloro-8-(1-ethyl-5-methyl-1H-pyrazol-4-yl)-9-methyl-9H-purine, and related 6-chloropurines, see Preparation of heterocyclyl-substituted purine derivatives as inhibitors of PI3k-delta for the treatment of cancer. Patrick, Kearney. PCT Int. Appl. (2012); WO 2012/037226.

[2] Many of the compounds claimed exist as a mixture of rotamers in solution at room temperature, which complicates their analyses by $^1$H-NMR spectroscopy. In these cases, the peak shifts are listed as ranges of multiplets that encompass the signals from both rotamers, rather than describing individual rotamer peaks.

Example 1A: Preparation of Compound 1-13

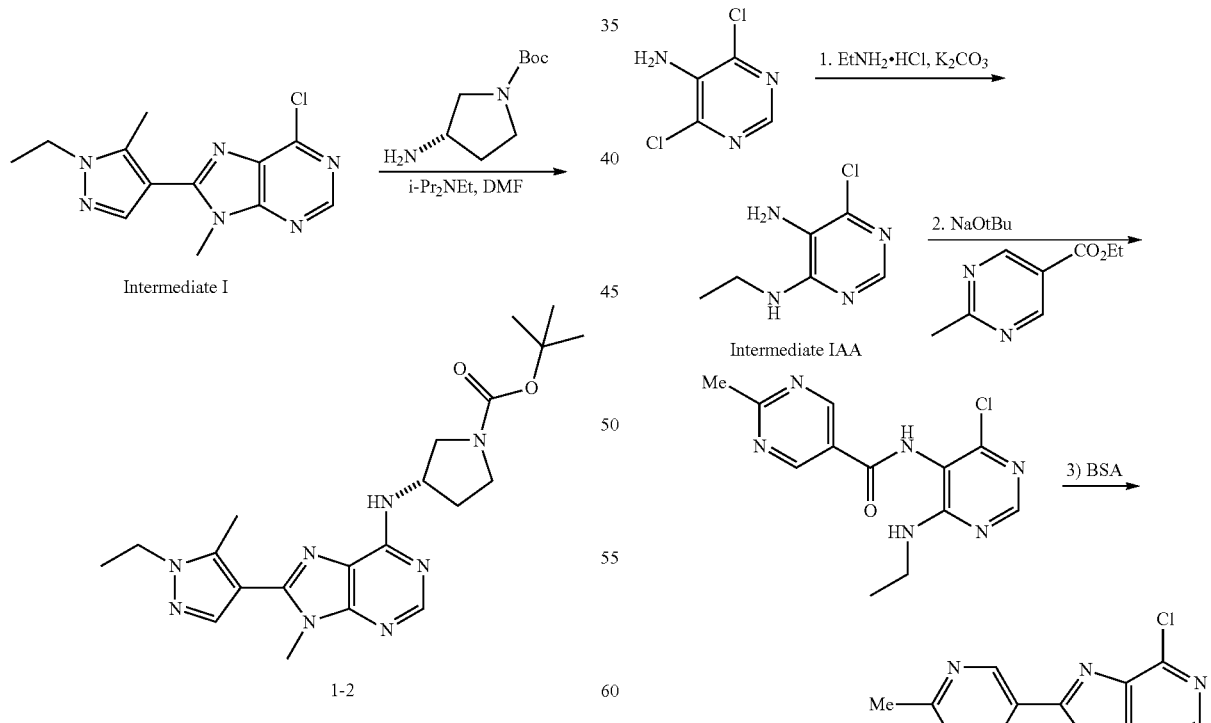

To a solution of Intermediate I[1] (6-chloro-8-(1-ethyl-5-methyl-1H-pyrazol-4-yl)-9-methyl-9H-purine; 500 mg, 1.8 mmol) in 18 mL of DMF were added i-Pr$_2$NEt (0.80 mL, 4.6 mmol) and (S)-tert-butyl 3-aminopyrrolidine-1-carboxylate (0.34 ml, 1.9 mmol). The mixture was stirred at room

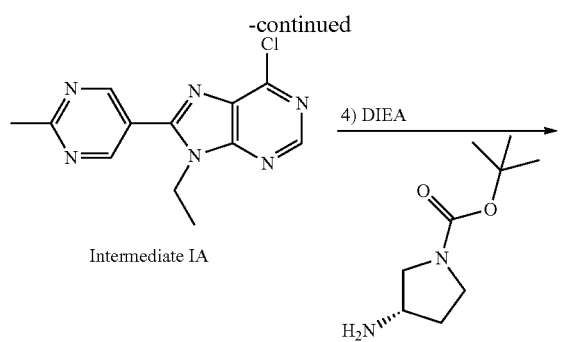

Intermediate IA 1-13

Step 1: Preparation of 6-chloro-N⁴-ethylpyrimidine-4,5-diamine (Intermediate IAA)

A mixture of 4,6-dichloropyrimidin-5-amine (20.0 g, 122 mmol), ethanamine hydrochloride (19.9 g, 243 mmol), and potassium carbonate (50.7 g, 367 mmol) in ethanol (100 mL) was heated to 50° C. for 39 h. The reaction mixture was then cooled to RT, after which it was diluted with DCM (750 mL) and filtered. The filter cake was washed with DCM (250 mL). The combined filtrate was concentrated to dryness to provide 6-chloro-N⁴-ethylpyrimidine-4,5-diamine (Intermediate 1AA). MS (ESI) calc'd for $C_6H_{10}ClN_4$ [M+H]$^+$: 173. found: 173.

Step 2: Preparation of N-(4-chloro-6-(ethylamino)pyrimidin-5-yl)-2-methylpyrimidine-5-carboxamide To a mixture of 6-chloro-N⁴-ethylpyrimidine-4,5-diamine (16 g, 91 mmol) and ethyl-2-methylpyrimidine-5-carboxylate (15 g, 90 mmol) in 50 mL of dimethyl ether at RT, a slurry of sodium tert-butoxide (9.1 g, 92 mmol) in dimethyl ether (25 mL) was added over the course of 1 min (reaction internal temperature rose to 43° C.). The reaction mixture was then stirred at RT for 2 h, after which it was quenched by the addition of water (75 mL) and EtOAc (75 mL). The reaction mixture was extracted with EtOAc (75 mL×2). The aqueous layer was then charged with acetic acid (5.3 ml, 92 mmol) and a slurry formed. The solid was collected by filtration, then washed with 75 mL of 1:1 DME:water, after which it was dried under vacuum at 35° C. for 16 h to provide N-(4-chloro-6-(ethylamino)pyrimidin-5-yl)-2-methylpyrimidine-5-carboxamide. MS (ESI) calc'd for $C_{12}H_{14}ClN_6O$ [M+H]$^+$: 293. found: 293.

Step 3: Preparation of 6-chloro-9-ethyl-8-(2-methyl-pyrimidin-5-yl)-9H-purine (Intermediate IA)

A vial was charged with BSA (22. mL, 91 mmol), after which N-(4-chloro-6-(ethylamino)pyrimidin-5-yl)-2-methylpyrimidine-5-carboxamide (5.0 g, 17 mmol) was added in portions. The reaction solution was then heated to 55° C. for 1 h, after which it was cooled down to RT. The formed solid was collected by filtration and washed with heptane (15 mL). The solid was then dried under vacuum at 50° C. for 16 h to provide 6-chloro-9-ethyl-8-(2-methylpyrimidin-5-yl)-9H-purine. MS (ESI) calc'd for $C_{12}H_{12}ClN_6$ [M+H]$^+$: 275. found: 275.

Step 4: Preparation of Compound 1-13

To a vial were added 6-chloro-9-ethyl-8-(2-methylpyrimidin-5-yl)-9H-purine (200 mg, 0.73 mmol), (S)-tert-butyl 3-aminopyrrolidine-1-carboxylate (300 mg, 1.4 mmol), DMF (5.2 ml) and DIEA (0.8 ml, 4.6 mmol). The resulting mixture was stirred at 60° C. for 48 h. The solvent was then evaporated in vacuo to afford a residue which was purified by chromatography on silica gel (0-10% MeOH in DCM) to afford (S)-tert-butyl 3-((9-ethyl-8-(2-methylpyrimidin-5-yl)-9H-purin-6-yl)amino)pyrrolidine-1-carboxylate (1-13). $^1$H NMR (600 MHz, DMSO-d$_6$) δ 9.08 (s, 2H), 8.18 (s, 1H), 4.75-4.60 (m, 1H), 4.26 (q, J=7.2 Hz, 2H), 3.62-3.50 (m, 1H), 3.50-3.38 (m, 1H), 3.35-3.20 (m, 3H), 2.70 (s, 3H), 2.20-2.04 (m, 1H), 2.04-1.92 (m, 1H), 1.40-1.30 (m, 9H), 1.27 (t, J=7.2 Hz, 3H); MS (EI) Calc'd for $C_{21}H_{29}N_8O_2$ [M+H]$^+$, 425. found 425.

Example 1A-2: Alternative Preparation of Compound 1-13

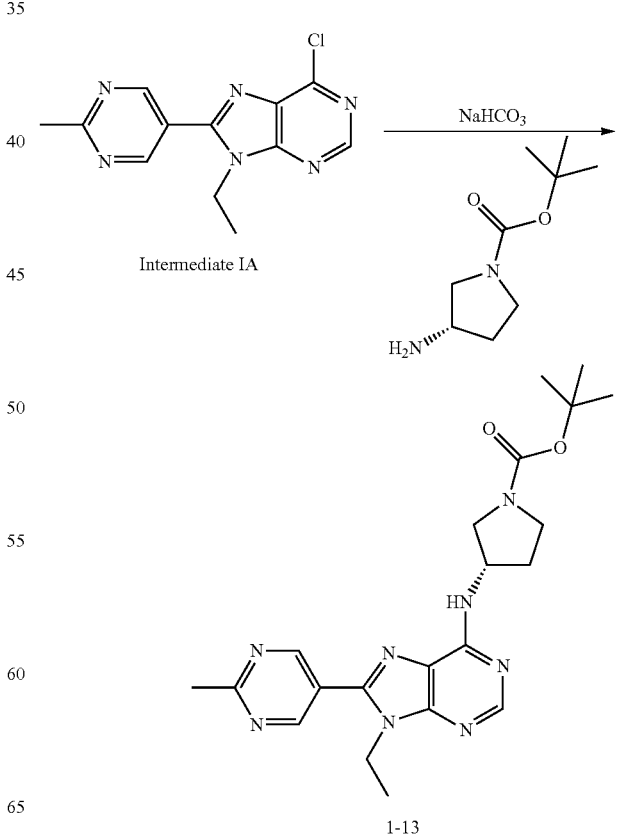

Intermediate IA 1-13

To a round bottom flask charged with Intermediate IA (250 mg, 0.91 mmol), (S)-tert-butyl 3-aminopyrrolidine-1-carboxylate (0.184 ml, 1.00 mmol), and sodium bicarbonate (268 mg, 3.19 mmol) was added 2-methyl-2-butanol (3 mL). The resulting suspension was heated to 80° C. overnight. The reaction mixture was then concentrated and the residue was purified by silica gel chromatography, eluting 0-50% ethyl acetate in hexanes to afford compound 1-13. MS (EI) Calc'd for $C_{21}H_{29}N_8O_2$ [M+H]$^+$, 425. found 425.

Example 1B: Preparation of Compound 1-15

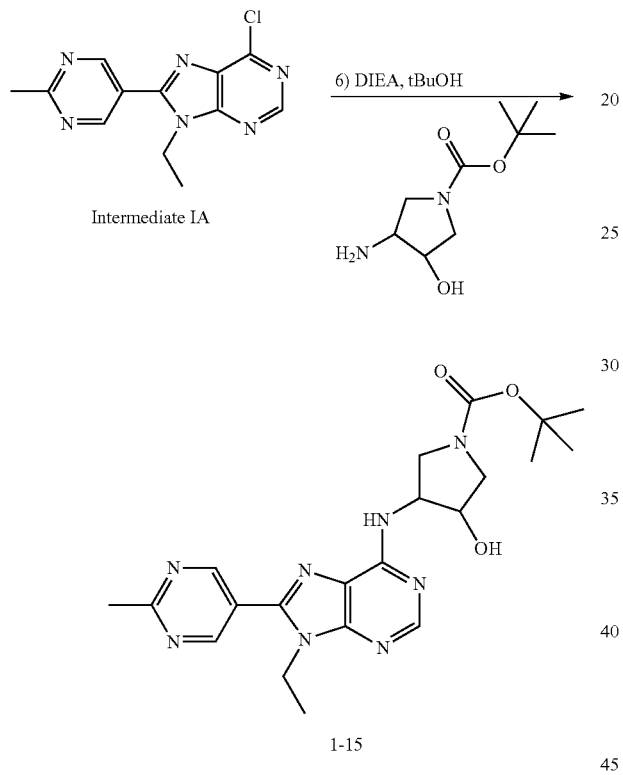

1-15

To a solution of tert-butyl (3R,4R and 3S,4S)-3-amino-4-hydroxypyrrolidine-1-carboxylate (commercially available from Advanced Chemblocks Inc.) in t-BuOH (5 mL) at RT was added DIEA (0.37 mL, 2 mmol) and Intermediate IA (130 mg, 0.5 mmol). The mixture was heated to 90° C. and stirred at this temperature for 15 h. The reaction was then cooled and the solvents were removed under reduced pressure. The residue thus obtained was purified with reverse-phase preparative HPLC (Column: Xbridge Prep C18 10 um OBD, 19×250 mm; Mobile phase: A: water (10 mM NH$_4$HCO$_3$), B: MeCN; Flow rate: 30 mL/min; UV detection: 214/254 nm) to afford ((3R,4R)- and (3 S,4S))-tert-butyl 3-{[9-ethyl-8-(2-methylpyrimidin-5-yl)-9H-purin-6-yl]amino}-4-hydroxypyrrolidine-1-carboxylate (1-15). $^1$H NMR (400 MHz, CDCl$_3$) δ 9.02 (s, 2H), 8.43 (s, 1H), 6.18-5.94 (m, 1H), 4.57-4.29 (m, 4H), 4.10-3.82 (m, 2H), 3.51-3.29 (m, 2H), 2.87 (s, 3H), 2.00-1.90 (m, 2H) 1.52-1.40 (m, 12H). MS (ESI) calc'd for ($C_{21}H_{29}N_8O_3$) [M+H]$^+$, 441. found, 441.

Example 1C: Preparation of Compound 1-21

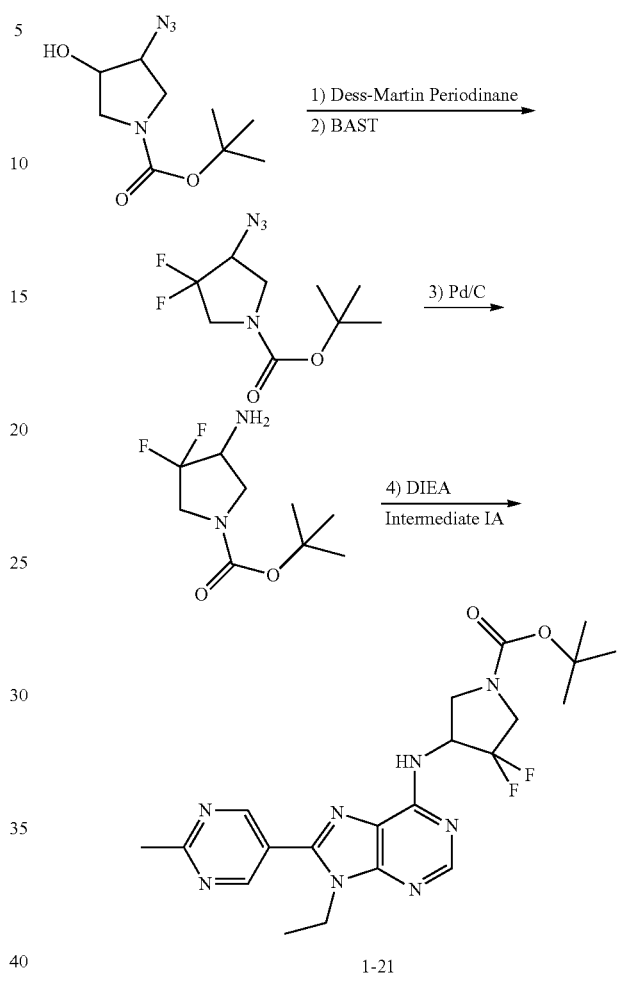

1-21

Step 1: Preparation of tert-butyl 3-azido-4-oxopyrrolidine-1-carboxylate

To a stirred solution of tert-butyl 3-azido-4-hydroxypyrrolidine-1-carboxylate (commercially available from VWR) (2.8 g, 12.3 mmol) in DCM (100 ml) was added a solution of Dess-Martin periodinane (10.4 g, 24.5 mmol) in DCM (10 mL) at 0° C. The resulting mixture was then allowed to warm to RT and stirred for 16 h. The reaction mixture was then cooled to 0° C. and treated with a 1:1 mixture of saturated aqueous sodium bicarbonate solution and saturated aqueous sodium thiosulfate solution (100 ml), after which it was stirred for 1 h. The organic layer was then separated, and the aqueous layer was extracted with DCM (2×30 mL). The combined organic layers were dried over magnesium sulfate, filtered, and the solvent was removed in vacuo to afford tert-butyl 3-azido-4-oxopyrrolidine-1-carboxylate. MS (ESI) calc'd for ($C_5H_7N_4O_3$) [M-tBu+2H]$^+$, 171. found, 171.

Step 2: Preparation of tert-butyl 4-azido-3,3-difluoropyrrolidine-1-carboxylate

To a stirred solution of tert-butyl 3-azido-4-oxopyrrolidine-1-carboxylate (2.3 g, 10 mmol) in DCM (50 ml) was added BAST (4.5 ml, 25 mmol) at 0° C. The resulting mixture was warmed to RT and stirred for 36 h. The mixture was then washed with saturated NaHCO$_3$, brine, then dried over sodium sulfate. The organics were then filtered and the solution was concentrated in vacuo to give the crude product which was purified by column chromatography on silica gel (PE:EtOAc=20:1) to afford tert-butyl 4-azido-3, 3-difluoro-pyrrolidine-1-carboxylate. MS (ESI) calc'd for (C$_5$H$_7$F$_2$N$_4$O$_2$) [M-tBu+2H]$^+$, 193. found, 193.

Step 3: Preparation of tert-butyl 4-amino-3, 3-difluoropyrrolidine-1-carboxylate To a stirred solution of tert-butyl 4-azido-3, 3-difluoro-pyrrolidine-1-carboxylate (1.4 g, 5.6 mmol) in MeOH (10 mL) was added Pd/C (10% by weight) (0.2 g, 10% by weight, 0.188 mmol) at RT. The mixture was degassed with nitrogen, and subsequently the mixture was stirred under a H$_2$ balloon at RT for 15 h. The mixture was filtered through a pad of Celite and the filtrate was concentrated in vacuo to provide tert-butyl 4-amino-3, 3-difluoropyrrolidine-1-carboxylate. MS (ESI) calc'd for (C$_5$H$_9$F$_2$N$_2$O$_2$) [M-tBu+2H]$^+$, 167. found, 167.

Step 4: Preparation of tert-butyl 4-(9-ethyl-8-(2-methylpyrimidin-5-yl)-9H-purin-6-ylamino)-3,3-difluoropyrrolidine-1-carboxylate (1-21)

To a solution of tert-butyl 4-amino-3, 3-difluoropyrrolidine-1-carboxylate (880 mg, 4 mmol) in t-BuOH (5 mL) was added DIEA (0.7 mL, 4 mmol) and Intermediate IA (400 mg, 1.5 mmol) at RT. The mixture was heated to 90° C. and stirred at this temperature for 5 days. The solution was then cooled and the solvents were removed under reduced pressure. The residue obtained was purified by reverse-phase preparative HPLC (Column: Xbridge Prep C18 10 um OBD, 19×250 mm; Mobile phase: A: water (10 mM NH$_4$HCO$_3$), B: MeCN; Flow rate: 30 mL/min; UV detection: 214/254 nm) to afford tert-butyl 4-(9-ethyl-8-(2-methylpyrimidin-5-yl)-9H-purin-6-ylamino)-3,3-difluoropyrrolidine-1-carboxylate (1-21). $^1$H NMR (400 MHz, CD$_3$OD) δ 9.22-9.10 (m, 2H), 8.39 (s, 1H), 5.52-5.43 (m, 1H), 4.41 (q, J=7.2 Hz, 2H), 4.10-3.73 (m, 3H), 3.52-3.39 (m, 1H), 2.83 (s, 3H), 1.49 (s, 9H), 1.46 (t, J=7.2 Hz, 3H). MS (ESI) calc'd for (C$_{21}$H$_{27}$F$_2$N$_8$O$_2$) [M+H]$^+$, 461. found, 461.

Example 1D: Preparation of Compound 1-22

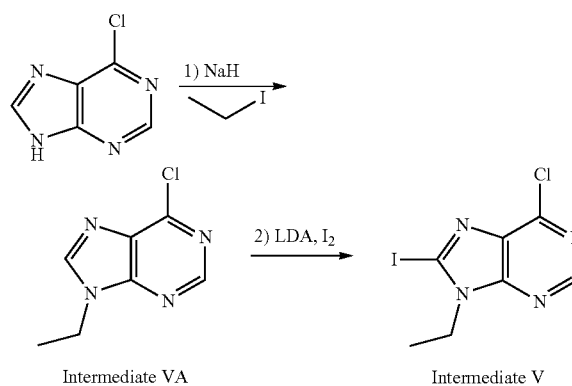

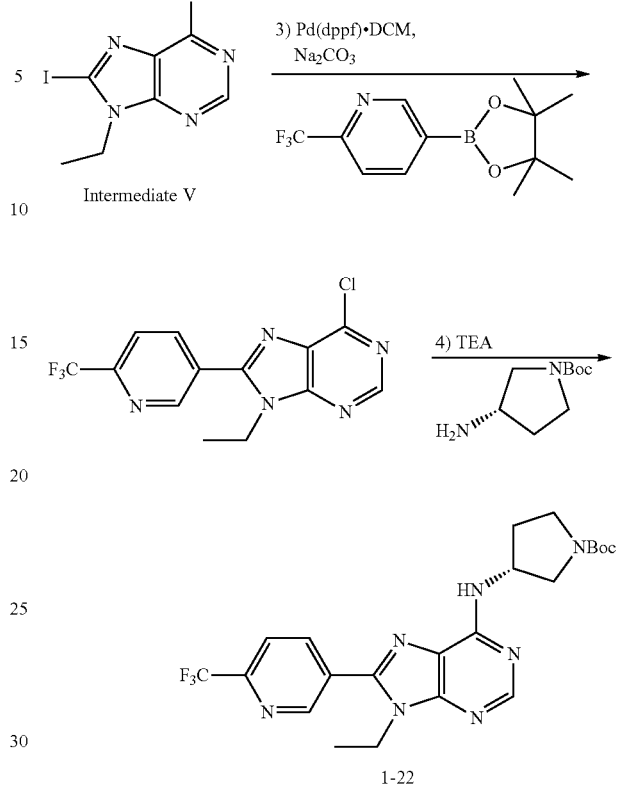

Step 1: Preparation of 6-chloro-9-ethyl-9H-purine (Intermediate VA)

To a solution of 6-chloro-9H-purine (31 g, 0.20 mol) dissolved in DMF (200 mL) was added NaH (60% w/t in mineral oil, 8.8 g, 0.22 mol) at 0° C. under nitrogen in portions. The mixture was warmed up to room temperature and stirred for 1 hour, after which it was cooled to 0° C. and CH$_3$CH$_2$I (34 g, 0.22 mol) was added slowly. Then the mixture was stirred at room temperature for 2 hours. The reaction was quenched with saturated aqueous ammonium chloride and was extracted with EtOAc. The organic layer was washed with brine, dried over sodium sulfate, filtered, and concentrated in vacuo. The crude product was then purified by column chromatography on silica gel (eluting PE:EtOAc=3:1) to give 6-chloro-9-ethyl-9H-purine.

Step 2: Preparation of 6-chloro-9-ethyl-8-iodo-9H-purine (Intermediate V)

To a stirred solution of 6-chloro-9-ethyl-9H-purine (Intermediate VA) (10.0 g, 54.9 mmol) in THF (150 mL) cooled to −78° C., LDA (82 mL, 82 mmol) was added slowly under nitrogen. The reaction was stirred at −78° C. for 1.5 hours, after which I$_2$ (21.0 g, 82.4 mol) in THF (100 mL) was added. The reaction was further stirred for 2 hours, after which it was quenched with saturated ammonium chloride. The mixture was then extracted with EtOAc and the organic layer was washed with brine, dried over sodium sulfate, filtered, and concentrated in vacuo to obtain 6-chloro-9-ethyl-8-iodo-9H-purine (Intermediate V).

Step 3: Preparation of 6-chloro-9-ethyl-8-(6-(trifluoromethyl)pyridin-3-yl)-9H-purine A vial was charged with 4-chloro-1-ethyl-2-iodo-1H-imidazo[4,5-c]pyridine (85 mg, 0.28 mmol), 5-(4,4,5,5-tetramethyl-1,3,2-dioxaborolan-2-yl)-2-(trifluoromethyl)pyridine (75 mg, 0.28 mmol), and [1,1'-bis(diphenylphosphino)ferrocene]dichloropalladium (II) dichloromethane adduct (20.2 mg, 0.028 mmol). The flask was degassed by evacuating under vacuum and backfilling with argon (3 times). Dioxane (2.76 mL) was then added, followed by aqueous sodium carbonate (276 µl, 2M solution, 0.553 mmol) and the mixture was degassed again. The reaction mixture was heated to 85° C. for 16 h. The reaction mixture was then cooled and filtered through a Celite plug, after which the filtrate was evaporated to dryness. The residue thus obtained was used in the next step without further purification. MS (EI) Calc'd for $C_{13}H_{10}ClF_3N_5[M+H]^+$, 328. found 328.

Step 4: Preparation of Compound 1-22

To a vial was added (S)-tert-butyl 3-aminopyrrolidine-1-carboxylate (114 mg, 0.610 mmol), 6-chloro-9-ethyl-8-(6-(trifluoromethyl)pyridin-3-yl)-9H-purine (100 mg, 0.31 mmol), DIEA (0.266 mL, 1.53 mmol) and DMF (2 mL). The mixture was heated at 90° C. for 16 hours. The reaction mixture was then cooled to room temperature, filtered, and purified by reverse-phase preparative HPLC (0:100 to 95:5 acetonitrile:water: 0.1% v/v TFA modifier) to afford the title compound (1-22) as the TFA salt. $^1$H NMR (600 MHz, DMSO-d$_6$) δ 9.17-9.15 (m, 1H), 8.52-8.45 (m, 1H), 8.43-8.22 (m, 2H), 8.13-8.08 (m, 1H), 4.74-4.60 (m, 1H), 4.32-4.26 (m, 2H), 3.66-3.52 (m, 1H), 3.51-3.39 (m, 1H), 3.34-3.18 (m, 2H), 2.22-2.06 (m, 1H), 2.05-1.94 (m, 1H), 1.40-1.32 (m, 9H), 1.31-1.25 (m, 3H). MS (EI) Calc'd for $C_{22}H_{27}F_3N_7O_2[M+H]^+$, 478. found 478.

Compounds 1-1 through 1-12 and 1-14 were prepared in an analogous fashion to Example 1 from the corresponding amine.

Compound 1-16 was prepared in an analogous fashion to Example 1B from the corresponding amine.

Compounds 1-17, 1-19, and 1-20 were prepared in an analogous fashion to Example 1A from the corresponding amine except that the reactions were stirred at 80° C.

Compound 1-18 was prepared from compound 1-17 using lithium hydroxide under standard ester hydrolysis conditions.

Compounds 1-23 and 1-24 were prepared in an analogous fashion to Example 1D from the corresponding boronic esters.

TABLE 1

| Compound | Structure | Compound Name | MS [M + H]$^+$ |
|---|---|---|---|
| 1-1 | 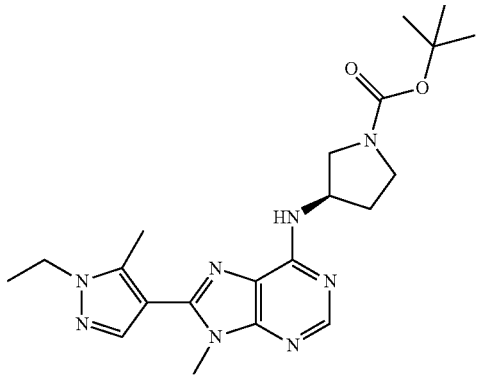 [SMILES: CCn1ncc(-c2nc3c(N[C@@H]4CCN(C(=O)OC(C)(C)C)C4)ncnc3n2C)c1C] | tert-butyl (3R)-3-{[8-(1-ethyl-5-methyl-1H-pyrazol-4-yl)-9-methyl-9H-purin-6-yl]amino}pyrrolidine-1-carboxylate | Calc'd 427, found 427 |
| 1-2 | 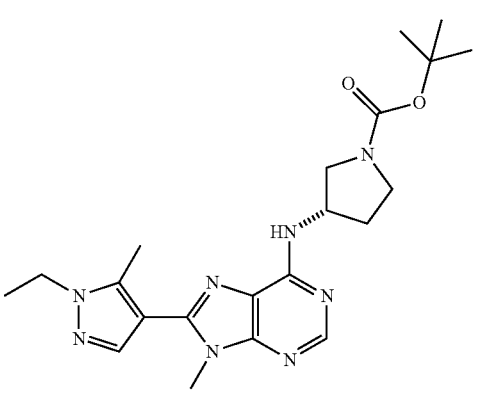 | tert-butyl (3S)-3-{[8-(1-ethyl-5-methyl-1H-pyrazol-4-yl)-9-methyl-9H-purin-6-yl]amino}pyrrolidine-1-carboxylate | Calc'd 427, found 427 |

TABLE 1-continued

| Compound | Structure | Compound Name | MS [M + H]+ |
|---|---|---|---|
| 1-3 | 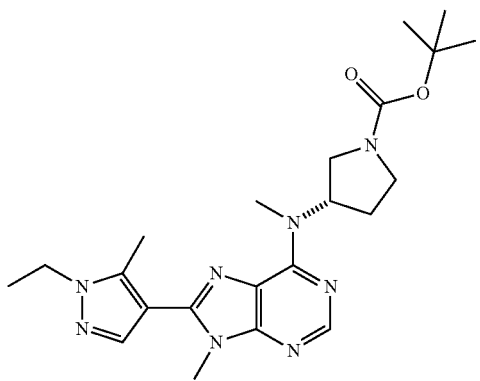 | (S)-tert-butyl 3-((8-(1-ethyl-5-methyl-1H-pyrazol-4-yl)-9-methyl-9H-purin-6-yl)(methyl)amino)pyrrolidine-1-carboxylate | Calc'd 441, found 441 |
| 1-4 | 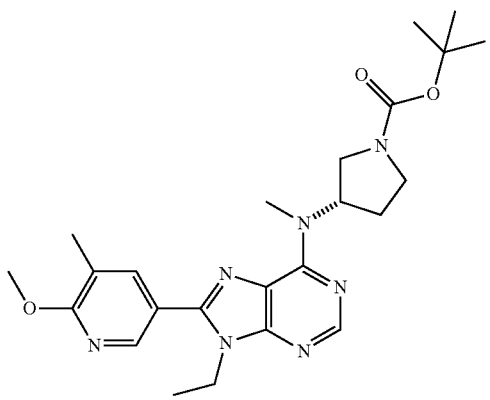 | (S)-tert-butyl 3-((9-ethyl-8-(6-methoxy-5-methylpyridin-3-yl)-9H-purin-6-yl)(methyl)amino)pyrrolidine-1-carboxylate | Calc'd 468, found 468 |
| 1-5 | 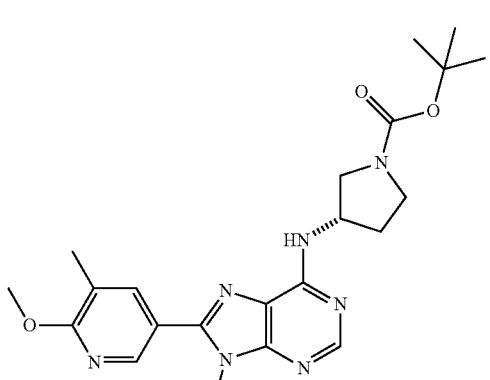 | (S)-tert-butyl 3-((9-ethyl-8-(6-methoxy-5-methylpyridin-3-yl)-9H-purin-6-yl)amino)pyrrolidine-1-carboxylate | Calc'd 454, found 454 |
| 1-6 | 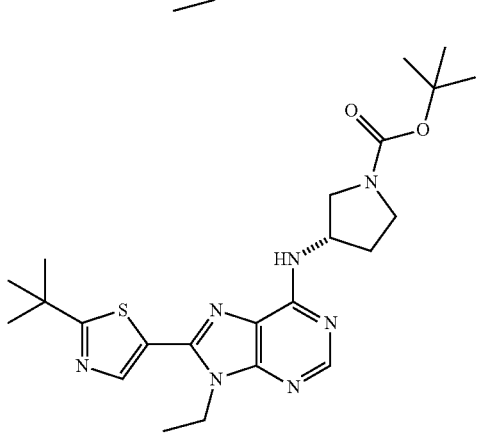 | (S)-tert-butyl 3-((8-(2-(tert-butyl)thiazol-5-yl)-9-ethyl-9H-purin-6-yl)amino)pyrrolidine-1-carboxylate | Calc'd 472, found 472 |

TABLE 1-continued

| Compound | Structure | Compound Name | MS [M + H]+ |
|---|---|---|---|
| 1-7 | 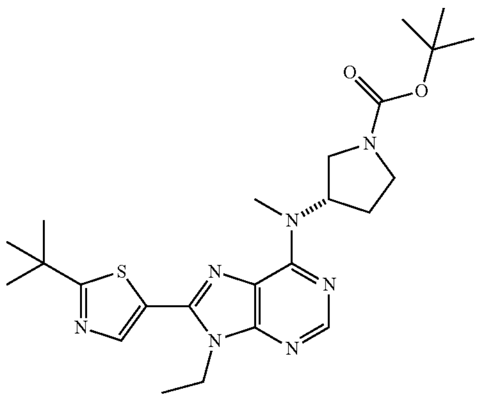 | (S)-tert-butyl 3-((8-(2-(tert-butyl)thiazol-5-yl)-9-ethyl-9H-purin-6-yl)(methyl)amino)pyrrolidine-1-carboxylate | Calc'd 486, found 486 |
| 1-8 | 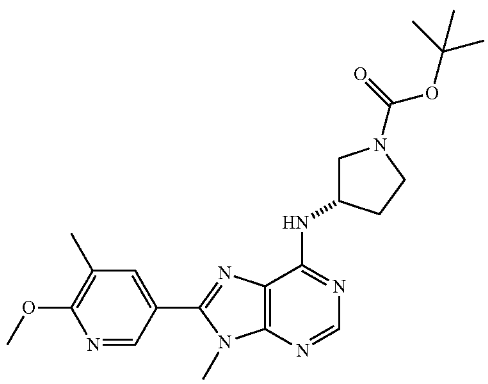 | (S)-tert-butyl 3-((8-(6-methoxy-5-methylpyridin-3-yl)-9-methyl-9H-purin-6-yl)amino)pyrrolidine-1-carboxylate | Calc'd 440, found 440 |
| 1-9 | 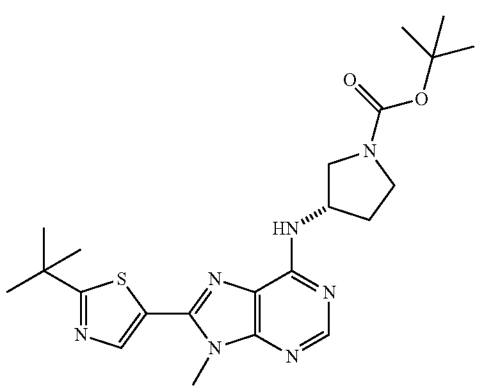 | (S)-tert-butyl 3-((8-(2-(tert-butyl)thiazol-5-yl)-9-methyl-9H-purin-6-yl)amino)pyrrolidine-1-carboxylate | Calc'd 458, found 458 |
| 1-10 | 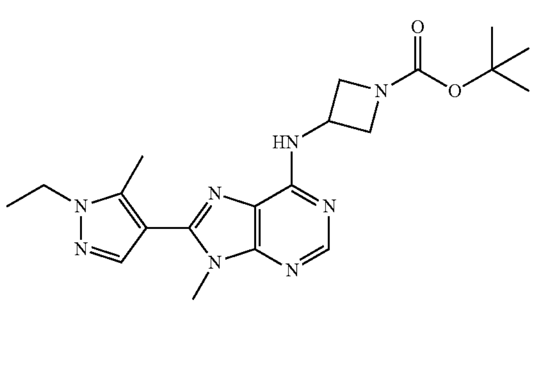 [SMILES: CCn1ncc(-c2nc3c(NC4CN(C(=O)OC(C)(C)C)C4)ncnc3n2C)c1C] | tert-butyl 3-((8-(1-ethyl-5-methyl-1H-pyrazol-4-yl)-9-methyl-9H-purin-6-yl)amino)azetidine-1-carboxylate | Calc'd 413, found 413 |

TABLE 1-continued

| Compound | Structure | Compound Name | MS [M + H]+ |
|---|---|---|---|
| 1-11 | 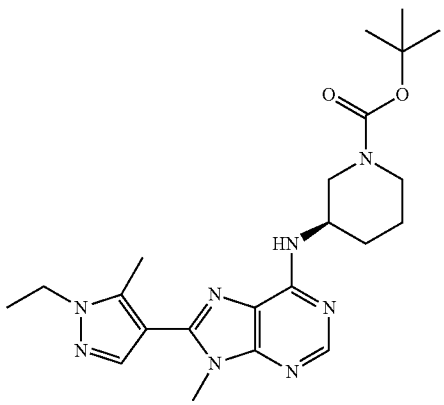 [SMILES: CCn1ncc(-c2nc3c(N[C@@H]4CCCN(C(=O)OC(C)(C)C)C4)ncnc3n2C)c1C] | (R)-tert-butyl 3-((8-(1-ethyl-5-methyl-1H-pyrazol-4-yl)-9-methyl-9H-purin-6-yl)amino)piperidine-1-carboxylate | Calc'd 441, found 441 |
| 1-12 | 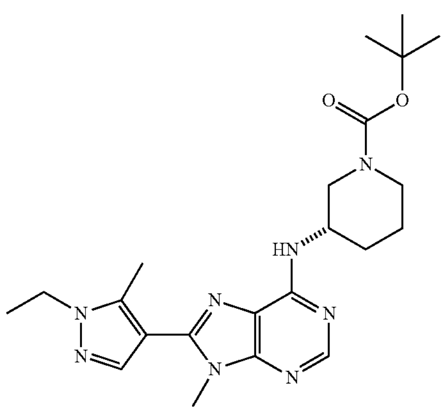 | (S)-tert-butyl 3-((8-(1-ethyl-5-methyl-1H-pyrazol-4-yl)-9-methyl-9H-purin-6-yl)amino)piperidine-1-carboxylate | Calc'd 441, found 441 |
| 1-13 | 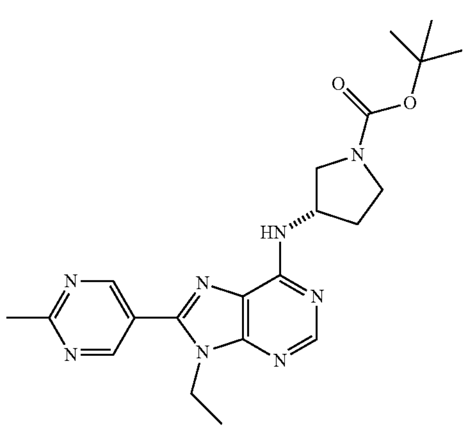 | (S)-tert-butyl 3-((9-ethyl-8-(2-methylpyrimidin-5-yl)-9H-purin-6-yl)amino)pyrrolidine-1-carboxylate | Calc'd 425, found 425 |

TABLE 1-continued

| Compound | Structure | Compound Name | MS [M + H]+ |
|---|---|---|---|
| 1-14 | 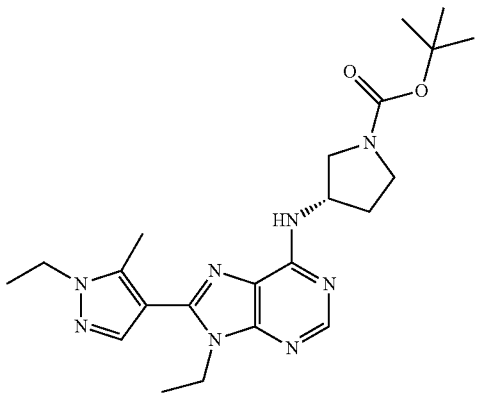 [SMILES: CCn1ncc(-c2nc3c(N[C@H]4CCN(C(=O)OC(C)(C)C)C4)ncnc3n2CC)c1C] | tert-butyl (3S)-3-{[9-ethyl-8-(1-ethyl-5-methyl-1H-pyrazol-4-yl)-9H-purin-6-yl]amino}pyrrolidine-1-carboxylate | Calc'd 441, found 441 |
| 1-15 | 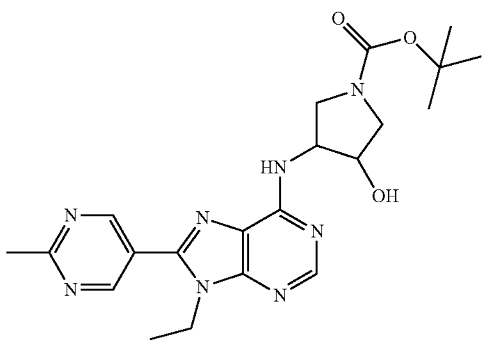 [SMILES: CCn1c(-c2cnc(C)nc2)nc2c(NC3CN(C(=O)OC(C)(C)C)CC3O)ncnc21] | ((3R,4R) and (3S,4S))-tert-butyl 3-{[9-ethyl-8-(2-methylpyrimidin-5-yl)-9H-purin-6-yl]amino}-4-hydroxypyrrolidine-1-carboxylate | Calc'd 441, found 441 |
| 1-16 | 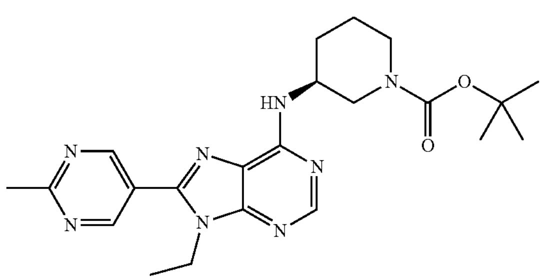 [SMILES: CCn1c(-c2cnc(C)nc2)nc2c(N[C@H]3CCCN(C(=O)OC(C)(C)C)C3)ncnc21] | tert-butyl (3S)-3-{[9-ethyl-8-(2-methylpyrimidin-5-yl)-9H-purin-6-yl]amino}piperidine-1-carboxylate | Calc'd 439, found 439 |
| 1-17 | 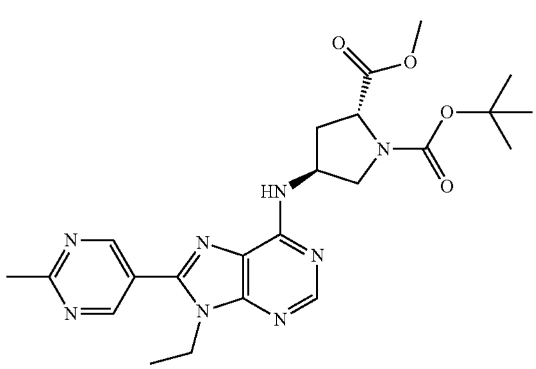 [SMILES: CCn1c(-c2cnc(C)nc2)nc2c(N[C@H]3C[C@H](C(=O)OC)N(C(=O)OC(C)(C)C)C3)ncnc21] | 1-tert-butyl 2-methyl (2R,4S)-4-{[9-ethyl-8-(2-methylpyrimidin-5-yl)-9H-purin-6-yl]amino}pyrrolidine-1,2-dicarboxylate | Calc'd 483, found 483 |

TABLE 1-continued

| Compound | Structure | Compound Name | MS [M + H]+ |
|---|---|---|---|
| 1-18 | 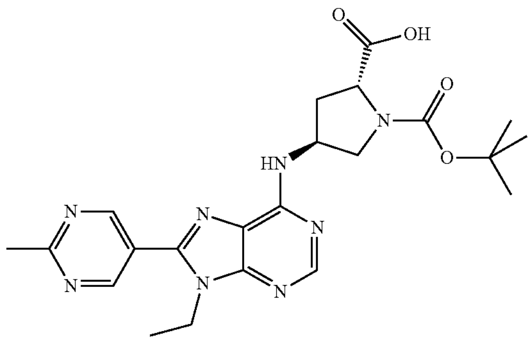 [SMILES: CCn1c(-c2cnc(C)nc2)nc2c(N[C@H]3C[C@H](C(=O)O)N(C(=O)OC(C)(C)C)C3)ncnc21] | (4S)-1-(tert-butoxycarbonyl)-4-{[9-ethyl-8-(2-methylpyrimidin-5-yl)-9H-purin-6-yl]amino}-D-proline | Calc'd 469, found 469 |
| 1-19 | 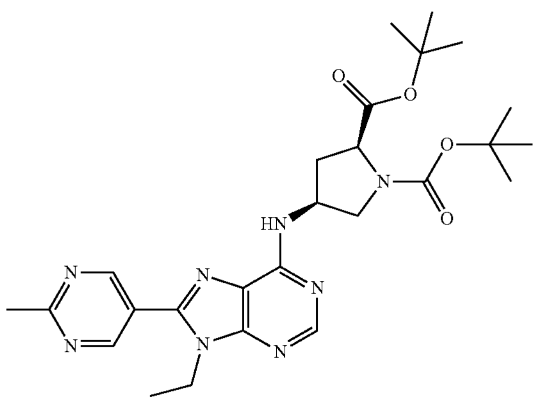 [SMILES: CCn1c(-c2cnc(C)nc2)nc2c(N[C@H]3C[C@@H](C(=O)OC(C)(C)C)N(C(=O)OC(C)(C)C)C3)ncnc21] | 1-tert-butyl 2-methyl (2S,4S)-4-{[9-ethyl-8-(2-methylpyrimidin-5-yl)-9H-purin-6-yl]amino}pyrrolidine-1,2-dicarboxylate | Calc'd 483, found 483 |
| 1-20 | 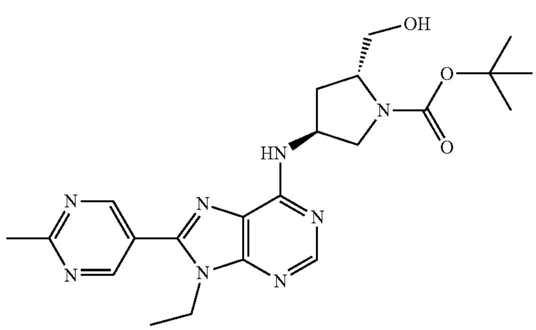 [SMILES: CCn1c(-c2cnc(C)nc2)nc2c(N[C@H]3C[C@H](CO)N(C(=O)OC(C)(C)C)C3)ncnc21] | tert-butyl (2R,4S)-4-{[9-ethyl-8-(2-methylpyrimidin-5-yl)-9H-purin-6-yl]amino}-2-(hydroxymethyl)pyrrolidine-1-carboxylate | Calc'd 455, found 455 |
| 1-21 | 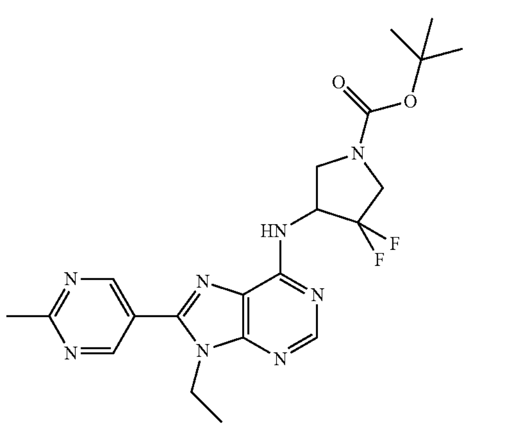 [SMILES: CCn1c(-c2cnc(C)nc2)nc2c(NC3CN(C(=O)OC(C)(C)C)CC3(F)F)ncnc21] | (R and S)-tert-butyl 4-{[9-ethyl-8-(2-methylpyrimidin-5-yl)-9H-purin-6-yl]amino}-3,3-difluoropyrrolidine-1-carboxylate | Calc'd 461, found 461 |

TABLE 1-continued

| Compound | Structure | Compound Name | MS [M + H]+ |
|---|---|---|---|
| 1-22 | 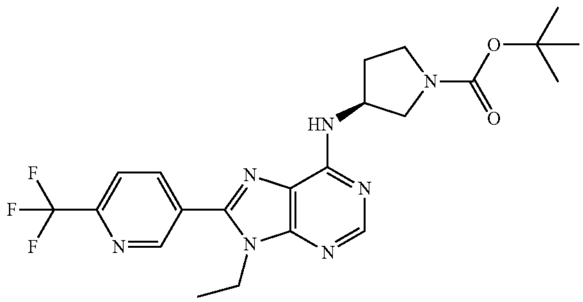 [SMILES: CCn1c(-c2ccc(C(F)(F)F)nc2)nc2c(N[C@H]3CCN(C(=O)OC(C)(C)C)C3)ncnc21] | tert-butyl (3S)-3-({9-ethyl-8-[6-(trifluoromethyl)pyridin-3-yl]-9H-purin-6-yl}amino)pyrrolidine-1-carboxylate | Calc'd 478, found 478 |
| 1-23 | 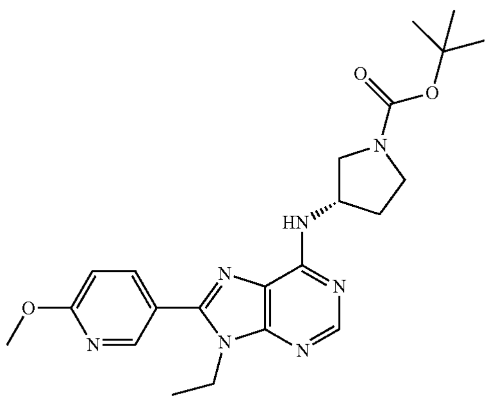 [SMILES: CCn1c(-c2ccc(OC)nc2)nc2c(N[C@H]3CCN(C(=O)OC(C)(C)C)C3)ncnc21] | tert-butyl (3S)-3-{[9-ethyl-8-(6-methoxypyridin-3-yl)-9H-purin-6-yl]amino}pyrrolidine-1-carboxylate | Calc'd 440, found 440 |
| 1-24 | 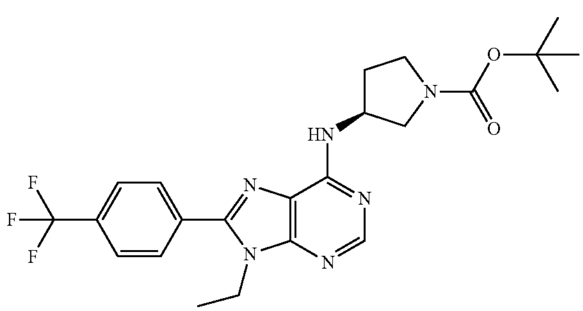 | tert-butyl (3S)-3-({9-ethyl-8-[4-(trifluoromethyl)phenyl]-9H-purin-6-yl}amino)pyrrolidine-1-carboxylate | Calc'd 477, found 477 |

Compound Examples of Table 2

Example 2: Preparation of Compound 2-3

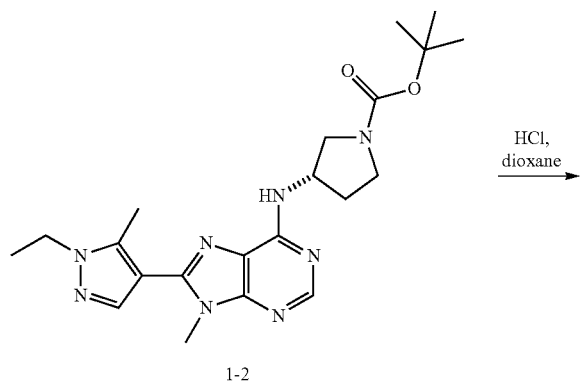

Step 2: Preparation of 2-3; (S)-1-(3-((8-(1-ethyl-5-methyl-1H-pyrazol-4-yl)-9-methyl-9H-purin-6-yl)amino)pyrrolidin-1-yl)propan-1-one To a glass reaction vial were added (S)-8-(1-ethyl-5-methyl-1H-pyrazol-4-yl)-9-methyl-N-(pyrrolidin-3-yl)-9H-purin-6-amine, 2HCl (20 mg, 0.05 mmol), DMF (0.5 mL), propionyl chloride (5 μl, 0.06 mmol) and triethylamine (0.050 ml, 0.36 mmol). The mixture was stirred at room temperature for 16 hours, filtered through a 0.45 μm Whatman filter and purified by reverse phase chromatography (acetonitrile/water with 0.1% TFA) to afford the TFA salt of 2-3 (S)-1-(3-((8-(1-ethyl-5-methyl-1H-pyrazol-4-yl)-9-methyl-9H-purin-6-yl)amino)pyrrolidin-1-yl)propan-1-one. $^1$H NMR (600 MHz, DMSO-d$_6$) δ 8.32 (s, 1H), 7.93 (s, 1H), 4.14 (q, J=7.2 Hz, 2H), 3.81-3.72 (m, 3H), 3.70-3.64 (m, 1H), 3.64-3.56 (m, 1H), 3.54-3.44 (m, 2H), 3.42-3.30 (m, 1H), 2.52 (s, 3H), 2.30-1.95 (m, 4H), 1.32 (t, J=7.2 Hz, 3H), 0.98-0.91 (m, 3H); MS (EI) Calc'd for $C_{19}H_{27}N_8O$ [M+H]$^+$, 383. found 383.

Example 3: Preparation of Compound 2-7

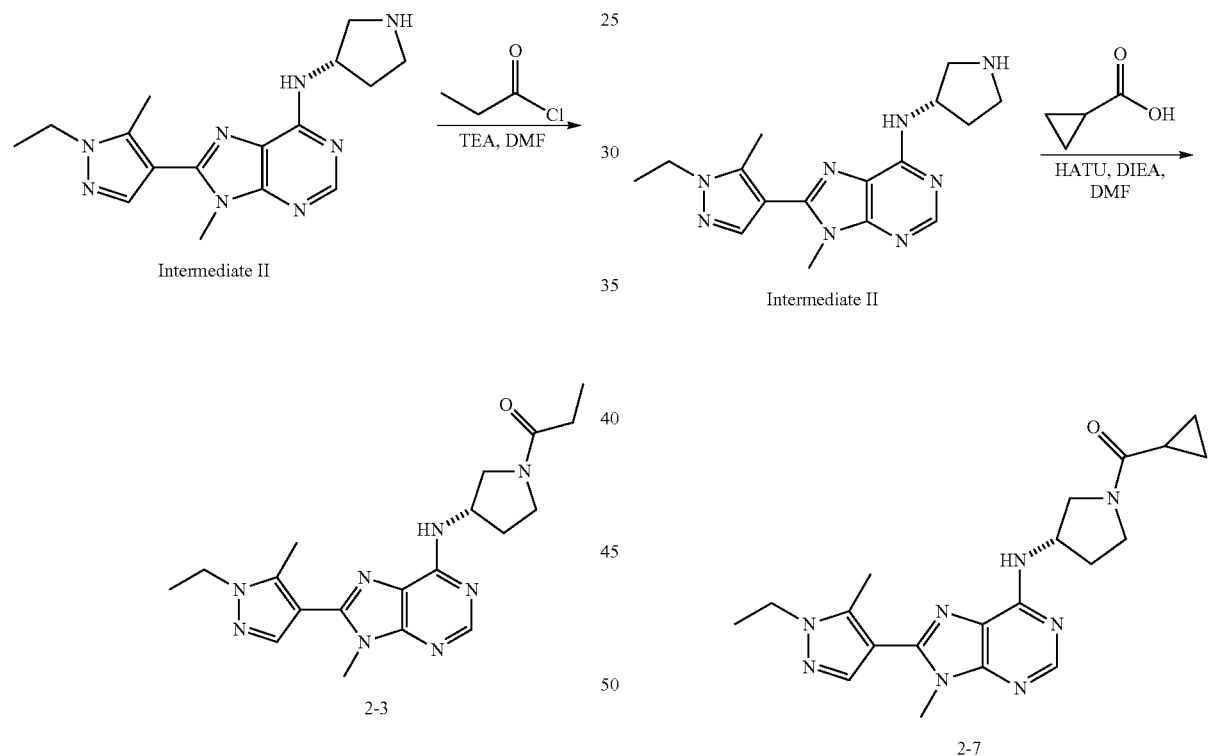

Step 1: Preparation of Intermediate II; (S)-8-(1-ethyl-5-methyl-1H-pyrazol-4-yl)-9-methyl-N-(pyrrolidin-3-yl)-9H-purin-6-amine To a solution of (S)-tert-butyl 3-((8-(1-ethyl-5-methyl-1H-pyrazol-4-yl)-9-methyl-9H-purin-6-yl)amino)pyrrolidine-1-carboxylate 1-2 (345 mg, 0.809 mmol) in 2 mL of dioxane was added a 4 M solution of HCl in dioxane (1.0 mL, 4.0 mmol). The mixture was stirred at room temperature for 2 days and concentrated to dryness to afford (S)-8-(1-ethyl-5-methyl-1H-pyrazol-4-yl)-9-methyl-N-(pyrrolidin-3-yl)-9H-purin-6-amine, 2HCl. MS (EI) Calc'd for $C_{16}H_{23}N_8$ [M+H]$^+$, 327. found 327.

To a reaction vial were added (S)-8-(1-ethyl-5-methyl-1H-pyrazol-4-yl)-9-methyl-N-(pyrrolidin-3-yl)-9H-purin-6-amine, 2HCl (Intermediate II) (16 mg, 0.040 mmol), cyclopropanecarboxylic acid (12 mg, 0.139 mmol), HATU (18 mg, 0.047 mmol), DMF (0.3 mL) and DIEA (0.05 mL, 0.286 mmol). The mixture was stirred at room temperature for 4 hours, filtered and purified by reverse phase chromatography (acetonitrile/water with 0.1% TFA) to afford the TFA salt of 2-7. $^1$H NMR (600 MHz, DMSO-d$_6$) δ 8.33 (s, 1H), 7.94 (broad s, 1H), 4.15 (q, J=7.2 Hz, 2H), 4.10-3.25 (m, 7H), 2.53 (s, 3H), 2.50-1.60 (m, 4H), 1.32 (t, J=7.2 Hz, 3H), 0.80-0.60 (m, 4H). MS (EI) Calc'd for $C_{20}H_{27}N_8O$ [M+H]$^+$, 395. found 395.

Example 3B: Preparation of Compound 2-36

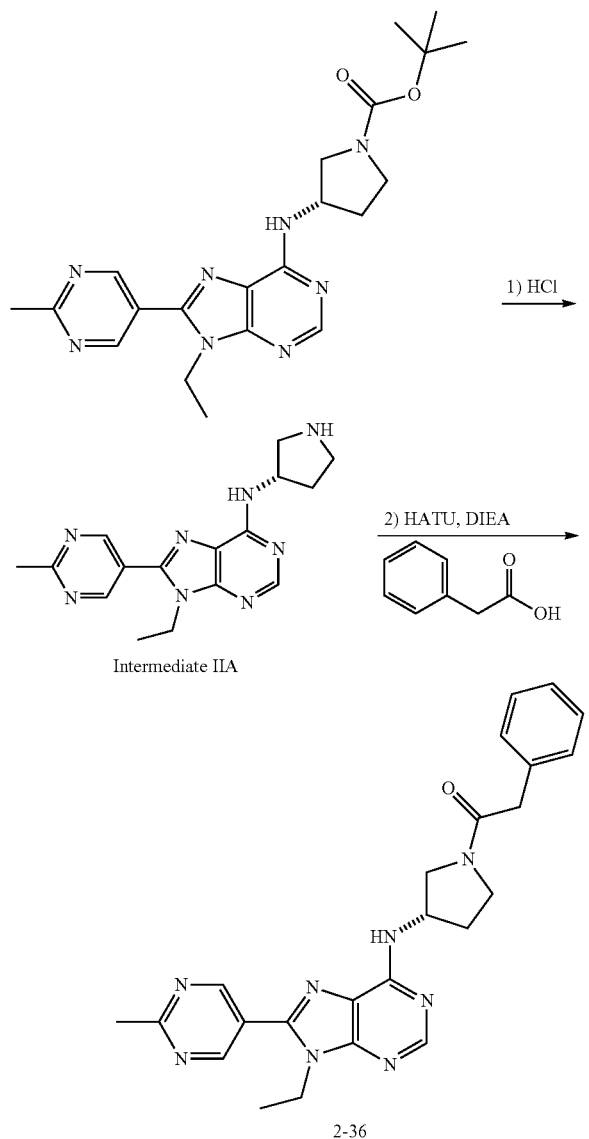

Step 1: Preparation of Intermediate IIA; (S)-9-ethyl-8-(2-methylpyrimidin-5-yl)-N-(pyrrolidin-3-yl)-9H-purin-6-amine, 2HCl A round-bottom flask was charged with (S)-tert-butyl 3-((9-ethyl-8-(2-methylpyrimidin-5-yl)-9H-purin-6-yl) amino)pyrrolidine-1-carboxylate (1-13) (0.730 g, 1.72 mmol), and dioxane (8.60 ml). To this solution was added HCl (4M in dioxane, 4.30 ml, 17.2 mmol). The reaction become a slurry, which was stirred vigorously for 16 h. The solvent was then removed in vacuo to afford Intermediate IIA as the HCl salt. Calc'd for $C_{16}H_{21}N_8$ [M+H]$^+$, 325. found 325.

Step 2: Preparation of 2-36

To a vial at RT were added (S)-9-ethyl-8-(2-methylpyrimidin-5-yl)-N-(pyrrolidin-3-yl)-9H-purin-6-amine, 2HCl (Intermediate IIA) (30 mg, 0.076 mmol) and 2-phenylacetic acid (10.28 mg, 0.076 mmol) followed by DMF (700 μl) and DIEA (92 μl, 0.53 mmol). HATU (31.6 mg, 0.083 mmol) was then added and the mixture was stirred at RT for 16 h. The reaction mixture was then diluted with 1.2 ml of DMSO and purified via reverse phase preparative HPLC (0:100 to 95:5 acetonitrile:water: 0.1% v/v TFA modifier). The TFA salt thus obtained was dissolved in MeOH and eluted through a 1 g SiliaPrep™ silicon-carbonate cartridge, after which it was lyophilized from a mixture of MeOH and water to afford 9-ethyl-8-(2-methylpyrimidin-5-yl)-N-[(3S)-1-(phenylacetyl)pyrrolidin-3-yl]-9H-purin-6-amine (2-36). $^1$H NMR (500 MHz, DMSO-d$_6$) δ 9.14-9.08 (m, 2H), 8.37-8.18 (m, 2H), 7.33-7.11 (m, 5H), 4.87-4.61 (m, 1H), 4.33-4.23 (m, 2H), 3.89-3.48 (m, 5H), 3.40-3.32 (m, 1H), 2.75-2.70 (m, 3H), 2.30-1.94 (m, 2H), 1.35-1.24 (m, 3H). Calc'd for $C_{24}H_{27}N_8O$ [M+H]$^+$, 443. found 443.

Example 3C: Preparation of Compound 2-76

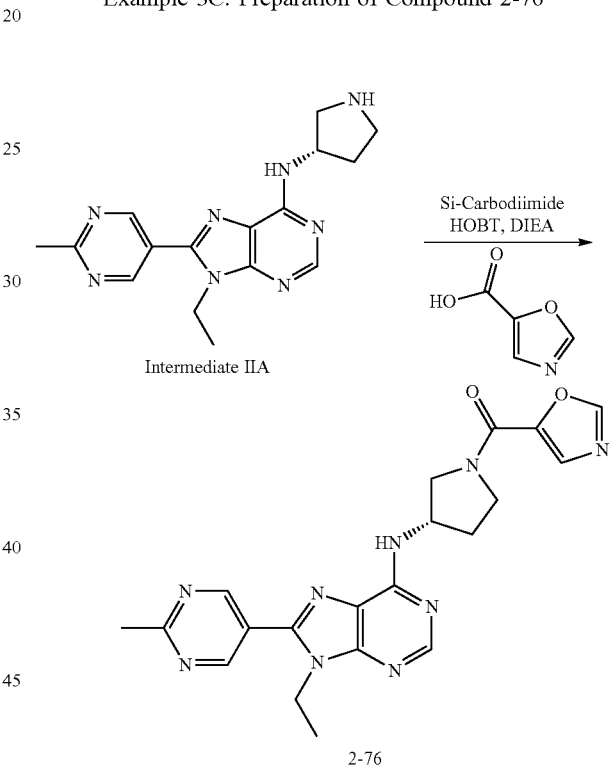

A solution of (S)-9-ethyl-8-(2-methylpyrimidin-5-yl)-N-(pyrrolidin-3-yl)-9H-purin-6-amine, 2HCl (Intermediate IIA) (25 mg, 0.06 mmol) in DMF (771 L) was added to a 2 dram vial containing Si-Carbodiimide (209 mg, 0.193 mmol), HOBT (17.70 mg, 0.116 mmol), DIEA (53.8 μl, 0.308 mmol) and oxazole-5-carboxylic acid (11 mg, 0.095 mmol). The vial was sealed and its contents were allowed to stir overnight at room temperature. Si-Carbonate (209 mg, 0.92 mmol) was added to the vial along with 1 mL of DMF (to scavenge any HOBt or unreacted carboxylic acid) and the vial was resealed and its contents were allowed to stir for 7 hours at room temperature. The reaction mixture was filtered through a 10 micron Whatman filter and washed with DMSO (1 mL). The filtered liquid was directly was purified by HPLC (0:100 to 95:5 acetonitrile:water: 0.1% v/v TFA modifier). The purified fraction was concentrated in vacuo to afford (R)-(3-((9-ethyl-8-(2-methylpyrimidin-5-yl)-9H-purin-6-yl)amino)pyrrolidin-1-yl)(oxazol-5-yl)methanone as a TFA salt. $^1$H NMR (600 MHz, DMSO-$d_6$) δ 9.10-9.06 (m, 2H), 8.55-8.50 (m, 1H), 8.37-8.25 (m, 1H), 7.78-7.69 (m, 1H), 4.86-4.70 (m, 1H), 4.32-4.21 (m, 2H), 4.11-3.35 (m, 5H), 2.73-2.67 (m, 3H), 2.36-2.02 (m, 2H), 1.32-1.23 (m, 3H). Calc'd for $C_{20}H_{22}N_9O_2$ [M+H]$^+$, 420. found 420.

Example 3D: Preparation of Compound 2-87

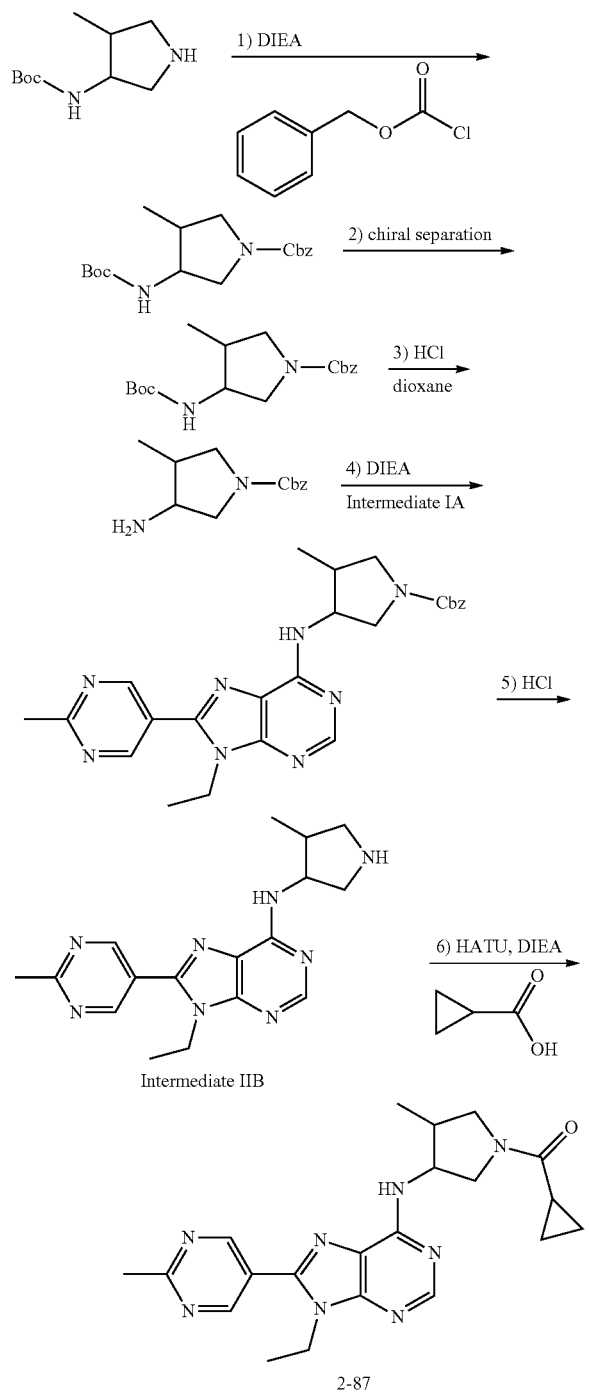

Step 1: Preparation of (3S,4R and 3R,4S)-benzyl 3-((tert-butoxycarbonyl)amino)-4-methylpyrrolidine-1-carboxylate Tert-butyl ((3S,4R and 3R,4S)-4-methylpyrrolidin-3-yl) carbamate (commercially available from A&C Pharmtech, Inc.) (10 g, 34.4 mmol) was suspended in DCM (180 ml) and DIEA (24 ml, 137 mmol) was added. The resulting solution was cooled to 0° C., benzyl carbonochloridate (9.0 ml, 63.0 mmol) was added drop wise and the solution was warmed to room temperature and stirred for 16 hours. The solvent was partially removed in vacuo and the mixture was purified mixture by chromatography on $SiO_2$ (30% EtOAc in hexane) to afford (3S,4R AND 3R,4S)-benzyl 3-((tert-butoxycarbonyl)amino)-4-methylpyrrolidine-1-carboxylate. MS (EI) Calc'd for $C_{14}H_{19}N_2O_4$ [M+2H-tBu]$^+$, 279. found 279.

Step 2: Preparation of (3S,4R or 3R,4S)-benzyl 3-((tert-butoxycarbonyl)amino)-4-methylpyrrolidine-1-carboxylate (3S,4R and 3R,4S)-benzyl 3-((tert-butoxycarbonyl)amino)-4-methylpyrrolidine-1-carboxylate (10.1 g) was purified by chiral SFC (Column & Dimensions: Phenomenex, Lux-4, 21×250 mm; 70 ml/min flow rate; 20% Methanol in $CO_2$) to afford (3S,4R or 3R,4S)-benzyl 3-((tert-butoxycarbonyl)amino)-4-methylpyrrolidine-1-carboxylate (retention time 2.4 min). MS (EI) Calc'd for $C_{14}H_{19}N_2O_4$ [M+2H-tBu]$^+$, 279. found 279.

Step 3: Preparation of (3S,4R or 3R,4S)-benzyl 3-amino-4-methylpyrrolidine-1-carboxylate A reaction vial was charged with (3S,4R or 3R,4S)-benzyl 3-((tert-butoxycarbonyl)amino)-4-methylpyrrolidine-1-carboxylate (100 mg, 0.299 mmol), dioxane (1 ml) and HCl (1 ml, 4.00 mmol, 4M in dioxane). The resulting mixture was stirred at room temperature for 5 hours. The solvent was then removed in vacuo to afford crude (3S,4R or 3R,4S)-benzyl 3-amino-4-methylpyrrolidine-1-carboxylate, HCl, which was used in next step without further purification. MS (EI) Calc'd for $C_{13}H_{19}N_2O_2$ [M+H]$^+$, 235. found 235.

Step 4: Preparation of (3S,4R or 3R,4S)-benzyl 3-((9-ethyl-8-(2-methylpyrimidin-5-yl)-9H-purin-6-yl)amino)-4-methylpyrrolidine-1-carboxylate, TFA A reaction vial was charged with (3S,4R or 3R,4S)-benzyl 3-amino-4-methylpyrrolidine-1-carboxylate, HCl (70 mg, 0.259 mmol), 6-chloro-9-ethyl-8-(2-methylpyrimidin-5-yl)-9H-purine (85 mg, 0.310 mmol), DMF (1.4 ml) and DIEA (0.3 ml, 1.718 mmol). The mixture was stirred at 80° C. for 24 h, after which it was cooled, filtered, and purified directly by reverse phase preparative HPLC (0:100 to 95:5 acetonitrile:water: 0.1% v/v TFA modifier) to afford 3S,4R or 3R,4S)-benzyl 3-((9-ethyl-8-(2-methylpyrimidin-5-yl)-9H-purin-6-yl)amino)-4-methylpyrrolidine-1-carboxylate as the TFA salt. MS (EI) Calc'd for $C_{25}H_{29}N_8O_2$[M+H]$^+$, 473. found 473.

Step 5: Preparation of 9-ethyl-8-(2-methylpyrimidin-5-yl)-N-((3S,4R or 3R,4S)-4-methylpyrrolidin-3-yl)-9H-purin-6-amine, TFA (Intermediate IIB)

To the solution of (3S,4R or 3R,4S)-benzyl 3-((9-ethyl-8-(2-methylpyrimidin-5-yl)-9H-purin-6-yl)amino)-4-methylpyrrolidine-1-carboxylate, TFA (71.2 mg, 0.121 mmol) in dioxane (1.6 ml) was added 12 M HCl (500 μl, 6.09 mmol). The mixture was stirred at 90° C. for 3 h. The reaction was then cooled and the solvent was removed in vacuo to afford a residue, which was dissolved into MeOH and purified by reverse phase preparative HPLC (0:100 to 95:5 acetonitrile: water: 0.1% v/v TFA modifier) to afford 9-ethyl-8-(2-methylpyrimidin-5-yl)-N-((3S,4R or 3R,4S)-4-methylpyrrolidin-3-yl)-9H-purin-6-amine as the TFA salt. MS (EI) Calc'd for $C_{17}H_{23}N_8[M+H]^+$, 339. found 339.

Step 6: Preparation of Compound 2-87

A reaction vial was charged with 9-ethyl-8-(2-methylpyrimidin-5-yl)-N-((3S,4R or 3R,4S)-4-methylpyrrolidin-3-yl)-9H-purin-6-amine, TFA (18.6 mg, 0.041 mmol), cyclopropanecarboxylic acid (8.7 mg, 0.10 mmol), HATU (18 mg, 0.047 mmol), DMF (400 μl) and DIEA (40 μl, 0.23 mmol). The resulting mixture was stirred at room temperature for 2 h. The mixture was filtered and purified directly by reverse phase preparative HPLC (0:100 to 95:5 acetonitrile: water: 0.1% v/v TFA modifier) to afford compound 2-87 as the TFA salt. $^1$H NMR (600 MHz, DMSO-d$_6$) δ 9.14-9.05 (m, 2H), 8.46-8.35 (m, 1H), 8.34-8.26 (m, 1H), 4.55-4.35 (m, 1H), 4.32-4.20 (m, 2H), 4.10-3.20 (m, 3H), 3.20-2.85 (m, 1H), 2.71 (s, 3H), 1.80-1.60 (m, 1H), 1.35-1.24 (m, 3H), 1.24-1.15 (m, 1H), 1.10-0.90 (m, 3H), 0.75-0.6 (m, 4H); MS (EI) Calc'd for $C_{21}H_{27}N_8O$ [M+H]$^+$, 407. found 407.

Example 3E: Preparation of Compound 2-92

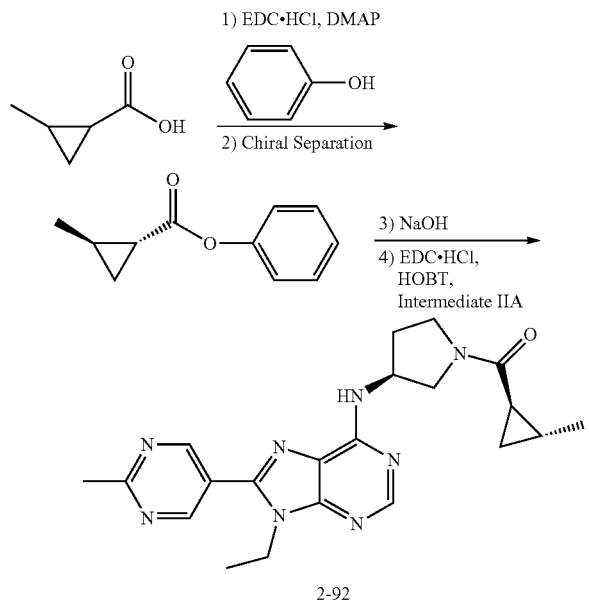

2-92

Step 1: Synthesis of phenyl 2-methylcyclopropanecarboxylate

Rac-cis and trans-2-methylcyclopropanecarboxylic acid (1.00 g, 10 mmol), phenol (1.20 g, 13 mmol), EDC.HCl (2.50 g, 13 mmol), and DMAP (120 mg, 1 mmol) were mixed in DCM (20 ml) and stirred at room temperature for 16 h. The mixture was then successively washed with hydrochloric acid aqueous solution (1M) (10 mL×3) and brine (10 mL×3). The organic layers were dried over anhydrous Na$_2$SO$_4$ and concentrated under reduced pressure. The residue product was purified by chromatography on silica gel with PE/EtOAc (20:1) as eluent, which afforded phenyl 2-methylcyclopropanecarboxylate as a racemic mixture of diastereomers. MS (ESI) calc'd for $(C_{11}H_{13}O_2)$ [M+H]$^+$, 177. found, 177.

Step 2: Resolution of phenyl 2-methylcyclopropanecarboxylate

The racemic mixture of diastereomeric products was resolved by chiral HPLC (Column: OJ-H (250×4.6 mm 5 um); Mobile Phase: Heptane:IPA=90:10; Flow: 1.0 ml/min; Temperature: 40° C.) to afford (1R,2R)-phenyl 2-methylcyclopropanecarboxylate (retention time=7.87 min); (1S,2S)-phenyl 2-methylcyclopropanecarboxylate (retention time=10.24 min); (1R,2S)-phenyl 2-methylcyclopropanecarboxylate (retention time=13.98 min); and (1S,2R)-phenyl 2-methylcyclopropanecarboxylate (retention time=14.72 min).

Step 3: Synthesis of (−)-(1R,2R)-2-methylcyclopropanecarboxylic Acid (1R,2R)-phenyl 2-methylcyclopropanecarboxylate (30 mg, 0.17 mmol) and NaOH (20 mg, 0.50 mmol) were combined in H$_2$O (1 mL) and THF (1 mL), and the mixture was stirred at 65° C. for 2 h. The solvents were then removed under reduced pressure, after which EtOH (10 mL) was added. The solution was then adjusted to pH=6 using concentrated hydrochloric acid. The precipitate formed was removed by filtration, and the organic layer was concentrated under reduced pressure. Stereochemical assignment for each acid (and the esters in Step 2) was determined by comparison to literature values (*Tetrahedron* 1996, 52, 13327-13338; *Bulletin of the Chemical Society of Japan* 1966, 39, 1075-1076)

Step 4: Synthesis of ((S)-3-(9-ethyl-8-(2-methylpyrimidin-5-yl)-9H-purin-6-ylamino)pyrrolidin-1-yl) ((1R,2R)-2-methylcyclopropyl)methanone (2-92)

(−)-(1R,2R)-2-methylcyclopropanecarboxylic acid (17 mg, 0.17 mmol) and 4-methylmorpholine (0.2 mL) were mixed in DMF (0.25 mL), followed by addition of HOBT (50 mg, 0.37 mmol). After 10 min at RT, EDC.HCl (80 mg, 0.41 mmol) was added. The mixture was stirred for 30 min at RT, then (S)-9-ethyl-8-(2-methylpyrimidin-5-yl)-N-(pyrrolidin-3-yl)-9H-purin-6-amine Intermediate IIA (in its neutral form) (60 mg, 0.13 mmol) in DMF (0.25 mL) was added drop wise. The whole mixture was stirred for 16 h at RT, after which the mixture was purified by reverse phase chromatography (Mobile phase: MeOH/water (10 mM NH$_4$HCO$_3$)) to afford ((S)-3-(9-ethyl-8-(2-methylpyrimidin-5-yl)-9H-purin-6-ylamino)pyrrolidin-1-yl)((1R,2R)-2-methylcyclopropyl)methanone (2-92) $^1$H NMR (CD$_3$OD, 400 MHz): δ 9.13 (s, 2H), 8.45-8.35 (m, 1H), 4.50-4.35 (m, 2H), 4.25-3.43 (m, 4H), 2.82 (s, 3H), 2.55-2.10 (m, 2H), 1.65-1.50 (m, 1H), 1.45 (m, 3H), 1.40-1.00 (m, 6H), 0.70-0.60 (m, 1H). MS (ESI) calc'd for $(C_{21}H_{27}N_8O)$ [M+H]$^+$, 407. found, 407.

Example 3F: Preparation of Compound 2-94

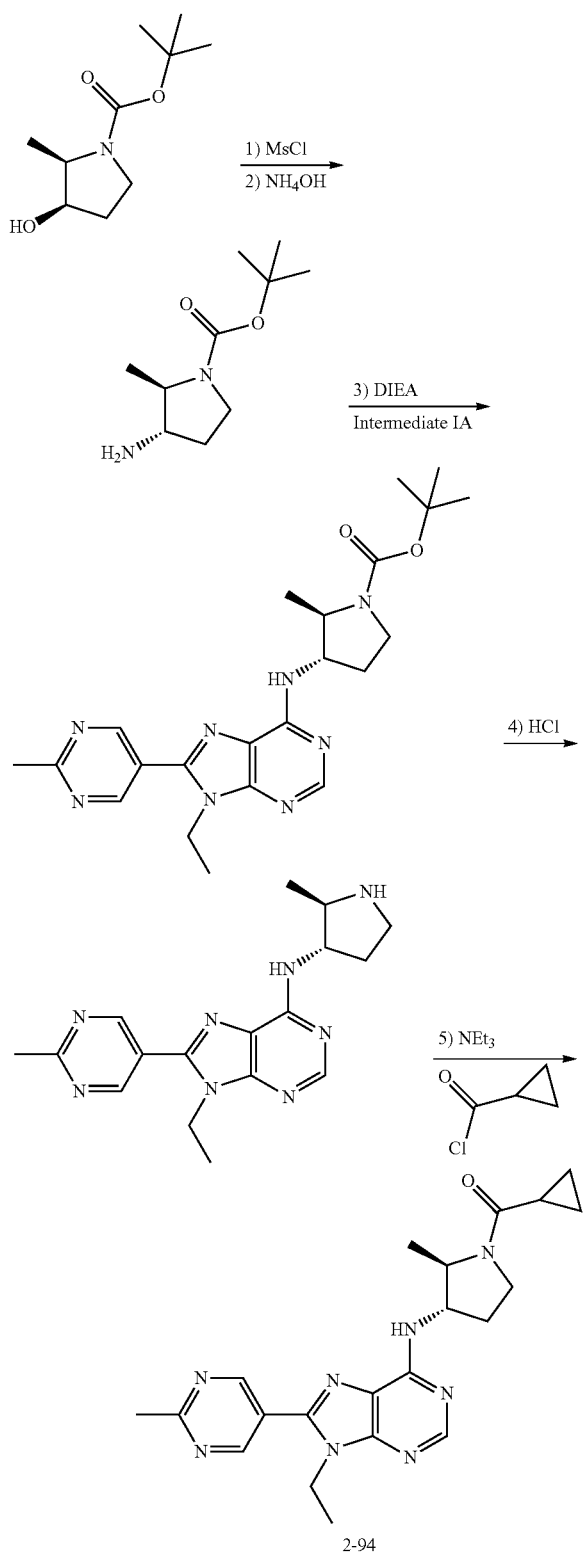

Step 1: Preparation of (2R,3R)-tert-butyl 2-methyl-3-(methylsulfonyloxy)pyrrolidine-1-carboxylate Methanesulfonyl chloride (0.25 ml, 3.21 mmol) was added to a stirred, cooled 0° C. mixture of (2R,3R)-tert-butyl 3-hydroxy-2-methylpyrrolidine-1-carboxylate (200 mg, 0.994 mmol) (Synthesized as in WO2004/112793) in DCM (10 ml) and the mixture was stirred at room temperature for 15 h. The solvents were removed under reduced pressure to give (2R,3R)-tert-butyl 2-methyl-3-(methylsulfonyloxy)pyrrolidine-1-carboxylate which was used directly for next step.

Step 2: Preparation of (2R,3S)-tert-butyl 3-amino-2-methylpyrrolidine-1-carboxylate A tube charged with (2R,3R)-tert-butyl 2-methyl-3-((methylsulfonyl)oxy)pyrrolidine-1-carboxylate (300 mg, 1.0 mmol) and ammonium hydroxide (5 mL, 28-35% aqueous) was sealed and heated to 80° C. for 15 h. The solvents were removed in vacuo to give crude (2R,3S)-tert-butyl 3-amino-2-methylpyrrolidine-1-carboxylate which was used directly in the next step Step 3: Preparation of (2R,3S)-tert-butyl 3-(9-ethyl-8-(2-methylpyrimidin-5-yl)-9H-purin-6-ylamino)-2-methylpyrrolidine-1-carboxylate To a stirred solution of (2R,3S)-tert-butyl 3-amino-2-methylpyrrolidine-1-carboxylate (180 mg, 0.9 mmol) in t-BuOH (5 ml) at RT were added Intermediate IA (100 mg, 0.36 mmol) and DIEA (0.5 ml, 2.8 mmol). The reaction mixture was then heated to 80° C. for 15 h. The solvent was then removed in vacuo to give the crude product which was purified by reverse phase preparative HPLC (Mobile phase; A: water (10 mmol $NH_4HCO_3$), B: MeCN) to afford (2R,3S)-tert-butyl 3-(9-ethyl-8-(2-methylpyrimidin-5-yl)-9H-purin-6-ylamino)-2-methylpyrrolidine-1-carboxylate. MS (ESI) calc'd for ($C_{22}H_{31}N_8O_2$) $[M+H]^+$, 439. found, 439.

Step 4: Preparation of 9-ethyl-8-(2-methylpyrimidin-5-yl)-N-((2R,3S)-2-methylpyrrolidin-3-yl)-9H-purin-6-amine Hydrochloride Into a 25-mL round bottom flask containing a solution of (2R,3S)-tert-butyl 3-(9-ethyl-8-(2-methylpyrimidin-5-yl)-9H-purin-6-ylamino)-2-methylpyrrolidine-1-carboxylate (90 mg, 0.2 mmol) in anhydrous dichloromethane (5 mL) was added HCl/dioxane (0.5 mL, 4.0 M in dioxane) and the contents were allowed to stir at ambient temperature for 2 h. The volatiles were then removed under reduced pressure and the residue was triturated with diethyl ether (2×5 mL) to furnish the title compound of 9-ethyl-8-(2-methylpyrimidin-5-yl)-N-((2R,3S)-2-methylpyrrolidin-3-yl)-9H-purin-6-amine, 2HCl as a solid. MS (ESI) calc'd for ($C_{17}H_{23}N_8$) $[M+H]^+$, 339. found, 339.

Step 5: Synthesis of cyclopropyl((2R,3S)-3-(9-ethyl-8-(2-methylpyrimidin-5-yl)-9H-purin-6-ylamino)-2-methylpyrrolidin-1-yl)methanone (2-94)

To a solution of 9-ethyl-8-(2-methylpyrimidin-5-yl)-N-((2R,3S)-2-methylpyrrolidin-3-yl)-9H-purin-6-amine, 2HCl (80 mg, 0.20 mmol) in DCM (3 ml) at 0° C. was added triethylamine (0.1 ml, 0.72 mmol), after which cyclopropanecarbonyl chloride (0.022 ml, 0.230 mmol) was added drop-wise. The resulting mixture was allowed to warm to RT and stirred for 1 h. The reaction mixture was then concentrated in vacuo to give a residue which was purified by reverse phase preparative HPLC [Column: Xbridge Prep C18 10 um OBD, 19×250 mm; Mobile phase: A: Water (10 mmol $NH_4HCO_3$), B: MeCN; Flow rate: 30 mL/min; UV detection: 214/254 nm] to afford cyclopropyl((2R,3S)-3-(9-ethyl-8-(2-methylpyrimidin-5-yl)-9H-purin-6-ylamino)-2-methylpyrrolidin-1-yl)methanone (2-94). $^1$H NMR (400 MHz, $CD_3OD$) δ 9.15-9.10 (m, 2H), 8.40-8.35 (m, 1H), 4.65-4.45 (m, 1H), 4.45-4.40 (m, 2H), 4.40-3.80 (m, 3H), 2.95 (s, 3H), 2.65-2.45 (m, 1H), 2.26-2.08 (m, 1H), 1.93-1.73 (m, 1H), 1.54-1.30 (m, 6H), 0.98-0.70 (m, 4H). MS (ESI) calc'd for ($C_{21}H_{27}N_8O$) [M+H]$^+$, 407. found, 407.

Example 3G: Preparation of Compound 2-100

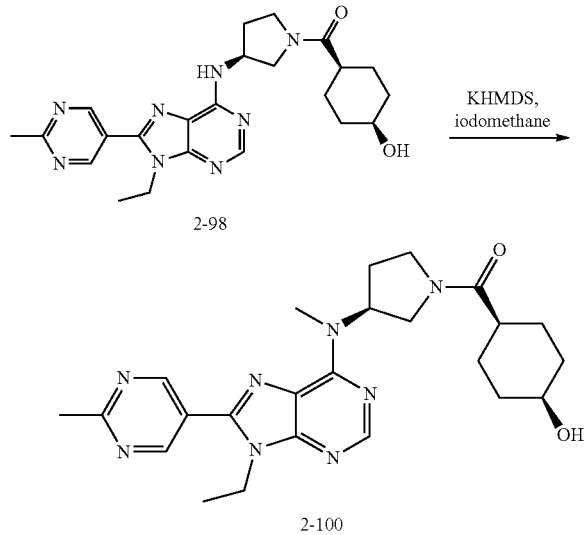

To a solution of compound 2-98 (50.0 mg, 0.11 mmol) in dry tetrahydrofuran (2 mL) at −50° C. was added potassium bis(trimethylsilyl)amide (0.13 mL, 1 M in tetrahydrofuran, 0.13 mmol). The mixture was stirred for 30 min at −50° C., after which iodomethane (7 μL, 0.11 mmol) was added. The mixture was allowed to warm to RT and allowed to stir for 2 h. The mixture was quenched with ethanol (10 mL) and water (20 mL), after which it was extracted with ethyl acetate (3×40 mL). The combined organic layers were dried over anhydrous sodium sulfate, filtered and concentrated under vacuum. The residue was purified by silica gel column chromatography with 1%-10% methanol in dichloromethane to afford ((S)-3-((9-ethyl-8-(2-methylpyrimidin-5-yl)-9H-purin-6-yl)(methyl)amino)pyrrolidin-1-yl)((1S,4R)-4-hydroxycyclohexyl)methanone (2-100) as a solid. $^1$H NMR (300 MHz, DMSO-$d_6$) δ 9.12 (s, 2H), 8.40-8.30 (m, 1H), 6.05-5.95 (m, 1H), 4.38-4.29 (q, J=7.2 Hz, 2H), 4.32-4.29 (m, 1H), 3.90-3.53 (m, 4H) 3.39 (s, 3H), 2.74 (s, 3H), 2.50-2.39 (m, 1H), 2.27-2.10 (m, 2H), 1.82-1.67 (m, 4H), 1.49-1.33 (m, 5H), 1.31 (t, J=7.2 Hz, 3H). MS (ESI) calc'd for ($C_{24}H_{33}N_8O_2$) [M+H]$^+$, 465. found, 465.

Example 3H: Preparation of Compounds 2-103 and 2-104

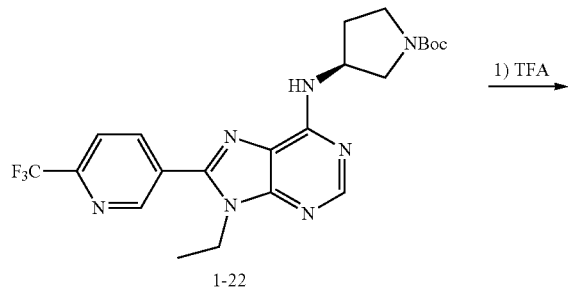

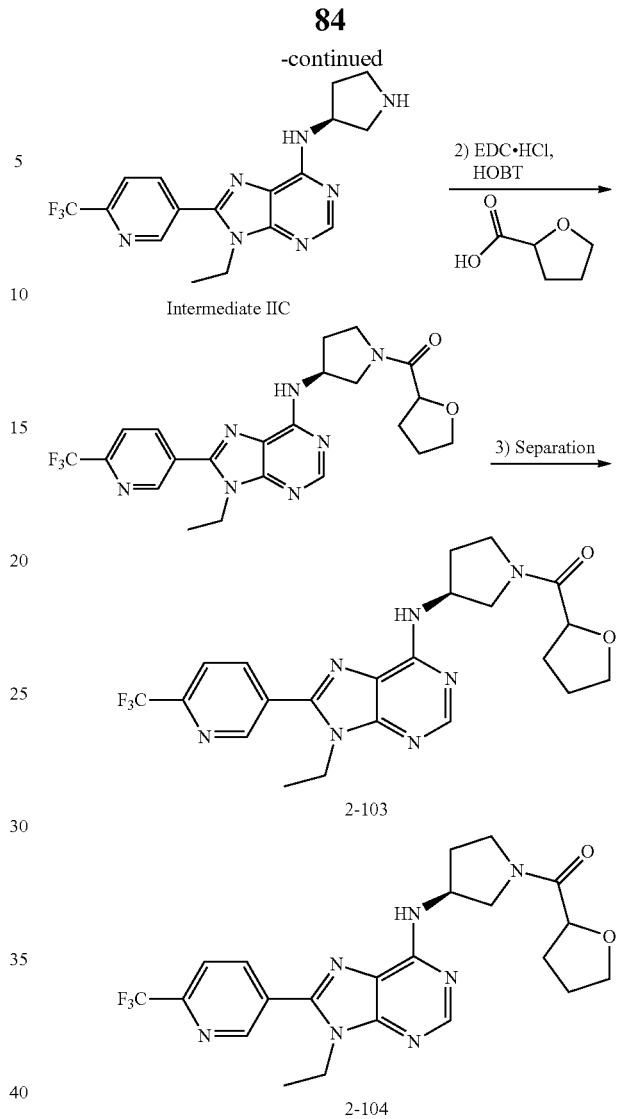

Step 1: Preparation of (S)-9-ethyl-N-(pyrrolidin-3-yl)-8-(6-(trifluoromethyl)pyridin-3-yl)-9H-purin-6-amine (Intermediate IIC)

To a solution of 1-22 (5 g, 0.01 mol) in dichloromethane (50 mL) was added 2,2,2-trifluoroacetic acid (10 mL). The resulting solution was stirred for 2 h at RT. The resulting mixture was then concentrated under vacuum, quenched by the addition of water (20 mL), adjusted to pH 8 with saturated potassium carbonate, and extracted with 10% methanol in dichloromethane (5×100 mL). The organic layers were combined, dried over anhydrous magnesium sulfate and filtered. The filtrate was concentrated under vacuum to afford (S)-9-ethyl-N-(pyrrolidin-3-yl)-8-(6-(trifluoromethyl)pyridin-3-yl)-9H-purin-6-amine. MS (ESI) calc'd for ($C_{17}H_{19}F_3N_7$) [M+H]$^+$, 378. found, 378.

Step 2: Preparation of ((S)-3-(9-ethyl-8-(6-(trifluoromethyl)pyridin-3-yl)-9H-purin-6-ylamino)pyrrolidin-1-yl)((S and R)-tetrahydrofuran-2-yl)methanone To a solution of (S)-9-ethyl-N-(pyrrolidin-3-yl)-8-(6-(trifluoromethyl)pyridin-3-yl)-9H-purin-6-amine (200 mg, 0.53 mmol) in dichloromethane (50 mL) were added rac-tetrahydrofuran-2-carboxylic acid (61 mg, 0.53 mmol), N-(3-dimethylaminopropyl)-N'-ethylcarbodiimide hydrochloride (152 mg, 0.795 mmol), 1H-benzo[d][1,2,3]triazol-1-ol (107 mg, 0.795 mmol) and triethylamine (160 mg, 1.59 mmol). The resulting mixture was stirred for 4 h at ambient temperature. The reaction was quenched by the addition of water (100 mL) and extracted with dichloromethane (3×50 mL). The organic layers were combined, dried over anhydrous magnesium sulfate and filtered. The filtrate was concentrated under vacuum to give a residue, which was purified by silica gel column chromatography with 3% methanol in dichloromethane to afford a mixture containing both epimers of ((S)-3-(9-ethyl-8-(6-(trifluoromethyl)pyridin-3-yl)-9H-purin-6-ylamino)pyrrolidin-1-yl)((S and R)-tetrahydrofuran-2-yl)methanone.

Step 3: Purification to afford 2-103 and 2-104

The mixture of diastereomers of ((S)-3-(9-ethyl-8-(6-(trifluoromethyl)pyridin-3-yl)-9H-purin-6-ylamino)pyrrolidin-1-yl)(tetrahydrofuran-2-yl)methanone was purified by preparative Chiral HPLC with the following conditions: Column: Lux Cellulose-2, 0.46×10 cm, Mobile phase: 25% EtOH in hexane (0.2% IPA)] to afford 2-103 (retention time 13.1 min) as a solid and 2-104 (retention time 17.7 min) as a solid. For 2-103: $^1$H NMR (400 MHz, DMSO-$d_6$): δ 9.23 (s, 1H), 8.56 (dd, J=1.2, 8.4 Hz, 1H), 8.40-8.30 (m, 2H), 8.18 (d, J=8.4 Hz, 1H), 4.96-4.72 (m, 1H), 4.56-4.54 (m, 1H), 4.53 (m, 2H), 3.83-3.42 (m, 6H), 2.53-1.84 (m, 6H), 1.37 (m, 3H). MS (ESI) calc'd for ($C_{22}H_{24}F_3N_7O_2$) [M+H]$^+$, 476. found, 476. For 2-104: $^1$H NMR (400 MHz, DMSO-$d_6$) δ 9.23 (s, 1H), 8.56 (d, J=8.0 Hz, 1H), 8.40-8.30 (m, 2H), 8.17 (d, J=8.0 Hz, 1H), 4.96-4.72 (m, 1H), 4.58-4.52 (m, 1H), 4.38 (m, 2H), 3.82-3.41 (m, 6H), 2.40-2.00 (m, 4H), 1.88-1.83 (m, 2H), 1.37 (m, 3H). MS (ESI) calc'd for ($C_{22}H_{25}F_3N_7O_2$) [M+H]$^+$, 476. found, 476.

Compounds 2-1 through 2-5, 2-8 through 2-19, 2-25, 2-27 through 2-29, and 2-44 were prepared in an analogous fashion to Example 2 using the corresponding acid chloride.

Compounds 2-6, 2-7, and 2-20 through 2-24 were prepared in an analogous fashion to Example 3 using the corresponding acid.

Compound 2-26 was prepared from racemic compound 2-25 by chiral preparative SFC using the following conditions: Column: OD-H 4.6×250 mm, 5 um; CO$_2$ Flow Rate: 2.25 mL/min; Co-Solvent MeOH (0.1% diethylamine); Co-Solvent Flow Rate 0.75 mL/min; Column Temperature 40° C., to afford 2-26 (retention time 4.8 min).

Compounds 2-30, 2-31, 2-37, and 2-40 through 2-43 were prepared in an analogous fashion to Example 3B using the corresponding acid.

Compounds 2-32 and 3-33 were prepared in an analogous fashion to Example 3B using racemic tetrahydrofuran-2-carboxylic acid. The resulting mix of two diastereomers were separated by chiral SFC using the following conditions: Chiralpak AS-H, 21×250 mm column, 70 mL/min flow rate, 25% MeOH in CO$_2$ to afford 2-32 (retention time 2.7 min) and 2-33 (retention time 3.6 min).

Compounds 2-34 and 3-35 were prepared in an analogous fashion to Example 3B using racemic spiro[2.4]heptane-1-carboxylic acid (available from Chembridge Corp.). The resulting mix of two diastereomers was separated by chiral SFC using the following conditions: Chiralpak IA, 21×250 mm column, 70 ml/min flow rate, 35% MeOH in CO$_2$ to afford 2-34 (retention time 4.4) and 2-35 (retention time 6.0 min).

Compounds 2-38 and 3-39 were prepared in an analogous fashion to Example 3B using a mixture of cis and trans 3-methoxycyclobutanecarboxylic acid (available from Parkway Scientific). The resulting mix of two diastereomers were separated by chiral SFC using the following conditions: ES Industries Pyridyl Amide, 21×250 mm column, 70 ml/min flow rate, 10% (MeOH+0.25% dimethylethyl amine) in CO$_2$ to provide 2-38 (retention time 3.2 min) and 2-39 (retention time 4.0 min).

Compounds 2-44 through 2-46 were prepared according to the first step in Example 3H and the second step in Example 3 using the corresponding compounds from Table 1 and the corresponding acid chlorides.

Compounds 2-47, 2-55 through 2-76, 2-79, and 2-81 were prepared in an analogous fashion to Example 3C using the corresponding acids.

Compounds 2-48 through 2-54 were prepared according to the first step in Example 3H and the second step in Example 3B using the corresponding compounds from Table 1 and the corresponding carboxylic acids.

Compound 2-77 was synthesized according to Example 3C using bicyclo[1.1.1]pentane-1-carboxylic acid (available from FCH Group Company).

Compounds 2-78, 2-80, 2-82, and 2-83 through 2-86 were prepared in an analogous fashion to Example 3C using the corresponding acids which contained N-Boc groups. In these cases, DCM was substituted in for DMF and, following the coupling reaction and scavenging step, TFA was added to the reaction mixture to remove the Boc groups. The reaction mixtures were then concentrated and purified as indicated in Example 3C.

Compounds 2-88 and 2-89 were prepared in an analogous fashion to Example 3D using the corresponding acids.

Compounds 2-90, 2-91, and 2-93 were prepared in an analogous fashion to Example 3E using the corresponding resolved acids prepared as described.

Compounds 2-95 and 2-96 were prepared in an analogous fashion to Example 3F following steps 3 through 5 with commercially-available amines. (The amine for 2-95 is commercially available from VWR, the amine for 2-96 from Advanced Chemblocks Inc.)

Compound 2-97 was obtained from 2-96 by chiral SFC using the following conditions: Column OJ-H 4.6×250 mm 5 um, CO$_2$ Flow Rate 2.55, Co-Solvent MeOH:MECN=1:1 (0.1% diethylamine), Co-Solvent Flow Rate 0.45, Column Temperature 40° C. to afford the single enantiomer (retention time 4.0 min).

Compounds 2-98 and 2-99 were prepared from Intermediate IIA using the coupling conditions described in Example 3E, step 4.

Compounds 2-101 and 2-102 were prepared using an analogous procedure to Example 3H to afford 2-101 (retention time 4.0 min) and 2-102 (retention time 7.9 min).

Compounds 2-105 and 2-106 were prepared from Intermediate IIC using an analogous procedure to Example 3H, step 2.

TABLE 2

| Compound | Structure | Compound Name | MS [M + H]+ |
|---|---|---|---|
| 2-1 | 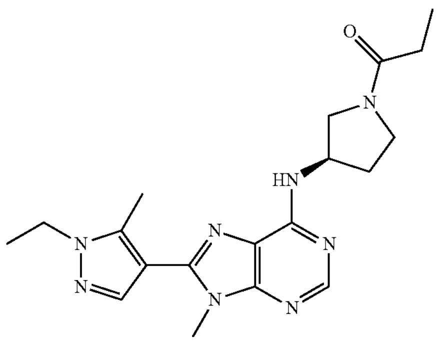 [SMILES: CCC(=O)N1CC[C@@H](Nc2ncnc3c2nc(-c2cnn(CC)c2C)n3C)C1] | 8-(1-ethyl-5-methyl-1H-pyrazol-4-yl)-9-methyl-N-[(3R)-1-propanoylpyrrolidin-3-yl]-9H-purin-6-amine | Calc'd 383, found 383 |
| 2-2 | 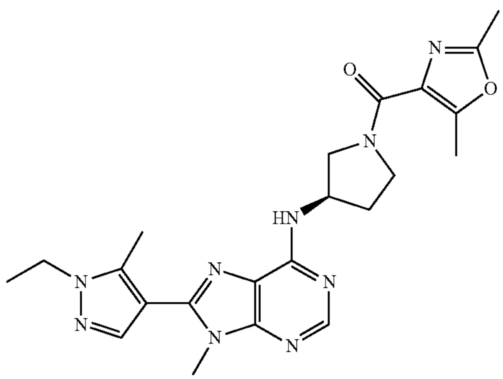 [SMILES: CCn1ncc(-c2nc3c(N[C@@H]4CCN(C(=O)c5nc(C)oc5C)C4)ncnc3n2C)c1C] | N-{(3R)-1-[(2,5-dimethyl-1,3-oxazol-4-yl)carbonyl]pyrrolidin-3-yl}-8-(1-ethyl-5-methyl-1H-pyrazol-4-yl)-9-methyl-9H-purin-6-amine | Calc'd 450, found 450 |
| 2-3 | 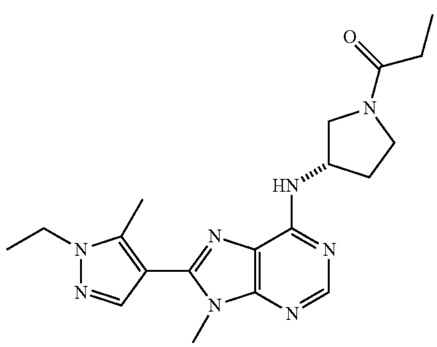 | 8-(1-ethyl-5-methyl-1H-pyrazol-4-yl)-9-methyl-N-[(3S)-1-propanoylpyrrolidin-3-yl]-9H-purin-6-amine | Calc'd 383, found 383 |
| 2-4 | 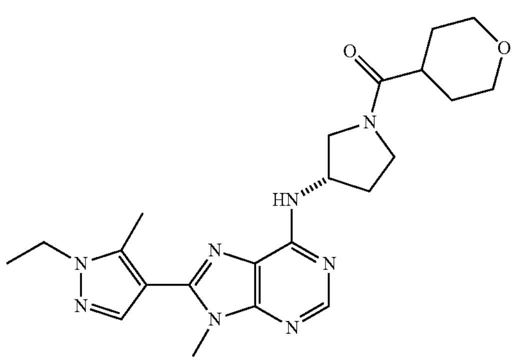 | 8-(1-ethyl-5-methyl-1H-pyrazol-4-yl)-9-methyl-N-[(3S)-1-(tetrahydro-2H-pyran-4-ylcarbonyl)pyrrolidin-3-yl]-9H-purin-6-amine | Calc'd 439, found 439 |

TABLE 2-continued

| Compound | Structure | Compound Name | MS [M + H]+ |
|---|---|---|---|
| 2-5 | 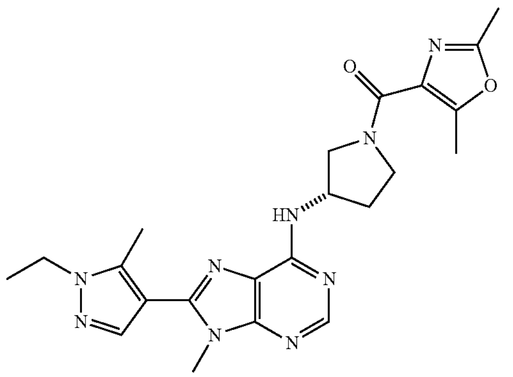 | N-{(3S)-1-[(2,5-dimethyl-1,3-oxazol-4-yl)carbonyl]pyrrolidin-3-yl}-8-(1-ethyl-5-methyl-1H-pyrazol-4-yl)-9-methyl-9H-purin-6-amine | Calc'd 450, found 450 |
| 2-6 | 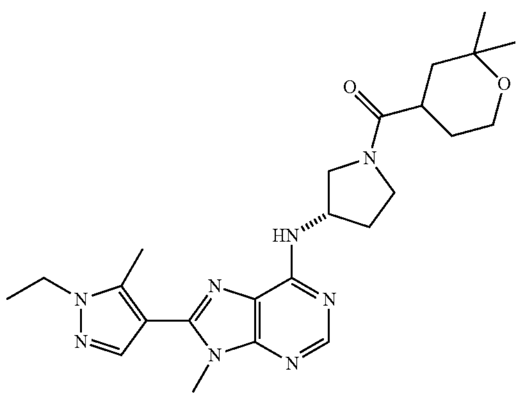 | N-{(3S)-1-[(2,2-dimethyltetrahydro-2H-pyran-4-yl)carbonyl]pyrrolidin-3-yl}-8-(1-ethyl-5-methyl-1H-pyrazol-4-yl)-9-methyl-9H-purin-6-amine | Calc'd 467, found 467 |
| 2-7 | 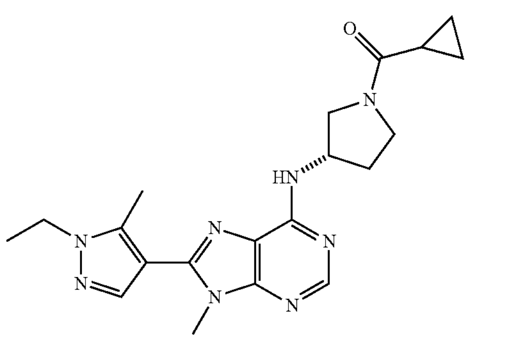 | N-[(3S)-1-(cyclopropylcarbonyl)pyrrolidin-3-yl]-8-(1-ethyl-5-methyl-1H-pyrazol-4-yl)-9-methyl-9H-purin-6-amine | Calc'd 395, found 395 |
| 2-8 | 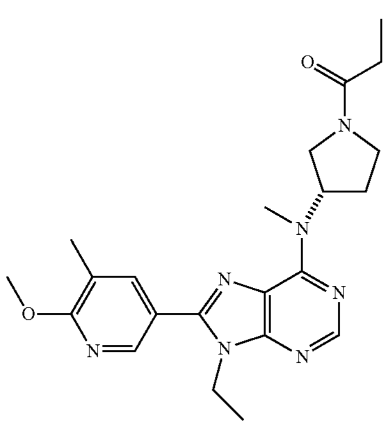 | (S)-1-(3-((9-ethyl-8-(6-methoxy-5-methylpyridin-3-yl)-9H-purin-6-yl)(methyl)amino)pyrrolidin-1-yl)propan-1-one | Calc'd 424, found 424 |

TABLE 2-continued

| Compound | Structure | Compound Name | MS [M + H]+ |
|---|---|---|---|
| 2-9 | 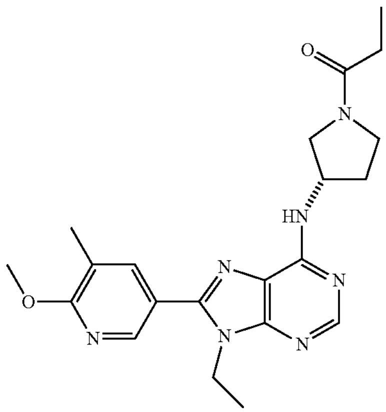 | (S)-1-(3-((9-ethyl-8-(6-methoxy-5-methylpyridin-3-yl)-9H-purin-6-yl)amino)pyrrolidin-1-yl)propan-1-one | Calc'd 410, found 410 |
| 2-10 | 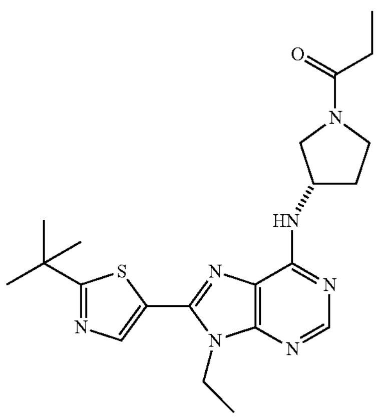 | (S)-1-(3-((8-(2-(tert-butyl)thiazol-5-yl)-9-ethyl-9H-purin-6-yl)amino)pyrrolidin-1-yl)propan-1-one | Calc'd 428, found 428 |
| 2-11 | 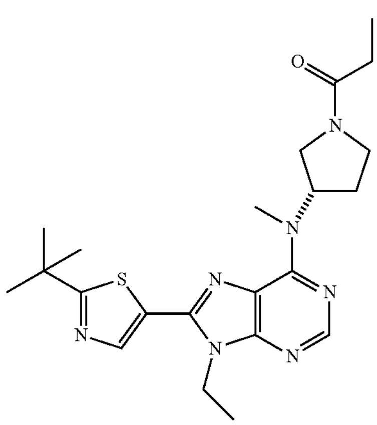 | (S)-1-(3-((8-(2-(tert-butyl)thiazol-5-yl)-9-ethyl-9H-purin-6-yl)(methyl)amino)pyrrolidin-1-yl)propan-1-one | Calc'd 442, found 442 |

TABLE 2-continued

| Compound | Structure | Compound Name | MS [M + H]+ |
|---|---|---|---|
| 2-12 | 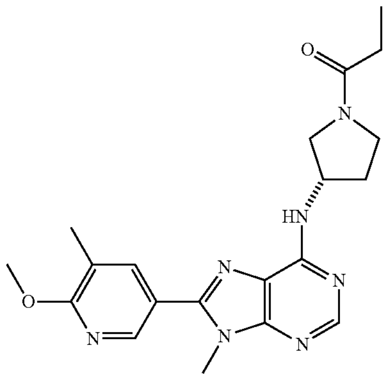 | (S)-1-(3-((8-(6-methoxy-5-methylpyridin-3-yl)-9-methyl-9H-purin-6-yl)amino)pyrrolidin-1-yl)propan-1-one | Calc'd 396, found 396 |
| 2-13 | 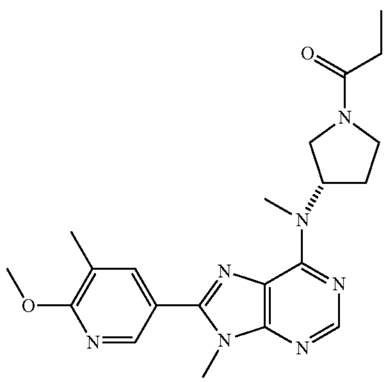 | (S)-1-(3-((8-(6-methoxy-5-methylpyridin-3-yl)-9-methyl-9H-purin-6-yl)(methyl)amino)pyrrolidin-1-yl)propan-1-one | Calc'd 410, found 410 |
| 2-14 | 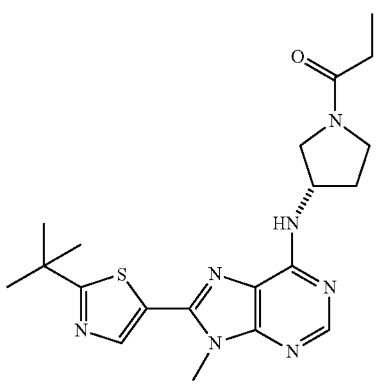 | (S)-1-(3-((8-(2-(tert-butyl)thiazol-5-yl)-9-methyl-9H-purin-6-yl)amino)pyrrolidin-1-yl)propan-1-one | Calc'd 414, found 414 |
| 2-15 | 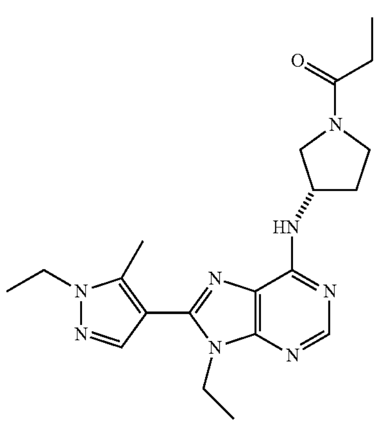 | (S)-1-(3-((9-ethyl-8-(1-ethyl-5-methyl-1H-pyrazol-4-yl)-9H-purin-6-yl)amino)pyrrolidin-1-yl)propan-1-one | Calc'd 397, found 397 |

TABLE 2-continued

| Compound | Structure | Compound Name | MS [M + H]+ |
|---|---|---|---|
| 2-16 | 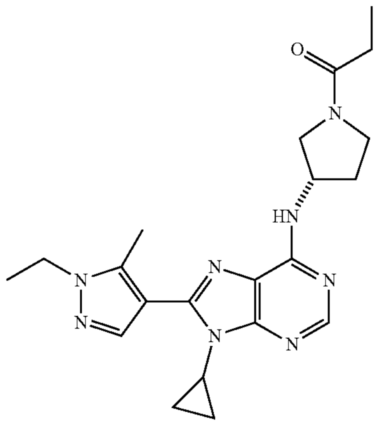 | (S)-1-(3-((9-cyclopropyl-8-(1-ethyl-5-methyl-1H-pyrazol-4-yl)-9H-purin-6-yl)amino)pyrrolidin-1-yl)propan-1-one | Calc'd 409, found 409 |
| 2-17 | 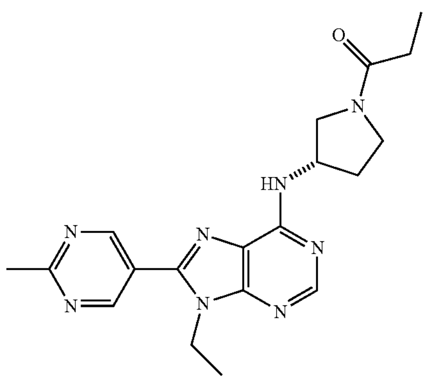 | (S)-1-(3-((9-ethyl-8-(2-methylpyrimidin-5-yl)-9H-purin-6-yl)amino)pyrrolidin-1-yl)propan-1-one | Calc'd 381, found 381 |
| 2-18 | 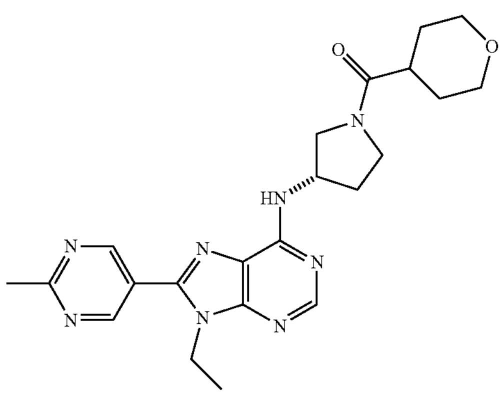 | (S)-(3-((9-ethyl-8-(2-methylpyrimidin-5-yl)-9H-purin-6-yl)amino)pyrrolidin-1-yl)(tetrahydro-2H-pyran-4-yl)methanone | Calc'd 437, found 437 |
| 2-19 | 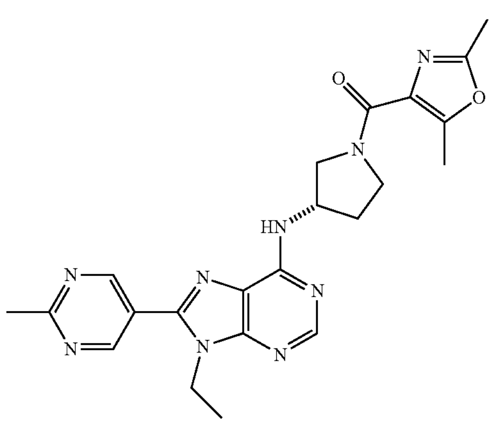 | (S)-(2,5-dimethyloxazol-4-yl)(3-((9-ethyl-8-(2-methylpyrimidin-5-yl)-9H-purin-6-yl)amino)pyrrolidin-1-yl)methanone | Calc'd 448, found 448 |

TABLE 2-continued

| Compound | Structure | Compound Name | MS [M + H]+ |
|---|---|---|---|
| 2-20 | 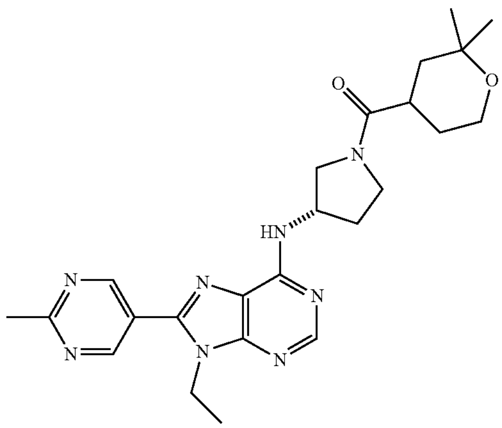 | ((S and R)-2,2-dimethyltetrahydro-2H-pyran-4-yl)((S)-3-((9-ethyl-8-(2-methylpyrimidin-5-yl)-9H-purin-6-yl)amino)pyrrolidin-1-yl)methanone | Calc'd 465, found 465 |
| 2-21 | 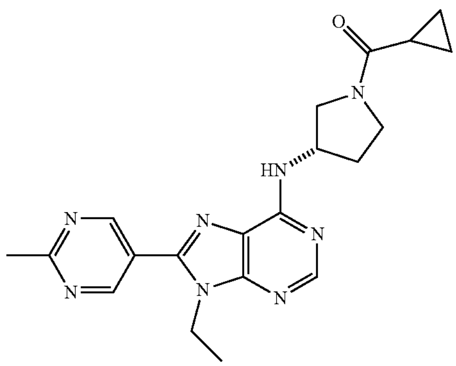 | (S)-cyclopropyl(3-((9-ethyl-8-(2-methylpyrimidin-5-yl)-9H-purin-6-yl)amino)pyrrolidin-1-yl)methanone | Calc'd 393, found 393 |
| 2-22 | 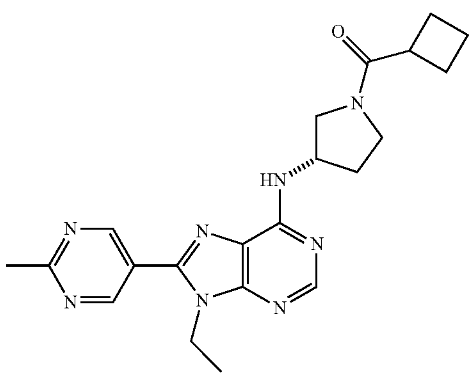 | (S)-cyclobutyl(3-((9-ethyl-8-(2-methylpyrimidin-5-yl)-9H-purin-6-yl)amino)pyrrolidin-1-yl)methanone | Calc'd 407, found 407 |
| 2-23 | 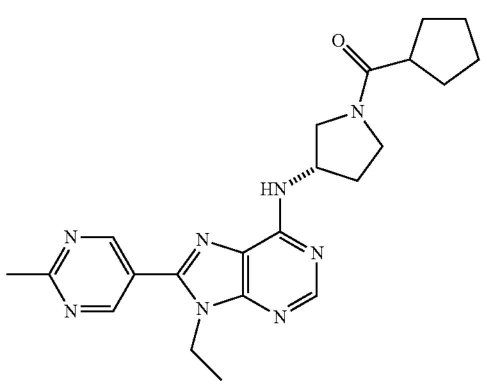 | (S)-cyclopentyl(3-((9-ethyl-8-(2-methylpyrimidin-5-yl)-9H-purin-6-yl)amino)pyrrolidin-1-yl)methanone | Calc'd 421, found 421 |

TABLE 2-continued

| Compound | Structure | Compound Name | MS [M + H]+ |
|---|---|---|---|
| 2-24 | 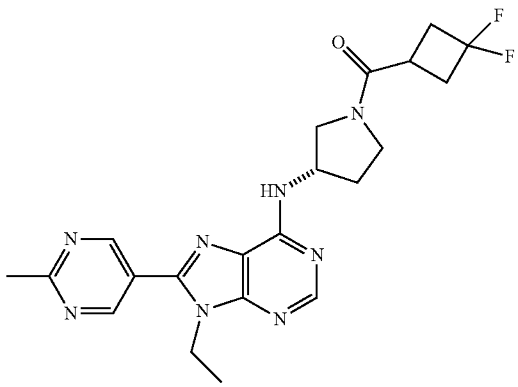 | (S)-(3,3-difluorocyclobutyl)(3-((9-ethyl-8-(2-methylpyrimidin-5-yl)-9H-purin-6-yl)amino)pyrrolidin-1-yl)methanone | Calc'd 443, found 443 |
| 2-25 | 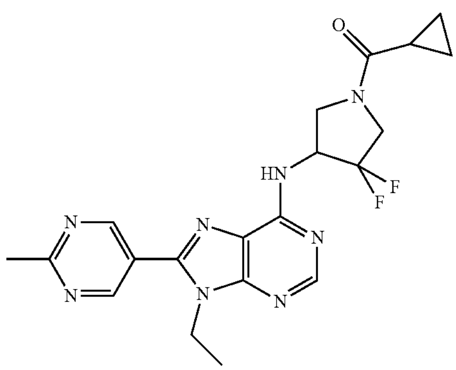 [SMILES: CCn1c(-c2cnc(C)nc2)nc2c(NC3CN(C(=O)C4CC4)CC3(F)F)ncnc21] | N-[(3S and 3R)-1-(cyclopropylcarbonyl)-4,4-difluoropyrrolidin-3-yl]-9-ethyl-8-(2-methylpyrimidin-5-yl)-9H-purin-6-amine | Calc'd 429, found 429 |
| 2-26 | 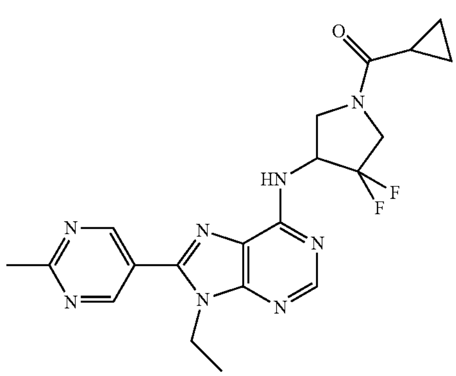 [SMILES: CCn1c(-c2cnc(C)nc2)nc2c(NC3CN(C(=O)C4CC4)CC3(F)F)ncnc21] | N-[(3S or 3R)-1-(cyclopropylcarbonyl)-4,4-difluoropyrrolidin-3-yl]-9-ethyl-8-(2-methylpyrimidin-5-yl)-9H-purin-6-amine | Calc'd 429, found 429 |
| 2-27 | 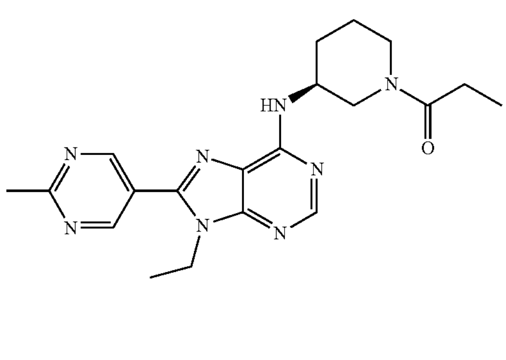 [SMILES: CCC(=O)N1CCC[C@H](Nc2ncnc3c2nc(-c2cnc(C)nc2)n3CC)C1] | 9-ethyl-8-(2-methylpyrimidin-5-yl)-N-[(3S)-1-propanoylpiperidin-3-yl]-9H-purin-6-amine | Calc'd 395, found 395 |

TABLE 2-continued

| Compound | Structure | Compound Name | MS [M + H]+ |
|---|---|---|---|
| 2-28 | 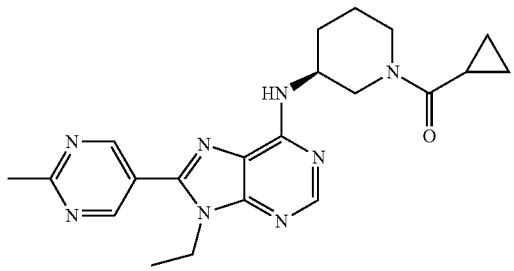 [SMILES: CCn1c(-c2cnc(C)nc2)nc2c(N[C@H]3CCCN(C(=O)C4CC4)C3)ncnc21] | N-[(3S)-1-(cyclopropylcarbonyl)piperidin-3-yl]-9-ethyl-8-(2-methylpyrimn-5-yl)-9H-purin-6-amine | Calc'd 407, found 407 |
| 2-29 | 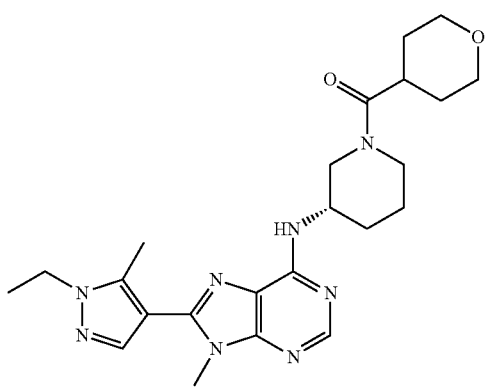 [SMILES: CCn1ncc(-c2nc3c(N[C@H]4CCCN(C(=O)C5CCOCC5)C4)ncnc3n2C)c1C] | 8-(1-ethyl-5-methyl-1H-pyrazol-4-yl)-9-methyl-N-[(3S)-1-(tetrahydro-2H-pyran-4-ylcarbonyl)piperidin-3-yl]-9H-purin-6-amine | Calc'd 453, found 453 |
| 2-30 | 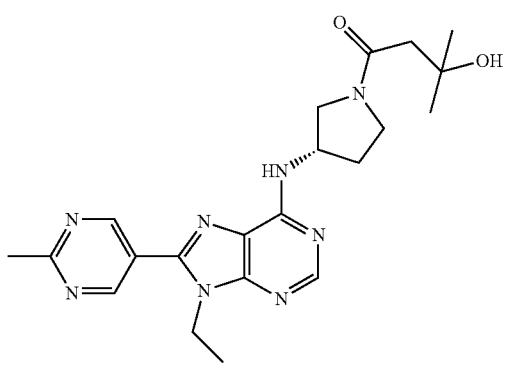 [SMILES: CCn1c(-c2cnc(C)nc2)nc2c(N[C@H]3CCN(C(=O)CC(C)(C)O)C3)ncnc21] | 4-[(3S)-3-{[9-ethyl-8-(2-methylpyrimidin-5-yl)-9H-purin-6-yl]amino}pyrrolidin-1-yl]-2-methyl-4-oxobutan-2-ol | Calc'd 425, found 425 |
| 2-31 | 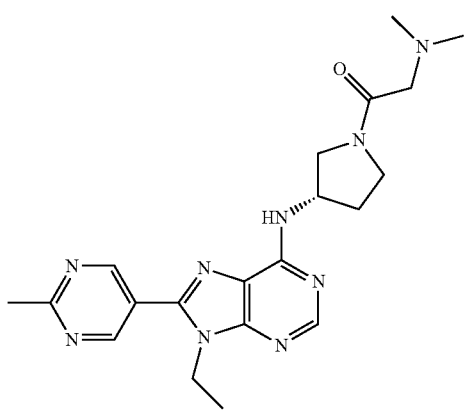 | N-{(3S)-1-[(dimethylamino)acetyl]pyrrolidin-3-yl}-9-ethyl-8-(2-methylpyrimidin-5-yl)-9H-purin-6-amine | Calc'd 410, found 410 |

TABLE 2-continued

| Compound | Structure | Compound Name | MS [M + H]+ |
|---|---|---|---|
| 2-32 | 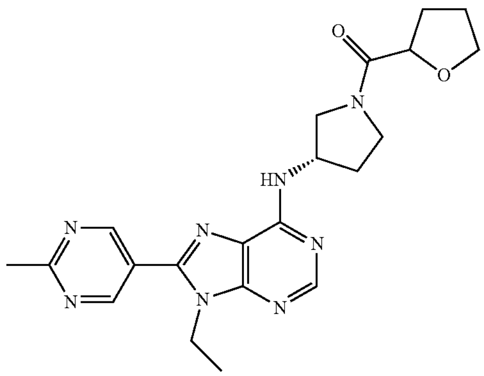 | 9-ethyl-8-(2-methylpyrimidin-5-yl)-N-[(3S)-1-((S or R)-tetrahydrofuran-2-ylcarbonyl)pyrrolidin-3-yl]-9H-purin-6-amine | Calc'd 423, found 423 |
| 2-33 | 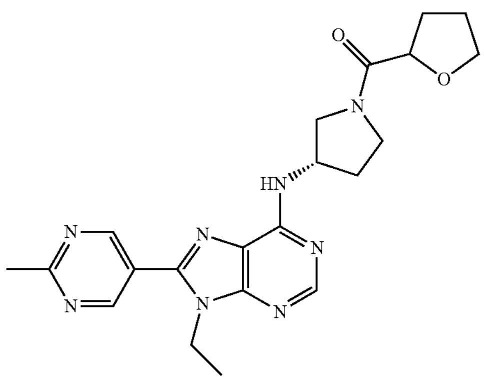 [SMILES: CCn1c(-c2cnc(C)nc2)nc2c(N[C@H]3CCN(C(=O)C4CCCO4)C3)ncnc21] | 9-ethyl-8-(2-methylpyrimidin-5-yl)-N-[(3S)-1-((R or S)-tetrahydrofuran-2-ylcarbonyl)pyrrolidin-3-yl]-9H-purin-6-amine | Calc'd 423, found 423 |
| 2-34 | 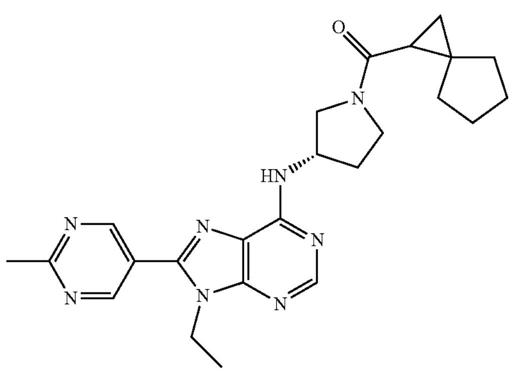 [SMILES: CCn1c(-c2cnc(C)nc2)nc2c(N[C@H]3CCN(C(=O)C4CC45CCCC5)C3)ncnc21] | 9-ethyl-8-(2-methylpyrimidin-5-yl)-N-[(3S)-1-((R or S)-spiro[2.4]hept-1-ylcarbonyl)pyrrolidin-3-yl]-9H-purin-6-amine | Calc'd 447, found 447 |
| 2-35 | 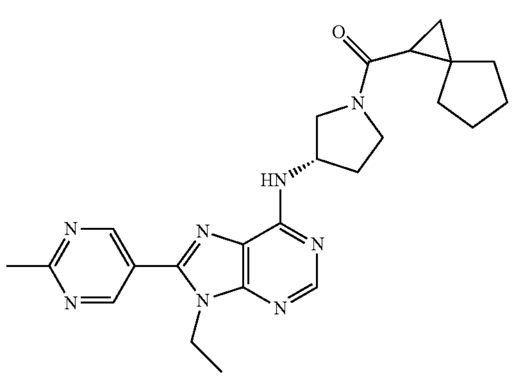 [SMILES: CCn1c(-c2cnc(C)nc2)nc2c(N[C@H]3CCN(C(=O)C4CC45CCCC5)C3)ncnc21] | 9-ethyl-8-(2-methylpyrimidin-5-yl)-N-[(3S)-1-((R or S)-spiro[2.4]hept-1-ylcarbonyl)pyrrolidin-3-yl]-9H-purin-6-amine | Calc'd 447, found 447 |

TABLE 2-continued

| Compound | Structure | Compound Name | MS [M + H]+ |
|---|---|---|---|
| 2-36 | 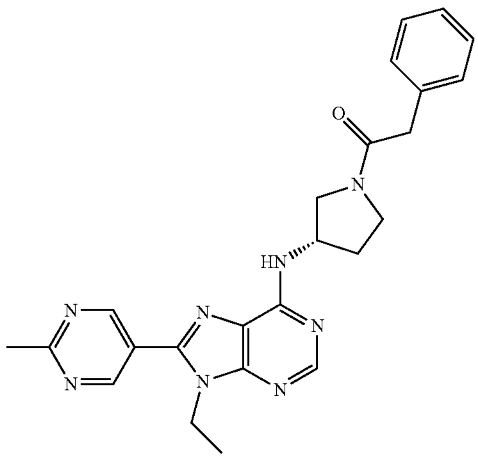 [SMILES: CCn1c(-c2cnc(C)nc2)nc2c(N[C@H]3CCN(C(=O)Cc4ccccc4)C3)ncnc21] | 9-ethyl-8-(2-methylpyrimidin-5-yl)-N-[(3S)-1-(phenylacetyl)pyrrolidin-3-yl]-9H-purin-6-amine | Calc'd 443, found 443 |
| 2-37 | 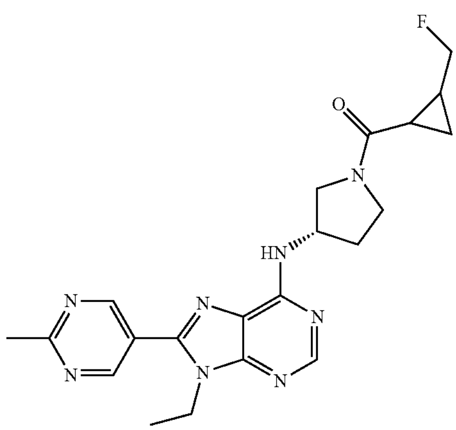 [SMILES: CCn1c(-c2cnc(C)nc2)nc2c(N[C@H]3CCN(C(=O)C4CC4CF)C3)ncnc21] | ((S)-3-((9-ethyl-8-(2-methylpyrimidin-5-yl)-9H-purin-6-yl)amino)pyrrolidin-1-yl)((1S,2S and 1R,2R)-2-(fluoromethyl)cyclopropyl)methanone | Calc'd 425, found 425 |
| 2-38 | 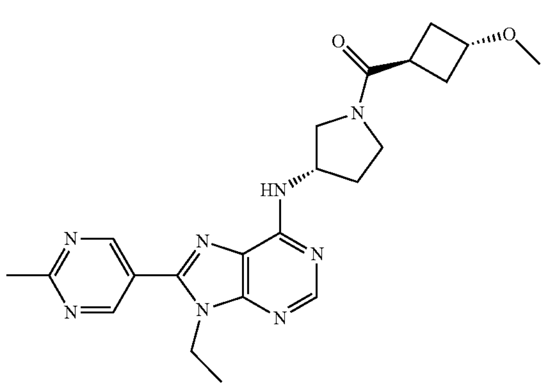 | 9-ethyl-N-{(3S)-1-[(trans-3-methoxycyclobutyl)carbonyl]pyrrolidin-3-yl}-8-(2-methylpyrimidin-5-yl)-9H-purin-6-amine | Calc'd 437, found 437 |

TABLE 2-continued

| Compound | Compound Name | MS [M + H]+ |
|---|---|---|
| 2-39 | 9-ethyl-N-{(3S)-1-[(cis-3-methoxycyclobutyl)carbonyl]pyrrolidin-3-yl}-8-(2-methylpyrimidin-5-yl)-9H-purin-6-amine | Calc'd 437, found 437 |
| 2-40 | 9-ethyl-8-(2-methylpyrimidin-5-yl)-N-{(3S)-1-[(3R)-tetrahydrofuran-3-ylcarbonyl]pyrrolidin-3-yl}-9H-purin-6-amine | Calc'd 423, found 423 |
| 2-41 | 9-ethyl-8-(2-methylpyrimidin-5-yl)-N-{(3S)-1-[(3S)-tetrahydrofuran-3-ylcarbonyl]pyrrolidin-3-yl}-9H-purin-6-amine | Calc'd 423, found 423 |
| 2-42 | 9-ethyl-N-[(3S)-1-(1-methyl-D-prolyl)pyrrolidin-3-yl]-8-(2-methylpyrimidin-5-yl)-9H-purin-6-amine | Calc'd 436, found 436 |

TABLE 2-continued

| Compound | Structure | Compound Name | MS [M + H]+ |
|---|---|---|---|
| 2-43 | 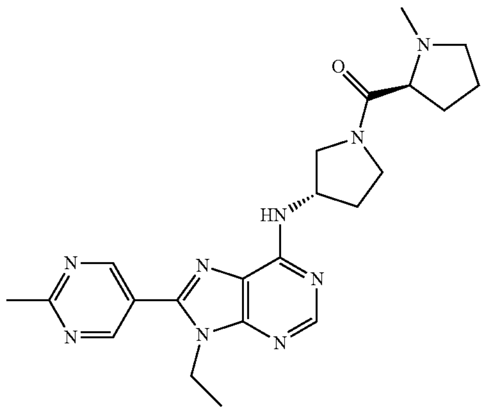 [SMILES: CCn1c(-c2cnc(C)nc2)nc2c(N[C@H]3CCN(C(=O)[C@@H]4CCCN4C)C3)ncnc21] | 9-ethyl-N-[(3S)-1-(1-methyl-L-prolyl)pyrrolidin-3-yl]-8-(2-methylpyrimidin-5-yl)-9H-purin-6-amine | Calc'd 436, found 436 |
| 2-44 | 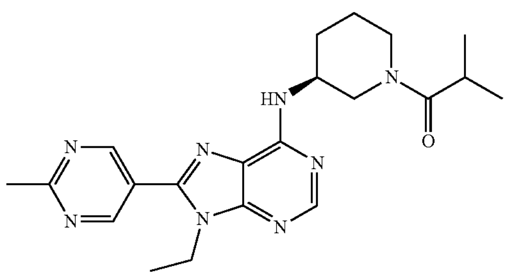 [SMILES: CCn1c(-c2cnc(C)nc2)nc2c(N[C@H]3CCCN(C(=O)C(C)C)C3)ncnc21] | 9-ethyl-N-[(3S)-1-(2-methylpropanoyl)piperidin-3-yl]-8-(2-methylpyrimidin-5-yl)-9H-purin-6-amine | Calc'd 409, found 409 |
| 2-45 | 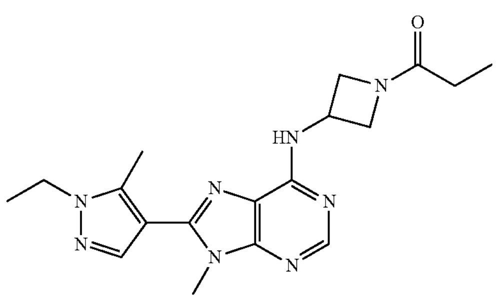 [SMILES: CCC(=O)N1CC(Nc2ncnc3c2nc(-c2cnn(CC)c2C)n3C)C1] | 8-(1-ethyl-5-methyl-1H-pyrazol-4-yl)-9-methyl-N-(1-propanoylazetidin-3-yl)-9H-purin-6-amine | Calc'd 369, found 369 |
| 2-46 | 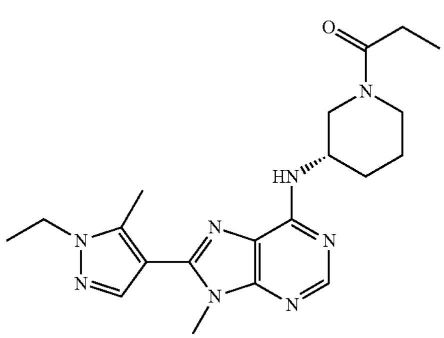 [SMILES: CCC(=O)N1CCC[C@H](Nc2ncnc3c2nc(-c2cnn(CC)c2C)n3C)C1] | 8-(1-ethyl-5-methyl-1H-pyrazol-4-yl)-9-methyl-N-[(3S)-1-propanoylpiperidin-3-yl]-9H-purin-6-amine | Calc'd 397, found 397 |

TABLE 2-continued

| Compound | Structure | Compound Name | MS [M + H]⁺ |
|---|---|---|---|
| 2-47 | 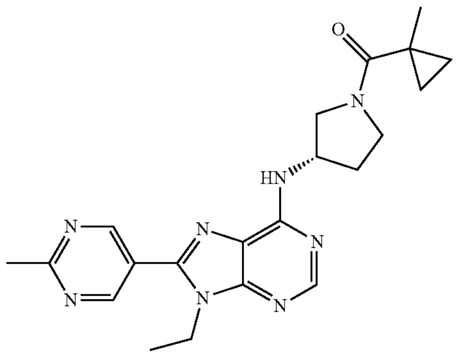 [SMILES: CCn1c(-c2cnc(C)nc2)nc2c(N[C@H]3CCN(C(=O)C4(C)CC4)C3)ncnc21] | 9-ethyl-N-{(3S)-1-[(1-methylcyclopropyl)carbonyl]pyrrolidin-3-yl}-8-(2-methylpyrimidin-5-yl)-9H-purin-6-amine | Calc'd 407, found 407 |
| 2-48 | 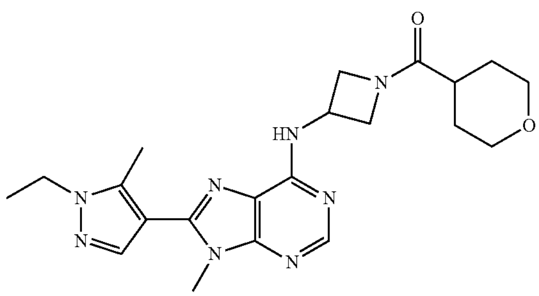 [SMILES: CCn1ncc(-c2nc3c(NC4CN(C(=O)C5CCOCC5)C4)ncnc3n2C)c1C] | 8-(1-ethyl-5-methyl-1H-pyrazol-4-yl)-9-methyl-N-[1-(tetrahydro-2H-pyran-4-ylcarbonyl)azetidin-3-yl]-9H-purin-6-amine | Calc'd 425, found 425 |
| 2-49 | 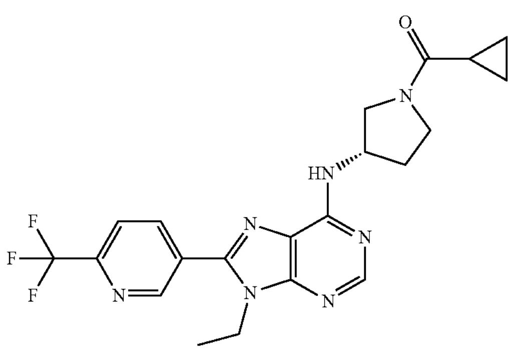 [SMILES: CCn1c(-c2ccc(C(F)(F)F)nc2)nc2c(N[C@H]3CCN(C(=O)C4CC4)C3)ncnc21] | N-[(3S)-1-(cyclopropylcarbonyl)pyrrolidin-3-yl]-9-ethyl-8-[6-(trifluoromethyl)pyridin-3-yl]-9H-purin-6-amine | Calc'd 446, found 446 |
| 2-50 | 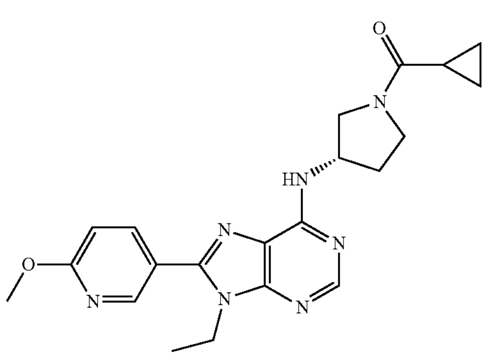 [SMILES: CCn1c(-c2ccc(OC)nc2)nc2c(N[C@H]3CCN(C(=O)C4CC4)C3)ncnc21] | N-[(3S)-1-(cyclopropylcarbonyl)pyrrolidin-3-yl]-9-ethyl-8-(6-methoxypyridin-3-yl)-9H-purin-6-amine | Calc'd 408, found 408 |

TABLE 2-continued

| Compound | Structure | Compound Name | MS [M + H]+ |
|---|---|---|---|
| 2-51 | 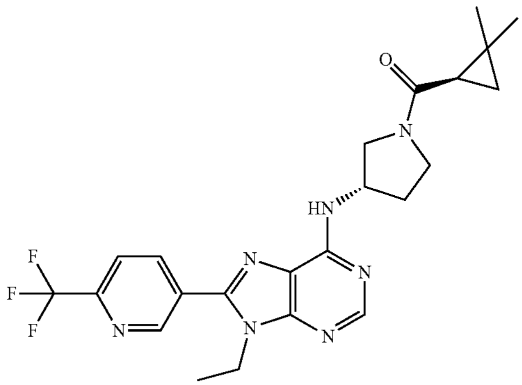 [SMILES: CCn1c(-c2ccc(C(F)(F)F)nc2)nc2c(N[C@H]3CCN(C(=O)[C@@H]4CC4(C)C)C3)ncnc21] | N-[(3S)-1-{[(1R)-2,2-dimethylcyclopropyl]carbonyl}pyrrolidin-3-yl]-9-ethyl-8-[6-(trifluoromethyl)pyridin-3-yl]-9H-purin-6-amine | Calc'd 474, found 474 |
| 2-52 | 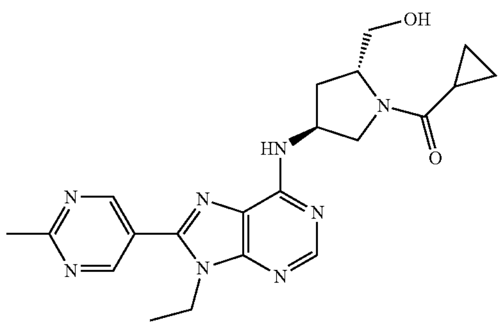 [SMILES: CCn1c(-c2cnc(C)nc2)nc2c(N[C@H]3C[C@H](CO)N(C(=O)C4CC4)C3)ncnc21] | [(2R,4S)-1-(cyclopropylcarbonyl)-4-{[9-ethyl-8-(2-methylpyrimidin-5-yl)-9H-purin-6-yl]amino}pyrrolidin-2-yl]methanol | Calc'd 423, found 423 |
| 2-53 | 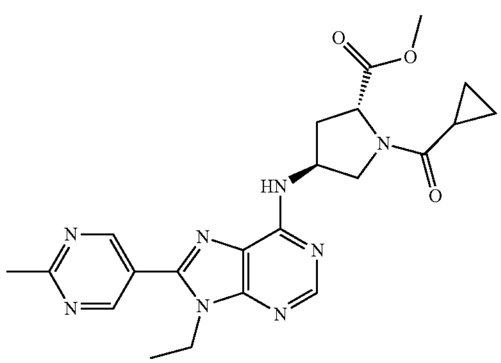 [SMILES: CCn1c(-c2cnc(C)nc2)nc2c(N[C@H]3C[C@H](C(=O)OC)N(C(=O)C4CC4)C3)ncnc21] | methyl (4S)-1-(cyclopropylcarbonyl)-4-{[9-ethyl-8-(2-methylpyrimidin-5-yl)-9H-purin-6-yl]amino}-D-prolinate | Calc'd 451, found 451 |
| 2-54 | 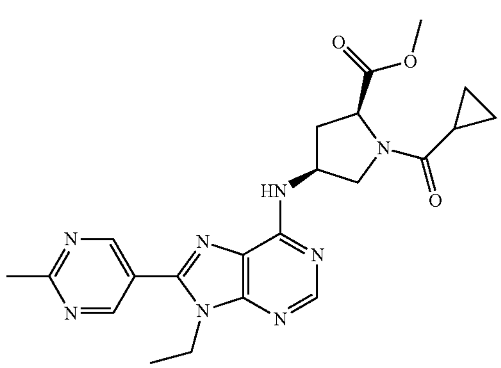 [SMILES: CCn1c(-c2cnc(C)nc2)nc2c(N[C@H]3C[C@@H](C(=O)OC)N(C(=O)C4CC4)C3)ncnc21] | methyl (4S)-1-(cyclopropylcarbonyl)-4-{[9-ethyl-8-(2-methylpyrimidin-5-yl)-9H-purin-6-yl]amino}-L-prolinate | Calc'd 451, found 451 |

TABLE 2-continued

| Compound | Structure | Compound Name | MS [M + H]+ |
|---|---|---|---|
| 2-55 | 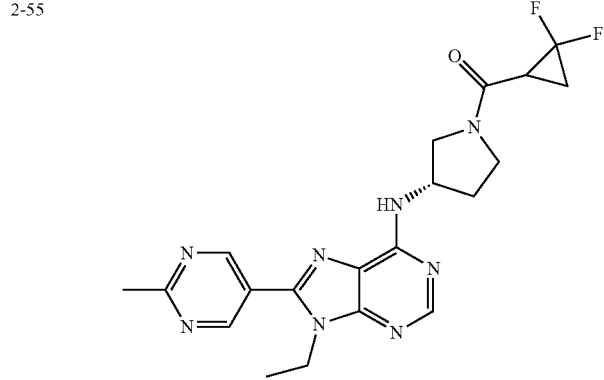 | N-{(3S)-1-[((R and S)-2,2-difluorocyclopropyl)carbonyl]pyrrolidin-3-yl}-9-ethyl-8-(2-methylpyrimidin-5-yl)-9H-purin-6-amine | Calc'd 429, found 429 |
| 2-56 | 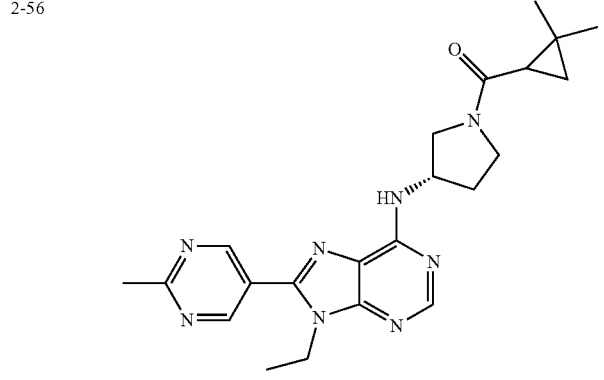 | N-{(3S)-1-[((R and S)-2,2-dimethylcyclopropyl)carbonyl]pyrrolidin-3-yl}-9-ethyl-8-(2-methylpyrimidin-5-yl)-9H-purin-6-amine | Calc'd 421, found 421 |
| 2-57 | 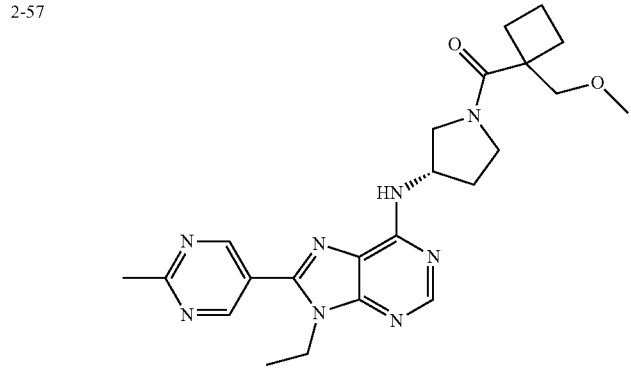 | 9-ethyl-N-[(3S)-1-{[1-(methoxymethyl)cyclobutyl]carbonyl}pyrrolidin-3-yl]-8-(2-methylpyrimidin-5-yl)-9H-purin-6-amine | Calc'd 451, found 451 |
| 2-58 | 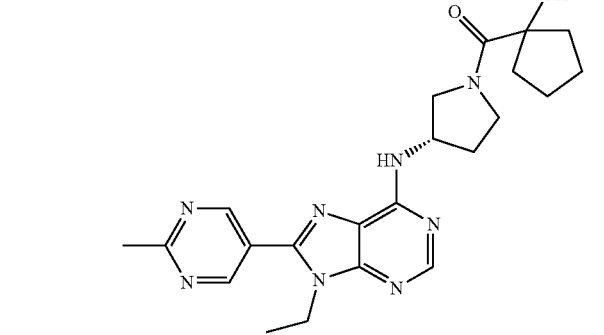 | 1-{[(3S)-3-{[9-ethyl-8-(2-methylpyrimidin-5-yl)-9H-purin-6-yl]amino}pyrrolidin-1-yl]carbonyl}cyclopentanol | Calc'd 437, found 437 |

TABLE 2-continued

| Compound | Structure | Compound Name | MS [M + H]+ |
|---|---|---|---|
| 2-59 | 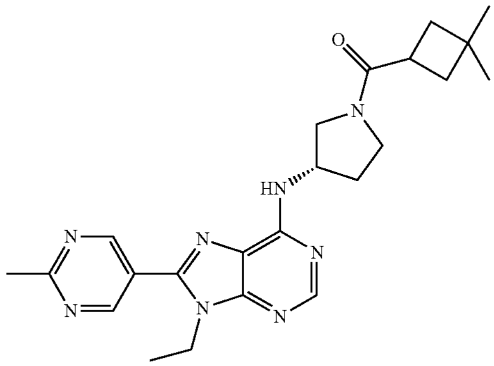 | N-{(3S)-1-[(3,3-dimethylcyclobutyl)carbonyl]pyrrolidin-3-yl}-9-ethyl-8-(2-methylpyrimidin-5-yl)-9H-purin-6-amine | Calc'd 435, found 435 |
| 2-60 | 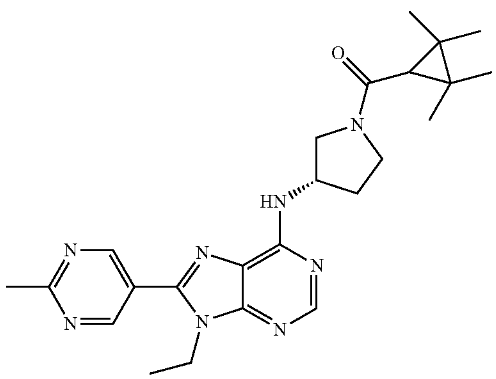 | 9-ethyl-8-(2-methylpyrimidin-5-yl)-N-{(3S)-1-[(2,2,3,3-tetramethylcyclopropyl)carbonyl]pyrrolidin-3-yl}-9H-purin-6-amine | Calc'd 449, found 449 |
| 2-61 | 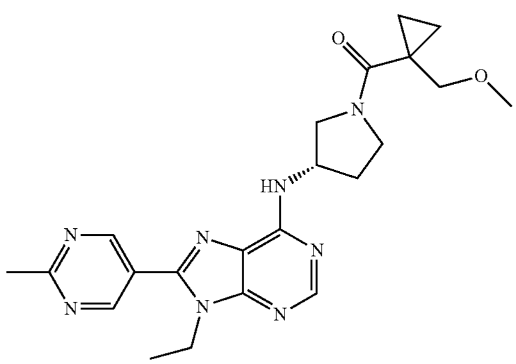 | 9-ethyl-N-[(3S)-1-{[1-(methoxymethyl)cyclopropyl]carbonyl}pyrrolidin-3-yl]-8-(2-methylpyrimidin-5-yl)-9H-purin-6-amine | Calc'd 437, found 437 |
| 2-62 | 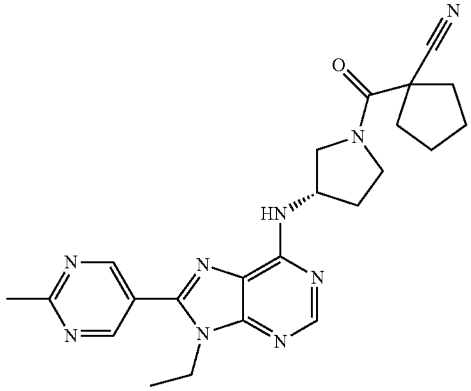 [SMILES: CCn1c(-c2cnc(C)nc2)nc2c(N[C@H]3CCN(C(=O)C4(C#N)CCCC4)C3)ncnc21] | 1-{[(3S)-3-{[9-ethyl-8-(2-methylpyrimidin-5-yl)-9H-purin-6-yl]amino}pyrrolidin-1-yl]carbonyl}cyclopentanecarbonitrile | Calc'd 446, found 446 |

TABLE 2-continued

| Compound | Structure | Compound Name | MS [M + H]+ |
|---|---|---|---|
| 2-63 | 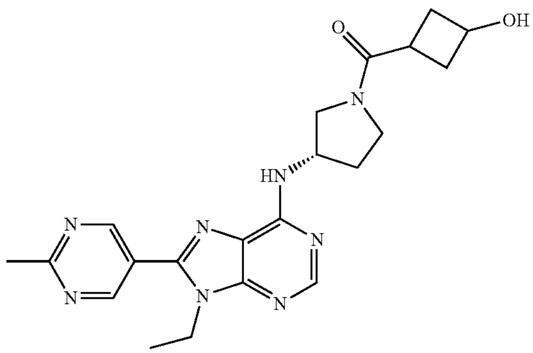 [SMILES: CCn1c(-c2cnc(C)nc2)nc2c(N[C@H]3CCN(C(=O)C4CC(O)C4)C3)ncnc21] | (cis and trans)-3-{[(3S)-3-{[9-ethyl-8-(2-methylpyrimidin-5-yl)-9H-purin-6-yl]amino}pyrrolidin-1-yl]carbonyl}cyclobutanol | Calc'd 423, found 423 |
| 2-64 | 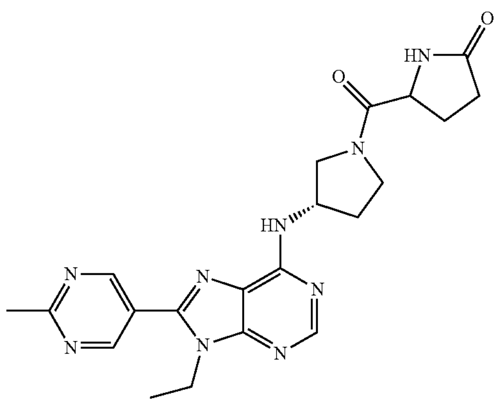 [SMILES: CCn1c(-c2cnc(C)nc2)nc2c(N[C@H]3CCN(C(=O)C4CCC(=O)N4)C3)ncnc21] | (R and S)-5-{[(3S)-3-{[9-ethyl-8-(2-methylpyrimidin-5-yl)-9H-purin-6-yl]amino}pyrrolidin-1-yl]carbonyl}pyrrolidin-2-one | Calc'd 436, found 436 |
| 2-65 | 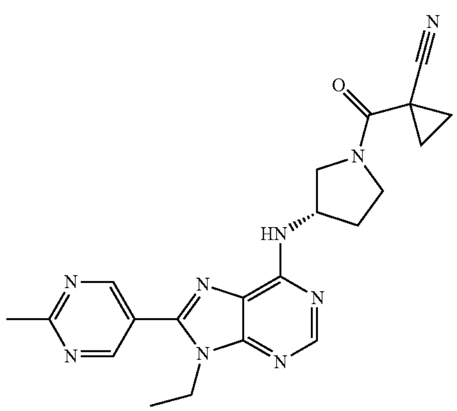 [SMILES: CCn1c(-c2cnc(C)nc2)nc2c(N[C@H]3CCN(C(=O)C4(C#N)CC4)C3)ncnc21] | 1-{[(3S)-3-{[9-ethyl-8-(2-methylpyrimidin-5-yl)-9H-purin-6-yl]amino}pyrrolidin-1-yl]carbonyl}cyclopropanecarbonitrile | Calc'd 418, found 418 |
| 2-66 | 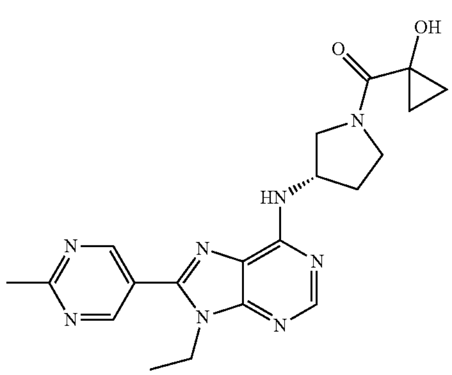 [SMILES: CCn1c(-c2cnc(C)nc2)nc2c(N[C@H]3CCN(C(=O)C4(O)CC4)C3)ncnc21] | 1-{[(3S)-3-{[9-ethyl-8-(2-methylpyrimidin-5-yl)-9H-purin-6-yl]amino}pyrrolidin-1-yl]carbonyl}cyclopropanol | Calc'd 409, found 409 |

TABLE 2-continued

| Compound | Compound Name | MS [M + H]+ |
|---|---|---|
| 2-67 | (R and S)-4-{[(3S)-3-{[9-ethyl-8-(2-methylpyrimidin-5-yl)-9H-purin-6-yl]amino}pyrrolidin-1-yl]carbonyl}-3,3-dimethylazetidin-2-one | Calc'd 450, found 450 |
| 2-68 | 9-ethyl-8-(2-methylpyrimidin-5-yl)-N-{(3S)-1-[((S and R)-2-methyltetrahydrofuran-2-yl)carbonyl]pyrrolidin-3-yl}-9H-purin-6-amine | Calc'd 437, found 437 |
| 2-69 | [(3S)-3-{[9-ethyl-8-(2-methylpyrimidin-5-yl)-9H-purin-6-yl]amino}pyrrolidin-1-yl](1-methyl-1H-imidazol-5-yl)methanone | Calc'd 433, found 433 |
| 2-70 | 9-ethyl-N-{(3S)-1-[(5-methylisoxazol-3-yl)carbonyl]pyrrolidin-3-yl}-8-(2-methylpyrimidin-5-yl)-9H-purin-6-amine | Calc'd 434, found 434 |

TABLE 2-continued

| Compound | Structure | Compound Name | MS [M + H]+ |
|---|---|---|---|
| 2-71 | 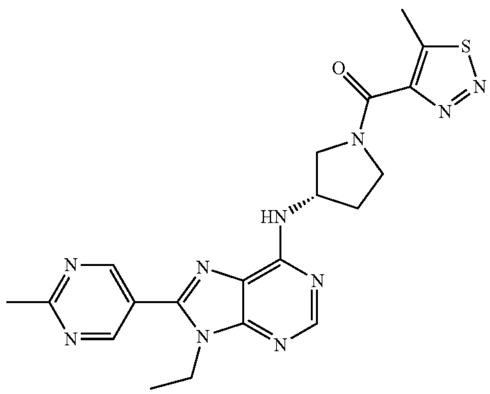 [SMILES: CCn1c(-c2cnc(C)nc2)nc2c(N[C@H]3CCN(C(=O)c4nnsc4C)C3)ncnc21] | 9-ethyl-8-(2-methylpyrimidin-5-yl)-N-{(3S)-1-[(5-methyl-1,2,3-thiadiazol-4-yl)carbonyl]pyrrolidin-3-yl}-9H-purin-6-amine | Calc'd 451, found 451 |
| 2-72 | 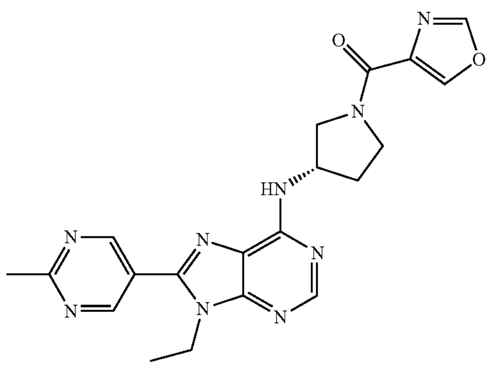 [SMILES: CCn1c(-c2cnc(C)nc2)nc2c(N[C@H]3CCN(C(=O)c4cocn4)C3)ncnc21] | 9-ethyl-8-(2-methylpyrimidin-5-yl)-N-[(3S)-1-(1,3-oxazol-4-ylcarbonyl)pyrrolidin-3-yl]-9H-purin-6-amine | Calc'd 420, found 420 |
| 2-73 | 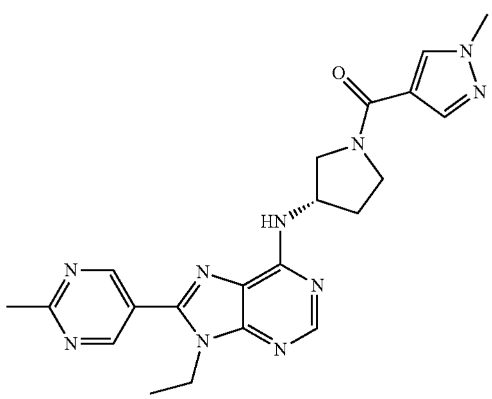 | 9-ethyl-N-{(3S)-1-[(1-methyl-1H-pyrazol-4-yl)carbonyl]pyrrolidin-3-yl}-8-(2-methylpyrimidin-5-yl)-9H-purin-6-amine | Calc'd 433, found 433 |
| 2-74 | 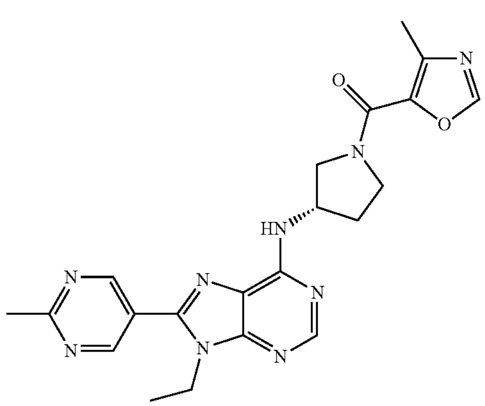 [SMILES: CCn1c(-c2cnc(C)nc2)nc2c(N[C@H]3CCN(C(=O)c4ocnc4C)C3)ncnc21] | 9-ethyl-N-{(3S)-1-[(4-methyl-1,3-oxazol-5-yl)carbonyl]pyrrolidin-3-yl}-8-(2-methylpyrimidin-5-yl)-9H-purin-6-amine | Calc'd 434, found 434 |

TABLE 2-continued

| Compound | Compound Name | MS [M + H]+ |
|---|---|---|
| 2-75 | 9-ethyl-8-(2-methylpyrimidin-5-yl)-N-{(3S)-1-[(1-methyl-1H-1,2,3-triazol-4-yl)carbonyl]pyrrolidin-3-yl}-9H-purin-6-amine | Calc'd 434, found 434 |
| 2-76 | 9-ethyl-8-(2-methylpyrimidin-5-yl)-N-[(3S)-1-(1,3-oxazol-5-ylcarbonyl)pyrrolidin-3-yl]-9H-purin-6-amine | Calc'd 420, found 420 |
| 2-77 | N-[(3S)-1-(bicyclo[1.1.1]pent-1-ylcarbonyl)pyrrolidin-3-yl]-9-ethyl-8-(2-methylpyrimidin-5-yl)-9H-purin-6-amine | Calc'd 419, found 419 |
| 2-78 | 9-ethyl-8-(2-methylpyrimidin-5-yl)-N-[(3S)-1-(piperidin-4-ylcarbonyl)pyrrolidin-3-yl]-9H-purin-6-amine | Calc'd 436, found 436 |

TABLE 2-continued

| Compound | Structure | Compound Name | MS [M + H]+ |
|---|---|---|---|
| 2-79 | 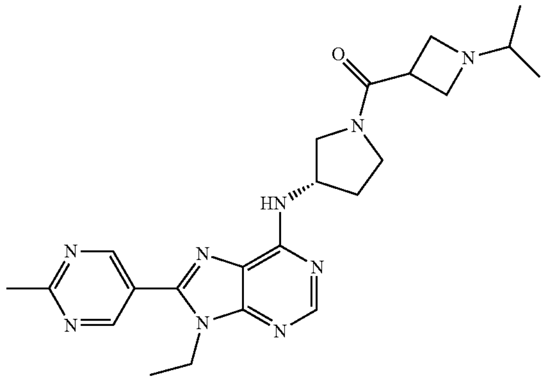 [SMILES: CCn1c(-c2cnc(C)nc2)nc2c(N[C@H]3CCN(C(=O)C4CN(C(C)C)C4)C3)ncnc21] | 9-ethyl-N-[(3S)-1-{[1-(1-methylethyl)azetidin-3-yl]carbonyl}pyrrolidin-3-yl]-8-(2-methylpyrimidin-5-yl)-9H-purin-6-amine | Calc'd 450, found 450 |
| 2-80 | 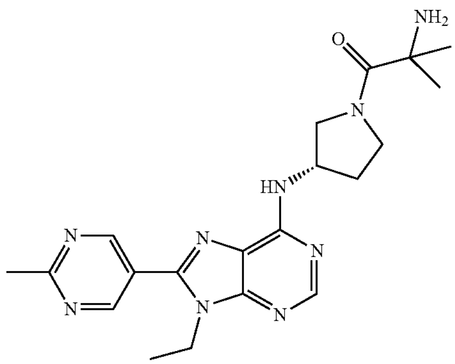 [SMILES: CCn1c(-c2cnc(C)nc2)nc2c(N[C@H]3CCN(C(=O)C(C)(C)N)C3)ncnc21] | N-[(3S)-1-(2-amino-2-methylpropanoyl)pyrrolidin-3-yl]-9-ethyl-8-(2-methylpyrimidin-5-yl)-9H-purin-6-amine | Calc'd 410, found 410 |
| 2-81 | 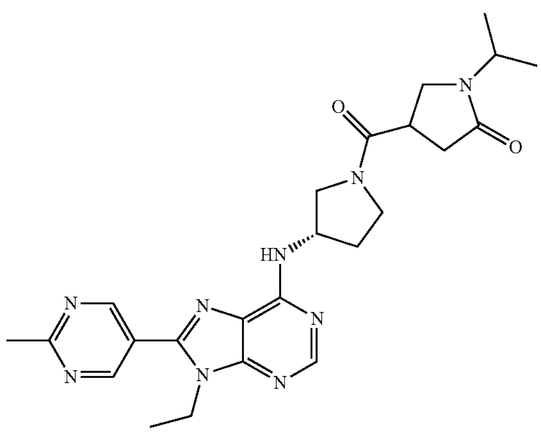 [SMILES: CCn1c(-c2cnc(C)nc2)nc2c(N[C@H]3CCN(C(=O)C4CC(=O)N(C(C)C)C4)C3)ncnc21] | (R and S)-4-{[(3S)-3-{[9-ethyl-8-(2-methylpyrimidin-5-yl)-9H-purin-6-yl]amino}pyrrolidin-1-yl]carbonyl}-1-(1-methylethyl)pyrrolidin-2-one | Calc'd 478, found 478 |
| 2-82 | 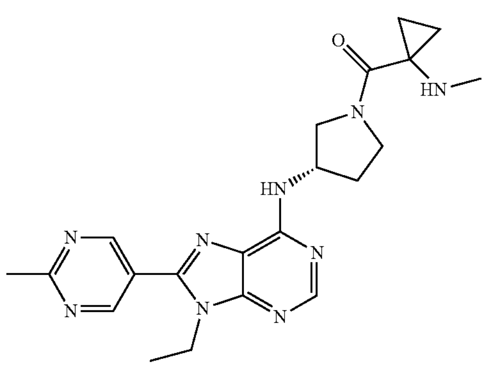 | 9-ethyl-N-[(3S)-1-{[1-(methylamino)cyclopropyl]carbonyl}pyrrolidin-3-yl]-8-(2-methylpyrimidin-5-yl)-9H-purin-6-amine | Calc'd 422, found 422 |

TABLE 2-continued

| Compound | Structure | Compound Name | MS [M + H]+ |
|---|---|---|---|
| 2-83 | 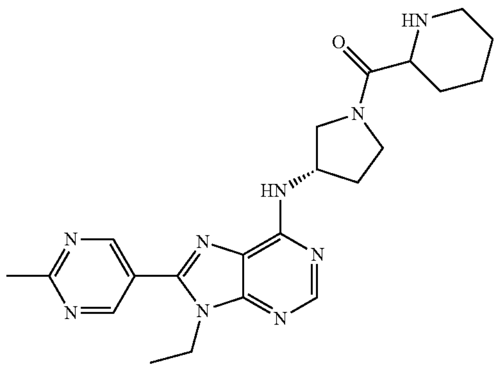 [SMILES: CCn1c(-c2cnc(C)nc2)nc2c(N[C@H]3CCN(C(=O)C4CCCCN4)C3)ncnc21] | 9-ethyl-8-(2-methylpyrimidin-5-yl)-N-[(3S)-1-((R and S)-piperidin-2-ylcarbonyl)pyrrolidin-3-yl]-9H-purin-6-amine | Calc'd 436, found 436 |
| 2-84 | 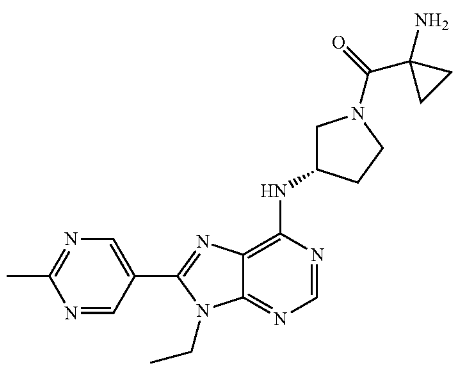 [SMILES: CCn1c(-c2cnc(C)nc2)nc2c(N[C@H]3CCN(C(=O)C4(N)CC4)C3)ncnc21] | N-{(3S)-1-[(1-aminocyclopropyl)carbonyl]pyrrolidin-3-yl}-9-ethyl-8-(2-methylpyrimidin-5-yl)-9H-purin-6-amine | Calc'd 408, found 408 |
| 2-85 | 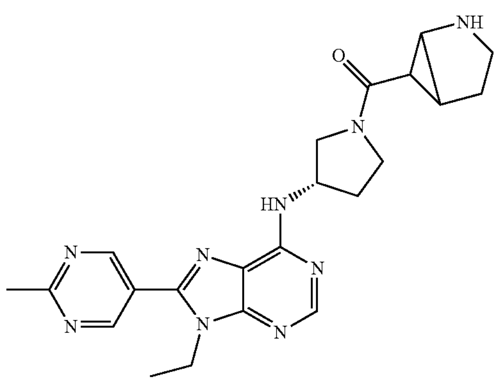 [SMILES: CCn1c(-c2cnc(C)nc2)nc2c(N[C@H]3CCN(C(=O)C4C5CCNC54)C3)ncnc21] | N-[(3S)-1-(1(R and S), 5(R and S), 6(R and S)-2-azabicyclo[3.1.0]hex-6-ylcarbonyl)pyrrolidin-3-yl]-9-ethyl-8-(2-methylpyrimidin-5-yl)-9H-purin-6-amine | Calc'd 434, found 434 |
| 2-86 | 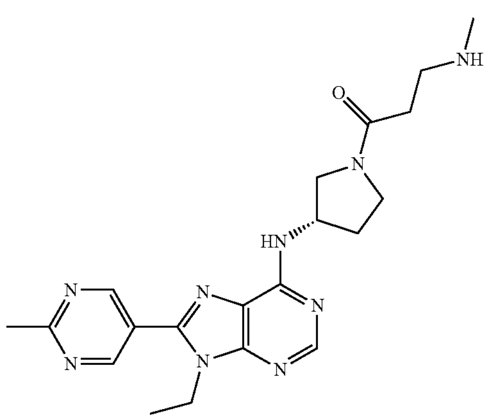 | 9-ethyl-N-{(3S)-1-[3-(methylamino)propanoyl]pyrrolidin-3-yl}-8-(2-methylpyrimidin-5-yl)-9H-purin-6-amine | Calc'd 410, found 410 |

TABLE 2-continued

| Compound | Structure | Compound Name | MS [M + H]+ |
|---|---|---|---|
| 2-87 | 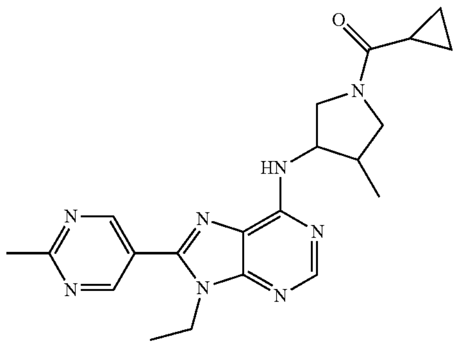 [SMILES: CCn1c(-c2cnc(C)nc2)nc2c(NC3CN(C(=O)C4CC4)CC3C)ncnc21] | N-[(3S,4R or 3R,4S)-1-(cyclopropylcarbonyl)-4-methylpyrrolidin-3-yl]-9-ethyl-8-(2-methylpyrimidin-5-yl)-9H-purin-6-amine | Calc'd 407, found 407 |
| 2-88 | 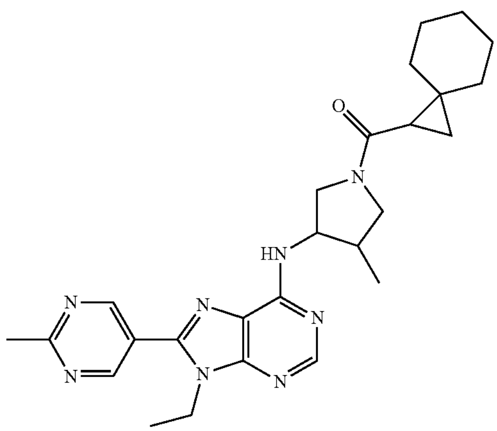 [SMILES: CCn1c(-c2cnc(C)nc2)nc2c(NC3CN(C(=O)C4CC45CCCCC5)CC3C)ncnc21] | 9-ethyl-8-(2-methylpyrimidin-5-yl)-N-[(3S,4R or 3R,4S)-4-methyl-1-((S and R)-spiro[2.5]oct-1-ylcarbonyl)pyrrolidin-3-yl]-9H-purin-6-amine | Calc'd 475, found 475 |
| 2-89 | 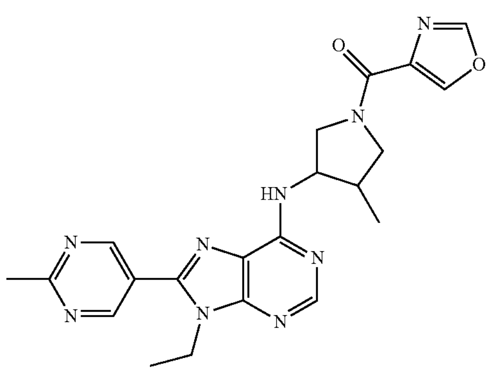 [SMILES: CCn1c(-c2cnc(C)nc2)nc2c(NC3CN(C(=O)c4cocn4)CC3C)ncnc21] | 9-ethyl-N-[-{(3S,4R or 3R,4S)-4-methyl-1-(1,3-oxazol-4-ylcarbonyl)pyrrolidin-3-yl]-8-(2-methylpyrimidin-5-yl)-9H-purin-6-amine | Calc'd 434, found 434 |
| 2-90 | 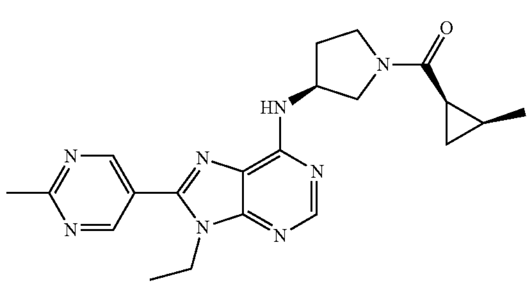 | 9-ethyl-N-[(3S)-1-{[(1R,2S)-2-methylcyclopropyl]carbonyl}pyrrolidin-3-yl]-8(2-methylpyrimidin-5-yl)-9H-purin-6-amine | Calc'd 407, found 407 |

TABLE 2-continued

| Compound | Structure | Compound Name | MS [M + H]+ |
|---|---|---|---|
| 2-91 | 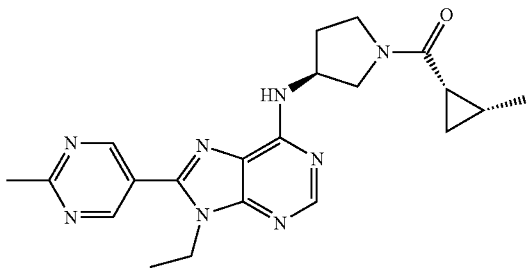 | 9-ethyl-N-[(3S)-1-{[(1S,2R)-2-methylcyclopropyl]carbonyl}pyrrolidin-3-yl]-8-(2-methylpyrimidin-5-yl)-9H-purin-6-amine | Calc'd 407, found 407 |
| 2-92 | 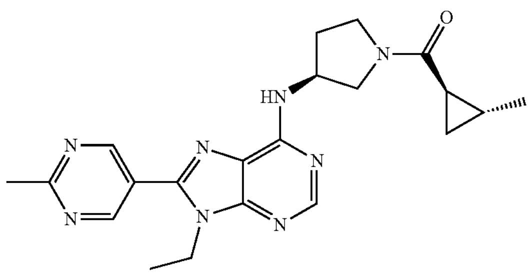 | 9-ethyl-N-[(3S)-1-{[(1R,2R)-2-methylcyclopropyl]carbonyl}pyrrolidin-3-yl]-8-(2-methylpyrimidin-5-yl)-9H-purin-6-amine | Calc'd 407, found 407 |
| 2-93 | 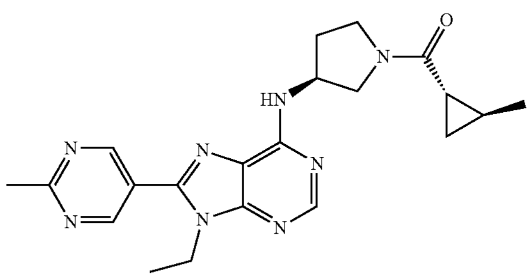 | 9-ethyl-N-[(3S)-1-{[(1S,2S)-2-methylcyclopropyl]carbonyl}pyrrolidin-3-yl]-8-(2-methylpyrimidin-5-yl)-9H-purin-6-amine | Calc'd 407, found 407 |
| 2-94 | 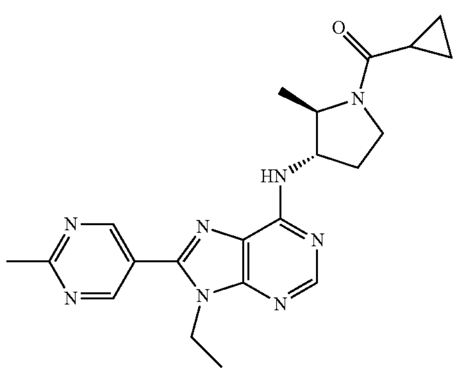 [SMILES: CCn1c(-c2cnc(C)nc2)nc2c(N[C@H]3CCN(C(=O)C4CC4)[C@@H]3C)ncnc21] | N-[(2R,3S)-1-(cyclopropylcarbonyl)-2-methylpyrrolidin-3-yl]-9-ethyl-8-(2-methylpyrimidin-5-yl)-9H-purin-6-amine | Calc'd 407, found 407 |
| 2-95 | 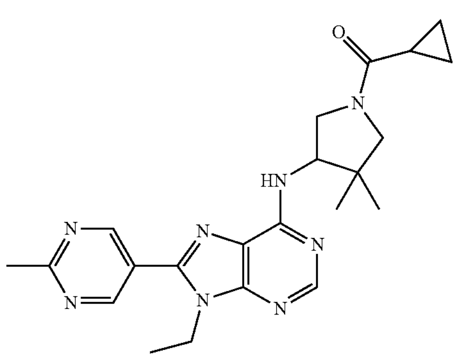 [SMILES: CCn1c(-c2cnc(C)nc2)nc2c(NC3CN(C(=O)C4CC4)CC3(C)C)ncnc21] | (R and S)-N-[1-(cyclopropylcarbonyl)-4,4-dimethylpyrrolidin-3-yl]-9-ethyl-8-(2-methylpyrimidin-5-yl)-9H-purin-6-amine | Calc'd 421, found 421 |

TABLE 2-continued

| Compound | Structure | Compound Name | MS [M + H]+ |
|---|---|---|---|
| 2-96 | 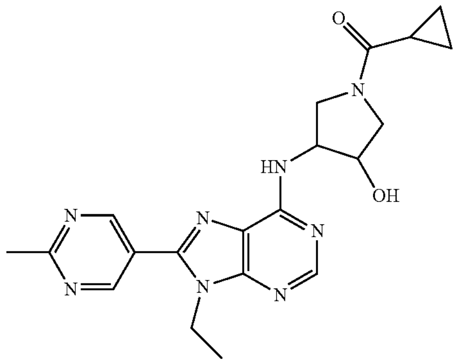 [SMILES: CCn1c(-c2cnc(C)nc2)nc2c(NC3CN(C(=O)C4CC4)CC3O)ncnc21] | 1-(cyclopropylcarbonyl)-4-{(3R,4R) and (3S,4S)-[9-ethyl-8-(2-methylpyrimidin-5-yl)-9H-purin-6-yl]amino}pyrrolidin-3-ol | Calc'd 409, found 409 |
| 2-97 | 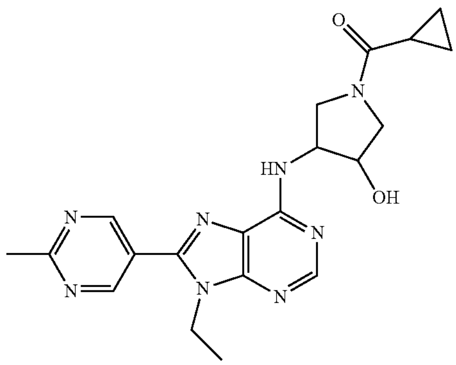 [SMILES: CCn1c(-c2cnc(C)nc2)nc2c(NC3CN(C(=O)C4CC4)CC3O)ncnc21] | 1-(cyclopropylcarbonyl)-4-{(3R,4R) or (3S,4S)-[9-ethyl-8-(2-methylpyrimidin-5-yl)-9H-purin-6-yl]amino}pyrrolidin-3-ol | Calc'd 409, found 409 |
| 2-98 | 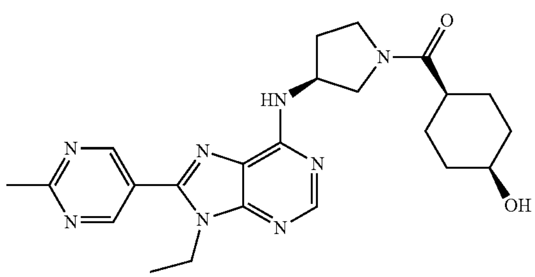 [SMILES: CCn1c(-c2cnc(C)nc2)nc2c(N[C@H]3CCN(C(=O)[C@H]4CC[C@@H](O)CC4)C3)ncnc21] | cis-4-{[(3S)-3-{[9-ethyl-8-(2-methylpyrimidin-5-yl)-9H-purin-6-yl]amino}pyrrolidin-1-yl]carbonyl}cyclohexanol | Calc'd 451, found 451 |
| 2-99 | 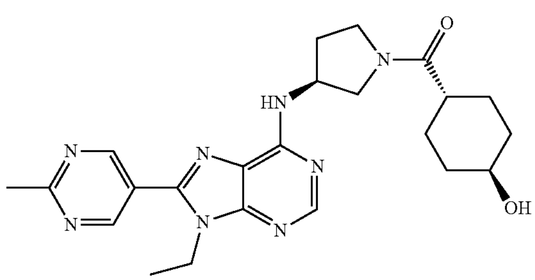 [SMILES: CCn1c(-c2cnc(C)nc2)nc2c(N[C@H]3CCN(C(=O)[C@H]4CC[C@H](O)CC4)C3)ncnc21] | trans-4-{[(3S)-3-{[9-ethyl-8-(2-methylpyrimidin-5-yl)-9H-purin-6-yl]amino}pyrrolidin-1-yl]carbonyl}cyclohexanol | Calc'd 451, found 451 |
| 2-100 | 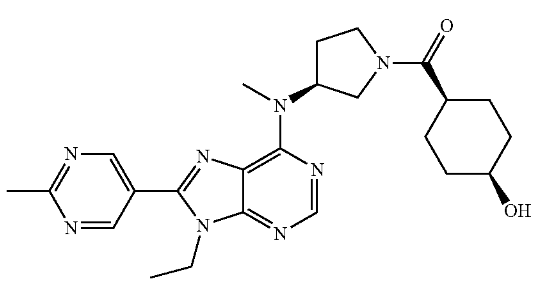 [SMILES: CCn1c(-c2cnc(C)nc2)nc2c(N(C)[C@H]3CCN(C(=O)[C@H]4CC[C@@H](O)CC4)C3)ncnc21] | cis-4-{[(3S)-3-{[9-ethyl-8-(2-methylpyrimidin-5-yl)-9H-purin-6-yl](methyl)amino}pyrrolidin-1-yl]carbonyl}cyclohexanol | Calc'd 465, found 465 |

TABLE 2-continued

| Compound | Structure | Compound Name | MS [M + H]+ |
|---|---|---|---|
| 2-101 | 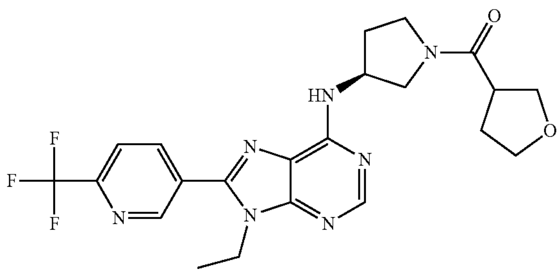 [SMILES: CCn1c(-c2ccc(C(F)(F)F)nc2)nc2c(N[C@H]3CCN(C(=O)C4CCOC4)C3)ncnc21] | 9-ethyl-N-{(3S)-1-[(3R or 3S)-tetrahydrofuran-3-ylcarbonyl]pyrrolidin-3-yl}-8-[6-(trifluoromethyl)pyridin-3-yl]-9H-purin-6-amine | Calc'd 476 found 476 |
| 2-102 | 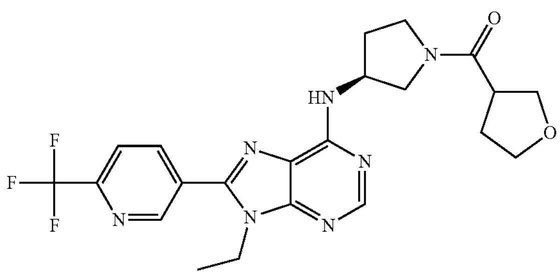 [SMILES: CCn1c(-c2ccc(C(F)(F)F)nc2)nc2c(N[C@H]3CCN(C(=O)C4CCOC4)C3)ncnc21] | 9-ethyl-N-{(3S)-1-[(3S or 3R)-tetrahydrofuran-3-ylcarbonyl]pyrrolidin-3-yl}-8-[6-(trifluoromethyl)pyridin-3-yl]-9H-purin-6-amine | Calc'd 476, found 476 |
| 2-103 | 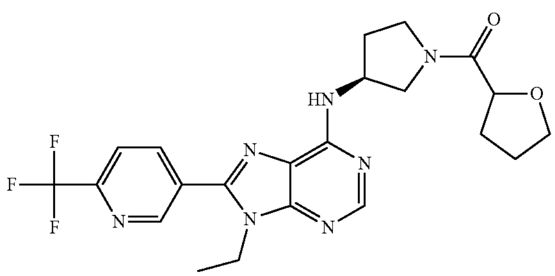 [SMILES: CCn1c(-c2ccc(C(F)(F)F)nc2)nc2c(N[C@H]3CCN(C(=O)C4CCCO4)C3)ncnc21] | 9-ethyl-N-{(3S)-1-[(2S or 2R)-tetrahydrofuran-2-ylcarbonyl]pyrrolidin-3-yl}-8-[6-(trifluoromethyl)pyridin-3-yl]-9H-purin-6-amine | Calc'd 476, found 476 |
| 2-104 | 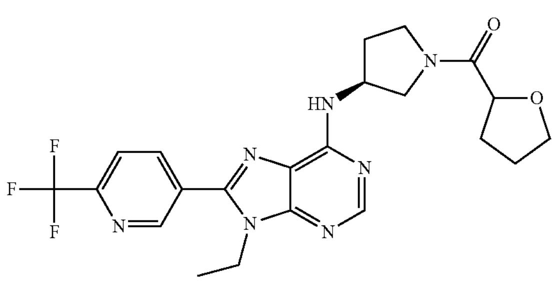 [SMILES: CCn1c(-c2ccc(C(F)(F)F)nc2)nc2c(N[C@H]3CCN(C(=O)C4CCCO4)C3)ncnc21] | 9-ethyl-N-{(3S)-1-[(2R or 2S)-tetrahydrofuran-2-ylcarbonyl]pyrrolidin-3-yl}-8-[6-(trifluoromethyl)pyridin-3-yl]-9H-purin-6-amine | Calc'd 476, found 476 |
| 2-105 | 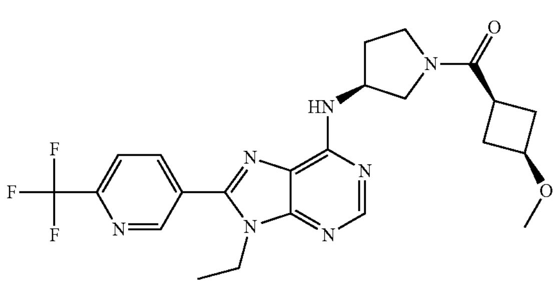 [SMILES: CCn1c(-c2ccc(C(F)(F)F)nc2)nc2c(N[C@H]3CCN(C(=O)[C@H]4C[C@@H](OC)C4)C3)ncnc21] | 9-ethyl-N-{(3S)-1-[(cis-3-methoxycyclobutyl)carbonyl]pyrrolidin-3-yl}-8-[6-(trifluoromethyl)pyridin-3-yl]-9H-purin-6-amine | Calc'd 490, found 490 |

TABLE 2-continued

| Compound | Structure | Compound Name | MS [M + H]+ |
|---|---|---|---|
| 2-106 | 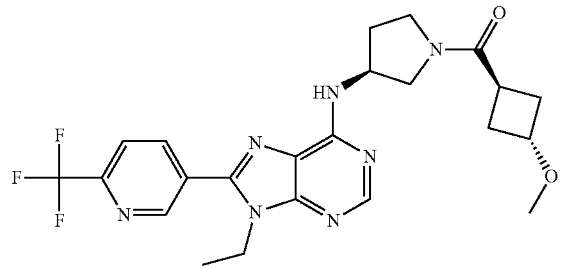 [SMILES: CCn1c(-c2ccc(C(F)(F)F)nc2)nc2c(N[C@H]3CCN(C(=O)[C@H]4C[C@H](OC)C4)C3)ncnc21] | 9-ethyl-N-{(3S)-1-[(trans-3-methoxycyclobutyl)carbonyl]pyrrolidin-3-yl}-8-[6-(trifluoromethyl)pyridin-3-yl]-9H-purin-6-amine | Calc'd 490, found 490 |

Compound Examples of Table 3

Example 4: Preparation of Compound 3-1

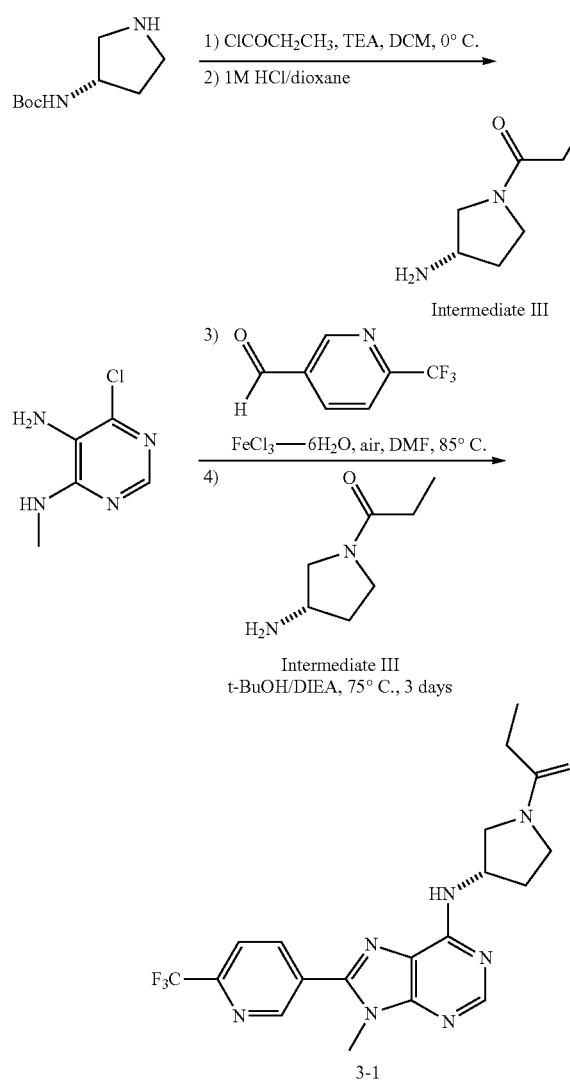

Step 1: Preparation of (S)-tert-butyl (1-propionylpyrrolidin-3-yl)carbamate

A solution of propionyl chloride (2.19 g, 23.6 mmol) in dry DCM (3 mL) was added to a solution of (S)-tert-butyl pyrrolidin-3-ylcarbamate (4.00 g, 21.5 mmol) (available from Alfa Aesar) and triethylamine (4.34 g, 43.0 mmol) in dry DCM (17 mL) portion wise at 0° C. The reaction mixture was allowed to warm to room temperature and stirred for 3 hours under a nitrogen atmosphere. Then, water (30 mL) was added and the mixture extracted with DCM (30 mL×2), dried with $Na_2SO_4$, filtered and concentrated under reduced pressure to obtain (S)-tert-butyl (1-propionylpyrrolidin-3-yl)carbamate; which was used in next step without further purification.

Step 2: Preparation of Intermediate III; (S)-1-(3-aminopyrrolidin-1-yl)propan-1-one To a solution of (S)-tert-butyl (1-propionylpyrrolidin-3-yl)carbamate (4.5 g, 18 mmol) in dioxane (5 mL), was added 1 N HCl in dioxane (10 mL) and the mixture was stirred for 2 hours at room temperature. The pH of the mixture was adjusted to 9-10 with saturated aqueous $Na_2CO_3$. The aqueous layer was dried in vacuo, extracted with MeOH (30 mL×2), and concentrated under reduced pressure to obtain (S)-1-(3-aminopyrrolidin-1-yl)propan-1-one (Intermediate III); which was used in next step without further purification.

Step 3: Preparation of 6-chloro-9-methyl-8-(6-(trifluoromethyl)pyridin-3-yl)-9H-purine A solution of 6-chloro-$N^4$-methylpyrimidine-4,5-diamine (300 mg, 1.89 mmol) in DMF (1 mL) was treated with iron(III) chloride hexahydrate (204 mg, 0.756 mmol), followed by 6-(trifluoromethyl)nicotinaldehyde (364 mg, 2.08 mmol). The reaction mixture was heated at 85° C. with air bubbling through reaction mixture for 48 hours. Next, the mixture was cooled to room temperature and water (30 mL) added. The mixture was extracted with DCM (30 mL×2), dried with $Na_2SO_4$, filtered and concentrated in vacuo. The residue was purified by chromatography on $SiO_2$ (MeOH/DCM; 1/60 to 1/40) to give 6-chloro-9-methyl-8-(6-(trifluoromethyl)pyridin-3-yl)-9H-purine. $^1$H NMR (400 MHz, $CDCl_3$) δ 9.25 (s, 1H), 8.85 (s, 1H), 8.51-8.49 (m, 1H), 7.97-7.95 (m, 1H), 4.09 (s, 3H); MS (EI) Calc'd for $C_{12}H_8ClF_3N_5$ [M+H]+, 314. found, 314.

Step 4: Preparation of 3-1; (S)-1-(3-((9-methyl-8-(6-(trifluoromethyl)pyridin-3-yl)-9H-purin-6-yl)amino)pyrrolidin-1-yl)propan-1-one 6-chloro-9-methyl-8-(6-(trifluoromethyl)pyridin-3-yl)-9H-purine (50 mg, 0.16 mmol) and Intermediate III, (S)-1-(3-aminopyrrolidin-1-yl)propan-1-one (28.0 mg, 0.192 mmol) were added to a mixture of 1:1 t-BuOH/DIEA (2 mL). The reaction mixture was heated at 75° C. for 3 days under a nitrogen atmosphere. The resulting mixture was cooled to room temperature, and the solvent evaporated to afford crude residue, which was purified by prep-TLC (MeOH/DCM=1/20) to give 3-1. $^1$H NMR (400 MHz, CDCl$_3$) δ 9.19 (s, 1H), 8.49-8.48 (m, 1H), 8.36-8.34 (m, 1H), 7.92-7.90 (m, 1H), 5.99-5.98 (m, 1H), 4.99 (s, 1H), 4.00-3.97 (m, 3H), 3.95-3.76 (m, 1H), 3.70-3.63 (m, 2H), 3.51-3.48 (m, 1H), 2.48-2.28 (m, 3H), 2.20-2.16 (m, 1H), 1.21-1.16 (m, 3H); MS (EI) Calc'd for C$_{19}$H$_{21}$F$_3$N$_7$O [M+H]$^+$, 420. found, 420.

Example 4A: Preparation of Intermediate IIIA

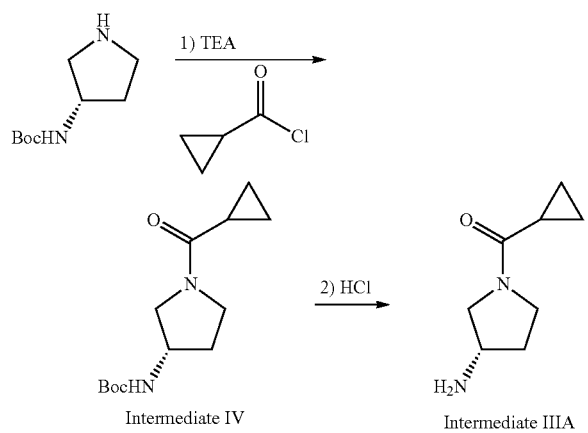

Step 1: Preparation of Intermediate IV

To a mixture of (S)-tert-butyl pyrrolidin-3-ylcarbamate (available from Alfa Aesar) (8.1 g, 44 mmol) and triethylamine (9 ml, 44 mmol) in DCM (100 mL) was added cyclopropanecarbonyl chloride (5.0 g, 48 mmol) drop wise at 0° C. After addition, the resulting mixture was stirred at RT for 4 h. The reaction mixture was then diluted with DCM (200 ml), washed with aq. NaHCO$_3$ (100 mL×2) and brine (100 mL) and dried over sodium sulfate. After removal the solvent, (S)-tert-butyl (1-(cyclopropanecarbonyl)pyrrolidin-3-yl)carbamate (Intermediate IV) was obtained. MS (ESI) calc'd for C$_{13}$H$_{23}$N$_2$O$_3$ [M+H]$^+$: 255. found: 255.

Step 2: Preparation of Intermediate IIIA

To a solution of (S)-tert-butyl (1-(cyclopropanecarbonyl)pyrrolidin-3-yl)carbamate (6.35 g, 24.9 mmol) in DCM (20 mL), 20 mL of HCl in dioxane was added. The reaction solution was stirred at r.t for 16 hr. After removal the solvent, (S)-(3-aminopyrrolidin-1-yl)(cyclopropyl)methanone hydrogen chloride (Intermediate IIIA) was obtained as an oil. MS (ESI) calc'd for C$_8$H$_{15}$N$_2$O [M+H]$^+$: 155. found: 155.

Example 4B: Preparation of Compounds 3-19 and 3-20

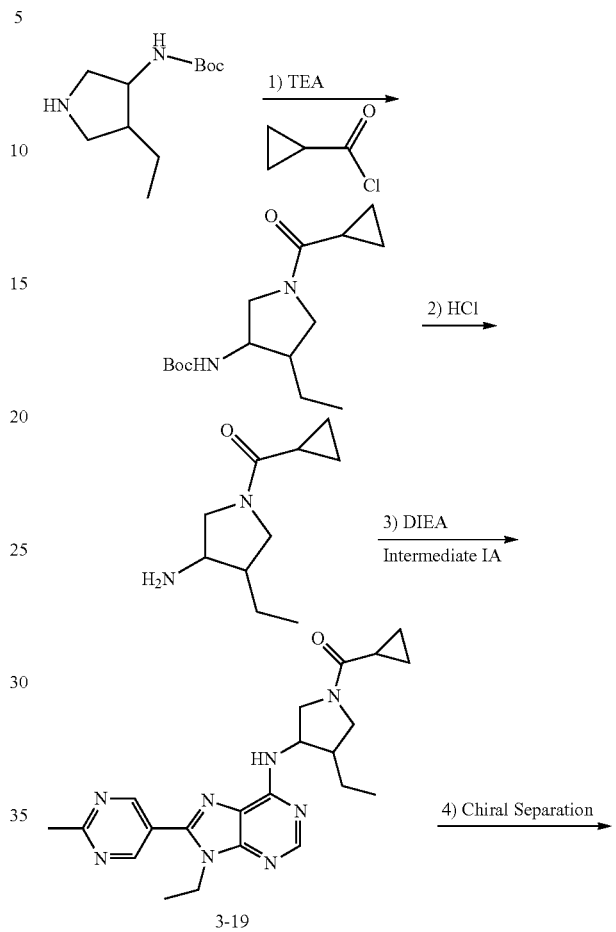

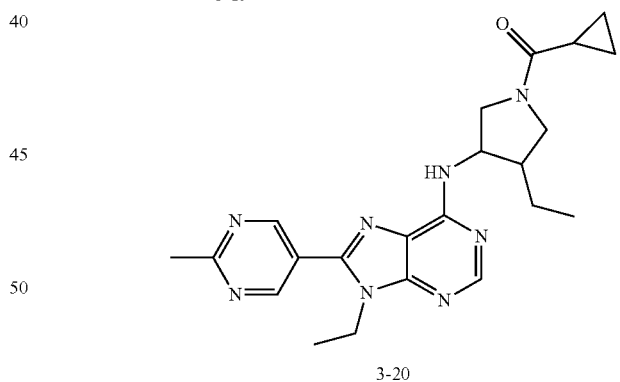

Step 1: Preparation of tert-butyl 1-(cyclopropanecarbonyl)-(3R,4S AND 3S,4R)-4-ethylpyrrolidin-3-ylcarbamate To a solution of tert-butyl 4-ethylpyrrolidin-3-ylcarbamate (500 mg, 2.3 mmol) (described in EP1757598 A1 2007 Col 16) in DCM (3 mL) was added TEA (0.64 mL, 4.6 mmol) and cyclopropanecarbonyl chloride (0.23 mL, 2.5 mmol) at 0° C. The resulting mixture was kept at this temperature for 1 h. The reaction was then concentrated to give a residue which was purified with silica gel (eluting with PE:EA=4:1) to afford tert-butyl 1-(cyclopropanecarbonyl)-(3R,4S AND 3S,4R)-4-ethylpyrrolidin-3-ylcarbamate. MS (ESI) calc'd for ($C_{12}H_{27}N_2O_3$) [M+H]$^+$, 283. found, 283.

Step 2: Preparation of (3R,4S AND 3S,4R)-(3-amino-4-ethylpyrrolidin-1-yl)(cyclopropyl)methanone Hydrochloride Into a 25-mL round bottom flask containing a solution of tert-butyl 1-(cyclopropanecarbonyl)-(3R,4S AND 3S,4R)-4-ethylpyrrolidin-3-ylcarbamate (500 mg, 1.8 mmol) in anhydrous dichloromethane (5 mL) was added HCl/dioxane (2 mL, 4.0 M in dioxane) and the contents were allowed to stir at RT for 2 h. The volatiles were then removed under reduced pressure and the residue was triturated with diethyl ether (2×5 mL) to furnish (3R,4S AND 3S,4R)-(3-amino-4-ethylpyrrolidin-1-yl)(cyclopropyl)methanone hydrochloride. MS (ESI) calc'd for ($C_{10}H_{19}N_2O$) [M+H]$^+$, 183. found, 183.

Step 3: Preparation of 3-19

To a solution of (3R,4S AND 3S,4R)-(3-amino-4-ethylpyrrolidin-1-yl)(cyclopropyl)methanone hydrochloride (100 mg, 0.46 mmol) in t-BuOH (5 mL) was added DIEA (0.7 mL, 4 mmol) and Intermediate IA (110 mg, 0.4 mmol) at RT. The mixture was heated to 85° C. and stirred at this temperature for 15 h. The solvents were then removed under reduced pressure, and the residue thus obtained was purified with preparative HPLC [Column: Xbridge Prep C18 10 um OBD, 19×250 mm; Mobile phase: A: Water (10 mM $NH_4HCO_3$), B: MeCN; Flow rate: 30 mL/min; UV detection: 214/254 nm] to afford 3-19. $^1$H NMR (400 MHz, $CD_3OD$): δ 9.14 (m, 2H), 8.30 (m, 1H), 4.80-4.50 (m, 1H), 4.43-4.40 (m, 2H), 4.40-3.87 (m, 2H), 3.58-3.48 (m, 1H), 3.40-3.10 (m, 1H), 2.83 (s, 3H), 2.41-2.29 (m, 1H), 2.00-1.70 (m, 2H), 1.60-1.25 (m, 4H), 1.07-1.01 (m, 3H), 0.91-0.86 (m, 4H). MS (ESI) calc'd for ($C_{22}H_{29}N_8O$) [M+H]$^+$, 421. found, 421.

Step 4: Preparation of 3-20

Compound 3-19 was separated by chiral column chromatography using the following conditions: Column OJ-H 4.6×250 mm 5 um, $CO_2$ Flow Rate=2.55, Co-Solvent: MeOH:MeCN=1:1 (0.1% DEA), Co-Solvent Flow Rate 0.45, Column Temperature 40° C. to afford 3-20 (elution time 4.0 min). $^1$H NMR (400 MHz, $CD_3OD$): δ 9.14 (m, 2H), 8.30 (m, 1H), 4.80-4.50 (m, 1H), 4.43-4.40 (m, 2H), 4.40-3.87 (m, 2H), 3.58-3.48 (m, 1H), 3.40-3.10 (m, 1H), 2.83 (s, 3H), 2.41-2.29 (m, 1H), 2.00-1.70 (m, 2H), 1.60-1.25 (m, 4H), 1.07-1.01 (m, 3H), 0.91-0.86 (m, 4H). MS (ESI) calc'd for ($C_{22}H_{29}N_8O$) [M+H]$^+$, 421. found, 421.

Example 4C: Preparation of Compound 3-28

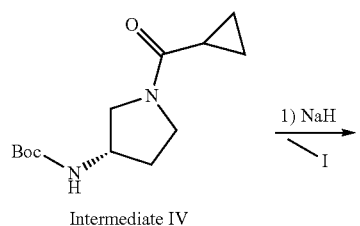

Intermediate IV

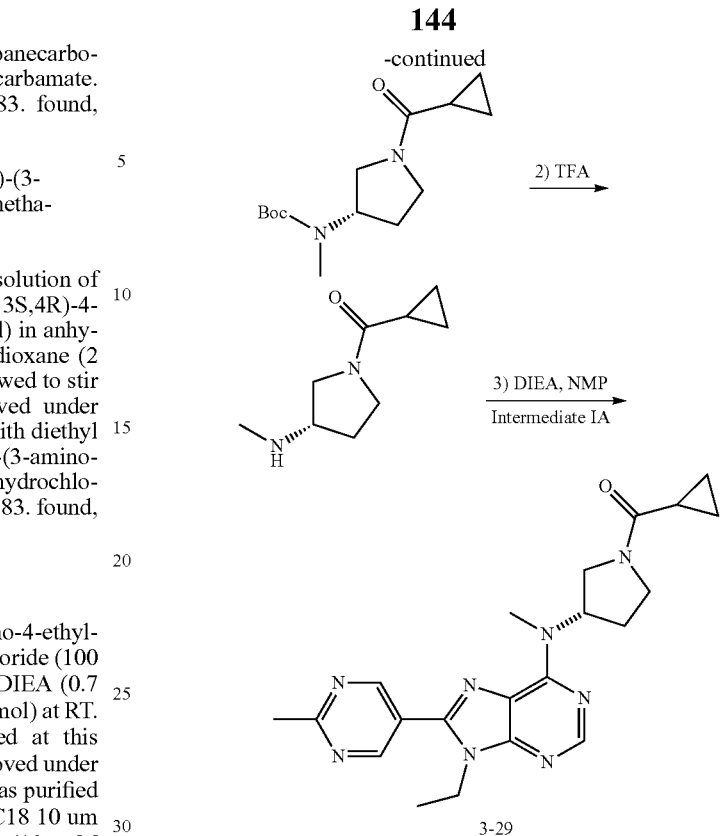

3-29

Step 1: Preparation of (S)-tert-butyl 1-(cyclopropanecarbonyl)pyrrolidin-3-yl(methyl)carbamate Iodomethane (123 mg, 0.865 mmol) was added to a solution of Intermediate IV (200 mg, 0.79 mmol) and sodium hydride (62.9 mg, 1.57 mmol) in DMF (3 ml) at room temperature and the mixture was stirred at 30° C. for 12 h. The mixture was quenched by the addition of saturated aqueous ammonium chloride (10 mL) and the mixture was then extracted with ethyl acetate (3×10 mL). The combined organic fractions were washed with brine, dried over sodium sulfate, filtered, and the solvent was evaporated under reduced pressure. The crude (S)-tert-butyl 1-(cyclopropanecarbonyl)pyrrolidin-3-yl(methyl)carbamate was used directly for next step. MS (ESI) calc'd for ($C_{14}H_{25}N_2O_3$) [M+H]$^+$, 269. found, 269.

Step 2: Preparation of (S)-cyclopropyl(3-(methylamino)pyrrolidin-1-yl)methanone, Trifluoroacetate Salt 2,2,2-trifluoroacetic acid (76 mg, 0.67 mmol) was added to a solution of (S)-tert-butyl (1-(cyclopropanecarbonyl) pyrrolidin-3-yl)(methyl)carbamate (180 mg, 0.67 mmol) in DCM (6 ml) at 0° C. and the mixture was stirred at 30° C. for 1 h. The reaction mixture was then concentrated in vacuo to afford (S)-cyclopropyl(3-(methylamino)pyrrolidin-1-yl) methanone, trifluoroacetate salt which was used directly for next step. MS (ESI) calc'd for ($C_9H_{17}N_2O$) [M+H]$^+$, 169. found, 169.

Step 3: Preparation of Compound 3-29

N-ethyl-N-isopropylpropan-2-amine (307 mg, 2.38 mmol) was added to a solution of 6-chloro-9-ethyl-8-(2-methylpyrimidin-5-yl)-9H-purine (Intermediate IA) (131 mg, 0.476 mmol) and (S)-cyclopropyl(3-(methylamino)pyrrolidin-1-yl)methanone, trifluoroacetate salt (80 mg, 0.30 mmol) in NMP (5 ml) at room temperature and the mixture was stirred at 120° C. for 12 h. The residue was purified by reverse phase preparative HPLC (C-18), eluting with Acetonitrile/Water+0.05% NH$_3$, to give compound 3-29. $^1$H NMR (400 MHz, CD$_3$OD): δ 9.13 (s, 2H), 8.34 (m, 1H), 6.30-6.20 (s, 1H), 4.43-4.41 (m, 2H), 4.32-3.40 (m, 7H), 2.82 (s, 3H), 2.51-2.20 (m, 2H), 1.87-1.70 (m, 1H), 1.43 (m, 3H), 0.95-0.84 (m, 4H). MS (ESI) calc'd for (C$_{21}$H$_{27}$N$_8$O) [M+H]$^+$, 407. found, 407.

Example 4D: Preparation of Compound 3-32

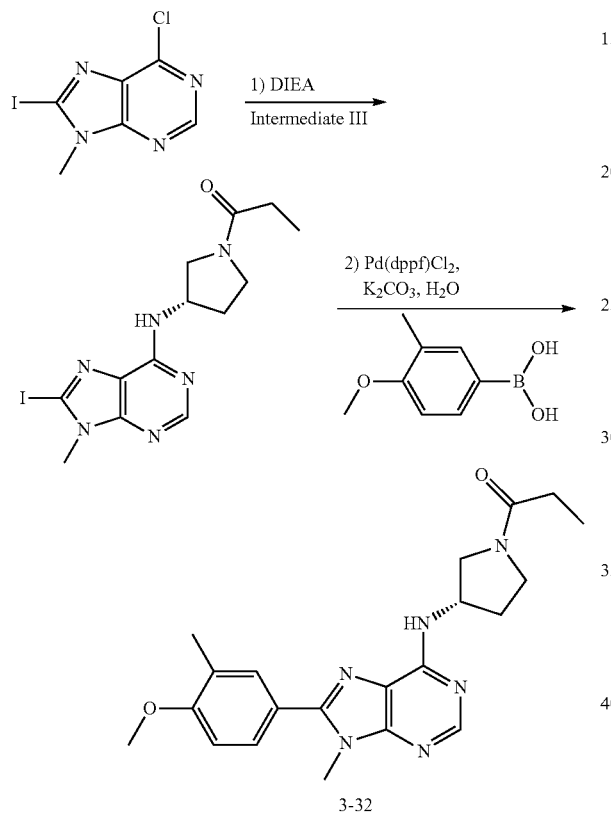

Step 1: Preparation of (S)-1-(3-(8-iodo-9-methyl-9H-purin-6-ylamino)pyrrolidin-1-yl)propan-1-one 6-chloro-8-iodo-9-methyl-9H-purine (Preparation of this material is described in Jin, Chunyang; Burgess, Jason P.; Rehder, Kenneth S.; Brine, George A. *Synthesis*, 2007, 2, p. 219-224) (500 mg, 1.7 mmol) and (S)-1-(3-aminopyrrolidin-1-yl)propan-1-one (Intermediate III) (in its neutral form) (266 mg, 1.87 mmol) were added to the mixture of t-BuOH: DIPEA (1:1, 6 mL). The reaction mixture was heated to 80° C. for 36 h under a N$_2$ atmosphere. The reaction mixture was cooled to room temperature and the solvent was removed under reduced pressure. The residue was purified by column chromatography on silica gel (EtOAc:hexane=10:10) to give (S)-1-(3-(8-iodo-9-methyl-9H-purin-6-ylamino)pyrrolidin-1-yl)propan-1-one. MS (ESI) calc'd for (C$_{13}$H$_{18}$IN$_6$O) [M+H]$^+$, 401. found, 401.

Step 2: Preparation of 3-32

A mixture of (S)-1-(3-(8-iodo-9-methyl-9H-purin-6-ylamino)pyrrolidin-1-yl)propan-1-one (100 mg, 0.26 mmol), 4-methoxy-3-methylphenylboronic acid (47 mg, 0.28 mmol), Pd(dppf)Cl$_2$ (11 mg, 0.013 mmol) and K$_2$CO$_3$ (110 mg, 0.78 mmol) in H$_2$O (1.5 mL) and dioxane (5 mL) was heated at 110° C. under nitrogen atmosphere for 15 h. The reaction mixture was quenched with water (5 mL) and extracted with EtOAc (5 mL×3). The organic layer was washed with brine, dried over Na$_2$SO$_4$, filtered and concentrated in vacuo. The residue was purified by column chromatography on silica gel (EtOAc:hexane=5:10) to give 3-32. $^1$H NMR (400 MHz, MeOD-d$_4$) δ 8.31 (s, 1H), 7.64 (d, J=8.4 Hz, 1H), 7.61 (s, 1H), 7.11 (d, J=8.4 Hz, 1H), 4.95-4.80 (m, 1H), 3.94 (s, 3H), 3.87 (s, 3H), 4.00-3.55 (m, 4H), 2.50-2.39 (m, 3H), 2.38 (s, 3H), 2.30-2.36 (m, 1H), 1.18-1.11 (m, 3H). MS (ESI) calc'd for (C$_{21}$H$_{27}$N$_6$O$_2$) [M+H]$^+$, 395. found, 395.

Example 4E: Preparation of Compound 3-36

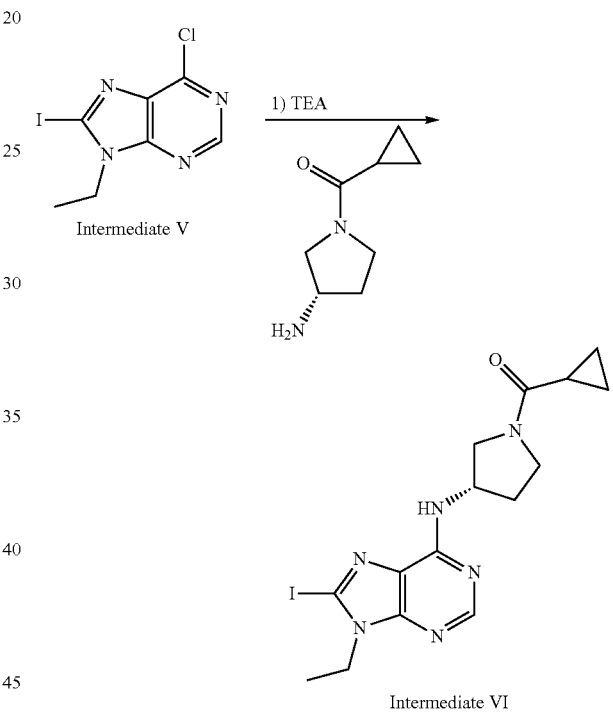

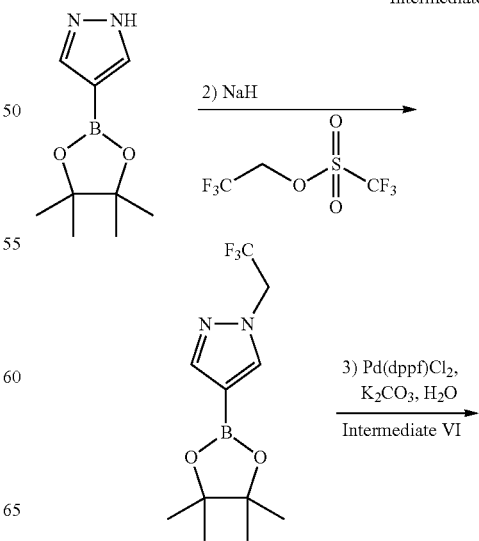

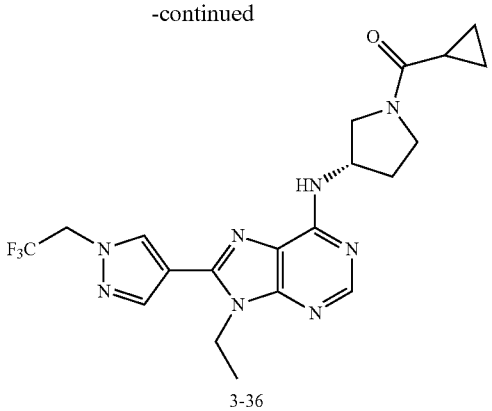

3-36

Step 1: Preparation of (S)-cyclopropyl(3-((9-ethyl-8-iodo-9H-purin-6-yl)amino)pyrrolidin-1-yl)methanone A mixture of Intermediate V (0.5 g, 2 mmol), Intermediate IIIA (in its neutral form) (0.250 g, 1.62 mmol), and triethylamine (3 ml, 21 mmol) in t-BuOH (5 ml) was heated to reflux for 2 days. The reaction was then cooled and concentrated in vacuo, after which DCM (30 ml) was added and the organic layer was washed with water (20 ml), dried over sodium sulfate, filtered, and concentrated in vacuo. The residue was purified by column chromatography on silica gel, eluting with DCM:MeOH=30:1, to give (S)-cyclopropyl (3-((9-ethyl-8-iodo-9H-purin-6-yl)amino)pyrrolidin-1-yl) methanone (Intermediate VI). MS (ESI) calc'd for $(C_{15}H_{20}IN_6O)$ $[M+H]^+$, 427. found, 427.

Step 2: Preparation of 4-(4,4,5,5-tetramethyl-1,3,2-dioxaborolan-2-yl)-1-(2,2,2-trifluoroethyl)-1H-pyrazole Sodium hydride (61.8 mg, 1.55 mmol) was added to a solution of 4-(4,4,5,5-tetramethyl-1,3,2-dioxaborolan-2-yl)-1H-pyrazole (150 mg, 0.77 mmol) and 2,2,2-trifluoroethyl trifluoromethanesulfonate (269 mg, 1.16 mmol) in DMF (5 ml) at 0° C. and the mixture was stirred at 20° C. for 12 h. The mixture was quenched with aqueous saturated ammonium chloride (6 mL) and extracted with ethyl acetate (3×8 mL). The combined organic fractions were washed with brine, dried over sodium sulfate, filtered, and the solvent was evaporated under reduced pressure to give 4-(4,4,5,5-tetramethyl-1,3,2-dioxaborolan-2-yl)-1-(2,2,2-trifluoroethyl)-1H-pyrazole. MS (ESI) calc'd for $(C_{11}H_{17}BF_3N_2O_2)$ $[M+H]^+$, 277. found, 277.

Step 3: Preparation of 3-36

PdCl2(dppf) (11 mg, 0.014 mmol) was added to a mixture of 4-(4,4,5,5-tetramethyl-1,3,2-dioxaborolan-2-yl)-1-(2,2,2-trifluoroethyl)-1H-pyrazole (50 mg, 0.18 mmol), Intermediate VI (77 mg, 0.18 mmol) and $K_2CO_3$ (62.6 mg, 0.453 mmol) in dioxane (5 ml) at room temperature and the mixture was stirred at 80° C. under $N_2$ for 18 h. The mixture was quenched with aqueous saturated ammonium chloride (6 mL) and extracted with ethyl acetate (3×6 mL). The combined organic fractions were washed with brine, dried over sodium sulfate, filtered, and the solvent was evaporated under reduced pressure. The residue was purified by preparative Reverse phase HPLC (C-18), eluting with Acetonitrile/Water+0.05% $NH_3$, to give 3-37. $^1$H NMR (400 MHz, $CD_3OD$): δ 8.46 (s, 1H), 8.33 (m, 1H), 8.17 (s, 1H), 5.13 (q, J=8.8 Hz, 2H), 5.05-4.90 (m, 1H), 4.48-4.42 (m, 2H), 4.21-3.60 (m, 4H), 2.52-2.05 (m, 2H), 1.95-1.70 (m, 1H), 1.45 (t, J=8.8 Hz, 3H), 0.95-0.75 (m, 4H). MS (ESI) calc'd for $(C_{20}H_{24}F_3N_8O)$ $[M+H]^+$, 449. found, 449.

Example 4F: Preparation of Compound 3-38

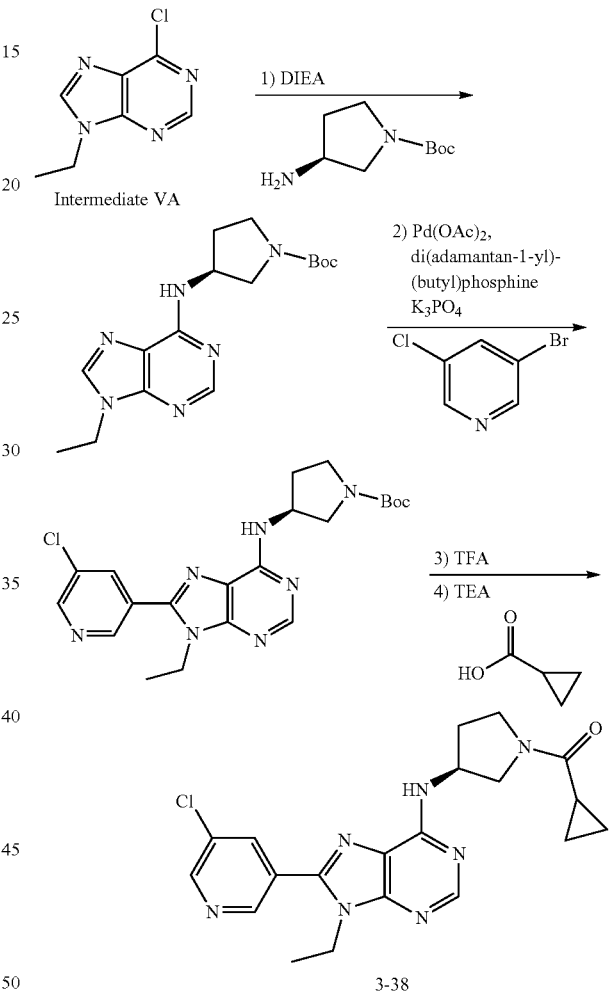

3-38

Step 1: Synthesis of (S)-tert-butyl 3-(9-ethyl-9H-purin-6-ylamino)pyrrolidine-1-carboxylate N-ethyl-N-isopropylpropan-2-amine (5.31 g, 41.1 mmol) was added to a solution of Intermediate VA (2.5 g, 14 mmol) and (S)-tert-butyl 3-aminopyrrolidine-1-carboxylate (3.06 g, 16.4 mmol) in t-BuOH (25 ml) at RT and the mixture was stirred at 85° C. for 18 h. The reaction mixture was then concentrated, and the residue was recrystallized from diethyl ether (30 mL). The solid was collected and dried in vacuo at room temperature to give (S)-tert-butyl 3-(9-ethyl-9H-purin-6-ylamino)pyrrolidine-1-carboxylate. MS (ESI) calc'd for $(C_{16}H_{25}N_6O_2)$ $[M+H]^+$, 333. found, 333.

Step 2: Synthesis of (S)-tert-butyl 3-(8-(5-chloro-pyridin-3-yl)-9-ethyl-9H-purin-6-ylamino)pyrrolidine-1-carboxylate Diacetoxypalladium (40.5 mg, 0.181 mmol) and di(adamantan-1-yl)-(butyl)phosphine (129 mg, 0.361 mmol) in DMA (3 ml) was degassed for two minutes and stirred at RT under $N_2$ for 15 minutes. Under $N_2$, a mixture of (S)-tert-butyl 3-((9-ethyl-9H-purin-6-yl)amino)pyrrolidine-1-carboxylate (300 mg, 0.90 mmol), 3-bromo-5-chloropyridine (521 mg, 2.71 mmol), pivalic acid (138 mg, 1.35 mmol) and potassium carbonate (575 mg, 2.71 mmol) was added to the catalyst mixture at RT. The reaction mixture was then degassed with $N_2$ and the mixture was heated to 130° C. with stirring for 16 h. The reaction mixture was then cooled and filtered. The solids were washed with ethyl acetate and the combined filtrates were concentrated in vacuo. The residue was purified by column chromatography on silica gel Isolute Flash Si; 10 g pre-packed, eluting with EtOAc:hexanes (3:1) to give the title compound. MS (ESI) calc'd for $(C_{21}H_{27}ClN_7O_2)$ [M+H]$^+$, 444. found, 444.

Step 3: Synthesis of (S)-8-(5-chloropyridin-3-yl)-9-ethyl-N-(pyrrolidin-3-yl)-9H-purin-6-amine, TFA 2,2,2-trifluoroacetic acid (231 mg, 2.03 mmol) was added to a solution of (S)-tert-butyl 3-((8-(5-chloropyridin-3-yl)-9-ethyl-9H-purin-6-yl)amino)pyrrolidine-1-carboxylate (180 mg, 0.41 mmol) in DCM (3 ml) at 0° C. and the mixture was allowed to come to 25° C. where it was stirred for 2 h. The reaction mixture was then concentrated and washed with ether to give (S)-8-(5-chloropyridin-3-yl)-9-ethyl-N-(pyrrolidin-3-yl)-9H-purin-6-amine as the TFA salt. MS (ESI) calc'd for $(C_{16}H_{19}ClN_7)$ [M+H]$^+$, 344. found, 344.

Step 4: Synthesis of (S)-(3-(8-(5-chloropyridin-3-yl)-9-ethyl-9H-purin-6-ylamino)pyrrolidin-1-yl)(cyclopropyl)methanone (3-38)

Cyclopropanecarbonyl chloride (25.1 mg, 0.240 mmol) was added to a solution of (S)-8-(5-chloropyridin-3-yl)-9-ethyl-N-(pyrrolidin-3-yl)-9H-purin-6-amine (75 mg, 0.22 mmol) and triethylamine (66.2 mg, 0.654 mmol) in DCM (3 ml) at room temperature and the mixture was stirred at 25° C. for 1 h. The reaction mixture was then quenched with methanol and concentrated. The residue was purified by preparative Reverse phase HPLC (C-18), eluting with Acetonitrile/Water+0.05% $NH_3$, to give compound 3-38. $^1$H NMR (400 MHz, DMSO-d$_6$): δ 8.97 (m, 1H), 8.85 (s, 1H), 8.39-8.33 (m, 3H), 4.95-4.60 (m, 1H), 4.34-4.29 (m, 2H), 4.05-3.30 (m, 4H), 2.40-1.95 (m, 2H), 1.75-1.65 (m, 1H), 1.32-1.28 (m, 3H), 0.73-0.69 (m, 4H). MS (ESI) calc'd for $(C_{20}H_{23}ClN_7O)$ [M+H]$^+$, 412. found, 412.

Example 4G: Preparation of Compound 3-39

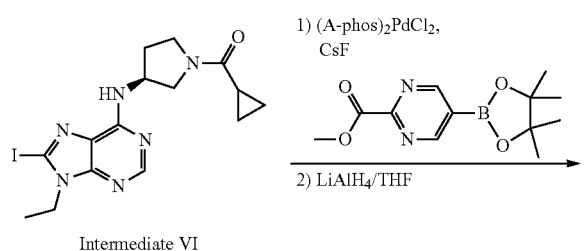

Intermediate VI

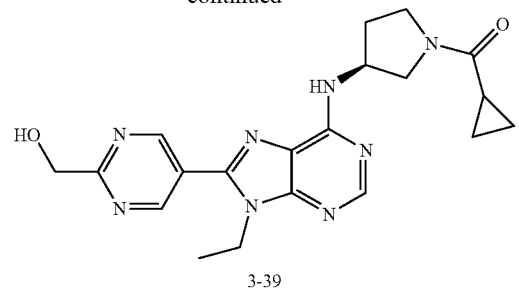

3-39

Step 1: Preparation of (S)-methyl 5-(6-(1-(cyclopropanecarbonyl)pyrrolidin-3-ylamino)-9-ethyl-9H-purin-8-yl)pyrimidine-2-carboxylate To a solution of Intermediate VI (500 mg, 1.2 mmol) in ethylene glycol dimethyl ether (20 mL) and methanol (5 mL) were added methyl 5-(4,4,5,5-tetramethyl-1,3,2-dioxaborolan-2-yl)pyrimidine-2-carboxylate (930 mg, 3.5 mmol) (Source: WO2007/84786 A1), bis(di-tert-butyl(4-dimethylaminophenyl)phosphine)dichloropalladium(II) ((A-phos)$_2$PdCl$_2$) (84 mg, 0.12 mmol) and cesium fluoride (720 mg, 4.8 mmol). The resulting mixture was stirred in a microwave reactor (50 Watt) for 3 h at 110° C. under a nitrogen atmosphere. The resulting mixture was concentrated under vacuum to give a residue, which was purified by silica gel column chromatography (eluting with 1-2% methanol in dichloromethane) to afford (S)-methyl 5-(6-(1-(cyclopropanecarbonyl)pyrrolidin-3-ylamino)-9-ethyl-9H-purin-8-yl)pyrimidine-2-carboxylate. MS (ESI) calc'd for $(C_{21}H_{25}N_8O_3)$ [M+H]$^+$, 437. found, 437.

Step 2: Preparation of 3-39

To a solution of (S)-methyl 5-(6-(1-(cyclopropanecarbonyl)pyrrolidin-3-ylamino)-9-ethyl-9H-purin-8-yl)pyrimidine-2-carboxylate (46 mg, 0.11 mmol) in tetrahydrofuran (10 mL) was added lithium aluminum hydride (8 mg, 0.2 mmol) at 0° C. The mixture was stirred for 15 min at ambient temperature and then at 40° C. for 15 h. The reaction was quenched by the addition of water (0.5 mL) at 0° C. and filtered. The filter cake was washed with tetrahydrofuran (100 mL). The filtrate was dried over anhydrous sodium sulfate and concentrated under vacuum to give a residue, which was purified by Prep-HPLC [Column: XBridge Prep C$_{18}$ OBD 19×100 mm 5 m; Mobile phase: A: Water with 10 mmol Ammonium bicarbonate, B: Acetonitrile (22%-40%); Flow rate: 30 mL/min; UV detection: 254/220 nm] to give 3-39. $^1$H NMR (300 MHz, CD$_3$OD): δ 9.23 (s, 2H), 8.37 (m, 1H), 5.00-4.80 (m, 3H), 4.47 (q, J=6.0 Hz, 2H), 4.30-3.50 (m, 4H), 2.52-2.10 (m, 2H), 1.87-1.80 (m, 1H), 1.48 (m, 3H), 0.94-0.82 (m, 4H). MS (ESI) calc'd for $(C_{20}H_{25}N_8O_2)$ [M+H]$^+$, 409. found, 409.

Compounds 3-1 through 3-15, 3-23 through 3-25, 3-27 were prepared in an analogous fashion to Example 4, using the corresponding aldehyde and Intermediate III or IIIA.

Compounds 3-16 through 3-18, 3-22, 3-26, were prepared in an analogous fashion to Example 4B, using the corresponding Boc-protected amine.

Compound 3-21 was prepared in an analogous fashion to Example 4B using trans-(4-fluoropyrrolidin-3-yl)-carbamic acid tert-butyl ester (available from Synnovator, Inc.). The racemic mixture was then separated on chiral SFC using the following conditions: Column OD-H 6×250 mm 5 um, CO₂ Flow Rate 2.1, Co-Solvent MeOH, Co-Solvent Flow Rate 0.9, Column Temperature 40° C. to afford the single enantiomer (retention time 3.7 min).

Compound 3-28 was prepared in an analogous fashion to Example 4C, except iodoethane was used in place of iodomethane.

Compound 3-30 was prepared in an analogous fashion to Example 4, step 4 from Intermediate IIIA and 6-chloro-9-ethyl-8-(4-(trifluoromethyl)phenyl)-9H-purine. 6-chloro-9-ethyl-8-(4-(trifluoromethyl)phenyl)-9H-purine was prepared in an analogous fashion to Example 1E, step 3 from Intermediate V and 4,4,5,5-tetramethyl-2-(4-(trifluoromethyl)phenyl)-1,3,2-dioxaborolane.

Compounds 3-31 and 3-33 through 3-35 were prepared in an analogous fashion to Example 4D.

Compound 3-36 was prepared in an analogous fashion to Example 4E, step 3.

Compound 3-37 was prepared in an analogous fashion to Example 4G, step 1.

TABLE 3

| Compound | Structure | Compound Name | MS [M + H]⁺ |
| --- | --- | --- | --- |
| 3-1 | 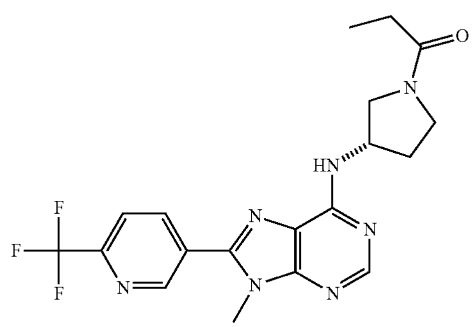 | (S)-1-(3-((9-methyl-8-(6-(trifluoromethyl)pyridin-3-yl)-9H-purin-6-yl)amino)pyrrolidin-1-yl)propan-1-one | Calc'd 420, found 420 |
| 3-2 | 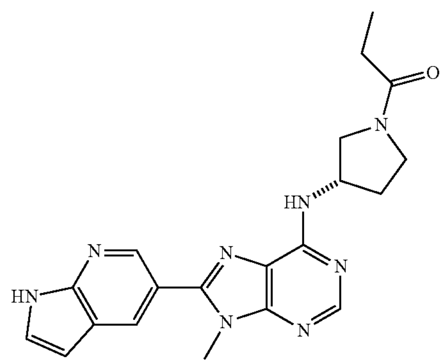 | (S)-1-(3-((9-methyl-8-(1H-pyrrolo[2,3-b]pyridin-5-yl)-9H-purin-6-yl)amino)pyrrolidin-1-yl)propan-1-one | Calc'd 391, found 391 |
| 3-3 | 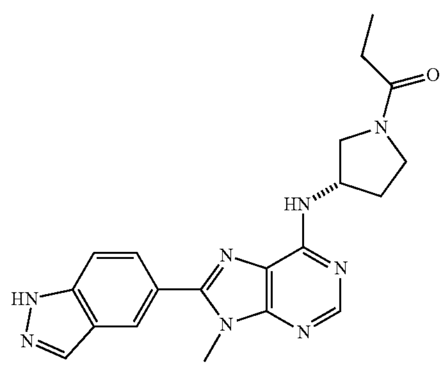 | (S)-1-(3-((8-(1H-indazol-5-yl)-9-methyl-9H-purin-6-yl)amino)pyrrolidin-1-yl)propan-1-one | Calc'd 391, found 391 |

TABLE 3-continued

| Compound | Structure | Compound Name | MS [M + H]+ |
|---|---|---|---|
| 3-4 | 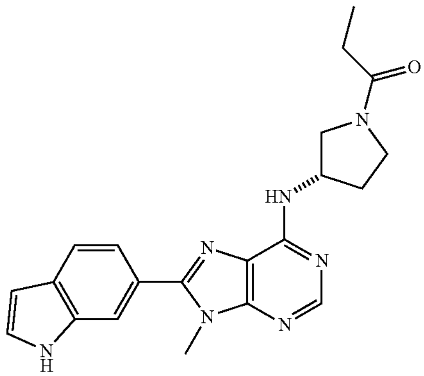 | (S)-1-(3-((8-(1H-indol-6-yl)-9-methyl-9H-purin-6-yl)amino)pyrrolidin-1-yl)propan-1-one | Calc'd 390, found 390 |
| 3-5 | 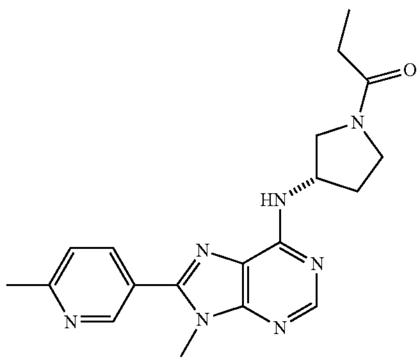 | (S)-1-(3-((9-methyl-8-(6-methylpyridin-3-yl)-9H-purin-6-yl)amino)pyrrolidin-1-yl)propan-1-one | Calc'd 366, found 366 |
| 3-6 | 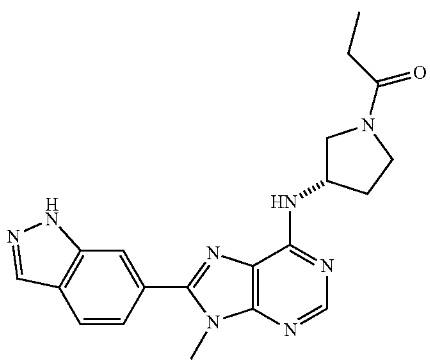 | (S)-1-(3-((8-(1H-indazol-6-yl)-9-methyl-9H-purin-6-yl)amino)pyrrolidin-1-yl)propan-1-one | Calc'd 391, found 391 |
| 3-7 | 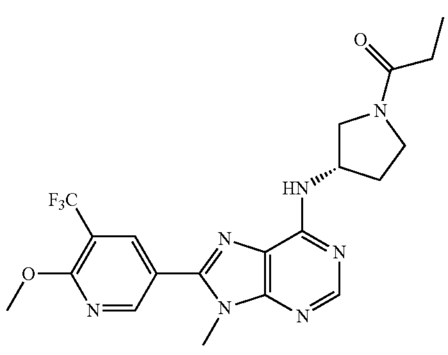 [SMILES: CCC(=O)N1CC[C@H](Nc2ncnc3c2nc(-c2cnc(OC)c(C(F)(F)F)c2)n3C)C1] | (S)-1-(3-((8-(6-methoxy-5-(trifluoromethyl)pyridin-3-yl)-9-methyl-9H-purin-6-yl)amino)pyrrolidin-1-yl)propan-1-one | Calc'd 450, found 450 |

TABLE 3-continued

| Compound | Structure | Compound Name | MS [M + H]+ |
|---|---|---|---|
| 3-8 | 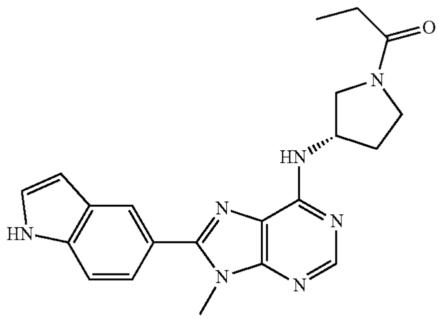 [SMILES: CCC(=O)N1CC[C@H](Nc2ncnc3c2nc(-c2ccc4[nH]ccc4c2)n3C)C1] | (S)-1-(3-((8-(1H-indol-5-yl)-9-methyl-9H-purin-6-yl)amino)pyrrolidin-1-yl)propan-1-one | Calc'd 390, found 390 |
| 3-9 | 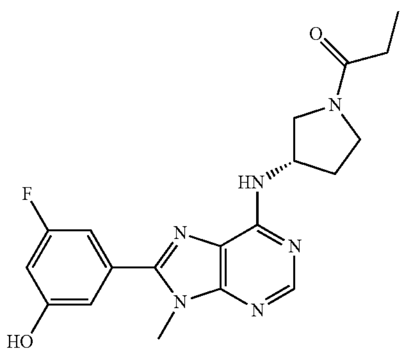 [SMILES: CCC(=O)N1CC[C@H](Nc2ncnc3c2nc(-c2cc(O)cc(F)c2)n3C)C1] | 3-fluoro-5-(9-methyl-6-{[(3S)-1-propanoylpyrrolidin-3-yl]amino}-9H-purin-8-yl)phenol | Calc'd 385, found 385 |
| 3-10 | 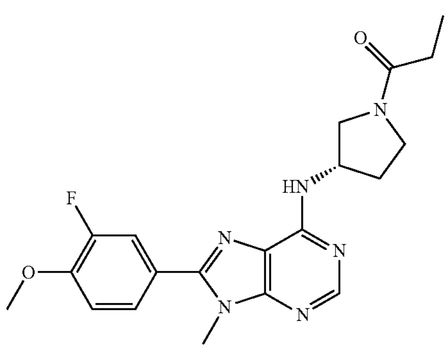 [SMILES: CCC(=O)N1CC[C@H](Nc2ncnc3c2nc(-c2ccc(OC)c(F)c2)n3C)C1] | 8-(3-fluoro-4-methoxyphenyl)-9-methyl-N-[(3S)-1-propanoylpyrrolidin-3-yl]-9H-purin-6-amine | Calc'd 399, found 399 |
| 3-11 | 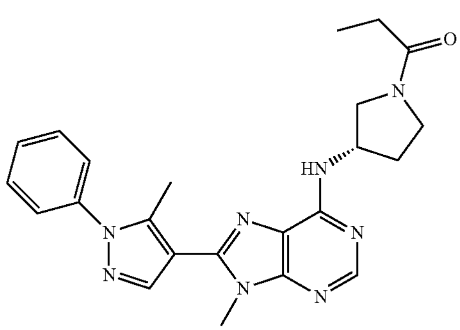 [SMILES: CCC(=O)N1CC[C@H](Nc2ncnc3c2nc(-c2cnn(-c4ccccc4)c2C)n3C)C1] | 9-methyl-8-(5-methyl-1-phenyl-1H-pyrazol-4-yl)-N-[(3S)-1-propanoylpyrrolidin-3-yl]-9H-purin-6-amine | Calc'd 431, found 431 |

TABLE 3-continued

| Compound | Structure | Compound Name | MS [M + H]+ |
|---|---|---|---|
| 3-12 | 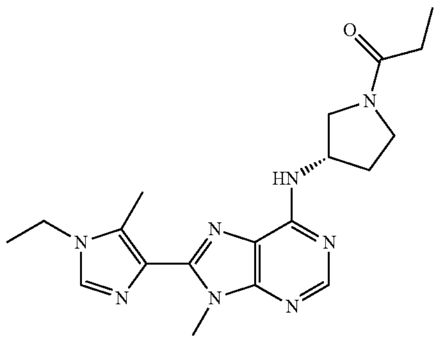 [SMILES: CCC(=O)N1CC[C@H](Nc2ncnc3c2nc(-c2ncn(CC)c2C)n3C)C1] | 8-(1-ethyl-5-methyl-1H-imidazol-4-yl)-9-methyl-N-[(3S)-1-propanoylpyrrolidin-3-yl]-9H-purin-6-amine | Calc'd 383, found 383 |
| 3-13 | 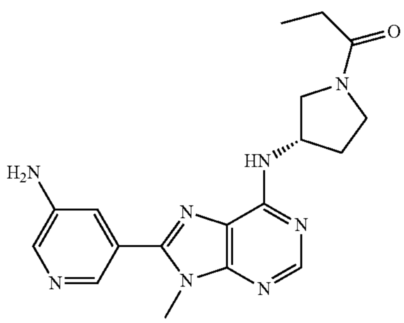 [SMILES: CCC(=O)N1CC[C@H](Nc2ncnc3c2nc(-c2cncc(N)c2)n3C)C1] | 8-(5-aminopyridin-3-yl)-9-methyl-N-[(3S)-1-propanoylpyrrolidin-3-yl]-9H-purin-6-amine | Calc'd 367, found 367 |
| 3-14 | 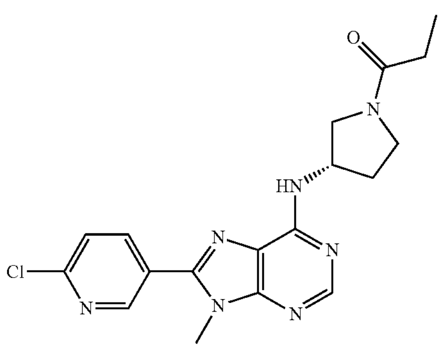 [SMILES: CCC(=O)N1CC[C@H](Nc2ncnc3c2nc(-c2ccc(Cl)nc2)n3C)C1] | 8-(6-chloropyridin-3-yl)-9-methyl-N-[(3S)-1-propanoylpyrrolidin-3-yl]-9H-purin-6-amine | Calc'd 386, found 386 |
| 3-15 | 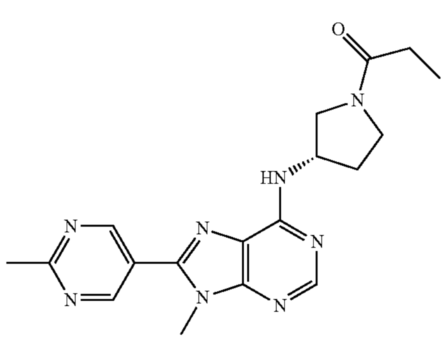 [SMILES: CCC(=O)N1CC[C@H](Nc2ncnc3c2nc(-c2cnc(C)nc2)n3C)C1] | 9-methyl-8-(2-methylpyrimidin-5-yl)-N-[(3S)-1-propanoylpyrrolidin-3-yl]-9H-purin-6-amine | Calc'd 367, found 367 |

TABLE 3-continued

| Compound | Structure | Compound Name | MS [M + H]+ |
|---|---|---|---|
| 3-16 | 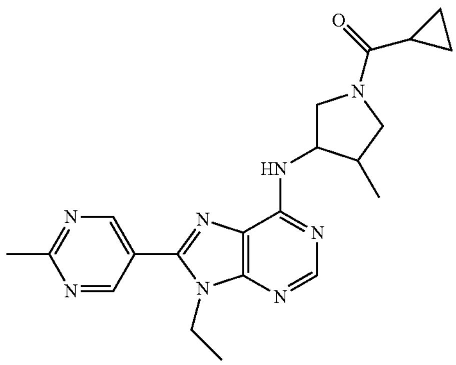 [SMILES: CCn1c(-c2cnc(C)nc2)nc2c(NC3CN(C(=O)C4CC4)CC3C)ncnc21] | N-[(3R,4R and 3S,4S)-1-(cyclopropylcarbonyl)-4-methylpyrrolidin-3-yl]-9-ethyl-8-(2-methylpyrimidin-5-yl)-9H-purin-6-amine | Calc'd 407, found 407 |
| 3-17 | 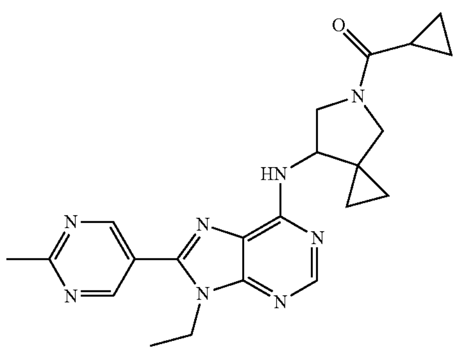 [SMILES: CCn1c(-c2cnc(C)nc2)nc2c(NC3CN(C(=O)C4CC4)CC34CC4)ncnc21] | (R and S)-N-[5-(cyclopropylcarbonyl)-5-azaspiro[2.4]hept-7-yl]-9-ethyl-8-(2-methylpyrimidin-5-yl)-9H-purin-6-amine | Calc'd 419, found 419 |
| 3-18 | 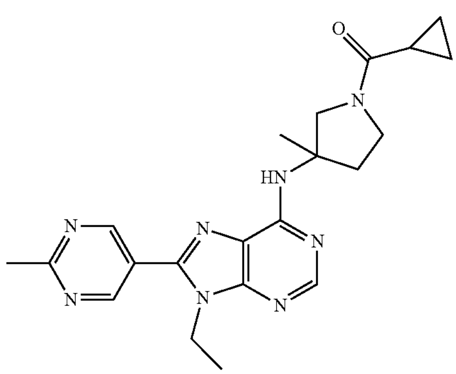 [SMILES: CCn1c(-c2cnc(C)nc2)nc2c(NC3(C)CCN(C(=O)C4CC4)C3)ncnc21] | N-[(R and S)-1-(cyclopropylcarbonyl)-3-methylpyrrolidin-3-yl]-9-ethyl-8-(2-methylpyrimidin-5-yl)-9H-purin-6-amine | Calc'd 407, found 407 |
| 3-19 | 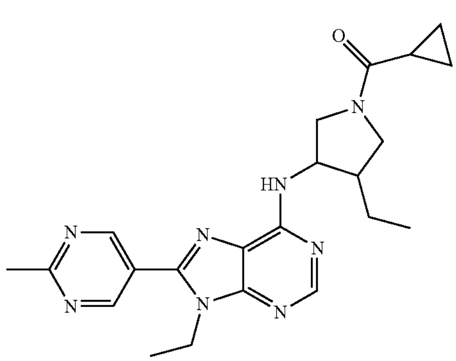 [SMILES: CCC1CN(C(=O)C2CC2)CC1Nc1ncnc2c1nc(-c1cnc(C)nc1)n2CC] | N-[(3R,4S and 3S,4R)-1-(cyclopropylcarbonyl)-4-ethylpyrrolidin-3-yl]-9-ethyl-8-(2-methylpyrimidin-5-yl)-9H-purin-6-amine | Calc'd 421, found 421 |

TABLE 3-continued

| Compound | Structure | Compound Name | MS [M + H]⁺ |
|---|---|---|---|
| 3-20 | 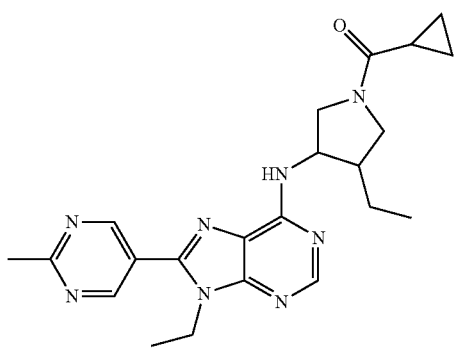 [SMILES: CCC1CN(C(=O)C2CC2)CC1Nc1ncnc2c1nc(-c1cnc(C)nc1)n2CC] | N-[(3R,4S or 3S,4R)-1-(cyclopropylcarbonyl)-4-ethylpyrrolidin-3-yl]-9-ethyl-8-(2-methylpyrimidin-5-yl)-9H-purin-6-amine | Calc'd 421, found 421 |
| 3-21 | 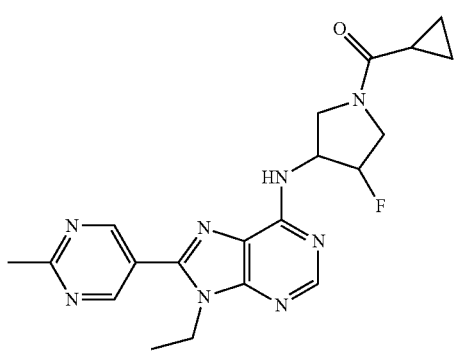 [SMILES: CCn1c(-c2cnc(C)nc2)nc2c(NC3CN(C(=O)C4CC4)CC3F)ncnc21] | N-[(3R,4R or 3S,4S)-1-(cyclopropylcarbonyl)-4-fluoropyrrolidin-3-yl]-9-ethyl-8-(2-methylpyrimidin-5-yl)-9H-purin-6-amine | Calc'd 411, found 411 |
| 3-22 | 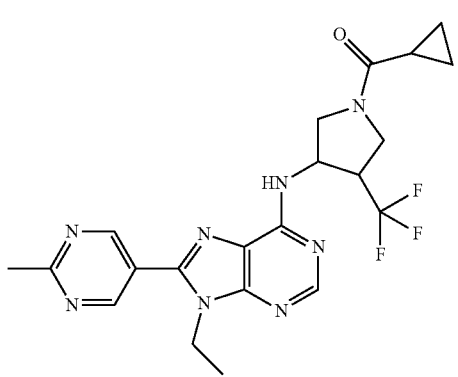 [SMILES: CCn1c(-c2cnc(C)nc2)nc2c(NC3CN(C(=O)C4CC4)CC3C(F)(F)F)ncnc21] | N-[(3R,4S and 3S,4R)-1-(cyclopropylcarbonyl)-4-(trifluoromethyl)pyrrolidin-3-yl]-9-ethyl-8-(2-methylpyrimidin-5-yl)-9H-purin-6-amine | Calc'd 461, found 461 |
| 3-23 | 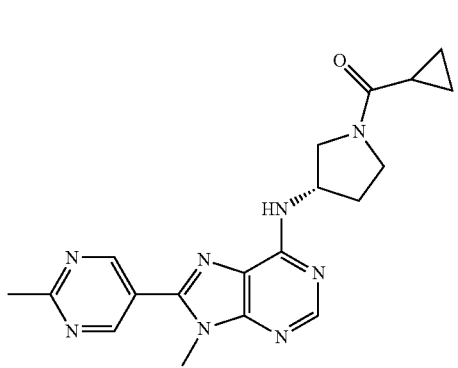 [SMILES: Cc1ncc(-c2nc3c(N[C@H]4CCN(C(=O)C5CC5)C4)ncnc3n2C)cn1] | N-[(3S)-1-(cyclopropylcarbonyl)pyrrolidin-3-yl]-9-methyl-8-(2-methylpyrimidin-5-yl)-9H-purin-6-amine | Calc'd 379, found 379 |

TABLE 3-continued

| Compound | Structure | Compound Name | MS [M + H]+ |
|---|---|---|---|
| 3-24 | 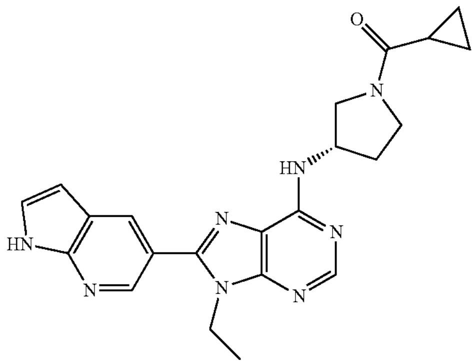 [SMILES: CCn1c(-c2cnc3[nH]ccc3c2)nc2c(N[C@H]3CCN(C(=O)C4CC4)C3)ncnc21] | N-[(3S)-1-(cyclopropylcarbonyl)pyrrolidin-3-yl]-9-ethyl-8-(1H-pyrrolo[2,3-b]pyridin-5-yl)-9H-purin-6-amine | Calc'd 417, found 417 |
| 3-25 | 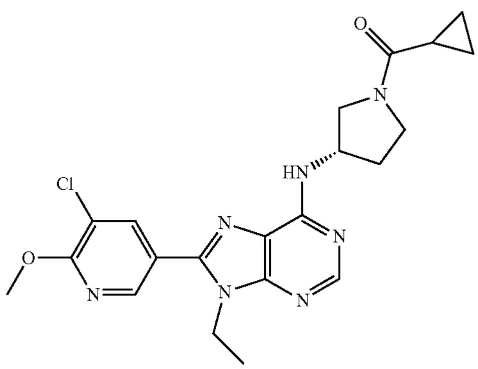 [SMILES: CCn1c(-c2cnc(OC)c(Cl)c2)nc2c(N[C@H]3CCN(C(=O)C4CC4)C3)ncnc21] | 8-(5-chloro-6-methoxypyridin-3-yl)-N-[(3S)-1-(cyclopropylcarbonyl)pyrrolidin-3-yl]-9-ethyl-9H-purin-6-amine | Calc'd 442, found 442 |
| 3-26 | 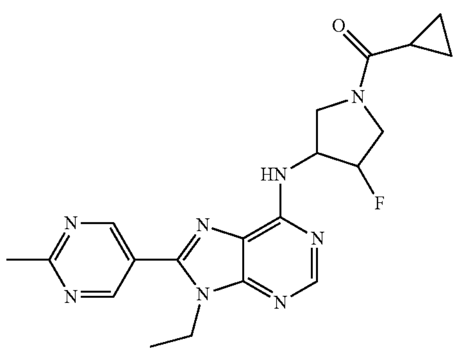 [SMILES: CCn1c(-c2cnc(C)nc2)nc2c(NC3CN(C(=O)C4CC4)CC3F)ncnc21] | N-[(3R,4S and 3S,4R)-1-(cyclopropylcarbonyl)-4-fluoropyrrolidin-3-yl]-9-ethyl-8-(2-methylpyrimidin-5-yl)-9H-purin-6-amine | Calc'd 411, found 411 |
| 3-27 | 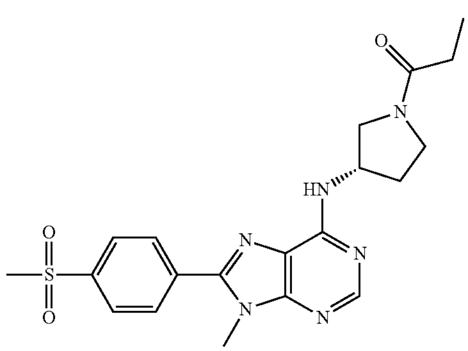 [SMILES: CCC(=O)N1CC[C@H](Nc2ncnc3c2nc(-c2ccc(S(C)(=O)=O)cc2)n3C)C1] | 9-methyl-8-[4-(methylsulfonyl)phenyl]-N-[(3S)-1-propanoylpyrrolidin-3-yl]-9H-purin-6-amine | Calc'd 429, found 429 |

TABLE 3-continued

| Compound | Structure | Compound Name | MS [M + H]+ |
|---|---|---|---|
| 3-28 | 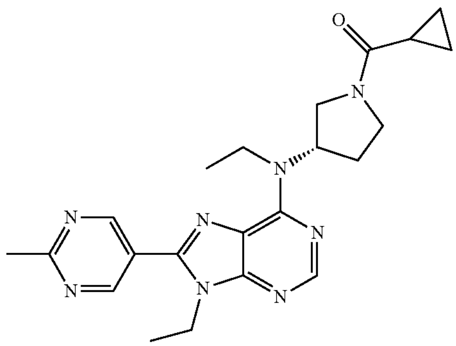 [SMILES: CCN(c1ncnc2c1nc(-c1cnc(C)nc1)n2CC)[C@H]1CCN(C(=O)C2CC2)C1] | N-[(3S)-1-(cyclopropylcarbonyl)pyrrolidin-3-yl]-N,9-diethyl-8-(2-methylpyrimidin-5-yl)-9H-purin-6-amine | Calc'd 421, found 421 |
| 3-29 | 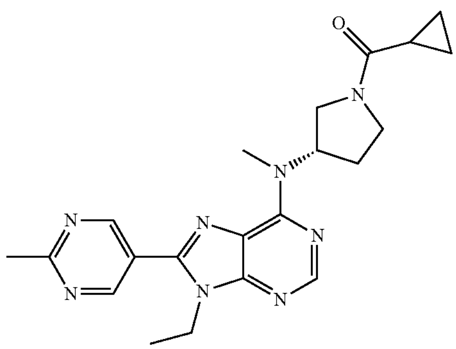 [SMILES: CCn1c(-c2cnc(C)nc2)nc2c(N(C)[C@H]3CCN(C(=O)C4CC4)C3)ncnc21] | N-[(3S)-1-(cyclopropylcarbonyl)pyrrolidin-3-yl]-9-ethyl-N-methyl-8-(2-methylpyrimidin-5-yl)-9H-purin-6-amine | Calc'd 407, found 407 |
| 3-30 | 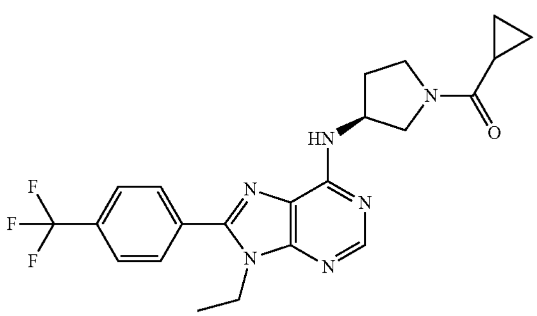 [SMILES: CCn1c(-c2ccc(C(F)(F)F)cc2)nc2c(N[C@H]3CCN(C(=O)C4CC4)C3)ncnc21] | N-[(3S)-1-(cyclopropylcarbonyl)pyrrolidin-3-yl]-9-ethyl-8-[4-(trifluoromethyl)phenyl]-9H-purin-6-amine | Calc'd 445, found 445 |
| 3-31 | 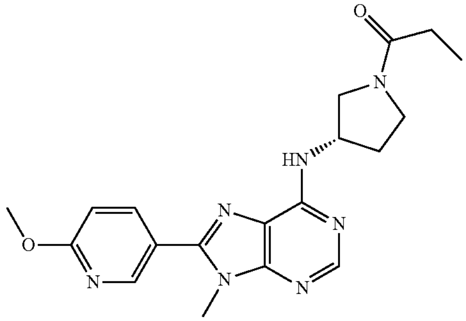 [SMILES: CCC(=O)N1CC[C@H](Nc2ncnc3c2nc(-c2ccc(OC)nc2)n3C)C1] | 8-(6-methoxypyridin-3-yl)-9-methyl-N-[(3S)-1-propanoylpyrrolidin-3-yl]-9H-purin-6-amine | Calc'd 382, found 382 |

TABLE 3-continued

| Compound | Structure | Compound Name | MS [M + H]+ |
|---|---|---|---|
| 3-32 | 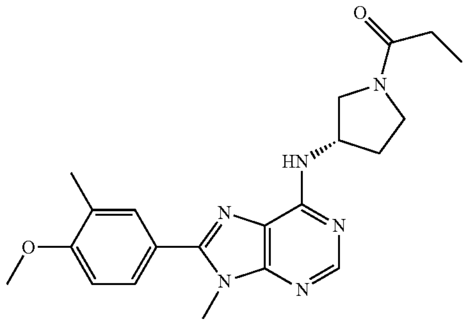 [SMILES: CCC(=O)N1CC[C@H](Nc2ncnc3c2nc(-c2ccc(OC)c(C)c2)n3C)C1] | 8-(4-methoxy-3-methylphenyl)-9-methyl-N-[(3S)-1-propanoylpyrrolidin-3-yl]-9H-purin-6-amine | Calc'd 395, found 395 |
| 3-33 | 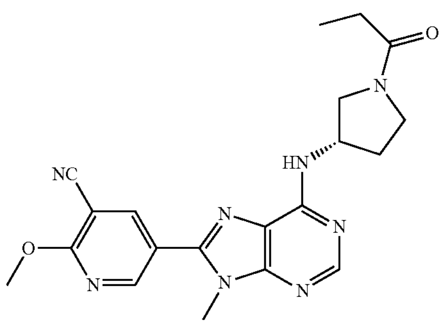 [SMILES: CCC(=O)N1CC[C@H](Nc2ncnc3c2nc(-c2cnc(OC)c(C#N)c2)n3C)C1] | 2-methoxy-5-(9-methyl-6-{[(3S)-1-propanoylpyrrolidin-3-yl]amino}-9H-purin-8-yl)pyridine-3-carbonitrile | Calc'd 407, found 407 |
| 3-34 | 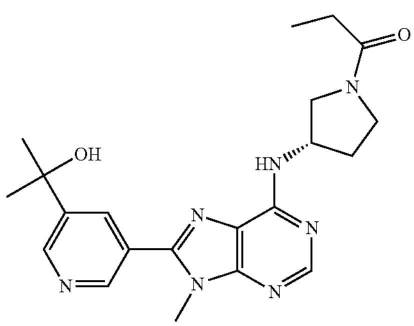 [SMILES: CCC(=O)N1CC[C@H](Nc2ncnc3c2nc(-c2cncc(C(C)(C)O)c2)n3C)C1] | 2-[5-(9-methyl-6-{[(3S)-1-propanoylpyrrolidin-3-yl]amino}-9H-purin-8-yl)pyridin-3-yl]propan-2-ol | Calc'd 410, found 410 |
| 3-35 | 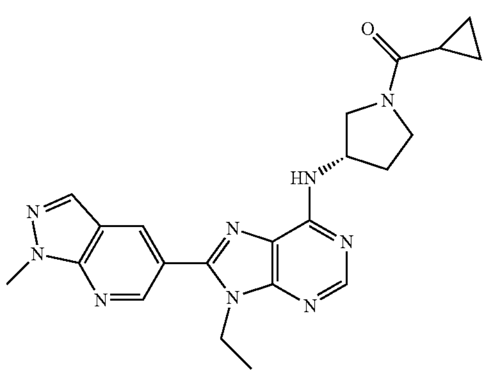 [SMILES: CCn1c(-c2cnc3c(cnn3C)c2)nc2c(N[C@H]3CCN(C(=O)C4CC4)C3)ncnc21] | N-[(3S)-1-(cyclopropylcarbonyl)pyrrolidin-3-yl]-9-ethyl-8-(1-methyl-1H-pyrazolo[3,4-b]pyridin-5-yl)-9H-purin-6-amine | Calc'd 432, found 432 |

TABLE 3-continued

| Compound | Structure | Compound Name | MS [M + H]+ |
|---|---|---|---|
| 3-36 | 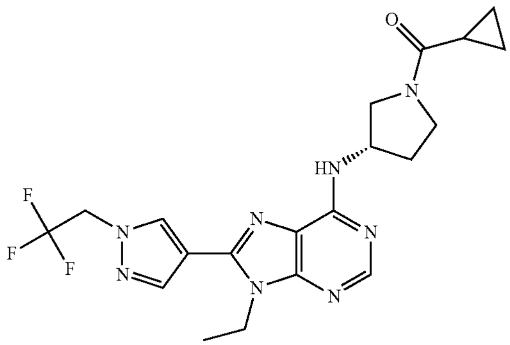 [SMILES: CCn1c(-c2cnn(CC(F)(F)F)c2)nc2c(N[C@H]3CCN(C(=O)C4CC4)C3)ncnc21] | N-[(3S)-1-(cyclopropylcarbonyl)pyrrolidin-3-yl]-9-ethyl-8-[1-(2,2,2-trifluoroethyl)-1H-pyrazol-4-yl]-9H-purin-6-amine | Calc'd 449, found 449 |
| 3-37 | 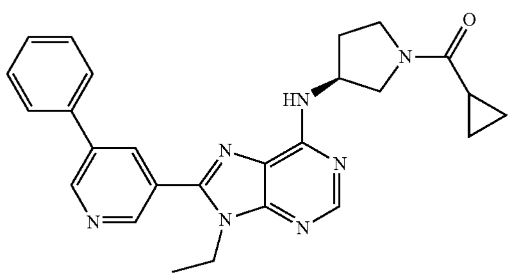 [SMILES: CCn1c(-c2cncc(-c3ccccc3)c2)nc2c(N[C@H]3CCN(C(=O)C4CC4)C3)ncnc21] | N-[(3S)-1-(cyclopropylcarbonyl)pyrrolidin-3-yl]-9-ethyl-8-(5-phenylpyridin-3-yl)-9H-purin-6-amine | Calc'd 454, found 454 |
| 3-38 | 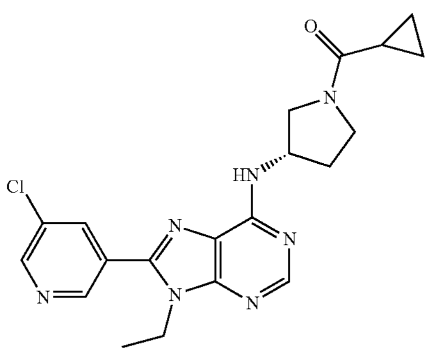 [SMILES: CCn1c(-c2cncc(Cl)c2)nc2c(N[C@H]3CCN(C(=O)C4CC4)C3)ncnc21] | 8-(5-chloropyridin-3-yl)-N-[(3S)-1-(cyclopropylcarbonyl)pyrrolidin-3-yl]-9-ethyl-9H-purin-6-amine | Calc'd 412, found 412 |
| 3-39 | 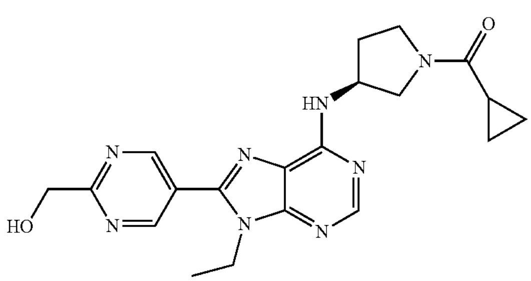 [SMILES: CCn1c(-c2cnc(CO)nc2)nc2c(N[C@H]3CCN(C(=O)C4CC4)C3)ncnc21] | [5-(6-{[(3S)-1-(cyclopropylcarbonyl)pyrrolidin-3-yl]amino}-9-ethyl-9H-purin-8-yl)pyrimidin-2-yl]methanol | Calc'd 409, found 409 |

Compound Examples of Table 3A

Example 5: Preparation of Compound 3A-1

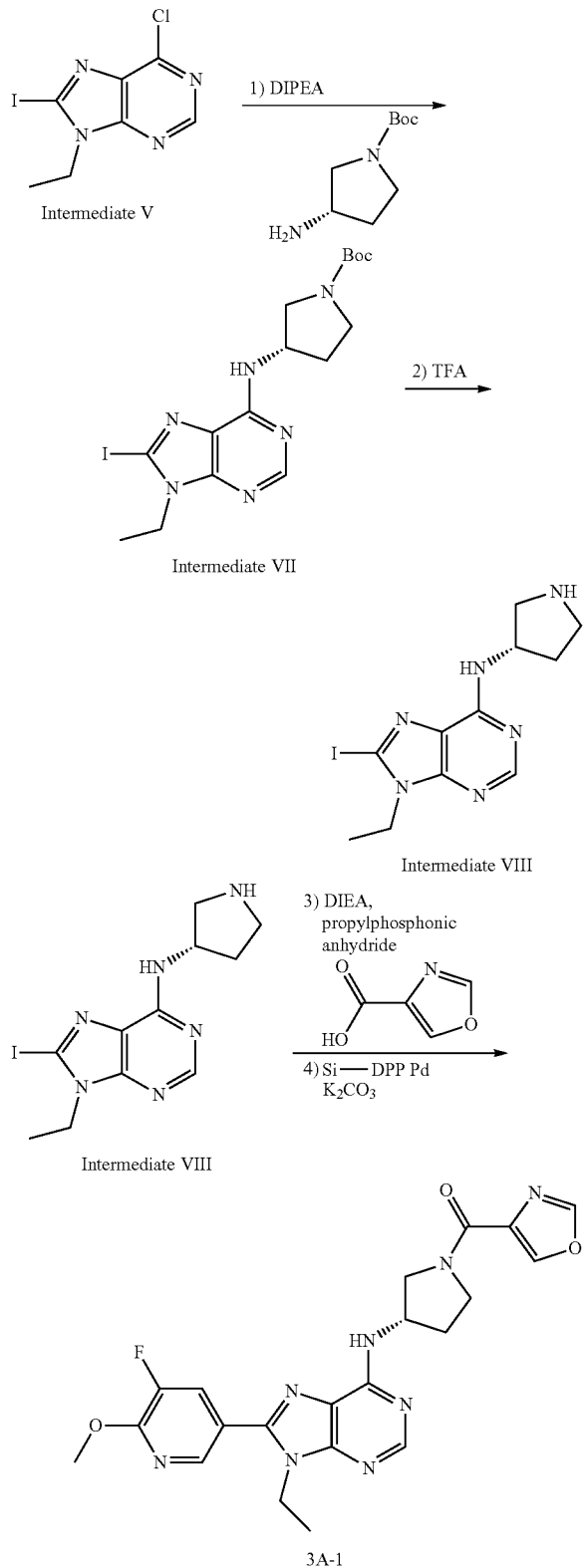

Step 1: Preparation of (S)-tert-butyl 3-(9-ethyl-8-iodo-9H-purin-6-ylamino)pyrrolidine-1-carboxylate (Intermediate VII)

To a solution of Intermediate V (30 g, 0.097 mol) in 2-methylpropan-2-ol (200 mL) were added N-ethyl-N-isopropylpropan-2-amine (37.4 g, 0.292 mol) and (S)-tert-butyl 3-aminopyrrolidine-1-carboxylate (18 g, 0.097 mol). The mixture was stirred for 12 h at 85° C. The reaction was then cooled and quenched by the addition of water (300 mL), extracted with ethyl acetate (3×200 mL), and the organic layers were combined and dried over anhydrous magnesium sulfate. The solids were filtered, and the filtrate was concentrated under reduced pressure to give a residue which was purified by silica gel column chromatography, eluting with 3% methanol in dichloromethane to afford (S)-tert-butyl 3-(9-ethyl-8-iodo-9H-purin-6-ylamino)pyrrolidine-1-carboxylate (Intermediate VII). MS (ESI) calc'd for ($C_{16}H_{24}IN_6O_2$) [M+H]$^+$, 459. found, 459.

Step 2: Preparation of (S)-9-ethyl-8-iodo-N-(pyrrolidin-3-yl)-9H-purin-6-amine, TFA (Intermediate VIII)

To a round bottom flask was added (S)-tert-butyl 3-((9-ethyl-8-iodo-9H-purin-6-yl)amino)pyrrolidine-1-carboxylate (Intermediate VII) (1.0 g, 2.2 mmol) dissolved in DCM (35 mL). To the reaction was added TFA (3.4 mL, 44 mmol) drop-wise at ambient temperature. The reaction was allowed to stir at ambient temperature for 3 hours. The reaction was then concentrated in vacuo to afford (S)-9-ethyl-8-iodo-N-(pyrrolidin-3-yl)-9H-purin-6-amine (Intermediate VIII) as the TFA salt. MS ESI calc'd. for $C_{11}H_{16}IN_6$ [M+H]$^+$ 359. found 359.

Step 3: Preparation of (S)-(3-((9-ethyl-8-iodo-9H-purin-6-yl)amino)pyrrolidin-1-yl)(oxazol-4-yl)methanone A reaction vessel was charged with Intermediate VIII (as the TFA salt) (0.052 g, 0.11 mmol) and oxazole-4-carboxylic acid (0.024 g, 0.21 mmol). Next was added DCM (1.1 mL), and DIEA (0.060 mL, 0.32 mmol) and the reaction was allowed to stir for 5 minutes. Next was added propylphosphonic anhydride solution (0.10 mL, 50% w/w in DMF). The reaction vessel was capped and stirred at ambient temperature for 6 hours. The reaction was diluted with water (2.0 mL), and was extracted with DCM (5.0 mL) using a phase separator SPE cartridge. The collected organics were concentrated in vacuo to afford (S)-(3-((9-ethyl-8-iodo-9H-purin-6-yl)amino)pyrrolidin-1-yl)(oxazol-4-yl)methanone as a crude residue. MS ESI calc'd. for $C_{15}H_{17}IN_7O_2$[M+H]$^+$ 454. found 454.

Step 4: Synthesis of 3A-1

To a microwave vial was added (S)-(3-((9-ethyl-8-iodo-9H-purin-6-yl)amino)pyrrolidin-1-yl)(oxazol-4-yl)methanone (0.050 g, 0.11 mmol), 3-fluoro-2-methoxy-5-(4,4,5,5-tetramethyl-1,3,2-dioxaborolan-2-yl)pyridine (0.090 g, 0.35 mmol), potassium phosphate tribasic (0.075 g, 0.35 mmol), SiliaCat® DPP-Pd (0.090 g, 0.023 mmol, 0.26 mmol/g) (available from Silicycle), dioxane (1.0 mL), and water (0.30 mL). The reaction vial was sealed and irradiated in the microwave for 20 minutes at 150° C. The reaction was then diluted with water (2.0 mL) and extracted with DCM (5.0 mL) using a phase separator SPE cartridge. The collected eluent was concentrated in vacuo, the residue was taken up in DMSO (1.0 mL), passed through a syringe filter and the filtrate was purified by reverse phase preparative HPLC (0:100 to 95:5 acetonitrile:water: 0.1% v/v TFA modifier) to afford 3A-1. $^1$H NMR (500 MHz, DMSO-d$_6$): δ 8.62-8.60 (m, 1H), 8.48-8.43 (m, 1H), 8.41-8.39 (m, 1H), 8.33-8.28 (m, 1H), 8.12-8.08 (m, 1H), 4.81-4.71 (m, 1H), 4.28-4.23 (m, 2H), 4.19-4.13 (m, 1H), 4.03 (s, 3H), 3.97-3.82 (m, 2H), 3.73-3.67 (m, 1H), 3.62-3.52 (m, 1H), 2.28-2.07 (m, 2H), 1.28-1.24 (m, 3H). MS ESI calc'd. for $C_{21}H_{22}FN_8O_3$[M+H]$^+$ 453. found 453.

Compounds 3A-2 through 3A-8 were prepared in an analogous fashion to Example 5.

TABLE 3A

| Compound | Structure | Compound Name | Exact Mass [M + H]+ |
|---|---|---|---|
| 3A-1 | 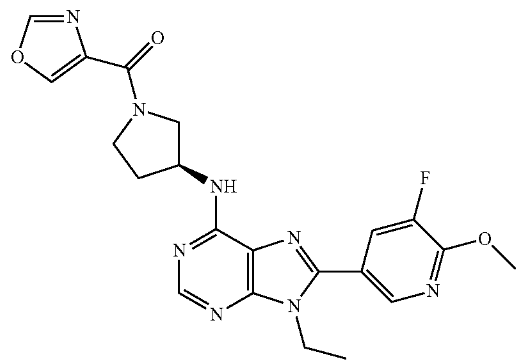 [SMILES: CCn1c(-c2cnc(OC)c(F)c2)nc2c(N[C@H]3CCN(C(=O)c4cocn4)C3)ncnc21] | 9-ethyl-8-(5-fluoro-6-methoxypyridin-3-yl)-N-[(3S)-1-(1,3-oxazol-4-ylcarbonyl)pyrrolidin-3-yl]-9H-purin-6-amine | Calc'd 453, found 453 |
| 3A-2 | 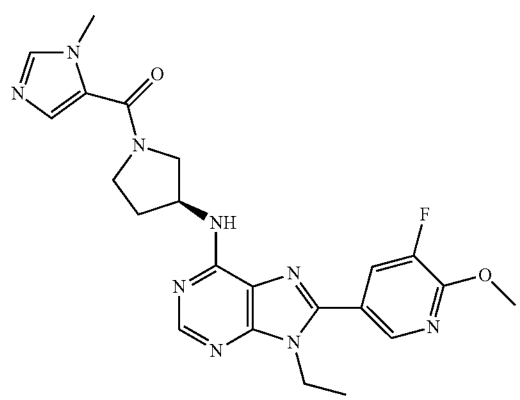 [SMILES: CCn1c(-c2cnc(OC)c(F)c2)nc2c(N[C@H]3CCN(C(=O)c4cncn4C)C3)ncnc21] | 9-ethyl-8-(5-fluoro-6-methoxypyridin-3-yl)-N-{(3S)-1-[(1-methyl-1H-imidazol-5-yl)carbonyl]pyrrolidin-3-yl}-9H-purin-6-amine | Calc'd 466, found 466 |
| 3A-3 | 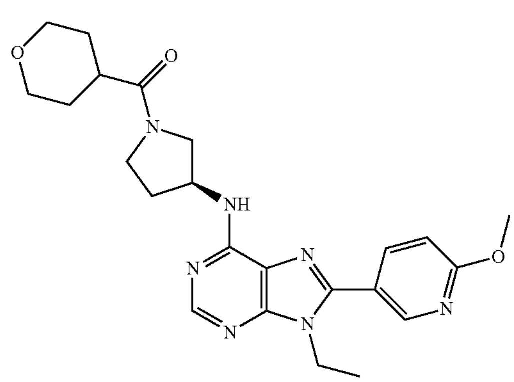 [SMILES: CCn1c(-c2ccc(OC)nc2)nc2c(N[C@H]3CCN(C(=O)C4CCOCC4)C3)ncnc21] | 9-ethyl-8-(6-methoxypyridin-3-yl)-N-[(3S)-1-(tetrahydro-2H-pyran-4-ylcarbonyl)pyrrolidin-3-yl]-9H-purin-6-amine | Calc'd 452, found 452 |

TABLE 3A-continued

| Compound | Structure | Compound Name | Exact Mass [M + H]+ |
|---|---|---|---|
| 3A-4 | 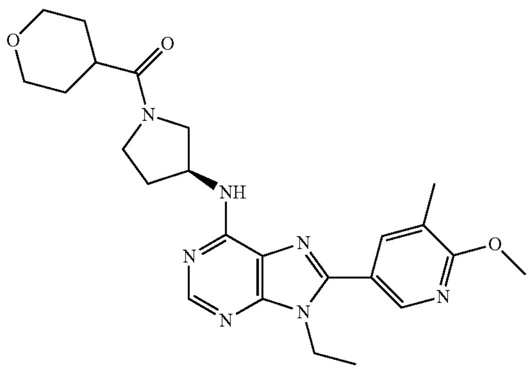 [SMILES: CCn1c(-c2cnc(OC)c(C)c2)nc2c(N[C@H]3CCN(C(=O)C4CCOCC4)C3)ncnc21] | 9-ethyl-8-(6-methoxy-5-methylpyridin-3-yl)-N-[(3S)-1-(tetrahydro-2H-pyran-4-ylcarbonyl)pyrrolidin-3-yl]-9H-purin-6-amine | Calc'd 466, found 466 |
| 3A-5 | 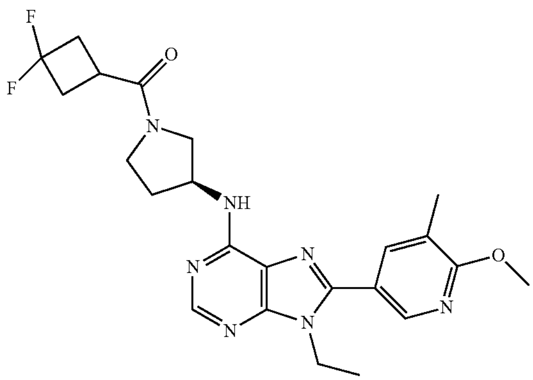 | N-{(3S)-1-[(3,3-difluorocyclobutyl)carbonyl]pyrrolidin-3-yl}-9-ethyl-8-(6-methoxy-5-methylpyridin-3-yl)-9H-purin-6-amine | Calc'd 472, found 472 |
| 3A-6 | 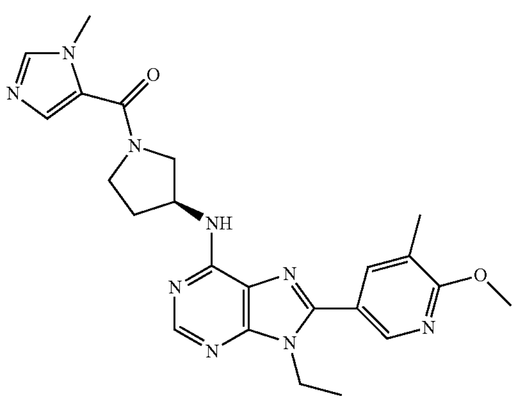 [SMILES: CCn1c(-c2cnc(OC)c(C)c2)nc2c(N[C@H]3CCN(C(=O)c4cncn4C)C3)ncnc21] | 9-ethyl-8-(6-methoxy-5-methylpyridin-3-yl)-N-{(3S)-1-[(1-methyl-1H-imidazol-5-yl)carbonyl]pyrrolidin-3-yl}-9H-purin-6-amine | Calc'd 462, found 462 |
| 3A-7 | 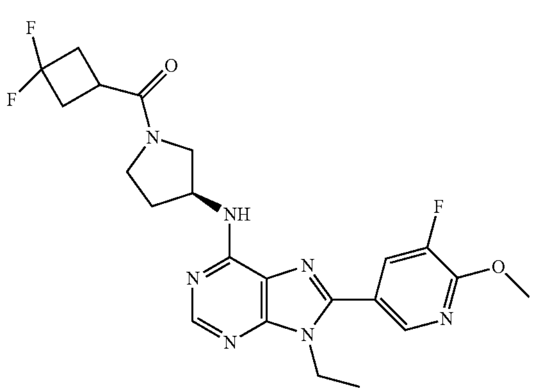 [SMILES: CCn1c(-c2cnc(OC)c(F)c2)nc2c(N[C@H]3CCN(C(=O)C4CC(F)(F)C4)C3)ncnc21] | N-{(3S)-1-[(3,3-difluorocyclobutyl)carbonyl]pyrrolidin-3-yl}-9-ethyl-8-(5-fluoro-6-methoxypyridin-3-yl)-9H-purin-6-amine | Calc'd 476, found 476 |

TABLE 3A-continued

| Compound | Structure | Compound Name | Exact Mass [M + H]+ |
|---|---|---|---|
| 3A-8 | 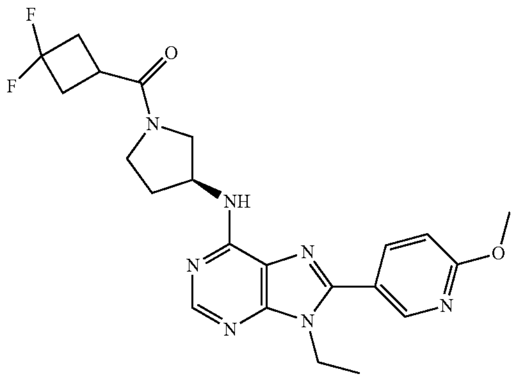 [SMILES: CCn1c(-c2ccc(OC)nc2)nc2c(N[C@H]3CCN(C(=O)C4CC(F)(F)C4)C3)ncnc21] | N-{(3S)-1-[(3,3-difluorocyclobutyl)carbonyl]pyrrolidin-3-yl}-9-ethyl-8-(6-methoxypyridin-3-yl)-9H-purin-6-amine | Calc'd 458, found 458 |

Compound Examples of Table 4

Example 6: Preparation of Compound 4-1

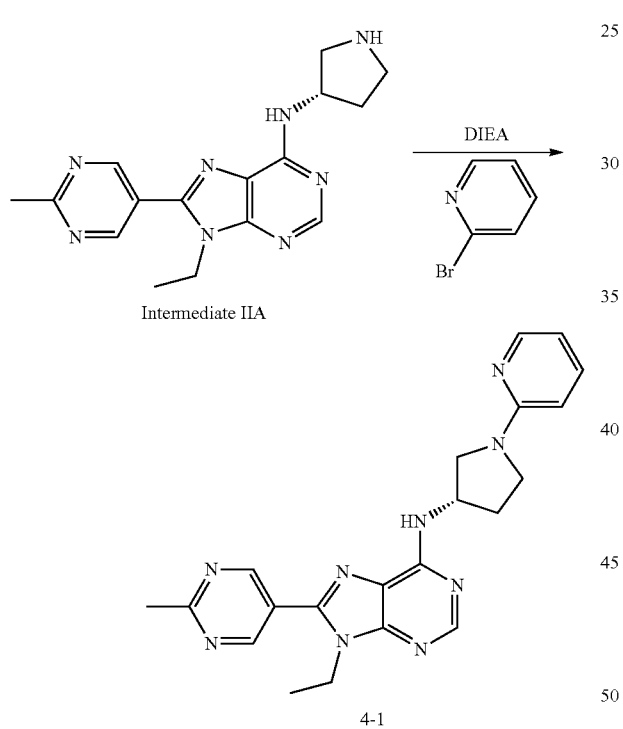

To a solution of (S)-9-ethyl-8-(2-methylpyrimidin-5-yl)-N-(pyrrolidin-3-yl)-9H-purin-6-amine Intermediate IIA (in its neutral form) (60 mg, 0.185 mmol) in DIEA (2 mL) was added 2-bromopyridine (292 mg, 1.85 mmol). After addition, the reaction mixture was heated to 90° C. for 10 h. The reaction was then cooled and quenched with water (30 mL), extracted with EtOAc (2×50 mL), and the organic layer was washed with brine, dried over sodium sulfate, filtered, and concentrated in vacuo to afford an oil which was purified by reverse phase preparative HPLC (Mobile phase; A: water (10 mM $NH_4HCO_3$), B: MeCN) to provide 4-1. $^1$H NMR (400 MHz, MeOD-$d_4$) δ 9.12 (s, 2H), 8.37 (s, 1H), 8.04-8.00 (m, 1H), 7.59-7.51 (m, 1H), 6.63-6.54 (m, 2H), 5.05-4.95 (m, 1H), 4.41 (q, J=7.4 Hz, 2H), 3.95-3.54 (m, 4H), 2.83 (s, 3H), 2.54-2.22 (m, 2H), 1.45 (t, J=7.4 Hz, 3H). MS (ESI) calc'd for ($C_{21}H_{24}N_9$) [M+H]$^+$, 402. found, 402.

Example 7: Preparation of Compound 4-3

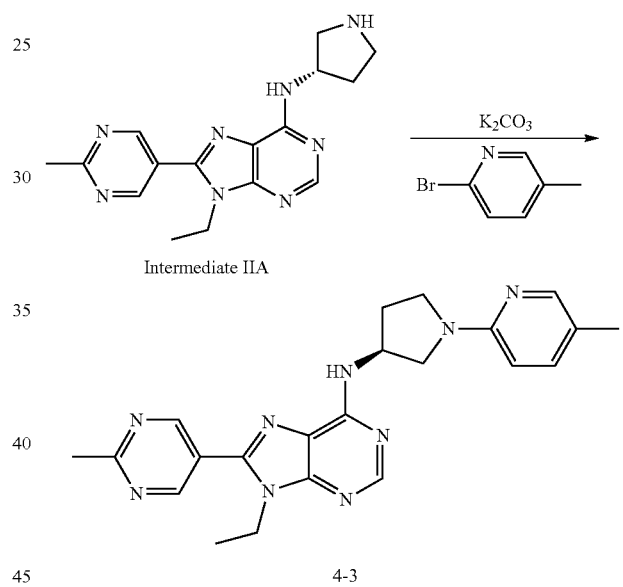

A reaction mixture of Intermediate IIA (100 mg, 0.31 mmol), 2-bromo-5-methylpyridine (58.0 mg, 0.34 mmol, commercially available from Beijing Wisdom Chemicals Co. Ltd.) and potassium carbonate (85.2 mg, 0.62 mmol) in N-methylpyrrolidone (3 mL) was irradiated with microwave radiation (200 Watt) for 30 minutes at 150° C. The mixture was cooled, and water (8 mL) was added and the mixture was extracted with dichloromethane (3×8 mL). The combined organic extracts were concentrated under reduced pressure. The residue was purified by preparative reverse-phase HPLC with the following conditions: [(Waters-2767-Prep): Column: Xbridge C 18, 19×150 mm; Mobile phase: 10-55% acetonitrile in water with 0.05% ammonium bicarbonate] to afford (S)-9-ethyl-N-(1-(5-methylpyridin-2-yl)pyrrolidin-3-yl)-8-(2-methylpyrimidin-5-yl)-9H-purin-6-amine (4-3). $^1$H NMR (300 MHz, DMSO-$d_6$) δ 9.08 (s, 2H), 8.29 (s, 1H), 8.22 (br, 1H), 7.84 (d, J=2.1 Hz, 1H), 7.27 (dd, J=8.7, 2.1 Hz, 1H), 6.33 (d, J=8.7 Hz, 1H), 4.88-4.84 (m, 1H), 4.30 (q, J=7.2 Hz, 2H), 3.81-3.76 (m, 1H), 3.60-3.51 (m, 1H), 3.40-3.36 (m, 2H), 2.70 (s, 3H), 2.28-2.21 (m, 2H), 2.08 (s, 3H), 1.31 (t, J=7.2 Hz, 3H). MS (ESI) calc'd for ($C_{22}H_{26}N_9$) [M+H]$^+$, 416. found, 416.

Example 8: Preparation of Compound 4-12

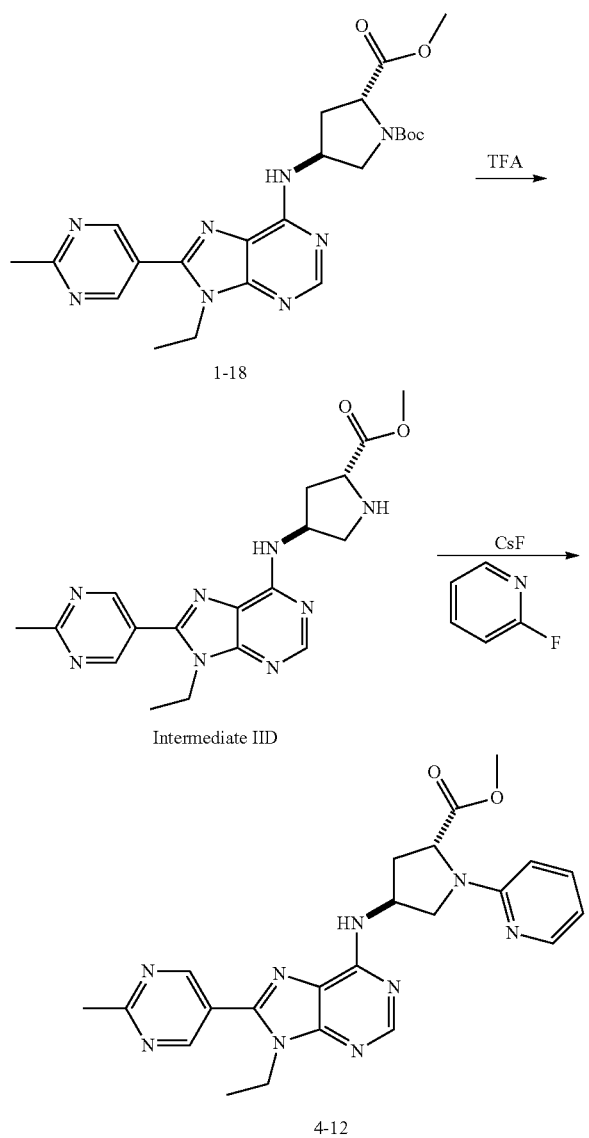

Step 1: Preparation of (2R,4S)-methyl-4-((9-ethyl-8-(2-methylpyrimidin-5-yl)-9H-purin-6-yl)amino)pyrrolidine-2-carboxylate, TFA (Intermediate IID)

A vial was charged with (2R,4S)-1-tert-butyl 2-methyl 4-((9-ethyl-8-(2-methylpyrimidin-5-yl)-9H-purin-6-yl)amino)pyrrolidine-1,2-dicarboxylate (compound 1-18) (500 mg, 1.036 mmol) in DCM (5 mL). To this solution was added TFA (1.597 mL, 20.72 mmol). The reaction mixture was stirred at 25° C. for 16 hours. The reaction mixture was then concentrated in vacuo to give (2R,4S)-methyl-4-((9-ethyl-8-(2-methylpyrimidin-5-yl)-9H-purin-6-yl)amino)pyrrolidine-2-carboxylate, as the TFA salt (Intermediate IID) which was used without further purification in the next step. MS (ESI) calc'd for ($C_{18}H_{23}N_8O_2$) [M+H]$^+$, 383. found, 383.

Step 2: Preparation of Compound 4-12

To a solution of (2R,4S)-methyl 4-((9-ethyl-8-(2-methylpyrimidin-5-yl)-9H-purin-6-yl)amino)pyrrolidine-2-carboxylate (Intermediate IID) (850 mg, 1.77 mmol) and DIEA (1.941 mL, 11.11 mmol) in acetonitrile (5 mL) was added 2-fluoropyridine (1.913 mL, 22.23 mmol) and cesium fluoride (338 mg, 2.223 mmol). The resulting mixture was stirred at 130° C. for 48 h. The reaction mixture was then filtered and the filtrate purified by reverse phase preparative HPLC (MECN/water with 0.1% TFA modifier) to afford the compound 4-12 as the TFA salt. $^1$H NMR (400 MHz, DMSO-$d_6$): δ 9.08 (s, 2H), 8.57-8.44 (m, 1H), 8.34 (broad s, 1H), 8.05-7.98 (m, 1H), 7.77 (broad s, 1H), 6.80 (broad s, 2H), 5.02-4.81 (m, 2H), 4.33-4.21 (m, 2H), 4.02-3.92 (m, 1H), 3.70-3.51 (m, 4H), 2.74-2.66 (m, 3H), 2.64-2.38 (m, 2H), 1.33-1.22 (m, 3H). MS (EI) Calc'd for $C_{23}H_{26}N_9O_2$ [M+H]$^+$, 460. found 460.

Compound 4-2 was prepared in an analogous fashion to Example 6.

Compounds 4-4 through 4-11 were prepared in an analogous fashion to Example 7.

Compound 4-13 was prepared in an analogous fashion to Example 7 except that cesium carbonate was used in place of potassium carbonate and the reaction was stirred at 100° C., in the absence of microwave irradiation, for 24 h. The compound was purified via reverse phase preparative HPLC (0:100 to 95:5 acetonitrile:water: 0.1% v/v TFA modifier).

TABLE 4

| Compound | Structure | Compound Name | Exact Mass [M + H]+ |
|---|---|---|---|
| 4-1 | 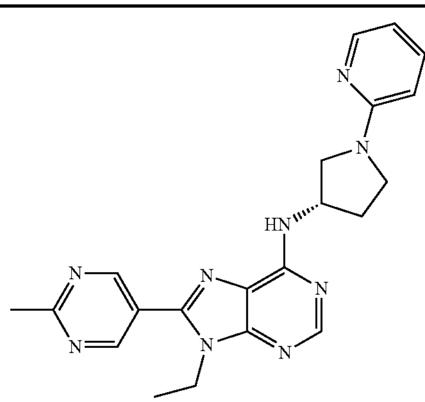 | 9-ethyl-8-(2-methylpyrimidin-5-yl)-N-[(3S)-1-pyridin-2-ylpyrrolidin-3-yl]-9H-purin-6-amine | Calc'd 402, found 402 |

TABLE 4-continued

| Compound | Structure | Compound Name | Exact Mass [M + H]+ |
|---|---|---|---|
| 4-2 | 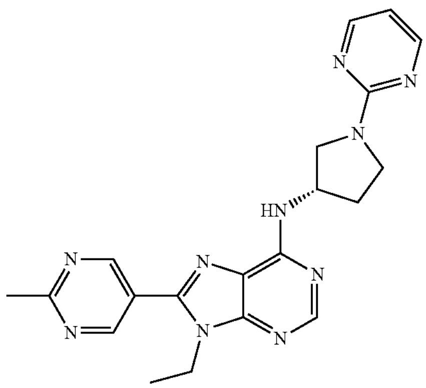 [SMILES: CCn1c(-c2cnc(C)nc2)nc2c(N[C@H]3CCN(c4ncccn4)C3)ncnc21] | 9-ethyl-8-(2-methylpyrimidin-5-yl)-N-[(3S)-1-pyrimidin-2-ylpyrrolidin-3-yl]-9H-purin-6-amine | Calc'd 403, found 403 |
| 4-3 | 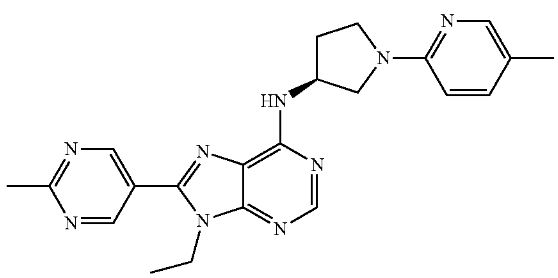 | 9-ethyl-N-[(3S)-1-(5-methylpyridin-2-yl)pyrrolidin-3-yl]-8-(2-methylpyrimidin-5-yl)-9H-purin-6-amine | Calc'd 416, found 416 |
| 4-4 | 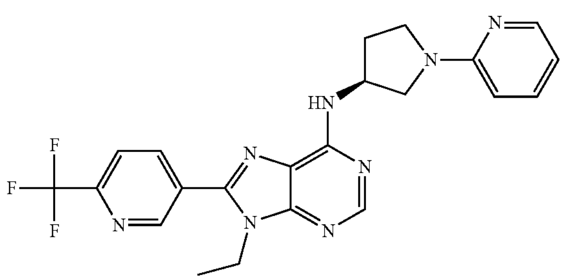 [SMILES: CCn1c(-c2ccc(C(F)(F)F)nc2)nc2c(N[C@H]3CCN(c4ccccn4)C3)ncnc21] | 9-ethyl-N-[(3S)-1-pyridin-2-ylpyrrolidin-3-yl]-8-[6-(trifluoromethyl)pyridin-3-yl]-9H-purin-6-amine | Calc'd 455, found 455 |
| 4-5 | 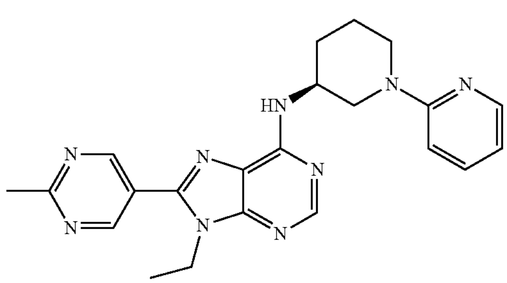 [SMILES: CCn1c(-c2cnc(C)nc2)nc2c(N[C@H]3CCCN(c4ccccn4)C3)ncnc21] | 9-ethyl-8-(2-methylpyrimidin-5-yl)-N-[(3S)-1-pyridin-2-ylpiperidin-3-yl]-9H-purin-6-amine | Calc'd 416, found 416 |
| 4-6 | 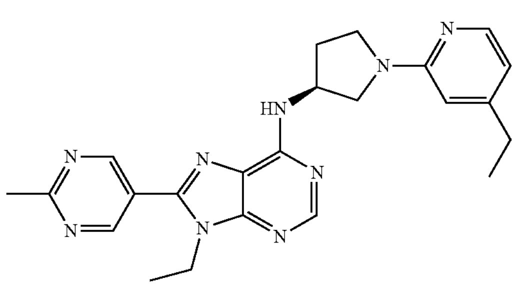 [SMILES: CCc1ccnc(N2CC[C@H](Nc3ncnc4c3nc(-c3cnc(C)nc3)n4CC)C2)c1] | 9-ethyl-N-[(3S)-1-(4-ethylpyridin-2-yl)pyrrolidin-3-yl]-8-(2-methylpyrimidin-5-yl)-9H-purin-6-amine | Calc'd 430, found 430 |

TABLE 4-continued

| Compound | Structure | Compound Name | Exact Mass [M + H]+ |
|---|---|---|---|
| 4-7 | 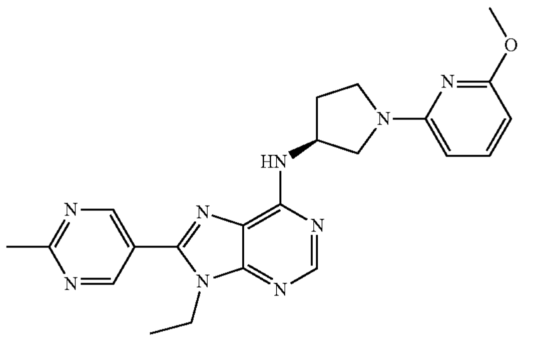 [SMILES: CCn1c(-c2cnc(C)nc2)nc2c(N[C@H]3CCN(c4cccc(OC)n4)C3)ncnc21] | 9-ethyl-N-[(3S)-1-(6-methoxypyridin-2-yl)pyrrolidin-3-yl]-8-(2-methylpyrimidin-5-yl)-9H-purin-6-amine | Calc'd 432, found 432 |
| 4-8 | 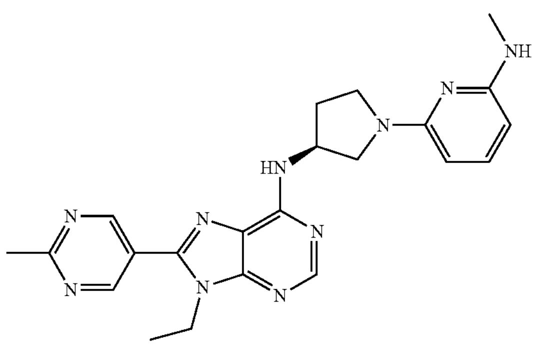 [SMILES: CCn1c(-c2cnc(C)nc2)nc2c(N[C@H]3CCN(c4cccc(NC)n4)C3)ncnc21] | 9-ethyl-N-{(3S)-1-[6-(methylamino)pyridin-2-yl]pyrrolidin-3-yl}-8-(2-methylpyrimidin-5-yl)-9H-purin-6-amine | Calc'd 431, found 431 |
| 4-9 | 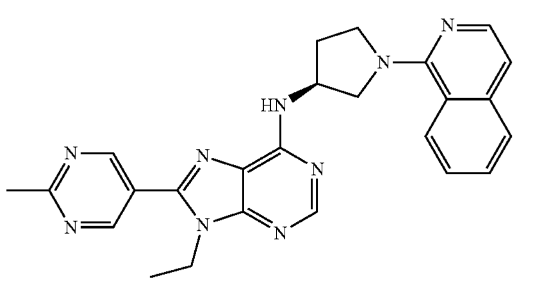 [SMILES: CCn1c(-c2cnc(C)nc2)nc2c(N[C@H]3CCN(c4nccc5ccccc45)C3)ncnc21] | 9-ethyl-N-[(3S)-1-isoquinolin-1-ylpyrrolidin-3-yl]-8-(2-methylpyrimidin-5-yl)-9H-purin-6-amine | Calc'd 452, found 452 |
| 4-10 | 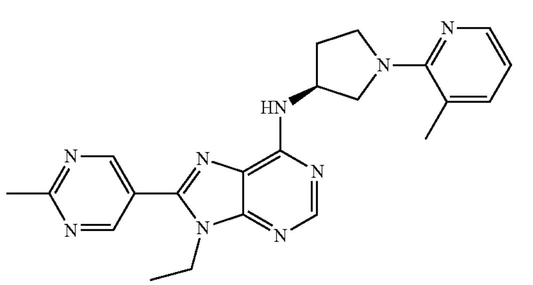 [SMILES: CCn1c(-c2cnc(C)nc2)nc2c(N[C@H]3CCN(c4ncccc4C)C3)ncnc21] | 9-ethyl-N-[(3S)-1-(3-methylpyridin-2-yl)pyrrolidin-3-yl]-8-(2-methylpyrimidin-5-yl)-9H-purin-6-amine | Calc'd 416, found 416 |

TABLE 4-continued

| Compound | Structure | Compound Name | Exact Mass [M + H]+ |
|---|---|---|---|
| 4-11 | 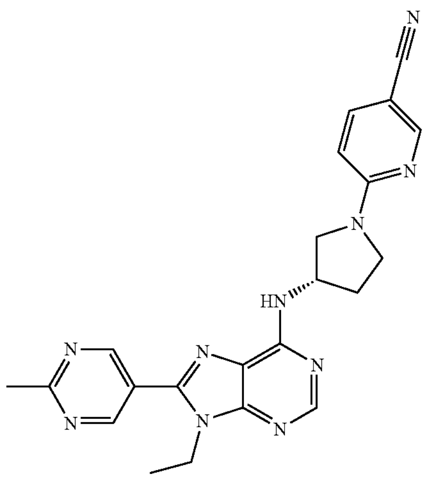 [SMILES: CCn1c(-c2cnc(C)nc2)nc2c(N[C@H]3CCN(c4ccc(C#N)cn4)C3)ncnc21] | 6-[(3S)-3-{[9-ethyl-8-(2-methylpyrimidin-5-yl)-9H-purin-6-yl]amino}pyrrolidin-1-yl]pyridine-3-carbonitrile | Calc'd 427, found 427 |
| 4-12 | 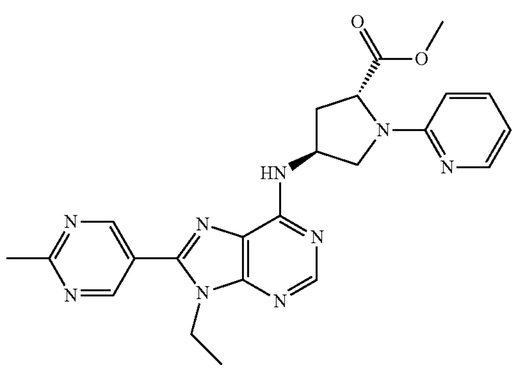 [SMILES: CCn1c(-c2cnc(C)nc2)nc2c(N[C@H]3C[C@H](C(=O)OC)N(c4ccccn4)C3)ncnc21] | methyl (4S)-4-{[9-ethyl-8-(2-methylpyrimidin-5-yl)-9H-purin-6-yl]amino}-1-pyridin-2-yl-D-prolinate | Calc'd 460, found 460 |
| 4-13 | 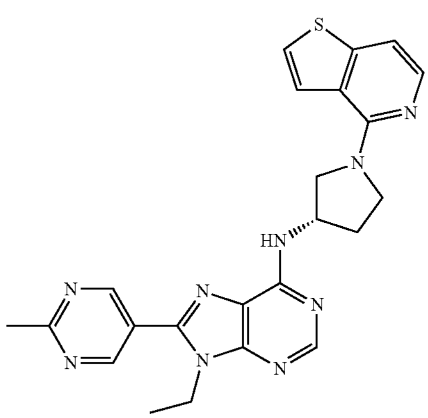 [SMILES: CCn1c(-c2cnc(C)nc2)nc2c(N[C@H]3CCN(c4nccc5sccc45)C3)ncnc21] | 9-ethyl-8-(2-methylpyrimidin-5-yl)-N-[(3S)-1-thieno[3,2-c]pyridin-4-y1pyrrolidin-3-yl]-9H-purin-6-amine | Calc'd 458, found 458 |

Compound Examples of Table 5

Example 8A: Preparation of Compound 5-1

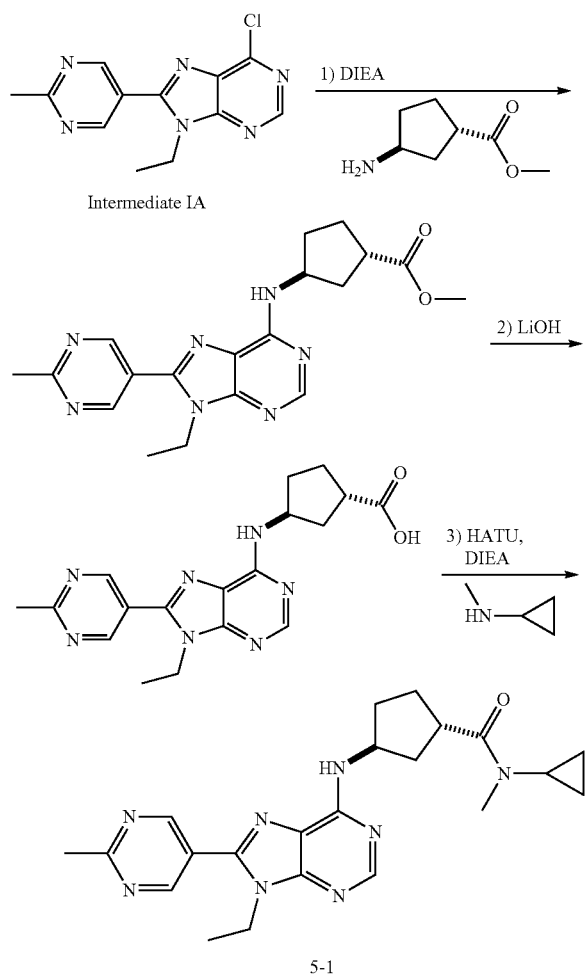

5-1

Step 1: Preparation of (1S,3S)-methyl 3-((9-ethyl-8-(2-methylpyrimidin-5-yl)-9H-purin-6-yl)amino)cyclopentanecarboxylate A reaction vial was charged with (1S,3S)-methyl 3-aminocyclopentanecarboxylate (250 mg, 1.75 mmol) (commercially available from Chemstep), 6-chloro-9-ethyl-8-(2-methylpyrimidin-5-yl)-9H-purine (Intermediate IA) (576 mg, 2.10 mmol), DMF (7 mL) and DIEA (1.53 mL, 8.73 mmol). The mixture was stirred at 80° C. for 24 hours. The reaction mixture was then cooled and concentrated in vacuo and the residue was purified by column chromatography on silica gel (eluting with 0-8% MeOH in DCM) to afford (1S,3S)-methyl-3-((9-ethyl-8-(2-methylpyrimidin-5-yl)-9H-purin-6-yl)amino)cyclopentanecarboxylate. MS (ESI) calc'd for ($C_{19}H_{24}N_7O_2$) [M+H]$^+$, 382. found, 382.

Step 2: Preparation of (1S,3S)-3-((9-ethyl-8-(2-methylpyrimidin-5-yl)-9H-purin-6-yl)amino)cyclopentanecarboxylic Acid Purine To a solution of (1S,3S)-methyl-3-((9-ethyl-8-(2-methylpyrimidin-5-yl)-9H-purin-6-yl)amino)cyclopentanecarboxylate (203 mg, 0.603 mmol) in THF (4 mL) and methanol (0.8 mL) was added an aqueous LiOH solution (1.544 mL of 1M, 1.544 mmol). The mixture was stirred at room temperature for 16 hours. The reaction mixture was then neutralized with an aqueous HCl solution (0.772 mL of 2M, 1.54 mmol). The reaction mixture was concentrated in vacuo and subsequently azeotroped twice with toluene. The crude product, which contained lithium chloride, and was used without further purification in the next step. MS (ESI) calc'd for ($C_{18}H_{22}N_7O_2$) [M+H]$^+$, 368.4. found, 368.3.

Step 3: Preparation of Compound 5-1

To a reaction vial were added (1S,3S)-3-((9-ethyl-8-(2-methylpyrimidin-5-yl)-9H-purin-6-yl)amino)cyclopentanecarboxylic acid (65 mg, 0.18 mmol) N-methylcyclopropanamine (commercially available from Enamine LLC). (15.1 mg, 0.212 mmol), HATU (81 mg, 0.21 mmol) in DMF (1 mL) was added DIEA (0.278 ml, 1.592 mmol). The mixture was stirred for 16 hours at 25° C. The mixture was then filtered and the filtrate was purified by mass-triggered reverse-phase HPLC (MeCN/water with 0.1% TFA modifier) to afford (S)-cyclopropyl(3-((9-ethyl-8-(4-(trifluoromethoxy)phenyl)-9H-purin-6-yl)oxy)pyrrolidin-1-yl)methanone (5-1) as the TFA salt. MS (ESI) calc'd for ($C_{22}H_{29}N_8O$) [M+H]$^+$, 421. found, 421.

Example 8B: Preparation of Compound 5-8

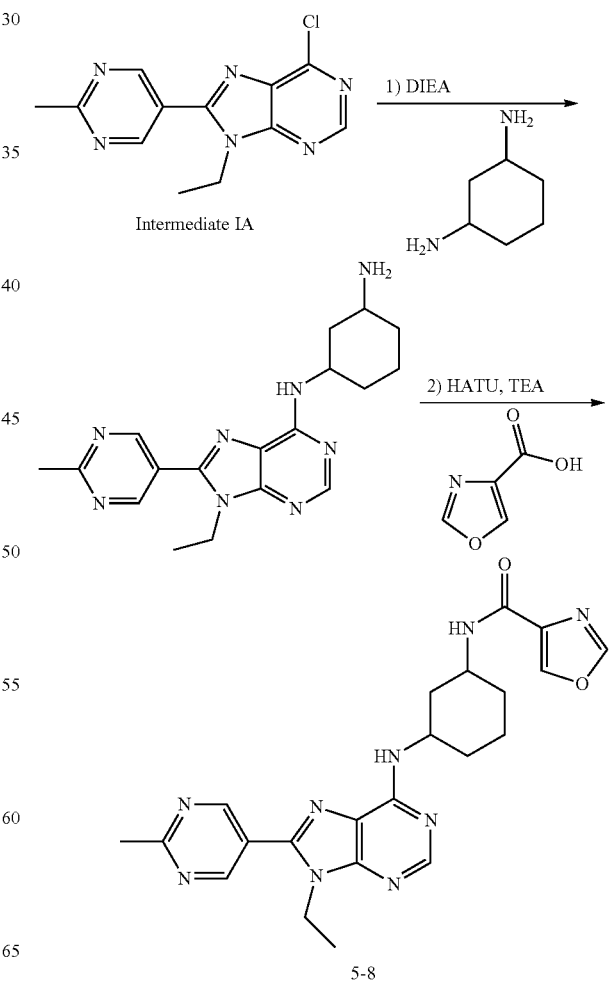

5-8

Step 1: Synthesis of (1(S and R), 3(S and R))—N¹-(9-ethyl-8-(2-methylpyrimidin-5-yl)-9H-purin-6-yl)cyclo-hexane-1,3-diamine To a stirred solution of cyclohexane-1,3-diamine (1.05 ml, 8.74 mmol) in t-BuOH (25 ml) was added DIEA (0.381 ml, 2.18 mmol) at RT, after which Intermediate IA (300 mg, 1.09 mmol) was added. The resulting mixture was stirred at 85° C. for 15 h. The reaction was then cooled and the solvent was evaporated under reduced pressure, after which water (5 mL) was added and the mixture was extracted with EtOAc (2×30 mL). The combined organic fractions were washed with water (2×20 mL), dried over sodium sulfate, filtered, and the solvent was evaporated under reduced pressure to give the crude product. The residue was purified by reverse-phase preparative HPLC (C-18, eluting with acetonitrile/water+0.05% NH₃) to give (1(S and R), 3(S and R))—N¹-(9-ethyl-8-(2-methylpyrimidin-5-yl)-9H-purin-6-yl)cyclo-hexane-1,3-diamine as a mixture of racemic diastereomers. MS (ESI) calc'd for ($C_{18}H_{25}N_8$) [M+H]⁺, 353. found, 353.

Step 2: Preparation of Compound 5-8

(1(S and R), 3(S and R))—N¹-(9-ethyl-8-(2-methylpyrimidin-5-yl)-9H-purin-6-yl)cyclo-hexane-1,3-diamine (230 mg, 0.653 mmol) was dissolved in DCM (10 ml) and TEA (0.364 ml, 2.61 mmol) was added, followed by oxazole-4-carboxylic acid (81 mg, 0.72 mmol) and HATU (273 mg, 0.718 mmol). The reaction was allowed to stir at room temperature for 16 h. The mixture was then concentrated and the residue was purified by silica gel chromatography (0-10% methanol in DCM) to afford N-(1(S and R), (3(S and R))-3-(3-{[9-ethyl-8-(2-methylpyrimidin-5-yl)-9H-purin-6-yl]amino}cyclohexyl)-1,3-oxazole-4-carboxamide as a mixture of racemic diastereomers. The mixture was then separated by chiral SFC (Chiralpak AD-H, 21×250 (mm), 70 ml/min, 20% (Ethanol+0.25% dimethyl ethyl amine) in $CO_2$) to provide N-((1S,3S) or (1R,3R))-3-(3-{[9-ethyl-8-(2-methylpyrimidin-5-yl)-9H-purin-6-yl]amino}cyclohexyl)-1,3-oxazole-4-carboxamide (5-8) (retention time 3.3 min). ¹H NMR (600 MHz, DMSO-d₆, 95° C.) δ 9.04 (s, 2H), 8.45 (s, 1H), 8.31 (broad s, 1H), 8.23 (s, 1H), 7.51 (d, J=7.5, 1H), 7.27 (d, J=7.2, 1H), 4.69-4.60 (m, 1H), 4.27 (q, J=7.2, 2H), 4.27-4.23 (m, 1H), 2.71 (s, 3H), 2.04-1.94 (m, 1H), 1.94-1.86 (m, 1H), 1.86-1.77 (m, 1H), 1.77-1.69 (m, 1H), 1.69-1.56 (m, 4H), 1.29 (t, J=7.2, 3H). MS (EI) Calc'd for $C_{22}H_{26}N_9O_2$ [M+H]⁺, 448. found 448.

Compound 5-2 was prepared in an analogous fashion to Example 8A using azetidine in place of N-methylcyclopropanamine.

Compound 5-3 was prepared in an analogous fashion to Example 8A, step 1 using (1R,3S)-methyl 3-aminocyclopentanecarboxylate (preparation is described in US2011/224225 A1, 2011).

Compounds 5-4 through 5-7 were prepared from compound 5-3 in an analogous fashion to Example 8A, steps 2 and 3.

TABLE 5

| Compound | Structure | Compound Name | Exact Mass [M + H]+ |
|---|---|---|---|
| 5-1 | 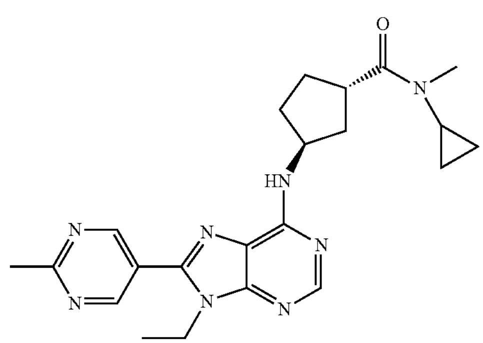 [SMILES: CCn1c(-c2cnc(C)nc2)nc2c(N[C@H]3CC[C@H](C(=O)N(C)C4CC4)C3)ncnc21] | (1S,3S)-N-cyclopropyl-3-{[9-ethyl-8-(2-methylpyrimidin-5-yl)-9H-purin-6-yl]amino}-N-methylcyclopentanecarboxamide | Calc'd 421, found 421 |
| 5-2 | 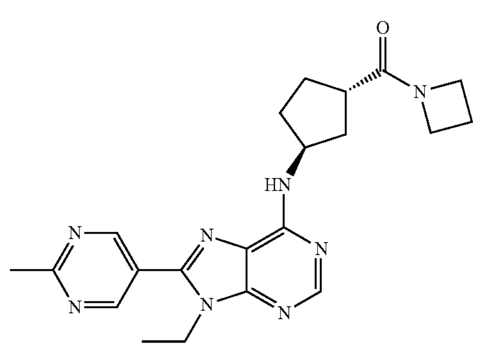 [SMILES: CCn1c(-c2cnc(C)nc2)nc2c(N[C@H]3CC[C@H](C(=O)N4CCC4)C3)ncnc21] | N-[(1S,3S)-3-(azetidin-1-ylcarbonyl)cyclopentyl]-9-ethyl-8-(2-methylpyrimidin-5-yl)-9H-purin-6-amine | Calc'd 407, found 407 |

TABLE 5-continued

| Compound | Structure | Compound Name | Exact Mass [M + H]+ |
|---|---|---|---|
| 5-3 | 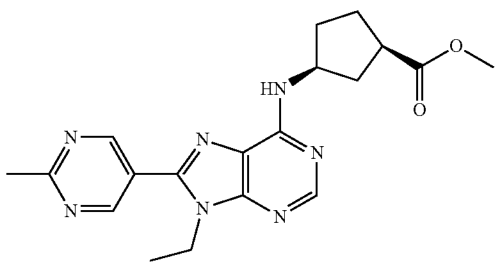 | methyl (1R,3S)-3-{[9-ethyl-8-(2-methylpyrimidin-5-yl)-9H-purin-6-yl]amino}cyclopentanecarboxylate | Calc'd 382, found 382 |
| 5-4 | 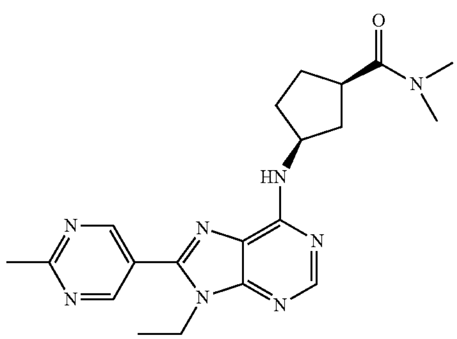 | (1R,3S)-3-{[9-ethyl-8-(2-methylpyrimidin-5-yl)-9H-purin-6-yl]amino}-N,N-dimethylcyclopentanecarboxamide | Calc'd 395, found 395 |
| 5-5 | 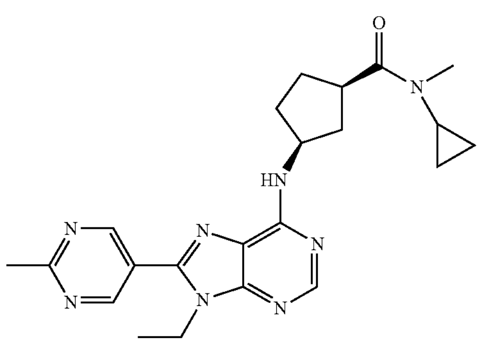 [SMILES: CCn1c(-c2cnc(C)nc2)nc2c(N[C@H]3CC[C@@H](C(=O)N(C)C4CC4)C3)ncnc21] | (1R,3S)-N-cyclopropyl-3-{[9-ethyl-8-(2-methylpyrimidin-5-yl)-9H-purin-6-yl]amino}-N-methylcyclopentanecarboxamide | Calc'd 421, found 421 |
| 5-6 | 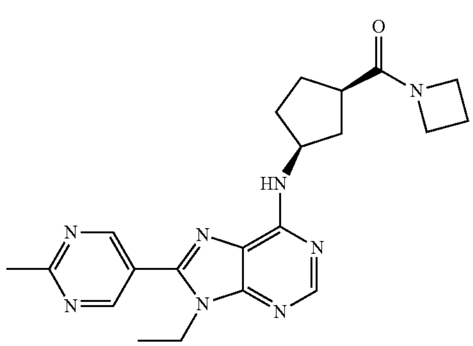 [SMILES: CCn1c(-c2cnc(C)nc2)nc2c(N[C@H]3CC[C@@H](C(=O)N4CCC4)C3)ncnc21] | N-[(1S,3R)-3-(azetidin-1-ylcarbonyl)cyclopentyl]-9-ethyl-8-(2-methylpyrimidin-5-yl)-9H-purin-6-amine | Calc'd 407, found 407 |

TABLE 5-continued

| Compound | Structure | Compound Name | Exact Mass [M + H]+ |
|---|---|---|---|
| 5-7 | 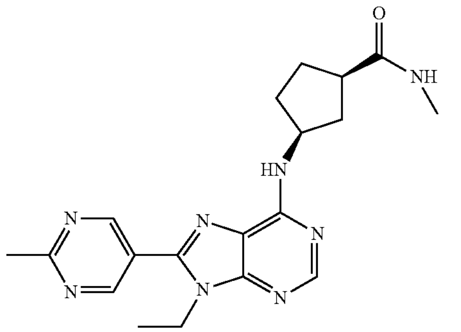 | (1R,3S)-3-{[9-ethyl-8-(2-ethylpyrimidin-5-yl)-9H-purin-6-yl]amino}-N-methylcyclopentanecarboxamide | Calc'd 381, found 381 |
| 5-8 | 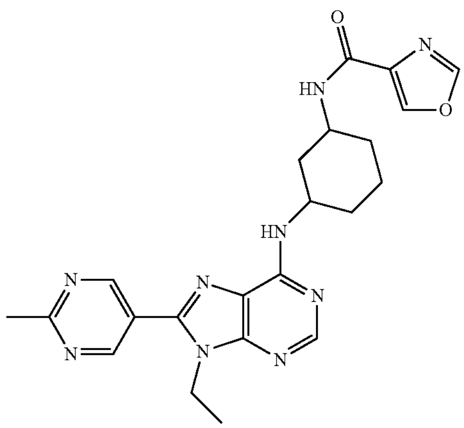 [SMILES: CCn1c(-c2cnc(C)nc2)nc2c(NC3CCCC(NC(=O)c4cocn4)C3)ncnc21] | N-(1S,3S or 1R,3R)-(3-{[9-ethyl-8-(2-methylpyrimidin-5-yl)-9H-purin-6-yl]amino}cyclohexyl)-1,3-oxazole-4-carboxamide | Calc'd 448, found 448 |

Compound Examples of Table 6

Example 9: Preparation of Compound 6-1

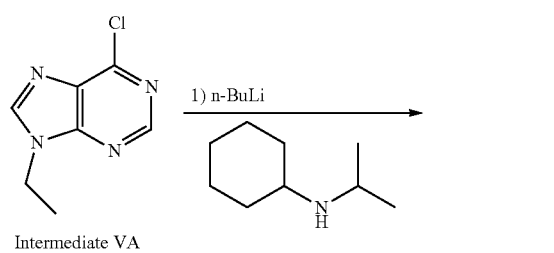

Intermediate VA

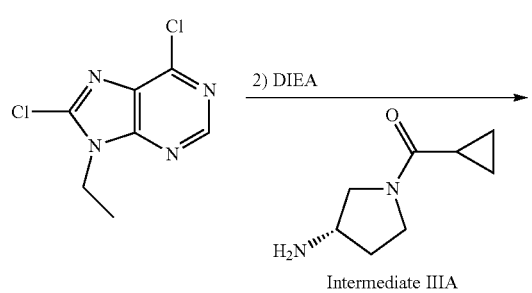

Intermediate IIIA

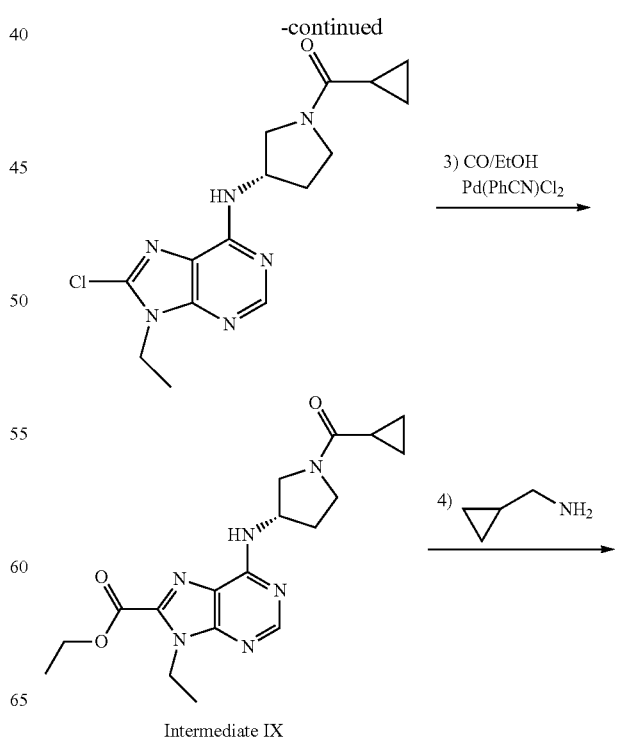

Intermediate IX

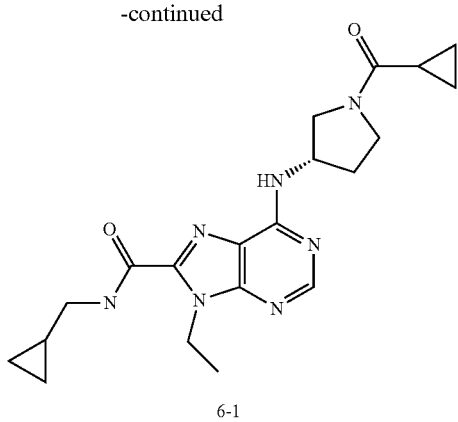

6-1

Step 1: Synthesis of 6,8-dichloro-9-ethyl-9H-purine

To a solution of N-isopropylcyclohexanamine (3.48 g, 24.64 mmol) in dry THF (30 ml) was added a solution of butyllithium (10 ml, 25 mmol, 2.5 M in hexane) at −70° C. and the resulting mixture was stirred for 15 min. A solution of Intermediate VA (3.0 g, 16.4 mmol) in dry THF (10 ml) was added and the temperature was maintained below −65° C. After the addition, the mixture was stirred for 40 min at −70° C. under a nitrogen atmosphere, after which it was treated with a solution of perchloroethane (5.83 g, 24.6 mmol) in dry THF (10 ml) at −70° C. The reaction mixture was stirred for 1 h at −70° C. After this time, the reaction was allowed to warm to ambient temperature and was quenched with aqueous ammonium chloride (50 mL) and diluted with DCM (50 mL). The layers were separated, and the aqueous layer was extracted with DCM (3×50 ml). The combined organic extracts were dried over anhydrous sodium sulfate, concentrated under reduced pressure, and the residue was purified by chromatography on silica gel (eluting with 20% EtOAc in PE) to afford 6,8-dichloro-9-ethyl-9H-purine. MS (ESI) calc'd for ($C_7H_7Cl_2N_4$) [M+H]$^+$, 217. found, 217.

Step 2: Preparation of (S)-(3-((8-chloro-9-ethyl-9H-purin-6-yl)amino)pyrrolidin-1-yl)(cyclopropyl)methanone 6,8-dichloro-9-ethyl-9H-purine (900 mg, 4.15 mmol) and (S)-(3-aminopyrrolidin-1-yl)(cyclopropyl)methanone (Intermediate IIIA) (in its neutral form) (767 mg, 4.5 mmol) were added to t-BuOH (10 ml) and DIEA (10 ml) and the reaction mixture was stirred and heated at 85° C. for 24 h. After this time, the solvent was removed in vacuo and the residue was purified by chromatography on silica gel (eluting with DCM/MeOH=60/1 (v/v)) to afford (S)-(3-((8-chloro-9-ethyl-9H-purin-6-yl)amino)pyrrolidin-1-yl)(cyclopropyl)methanone. MS (ESI) calc'd for ($C_{15}H_{20}ClN_6O$) [M+H], 335. found, 335.

Step 3: Preparation of (S)-ethyl 6-((1-(cyclopropanecarbonyl)pyrrolidin-3-yl)amino)-9-ethyl-9H-purine-8-carboxylate (Intermediate IX)

(S)-(3-((8-chloro-9-ethyl-9H-purin-6-yl)amino)pyrrolidin-1-yl)(cyclopropyl)methanone (900 mg, 2.69 mmol), bis(benzonitrile)palladium(II)chloride (103 mg, 0.269 mmol), 1,1'-bis(diphenylphosphino)ferrocene (149 mg, 0.269 mmol) and triethylamine (5 ml, 35.9 mmol) were combined in EtOH (100 ml) in a pressure vessel. The reaction was placed under 10 atm of CO and the mixture was heated to 120° C. for 8 h. After this time, the mixture was cooled to 25° C. and filtered. The filtrate was evaporated in vacuo, and the resulting residue was dissolved in EtOAc (50 ml), washed with water (30 ml) and brine (30 ml) and dried over anhydrous sodium sulfate. After filtration the solvent was evaporated under reduced pressure, and the residue was purified by chromatography on silica gel (eluting with EtOAc/PE=10/1) to afford (S)-ethyl 6-((1-(cyclopropanecarbonyl)pyrrolidin-3-yl)amino)-9-ethyl-9H-purine-8-carboxylate (Intermediate IX). MS (ESI) calc'd for ($C_{18}H_{24}N_6O_3$), [M+H], 373. found, 373.

Step 4: Preparation of (S)-6-((1-(cyclopropanecarbonyl)pyrrolidin-3-yl)amino)-N-(cyclopropylmethyl)-9-ethyl-9H-purine-8-carboxamide (6-1)

(S)-ethyl 6-((1-(cyclopropanecarbonyl)pyrrolidin-3-yl)amino)-9-ethyl-9H-purine-8-carboxylate (10 mg, 0.027 mmol) was added to cyclopropylmethanamine (0.5 ml, 5.84 mmol). and the reaction mixture was heated to 70° C. in a sealed tube for 30 h. After this time, the solvent was removed in vacuo and the residue was purified by preparative HPLC [Column: Xbridge Prep C18 10 um OBD, 19*250 mm; Mobile phase: A: Water (10 mmol $NH_4HCO_3$), B: MeCN; Flow rate: 30 mL/min; UV detection: 214/254 nm] to afford compound 6-1. $^1$H NMR (400 MHz, MeOD-$d_4$) δ 8.36 (m, 1H), 4.90-4.80 (m, 1H), 4.71-4.68 (m, 2H), 4.30-3.56 (m, 4H), 3.32-3.29 (m, 2H), 2.52-2.13 (m, 2H), 1.87-1.78 (m, 1H), 1.46-1.43 (m, 3H), 1.20-1.08 (m, 1H), 0.95-0.80 (m, 4H), 0.70-0.50 (2H, m), 0.40-0.30 (m, 2H). MS (ESI) calc'd for ($C_{20}H_{28}N_7O_2$), [M+H], 398. found, 398.

Example 10: Preparation of Compound 6-9

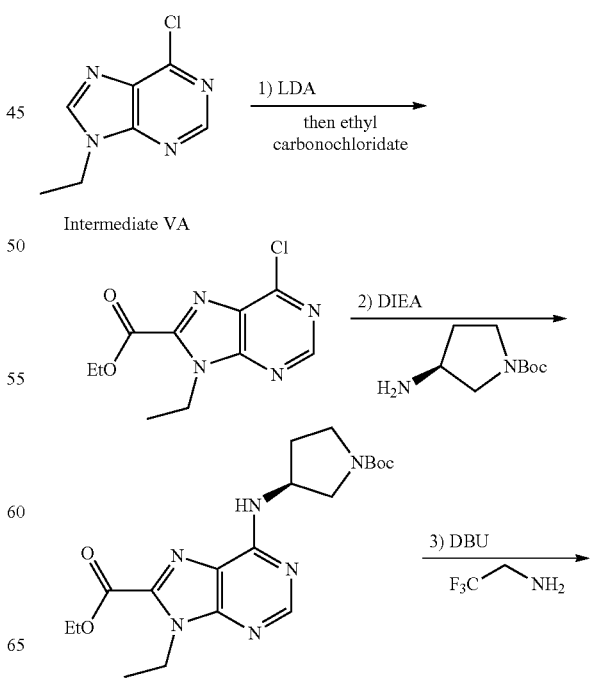

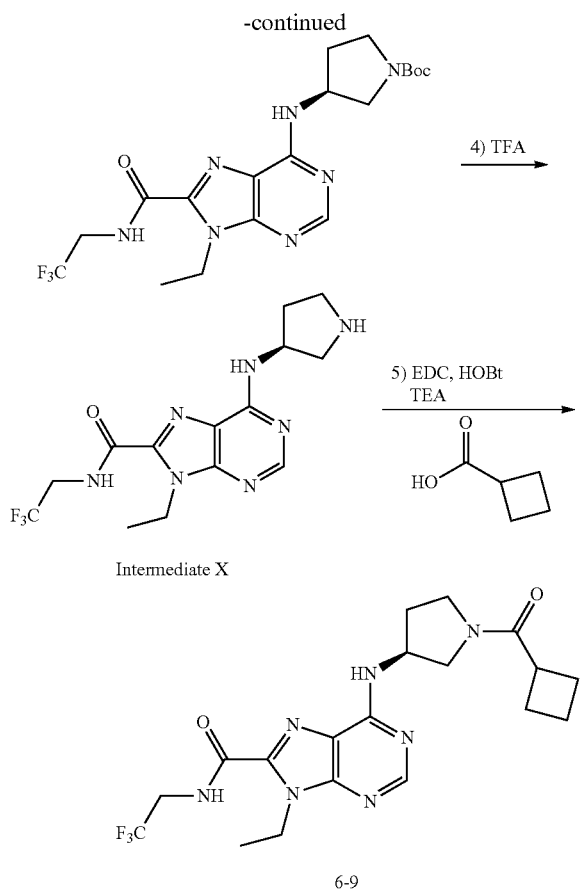

Intermediate X 6-9

Step 1: Preparation of ethyl 6-chloro-9-ethyl-9H-purine-8-carboxylate

To a solution of LDA (13 mL, 13.0 mmol) in THF (10 mL) at −78° C. was added Intermediate VA (2 g, 11.0 mmol) in THF (10 mL) drop wise with stirring. The resulting mixture was stirred for 2 h under nitrogen atmosphere. The reaction mixture was then transferred to a solution of ethyl carbonochloridate (2.4 g, 20.0 mmol) in THF (20 mL) at −78° C. and it was stirred for 3 h. The reaction mixture was then quenched by the addition of saturated aqueous ammonium chloride (50 mL) and the mixture was extracted with ethyl acetate (3×50 mL). The combined organic layers were washed with brine, dried over anhydrous sodium sulfate, and filtered. The filtrate was concentrated under vacuum to give a residue, which was purified by silica gel column chromatography eluting with 6% ethyl acetate in petroleum ether to afford ethyl 6-chloro-9-ethyl-9H-purine-8-. MS (ESI) calc'd for ($C_{10}H_{12}ClN_4O_2$) [M+H]$^+$, 255. found, 255.

Step 2: Preparation of (S)-ethyl 6-(1-(tert-butoxycarbonyl)pyrrolidin-3-ylamino)-9-ethyl-9H-purine-8-carboxylate To a solution of ethyl 6-chloro-9-ethyl-9H-purine-8-carboxylate (1.4 g, 5.5 mmol) and (S)-tert-butyl 3-aminopyrrolidine-1-carboxylate (1.07 g, 5.8 mmol, commercially available from Chengdu Firster Pharmaceutical Technology) in t-BuOH (30 mL) was added N,N-diisopropylethylamine (2.12 g, 16 mmol). The resulting mixture was stirred for 2 h at 85° C. The reaction mixture was then concentrated under vacuum, diluted with ethyl acetate (100 mL), washed with water (2×100 mL) and brine (100 mL), then dried over anhydrous sodium sulfate, and filtered. The filtrate was concentrated under vacuum to give a residue, which was purified by silica gel column chromatography, eluting with 33-50% ethyl acetate in petroleum ether to afford (S)-ethyl 6-(1-(tert-butoxycarbonyl)pyrrolidin-3-ylamino)-9-ethyl-9H-purine-8-carboxylate. MS (ESI) calc'd for ($C_{19}H_{29}N_6O_4$) [M+H]$^+$, 405. found, 405.

Step 3: Preparation of (S)-tert-butyl 3-(9-ethyl-8-(2,2,2-trifluoroethylcarbamoyl)-9H-purin-6-ylamino)pyrrolidine-1-carboxylate A 50 mL sealed tube was charged with (S)-ethyl 6-(1-(tert-butoxycarbonyl)pyrrolidin-3-ylamino)-9-ethyl-9H-purine-8-carboxylate (1.8 g, 4.5 mmol), 1,8-diazabicyclo[5.4.0]undec-7-ene (DBU) (1.35 g, 8.9 mmol), and 2,2,2-trifluoroethanamine (20 mL). The mixture was stirred for 24 h at 100° C. The reaction mixture was then concentrated under vacuum, diluted with ethyl acetate (100 mL), washed with water (2×100 mL) and brine (100 mL), then dried over anhydrous sodium sulfate, and filtered. The filtrate was concentrated under vacuum to give a residue, which was purified by silica gel column chromatography eluting with 33% ethyl acetate in petroleum ether to afford (S)-tert-butyl 3-(9-ethyl-8-(2,2,2-trifluoroethylcarbamoyl)-9H-purin-6-ylamino)pyrrolidine-1-carboxylate. MS (ESI) calc'd for ($C_{19}H_{27}F_3N_7O_3$) [M+H]$^+$, 458. found, 458.

Step 4: Preparation of (S)-9-ethyl-6-(pyrrolidin-3-ylamino)-N-(2,2,2-trifluoroethyl)-9H-purine-8-carboxamide (Intermediate X)

To a solution of (S)-tert-butyl 3-(9-ethyl-8-(2,2,2-trifluoroethylcarbamoyl)-9H-purin-6-ylamino)pyrrolidine-1-carboxylate (900 mg, 1.97 mmol) in dichloromethane (10 mL) was added TFA (2 mL). The resulting mixture was stirred for 1 h, after which it was concentrated under vacuum. Saturated aqueous sodium hydrogen carbonate (100 mL) was then added and the resulting mixture was extracted with ethyl acetate (10×100 mL). The organic layers were combined and concentrated under vacuum to afford (S)-9-ethyl-6-(pyrrolidin-3-ylamino)-N-(2,2,2-trifluoroethyl)-9H-purine-8-carboxamide (Intermediate X). MS (ESI) calc'd for ($C_{14}H_{19}F_3N_7O$) [M+H]$^+$, 358. found, 358.

Step 5: Preparation of Compound 6-9

To a solution of (S)-9-ethyl-6-(pyrrolidin-3-ylamino)-N-(2,2,2-trifluoroethyl)-9H-purine-8-carboxamide (40 mg, 0.11 mmol) in dichloromethane (2 mL) were added cyclobutanecarboxylic acid (11 mg, 0.11 mmol) (commercially available from Liaoyang Jiulong Pharmaceutical Chemical), EDC.HCl (32 mg, 0.17 mmol), HOBT (23 mg, 0.17 mmol) and triethylamine (34 mg, 0.34 mmol). The resulting mixture was stirred for 2 h at ambient temperature, after which it was diluted with dichloromethane (50 mL). The mixture was washed with water (2×20 mL) and saturated brine (20 mL), dried over anhydrous sodium sulfate, and filtered. The filtrate was concentrated in vacuo to give a residue, which was purified by preparative thin-layer chromatography, eluting with ethyl acetate, to afford compound 6-9. $^1$H NMR: (300 MHz, CDCl$_3$) δ 8.50-8.40 (m, 1H), 7.90-7.75 (m, 1H), 6.00-5.759 m, 1H), 5.05-4.80 (m, 1H), 4.75 (q, J=7.0 Hz, 2H), 4.20-4.00 (m, 2H), 3.95-3.30 (m, 4H), 3.30-3.10 (m, 1H), 2.50-1.75 (m, 8H), 1.48 (t, J=7.0 Hz, 3H). MS (ESI) calc'd for ($C_{19}H_{25}F_3N_7O_2$) [M+H]$^+$, 440. found, 440.

Example 10B: Preparation of Compound 6-10

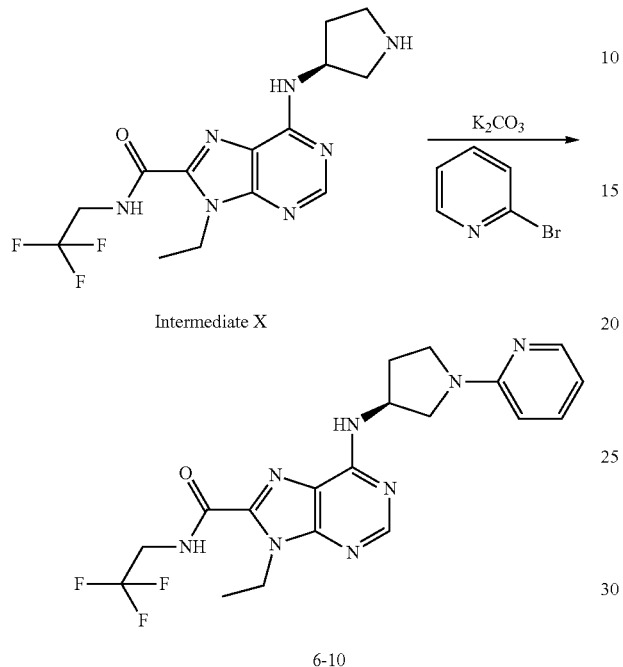

Intermediate X 6-10

To a solution of Intermediate X (200 mg, 0.56 mmol) in N,N-dimethylformamide (5 mL) were added 2-bromopyridine (177 mg, 1.12 mmol) and potassium carbonate (155 mg, 1.12 mmol). The resulting mixture was stirred for 24 h at 120° C. The reaction mixture was then diluted with ethyl acetate (100 mL), washed with water (100 mL) and brine (100 mL), dried over anhydrous sodium sulfate and filtered. The filtrate was concentrated under vacuum to give a residue, which was purified by preparative thin-layer chromatography, eluting with ethyl acetate, to afford compound 6-10. $^1$H NMR: (300 MHz, CDCl$_3$) δ 8.48 (s, 1H), 8.20 (d, J=3.6 Hz, 1H), 7.80 (m, 1H), 7.52 (m, 1H), 6.63-6.59 (m, 1H), 6.45 (d, J=8.4 Hz, 1H), 5.88 (d, J=6.9 Hz, 1H), 5.08 (s, 1H), 4.78 (q, J=7.0 Hz, 2H), 4.15-4.04 (m, 2H), 3.96-3.90 (m, 1H), 3.78-3.63 (m, 3H), 2.55-2.43 (m, 1H), 2.29-2.19 (m, 1H), 1.49 (t, J=7.0 Hz, 3H). MS (ESI) calc'd for ($C_{19}H_{22}F_3N_8O$) [M+H]$^+$, 435. found, 435.

Example 10C: Preparation of Compound 6-11

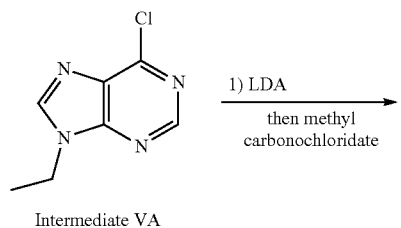

Intermediate VA

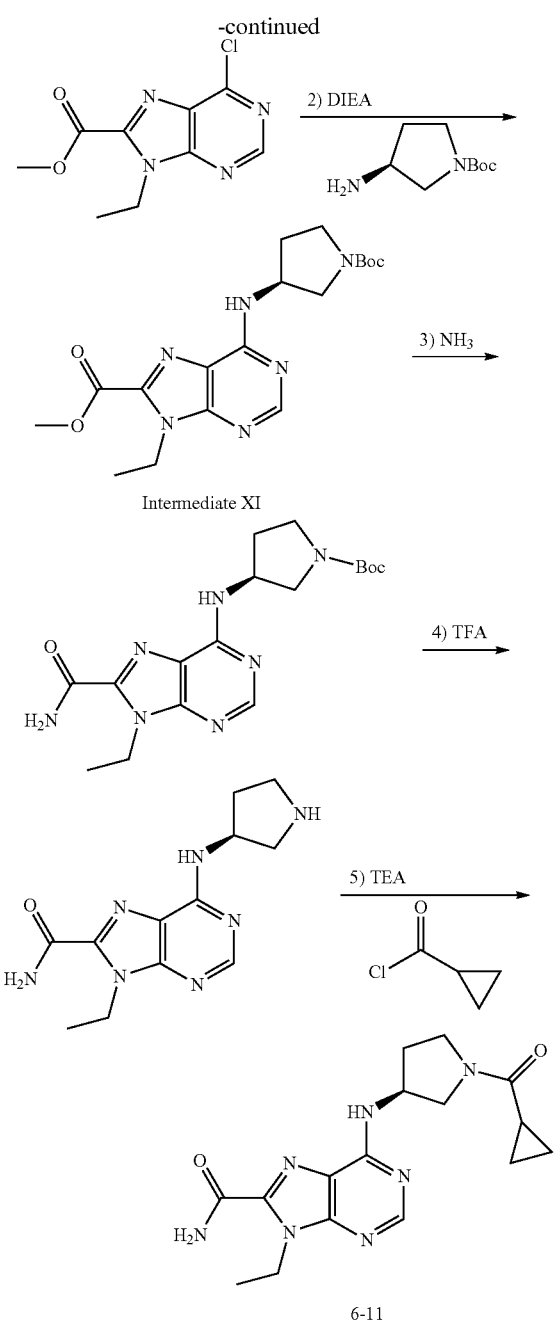

6-11

Step 1: Preparation of methyl 6-chloro-9-ethyl-9H-purine-8-carboxylate

To a solution of lithium diisopropylamide (LDA) (32.5 mL, 32.5 mmol) in THF (30 mL) was added Intermediate VA (5.0 g, 27.5 mmol) in THF (50 mL) drop wise with stirring at −78° C. The mixture was stirred for 2 h at −78° C. The reaction mixture was then transferred to a solution of methyl carbonochloridate (5.2 g, 55 mmol) in THF (50 mL) at −78° C. and stirred for 3 h. The reaction mixture was quenched by saturated aqueous ammonium chloride (100 mL) and extracted with ethyl acetate (3×100 mL). The combined organic layers were washed with brine, dried over anhydrous sodium sulfate, and filtered. The filtrate was concentrated under vacuum to give a residue, which was purified by silica gel column chromatography eluting with 6% ethyl acetate in petroleum ether to afford methyl 6-chloro-9-ethyl-9H-purine-8-carboxylate. MS (ESI) calc'd for ($C_9H_{10}ClN_4O_2$) [M+H]$^+$, 241. found, 241.

Step 2: Preparation of (S)-methyl 6-(1-(tert-butoxy-carbonyl)pyrrolidin-3-ylamino)-9-ethyl-9H-purine-8-carboxylate (Intermediate XI)

To a solution of methyl 6-chloro-9-ethyl-9H-purine-8-carboxylate (2.0 g, 8.3 mmol) and (S)-tert-butyl 3-aminopyrrolidine-1-carboxylate (1.58 g, 8.5 mmol) in tert-butanol (60 mL) was added N,N-diisopropylethylamine (3.23 g, 25 mmol). The resulting mixture was stirred for 7 h at 85° C. The reaction mixture was then cooled and concentrated under vacuum, diluted with ethyl acetate (150 mL), washed with water (2×100 mL) and brine (100 mL), dried over anhydrous sodium sulfate, and filtered. The filtrate was concentrated under vacuum to give a residue, which was purified by silica gel column chromatography eluting with 33%-50% ethyl acetate in petroleum ether to afford Intermediate XI. MS (ESI) calc'd for ($C_{18}H_{27}N_6O_4$) [M+H]$^+$, 391. found, 391.

Step 3: Preparation of (S)-tert-butyl 3-(8-carbamoyl-9-ethyl-9H-purin-6-ylamino)pyrrolidine-1-carboxylate To a solution of Intermediate XI (100 mg, 0.256 mmol) in THF (5 mL) was added ammonia (5 mL). The resulting solution was stirred for 1 h at ambient temperature. The resulting solution was concentrated under vacuum, after which the product was precipitated from water, collected by filtration, and washed with water (10 mL) to afford (S)-tert-butyl 3-(8-carbamoyl-9-ethyl-9H-purin-6-ylamino)pyrrolidine-1-carboxylate a. MS (ESI) calc'd for ($C_{17}H_{26}N_7O_3$) [M+H]$^+$, 376. found, 376.

Step 4: Preparation of (S)-9-ethyl-6-(pyrrolidin-3-ylamino)-9H-purine-8-carboxamide To a solution of (S)-tert-butyl 3-(8-carbamoyl-9-ethyl-9H-purin-6-ylamino)pyrrolidine-1-carboxylate (60 mg, 0.16 mmol) in dichloromethane (6 mL) was added 2,2,2-trifluoroacetic acid (2 mL). The resulting solution was stirred for 1 h at ambient temperature. The resulting solution was then concentrated under vacuum to afford (S)-9-ethyl-6-(pyrrolidin-3-ylamino)-9H-purine-8-carboxamide, TFA. MS (ESI) calc'd for ($C_{12}H_{18}N_7O$) [M+H]$^+$, 276. found, 276.

Step 5: Preparation of Compound 6-11

To a solution of (S)-9-ethyl-6-(pyrrolidin-3-ylamino)-9H-purine-8-carboxamide, TFA (200 mg, 0.54) and triethylamine (161.6 mg, 1.6 mmol) in dichloromethane (20 mL) was added cyclopropanecarbonyl chloride (16.6 mg, 0.16 mmol) drop wise at 0° C. The resulting mixture was stirred for 1 h at ambient temperature, after which it was quenched by the addition of water (30 mL). The resulting mixture was extracted with dichloromethane (3×20 mL) and the organic layers were combined, dried over anhydrous sodium sulfate and filtered. The filtrate was concentrated under vacuum. The residue was purified by preparative thin-layer chromatography eluting with 33% ethyl acetate in dichloromethane to afford Compound 6-11. $^1$H NMR (400 MHz, CDCl$_3$) δ 8.49-8.46 (m, 1H), 7.33 (s, 1H), 6.28-5.62 (m, 2H), 5.25-4.85 (m, 1H), 4.81 (m, 2H), 4.19-3.89 (m, 2H), 3.79-3.69 (m, 2H), 2.51-2.07 (m, 2H), 1.73-1.60 (m, 1H), 1.51 (t, J=6.8 Hz, 3H), 1.10-1.04 (m, 2H), 0.85-0.78 (m, 2H). MS (ESI) calc'd for ($C_{16}H_{22}N_7O_2$) [M+H]$^+$, 344. found, 344.

Example 11: Preparation of Compound 6-12

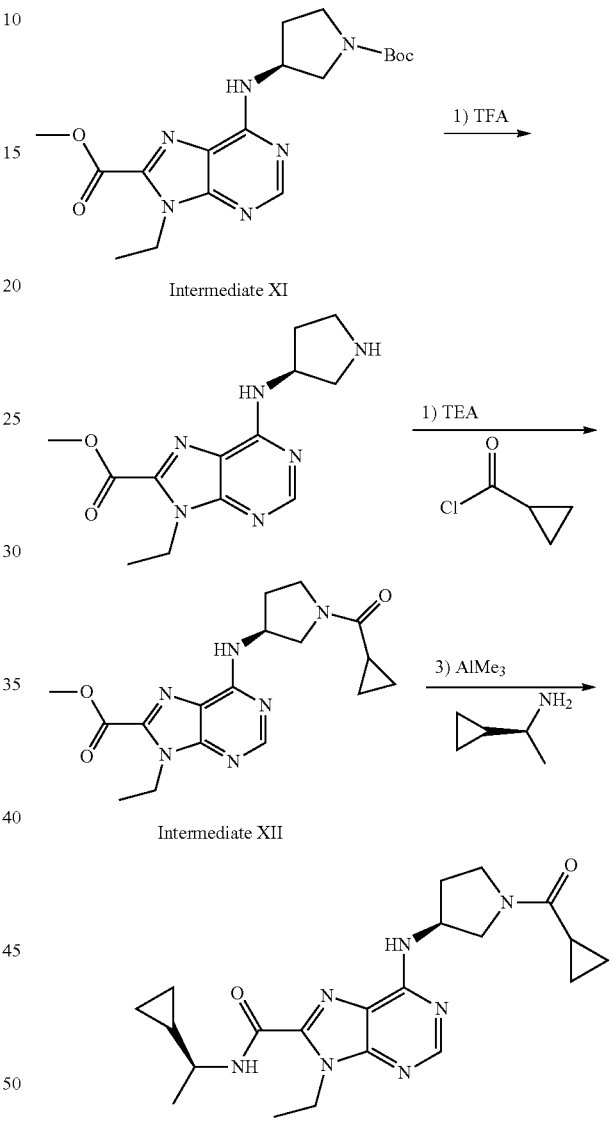

Step 1: Preparation of (S)-methyl 9-ethyl-6-(pyrrolidin-3-ylamino)-9H-purine-8-carboxylate To a solution of Intermediate XI (1 g, 2.56 mmol) in dichloromethane (8 mL) was added 2,2,2-trifluoroacetic acid (2 mL). The resulting solution was stirred for 30 min at ambient temperature. The reaction mixture was then concentrated under vacuum to afford (S)-methyl 9-ethyl-6-(pyrrolidin-3-ylamino)-9H-purine-8-carboxylate. MS (ESI) calc'd for ($C_{13}H_{19}N_6O_2$) [M+H]$^+$, 291. found, 291.

Step 2: Preparation of (S)-methyl 6-(1-(cyclopropanecarbonyl)pyrrolidin-3-ylamino)-9-ethyl-9H-purine-8-carboxylate (Intermediate XII)

To a solution of (S)-methyl 9-ethyl-6-(pyrrolidin-3-ylamino)-9H-purine-8-carboxylate (2.3 g, crude) in dichloromethane (20 mL) were added triethylamine (2.56 g, 25 mmol) and cyclopropanecarbonyl chloride (293 mg, 2.8 mmol). The reaction mixture was stirred for 30 min at ambient temperature, after which it was quenched with water (500 mL) and extracted with dichloromethane (2×500 mL). The organic layers were combined, washed with saturated aqueous sodium chloride (500 mL), dried over anhydrous sodium sulfate and filtered. The filtrate was concentrated under vacuum to give a residue, which was purified by silica gel column chromatography eluting with ethyl acetate to afford (Intermediate XII). MS (ESI) calc'd for ($C_{17}H_{23}N_6O_3$) [M+H]$^+$, 359. found, 359.

Step 3: Preparation of Compound 6-12

To a solution of (S)-1-cyclopropylethanamine (237 mg, 2.8 mmol) in dichloromethane (15 mL) was added a solution of trimethylaluminum (1.4 mL, 2.0 M solution in toluene, 2.8 mmol) at 0° C. The mixture was stirred at ambient temperature for 1 h and then cooled down to 0° C. To this solution was added Intermediate XII (100 mg, 0.28 mmol), and the mixture was stirred at ambient temperature for 24 h. The reaction was then quenched by the addition of saturated aqueous potassium sodium tartrate (100 mL) at 0° C. and the mixture was extracted with dichloromethane (2×100 mL). The combined organic layers were washed with brine (100 mL), dried over anhydrous sodium sulfate and filtered. The filtrate was concentrated under vacuum, and the residue was purified by preparative thin-layer chromatography eluting with ethyl acetate to afford 6-12. $^1$H NMR: (300 MHz, CD$_3$OD) δ 8.30 (m, 1H), 5.00-4.80 (m, 1H), 4.66-4.61 (m, 2H), 4.15-3.77 (m, 2H), 3.77-3.40 (m, 3H), 2.50-2.07 (m, 2H), 1.90-1.72 (m, 1H), 1.42 (t, J=7.2 Hz, 3H), 1.33 (d, J=6.6 Hz, 3H), 1.10-0.95 (m, 1H), 0.90-0.80 (m, 4H), 0.60-0.42 (m, 2H), 0.42-0.27 (m, 2H). MS (ESI) calc'd for ($C_{21}H_{30}N_7O_2$) [M+H]$^+$, 412. found, 412.

Example 12: Preparation of Compound 6-16

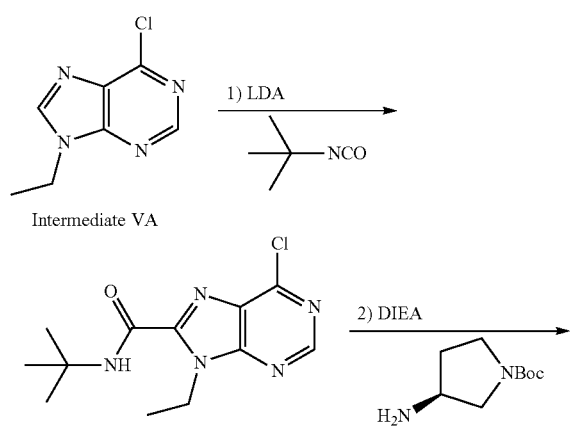

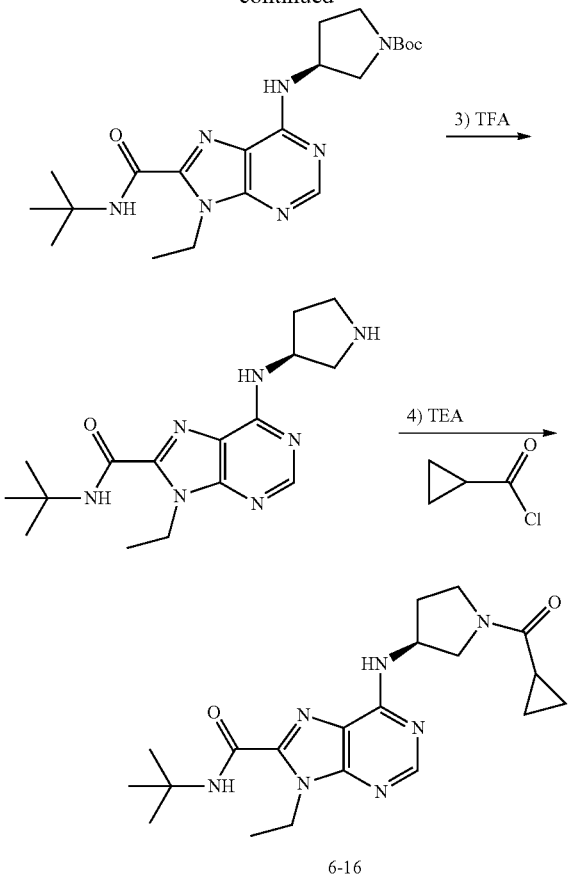

6-16

Step 1: Preparation of N-tert-butyl-6-chloro-9-ethyl-9H-purine-8-carboxamide To a solution of lithium diisopropylamide (550 mg, 5.27 mmol) in tetrahydrofuran (15 mL) was added Intermediate VA (0.8 g, 4.4 mmol) drop wise at −78° C. After stirring for 1.5 h at −78° C., 2-isocyanato-2-methylpropane (870 mg, 8.79 mmol, commercially available from Accela ChemBio) was added. After stirring for 1.5 h at ambient temperature, the reaction was quenched with water (30 mL), extracted with ethyl acetate (3×50 mL), dried over anhydrous magnesium sulfate and filtered. The filtrate was concentrated under vacuum to give a residue, which was purified by silica gel column chromatography eluting with 10%-30% ethyl acetate in petroleum ether to afford N-tert-butyl-6-chloro-9-ethyl-9H-purine-8-carboxamide. MS (ESI) calc'd for ($C_{12}H_{17}ClN_5O$) [M+H]$^+$, 282. found, 282.

Step 2: Preparation of (S)-tert-butyl 3-(8-(tert-butylcarbamoyl)-9-ethyl-9H-purin-6-ylamino)pyrrolidine-1-carboxylate To a solution of N-tert-butyl-6-chloro-9-ethyl-9H-purine-8-carboxamide (400 mg, 1.42 mmol) and (S)-tert-butyl 3-aminopyrrolidine-1-carboxylate (265 mg, 1.42 mmol, commercially available from Chengdu Firster Pharmaceutical Technology) in tert-butanol (10 mL) was added DIEA (550 mg, 4.26 mmol). After stirring for 12 h at 85° C., the resulting mixture was concentrated under vacuum, diluted with water (50 mL), extracted with dichloromethane (3×50 mL), dried over anhydrous sodium sulfate and filtered. The filtrate was concentrated under vacuum to give a residue, which was purified by silica gel column chromatography eluting with 4% methanol in dichloromethane to afford (S)-tert-butyl 3-(8-(tert-butylcarbamoyl)-9-ethyl-9H-purin-6-ylamino)pyrrolidine-1-carboxylate. MS (ESI) calc'd for ($C_{21}H_{34}N_7O_3$) [M+H]$^+$, 432. found, 432.

Step 3: Preparation of (S)—N-tert-butyl-9-ethyl-6-(pyrrolidin-3-ylamino)-9H-purine-8-carboxamide To a solution of (S)-tert-butyl 3-(8-(tert-butylcarbamoyl)-9-ethyl-9H-purin-6-ylamino)pyrrolidine-1-carboxylate (400 mg, 1.42 mmol) in dichloromethane (10 mL) was added trifluoroacetic acid (2 mL). After stirring for 2 h at ambient temperature, the resulting mixture was concentrated under vacuum and diluted with water (5 mL). The pH was adjusted to 12 with saturated aqueous sodium bicarbonate and the mixture was then extracted with 10% methanol in dichloromethane (5×50 mL), dried over anhydrous sodium sulfate and filtered. The filtrate was concentrated under vacuum to afford (S)—N-tert-butyl-9-ethyl-6-(pyrrolidin-3-ylamino)-9H-purine-8-carboxamide. MS (ESI) calc'd for ($C_{16}H_{26}N_7O$) [M+H]$^+$, 332. found, 332.

Step-4: Preparation of Compound 6-16

To a solution of (S)—N-tert-butyl-9-ethyl-6-(pyrrolidin-3-ylamino)-9H-purine-8-carboxamide (50 mg, 0.15 mmol) in dichloromethane (3 mL) were added triethylamine (48 mg, 0.45 mmol) and cyclopropanecarbonyl chloride (20 mg, 0.19 mmol). After stirring for 1 h at ambient temperature, the resulting mixture was diluted with water (20 mL), extracted with dichloromethane (3×20 mL), dried over anhydrous sodium sulfate and filtered. The filtrate was concentrated under vacuum to give a residue, which was purified by reverse phase preparative HPLC [Column: Xbridge Prep C18 5 m OBD, 19×150 mm; Mobile phase: A: Water (10 mmol/L NH$_4$HCO$_3$), B: Acetonitrile (22%-37%); Flow rate: 30 mL/min; UV detection: 220/254 nm] to afford 6-16. $^1$H NMR (300 MHz, DMSO-d$_6$) δ 8.34-8.33 (m, 2H), 7.91 (s, 1H), 4.85-4.65 (m, 1H), 4.53 (q, J=6.9 Hz, 2H), 3.99-3.85 (m, 1H), 3.73-3.30 (m, 3H), 2.40-2.00 (m, 2H), 1.80-1.69 (m, 1H), 1.42 (s, 9H), 1.33 (t, J=6.6 Hz, 3H), 0.74-0.67 (m, 4H). MS (ESI) calc'd for ($C_{20}H_{30}N_7O_2$) [M+H]$^+$, 400. found, 400.

Example 12B: Preparation of Compound 6-20

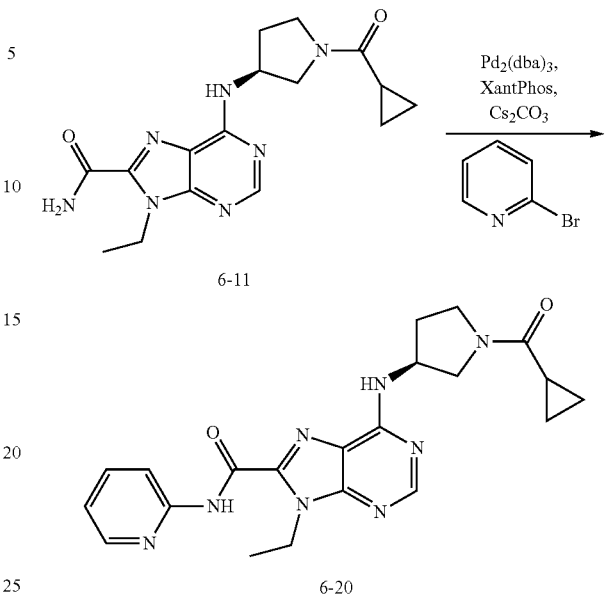

A mixture of compound 6-11 (50 mg, 0.14 mmol), 2-bromopyridine (28 mg, 0.16 mmol), tris(dibenzylideneacetone)dipalladium (15.0 mg, 0.01 mmol), (9,9-dimethyl-9H-xanthene-4,5-diyl)bis(diphenylphosphine) (XantPhos) (17 mg, 0.02 mmol), and cesium carbonate (142 mg, 0.42 mmol) in dioxane (5 mL) was stirred at 110° C. for 12 h. The reaction was then cooled to ambient temperature and quenched by the addition of water (2 mL) and extracted with dichloromethane (3×5 mL). The organic layers were combined, dried over anhydrous sodium sulfate, and filtered. The filtrate was concentrated under vacuum and the residue was purified by reverse phase preparative HPLC [Column: Xbridge Prep C18 5 m OBD, 19×150 mm; Mobile phase: A: Water (10 mM NH$_4$HCO$_3$), B: Acetonitrile; Flow rate: 20 mL/min; UV detection: 220/254 nm] to afford compound 6-20. $^1$H NMR (300 MHz, DMSO-d$_6$) δ 10.32 (s, 1H), 8.69-8.62 (m, 1H), 8.43-8.41 (m, 2H), 8.22 (d, J=8.4 Hz, 1H), 7.94-7.88 (m, 1H), 7.24-7.20 (m, 1H), 4.86-4.70 (m, 1H), 4.63 (q, J=7.2 Hz, 2H), 4.10-3.38 (m, 4H), 2.40-2.00 (m, 2H), 1.81-1.70 (m, 1H), 1.40 (t, J=7.2 Hz, 3H), 0.74-0.63 (m, 4H). MS (ESI) calc'd for ($C_{21}H_{25}N_8O_2$) [M+H]$^+$, 421. found, 421.

Compounds 6-2 through 6-6 were prepared in an analogous fashion to Example 9.

Compounds 6-13, 6-15, and 6-17 were prepared in an analogous fashion to Example 11 using the corresponding amine.

Compound 6-14 was prepared from Intermediate XII using the amide formation reaction described in Example 10, step 3, and using cyclohexylamine in place of trifluoroethylamine.

Compound 6-18 was prepared in an analogous fashion to Example 12 using isocyanatobenzene in place of 2-isocyanato-2-methylpropane.

Compound 6-19 was prepared in an analogous fashion to Example 9, step 4 from Intermediate IX and ethylamine.

Compound 6-21 was made in an analogous fashion to Example 12B except 3-bromopyridine was used instead of 2-bromopyridine.

TABLE 6

| Compound | Structure | Compound Name | Exact Mass [M + H]+ |
|---|---|---|---|
| 6-1 | 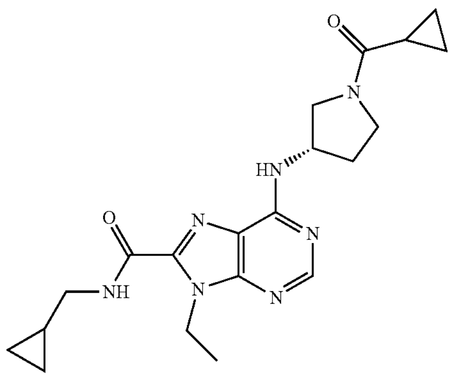 [SMILES: CCn1c(C(=O)NCC2CC2)nc2c(N[C@H]3CCN(C(=O)C4CC4)C3)ncnc21] | 6-{[(3S)-1-(cyclopropylcarbonyl)pyrrolidin-3-yl]amino}-N-(cyclopropylmethyl)-9-ethyl-9H-purine-8-carboxamide | Calc'd 398, found 398 |
| 6-2 | 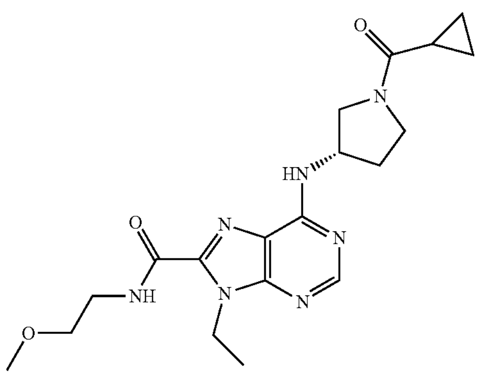 [SMILES: CCn1c(C(=O)NCCOC)nc2c(N[C@H]3CCN(C(=O)C4CC4)C3)ncnc21] | 6-{[(3S)-1-(cyclopropylcarbonyl)pyrrolidin-3-yl]amino}-9-ethyl-N-(2-methoxyethyl)-9H-purine-8-carboxamide | Calc'd 402, found 402 |
| 6-3 | 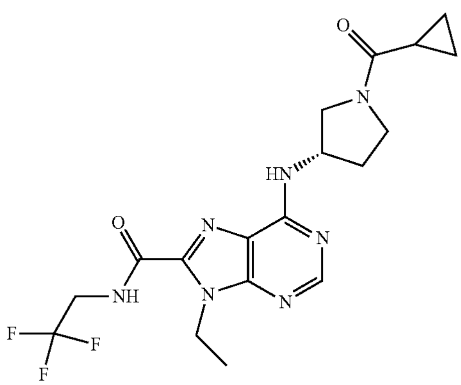 [SMILES: CCn1c(C(=O)NCC(F)(F)F)nc2c(N[C@H]3CCN(C(=O)C4CC4)C3)ncnc21] | 6-{[(3S)-1-(cyclopropylcarbonyl)pyrrolidin-3-yl]amino}-9-ethyl-N-(2,2,2-trifluoroethyl)-9H-purine-8-carboxamide | Calc'd 426, found 426 |
| 6-4 | 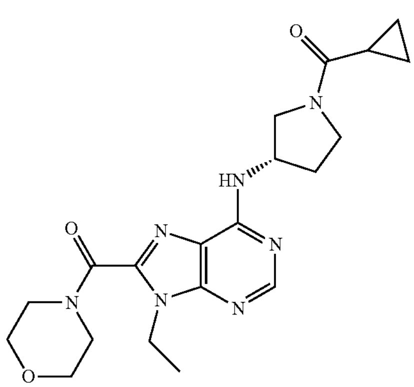 [SMILES: CCn1c(C(=O)N2CCOCC2)nc2c(N[C@H]3CCN(C(=O)C4CC4)C3)ncnc21] | N-[(3S)-1-(cyclopropylcarbonyl)pyrrolidin-3-yl]-9-ethyl-8-(morpholin-4-ylcarbonyl)-9H-purin-6-amine | Calc'd 414, found 414 |

TABLE 6-continued

| Compound | Structure | Compound Name | Exact Mass [M + H]+ |
|---|---|---|---|
| 6-5 | 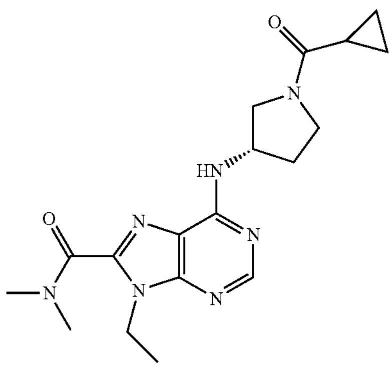 [SMILES: CCn1c(C(=O)N(C)C)nc2c(N[C@H]3CCN(C(=O)C4CC4)C3)ncnc21] | 6-{[(3S)-1-(cyclopropylcarbonyl)pyrrolidin-3-yl]amino}-9-ethyl-N,N-dimethyl-9H-purine-8-carboxamide | Calc'd 372, found 372 |
| 6-6 | 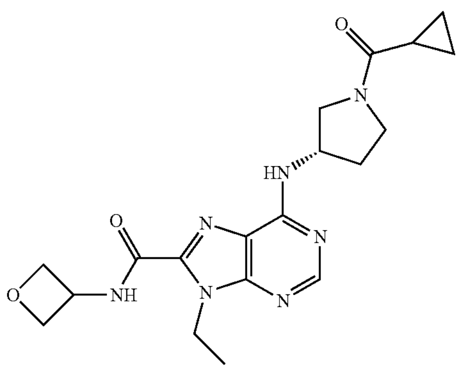 [SMILES: CCn1c(C(=O)NC2COC2)nc2c(N[C@H]3CCN(C(=O)C4CC4)C3)ncnc21] | 6-{[(3S)-1-(cyclopropylcarbonyl)pyrrolidin-3-yl]amino}-9-ethyl-N-oxetan-3-yl-9H-purine-8-carboxamide | Calc'd 400, found 400.0 |
| 6-7 | 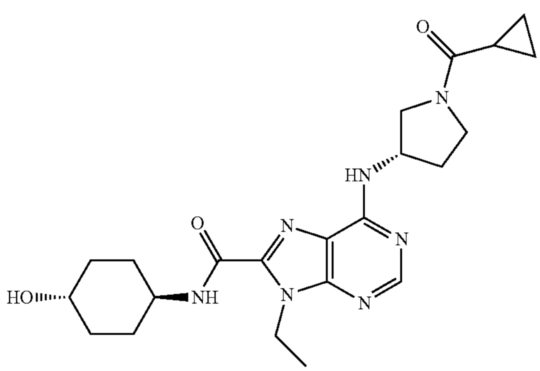 [SMILES: CCn1c(C(=O)N[C@H]2CC[C@H](O)CC2)nc2c(N[C@H]3CCN(C(=O)C4CC4)C3)ncnc21] | 6-{[(3S)-1-(cyclopropylcarbonyl)pyrrolidin-3-yl]amino}-9-ethyl-N-(trans-4-hydroxycyclohexyl)-9H-purine-8-carboxamide | Calc'd 442, found 442 |
| 6-8 | 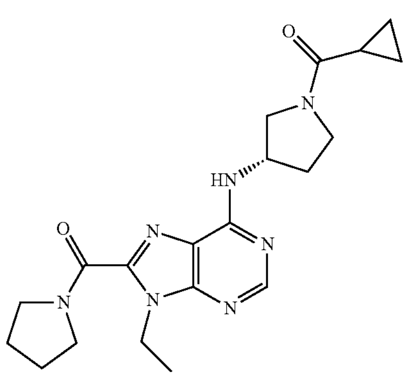 [SMILES: CCn1c(C(=O)N2CCCC2)nc2c(N[C@H]3CCN(C(=O)C4CC4)C3)ncnc21] | N-[(3S)-1-(cyclopropylcarbonyl)pyrrolidin-3-yl]-9-ethyl-8-(pyrrolidin-1-ylcarbonyl)-9H-purin-6-amine | Calc'd 398, found 398 |

TABLE 6-continued

| Compound | Compound Name | Exact Mass [M + H]+ |
|---|---|---|
| 6-9 | 6-{[(3S)-1-(cyclobutylcarbonyl)pyrrolidin-3-yl]amino}-9-ethyl-N-(2,2,2-trifluoroethyl)-9H-purine-8-carboxamide | Calc'd 440, found 440 |
| 6-10 | 9-ethyl-6-{[(3S)-1-pyridin-2-ylpyrrolidin-3-yl]amino}-N-(2,2,2-trifluoroethyl)-9H-purine-8-carboxamide | Calc'd 435, found 435 |
| 6-11 | 6-{[(3S)-1-(cyclopropylcarbonyl)pyrrolidin-3-yl]amino}-9-ethyl-9H-purine-8-carboxamide | Calc'd 344, found 344 |
| 6-12 | 6-{[(3S)-1-(cyclopropylcarbonyl)pyrrolidin-3-yl]amino}-N-[(1S)-1-cyclopropylethyl]-9-ethyl-9H-purine-8-carboxamide | Calc'd 412, found 412 |
| 6-13 | 6-{[(3S)-1-(cyclopropylcarbonyl)pyrrolidin-3-yl]amino}-N-[(1R)-1-cyclopropylethyl]-9-ethyl-9H-purine-8-carboxamide | Calc'd 412, found 412 |

| Compound | Structure | Compound Name | Exact Mass [M + H]+ |
|---|---|---|---|
| 6-14 | 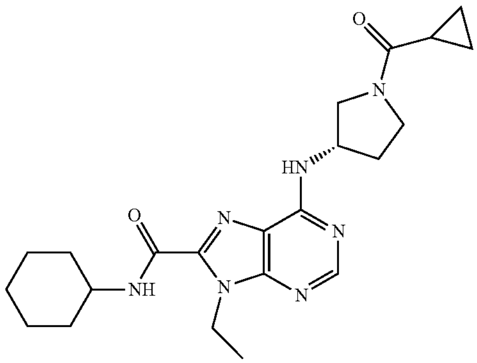 [SMILES: CCn1c(C(=O)NC2CCCCC2)nc2c(N[C@H]3CCN(C(=O)C4CC4)C3)ncnc21] | N-cyclohexyl-6-{[(3S)-1-(cyclopropylcarbonyl)pyrrolidin-3-yl]amino}-9-ethyl-9H-purine-8-carboxamide | Calc'd 426, found 426 |
| 6-15 | 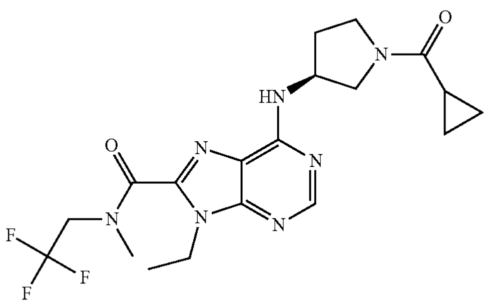 [SMILES: CCn1c(C(=O)N(C)CC(F)(F)F)nc2c(N[C@H]3CCN(C(=O)C4CC4)C3)ncnc21] | 6-{[(3S)-1-(cyclopropylcarbonyl)pyrrolidin-3-yl]amino}-9-ethyl-N-methyl-N-(2,2,2-trifluoroethyl)-9H-purine-8-carboxamide | Calc'd 440, found 440 |
| 6-16 | 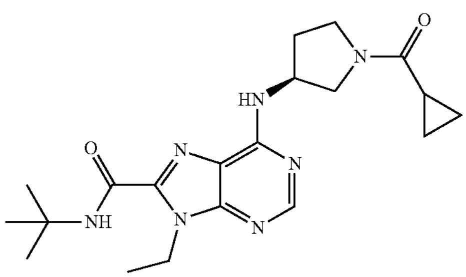 [SMILES: CCn1c(C(=O)NC(C)(C)C)nc2c(N[C@H]3CCN(C(=O)C4CC4)C3)ncnc21] | N-tert-butyl-6-{[(3S)-1-(cyclopropylcarbonyl)pyrrolidin-3-yl]amino}-9-ethyl-9H-purine-8-carboxamide | Calc'd 400, found 400 |
| 6-17 | 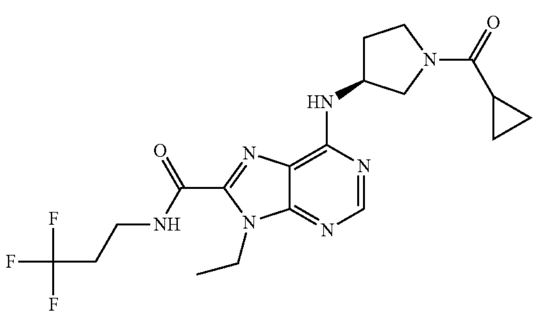 [SMILES: CCn1c(C(=O)NCCC(F)(F)F)nc2c(N[C@H]3CCN(C(=O)C4CC4)C3)ncnc21] | 6-{[(3S)-1-(cyclopropylcarbonyl)pyrrolidin-3-yl]amino}-9-ethyl-N-(3,3,3-trifluoropropyl)-9H-purine-8-carboxamide | Calc'd 440, found 440 |
| 6-18 | 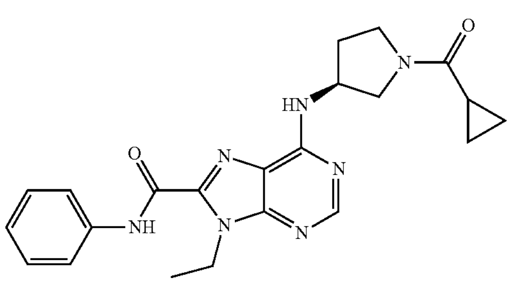 [SMILES: CCn1c(C(=O)Nc2ccccc2)nc2c(N[C@H]3CCN(C(=O)C4CC4)C3)ncnc21] | 6-{[(3S)-1-(cyclopropylcarbonyl)pyrrolidin-3-yl]amino}-9-ethyl-N-phenyl-9H-purine-8-carboxamide | Calc'd 420, found 420 |

TABLE 6-continued

| Compound | Structure | Compound Name | Exact Mass [M + H]+ |
|---|---|---|---|
| 6-19 | 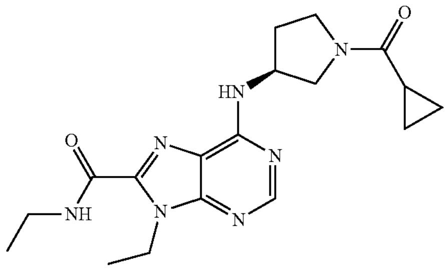 [SMILES: CCNC(=O)c1nc2c(N[C@H]3CCN(C(=O)C4CC4)C3)ncnc2n1CC] | 6-{[(3S)-1-(cyclopropylcarbonyl)pyrrolidin-3-yl]amino}-N,9-diethyl-9H-purine-8-carboxamide | Calc'd 372, found 372 |
| 6-20 | 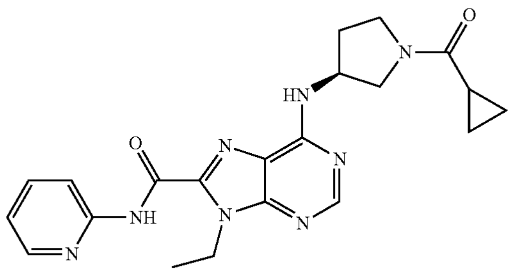 [SMILES: CCn1c(C(=O)Nc2ccccn2)nc2c(N[C@H]3CCN(C(=O)C4CC4)C3)ncnc21] | 6-{[(3S)-1-(cyclopropylcarbonyl)pyrrolidin-3-yl]amino}-9-ethyl-N-pyridin-2-yl-9H-purine-8-carboxamide | Calc'd 421, found 421 |
| 6-21 | 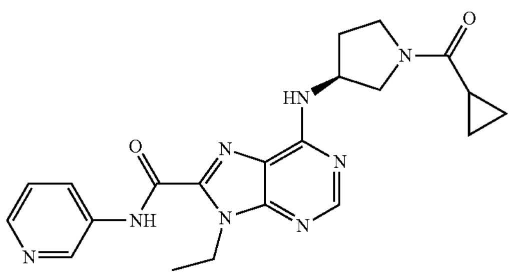 [SMILES: CCn1c(C(=O)Nc2cccnc2)nc2c(N[C@H]3CCN(C(=O)C4CC4)C3)ncnc21] | 6-{[(3S)-1-(cyclopropylcarbonyl)pyrrolidin-3-yl]amino}-9-ethyl-N-pyridin-3-yl-9H-purine-8-carboxamide | Calc'd 421, found 421 |

Compound Examples of Table 7

Example 13: Preparation of Compound 7-1

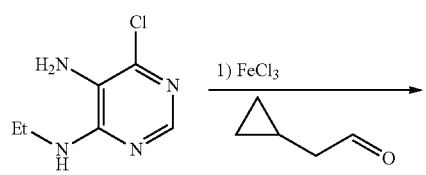

Intermediate IAA

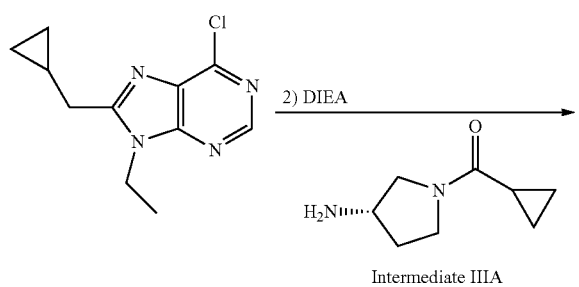

Intermediate IIIA

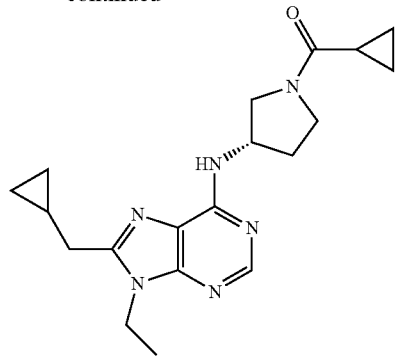

7-1

Step 1: Preparation of 6-chloro-8-(cyclopropylmethyl)-9-ethyl-9H-purine

FeCl$_3$·6H$_2$O (121 mg, 0.446 mmol) was added to a solution of 2-cyclopropylacetaldehyde (150 mg, 1.8 mmol) and Intermediate IAA (308 mg, 1.78 mmol) in DMF (5 ml) at room temperature and the mixture was stirred vigorously open to air at 80° C. for 12 h. The mixture was then quenched with aqueous ammonium chloride (saturated, 10 mL) and extracted with ethyl acetate (3×10 mL). The combined organic fractions were washed with brine, dried over sodium sulfate, filtered, and the solvent was evaporated under reduced pressure. The residue was purified by preparative thin-layer chromatography (eluting PE:EA=2:1) to give 6-chloro-8-(cyclopropylmethyl)-9-ethyl-9H-purine. MS (ESI) calc'd for ($C_{11}H_{14}ClN_4$) [M+H]$^+$, 237. found, 237.

Step 2: Preparation of Compound 7-1

DIEA (0.369 ml, 2.112 mmol) was added to a solution of 6-chloro-8-(cyclopropylmethyl)-9-ethyl-9H-purine (100 mg, 0.42 mmol) and Intermediate IIIA (in its neutral form) (85 mg, 0.55 mmol) in t-BuOH (6 ml) at room temperature and the mixture was then stirred at 80° C. for 12 h. The residue was purified by preparative reverse phase HPLC (C-18), eluting with Acetonitrile/Water+0.05% $NH_3$, to give 7-1. $^1$H NMR (400 MHz, $CD_3OD$): δ 8.28 (m, 1H), 4.90-4.78 (m, 1H), 4.29-4.23 (m, 2H), 4.28-3.62 (m, 4H), 2.88-2.86 (m, 2H), 2.50-2.11 (m, 2H), 1.86-1.75 (m, 1H), 1.43-1.41 (m, 3H), 1.38-1.25 (m, 1H), 0.95-0.73 (m, 6H), 0.35-0.30 (m, 2H). MS (ESI) calc'd for ($C_{19}H_{27}N_6O$) [M+H]$^+$, 355. found, 355.

Example 14: Preparation of Compound 7-11

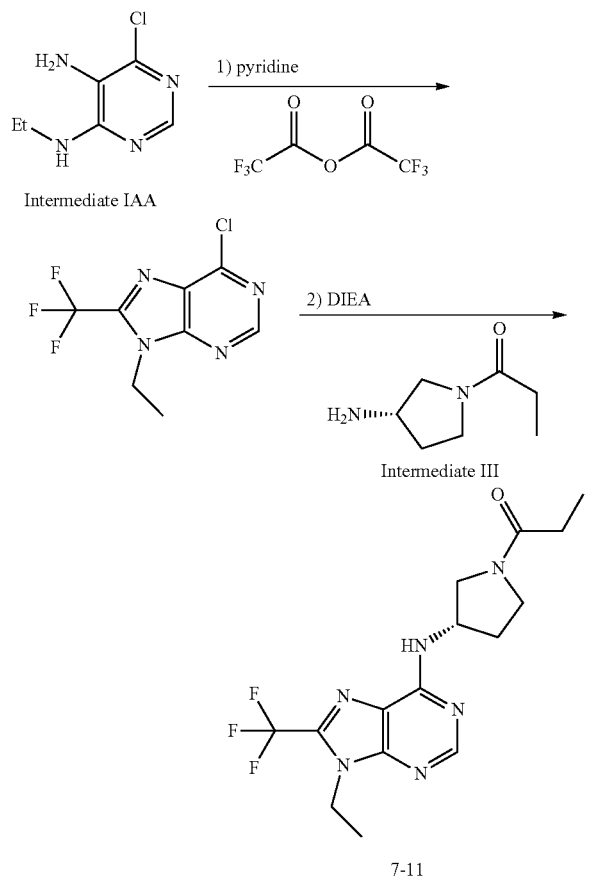

7-11

Step 1: Preparation of 6-chloro-9-ethyl-8-(trifluoromethyl)-9H-purine

Intermediate IAA (1.5 g, 8.7 mmol) was dissolved in dry DCM (20 ml) along with pyridine (14 ml, 17 mmol) followed by the addition of trifluoroacetic anhydride (3.65 g, 17.4 mmol). The reaction mixture was stirred for 16 h at room temperature. Another portion of trifluoroacetic anhydride (3.65 g, 17.4 mmol) was then added and the mixture was stirred for an additional 4 h at room temperature. Water (20 ml) was then added and the mixture was extracted with DCM (2×20 ml). The combined organic layers were dried over anhydrous sodium sulfate, filtered, and concentrated under reduced pressure. The residue was purified by chromatography on silica gel (eluting with PE/EA=70/30) to afford 6-chloro-9-ethyl-8-(trifluoromethyl)-9H-purine. MS (ESI) calc'd for ($C_8H_7ClF_3N_4$) [M+H]$^+$, 251. found, 251.

Step 2: Preparation of Compound 7-11

6-chloro-9-ethyl-8-methyl-9H-purine (50 mg, 0.2 mmol) and Intermediate III (34 mg, 0.24 mmol) were added to the solution of t-BuOH (1 ml) in DIEA (1 ml) in a 25-mL reaction vessel. The reaction mixture was heated to 85° C. for 48 h under a $N_2$ atmosphere. After this time, the mixture was cooled to room temperature and the solvent was removed in vacuo. The residue was purified by reverse phase preparative HPLC [Column: Xbridge Prep C18 10 um OBD, 19*250 mm; Mobile phase: A: Water (10 mmol $NH_4HCO_3$), B: MeCN; Flow rate: 30 mL/min; UV detection: 214/254 nm] to afford Compound 7-11. $^1$H NMR (400 MHz, $CDCl_3$) δ 8.52-8.41 (m, 1H), 6.23-6.12 (m, 1H), 5.05-4.75 (1H, m), 4.43-4.38 (m, 2H), 3.97-3.86 (m, 1H), 3.75-3.41 (m, 3H), 2.50-2.26 (m, 3H), 2.26-1.90 (m, 1H), 1.51-1.47 (m, 3H), 1.18-1.12 (m, 3H). MS (ESI) calc'd for ($C_{15}H_{20}F_3N_6O$) [M+H]$^+$, 357. found, 357.

Example 15: Preparation of Compound 7-12

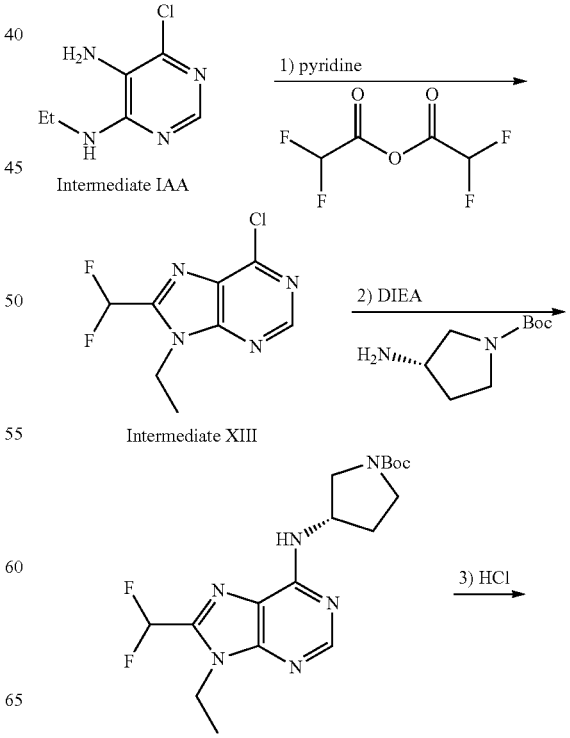

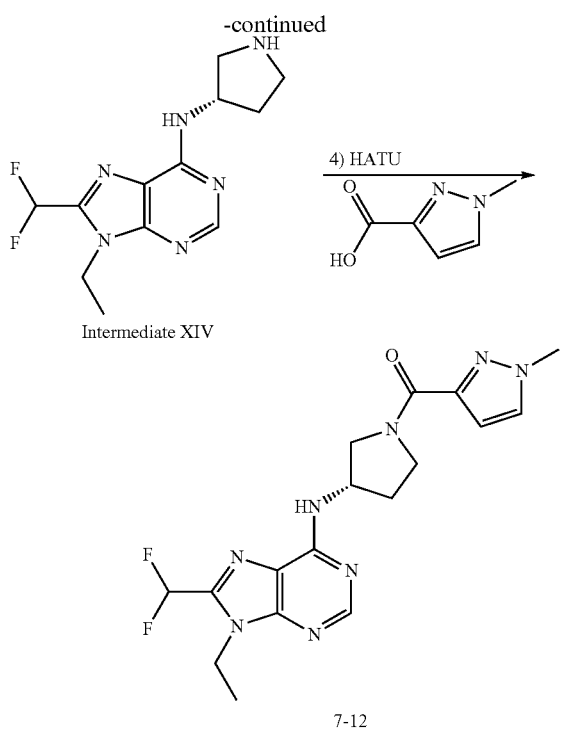

Step 1: Preparation of 6-chloro-8-(difluoromethyl)-9-ethyl-9H-purine (Intermediate XIII)

Intermediate IAA (5 g, 30 mmol) was dissolved in dry DCM (120 ml) along with pyridine (47 ml, 58 mmol) followed by 2,2-difluoroacetic anhydride (10 g, 58 mmol), the mixture was stirred for 16 h at 25° C. under a nitrogen atmosphere. After this time, another portion 2,2-difluoroacetic anhydride (10 g, 58 mmol) was added and the reaction was stirred for an additional 4 h at 25° C., after which the solvent was removed in vacuo. The residue was then re-dissolved in DCM (50 ml) and water (40 ml), the layers were separated and the aqueous layer was extracted with DCM (2×40 ml). The combined organic layers were dried over anhydrous sodium sulfate and filtered, and the filtrate was concentrated under reduced pressure. The residue was purified by chromatography on silica gel (eluting with EA/PE=1/5) to provide Intermediate XIII. MS (ESI) calc'd for ($C_8H_8ClF_2N_4$) [M+H]$^+$, 233. found, 233.

Step 2: Preparation of (S)-tert-butyl 3-((8-(difluoromethyl)-9-ethyl-9H-purin-6-yl)amino)pyrrolidine-1-carboxylate 6-chloro-8-(difluoromethyl)-9-ethyl-9H-purine (1.0 g, 4.3 mmol) and (S)-tert-butyl 3-aminopyrrolidine-1-carboxylate (0.96 g, 5.1 mmol) were added to a mixture of t-BuOH (2 ml) and DIPEA (1 ml). The reaction mixture was allowed to heat to 85° C. for 30 h. After this time, the reaction was cooled to 25° C. and the solvent was removed in vacuo. The residue was re-dissolved in DCM (30 ml), washed with brine (20 ml), and concentrated under reduced pressure. The residue was then purified by chromatography on silica gel (eluting with DCM/CH$_3$OH=100/5 (v/v)) to provide (S)-tert-butyl 3-((8-(difluoromethyl)-9-ethyl-9H-purin-6-yl)amino)pyrrolidine-1-carboxylate. MS (ESI) calc'd for ($C_{17}H_{25}F_2N_6O_2$) [M+H]$^+$, 383. found, 383.

Step 3: Synthesis of (S)-8-(difluoromethyl)-9-ethyl-N-(pyrrolidin-3-yl)-9H-purin-6-amine (Intermediate XIV)

To a solution of (S)-tert-butyl 3-((8-(difluoromethyl)-9-ethyl-9H-purin-6-yl)amino)pyrrolidine-1-carboxylate (1 g, 3 mmol) in DCM (4 ml) was added HCl in dioxane (2 ml, 4M in dioxane), and the mixture was stirred at 20° C. for 2 h. The mixture was then cooled in an ice bath and saturated aqueous sodium hydrogen carbonate was added and the mixture was extracted with dichloromethane (2×100 mL). The organic layer was separated and the solvent was removed in vacuo to provide a residue which was purified by preparative reverse phase HPLC [Column: Xbridge Prep C18 10 um OBD, 19×250 mm; Mobile phase A: Water (10 mM NH$_4$HCO$_3$), B: MeCN; Flow rate: 30 mL/min; UV detection: 214/254 nm] to afford Intermediate XIV. MS (ESI) calc'd for ($C_{12}H_{17}F_2N_6$) [M+H]$^+$, 283. found, 283.

Step 4: Preparation of Compound 7-12

To a solution of 1-methyl-1H-pyrazole-3-carboxylic acid (30 mg, 0.23 mmol, commercially available from Chembridge) in DMF (2 ml) was added HATU (100 mg, 0.26 mmol) and 4-methylmorpholine (0.04 ml, 0.4 mmol). The mixed solution was stirred at 30° C. for 15 min, then Intermediate XIV (50 mg, 0.17 mmol) was added, the solution was stirred at 30° C. for 15 h. The mixture was cooled, and water (10 mL) was added and the mixture was extracted with ethyl acetate (2×10 mL). The combined organic extracts were evaporated under reduced pressure. The residue was purified by preparative Reverse phase HPLC (Column: Xbridge Prep C18, 10 um OBD, 19×250 mm; Mobile phase A: Water (0.05% TFA), B: MeCN; Flow rate: 30 mL/min; UV detection: 214/254 nm) to afford Compound 7-12. $^1$H NMR (400 MHz, CD$_3$OD) δ 8.45 (d, J=8.0 Hz, 1H), 7.64 (dd, J=8.0, 2.0 Hz, 1H), 7.15 (t, J=52.2 Hz, 1H), 6.84-6.70 (m, 1H), 5.00-4.70 (m, 1H), 4.70-4.39 (m, 2H), 4.32-3.72 (m, 7H), 2.60-2.15 (m, 2H), 1.60-1.42 (m, 3H). MS (ESI) calc'd for ($C_{17}H_{21}F_2N_8O$) [M+H]$^+$, 391. found, 391.

Example 16: Preparation of Compounds 7-22 and 7-23

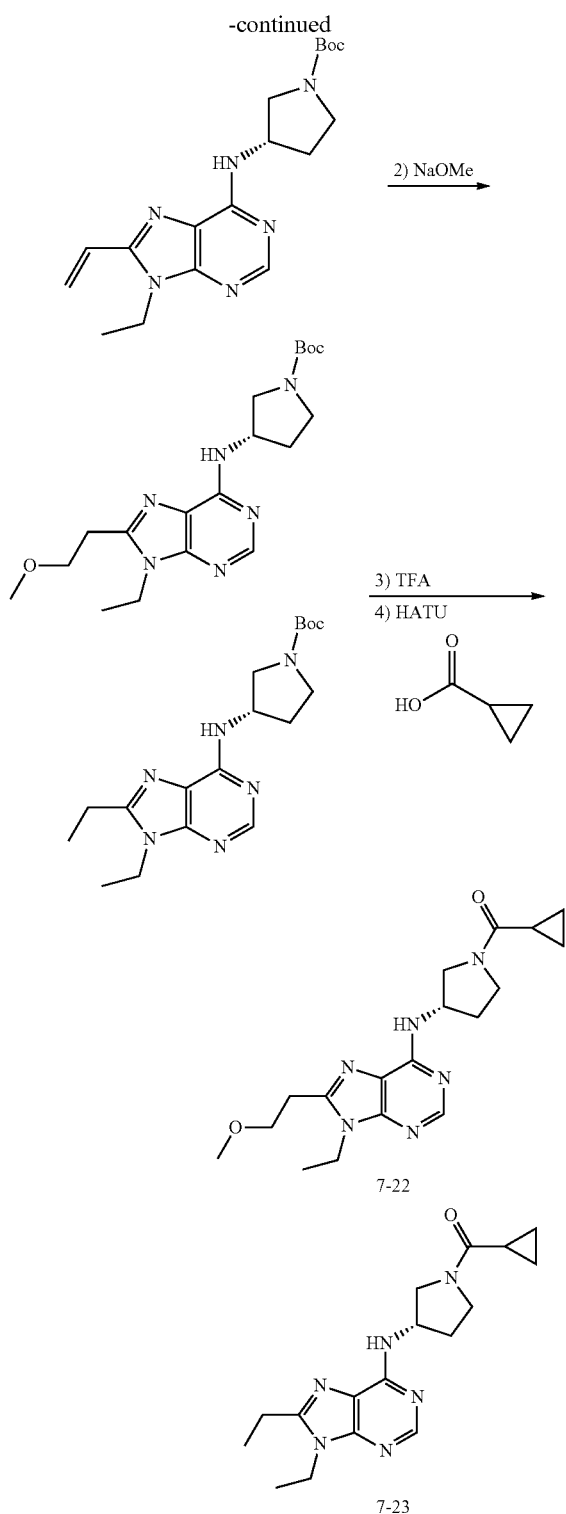

Step 1: Preparation of (S)-tert-butyl 3-((9-ethyl-8-vinyl-9H-purin-6-yl)amino)pyrrolidine-1-carboxylate A microwave vial was charged with Intermediate VII (100 mg, 0.22 mmol), PdCl$_2$(dppf).CH$_2$Cl$_2$ (18 mg, 0.022 mmol), and potassium phosphate (140 mg, 0.66 mmol). The tube was evacuated and backfilled with argon (3×). Fully degassed dioxane (1 mL) was then added, followed by 4,4,5,5-tetramethyl-2-vinyl-1,3,2-dioxaborolane (44.4 µl, 0.262 mmol) and degassed Water (100 µl). The vial was capped and heated at 50° C. overnight. The vial was then cooled to RT and partitioned between water and ethyl acetate. The organic layers were separated and washed with brine, dried over magnesium sulfate, filtered, and concentrated in vacuo. The residue was purified via silica gel chromatography, eluting 0-60% [10:1:1:1 EtOAc:MeOH:Acetone:Water] in EtOAc to provide of (S)-tert-butyl 3-((9-ethyl-8-vinyl-9H-purin-6-yl)amino)pyrrolidine-1-carboxylate. MS (ESI) calc'd for (C$_{18}$H$_{27}$N$_6$O$_2$) [M+H]$^+$, 359. found, 359.

Step 2: Preparation of (S)-tert-butyl 3-((9-ethyl-8-(2-methoxyethyl)-9H-purin-6-yl)amino)pyrrolidine-1-carboxylate and (S)-tert-butyl 3-((8,9-diethyl-9H-purin-6-yl)amino)pyrrolidine-1-carboxylate (S)-tert-butyl 3-((9-ethyl-8-vinyl-9H-purin-6-yl)amino)pyrrolidine-1-carboxylate (85 mg, 0.24 mmol) was taken up in MeOH (1 ml) at room temperature and sodium methoxide (25 wt % in methanol) (1.4 ml, 5.9 mmol) was added. The mixture was capped and heated to 75° C. for 60 h. The reaction was then diluted with EtOAc and saturated ammonium chloride was added. The reaction mixture was extracted with EtOAc, washed with brine, dried over magnesium sulfate, filtered, and concentrated in vacuo. The residue was purified via silica gel chromatography, eluting 0-30% [10:1:1:1 EtOAc:MeOH:Acetone:Water] in EtOAc to provide a mixture of (S)-tert-butyl 3-((9-ethyl-8-(2-methoxyethyl)-9H-purin-6-yl)amino)pyrrolidine-1-carboxylate and (S)-tert-butyl 3-((8,9-diethyl-9H-purin-6-yl)amino)pyrrolidine-1-carboxylate which was taken on to the next step without further purification.

Step 3: Preparation of (S)-9-ethyl-8-(2-methoxyethyl)-N-(pyrrolidin-3-yl)-9H-purin-6-amine, TFA and (S)-8,9-diethyl-N-(pyrrolidin-3-yl)-9H-purin-6-amine, TFA To a flask were added the crude mixture of (S)-tert-butyl 3-((9-ethyl-8-(2-methoxyethyl)-9H-purin-6-yl)amino)pyrrolidine-1-carboxylate and (S)-tert-butyl 3-((8,9-diethyl-9H-purin-6-yl)amino)pyrrolidine-1-carboxylate (obtained in Step 2) which were dissolved in Dichloromethane (400 µL). To this was added TFA (100 µL, 1.3 mmol). The reaction was stirred at RT for 3 h. The solvent was then removed in vacuo to afford the crude mixture of TFA salts which were taken into the next reaction without further purification.

Step 4: Preparation of Compounds 7-22 and 7-23

To a vial, were added the mixture (S)-9-ethyl-8-(2-methoxyethyl)-N-(pyrrolidin-3-yl)-9H-purin-6-amine, TFA and (S)-8,9-diethyl-N-(pyrrolidin-3-yl)-9H-purin-6-amine, TFA (obtained in step 3), cyclopropanecarboxylic acid (9.25 µl, 0.116 mmol), DMF (800 µl) and DIEA (150 µl, 0.86 mmol). HATU (47 mg, 0.12 mmol) was then added, and the mixture was stirred at RT for 16 h. DMSO (1 ml) was then added and the crude mixture was purified by SFC [Viridis, Fluoro-Phenyl, 21×250 (mm), 70 ml/min flow rate, 15% MeOH and 0.25% dimethylethylamine in CO$_2$] to provide 7-22 (retention time 3.8 min) and 7-23 (retention time 4.4 min). For 7-22: $^1$H NMR (500 MHz, DMSO-d$_6$) δ 8.24-8.12 (m, 1H), 7.91-7.73 (m, 1H), 4.94-4.53 (m, 1H), 4.23-4.09 (m, 2H), 4.02-3.80 (m, 1H), 3.79-3.72 (m, 2H), 3.71-3.43

(m, 2H), 3.38-3.28 (m, 1H), 3.28-3.21 (m, 3H), 3.14-3.03 (m, 2H), 2.29-1.93 (m, 2H), 1.80-1.61 (m, 1H), 1.33-1.24 (m, 3H), 0.75-0.60 (m, 4H). MS (ESI) calc'd for ($C_{18}H_{27}N_6O_2$) [M+H]$^+$, 359. found, 359. For 7-23: $^1$H NMR (500 MHz, DMSO-$d_6$) δ 8.30-8.08 (m, 1H), 7.88-7.67 (m, 1H), 4.93-4.54 (m, 1H), 4.19-4.07 (m, 2H), 4.01-3.80 (m, 1H), 3.70-3.45 (m, 2H), 3.40-3.27 (m, 1H), 2.90-2.77 (m, 2H), 2.30-1.93 (m, 2H), 1.79-1.62 (m, 1H), 1.36-1.21 (m, 6H), 0.75-0.60 (m, 4H). MS (ESI) calc'd for ($C_{17}H_{25}N_6O$) [M+H]$^+$, 329. found, 329.

Example 17: Preparation of Compound 7-24

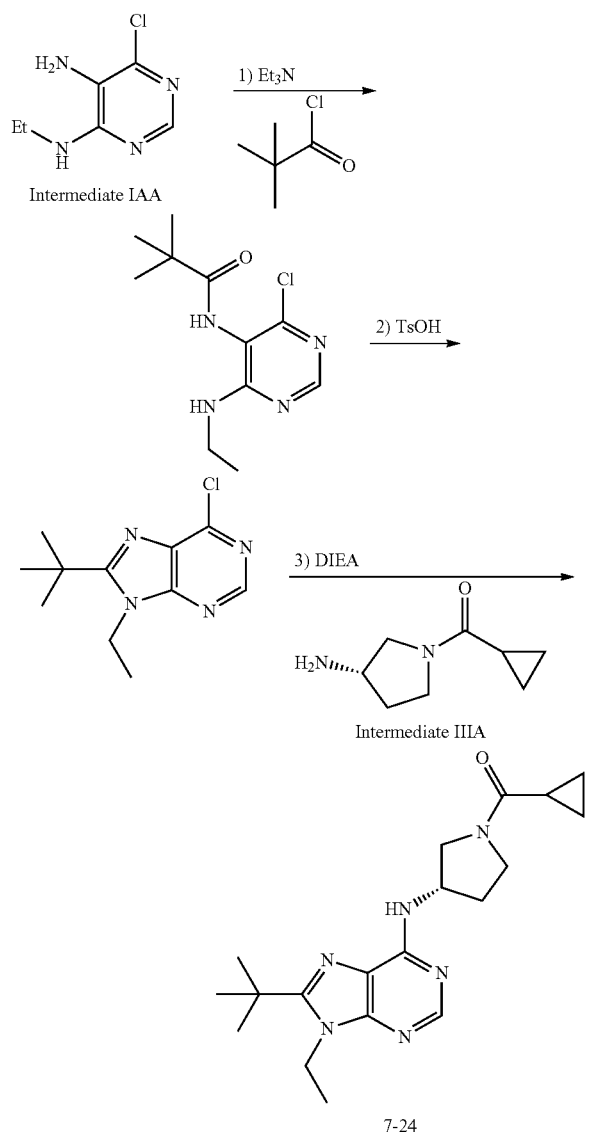

Step 1: Preparation of N-(4-chloro-6-(ethylamino)pyrimidin-5-yl)pivalamide

Pivaloyl chloride (220 mg, 1.8 mmol) was added to a solution of Intermediate IAA (300 mg, 1.7 mmol) and triethylamine (352 mg, 3.48 mmol) in DCM (10 ml) at 0° C. and the mixture was stirred at 40° C. for 16 hr. The mixture was then quenched with saturated aqueous ammonium chloride (10 mL) and extracted with dichloromethane (3×10 mL). The combined organic fractions were washed with brine, dried over sodium sulfate, filtered, and the solvent was evaporated under reduced pressure to give N-(4-chloro-6-(ethylamino)pyrimidin-5-yl)pivalamide. MS (ESI) calc'd for ($C_{11}H_{18}ClN_4O$) [M+H]$^+$, 257. found, 257.

Step 2: Preparation of 8-tert-butyl-6-chloro-9-ethyl-9H-purine 4-methylbenzenesulfonic acid (33.5 mg, 0.195 mmol) was added to a solution of N-(4-chloro-6-(ethylamino)pyrimidin-5-yl)pivalamide (200 mg, 0.78 mmol) in toluene (5 ml) at room temperature and the mixture was stirred at 105° C. for 18 h. The reaction mixture was then cooled and concentrated in vacuo. The resulting residue was purified by preparative thin-layer chromatography (eluting with PE:EA=4:1) to give 8-tert-butyl-6-chloro-9-ethyl-9H-purine. MS (ESI) calc'd for ($C_{11}H_{16}ClN_4$) [M+H]$^+$, 239. found, 239.

Step 3: Preparation of Compound 7-24

DIPEA (0.366 ml, 2.095 mmol) was added to a solution of 8-(tert-butyl)-6-chloro-9-ethyl-9H-purine (100 mg, 0.42 mmol) and (S)-(3-aminopyrrolidin-1-yl)(cyclopropyl)methanone Intermediate IIIA (in its neutral form) (129 mg, 0.838 mmol) in t-BuOH (6 ml) at room temperature and the mixture was stirred at 85° C. for 18 h. The reaction mixture was then concentrated, and the residue was purified by preparative reverse phase HPLC (C-18), eluting with Acetonitrile/Water+0.05% NH$_3$, to give as 7-24. $^1$H NMR (400 MHz, CD$_3$OD): δ 8.27 (m, 1H), 5.00-4.70 (m, 1H), 4.49-4.44 (m, 2H), 4.20-3.57 (m, 4H), 2.50-2.10 (m, 2H), 1.86-1.70 (m, 1H), 1.55 (s, 9H), 1.50-1.45 (m, 3H), 1.00-0.75 (m, 4H). MS (ESI) calc'd for ($C_{19}H_{29}N_6O$) [M+H]$^+$, 357. found, 357.

Example 18: Preparation of Compound 7-25

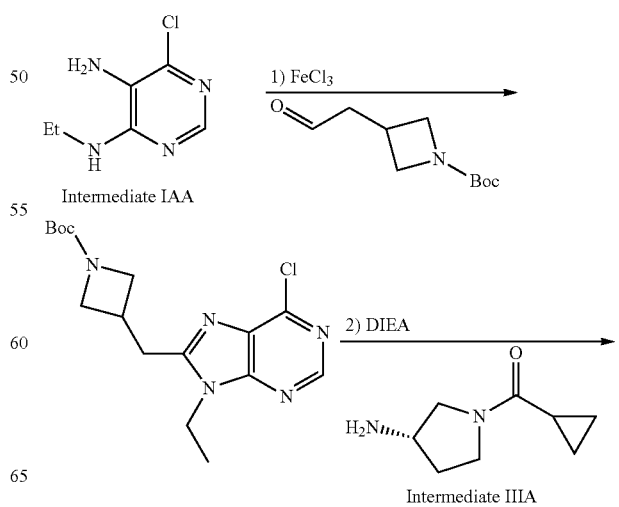

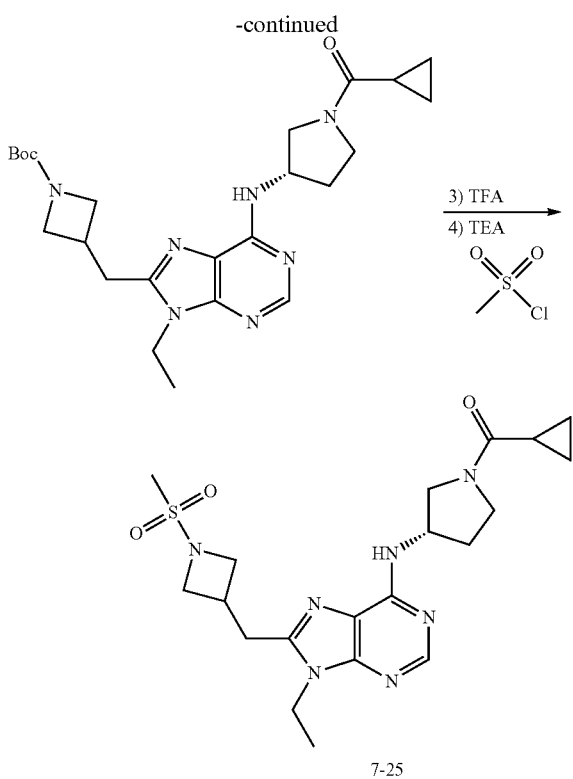

7-25

Step 1: Preparation of tert-butyl 3-((6-chloro-9-ethyl-9H-purin-8-yl)methyl)azetidine-1-carboxylate Intermediate IAA (200 mg, 1.2 mmol) and iron (III) chloride hexahydrate (81 mg, 0.30 mmol) were dissolved in DMF (1.2 ml). Tert-butyl 3-(2-oxoethyl)azetidine-1-carboxylate (300 mg, 1.5 mmol, available from Synnovator, Inc.) was then added. The mixture was heated to 75° C. and stirred vigorously in an open vial for 18 h. The reaction mixture was then cooled and partitioned between water and EtOAc. The organic layer was separated and the aqueous layer was further extracted EtOAc (×3). The combined organic layers were washed with brine, dried over magnesium sulfate, filtered, and concentrated in vacuo. The residue was purified by silica gel eluting with a 0-80% EtOAc in Hexanes to provide of tert-butyl 3-((6-chloro-9-ethyl-9H-purin-8-yl)methyl)azetidine-1-carboxylate. MS (ESI) calc'd for ($C_{16}H_{23}ClN_5O_2$) [M+H]$^+$, 352. found, 352.

Step 2: Preparation of (S)-tert-butyl 3-((6-((1-(cyclopropanecarbonyl)pyrrolidin-3-yl)amino)-9-ethyl-9H-purin-8-yl)methyl)azetidine-1-carboxylate Tert-butyl 3-((6-chloro-9-ethyl-9H-purin-8-yl)methyl)azetidine-1-carboxylate (235 mg, 0.668 mmol) and (S)-(3-aminopyrrolidin-1-yl)(cyclopropyl)methanone, HCl (Intermediate IIIA) (134 mg, 0.701 mmol) were suspended in t-BuOH (3340 µl) and DIEA (760 µl, 4.4 mmol) was added. The suspension was heated to 85° C. overnight. The reaction was then cooled and the solvent was removed in vacuo. The residue was re-dissolved in EtOAc and washed with water, brine, dried over magnesium sulfate, filtered, and concentrated directly onto silica gel. The residue was then purified via silica gel chromatography, eluting 10-100% EtOAc in Hexanes to provide (S)-tert-butyl 3-((6-((1-(cyclopropanecarbonyl)pyrrolidin-3-yl)amino)-9-ethyl-9H-purin-8-yl)methyl)azetidine-1-carboxylate. MS (ESI) calc'd for ($C_{24}H_{36}N_7O_3$) [M+H]$^+$, 470. found, 470.

Step 3: Preparation of (S)-(3-((8-(azetidin-3-ylmethyl)-9-ethyl-9H-purin-6-yl)amino)pyrrolidin-1-yl)(cyclopropyl)methanone, TFA (S)-tert-butyl 3-((6-((1-(cyclopropanecarbonyl)pyrrolidin-3-yl)amino)-9-ethyl-9H-purin-8-yl)methyl)azetidine-1-carboxylate (73 mg, 0.16 mmol) was dissolved in DCM (500 µl) and TFA (125 µl) was added. The reaction was stirred for 6 h at RT, after which another aliquot of TFA (100 µl) was added and the reaction was allowed to stir for an additional 1 h, after which the solvent was removed in vacuo to provide (S)-(3-((8-(azetidin-3-ylmethyl)-9-ethyl-9H-purin-6-yl)amino)pyrrolidin-1-yl)(cyclopropyl)methanone, TFA which was used in the next step without further purification. MS (ESI) calc'd for ($C_{19}H_{28}N_7O$) [M+H]$^+$, 370. found, 370.

Step 4: Preparation of Compound 7-25

(S)-(3-((8-(azetidin-3-ylmethyl)-9-ethyl-9H-purin-6-yl)amino)pyrrolidin-1-yl)(cyclopropyl)methanone, TFA (47 mg, 0.078 mmol) was dissolved in DCM (0.750 ml) and TEA (0.087 ml, 0.624 mmol) was added, followed by methanesulfonyl chloride (6.7 µl, 0.086 mmol). The reaction was allowed to stir at RT for 16 h, after which the mixture was concentrated in vacuo and re-dissolved in DMSO and purified by reverse phase preparative HPLC (0:100 to 95:5 acetonitrile:water: 0.1% v/v TFA modifier) to provide (S)cyclopropyl(3-(9-ethyl-8-((1-(methylsulfonyl)azetidin-3-yl)methyl)-9H-purin-6-yl)amino)pyrrolidin-1-yl)methanone as the TFA salt. The salt was then dissolved in MeOH and eluted through a 1 g SiliaPrep™ silicon-carbonate cartridge, after which it was lyophilized from a mixture of MeOH and water to afford 7-25. $^1$H NMR (499 MHz, DMSO-d$_6$) δ 8.29-8.05 (m, 1H), 7.82-7.65 (m, 1H), 4.93-4.58 (m, 1H), 4.19-4.11 (m, 2H), 4.09-3.48 (m, 8H), 3.23-3.09 (m, 3H), 3.03-2.96 (m, 3H), 2.33-1.88 (m, 2H), 1.82-1.60 (m, 1H), 1.31-1.25 (m, 3H), 0.76-0.61 (m, 4H). MS (ESI) calc'd for ($C_{20}H_{30}N_7O_3S$) [M+H]$^+$, 448. found, 448.

Example 19: Preparation of Compound 7-27

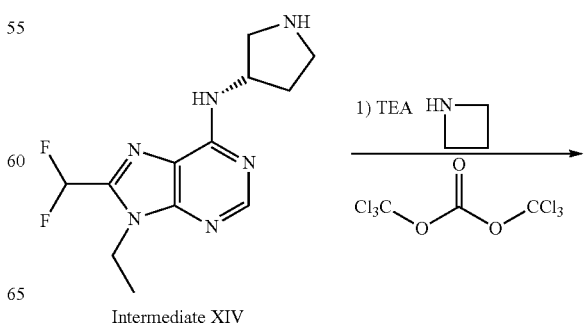

Intermediate XIV

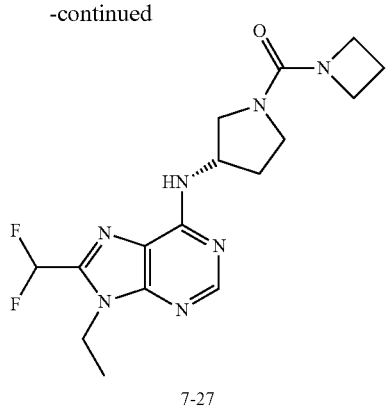

7-27

To a solution of azetidine (10 μL, 0.2 mmol) in 1 mL of DCM was added TEA (50 μL, 0.35 mmol) in an ice bath. Triphosgene (21 mg, 0.071 mmol), dissolved in 200 μL of DCM, was then added into the solution. The reaction was stirred at 0° C. for 30 min, after which it was allowed to warm to RT where it was stirred for 2 h. The solution was then cooled to 0° C. and TEA (50 μL, 0.35 mmol) and Intermediate XIV (50 mg, 0.18 mmol) were then added as a solution in DCM. The reaction was stirred at 0° C. for 30 min, after which it was allowed to warm to RT where it was stirred for 16 h. The reaction was then quenched by the addition of saturated sodium bicarbonate, and the organic layer was separated and concentrated in vacuo. The residue was then purified by silica gel chromatography, eluting 0-10% methanol in DCM, to afford compound 7-27. $^1$H NMR (499 MHz, CDCl$_3$) δ 8.46 (broad s, 1H); 6.81 (t, J=52.5 Hz, 1H); 5.90 (broad s, 1H); 4.86 (broad s, 1H); 4.45 (q, J=7.3 Hz, 2H); 4.10-3.94 (m, 4H); 3.79 (dd, J=10.5, 5.8 Hz, 1H); 3.63-3.46 (m, 2H); 3.40 (dd, J=11.2, 4.1 Hz, 1H); 2.35-2.19 (m, 3H); 2.15-1.93 (m, 1H); 1.51 (t, J=7.3 Hz, 3H); MS (EI) Calc'd for C$_{16}$H$_{22}$F$_2$N$_7$O [M+H]$^+$, 366. found 366.

Compounds 7-2 through 7-7 were prepared in an analogous fashion to Example 13 using the corresponding aldehydes and either Intermediate III or Intermediate IIIA.

Compound 7-8 was prepared in an analogous fashion to Example 13 except that the aldehyde was prepared in situ in the first step by adding 1,1,2-trimethoxyethane (4 equivalents) and a catalytic amount of 4-methylbenzenesulfonic acid to the reaction vessel and by conducting the first step in a 4:1 mixture of DMF:Ethanol.

Compound 7-9 was prepared in an analogous fashion to Example 4D (in table 3) using cyclopropylboronic acid instead of 4-methoxy-3-methylphenylboronic acid.

Compound 7-10 was prepared in an analogous fashion to Example 4E, step 3 (in table 3) using cyclopropylboronic acid instead of 4-(4,4,5,5-tetramethyl-1,3,2-dioxaborolan-2-yl)-1-(2,2,2-trifluoroethyl)-1H-pyrazole.

Compounds 7-13 and 7-14 were prepared in an analogous fashion to Example 15, step 2 using Intermediates III and IIIA, respectively.

Compounds 7-15, 7-16, and 7-19 were prepared in an analogous fashion to Example 15 using the corresponding acids.

Compounds 7-17 and 7-18 were prepared in an analogous fashion to Example 15 using a mixture of trans and cis 3-methoxycyclobutanecarboxylic acid. The mixture thus obtained was separated by chiral SFC [Chiralpak, IA, 21×250 (mm), 70 ml/min flow rate, 25% MeOH in CO$_2$] to provide compound 7-17 (retention time 3.2 min) and 7-18 (retention time 4.6 min).

Compounds 7-20 and 7-21 were prepared in an analogous fashion to Example 15 using racemic spiro[2.4]heptane-1-carboxylic acid. The mixture thus obtained was separated by chiral SFC [Chiralpak AD-H, 21×250 (mm), 70 ml/min, 20% MeOH in CO$_2$] to provide 7-20 (retention time 3.6 min) and 7-21 (retention time 4.8 min).

Compound 7-26 was prepared from Intermediate VIX and 2-bromopyridine in an analogous fashion to Example 7, using cesium carbonate instead of potassium carbonate and DMF instead of N-methylpyrrolidone.

Compound 7-28 was prepared in an analogous fashion to Example 19 using 3-methoxyazetidine hydrochloride instead of azetidine.

TABLE 7

| Compound | Structure | IUPAC Name | Exact Mass [M + H]+ |
|---|---|---|---|
| 7-1 | 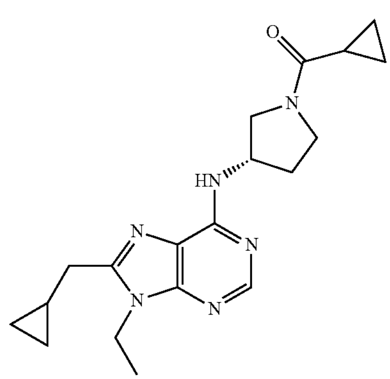 [SMILES: CCn1c(CC2CC2)nc2c(N[C@H]3CCN(C(=O)C4CC4)C3)ncnc21] | N-[(3S)-1-(cyclopropylcarbonyl)pyrrolidin-3-yl]-8-(cyclopropylmethyl)-9-ethyl-9H-purin-6-amine | Calc'd 355, found 355 |

TABLE 7-continued

| Compound | Structure | IUPAC Name | Exact Mass [M + H]+ |
|---|---|---|---|
| 7-2 | 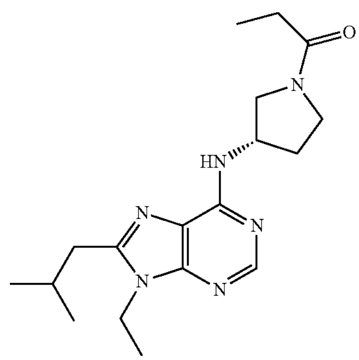 [SMILES: CCC(=O)N1CC[C@H](Nc2ncnc3c2nc(CC(C)C)n3CC)C1] | 9-ethyl-8-(2-methylpropyl)-N-[(3S)-1-propanoylpyrrolidin-3-yl]-9H-purin-6-amine | Calc'd 345, found 345 |
| 7-3 | 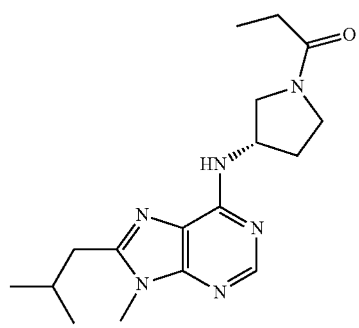 [SMILES: CCC(=O)N1CC[C@H](Nc2ncnc3c2nc(CC(C)C)n3C)C1] | 9-methyl-8-(2-methylpropyl)-N-[(3S)-1-propanoylpyrrolidin-3-yl]-9H-purin-6-amine | Calc'd 331, found 331 |
| 7-4 | 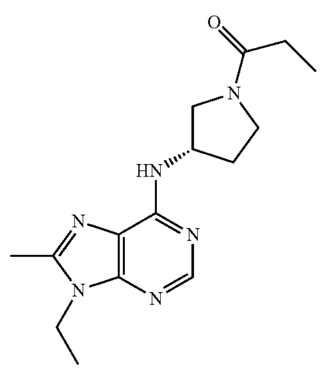 [SMILES: CCC(=O)N1CC[C@H](Nc2ncnc3c2nc(C)n3CC)C1] | 9-ethyl-8-methyl-N-[(3S)-1-propanoylpyrrolidin-3-yl]-9H-purin-6-amine | Calc'd 303, found 303 |
| 7-5 | 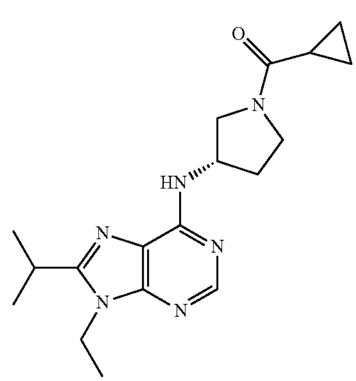 [SMILES: CCn1c(C(C)C)nc2c(N[C@H]3CCN(C(=O)C4CC4)C3)ncnc21] | N-[(3S)-1-(cyclopropylcarbonyl)pyrrolidin-3-yl]-9-ethyl-8-(1-methylethyl)-9H-purin-6-amine | Calc'd 343, found 343 |

TABLE 7-continued

| Compound | Structure | IUPAC Name | Exact Mass [M + H]+ |
|---|---|---|---|
| 7-6 | 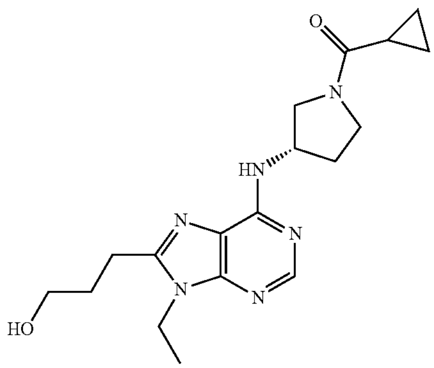 [SMILES: CCn1c(CCCO)nc2c(N[C@H]3CCN(C(=O)C4CC4)C3)ncnc21] | 3-(6-{[(3S)-1-(cyclopropylcarbonyl)pyrrolidin-3-yl]amino}-9-ethyl-9H-purin-8-yl)propan-1-ol | Calc'd 359, found 359 |
| 7-7 | 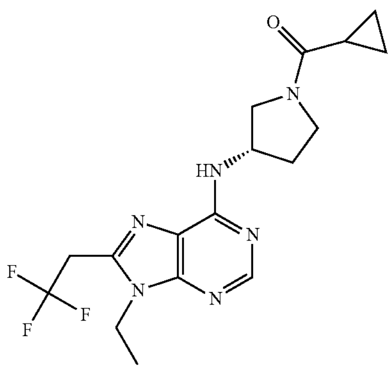 [SMILES: CCn1c(CC(F)(F)F)nc2c(N[C@H]3CCN(C(=O)C4CC4)C3)ncnc21] | N-[(3S)-1-(cyclopropylcarbonyl)pyrrolidin-3-yl]-9-ethyl-8-(2,2,2-trifluoroethyl)-9H-purin-6-amine | Calc'd 383, found 383 |
| 7-8 | 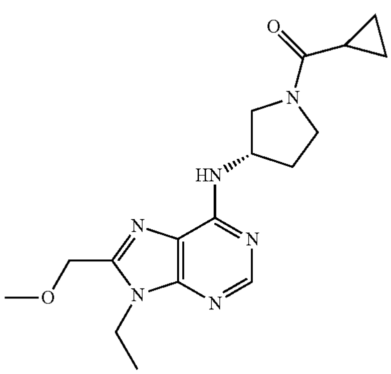 [SMILES: CCn1c(COC)nc2c(N[C@H]3CCN(C(=O)C4CC4)C3)ncnc21] | N-[(3S)-1-(cyclopropylcarbonyl)pyrrolidin-3-yl]-9-ethyl-8-(methoxymethyl)-9H-purin-6-amine | Calc'd 345, found 345 |
| 7-9 | 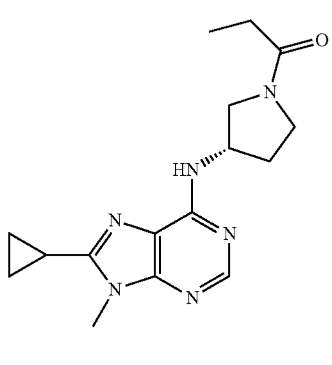 [SMILES: CCC(=O)N1CC[C@H](Nc2ncnc3c2nc(C2CC2)n3C)C1] | 8-cyclopropyl-9-methyl-N-[(3S)-1-propanoylpyrrolidin-3-yl]-9H-purin-6-amine | Calc'd 315, found 315 |

TABLE 7-continued

| Compound | Structure | IUPAC Name | Exact Mass [M + H]+ |
|---|---|---|---|
| 7-10 | 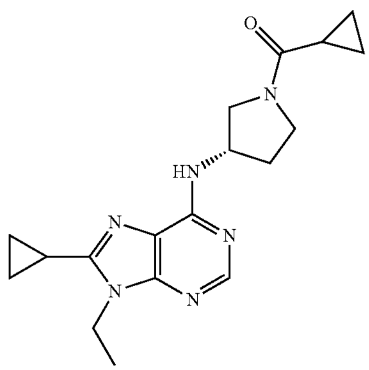 [SMILES: CCn1c(C2CC2)nc2c(N[C@H]3CCN(C(=O)C4CC4)C3)ncnc21] | 8-cyclopropyl-N-[(3S)-1-(cyclopropylcarbonyl)pyrrolidin-3-yl]-9-ethyl-9H-purin-6-amine | Calc'd 341, found 341 |
| 7-11 | 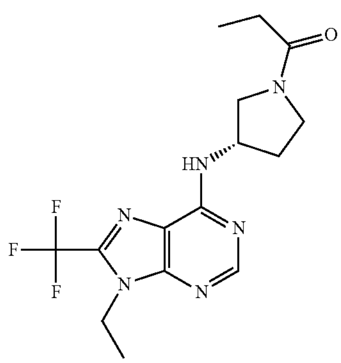 [SMILES: CCC(=O)N1CC[C@H](Nc2ncnc3c2nc(C(F)(F)F)n3CC)C1] | 9-ethyl-N-[(3S)-1-propanoylpyrrolidin-3-yl]-8-(trifluoromethyl)-9H-purin-6-amine | Calc'd 357, found 357 |
| 7-12 | 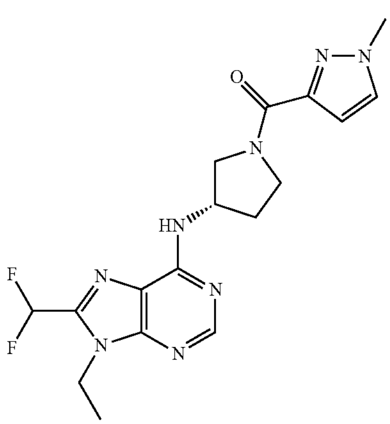 [SMILES: CCn1c(C(F)F)nc2c(N[C@H]3CCN(C(=O)c4ccn(C)n4)C3)ncnc21] | 8-(difluoromethyl)-9-ethyl-N-{(3S)-1-[(1-methyl-1H-pyrazol-3-yl)carbonyl]pyrrolidin-3-yl}-9H-purin-6-amine | Calc'd 391, found 391 |
| 7-13 | 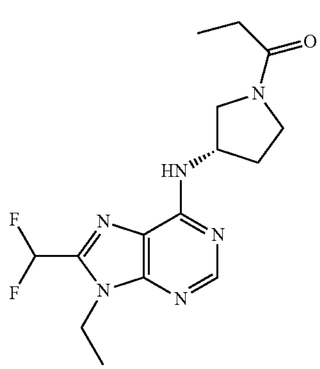 [SMILES: CCC(=O)N1CC[C@H](Nc2ncnc3c2nc(C(F)F)n3CC)C1] | 8-(difluoromethyl)-9-ethyl-N-[(3S)-1-propanoylpyrrolidin-3-yl]-9H-purin-6-amine | Calc'd 339, found 339 |

TABLE 7-continued

| Compound | Structure | IUPAC Name | Exact Mass [M + H]+ |
|---|---|---|---|
| 7-14 | 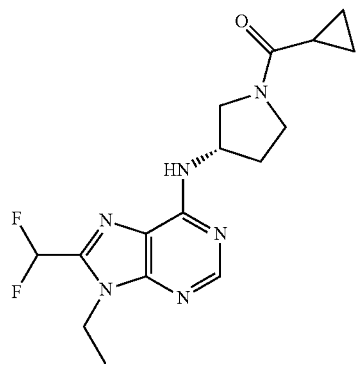 [SMILES: CCn1c(C(F)F)nc2c(N[C@H]3CCN(C(=O)C4CC4)C3)ncnc21] | N-[(3S)-1-(cyclopropylcarbonyl)pyrrolidin-3-yl]-8-(difluoromethyl)-9-ethyl-9H-purin-6-amine | Calc'd 351, found 351 |
| 7-15 | 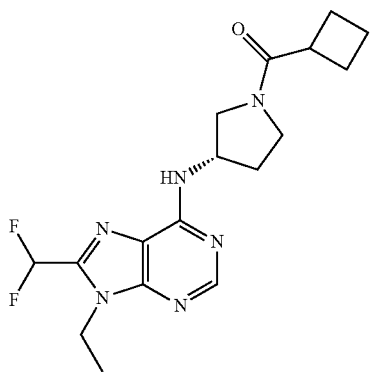 [SMILES: CCn1c(C(F)F)nc2c(N[C@H]3CCN(C(=O)C4CCC4)C3)ncnc21] | N-[(3S)-1-(cyclobutylcarbonyl)pyrrolidin-3-yl]-8-(difluoromethyl)-9-ethyl-9H-purin-6-amine | Calc'd 365, found 365 |
| 7-16 | 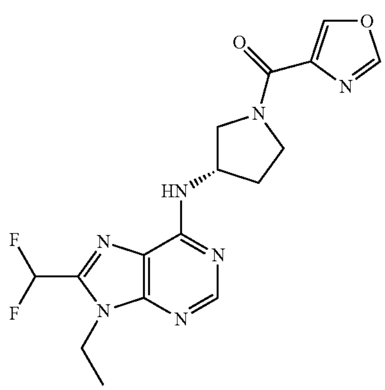 [SMILES: CCn1c(C(F)F)nc2c(N[C@H]3CCN(C(=O)c4cocn4)C3)ncnc21] | 8-(difluoromethyl)-9-ethyl-N-[(3S)-1-(1,3-oxazol-4-ylcarbonyl)pyrrolidin-3-yl]-9H-purin-6-amine | Calc'd 378, found 378 |
| 7-17 | 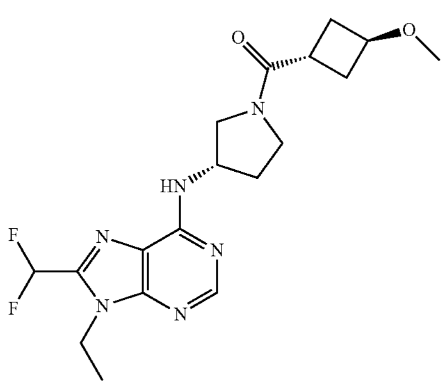 [SMILES: CCn1c(C(F)F)nc2c(N[C@H]3CCN(C(=O)[C@H]4C[C@H](OC)C4)C3)ncnc21] | 8-(difluoromethyl)-9-ethyl-N-{(3S)-1-[(trans-3-methoxycyclobutyl)carbonyl]-pyrrolidin-3-yl}-9H-purin-6-amine | Calc'd 395, found 395 |

TABLE 7-continued

| Compound | Structure | IUPAC Name | Exact Mass [M + H]+ |
|---|---|---|---|
| 7-18 | 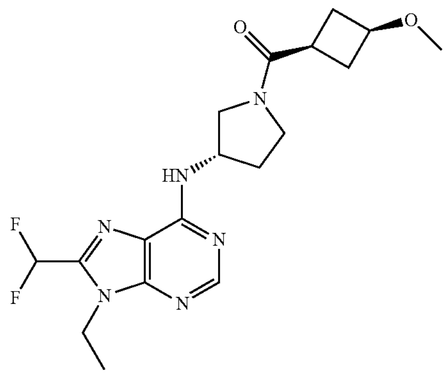 [SMILES: CCn1c(C(F)F)nc2c(N[C@H]3CCN(C(=O)[C@H]4C[C@@H](OC)C4)C3)ncnc21] | 8-(difluoromethyl)-9-ethyl-N-{(3S)-1-[(cis-3-methoxycyclobutyl)carbonyl]-pyrrolidin-3-yl}-9H-purin-6-amine | Calc'd 395, found 395 |
| 7-19 | 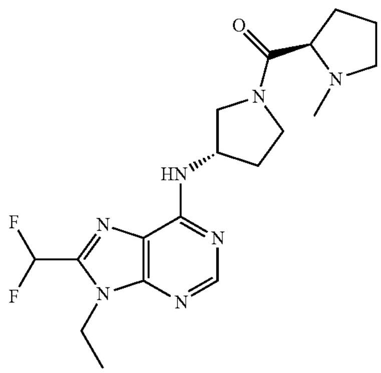 [SMILES: CCn1c(C(F)F)nc2c(N[C@H]3CCN(C(=O)[C@H]4CCCN4C)C3)ncnc21] | 8-(difluoromethyl)-9-ethyl-N-[(3S)-1-(1-methyl-D-prolyl)pyrrolidin-3-yl]-9H-purin-6-amine | Calc'd 394, found 394 |
| 7-20 | 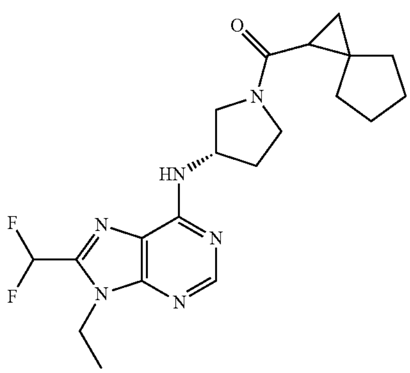 [SMILES: CCn1c(C(F)F)nc2c(N[C@H]3CCN(C(=O)C4CC45CCCC5)C3)ncnc21] | (S or R)-8-(difluoromethyl)-9-ethyl-N-[(3S)-1-(spiro[2.4]hept-1-ylcarbonyl)pyrrolidin-3-yl]-9H-purin-6-amine | Calc'd 405, found 405 |
| 7-21 | 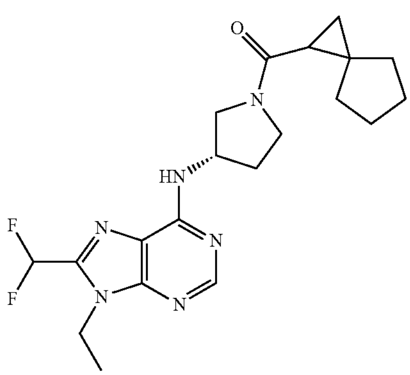 [SMILES: CCn1c(C(F)F)nc2c(N[C@H]3CCN(C(=O)C4CC45CCCC5)C3)ncnc21] | (S or R)-8-(difluoromethyl)-9-ethyl-N-[(3S)-1-(spiro[2.4]hept-1-ylcarbonyl)pyrrolidin-3-yl]-9H-purin-6-amine | Calc'd 405, found 405 |

TABLE 7-continued

| Compound | Structure | IUPAC Name | Exact Mass [M + H]+ |
|---|---|---|---|
| 7-22 | 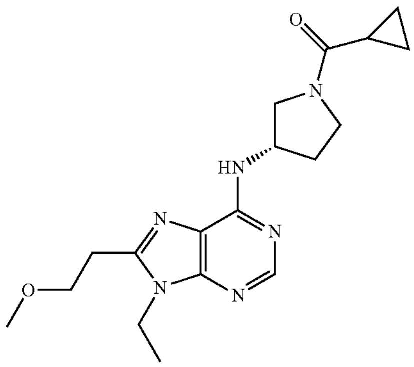 [SMILES: CCn1c(CCOC)nc2c(N[C@H]3CCN(C(=O)C4CC4)C3)ncnc21] | N-[(3S)-1-(cyclopropylcarbonyl)pyrrolidin-3-yl]-9-ethyl-8-(2-methoxyethyl)-9H-purin-6-amine | Calc'd 359, found 359 |
| 7-23 | 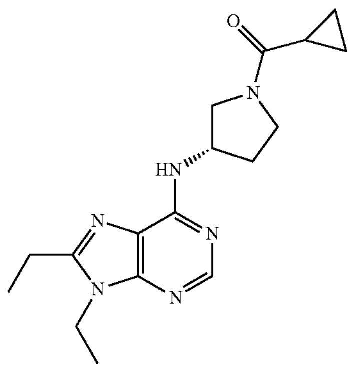 [SMILES: CCc1nc2c(N[C@H]3CCN(C(=O)C4CC4)C3)ncnc2n1CC] | N-[(3S)-1-(cyclopropylcarbonyl)pyrrolidin-3-yl]-8,9-diethyl-9H-purin-6-amine | Calc'd 329, found 329 |
| 7-24 | 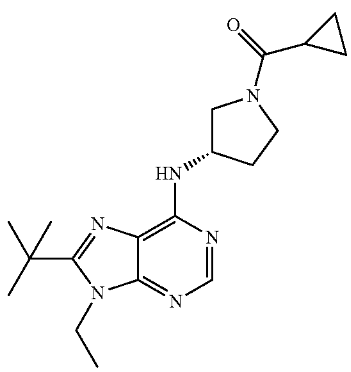 [SMILES: CCn1c(C(C)(C)C)nc2c(N[C@H]3CCN(C(=O)C4CC4)C3)ncnc21] | 8-tert-butyl-N-[(3S)-1-(cyclopropylcarbonyl)pyrrolidin-3-yl]-9-ethyl-9H-purin-6-amine | Calc'd 357, found 357 |
| 7-25 | 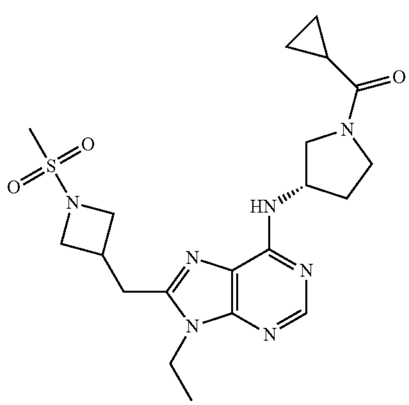 [SMILES: CCn1c(CC2CN(S(C)(=O)=O)C2)nc2c(N[C@H]3CCN(C(=O)C4CC4)C3)ncnc21] | N-[(3S)-1-(cyclopropylcarbonyl)pyrrolidin-3-yl]-9-ethyl-8-{[1-(methylsulfonyl)azetidin-3-yl]methyl}-9H-purin-6-amine | Calc'd 448, found 448 |

TABLE 7-continued

| Compound | Structure | IUPAC Name | Exact Mass [M + H]+ |
|---|---|---|---|
| 7-26 | 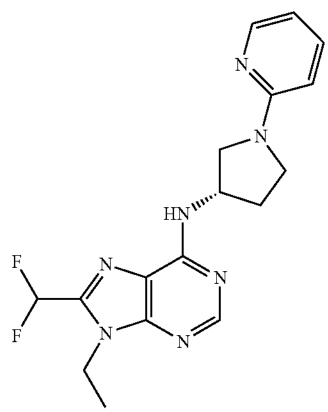 [SMILES: CCn1c(C(F)F)nc2c(N[C@H]3CCN(c4ccccn4)C3)ncnc21] | 8-(difluoromethyl)-9-ethyl-N-[(3S)-1-pyridin-2-ylpyrrolidin-3-yl]-9H-purin-6-amine | Calc'd 360, found 360 |
| 7-27 | 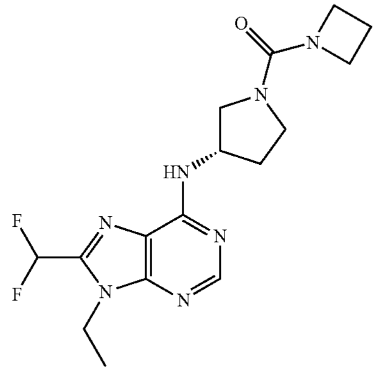 [SMILES: CCn1c(C(F)F)nc2c(N[C@H]3CCN(C(=O)N4CCC4)C3)ncnc21] | N-[(3S)-1-(azetidin-1-ylcarbonyl)pyrrolidin-3-yl]-8-(difluoromethyl)-9-ethyl-9H-purin-6-amine | Calc'd 366, found 366 |
| 7-28 | 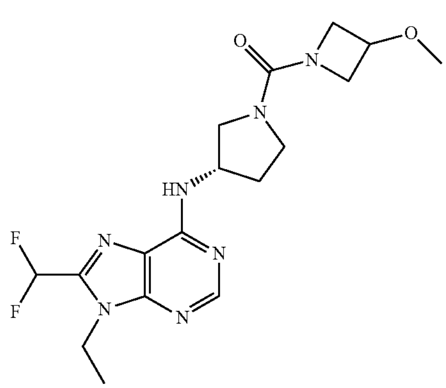 [SMILES: CCn1c(C(F)F)nc2c(N[C@H]3CCN(C(=O)N4CC(OC)C4)C3)ncnc21] | 8-(difluoromethyl)-9-ethyl-N-{(3S)-1-[(3-methoxyazetidin-1-yl)carbonyl]pyrrolidin-3-yl}-9H-purin-6-amine | Calc'd 396, found 396 |

Compound Examples of Table 8

Example 19A: Preparation of Compound 8-1

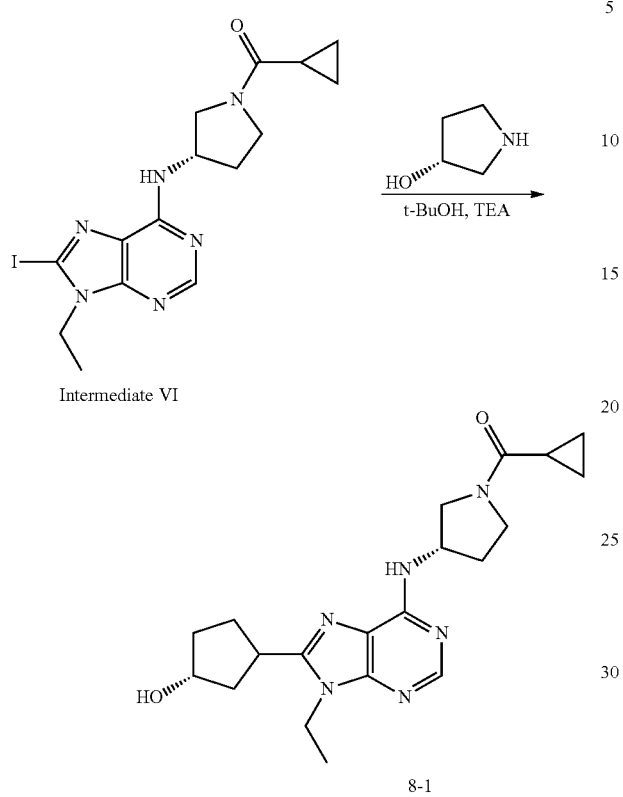

Intermediate VI 8-1

A mixture of (S)-cyclopropyl(3-((9-ethyl-8-iodo-9H-purin-6-yl)amino)pyrrolidin-1-yl)methanone (Intermediate VI) (0.050 g, 0.12 mmol), (R)-pyrrolidin-3-ol (0.013 g, 0.15 mmol), triethylamine (1.0 mL, 7.1 mmol) and t-BuOH (2.0 mL) was heated to 100° C. in a sealed tube for 15 h. The reaction was then cooled, concentrated in vacuo, and the residue was purified by preparative thin-layer chromatography (silica gel, DCM:MeOH=5:1) to afford compound 8-1. $^1$H NMR (400 MHz, CD$_3$OD) δ 8.15-8.14 (m, 1H), 4.84-4.58 (m, 2H), 4.37-3.55 (m, 10H), 2.47-1.74 (m, 5H), 1.41-1.37 (m, 3H), 0.95-0.79 (m, 4H). MS (ESI) calc'd for C$_{19}$H$_{28}$N$_7$O$_2$ [M+H]$^+$, 386. found, 386.

Example 19B: Preparation of Compound 8-4

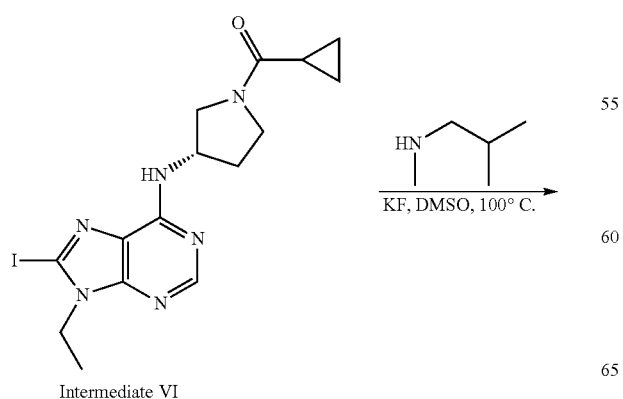

Intermediate VI

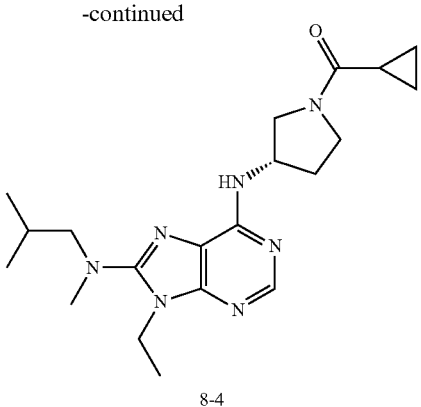

8-4

To a microwave vial was added (S)-cyclopropyl(3-((9-ethyl-8-iodo-9H-purin-6-yl)amino)pyrrolidin-1-yl)methanone (Intermediate VI) (0.023 g, 0.054 mmol), N,2-dimethylpropan-1-amine (0.019 mg, 0.22 mmol), potassium fluoride (0.032 g, 0.54 mmol) and DMSO (0.36 mL). The reaction vial was sealed and heated at 100° C. for 10 h. The reaction mixture was then cooled and passed through a syringe filter, after which it was directly purified by reverse phase preparative HPLC (0:100 to 95:5 acetonitrile:water: 0.1% v/v TFA modifier) to afford compound 8-4 as the TFA salt. $^1$H NMR (499 MHz, DMSO-d$_6$) δ 8.26 (s, 1H), 8.21-7.85 (m, 1H), 4.88-4.53 (m, 2H), 4.21-4.09 (m, 2H), 4.04-3.30 (m, 6H), 3.23-3.12 (m, 2H), 3.08-2.98 (m, 3H), 2.32-1.61 (m, 4H), 1.38-1.28 (m, 3H), 0.93-0.82 (m, 6H), 0.81-0.57 (m, 4H). MS (ESI) calc'd. for C$_{20}$H$_{32}$N$_7$O [M+H]$^+$ 386. found 386.

Example 19C: Preparation of Compound 8-5

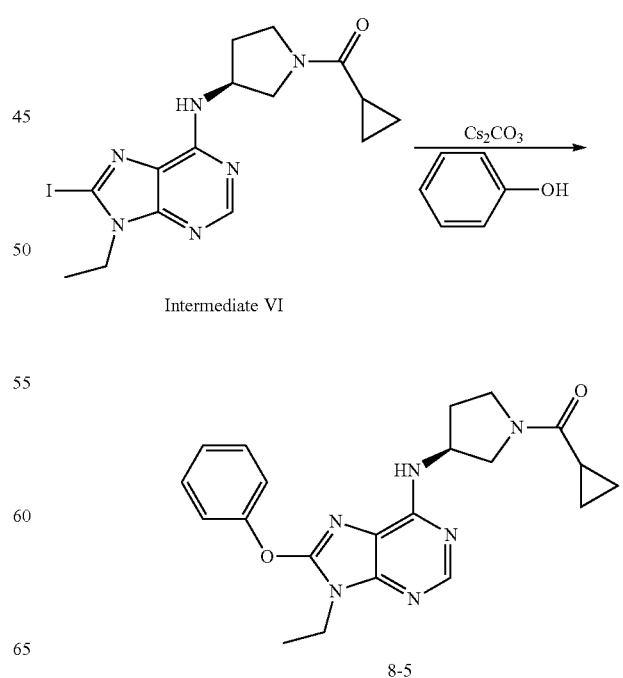

Intermediate VI 8-5

To a solution of Intermediate VI (50 mg, 0.12 mmol) in N,N-dimethylformamide (2 mL) were added phenol (17 mg, 0.18 mmol) and cesium carbonate (76 mg, 0.23 mmol). The resulting mixture was stirred for 12 h at 100° C. The reaction mixture was then cooled and quenched with water (50 mL), after which the reaction mixture was extracted with dichloromethane (3×25 mL). The organic extracts were combined, dried over anhydrous magnesium sulfate, and filtered. The filtrate was concentrated under vacuum to give a residue, which was purified by reverse phase preparative HPLC [Column: Xbridge Prep C18 5 m OBD, 19×150 mm; Mobile phase: A: Water (10 mM $NH_4HCO_3$), B: acetonitrile (22%-40%); Flow rate: 20 mL/min; UV detection: 220/254 nm] to afford compound 8-5. $^1$H NMR (300 MHz, DMSO-$d_6$) δ 8.22 (m, J=3.9 Hz, 1H), 7.64-7.56 (m, 1H), 7.49-7.39 (m, 4H), 7.29-7.25 (m, 1H), 4.82-4.61 (m, 1H), 4.14 (q, J=7.2 Hz, 2H), 3.97-3.75 (m, 1H), 3.63-3.20 (m, 3H), 2.22-1.90 (m, 2H), 1.79-1.65 (m, 1H), 1.37 (t, J=7.2 Hz, 3H), 0.70-0.66 (m, 4H). MS (ESI) calc'd for ($C_{21}H_{25}N_6O_2$) [M+H]$^+$, 393. found, 393.

Example 19D: Preparation of Compound 8-7

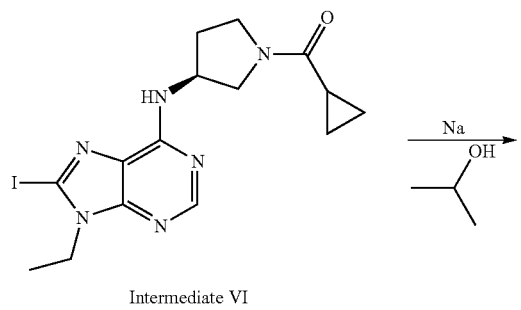

Intermediate VI

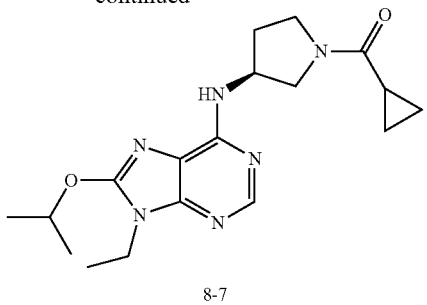

8-7

A mixture of propan-2-ol (2 mL) and sodium (27 mg, 1.20 mmol) was stirred at ambient temperature for 1 h, then Intermediate VI (100 mg, 0.24 mmol) was added. The resulting mixture was stirred for 5 h at 40° C. The resulting mixture was cooled and quenched with water (50 mL), after which the reaction mixture was extracted with ethyl acetate (3×30 mL). The organic extracts were combined, dried over anhydrous sodium sulfate, and filtered. The filtrate was concentrated under vacuum to give a residue, which was purified by reverse phase preparative HPLC [Column: Xbridge Prep C18 5 m OBD, 19×150 mm; Mobile phase: A: Water (10 mM $NH_4HCO_3$), B: acetonitrile (22%-40%); Flow rate: 20 mL/min; UV detection: 220/254 nm] to afford compound 8-7. $^1$H NMR (400 MHz, DMSO-$d_6$) δ 8.11 (m, 1H), 7.38 (m, 1H), 5.27 (m, 1H), 4.90-4.60 (m, 1H), 3.99-3.82 (m, 3H), 3.67-3.50 (m, 2H), 3.40-3.25 (m, 1H), 2.31-1.90 (m, 2H), 1.77-1.67 (m, 1H), 1.39 (d, J=6.0 Hz, 6H), 1.24 (t, J=7.2 Hz, 3H), 0.71-0.67 (m, 4H). MS (ESI) calc'd for ($C_{18}H_{27}N_6O_2$) [M+H]+, 359.2. found, 359.

Compounds 8-2 and 8-3 were prepared in an analogous fashion to Example 19A using the corresponding amines.

Compound 8-6 was prepared in an analogous fashion to Example 19C, using 3-fluoro-4-methoxyphenol instead of phenol.

Compound 8-8 was prepared in an analogous fashion to Example 19C, using 4,5,6,7-tetrahydro-1H-benzo[d]imidazole instead of phenol.

TABLE 8

| Compound | Structure | IUPAC Name | Exact Mass [M + H]+ |
|---|---|---|---|
| 8-1 | 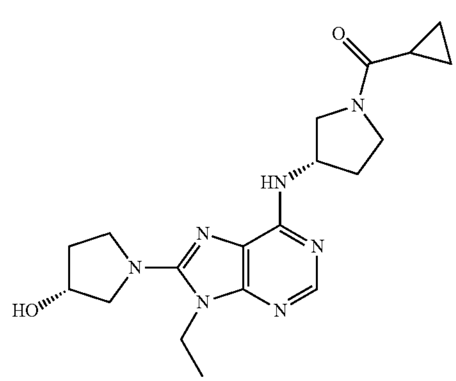 [SMILES: CCn1c(N2CC[C@@H](O)C2)nc2c(N[C@H]3CCN(C(=O)C4CC4)C3)ncnc21] | (3R)-1-(6-{[(3S)-1-(cyclopropylcarbonyl)pyrrolidin-3-yl]amino}-9-ethyl-9H-purin-8-yl)pyrrolidin-3-ol | Calc'd 386, found 386 |

TABLE 8-continued

| Compound | Structure | IUPAC Name | Exact Mass [M + H]+ |
|---|---|---|---|
| 8-2 | 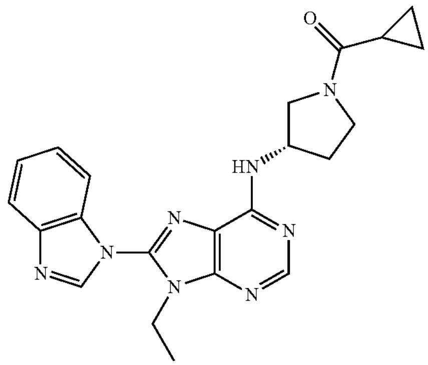 [SMILES: CCn1c(-n2cnc3ccccc32)nc2c(N[C@H]3CCN(C(=O)C4CC4)C3)ncnc21] | 8-(1H-benzimidazol-1-yl)-N-[(3S)-1-(cyclopropylcarbonyl)pyrrolidin-3-yl]-9-ethyl-9H-purin-6-amine | Calc'd 417, found 417 |
| 8-3 | 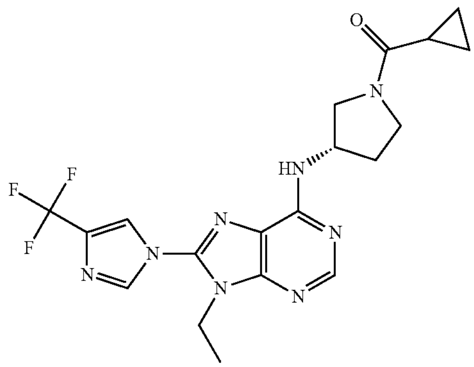 [SMILES: CCn1c(-n2cnc(C(F)(F)F)c2)nc2c(N[C@H]3CCN(C(=O)C4CC4)C3)ncnc21] | N-[(3S)-1-(cyclopropylcarbonyl)pyrrolidin-3-yl]-9-ethyl-8-[4-(trifluoromethyl)-1H-imidazol-1-yl]-9H-purin-6-amine | Calc'd 435, found 435 |
| 8-4 | 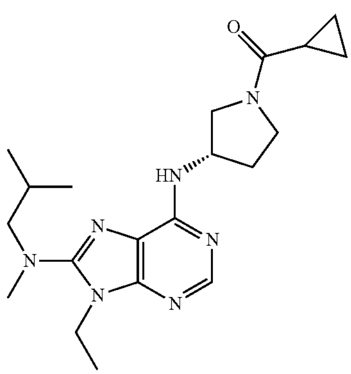 [SMILES: CCn1c(N(C)CC(C)C)nc2c(N[C@H]3CCN(C(=O)C4CC4)C3)ncnc21] | cyclopropyl[(3S)-3-({9-ethyl-8-[methyl(2-methylpropyl)amino]-9H-purin-6-yl}amino)pyrrolidin-1-yl]methanone | Calc'd 386, found 386 |
| 8-5 | 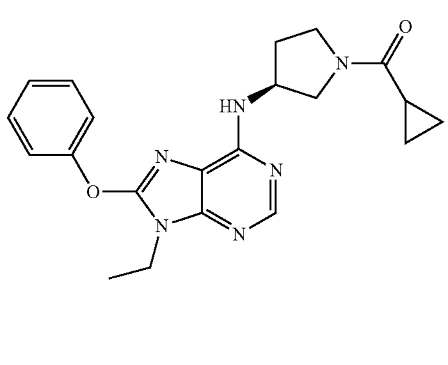 [SMILES: CCn1c(Oc2ccccc2)nc2c(N[C@H]3CCN(C(=O)C4CC4)C3)ncnc21] | N-[(3S)-1-(cyclopropylcarbonyl)pyrrolidin-3-yl]-9-ethyl-8-phenoxy-9H-purin-6-amine | Calc'd 393, found 393 |

TABLE 8-continued

| Compound | Structure | IUPAC Name | Exact Mass [M + H]+ |
|---|---|---|---|
| 8-6 | 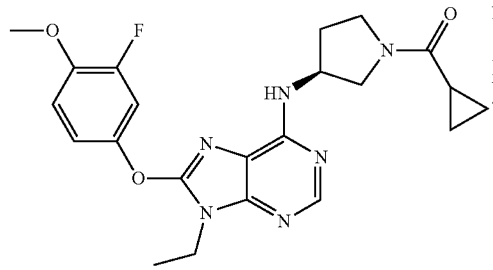 [SMILES: CCn1c(Oc2ccc(OC)c(F)c2)nc2c(N[C@H]3CCN(C(=O)C4CC4)C3)ncnc21] | N-[(3S)-1-(cyclopropylcarbonyl)pyrrolidin-3-yl]-9-ethyl-8-(3-fluoro-4-methoxyphenoxy)-9H-purin-6-amine | Calc'd 441, found 441 |
| 8-7 | 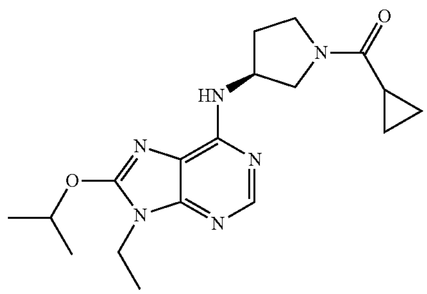 [SMILES: CCn1c(OC(C)C)nc2c(N[C@H]3CCN(C(=O)C4CC4)C3)ncnc21] | N-[(3S)-1-(cyclopropylcarbonyl)pyrrolidin-3-yl]-9-ethyl-8-(1-methylethoxy)-9H-purin-6-amine | Calc'd 359, found 359 |
| 8-8 | 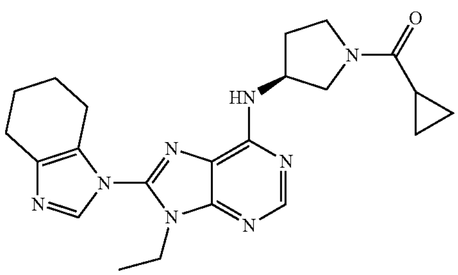 [SMILES: CCn1c(-n2cnc3c2CCCC3)nc2c(N[C@H]3CCN(C(=O)C4CC4)C3)ncnc21] | N-[(3S)-1-(cyclopropylcarbonyl)pyrrolidin-3-yl]-9-ethyl-8-(4,5,6,7-tetrahydro-1H-benzimidazol-1-yl)-9H-purin-6-amine | Calc'd 421, found 421 |

Compound Examples of Table 9

Example 20: Preparation of Compound 9-1

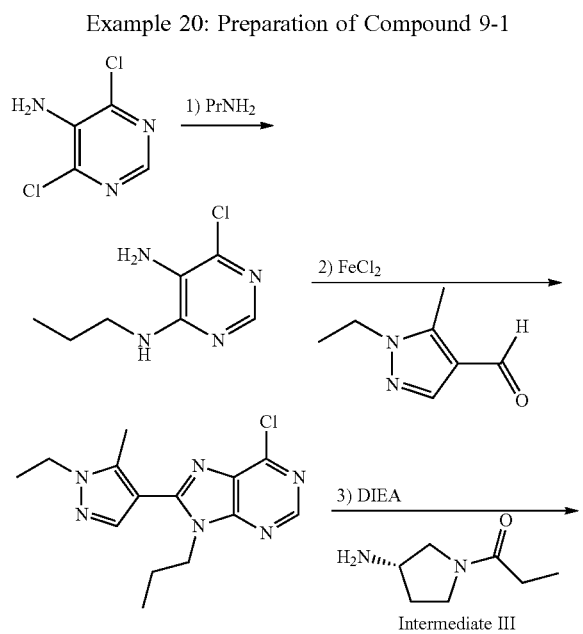

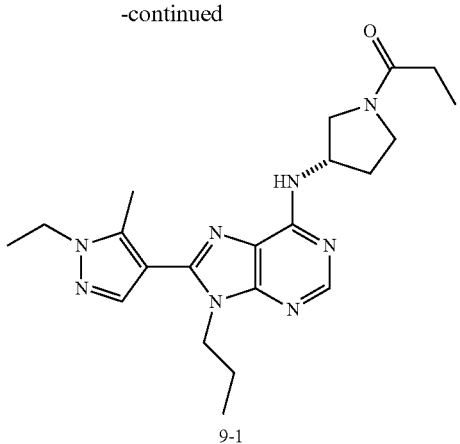

9-1

Step 1: Preparation of 6-chloro-N4-propylpyrimidine-4,5-diamine

A mixture of 4,6-dichloropyrimidin-5-amine (3.0 g, 18.3 mmol) and propan-1-amine (2.7 g, 45.7 mmol) in IPA (20 mL) and water (10 mL) was heated at 80° C. for 16 h. The reaction mixture was then cooled and concentrated under reduced pressure. The resulting residue was purified by chromatography on silica gel (eluting 5% MeOH in DCM) to afford 6-chloro-N4-propylpyrimidine-4,5-diamine. MS (ESI) calc'd for ($C_7H_{12}ClN_4$) [M+H]$^+$, 187. found, 187.

Step 2: Preparation of 6-chloro-8-(1-ethyl-5-methyl-1H-pyrazol-4-yl)-9-propyl-9H-purine To a solution of 6-chloro-N4-propylpyrimidine-4,5-diamine (600 mg, 3.2 mmol) and 6-methylnicotinaldehyde (1.3 g, 9.6 mmol) in DMF (10 mL) was added FeCl$_3$.6H$_2$O (216 mg, 0.8 mmol) slowly at room temperature. The resulting mixture was heated at 80° C. under and atmosphere of air for 16 h. The reaction was then cooled and quenched by the addition of water (10 mL) and the resulting mixture was extracted with DCM (10 mL×3). The organic extracts were washed with brine, dried over Na$_2$SO$_4$, filtered, and concentrated in vacuo. The residue was purified by chromatography on silica gel (eluting 10% MeOH in DCM) to give 6-chloro-8-(1-ethyl-5-methyl-1H-pyrazol-4-yl)-9-propyl-9H-purine. MS (ESI) calc'd for ($C_{14}H_{18}N_6$) [M+H]$^+$, 305. found, 305.

Step 3: Preparation of Compound 9-1

6-chloro-8-(1-ethyl-5-methyl-1H-pyrazol-4-yl)-9-propyl-9H-purine (200 mg, 0.65 mmol) and Intermediate III (373 mg, 2.62 mmol) were added to the mixture of t-BuOH: DIPEA (1:1, 4 mL). The reaction mixture was heated to 80° C. for 36 h under an atmosphere of nitrogen. The reaction mixture was then cooled to RT and the solvent was evaporated under reduced pressure. The residue was purified by reverse phase preparative HPLC (Mobile phase; A: water (10 mM NH$_4$HCO$_3$), B: MeCN) to give 9-1. $^1$H NMR (400 MHz, DMSO-d$_6$) δ 8.25 (s, 1H), 7.81-7.90 (m, 2H), 5.00-4.60 (s, 1H), 4.25-4.10 (m, 4H), 3.85-3.30 (m, 5H), 2.50 (s, 3H), 2.30-1.95 (m, 4H), 1.15-1.25 (m, 2H), 1.36 (t, J=7.2 Hz, 3H), 0.95 (q, J=7.2 Hz, 3H), 0.75 (t, J=8.0 Hz, 3H). MS (ESI) calc'd for ($C_{21}H_3$, $N_8O$) [M+H]$^+$, 411. found, 411.

Example 21: Preparation of Compound 9-5

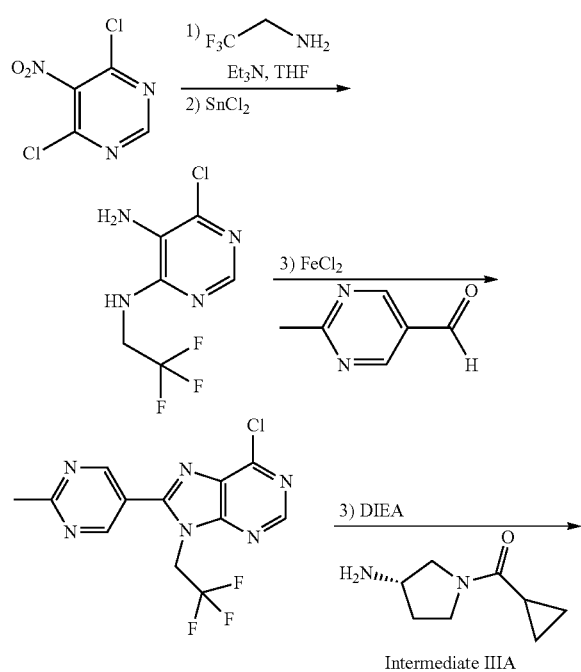

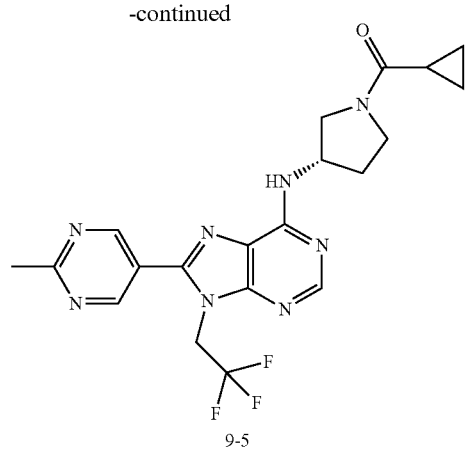

9-5

Step 1: Preparation of 6-chloro-5-nitro-N-(2,2,2-trifluoroethyl)pyrimidin-4-amine To a mixture of 4,6-dichloro-5-nitropyrimidine 1 (2.0 g, 10.3 mmol), TEA (2.87 mL, 20.6 mmol) and THF (40 mL) at 0° C. was added 2,2,2-trifluoroethanamine (0.92 g, 9.3 mmol) in THF (4 mL) drop wise. The resulting mixture was stirred at the same temperature for 1 h. The mixture was then evaporated under reduced pressure. The residue was purified by column chromatography on silica gel eluting with 10-25% EtOAc in petroleum ether to give 6-chloro-5-nitro-N-(2,2,2-trifluoroethyl)pyrimidin-4-amine. MS (ESI) calc'd for ($C_6H_5ClF_3N_4O_2$) [M+H]$^+$, 257. found, 257.

Step 2: Preparation of 6-chloro-N$^4$-(2,2,2-trifluoroethyl)pyrimidine-4,5-diamine A mixture of 6-chloro-5-nitro-N-(2,2,2-trifluoroethyl)pyrimidin-4-amine (1.3 g, 5.1 mmol), tin(II) chloride dihydrate (5.72 g, 25.3 mmol) and ethanol (40 mL) was heated to reflux for 1 h. The mixture was cooled, quenched with saturated aqueous sodium bicarbonate (300 mL). The mixture was then extracted with EtOAc (3×150 mL). The combined organic extracts were washed with brine (1×100 mL), dried over anhydrous Na$_2$SO$_4$, filtered, and the solvent evaporated under reduced pressure. The residue was purified by column chromatography eluting with 10-17% EtOAc in petroleum ether to give 6-chloro-N$^4$-(2,2,2-trifluoroethyl) pyrimidine-4,5-. MS (ESI) calc'd for ($C_6H_7ClF_3N4$) [M+H]$^+$, 227. found, 227.

Step 3: Preparation of 6-chloro-8-(2-methylpyrimidin-5-yl)-9-(2,2,2-trifluoroethyl)-9H-purine 6-chloro-N$^4$-(2,2,2-trifluoroethyl)pyrimidine-4,5-diamine 3 (220 mg, 0.97 mmol) was dissolved in DMF (5 mL) and treated with iron(III) chloride hexahydrate (79 mg, 0.29 mmol), followed by 2-methylpyrimidine-5-carbaldehyde (166 mg, 1.36 mmol). The reaction mixture was heated to 85° C. with good stirring for 18 h with air bubbling through the reaction mixture. The mixture was then cooled, diluted with DCM (30 mL), washed with brine (1×20 mL), dried over anhydrous Na$_2$SO$_4$, filtered, and the solvent was evaporated under reduced pressure. The residue was purified by column chromatography eluting with 50% EtOAc in petroleum ether to give 6-chloro-8-(2-methylpyrimidin-5-yl)-9-

(2, 2, 2-trifluoroethyl)-9H-purine. MS (ESI) calc'd for (C$_{12}$H$_9$ClF$_3$N$_6$) [M+H]$^+$, 329. found, 329.

Step 4: Preparation of Compound 9-5

A mixture of (S)-(3-aminopyrrolidin-1-yl)(cyclopropyl)methanone (Intermediate IIIA) (in its neutral form) (80 mg, 0.52 mmol), 6-chloro-8-(2-methylpyrimidin-5-yl)-9-(2,2,2-trifluoroethyl)-9H-purine (48 mg, 0.146 mmol), DIEA (0.10 mL, 0.57 mmol) and t-BuOH (8 mL) was heated at 85° C. for 12 h. The mixture was then cooled and the solvent was evaporated under reduced pressure. The residue was purified via reverse phase preparative HPLC (Mobile phase; A: water (10 mM NH$_4$HCO$_3$), B: MeCN) to give compound 9-5. $^1$H NMR (400 MHz, CDCl$_3$) δ 8.98 (s, 2H), 8.48 (m, 1H), 6.10-5.95 (m, 1H), 5.04-4.88 (m, 3H), 4.18-3.62 (m, 4H), 2.87 (s, 3H), 2.46-2.38 (m, 1H), 2.35-2.07 (m, 1H), 1.66-1.58 (m, 1H), 1.04-1.02 (m, 2H), 0.85-0.70 (m, 2H). MS (ESI) calc'd for (C$_{20}$H$_{22}$F$_3$N$_8$O) [M+H]$^+$, 447. found, 447.

Compounds 9-2 through 9-4 were prepared in an analogous fashion to Example 20, using the corresponding amines.

TABLE 9

| Compound | Structure | Compound Name | Exact Mass [M + H]+ |
|---|---|---|---|
| 9-1 | 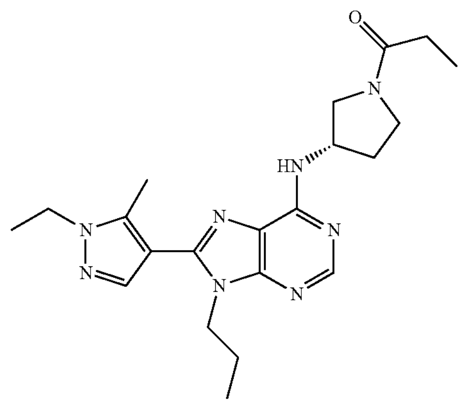 [SMILES: CCCn1c(-c2cnn(CC)c2C)nc2c(N[C@H]3CCN(C(=O)CC)C3)ncnc21] | 8-(1-ethyl-5-methyl-1H-pyrazol-4-yl)-N-[(3S)-1-propanoylpyrrolidin-3-yl]-9-propyl-9H-purin-6-amine | Calc'd 411, found 411 |
| 9-2 | 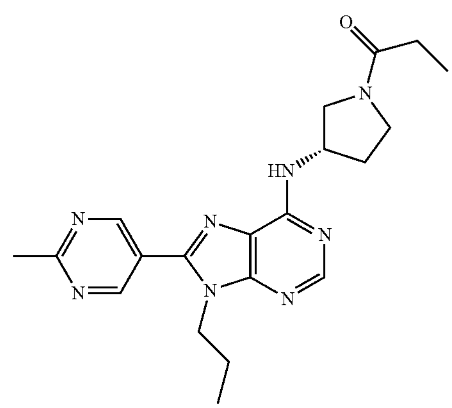 [SMILES: CCCn1c(-c2cnc(C)nc2)nc2c(N[C@H]3CCN(C(=O)CC)C3)ncnc21] | 8-(2-methylpyrimidin-5-yl)-N-[(3S)-1-propanoylpyrrolidin-3-yl]-9-propyl-9H-purin-6-amine | Calc'd 395, found 395 |
| 9-3 | 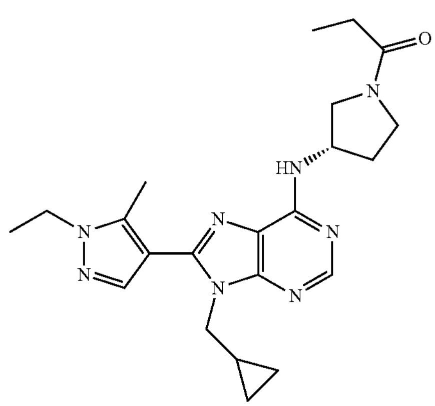 [SMILES: CCC(=O)N1CC[C@H](Nc2ncnc3c2nc(-c2cnn(CC)c2C)n3CC2CC2)C1] | 9-(cyclopropylmethyl)-8-(1-ethyl-5-methyl-1H-pyrazol-4-yl)-N-[(3S)-1-propanoylpyrrolidin-3-yl]-9H-purin-6-amine | Calc'd 423, found 423 |

TABLE 9-continued

| Compound | Structure | Compound Name | Exact Mass [M + H]+ |
|---|---|---|---|
| 9-4 | 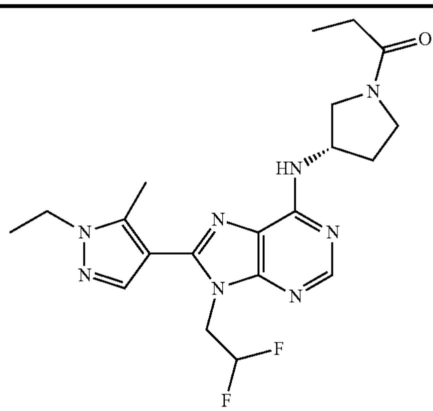 | 9-(2,2-difluoroethyl)-8-(1-ethyl-5-methyl-1H-pyrazol-4-yl)-N-[(3S)-1-propanoylpyrrolidin-3-yl]-9H-purin-6-amine | Calc'd 433, found 433 |
| 9-5 | 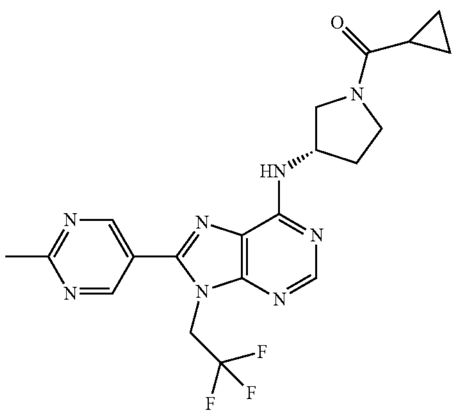 [SMILES: Cc1ncc(-c2nc3c(N[C@H]4CCN(C(=O)C5CC5)C4)ncnc3n2CC(F)(F)F)cn1] | N-[(3S)-1-(cyclopropylcarbonyl)pyrrolidin-3-yl]-8-(2-methylpyrimidin-5-yl)-9-(2,2,2-trifluoroethyl)-9H-purin-6-amine | Calc'd 447, found 447 |

Compound Examples of Table 10

Example 22: Preparation of Compound 10-1

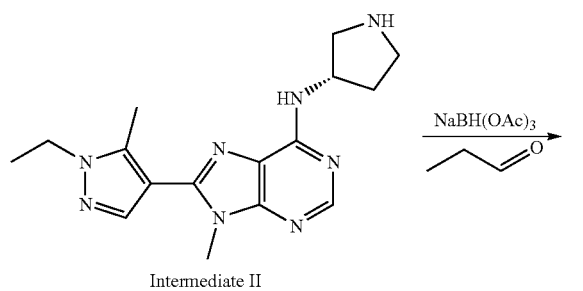

To a solution of (S)-8-(1-ethyl-5-methyl-1H-pyrazol-4-yl)-9-methyl-N-(pyrrolidin-3-yl)-9H-purin-6-amine (Intermediate II) (in its neutral form) (100 mg, 0.3 mmol) in DCM (3 mL) was added propionaldehyde (35 mg, 0.6 mmol) and acetic acid (0.2 mL). The resulting mixture was stirred for 30 min at room temperature under an atmosphere of nitrogen. Sodium triacetoxyborohydride (127 mg, 0.6 mmol) was then added and the reaction mixture was stirred at room temperature for 15 h. The reaction was then diluted with water (10 mL) and extracted with EtOAc (10 mL). The combined organic layers were dried over sodium sulfate, filtered, and concentrated. The residue was purified by reverse phase preparative HPLC (Mobile phase; A: water (10 mM $NH_4HCO_3$), B: MeCN) to afford 10-1. $^1$H NMR (400 MHz, DMSO-$d_6$) δ 8.14 (s, 1H), 7.79 (s, 1H), 4.14 (q, J=7.6 Hz, 2H), 3.70 (s, 3H), 3.20-3.21 (m, 1H), 2.95-3.05 (m, 1H), 2.80-2.85 (m, 1H), 2.57-2.67 (m, 2H), 2.50-2.25 (m, 6H), 1.78-1.81 (m, 1H), 1.40-1.52 (m, 2H), 1.34 (t, J=7.6 Hz, 3H), 0.85 (t, J=7.6 Hz, 3H). MS (ESI) calc'd for ($C_{19}H_{29}N_8$) [M+H]$^+$, 369. found, 369.

Example 23: Preparation of Compound 10-2

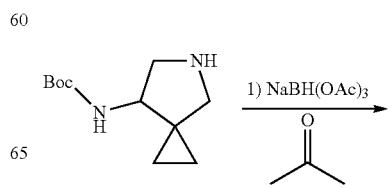

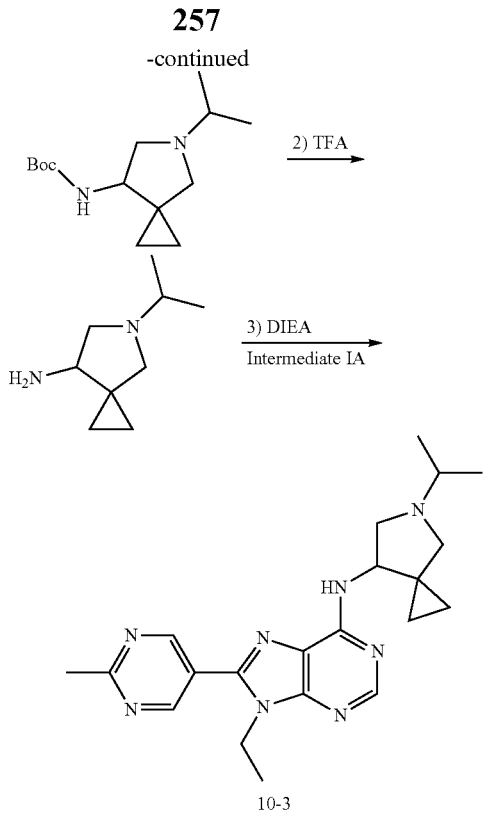

10-3

Step 1: Preparation of tert-butyl (5-isopropyl-5-azaspiro[2.4]heptan-7-yl)carbamate To a solution of rac-tert-butyl 5-azaspiro[2.4]heptan-7-ylcarbamate (150 mg, 0.7 mmol) in DCM (10 ml) was added acetic acid (1 drop) and propan-2-one (0.25 mL, 3.4 mmol). The mixed solution was stirred for 15 min, then sodium triacetoxyborohydride (450 mg, 2.1 mmol) was added, and the solution was stirred for 15 h. The mixture was then cooled, water (10 mL) was added, and the mixture was extracted with ethyl acetate (2×10 mL). The combined organic fractions were evaporated under reduced pressure to afford rac-tert-butyl (5-isopropyl-5-azaspiro[2.4]heptan-7-yl)carbamate that was directly used for next step without further purification MS (ESI) calc'd for ($C_{14}H_{27}N_2O_2$) $[M+H]^+$, 255. found, 255.

Step 2: Preparation of 5-isopropyl-5-azaspiro[2.4]heptan-7-amine Methanone

To a solution of rac-tert-butyl (5-isopropyl-5-azaspiro[2.4]heptan-7-yl)carbamate (150 mg, 0.59 mmol) in DCM (4 ml) was added TFA (1 ml). The mixed solution was stirred at 20° C. for 2 h. The mixture was then cooled, water (10 mL) was added and the mixture was extracted with dichloromethane (2×10 mL). The combined organic fractions were evaporated under reduced pressure to afford 5-isopropyl-5-azaspiro[2.4]heptan-7-amine methanone that was used directly for next step without further purification. MS (ESI) calc'd for ($C_9H_{19}N_2$) $[M+H]^+$, 155. found, 155.

Step 3: Preparation of Compound 10-3

To a solution of Intermediate II in t-BuOH (1 ml) and DIEA (3 ml) was added 5-isopropyl-5-azaspiro[2.4]heptan-7-amine (130 mg, 0.84 mmol). The mixed solution was stirred at 100° C. for 15 h. The mixture was then cooled, water (10 mL) was added and the mixture was extracted with ethyl acetate (2×10 mL). The combined organic fractions were evaporated under reduced pressure. The residue was purified by reverse phase preparative HPLC [Column: Xbridge Prep C18 10 um OBD, 19×250 mm; Mobile phase A: Water (10 mM $NH_4HCO_3$), B: MeCN; Flow rate: 30 mL/min; UV detection: 214/254 nm] to afford compound 10-3. $^1$H NMR (400 MHz, CD3OD) δ 9.14 (s, 2H), 8.27 (s, 1H), 4.73 (broad s, 1H), 4.40 (q, J=7.2 Hz, 2H), 3.43-3.36 (m, 1H), 2.95-2.90 (m, 1H), 2.86-2.79 (m, 4H), 2.73-2.68 (m, 1H), 2.57-2.48 (m, 1H), 1.44 (t, J=7.2 Hz, 3H), 1.20-1.14 (m, 6H), 0.97-0.57 (m, 4H). MS (ESI) calc'd for ($C_{21}H_{29}N_8$) $[M+H]^+$, 393. found, 393.

Compound 10-2 was made in an analogous fashion to Example 23 using the corresponding ketone.

TABLE 10

| Compound | Structure | Compound Name | Exact Mass [M + H]+ |
|---|---|---|---|
| 10-1 | 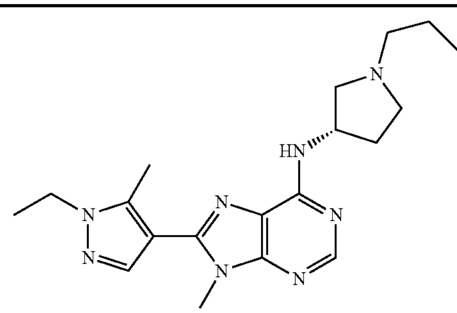 | 8-(1-ethyl-5-methyl-1H-pyrazol-4-yl)-9-methyl-N-[(3S)-1-propylpyrrolidin-3-yl]-9H-purin-6-amine | Calc'd 369, found 369 |

TABLE 10-continued

| Compound | Structure | Compound Name | Exact Mass [M + H]+ |
|---|---|---|---|
| 10-2 | 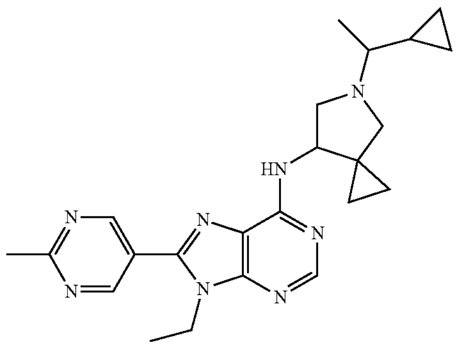 [SMILES: CCn1c(-c2cnc(C)nc2)nc2c(NC3CN(C(C)C4CC4)CC34CC4)ncnc21] | N(S AND R)-[5-(1-(S AND R)-cyclopropylethyl)-5-azaspiro[2.4]hept-7-yl]-9-ethyl-8-(2-methylpyrimidin-5-yl)-9H-purin-6-amine | Calc'd 419, found 419 |
| 10-3 | 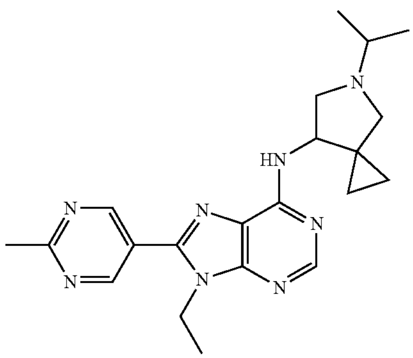 [SMILES: CCn1c(-c2cnc(C)nc2)nc2c(NC3CN(C(C)C)CC34CC4)ncnc21] | (R AND S)-9-ethyl-N-[5-(1-methylethyl)-5-azaspiro[2.4]hept-7-yl]-8-(2-methylpyrimidin-5-yl)-9H-purin-6-amine | Calc'd 393, found 393 |

Compound Examples of Table 11

Example 24: Preparation of Compound 11-1

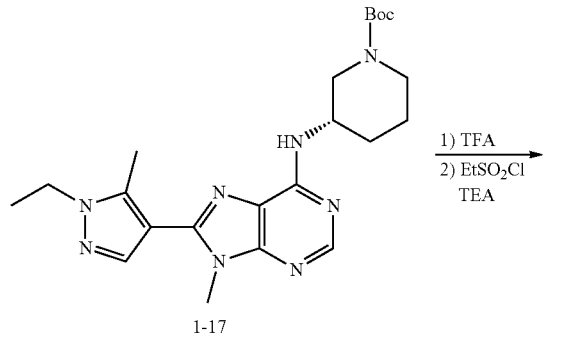

Step 1: Preparation of 8-(1-ethyl-5-methyl-1H-pyrazol-4-yl)-9-methyl-N—((S)-piperidin-3-yl)-9H-purin-6-amine To a solution of compound 1-17 (300 mg, 0.68 mmol) in DCM (4 mL) was added TFA (1 mL). The resulting mixture was stirred for 2 h at RT. The reaction was then washed with water (10 mL) and extracted with EA (10 mL). The organic layers were separated, dried over magnesium sulfate, filtered, and concentrated to afford 8-(1-ethyl-5-methyl-1H-pyrazol-4-yl)-9-methyl-N—((S)-piperidin-3-yl)-9H-purin-6-amine and was used in the next step without further purification. MS (ESI) calc'd for ($C_{17}H_{25}N_8$) [M+H]$^+$, 341. found, 341.

Step 2: Preparation of Compound 11-1

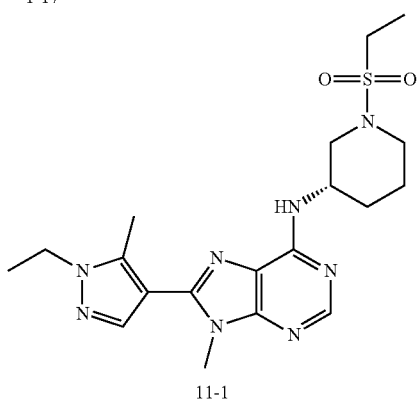

To a solution of 8-(1-ethyl-5-methyl-1H-pyrazol-4-yl)-9-methyl-N—((S)-piperidin-3-yl)-9H-purin-6-amine (50 mg, 0.15 mmol) in DCM (3 mL) was added ethanesulfonyl chloride (38 mg, 0.3 mmol) and TEA (46 mg, 0.45 mmol). The resulting mixture was stirred at RT for 15 h. The reaction was then washed with water (10 mL) and extracted with EtOAc (10 mL). The organic layers were separated, dried over magnesium sulfate, filtered, and concentrated in vacuo. The residue was purified via reverse phase preparative HPLC (Mobile phase; A: water (10 mM $NH_4HCO_3$), B: MeCN) to afford compound 11-1. $^1$H NMR (400 MHz, CDCl$_3$) δ 8.28 (s, 1H), 7.91 (s, 1H), 4.29-4.24 (m, 3H), 3.82-3.78 (m, 4H), 3.52-3.48 (m, 1H), 3.18-3.00 (m, 4H), 2.56 (s, 3H), 2.10-1.95 (m, 2H), 1.80-1.70 (m, 2H), 1.50-1.45 (m, 3H), 1.35-1.30 (m, 3H). MS (ESI) calc'd for ($C_{19}H_{29}N_8O_2S$) [M+H]$^+$, 433. found, 433.

TABLE 11

| Compound | Structure | Compound Name | Exact Mass [M + H]+ |
|---|---|---|---|
| 11-1 | 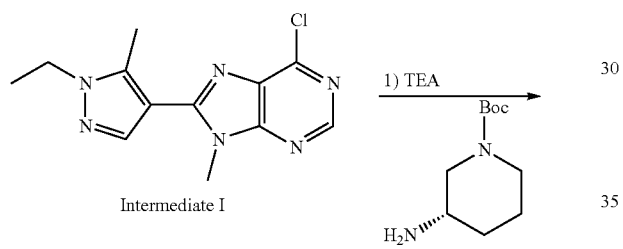 | 8-(1-ethyl-5-methyl-1H-pyrazol-4-yl)-N-[(3S)-1-(ethylsulfonyl)piperidin-3-yl]-9-methyl-9H-purin-6-amine | Calc'd 433, found 433 |

Compound Examples of Table 12

Example 24A: Preparation of Compound 12-1

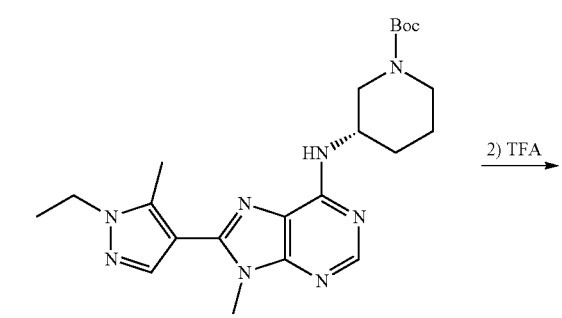

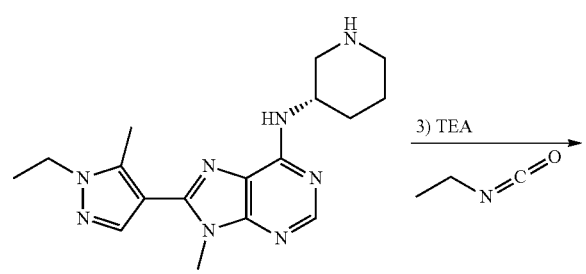

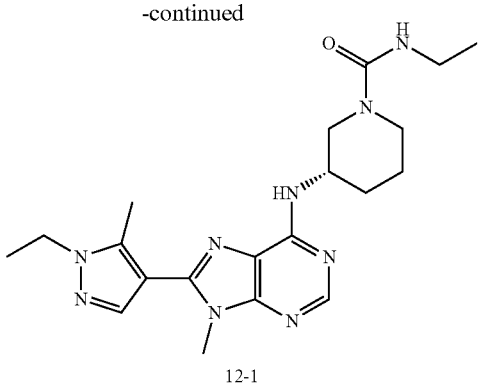

Step 1: Preparation of (3S)-tert-butyl3-(8-(1-ethyl-5-methyl-1H-pyrazol-4-yl)-9-methyl-9H-purin-6-ylamino)piperidine-1-carboxylate A solution of Intermediate I (0.77 g, 2.8 mmol) and (S)-tert-butyl 3-aminopiperidine-1-carboxylate (0.50 g, 2.5 mmol) in t-BuOH (5.0 mL) and TEA (10 mL) was stirred in sealed tube for 72 h at 110° C. The reaction mixture was then cooled to ambient temperature, water (10 mL) was added, and the mixture was extracted with EtOAc (10 mL). The organic layers were then separated, dried over magnesium sulfate, filtered, and concentrated in vacuo. The crude residue was then purified by silica gel chromatography (Ethyl Acetate:DCM=1:1) to afford (S)-tert-butyl 3-((8-(1-ethyl-5-methyl-1H-pyrazol-4-yl)-9-methyl-9H-purin-6-yl)amino)piperidine-1-carboxylate. MS (ESI) Calc'd for $C_{22}H_{33}N_8O_2$ [M+H]+, 441. found, 441.

Step 2: Preparation of 8-(1-ethyl-5-methyl-1H-pyrazol-4-yl)-9-methyl-N—((S)-piperidin-3-yl)-9H-purin-6-amine To a solution of (S)-tert-butyl 3-((8-(1-ethyl-5-methyl-1H-pyrazol-4-yl)-9-methyl-9H-purin-6-yl)amino)piperidine-1-carboxylate (0.30 g, 0.68 mmol) in DCM (4.0 mL) was added TFA (1.0 mL). The resulting mixture was stirred for 2 h at ambient temperature. The reaction was then washed with water (10 mL), and the aqueous layer was extracted with ethyl acetate (10 mL). The combined organic layers were separated, dried over magnesium sulfate, filtered, and concentrated in vacuo to afford 8-(1-ethyl-5-methyl-1H-pyrazol-4-yl)-9-methyl-N—((S)-piperidin-3-yl)-9H-purin-6-amine. MS (ESI) Calc'd for $C_{17}H_{25}N_8$[M+H]$^+$, 341. found, 341.

Step 3: Preparation of Compound 12-1

To a solution of 8-(1-ethyl-5-methyl-1H-pyrazol-4-yl)-9-methyl-N—((S)-piperidin-3-yl)-9H-purin-6-amine (0.050 g, 0.15 mmol) in DCM (3.0 mL) was added isocyanatoethane (0.022 mg, 0.30 mmol) and TEA (0.046 g, 0.45 mmol). The resulting mixture was stirred at ambient temperature for 15 h. The reaction was then washed with water (10 mL), and the aqueous layer was extracted with ethyl acetate (10 mL). The organic layers were separated, dried with MgSO$_4$, filtered and concentrated. The crude residue was purified by reverse phase preparative HPLC (0:100 to 95:5 acetonitrile:water: 10 mM NH$_4$HCO$_3$ modifier) to afford compound 12-1. $^1$H NMR (400 MHz, CDCl$_3$) δ 8.28 (s, 1H), 7.92 (s, 1H), 4.40-4.24 (m, 3H), 4.07-3.95 (m, 1H), 3.90-3.75 (m, 4H), 3.25-3.00 (m, 4H), 2.55 (s, 3H), 2.20-2.10 (m, 1H), 1.90-1.82 (m, 1H), 1.80-1.57 (m, 2H), 1.47 (m, 3H), 1.07 (s, 3H). MS (ESI) Calc'd for $C_{20}H_{30}N_9O$ [M+H]$^+$, 412. found, 412.

Example 24B: Preparation of Compound 12-2

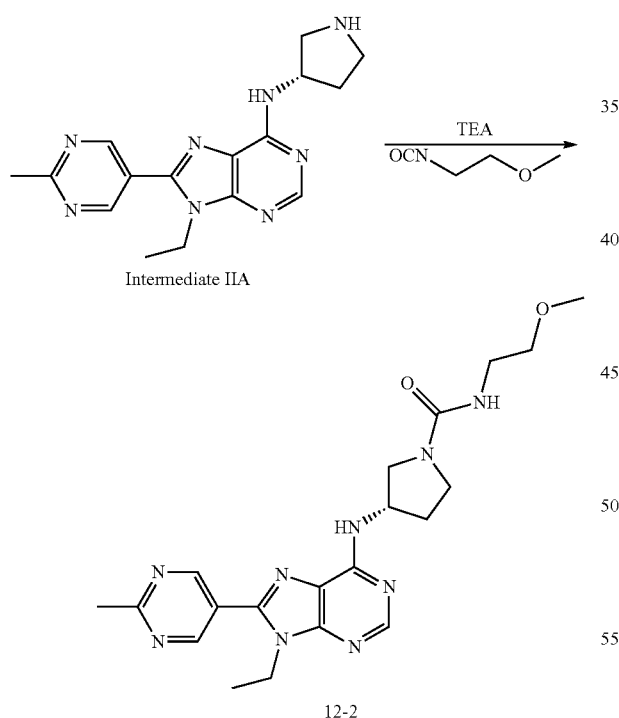

12-2

To a solution of (S)-9-ethyl-8-(2-methylpyrimidin-5-yl)-N-(pyrrolidin-3-yl)-9H-purin-6-amine (Intermediate IIA) (in its neutral form) (0.050 g, 0.15 mmol) and 1-isocyanato-2-methoxyethane (0.016 mg, 0.15 mmol) in DCM (20 mL) was added TEA (0.060 mL, 0.40 mmol). The reaction was stirred at ambient temperature for 3 h. The reaction was then quenched with H$_2$O (10 mL). The organic layer was separated and washed with brine, dried over sodium sulfate, filtered, and concentrated in vacuo. The crude residue was purified by reverse phase preparative HPLC (0:100 to 95:5 acetonitrile:water: 10 mM NH$_4$HCO$_3$ modifier) to afford compound 12-2. $^1$H NMR (400 MHz, MeOD) δ 9.13 (s, 2H), 8.35 (s, 1H), 5.05-4.85 (m, 1H), 4.41 (q, J=7.2 Hz, 2H), 3.81-3.77 (m, 1H), 3.66-3.32 (m, 10H), 2.82 (s, 3H), 2.40-2.15 (m, 2H), 1.45 (t, J=7.2 Hz, 3H). MS (ESI) Calc'd for $C_{20}H_{28}N_9O_2$ [M+H]$^+$, 426. found, 426.

Example 24C: Preparation of Compound 12-6

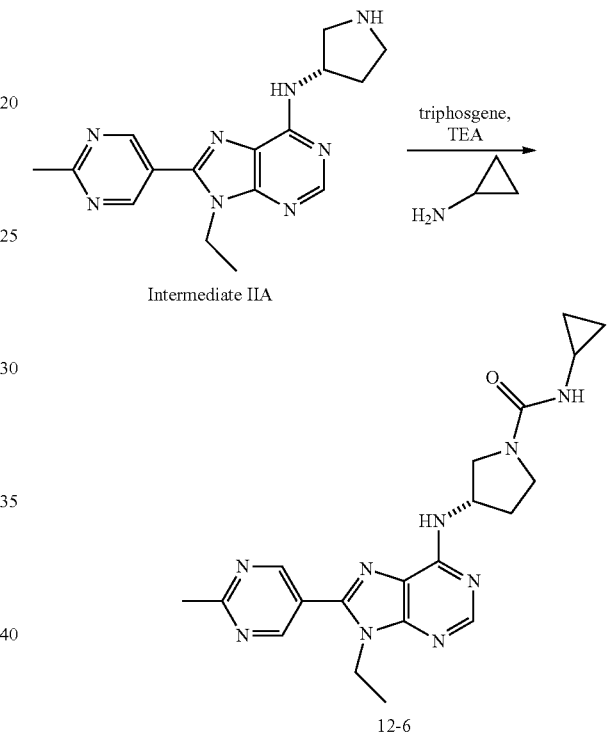

12-6

To a solution of cyclopropanamine (0.018 g, 0.31 mmol) in DCM (5.0 mL) and TEA (0.070 ml, 0.50 mmol) was added bis(trichloromethyl) carbonate (0.90 g, 0.10 mmol). The mixed solution was stirred at 20° C. for 0.5 h, then (S)-9-ethyl-8-(2-methylpyrimidin-5-yl)-N-(pyrrolidin-3-yl)-9H-purin-6-amine (Intermediate IIA, in its neutral form) (0.049 g, 0.15 mmol) was added. The reaction was then stirred at room temperature for 15 h. The solution was then evaporated under reduced pressure and the crude residue was purified by reverse phase preparative HPLC (0:100 to 95:5 acetonitrile:water: 10 mM NH$_4$HCO$_3$ modifier) to afford (S)—N-cyclopropyl-3-((9-ethyl-8-(2-methylpyrimidin-5-yl)-9H-purin-6-yl)amino)pyrrolidine-1-carboxamide (compound 12-6). 1H NMR (400 MHz, MeOD) δ 9.13 (s, 2H), 8.35 (s, 1H), 4.94-4.91 (m, 1H), 4.41 (q, J=7.2 Hz, 2H), 3.79-3.74 (m, 1H), 3.60-3.40 (m, 3H), 2.83 (s, 3H), 2.59-2.52 (m, 1H), 2.40-2.31 (m, 1H), 2.17-2.09 (m, 1H), 1.45 (t, J=7.2 Hz, 3H), 0.70-0.64 (m, 2H), 0.52-0.47 (m, 2H). MS (ESI) Calc'd for $C_{20}H_{26}N_9O$ [M+H]$^+$, 408. found, 408.

Example 24D: Preparation of Compound 12-11

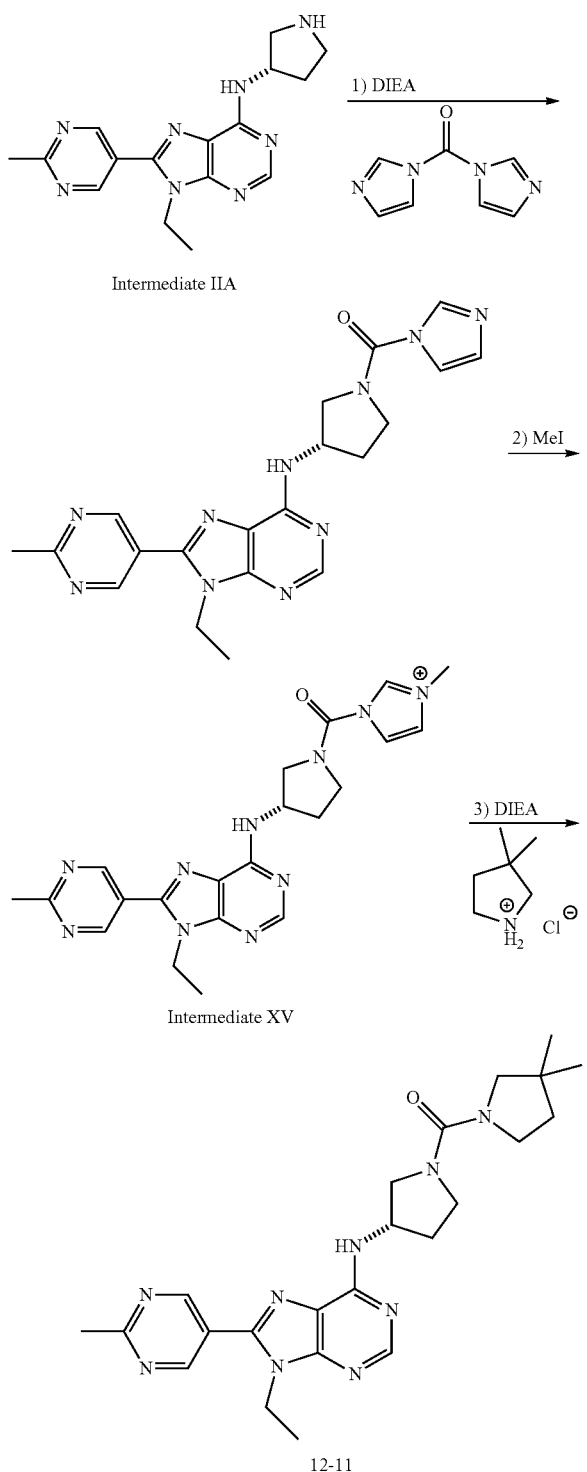

Intermediate IIA

Intermediate XV 12-11

Step 1: Preparation of (S)-(3-((9-ethyl-8-(2-methyl-pyrimidin-5-yl)-9H-purin-6-yl)amino)pyrrolidin-1-yl)(1H-imidazol-1-yl)methanone (S)-9-ethyl-8-(2-methylpyrimidin-5-yl)-N-(pyrrolidin-3-yl)-9H-purin-6-amine, 2HCl, (Intermediate IIA) (0.25 g, 0.63 mmol) was added to a 20 mL microwave vial along with 1,1'-carbonyldiimidazole (0.23 g, 1.4 mmol) and THF (3.0 mL). DIEA (0.36 mL, 2.1 mmol) was then added and the reaction mixture was heated to 75° C. for 12 hours. The reaction mixture was then concentrated in vacuo and was directly loaded onto a 50 g silica gel column, eluting with 0-10% MeOH in DCM to afford (S)-(3-((9-ethyl-8-(2-methylpyrimidin-5-yl)-9H-purin-6-yl)amino)pyrrolidin-1-yl)(1H-imidazol-1-yl)methanone. MS (ESI) Calc'd for $C_{20}H_{23}N_{10}O$ [M+H]$^+$, 419. found, 419.

Step 2: Preparation of (S)-1-(3-((9-ethyl-8-(2-methylpyrimidin-5-yl)-9H-purin-6-yl)amino)pyrrolidine-1-carbonyl)-3-methyl-1H-imidazol-3-ium (Intermediate XV)

A round-bottom flask was charged with (S)-(3-((9-ethyl-8-(2-methylpyrimidin-5-yl)-9H-purin-6-yl)amino)pyrrolidin-1-yl)(1H-imidazol-1-yl)methanone (0.21 g, 0.50 mmol) and acetonitrile (2.0 mL), followed by iodomethane (0.13 mL, 2.0 mmol). The reaction mixture was allowed to stir 12 hours at ambient temperature. The reaction was then concentrated under reduced pressure to afford (S)-1-(3-((9-ethyl-8-(2-methylpyrimidin-5-yl)-9H-purin-6-yl)amino)pyrrolidine-1-carbonyl)-3-methyl-1H-imidazol-3-ium (Intermediate XV). MS (ESI) calc'd for $C_{21}H_{25}N_{10}O^+$ [M]$^+$, 433. found, 433.

Step 3: Preparation of Compound 12-11

To a reaction vessel was added (S)-1-(3-((9-ethyl-8-(2-methylpyrimidin-5-yl)-9H-purin-6-yl)amino)pyrrolidine-1-carbonyl)-3-methyl-1H-imidazol-3-ium (Intermediate XV) (0.030 g, 0.069 mmol) and 3,3-dimethylpyrrolidine, HCl (0.0094 mg, 0.069 mmol), DMA (0.50 mL) and DIEA (0.024 mL, 0.14 mmol). The reaction mixture was heated to 55° C. for 12 hours. The reaction was then diluted with DMSO (0.50 mL) and was directly purified by reverse phase preparative HPLC (0:100 to 95:5 acetonitrile:water: 0.1% v/v TFA modifier) to afford N-{(3S)-1-[(3,3-dimethylpyrrolidin-1-yl)carbonyl]pyrrolidin-3-yl}-9-ethyl-8-(2-methylpyrimidin-5-yl)-9H-purin-6-amine as the TFA salt. $^1$H NMR (499 MHz, DMSO-d$_6$) δ 9.12 (s, 2H), 8.61-8.43 (broad s, 1H), 8.39-8.32 (broad s, 1H), 4.71-4.57 (m, 1H), 4.31 (m, 2H), 3.67-3.60 (m, 1H), 3.53-3.41 (m, 1H), 3.35 (m, 4H), 3.02 (q, J=9.9, 2H), 2.74 (s, 3H), 2.19-2.07 (m, 1H), 2.07-1.96 (m, 1H), 1.57 (t, J=7.1, 2H), 1.30 (t, J=7.2, 3H), 1.00 (s, 6H). MS (ESI) Calc'd for $C_{23}H_{32}N_9O$ [M+H]$^+$, 450. found 450.

Example 24E: Preparation of Compound 12-19

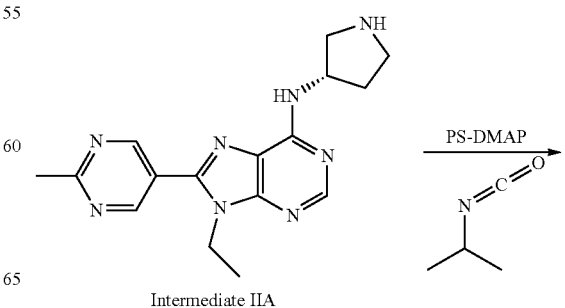

Intermediate IIA

-continued

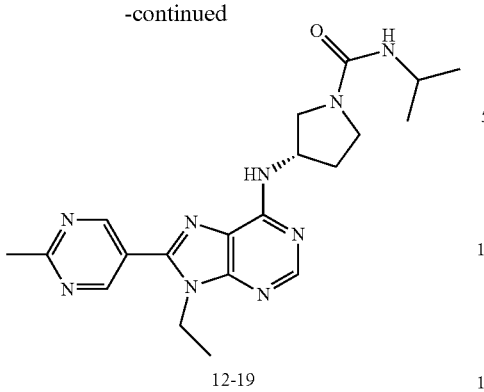

12-19

Polystyrene-bound-DMAP (0.19 g, 0.30 mmol) was added to a 2-dram vial along with isopropyl isocyanate (0.0090 g, 0.10 mmol). A solution of (S)-9-ethyl-8-(2-methylpyrimidin-5-yl)-N-(pyrrolidin-3-yl)-9H-purin-6-amine, 2HCl (Intermediate IIA) (0.032 g, 0.08 mmol) in DMF (1.5 ml) was added and the vial was sealed and its contents were allowed to react overnight at ambient temperature. The reaction mixture was then filtered, washing with DMSO (1.5 mL). The collected filtrate was purified by reverse phase preparative HPLC (0:100 to 95:5 acetonitrile: water: 0.1% v/v TFA modifier) to afford (R)-3-((9-ethyl-8-(2-methylpyrimidin-5-yl)-9H-purin-6-yl)amino)-N-isopropylpyrrolidine-1-carboxamide (compound 12-19) as the TFA salt. $^1$H NMR (600 MHz, DMSO-d$_6$) δ 9.09 (s, 2H), 8.44 (s, 1H), 8.32 (s, 1H), 4.72-4.57 (m, 1H), 4.27 (q, J=6.8, 2H), 3.76-3.18 (m, 5H), 2.95 (s, 1H), 2.71 (s, 3H), 2.18-1.96 (m, 2H), 1.27 (t, J=7.2, 3H), 1.01 (dd, J=3.8, 6.5, 6H). MS (ESI) Calc'd for C$_{20}$H$_{28}$N$_9$O [M+H]$^+$, 410. found 410.

Example 24F: Preparation of Compound 12-26

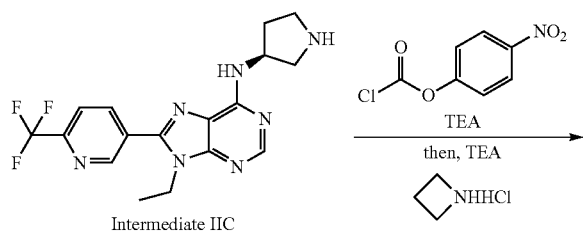

-continued

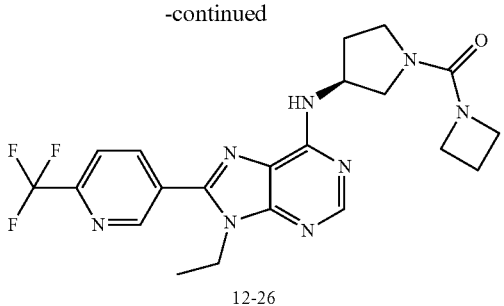

12-26

To a solution of (S)-9-ethyl-N-(pyrrolidin-3-yl)-8-(6-(trifluoromethyl)pyridin-3-yl)-9H-purin-6-amine (Intermediate IIC) (0.20 g, 0.53 mmol) in tetrahydrofuran (20 mL) was added triethylamine (0.080 g, 0.80 mmol) and 4-nitrophenyl carbonochloridate (0.11 g, 0.58 mmol). The resulting mixture was stirred for 1 h at ambient temperature. Then the reaction mixture was transferred into a sealed tube and triethylamine (0.43 g, 4.2 mmol) and azetidine hydrochloride (246 g, 2.7 mmol) was added and stirred for 16 h at 50° C. The reaction mixture was quenched by the addition of water (100 mL), extracted with ethyl acetate (3×50 mL). The organic layers were combined, dried over anhydrous sodium sulfate and filtered. The filtrate was concentrated under vacuum to give a residue, which was purified by preparative thin-layer chromatography (dichloromethane:methanol=30: 1) to afford compound 12-26. $^1$H NMR (300 MHz, DMSO-d$_6$) δ 9.21 (m, J=1.5 Hz, 1H), 8.52 (dd, J=8.0 and 1.5 Hz, 1H), 8.34 (s, 1H), 8.24 (br, 1H), 8.15 (d, J=8.0 Hz, 1H), 4.71 (m, 1H), 4.34 (q, J=7.2 Hz, 2H), 3.91-3.83 (m, 4H), 3.63-3.57 (m, 1H), 3.52-3.49 (m, 1H), 3.32-3.27 (m, 2H), 2.17-2.08 (m, 4H), 1.41 (t, J=7.2 Hz, 3H). MS (ESI) Calc'd for C$_{21}$H$_{24}$F$_3$N$_8$O [M+H]$^+$, 461. found, 461.

Compounds 12-3 through 12-5, and 12-7 through 12-9 were prepared in an analogous fashion as described in Example 24C using Intermediate IIA and the corresponding amine.

Compounds 12-10 and 12-12 through 12-15 were prepared in an analogous fashion as described in Example 24D using Intermediate XV and the corresponding amine.

Compounds 12-16 through 12-18 and 12-20 through 12-25 were prepared in an analogous fashion as described in Example 24E using Intermediate IIA and the corresponding isocyanate.

Compound 12-27 was prepared in an analogous fashion to that described in Example 24F using Intermediate X and 3-methoxyazetidine hydrochloride.

TABLE 12

| Compound | Structure | Compound Name | Exact Mass [M + H]+ |
|---|---|---|---|
| 12-1 | 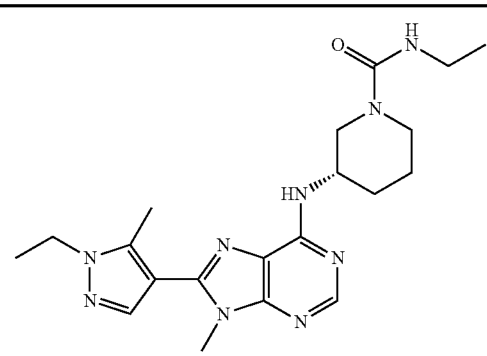 | (3S)-N-ethyl-3-{[8-(1-ethyl-5-methyl-1H-pyrazol-4-yl)-9-methyl-9H-purin-6-yl]amino}piperidine-1-carboxamide | Calc'd 412, found 412 |

TABLE 12-continued

| Compound | Structure | Compound Name | Exact Mass [M + H]+ |
|---|---|---|---|
| 12-2 | 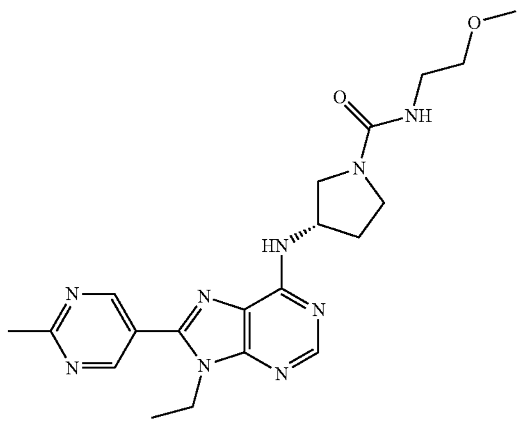 | (3S)-3-{[9-ethyl-8-(2-methylpyrimidin-5-yl)-9H-purin-6-yl]amino}-N-(2-methoxyethyl)pyrrolidine-1-carboxamide | Calc'd 426, found 426 |
| 12-3 | 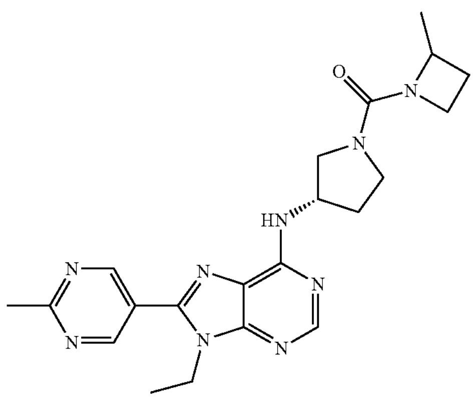 [SMILES: CCn1c(-c2cnc(C)nc2)nc2c(N[C@H]3CCN(C(=O)N4CCC4C)C3)ncnc21] | 9-ethyl-N-{(3S)-1-[((S and R)-2-methylazetidin-1-yl)carbonyl]pyrrolidin-3-yl}-8-(2-methylpyrimidin-5-yl)-9H-purin-6-amine | Calc'd 422, found 422 |
| 12-4 | 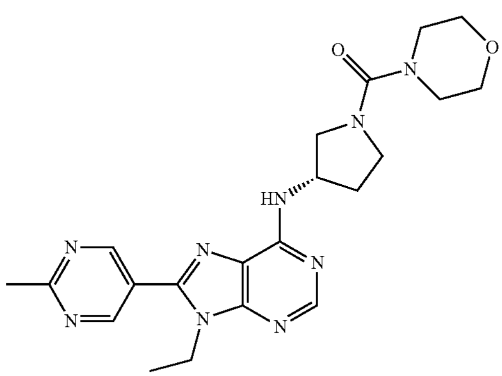 [SMILES: CCn1c(-c2cnc(C)nc2)nc2c(N[C@H]3CCN(C(=O)N4CCOCC4)C3)ncnc21] | 9-ethyl-8-(2-methylpyrimidin-5-yl)-N-[(3S)-1-(morpholin-4-ylcarbonyl)pyrrolidin-3-yl]-9H-purin-6-amine | Calc'd 438, found 438 |
| 12-5 | 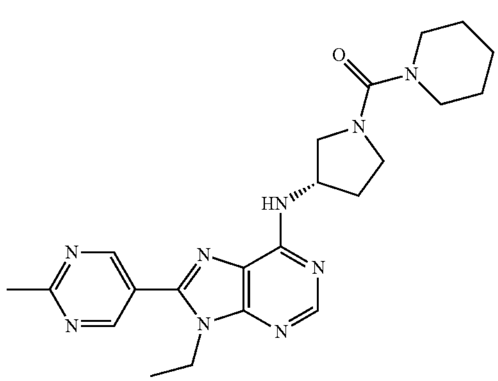 [SMILES: CCn1c(-c2cnc(C)nc2)nc2c(N[C@H]3CCN(C(=O)N4CCCCC4)C3)ncnc21] | 9-ethyl-8-(2-methylpyrimidin-5-yl)-N-[(3S)-1-(piperidin-1-ylcarbonyl)pyrrolidin-3-yl]-9H-purin-6-amine | Calc'd 436, found 436 |

TABLE 12-continued

| Compound | Structure | Compound Name | Exact Mass [M + H]+ |
|---|---|---|---|
| 12-6 | 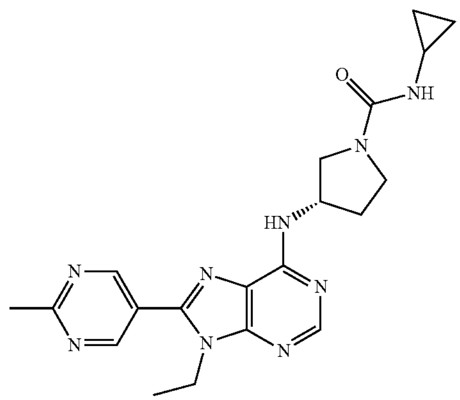 [SMILES: CCn1c(-c2cnc(C)nc2)nc2c(N[C@H]3CCN(C(=O)NC4CC4)C3)ncnc21] | (3S)-N-cyclopropyl-3-{[9-ethyl-8-(2-methylpyrimidin-5-yl)-9H-purin-6-yl]amino}pyrrolidine-1-carboxamide | Calc'd 408, found 408 |
| 12-7 | 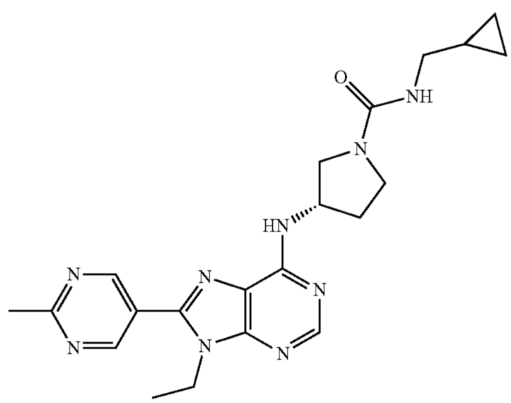 [SMILES: CCn1c(-c2cnc(C)nc2)nc2c(N[C@H]3CCN(C(=O)NCC4CC4)C3)ncnc21] | (3S)-N-(cyclopropylmethyl)-3-{[9-ethyl-8-(2-methylpyrimidin-5-yl)-9H-purin-6-yl]amino}pyrrolidine-1-carboxamide | Calc'd 422, found 422 |
| 12-8 | 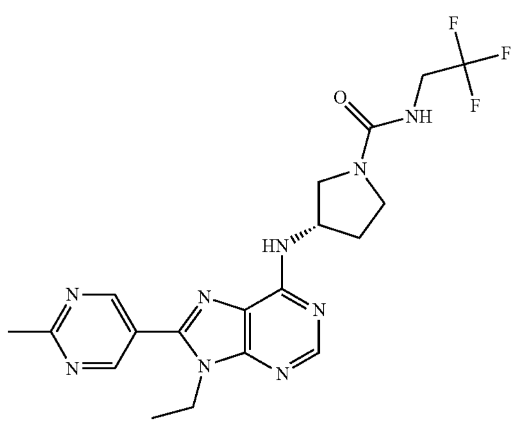 [SMILES: CCn1c(-c2cnc(C)nc2)nc2c(N[C@H]3CCN(C(=O)NCC(F)(F)F)C3)ncnc21] | (3S)-3-{[9-ethyl-8-(2-methylpyrimidin-5-yl)-9H-purin-6-yl]amino}-N-(2,2,2-trifluoroethyl)pyrrolidine-1-carboxamide | Calc'd 450, found 450 |
| 12-9 | 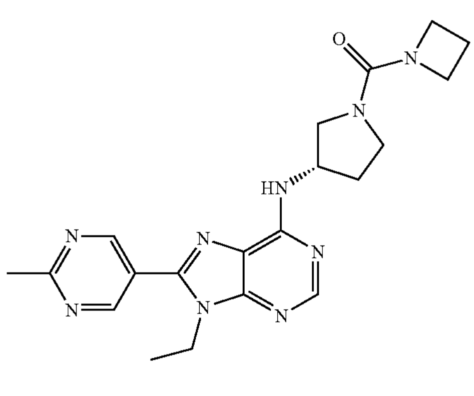 [SMILES: CCn1c(-c2cnc(C)nc2)nc2c(N[C@H]3CCN(C(=O)N4CCC4)C3)ncnc21] | N-[(3S)-1-(azetidin-1-ylcarbonyl)pyrrolidin-3-yl]-9-ethyl-8-(2-methylpyrimidin-5-yl)-9H-purin-6-amine | Calc'd 408, found 408 |

TABLE 12-continued

| Compound | Compound Name | Exact Mass [M + H]+ |
|---|---|---|
| 12-10 | 9-ethyl-N-{(3S)-1-[(3-methoxyazetidin-1-yl)carbonyl]pyrrolidin-3-yl}-8-(2-methylpyrimidin-5-yl)-9H-purin-6-amine | Calc'd 438, found 438 |
| 12-11 | N-{(3S)-1-[(3,3-dimethylpyrrolidin-1-yl)carbonyl]pyrrolidin-3-yl}-9-ethyl-8-(2-methylpyrimidin-5-yl)-9H-purin-6-amine | Calc'd 450, found 450 |
| 12-12 | 9-ethyl-N-[(3S)-1-{[(3R)-3-fluoropyrrolidin-1-yl]carbonyl}pyrrolidin-3-yl]-8-(2-methylpyrimidin-5-yl)-9H-purin-6-amine | Calc'd 440, found 440 |
| 12-13 | 9-ethyl-N-[(3S)-1-{[(3S)-3-fluoropyrrolidin-1-yl]carbonyl}pyrrolidin-3-yl]-8-(2-methylpyrimidin-5-yl)-9H-purin-6-amine | Calc'd 440, found 440 |

TABLE 12-continued

| Compound | Compound Name | Exact Mass [M + H]+ |
|---|---|---|
| 12-14 | 9-ethyl-N-[(3S)-1-{[(3S)-3-methoxypyrrolidin-1-yl]carbonyl}pyrrolidin-3-yl]-8-(2-methylpyrimidin-5-yl)-9H-purin-6-amine | Calc'd 452, found 452 |
| 12-15 | 9-ethyl-N-[(3S)-1-{[(3R)-3-methoxypyrrolidin-1-yl]carbonyl}pyrrolidin-3-yl]-8-(2-methylpyrimidin-5-yl)-9H-purin-6-amine | Calc'd 452, found 452 |
| 12-16 | (3S)-N-cyclohexyl-3-{[9-ethyl-8-(2-methylpyrimidin-5-yl)-9H-purin-6-yl]amino}pyrrolidine-1-carboxamide | Calc'd 450, found 450 |
| 12-17 | ethyl N-{[(3S)-3-{[9-ethyl-8-(2-methylpyrimidin-5-yl)-9H-purin-6-yl]amino}pyrrolidin-1-yl]carbonyl}-beta-alaninate | Calc'd 468, found 468 |

TABLE 12-continued

| Compound | Structure | Compound Name | Exact Mass [M + H]+ |
|---|---|---|---|
| 12-18 | 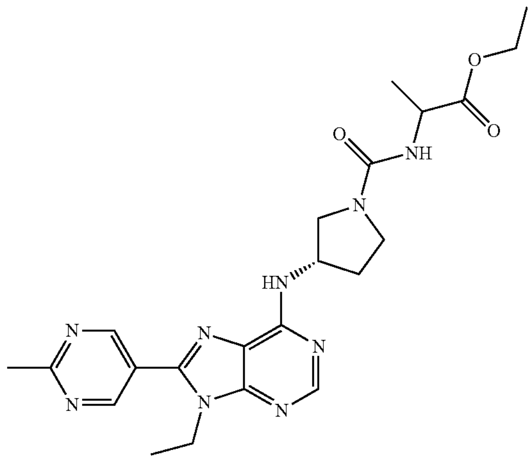 [SMILES: CCOC(=O)C(C)NC(=O)N1CC[C@H](Nc2ncnc3c2nc(-c2cnc(C)nc2)n3CC)C1] | ethyl N-{[(3S)-3-{[9-ethyl-8-(2-methylpyrimidin-5-yl)-9H-purin-6-yl]amino}pyrrolidin-1-yl]carbonyl}(D and L)-alaninate | Calc'd 468, found 468 |
| 12-19 | 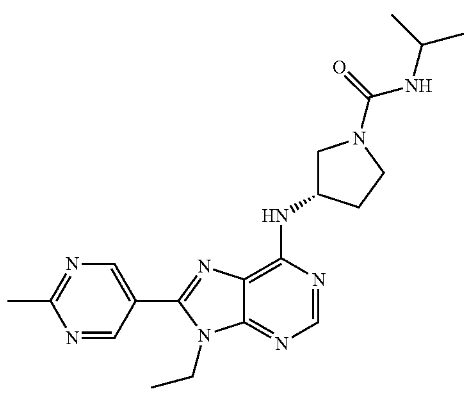 [SMILES: CCn1c(-c2cnc(C)nc2)nc2c(N[C@H]3CCN(C(=O)NC(C)C)C3)ncnc21] | (3S)-3-{[9-ethyl-8-(2-methylpyrimidin-5-yl)-9H-purin-6-yl]amino}-N-(1-methylethyl)pyrrolidine-1-carboxamide | Calc'd 410, found 410 |
| 12-20 | 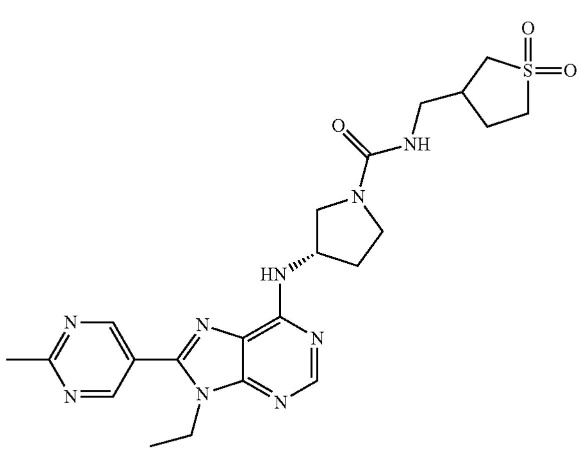 [SMILES: CCn1c(-c2cnc(C)nc2)nc2c(N[C@H]3CCN(C(=O)NCC4CCS(=O)(=O)C4)C3)ncnc21] | (3S)-N-[((S and R)-1,1-dioxidotetrahydrothiophen-3-yl)methyl]-3-{[9-ethyl-8-(2-methylpyrimidin-5-yl)-9H-purin-6-yl]amino}pyrrolidine-1-carboxamide | Calc'd 500, found 500 |

TABLE 12-continued

| Compound | Structure | Compound Name | Exact Mass [M + H]+ |
|---|---|---|---|
| 12-21 | 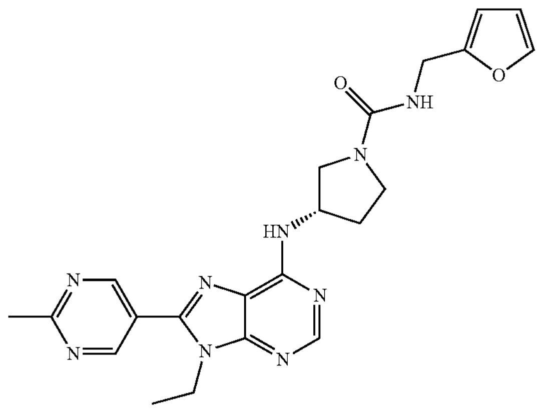 [SMILES: CCn1c(-c2cnc(C)nc2)nc2c(N[C@H]3CCN(C(=O)NCc4ccco4)C3)ncnc21] | (3S)-3-{[9-ethyl-8-(2-methylpyrimidin-5-yl)-9H-purin-6-yl]amino}-N-(furan-2-ylmethyl)pyrrolidine-1-carboxamide | Calc'd 448, found 448 |
| 12-22 | 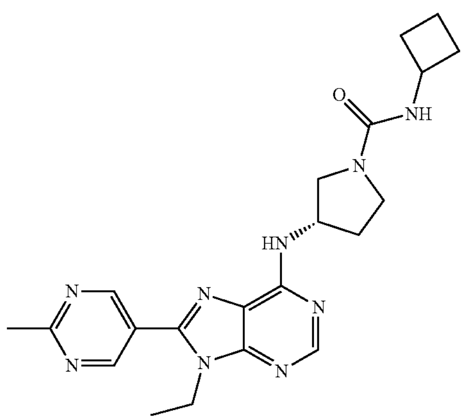 [SMILES: CCn1c(-c2cnc(C)nc2)nc2c(N[C@H]3CCN(C(=O)NC4CCC4)C3)ncnc21] | (3S)-N-cyclobutyl-3-{[9-ethyl-8-(2-methylpyrimidin-5-yl)-9H-purin-6-yl]amino}pyrrolidine-1-carboxamide | Calc'd 422, found 422 |
| 12-23 | 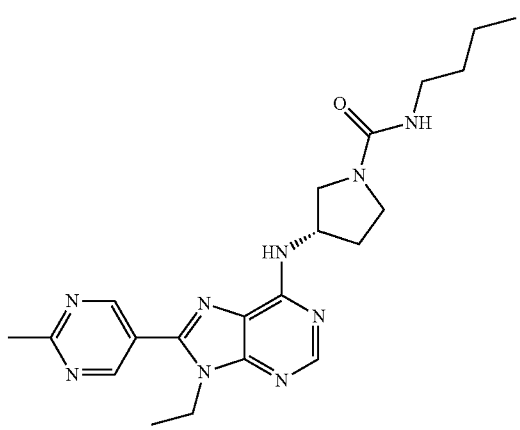 [SMILES: CCCCNC(=O)N1CC[C@H](Nc2ncnc3c2nc(-c2cnc(C)nc2)n3CC)C1] | (3S)-N-butyl-3-{[9-ethyl-8-(2-methylpyrimidin-5-yl)-9H-purin-6-yl]amino}pyrrolidine-1-carboxamide | Calc'd 424, found 424 |

TABLE 12-continued

| Compound | Compound Name | Exact Mass [M + H]+ |
|---|---|---|
| 12-24 | methyl N-{[(3S)-3-{[9-ethyl-8-(2-methylpyrimidin-5-yl)-9H-purin-6-yl]amino}pyrrolidin-1-yl]carbonyl}-2-methylalaninate | Calc'd 468, found 468 |
| 12-25 | (3S)-3-{[9-ethyl-8-(2-methylpyrimidin-5-yl)-9H-purin-6-yl]amino}-N-(1,1,3,3-tetramethylbutyl)pyrrolidine-1-carboxamide | Calc'd 480, found 480 |
| 12-26 | N-[(3S)-1-(azetidin-1-ylcarbonyl)pyrrolidin-3-yl]-9-ethyl-8-[6-(trifluoromethyl)pyridin-3-yl]-9H-purin-6-amine | Calc'd 461, found 461 |
| 12-27 | 9-ethyl-6-({(3S)-1-[(3-methoxyazetidin-1-yl)carbonyl]pyrrolidin-3-yl}amino)-N-(2,2,2-trifluoroethyl)-9H-purine-8-carboxamide | Calc'd 471, found 471 |

Compound Examples of Table 13

Example 24G: Preparation of Compound 13-2

Example 24H: Preparation of Compound 13-11

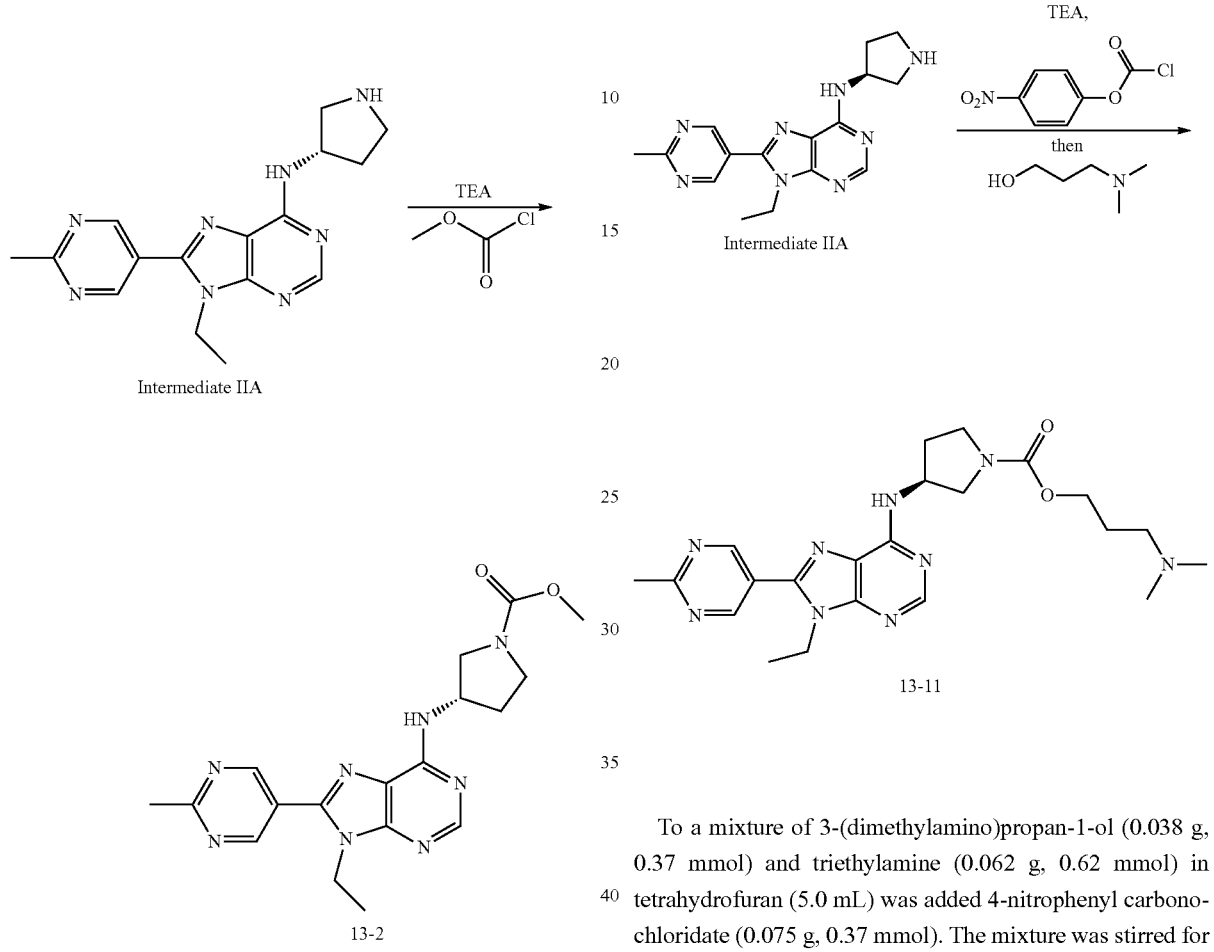

Intermediate IIA 13-2

13-11

Methyl chloroformate (0.0090 g, 0.10 mmol) was measured directly into a reaction vessel. A solution of (S)-9-ethyl-8-(2-methylpyrimidin-5-yl)-N-(pyrrolidin-3-yl)-9H-purin-6-amine, 2HCl (Intermediate IIA) (0.029 g, 0.073 mmol) in DMF (1.0 mL) was then added to the reaction vial along with triethylamine (0.025 ml, 0.18 mmol). The vial was sealed and its contents were allowed to stir overnight at room temperature. The reaction mixture was then filtered, washing with DMSO (1.0 mL). The filtrate was purified by reverse phase preparative HPLC (0:100 to 95:5 acetonitrile:water: 0.1% v/v TFA modifier) to afford compound 13-2 as the TFA salt. $^1$H NMR (600 MHz, DMSO) δ 9.08 (s, 2H), 8.45 (s, 1H), 8.31 (s, 1H), 4.66 (s, 1H), 4.27 (q, J=7.1, 2H), 3.70-2.93 (m, 7H), 2.71 (s, 3H), 2.21-1.93 (m, J=40.9, 46.2, 2H), 1.27 (t, J=7.2, 3H). MS (EI) Calc'd for $C_{18}H_{23}N_8O_2$ [M+H]$^+$, 383. found 383.

To a mixture of 3-(dimethylamino)propan-1-ol (0.038 g, 0.37 mmol) and triethylamine (0.062 g, 0.62 mmol) in tetrahydrofuran (5.0 mL) was added 4-nitrophenyl carbonochloridate (0.075 g, 0.37 mmol). The mixture was stirred for 1 hour, then (S)-9-ethyl-8-(2-methylpyrimidin-5-yl)-N-(pyrrolidin-3-yl)-9H-purin-6-amine (Intermediate IIA) (in its neutral form) (0.10 g, 0.31 mmol) in 1,2-dichloroethane (1.0 mL) was added to the reaction mixture. The reaction was stirred for 12 h at 70° C. The reaction was then cooled and concentrated in vacuo. The residue thus obtained was purified by reverse phase preparative HPLC (30:70 to 70:30 acetonitrile:water: 10 mM NH$_4$HCO$_3$ modifier) to afford compound 13-11. $^1$H NMR (400 MHz, CD$_3$OD): δ 9.13 (s, 2H), 8.36 (s, 1H), 5.00-4.60 (m, 1H), 4.41 (q, J=7.2 Hz, 2H), 4.16-4.12 (m, 2H), 3.85-3.48 (m, 4H), 2.83 (s, 3H), 2.50-2.30 (m, 3H), 2.28 (s, 3H), 2.24 (s, 3H), 2.17-2.14 (m, 1H), 1.95-1.80 (m, 2H), 1.45 (m, 3H). MS (ESI) calc'd for $C_{22}H_{32}N_9O_2$ [M+H]$^+$, 454. found, 454.

Compounds 13-1 and 13-3 through 13-10 were prepared in an analogous fashion as described in Example 24G using the corresponding chloroformate.

TABLE 13

| Compound | Structure | Compound Name | Exact Mass [M + H]+ |
|---|---|---|---|
| 13-1 | 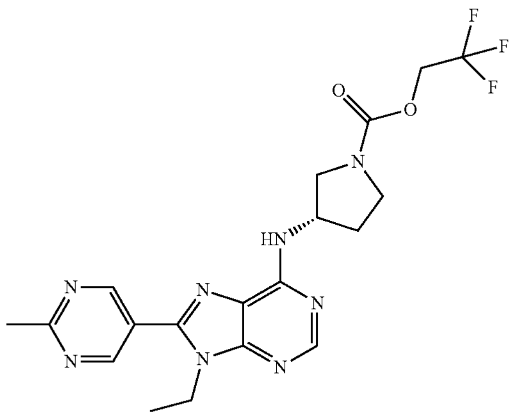 [SMILES: CCn1c(-c2cnc(C)nc2)nc2c(N[C@H]3CCN(C(=O)OCC(F)(F)F)C3)ncnc21] | 2,2,2-trifluoroethyl (3S)-3-{[9-ethyl-8-(2-methylpyrimidin-5-yl)-9H-purin-6-yl]amino}pyrrolidine-1-carboxylate | Calc'd 451, found 451 |
| 13-2 | 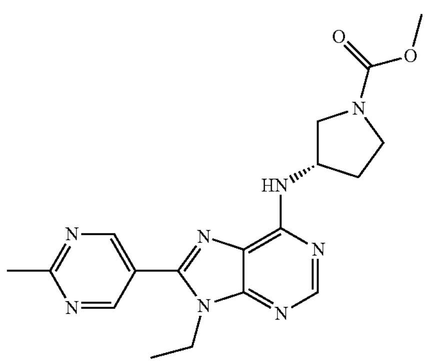 | methyl (3S)-3-{[9-ethyl-8-(2-methylpyrimidin-5-yl)-9H-purin-6-yl]amino}pyrrolidine-1-carboxylate | Calc'd 383, found 383 |
| 13-3 | 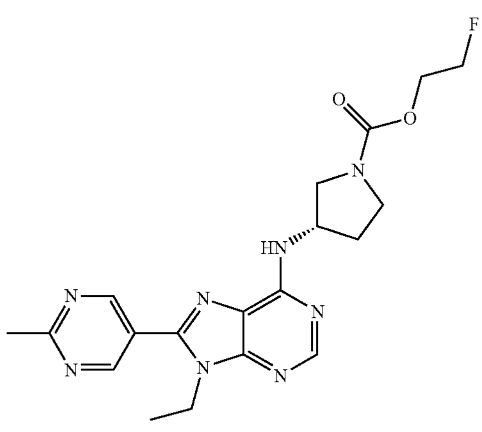 [SMILES: CCn1c(-c2cnc(C)nc2)nc2c(N[C@H]3CCN(C(=O)OCCF)C3)ncnc21] | 2-fluoroethyl (3S)-3-{[9-ethyl-8-(2-methylpyrimidin-5-yl)-9H-purin-6-yl]amino}pyrrolidine-1-carboxylate | Calc'd 415, found 415 |

TABLE 13-continued

| Compound | Structure | Compound Name | Exact Mass [M + H]+ |
|---|---|---|---|
| 13-4 | 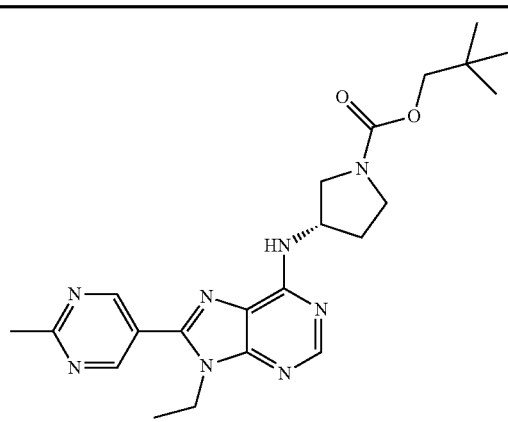 | 2,2-dimethylpropyl (3S)-3-{[9-ethyl-8-(2-methylpyrimidin-5-yl)-9H-purin-6-yl]amino}pyrrolidine-1-carboxylate | Calc'd 439, found 439 |
| 13-5 | 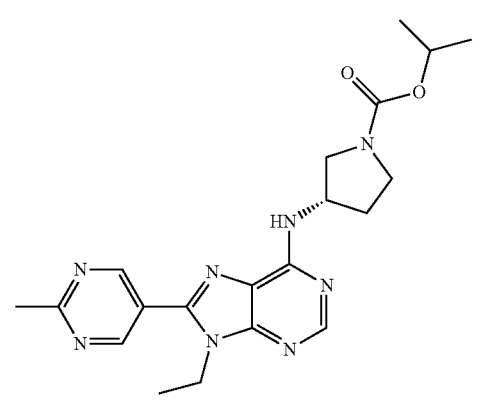 [SMILES: CCn1c(-c2cnc(C)nc2)nc2c(N[C@H]3CCN(C(=O)OC(C)C)C3)ncnc21] | 1-methylethyl (3S)-3-{[9-ethyl-8-(2-methylpyrimidin-5-yl)-9H-purin-6-yl]amino}pyrrolidine-1-carboxylate | Calc'd 411, found 411 |
| 13-6 | 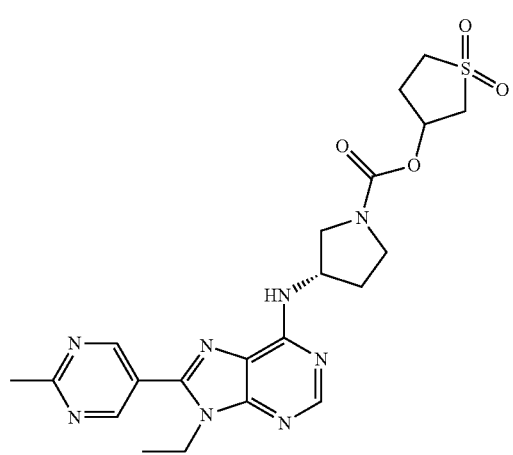 [SMILES: CCn1c(-c2cnc(C)nc2)nc2c(N[C@H]3CCN(C(=O)OC4CCS(=O)(=O)C4)C3)ncnc21] | (S and R)-1,1-dioxidotetrahydrothiophen-3-yl (3S)-3-{[9-ethyl-8-(2-methylpyrimidin-5-yl)-9H-purin-6-yl]amino}pyrrolidine-1-carboxylate | Calc'd 487, found 487 |

TABLE 13-continued

| Compound | Structure | Compound Name | Exact Mass [M + H]+ |
|---|---|---|---|
| 13-7 | 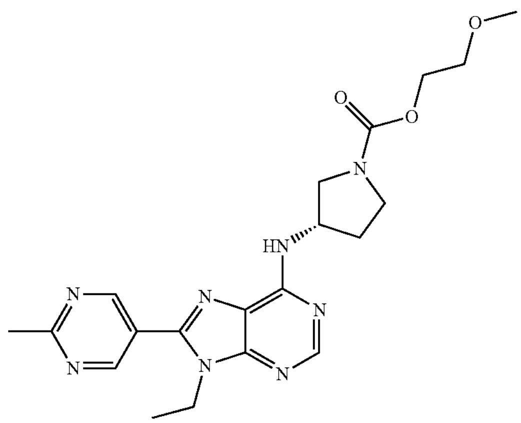 | 2-methoxyethyl (3S)-3-{[9-ethyl-8-(2-methylpyrimidin-5-yl)-9H-purin-6-yl]amino}pyrrolidine-1-carboxylate | Calc'd 427, found 427 |
| 13-8 | 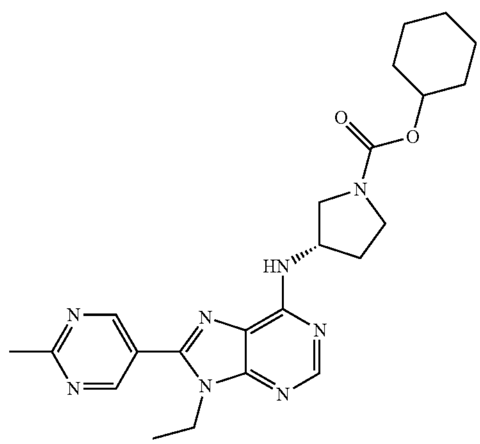 [SMILES: CCn1c(-c2cnc(C)nc2)nc2c(N[C@H]3CCN(C(=O)OC4CCCCC4)C3)ncnc21] | cyclohexyl (3S)-3-{[9-ethyl-8-(2-methylpyrimidin-5-yl)-9H-purin-6-yl]amino}pyrrolidine-1-carboxylate | Calc'd 451, found 451 |
| 13-9 | 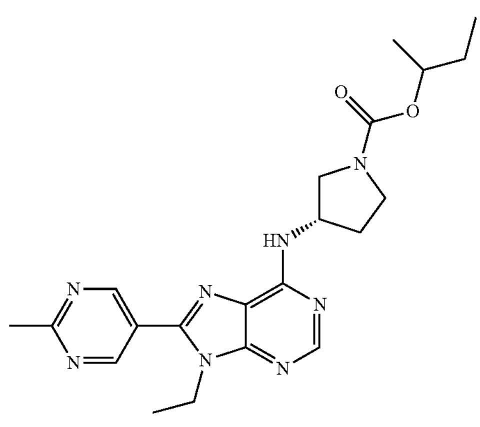 [SMILES: CCC(C)OC(=O)N1CC[C@H](Nc2ncnc3c2nc(-c2cnc(C)nc2)n3CC)C1] | (S and R)-1-methylpropyl (3S)-3-{[9-ethyl-8-(2-methylpyrimidin-5-yl)-9H-purin-6-yl]amino}pyrrolidine-1-carboxylate | Calc'd 425, found 425 |

TABLE 13-continued

| Compound | Structure | Compound Name | Exact Mass [M + H]+ |
|---|---|---|---|
| 13-10 | 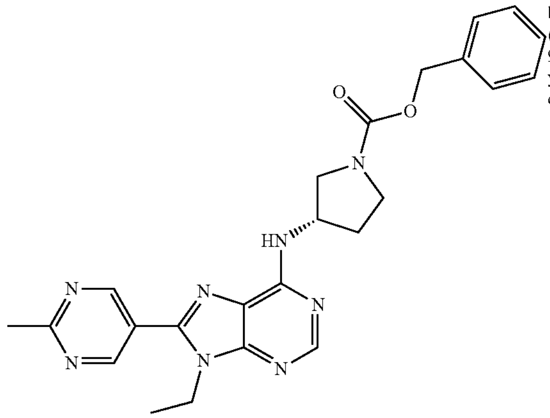 [SMILES: CCn1c(-c2cnc(C)nc2)nc2c(N[C@H]3CCN(C(=O)OCc4ccccc4)C3)ncnc21] | benzyl (3S)-3-{[9-ethyl-8-(2-methylpyrimidin-5-yl)-9H-purin-6-yl]amino}pyrrolidine-1-carboxylate | Calc'd 459, found 459 |
| 13-11 | 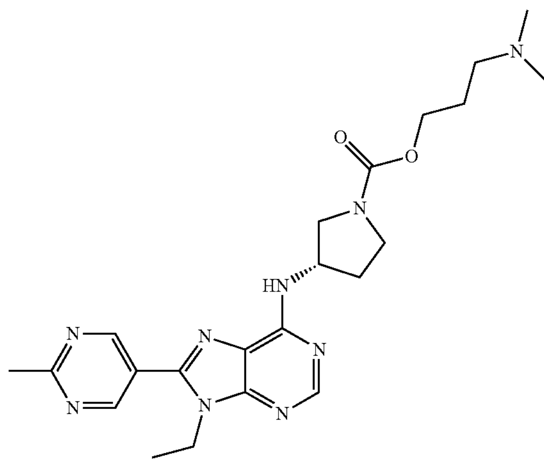 | 3-(dimethylamino)propyl (3S)-3-{[9-ethyl-8-(2-methylpyrimidin-5-yl)-9H-purin-6-yl]amino}pyrrolidine-1-carboxylate | Calc'd 454, found 454 |

Compound Examples of Table 14

Example 25: Preparation of Compound 14-1

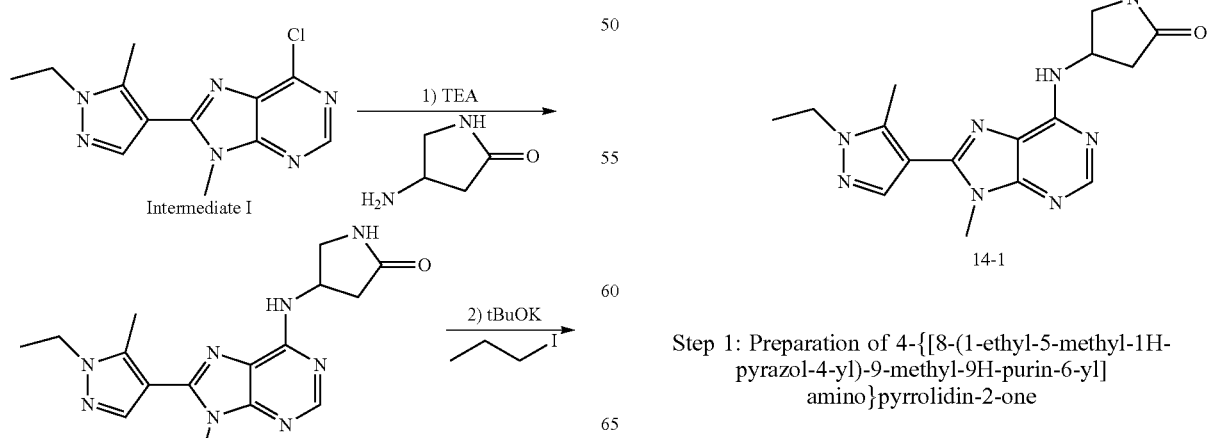

Step 1: Preparation of 4-{[8-(1-ethyl-5-methyl-1H-pyrazol-4-yl)-9-methyl-9H-purin-6-yl]amino}pyrrolidin-2-one A mixture of Intermediate I (100 mg, 0.36 mmol), 4-aminopyrrolidin-2-one hydrochloride (60 mg, 0.43 mmol), TEA (1.0 mL) and t-BuOH (1.0 mL) was heated to 100° C. for 48 h, after which the reaction solution was concentrated in vacuo. The residue was purified by preparative thin-layer chromatography, (silica gel, eluting with DCM:MeOH=10:1) to afford 4-{[8-(1-ethyl-5-methyl-1H-pyrazol-4-yl)-9-methyl-9H-purin-6-yl]amino}pyrrolidin-2-one. MS (ESI) calc'd for ($C_{16}H_{21}N_8O$) [M+H]$^+$, 341. found, 341.

Step 2: Preparation of Compound 14-1

To a mixture of 4-{[8-(1-ethyl-5-methyl-1H-pyrazol-4-yl)-9-methyl-9H-purin-6-yl]amino}pyrrolidin-2-one (30 mg, 0.088 mmol) and THF (2 mL) was added potassium tert-butoxide (20 mg, 0.18 mmol). The reaction mixture was stirred for 10 min at RT, after which 1-iodopropane (30 mg, 0.18 mmol) was added and the resulting mixture was allowed to stir for 15 h at RT. Water (5 mL) was then added and the reaction mixture was extracted with EtOAc (3×5 ml), and the combined organic layers were dried over sodium sulfate, filtered, and concentrated in vacuo. The residue thus obtained was purified by preparative thin-layer chromatography (silica gel, eluting DCM:MeOH=10:1) to afford 14-1. $^1$H NMR (400 MHz, MeOD-d$_4$) δ 8.19 (s, 1H), 7.81 (s, 1H), 4.95-4.80 (m, 1H) 4.19-4.13 (m, 2H), 3.88-3.83 (m, 1H), 3.73 (s, 3H), 3.40-3.35 (m, 1H), 3.22-3.19 (m, 2H), 2.88-2.84 (m, 1H), 2.48-2.46 (m, 4H), 1.52-1.47 (m, 2H), 1.35 (t, J=7.2 Hz, 3H), 0.82 (t, J=7.2 Hz, 3H). MS (ESI) calc'd for ($C_{19}H_{27}N_8O$) [M+H]$^+$, 383. found, 383.

Example 26: Preparation of Compound 14-3

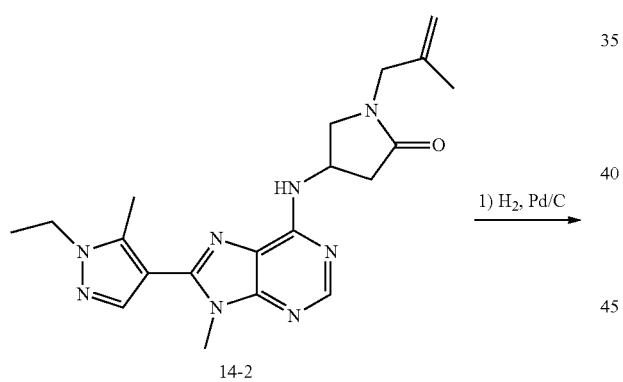

A mixture of compound 14-2 (5 mg, 0.01 mmol), 10% Pd/C (2 mg), and MeOH (5 ml) was stirred under a hydrogen atmosphere for 15 h at room temperature, after which it was filtered and concentrated in vacuo to provide compound 14-3. $^1$H NMR (400 MHz, MeOD-d$_4$) δ 8.30 (s, 1H), 7.91 (s, 1H), 5.12-4.98 (m, 1H) 4.29-4.23 (m, 2H), 3.95-3.90 (m, 1H), 3.83 (s, 3H), 3.53-3.48 (m, 1H), 3.16-3.12 (m, 2H), 3.00-2.90 (m, 1H), 2.65-2.45 (m, 4H), 1.99-1.89 (m, 1H), 1.46 (t, J=7.2 Hz, 3H), 0.94-0.90 (m, 6H). MS (ESI) calc'd for ($C_{20}H_{29}N_8O$) [M+H]$^+$, 397. found, 397.

Example 27: Preparation of Compound 14-6

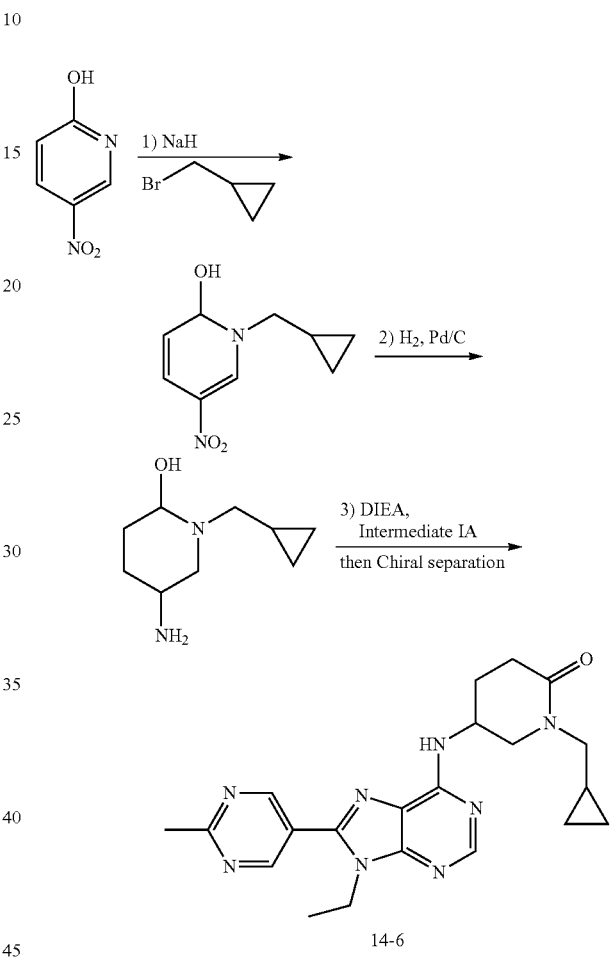

Step 1: Preparation of (1-(cyclopropylmethyl)-5-nitropyridin-2(1H)-one

To a solution of 5-nitropyridin-2-ol (2 g, 14 mmol, commercially available from Beijing Wisdom Chemical. Co. Ltd.) in N,N-dimethylformamide (30 mL) was added sodium hydride (571 mg, 60% in mineral oil, 14.3 mmol) in portions at 0° C. After stirring for 30 min at 0° C., (bromomethyl)cyclopropane (1.9 g, 14 mmol, commercially available from Sichuan Weibo Science and Technology Co. Ltd.) was added. The mixture was stirred for 15 h at 60° C. The reaction mixture was then quenched with water (100 mL), extracted with ethyl acetate (3×80 mL), dried over anhydrous sodium sulfate, filtered and concentrated under vacuum. The residue was purified by silica gel column chromatography, eluting with 2% ethyl acetate in petroleum ether to afford 1-(cyclopropylmethyl)-5-nitropyridin-2(1H)-one. MS (ESI) calc'd for ($C_9H_{11}N_2O_3$) [M+H]$^+$, 195. found, 195.

Step 2: Preparation of 5-amino-1-(cyclopropylmethyl)piperidin-2-one

To a solution of 1-(cyclopropylmethyl)-5-nitropyridin-2 (1H)-one (1.5 g, 7.7 mmol) in methanol (50 mL) was added Pd/C (300 mg). The reaction mixture was stirred for 50 h at ambient temperature under an atmosphere of hydrogen, after which the solution was filtered. The filtrate was concentrated under vacuum to afford 5-amino-1-(cyclopropylmethyl)piperidin-2-one. MS (ESI) calc'd for ($C_9H_{16}N_2O$) [M+H]$^+$, 169. found, 169.

Step 3: Preparation of Compound 14-6

To a mixture of 5-amino-1-(cyclopropylmethyl)piperidin-2-one (600 mg, 3.6 mmol) and Intermediate IA (500 mg, 1.8 mmol) in tert-butanol (10 mL) was added DIEA (706 mg, 5.47 mmol). The reaction mixture was stirred for 12 h at 85° C., after which it was concentrated under reduced pressure. The residue was re-dissolved in water (100 mL), extracted with dichloromethane (3×80 mL), dried over anhydrous sodium sulfate, and filtered. The filtrate was concentrated under reduced pressure. The residue was purified by silica gel column chromatography eluting with 3% methanol in dichloromethane to afford a product mixture, which was separated by preparative chiral HPLC using the following conditions: Column: Chiralpak AD-H (SFC1), 4.6×150 cm; Mobile phase: 0.1% diethylamine in methanol to afford compound 14-6 (retention time 2.27 min). $^1$H NMR (300 MHz, DMSO-$d_6$) δ 9.12 (s, 2H), 8.32 (s, 1H), 8.09 (m, 1H), 4.63 (m, 1H), 4.30 (q, J=7.2 Hz, 2H), 3.58-3.47 (m, 1H), 3.44-3.32 (m, 1H), 3.26-3.24 (m, 1H), 3.10-3.03 (m, 1H), 2.74 (s, 3H), 2.43-2.38 (m, 2H), 2.10-1.90 (m, 2H), 1.31 (t, J=7.2 Hz, 3H), 1.00-0.85 (m, 1H), 0.41-0.37 (m, 2H), 0.20-0.15 (m, 2H). MS (ESI) calc'd for ($C_{21}H_{27}N_8O$) [M+H]$^+$, 407. found, 407.

Example 28: Preparation of Compound 14-7

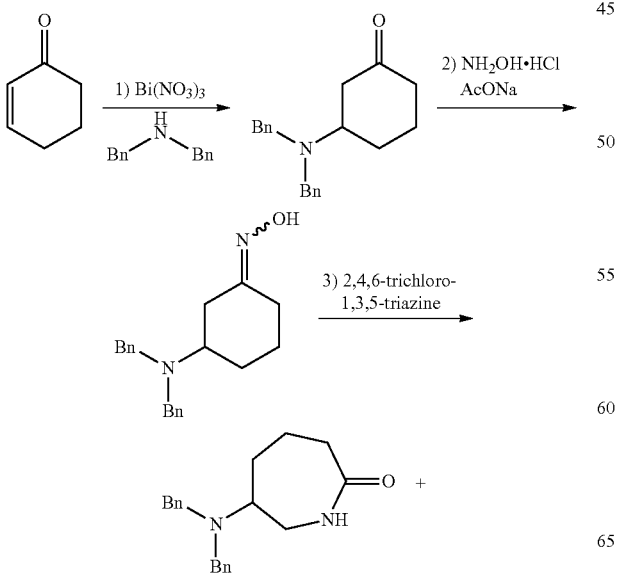

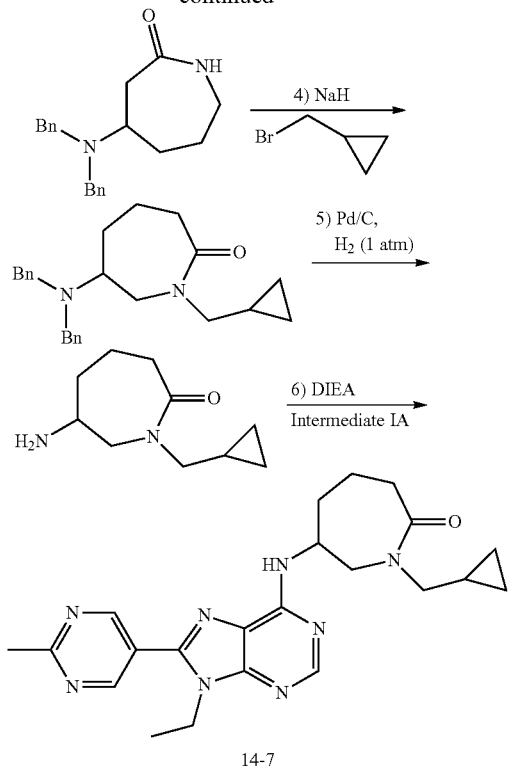

Step 1: Preparation of 3-(dibenzylamino)cyclohexanone

To a solution of cyclohex-2-enone (25 g, 0.26 mol) in dibenzylamine (51 g, 0.26 mol) was added tris(nitrooxy)bismuthine (15 g, 0.04 mol). The resulting mixture was stirred for 15 h at ambient temperature. The reaction was then quenched by the addition of water (500 mL), and the mixture was extracted with dichloromethane (3×500 mL). The combined organic layers were dried over anhydrous magnesium sulfate and filtered. The filtrate was concentrated to give a residue, which was purified by silica gel column chromatography, eluting with 3% ethyl acetate in petroleum ether to afford 3-(dibenzylamino)cyclohexanone. MS (ESI) calc'd for ($C_{20}H_{24}NO$) [M+H]$^+$, 294. found, 294.

Step 2: Preparation of 3-(dibenzylamino)cyclohexanone oxime

To a solution of 3-(dibenzylamino)cyclohexanone (7 g, 0.02 mol) in ethanol (100 mL) were added hydroxylamine hydrogen chloride (3.0 g, 0.043 mol) and sodium acetate (4 g, 0.05 mol). The resulting mixture was stirred for 1 h at ambient temperature. The reaction was then quenched by the addition of water (50 mL), and extracted with dichloromethane (3×50 mL). The organic layers were combined and dried over anhydrous magnesium sulfate and filtered. The filtrate was concentrated to give a residue, which was purified by silica gel column chromatography, eluting with 3% ethyl acetate in petroleum ether to afford 3-(dibenzylamino)cyclohexanone oxime. MS (ESI) calc'd for ($C_{20}H_{25}N_2O$) [M+H]$^+$, 309. found, 309.

Step 3: Preparation of 6-(dibenzylamino)azepan-2-one

A solution of 2,4,6-trichloro-1,3,5-triazine (2.08 g, 11.4 mmol) in N,N-dimethylformamide (20 mL) was stirred for 1 h at ambient temperature, then 3-(dibenzylamino)cyclohexanone oxime (3.5 g, 11 mmol) in N,N-dimethylformamide (30 mL) was added at 0° C. After stirring for 12 h at ambient temperature, the reaction was quenched by the addition of water (100 mL) and extracted with ethyl acetate (3×50 mL). The organic layers were combined, dried over anhydrous magnesium sulfate, and filtered. The filtrate was concentrated to give a residue, which was purified by silica gel column chromatography, eluting with 2% dichloromethane in methanol to afford 6-(dibenzylamino)azepan-2-one, along with isomer 4-(dibenzylamino)azepan-2-one, as a mixture which was carried into the next step without further purification. MS (ESI) calc'd for $(C_{20}H_{25}N_2O)$ $[M+H]^+$, 309. found, 309.

Step 4: Synthesis of 1-(cyclopropylmethyl)-6-(dibenzylamino)azepan-2-one

To a solution of a mixture of 6-(dibenzylamino)azepan-2-one and 4-(dibenzylamino)azepan-2-one (300 mg, 0.97 mmol) in N,N-dimethylformamide (10 mL) was added sodium hydride (60 mg, 1.5 mmol) at 0° C. After stirring for 30 min, (bromomethyl)cyclopropane (260 mg, 1.9 mmol) was added. The resulting mixture was stirred for 12 h at RT. The mixture was then quenched by the addition of water (20 mL) and extracted with ethyl acetate (3×50 mL). The organic layers were combined, dried over anhydrous magnesium sulfate, and filtered. The filtrate was concentrated under vacuum to give a residue, which was purified by silica gel column chromatography eluted with 10%-20% ethyl acetate in petroleum ether to afford 1-(cyclopropylmethyl)-6-(dibenzylamino)azepan-2-one. MS (ESI) calc'd for $(C_{24}H_{31}N_2O)$ $[M+H]^+$, 363. found, 363.

Step 5: Synthesis of 6-amino-1-(cyclopropylmethyl)azepan-2-one

To a solution of 1-(cyclopropylmethyl)-6-(dibenzylamino)azepan-2-one (100 mg, 0.28 mmol) in methanol (20 mL) was added palladium on carbon (10 wt %, 20 mg). The reaction mixture was stirred for 15 min at ambient temperature under a hydrogen atmosphere (1 atm), after which it was filtered and washed with methanol (20 mL). The filtrate was concentrated under reduced pressure to afford 6-amino-1-(cyclopropylmethyl)azepan-2-one which was used without further purification. MS (ESI) calc'd for $(C_{10}H_{19}N_2O)$ $[M+H]^+$, 183. found, 183.

Step 6: Preparation of Compound 14-7

To a solution of Intermediate IA (60 mg, 0.22 mmol) in 2-methylpropan-2-ol (20 mL) were added 6-amino-1-(cyclopropylmethyl)azepan-2-one (60 mg, crude) and N-ethyl-N-isopropylpropan-2-amine (85 mg, 0.66 mmol). The mixture was stirred for 12 h at 85° C. The reaction was then quenched by the addition of water (50 mL), and was extracted with dichloromethane (3×20 mL). The organic layers were combined, dried over anhydrous magnesium sulfate, and filtered. The filtrate was concentrated in vacuo to give a residue, which was purified by silica gel column chromatography (eluting with 3% methanol in dichloromethane) to afford (R and S)-1-(cyclopropylmethyl)-6-(9-ethyl-8-(2-methylpyrimidin-5-yl)-9H-purin-6-ylamino)azepan-2-one as a racemic mixture. The mixture was separated by preparative chiral HPLC (Column: CHIRALPAK IA 2×25 cm, 20 rtm, Mobile phase: A: Hex, B: IPA; Flow rate: 20 mL/min; UV detection: 254/220 nm) to afford (S or R)-1-(cyclopropylmethyl)-6-(9-ethyl-8-(2-methylpyrimidin-5-yl)-9H-purin-6-ylamino)azepan-2-one (14-7) (retention time 8.8 min). $^1$H NMR (300 MHz, DMSO-$d_6$) δ 9.11 (s, 2H), 8.30 (s, 1H), 7.92 (m, 1H), 4.36-4.20 (m, 3H), 3.72-3.64 (m, 1H), 3.51-3.27 (m, 1H), 3.26-3.16 (m, 2H), 2.75 (s, 3H), 2.57-2.50 (m, 1H), 2.36-2.25 (m, 1H), 2.10-1.80 (m, 3H), 1.56-1.48 (m, 1H), 1.37 (t, J=7.2 Hz, 3H), 1.21-1.03 (m, 1H), 0.50-0.35 (m, 2H), 0.30-0.10 (m, 2H). MS (ESI) calc'd for $(C_{22}H_{29}N_8O)$ $[M+H]^+$, 421. found, 421.

Compound 14-2 was prepared in an analogous fashion to Example 25 using the corresponding allyl iodide.

Compound 14-4 was prepared in an analogous fashion to Example 25 using Intermediate IA.

Compound 14-5 was prepared in an analogous fashion to Example 25 from Intermediate IA; enantioenriched 14-5 was obtained from the racemic product by chiral column chromatography using the following conditions: [Column AD-H 4.6×250 mm 5 um, 2.55 ml/min flow rate, co-Solvent MeOH:MECN=1:1 (0.1% DEA), co-solvent flow rate=0.45 ml/min, column temperature=40° C.] to afford 14-5 (retention time 6.0 min).

TABLE 14

| Compound | Structure | Compound Name | Exact Mass [M + H]+ |
| --- | --- | --- | --- |
| 14-1 | 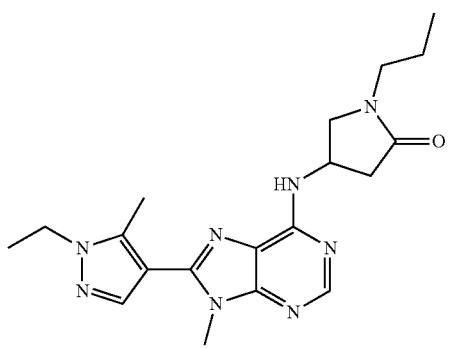 [SMILES: CCCN1CC(Nc2ncnc3c2nc(-c2cnn(CC)c2C)n3C)CC1=O] | 4(S and R)-{[8-(1-ethyl-5-methyl-1H-pyrazol-4-yl)-9-methyl-9H-purin-6-yl]amino}-1-propylpyrrolidin-2-one | Calc'd 383, found 383 |

TABLE 14-continued

| Compound | Structure | Compound Name | Exact Mass [M + H]+ |
|---|---|---|---|
| 14-2 | 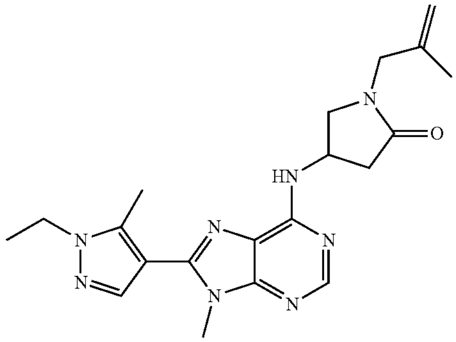 [SMILES: C=C(C)CN1CC(Nc2ncnc3c2nc(-c2cnn(CC)c2C)n3C)CC1=O] | 4(S and R)-{[8-(1-ethyl-5-methyl-1H-pyrazol-4-yl)-9-methyl-9H-purin-6-yl]amino}-1-(2-methylprop-2-en-1-yl)pyrrolidin-2-one | Calc'd 395, found 395 |
| 14-3 | 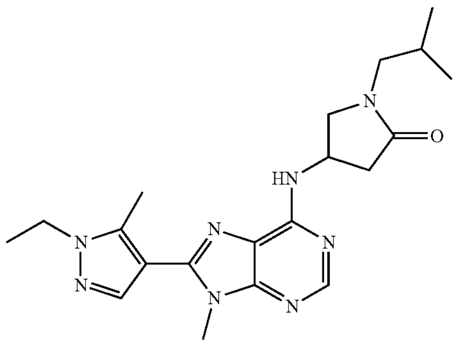 [SMILES: CCn1ncc(-c2nc3c(NC4CC(=O)N(CC(C)C)C4)ncnc3n2C)c1C] | 4(S and R)-{[8-(1-ethyl-5-methyl-1H-pyrazol-4-yl)-9-methyl-9H-purin-6-yl]amino}-1-(2-methylpropyl)pyrrolidin-2-one | Calc'd 397, found 397 |
| 14-4 | 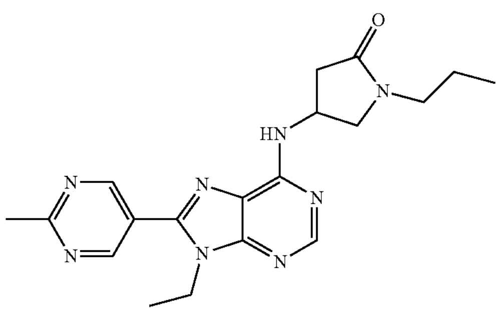 [SMILES: CCCN1CC(Nc2ncnc3c2nc(-c2cnc(C)nc2)n3CC)CC1=O] | 4(S and R)-{[9-ethyl-8-(2-methylpyrimidin-5-yl)-9H-purin-6-yl]amino}-1-propylpyrrolidin-2-one | Calc'd 381, found 381 |
| 14-5 | 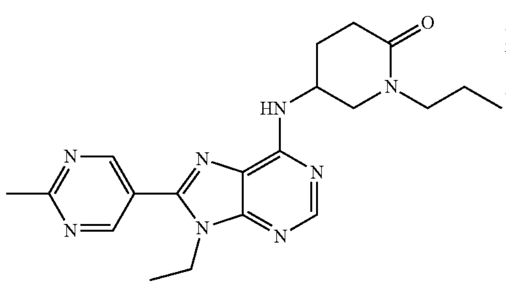 | 5(S and R)-{[9-ethyl-8-(2-methylpyrimidin-5-yl)-9H-purin-6-yl]amino}-1-propylpiperidin-2-one | Calc'd 395, found 395 |
| 14-6 | 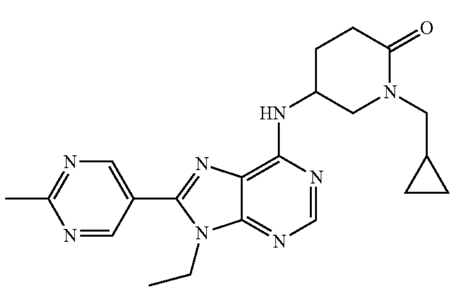 [SMILES: CCn1c(-c2cnc(C)nc2)nc2c(NC3CCC(=O)N(CC4CC4)C3)ncnc21] | 5(S or R)-1-(cyclopropylmethyl)-5-{[9-ethyl-8-(2-methylpyrimidin-5-yl)-9H-purin-6-yl]amino}piperidin-2-one | Calc'd 407, found 407 |

TABLE 14-continued
| Compound | Structure | Compound Name | Exact Mass [M + H]+ |
|---|---|---|---|
| 14-7 | 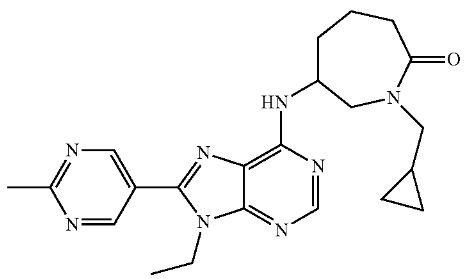 [SMILES: CCn1c(-c2cnc(C)nc2)nc2c(NC3CCCC(=O)N(CC4CC4)C3)ncnc21] | (R or S)-1-(cyclopropylmethyl)-6-{[9-ethyl-8-(2-methylpyrimidin-5-yl)-9H-purin-6-yl]amino}azepan-2-one | Calc'd 421, found 421 |
Compound Examples of Table 15
Example 29: Preparation of Compounds 15-1 and 15-2
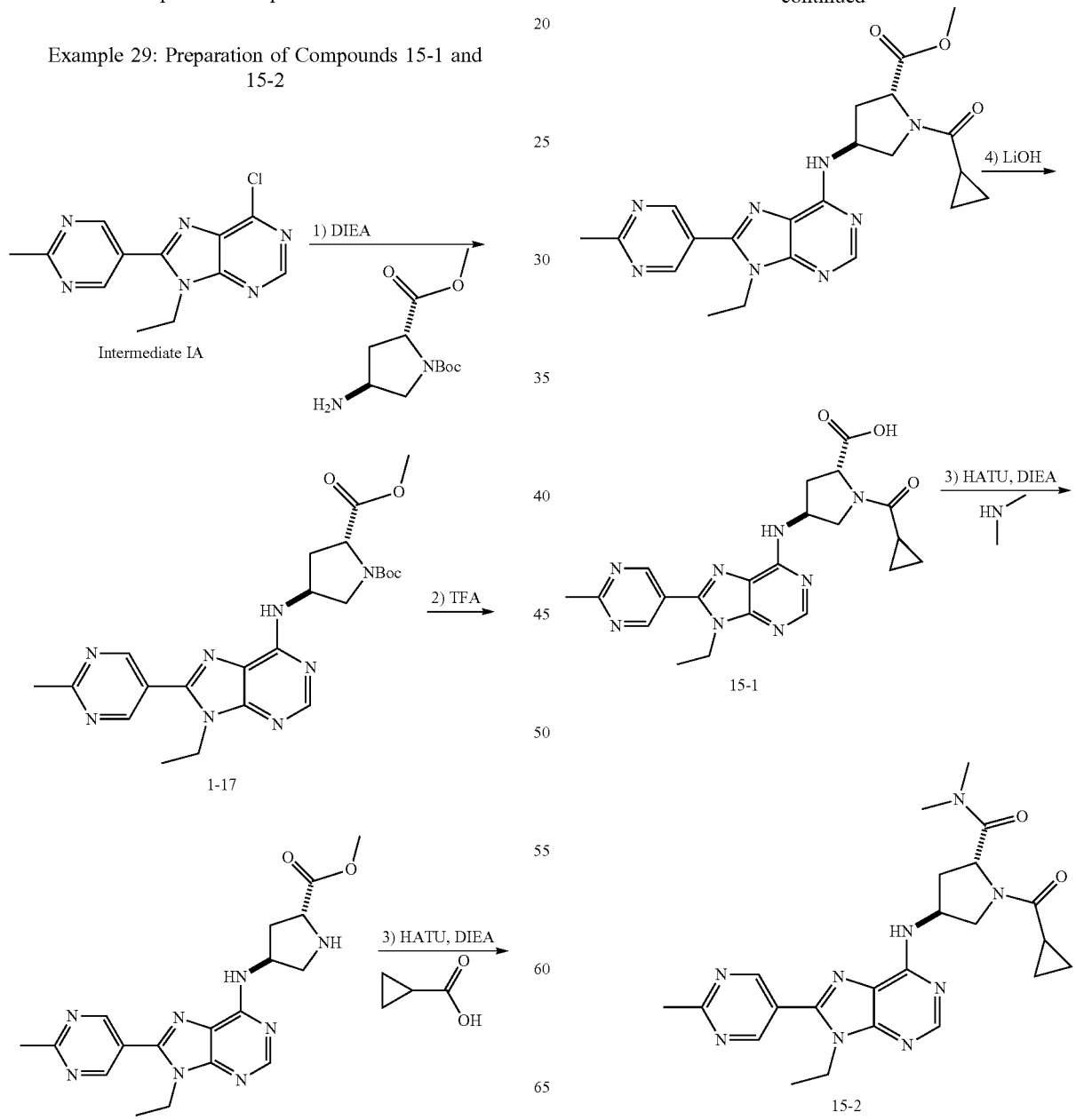

Step 1: Preparation of (2R,4S)-1-tert-butyl-2-methyl-4-((9-ethyl-8-(2-methylpyrimidin-5-yl)-9H-purin-6-yl)amino)pyrrolidine-1,2-dicarboxylate (1-17)

A vial was charged with (2R,4S)-1-tert-butyl 2-methyl-4-aminopyrrolidine-1,2-dicarboxylate (commercially available from D-L Chiral Chemicals LLC) (600 mg, 2.456 mmol), 6-chloro-9-ethyl-8-(2-methylpyrimidin-5-yl)-9H-purine (Intermediate IA) (810 mg, 2.95 mmol), DMF (20 mL) and DIEA (2.145 mL, 12.28 mmol). The mixture was stirred at 80° C. for 24 h. The reaction mixture was concentrated in vacuo and the residue was purified by mass triggered reverse phase HPLC (MECN/water with 0.1% TFA modifier) to afford compound 1-17 as the TFA salt. (400 MHz, DMSO-$d_6$): 9.08 (s, 2H), 8.39 (s, 1H), 8.30 (s, 1H), 4.80 (m, 1H), 4.41-4.38 (m, 1H), 4.26 (m, 2H), 3.70-3.62 (m, 5H), 2.70 (s, 3H), 2.19 (m, 1H), 1.33-1.25 (m, 14H). MS (ESI) calc'd for ($C_{23}H_{31}N_8O_4$) [M+H]$^+$, 482.4. found, 482.9.

Step 2: Preparation of (2R,4S)-methyl-4-((9-ethyl-8-(2-methylpyrimidin-5-yl)-9H-purin-6-yl)amino)pyrrolidine-2-carboxylate A vial was charged with (2R,4S)-1-tert-butyl 2-methyl 4-((9-ethyl-8-(2-methylpyrimidin-5-yl)-9H-purin-6-yl)amino)pyrrolidine-1,2-dicarboxylate, as its TFA salt (1-17) (500 mg, 0.84 mmol) in DCM (5 mL). TFA (1.6 mL, 20.7 mmol) was added and the reaction mixture was stirred at 25° C. for 16 h. The reaction mixture was evaporated in vacuo to give the product (2R,4S)-methyl-4-((9-ethyl-8-(2-methylpyrimidin-5-yl)-9H-purin-6-yl)amino)pyrrolidine-2-carboxylate as its trifluoroacetate salt which was used without further purification in the next step. MS (ESI) calc'd for ($C_{18}H_{23}N_8O_2$) [M+H]$^+$, 383. found, 383.

Step 3: Preparation of (2R,4S)-methyl 1-(cyclopropanecarbonyl)-4-((9-ethyl-8-(2-methylpyrimidin-5-yl)-9H-purin-6-yl)amino)pyrrolidine-2-carboxylate To a vial were added (2R,4S)-methyl 4-((9-ethyl-8-(2-methylpyrimidin-5-yl)-9H-purin-6-yl)amino)pyrrolidine-2-carboxylate, TFA salt (400 mg, 0.81 mmol), cyclopropanecarboxylic acid (0.082 mL, 1.046 mmol), HATU (477 mg, 1.255 mmol), DMF (5 mL) and DIEA (1.096 mL, 6.28 mmol). The mixture was stirred for 16 h at 25° C. The mixture was filtered and the filtrate was purified by reverse phase preparative HPLC (MECN/water with 0.1% TFA modifier) to afford (2R,4S)-methyl 1-(cyclopropanecarbonyl)-4-((9-ethyl-8-(2-methylpyrimidin-5-yl)-9H-purin-6-yl)amino)pyrrolidine-2-carboxylate as its trifluoroacetate salt. MS (ESI) calc'd for ($C_{22}H_{27}N_8O_3$) [M+H]$^+$, 451. found, 451.

Step 4: Preparation of Compound 15-1

To a solution of (2R,4S)-methyl-1-(cyclopropanecarbonyl)-4-((9-ethyl-8-(2-methylpyrimidin-5-yl)-9H-purin-6-yl)amino)pyrrolidine-2-carboxylate, TFA as its salt (160 mg, 0.29 mmol) in THF (4 mL) and Methanol (0.8 mL) was added aqueous lithium hydroxide (1.21 mL of 1M solution, 1.21 mmol). The mixture was stirred at room temperature for 16 h. A solution of aqueous HCl (0.605 mL of 2M, 1.21 mmol) was added to neutralize the reaction mixture. Toluene was then added and the reaction mixture was concentrated in vacuo. The residue was azeotroped twice more with toluene. The crude product, mixed with lithium chloride, was used without further purification in the next step. For assay analysis, a small amount of the product was purified by reverse phase preparative HPLC (MECN/water with 0.1% TFA modifier) to afford 15-1 as a TFA salt. $^1$H NMR (400 MHz, DMSO-$d_6$): δ) 9.10 (s, 2H), 8.47 (s, 1H), 5.00-4.80 (m, 1H), 4.60-3.40 (m, 3H), 2.74 (s, 3H), 2.65-2.10 (s, 2H), 1.80-1.40 (m, 1H), 1.28 (m, 3H), 0.81-0.66 (m, 4H). MS (ESI) calc'd for ($C_{21}H_{25}N_8O_3$) [M+H]$^+$, 437. found, 437.

Step 5: Preparation of Compound 15-2

To a vial, were added (2R,4S)-1-(cyclopropanecarbonyl)-4-((9-ethyl-8-(2-methylpyrimidin-5-yl)-9H-purin-6-yl)amino)pyrrolidine-2-carboxylic acid (60 mg, 0.137 mmol), dimethylamine (8.75 μl, 0.165 mmol), DMF (1 mL) and HATU (62.7 mg, 0.165 mmol). The mixture was stirred for 16 h at 25° C. The mixture was filtered and the filtrate was purified by reverse phase preparative HPLC (MECN/water with 0.1% TFA modifier) to afford 15-2 as a TFA salt. $^1$H NMR (400 MHz, DMSO-d): δ 9.08 (s, 2H), 8.57 (s, 1H), 8.33 (s, 1H), 5.31 (s, 1H), 4.97-4.92 (m, 2H), 4.27 (m, 2H), 4.04 (m, 1H), 3.71 (s, 3H), 2.78 (s, 3H), 2.71 (s, 3H), 2.01 (s, 2H), 1.68 (m, 1H), 1.27 (m, 4H), 0.66-059 (m, 4H). MS (ESI) calc'd for ($C_{23}H_{30}N_9O_2$) [M+H]$^+$, 464. found, 464.

Example 30: Preparation of Compound 15-14

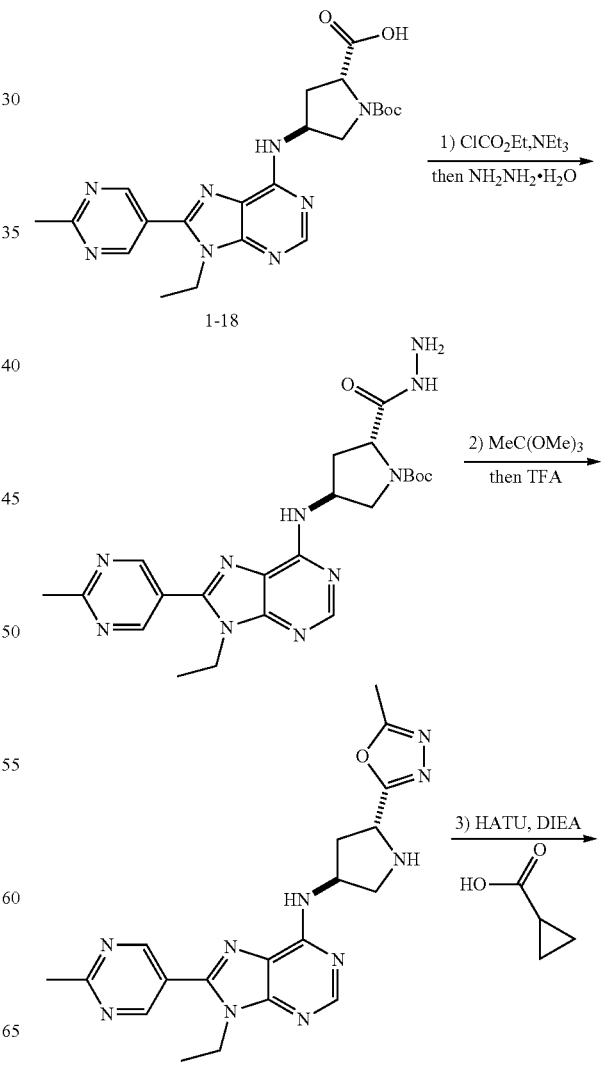

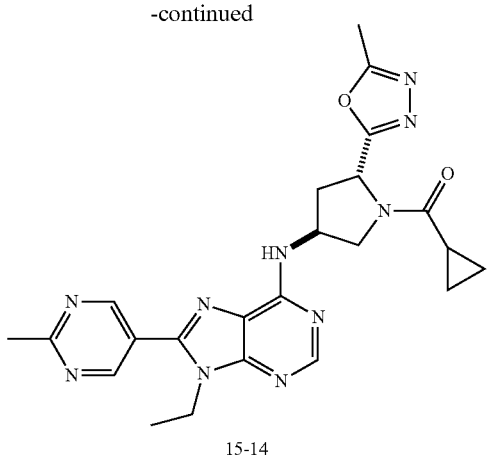

15-14

Step 1: Preparation of (2R,4S)-tert-butyl 4-((9-ethyl-8-(2-methylpyrimidin-5-yl)-9H-purin-6-yl)amino)-2-(hydrazinecarbonyl)pyrrolidine-1-carboxylate To a solution of (2R,4S)-1-(tert-butoxycarbonyl)-4-((9-ethyl-8-(2-methylpyrimidin-5-yl)-9H-purin-6-yl)amino)pyrrolidine-2-carboxylic acid (500 mg, 1.07 mmol) in THF (11 mL) at −10° C. was added Et$_3$N (0.171 mL, 1.23 mmol) followed by the slow addition of ethyl chloroformate (0.122 mL, 1.28 mmol). The reaction mixture was stirred at −10° C. for 20 min. The solid was then removed via filtration and was washed with THF. The combined filtrate was added into a solution of hydrazine hydrate (91 mg, 1.81 mmol) in THF (11 mL) at 0° C. The reaction was allowed to stir at ambient temperature for 2 h, after which the solvent was evaporated in vacuo and the residue was partitioned between 2-MeTHF and saturated aqueous sodium bicarbonate. The combined organic extract was washed with brine, dried over sodium sulfate, filtered, and concentrated in vacuo to afford crude product, which was used in the next step without further purification. MS (ESI) calc'd for (C$_{22}$H$_{31}$N$_{10}$O$_3$) [M+H]$^+$ 483. found 483.

Step 2: Preparation of 9-ethyl-N-((3S,5R)-5-(5-methyl-1,3,4-oxadiazol-2-yl)pyrrolidin-3-yl)-8-(2-methylpyrimidin-5-yl)-9H-purin-6-amine, TFA (2R,4S)-tert-butyl-4-((9-ethyl-8-(2-methylpyrimidin-5-yl)-9H-purin-6-yl)amino)-2-(hydrazinecarbonyl)pyrrolidine-1-carboxylate (120 mg, 0.249 mmol) was dissolved in 1,1,1-trimethoxyethane (1 mL, 0.25 mmol) and the mixture was refluxed for 24 h. The reaction mixture was then concentrated in vacuo. The residue was purified by reverse phase preparative HPLC (0:100 to 95:5 acetonitrile:water: 0.1% v/v TFA modifier) to afford a mixture of Boc-protected amine and the corresponding deprotected amine. This mixture was dissolved in DCM (1 mL) and TFA (0.192 mL, 2.49 mmol) was added and the mixture stirred at RT for 3 h. The solvent was evaporated in vacuo and the crude product as its TFA salt was used in the next step without further purification. MS (ESI) calc'd for (C$_{19}$H$_{23}$N$_{10}$O) [M+H]$^+$ 407. found 407.

Step 3: Preparation of Compound 15-14

To a vial were added 9-ethyl-N-((3S,5R)-5-(5-methyl-1,3,4-oxadiazol-2-yl)pyrrolidin-3-yl)-8-(2-methylpyrimidin-5-yl)-9H-purin-6-amine, TFA (20 mg, 0.037 mmol), cyclopropane carboxylic acid (5.9 µL, 0.074 mmol), HATU (28 mg, 0.074 mmol), DMF (1 mL) and DIEA (0.043 mL, 0.25 mmol), and the mixture was stirred at RT for 16 h. The solvent was evaporated in vacuo and the residue was purified by reverse phase preparative HPLC (0:100 to 95:5 acetonitrile:water: 0.1% v/v TFA modifier) to afford compound 15-14 as the TFA salt. (400 MHz, DMSO-d$_6$): δ 9.09 (s, 2H), 8.60-8.40 (m, 1H), 8.32-8.30 (m, 1H), 5.45-5.48 (m, 1H), 5.07-5.05 (m, 1H), 4.40-4.10 (m, 3H), 3.85-3.70 (m, 1H), 2.71 (s, 3H), 2.70-2.20 (m, 4H), 1.92-1.70 (m, 2H), 1.28-1.27 (m, 3H), 0.77-0.69 (m, 4H). MS (ESI) calc'd for (C$_{23}$H$_{27}$N$_{10}$O$_2$) [M+H]$^+$, 475. found, 475.

Compounds 15-3 through 15-8 were prepared in an analogous fashion to Example 29 using the corresponding amines.

Compounds 15-9 and 15-10 were prepared in an analogous fashion to Example 29 using (2S,4S)-1-tert-butyl 2-methyl-4-aminopyrrolidine-1,2-dicarboxylate (commercially available from D-L Chiral Chemicals LLC).

Compounds 15-11 and 15-12 were prepared in an analogous fashion to Example 29, steps 4 and 5 beginning from compound 4-12.

TABLE 15

| Compound | Structure | Compound Name | Exact Mass [M + H]+ |
| --- | --- | --- | --- |
| 15-1 | ![structure] | (4S)-1-(cyclopropylcarbonyl)-4-{[9-ethyl-8-(2-methylpyrimidin-5-yl)-9H-purin-6-yl]amino}-D-proline | Calc'd 437, found 437 |

TABLE 15-continued

| Compound | Structure | Compound Name | Exact Mass [M + H]+ |
|---|---|---|---|
| 15-2 | 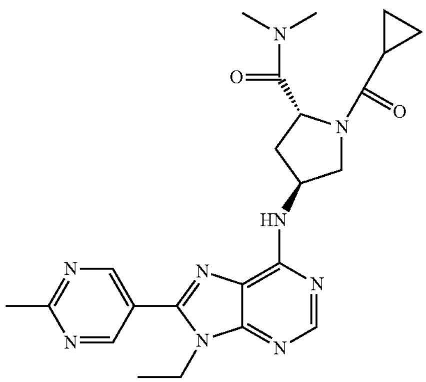 [SMILES: CCn1c(-c2cnc(C)nc2)nc2c(N[C@H]3C[C@H](C(=O)N(C)C)N(C(=O)C4CC4)C3)ncnc21] | (4S)-1-(cyclopropylcarbonyl)-4-{[9-ethyl-8-(2-methylpyrimidin-5-yl)-9H-purin-6-yl]amino}-N,N-dimethyl-D-prolinamide | Calc'd 464, found 464 |
| 15-3 | 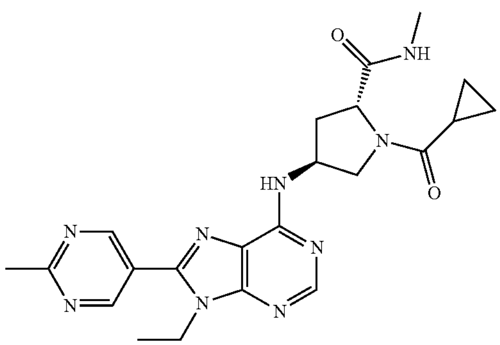 [SMILES: CCn1c(-c2cnc(C)nc2)nc2c(N[C@H]3C[C@H](C(=O)NC)N(C(=O)C4CC4)C3)ncnc21] | (4S)-1-(cyclopropylcarbonyl)-4-{[9-ethyl-8-(2-methylpyrimidin-5-yl)-9H-purin-6-yl]amino}-N-methyl-D-prolinamide | Calc'd 450, found 450 |
| 15-4 | 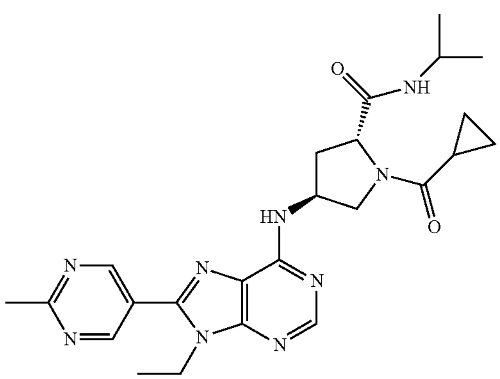 [SMILES: CCn1c(-c2cnc(C)nc2)nc2c(N[C@H]3C[C@H](C(=O)NC(C)C)N(C(=O)C4CC4)C3)ncnc21] | (4S)-1-(cyclopropylcarbonyl)-4-{[9-ethyl-8-(2-methylpyrimidin-5-yl)-9H-purin-6-yl]amino}-N-(1-methylethyl)-D-prolinamide | Calc'd 478, found 478 |
| 15-5 | 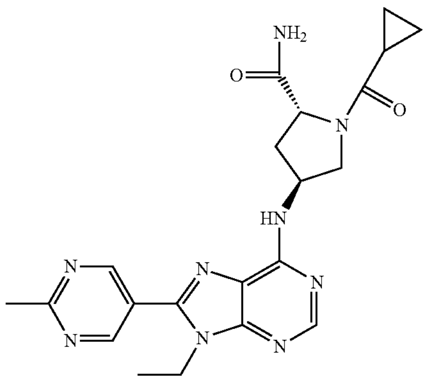 [SMILES: CCn1c(-c2cnc(C)nc2)nc2c(N[C@H]3C[C@H](C(N)=O)N(C(=O)C4CC4)C3)ncnc21] | (4S)-1-(cyclopropylcarbonyl)-4-{[9-ethyl-8-(2-methylpyrimidin-5-yl)-9H-purin-6-yl]amino}-D-prolinamide | Calc'd 436, found 436 |

TABLE 15-continued

| Compound | Structure | Compound Name | Exact Mass [M + H]+ |
|---|---|---|---|
| 15-6 | 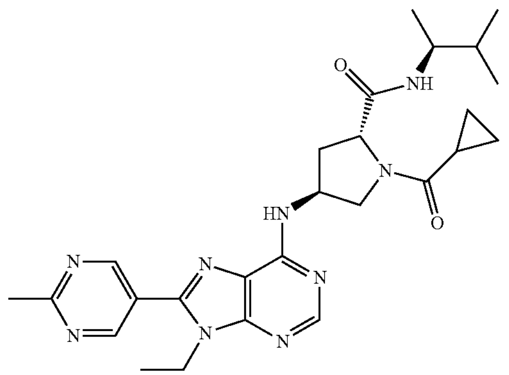 [SMILES: CCn1c(-c2cnc(C)nc2)nc2c(N[C@H]3C[C@H](C(=O)N[C@@H](C)C(C)C)N(C(=O)C4CC4)C3)ncnc21] | (4S)-1-(cyclopropylcarbonyl)-N-[(1S)-1,2-dimethylpropyl]-4-{[9-ethyl-8-(2-methylpyrimidin-5-yl)-9H-purin-6-yl]amino}-D-prolinamide | Calc'd 506, found 506 |
| 15-7 | 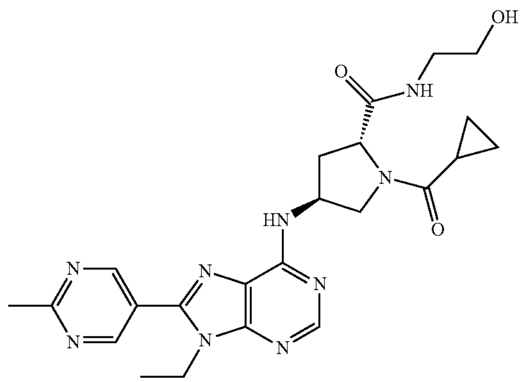 [SMILES: CCn1c(-c2cnc(C)nc2)nc2c(N[C@H]3C[C@H](C(=O)NCCO)N(C(=O)C4CC4)C3)ncnc21] | (4S)-1-(cyclopropylcarbonyl)-4-{[9-ethyl-8-(2-methylpyrimidin-5-yl)-9H-purin-6-yl]amino}-N-(2-hydroxyethyl)-D-prolinamide | Calc'd 480, found 480 |
| 15-8 | 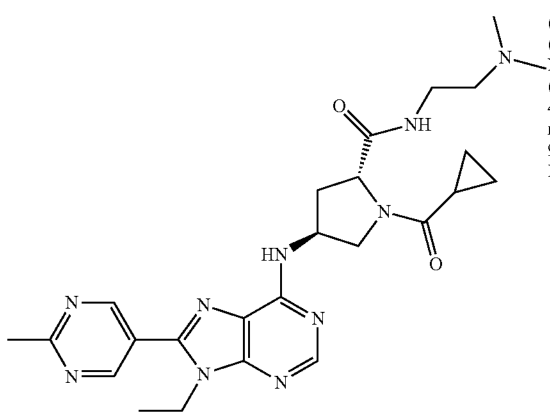 | (4S)-1-(cyclopropylcarbonyl)-N-[2-(dimethylamino)ethyl]-4-{[9-ethyl-8-(2-methylpyrimidin-5-yl)-9H-purin-6-yl]amino}-D-prolinamide | Calc'd 507, found 507 |
| 15-9 | 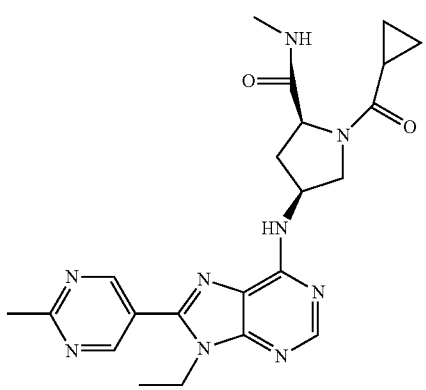 [SMILES: CCn1c(-c2cnc(C)nc2)nc2c(N[C@H]3C[C@@H](C(=O)NC)N(C(=O)C4CC4)C3)ncnc21] | (4S)-1-(cyclopropylcarbonyl)-4-{[9-ethyl-8-(2-methylpyrimidin-5-yl)-9H-purin-6-yl]amino}-N-methyl-L-prolinamide | Calc'd 450, found 450 |

TABLE 15-continued

| Compound | Structure | Compound Name | Exact Mass [M + H]+ |
|---|---|---|---|
| 15-10 | 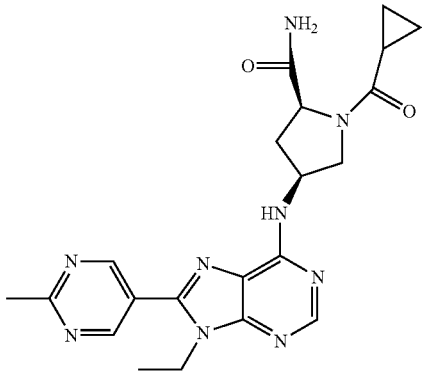 [SMILES: CCn1c(-c2cnc(C)nc2)nc2c(N[C@H]3C[C@@H](C(N)=O)N(C(=O)C4CC4)C3)ncnc21] | (4S)-1-(cyclopropylcarbonyl)-4-{[9-ethyl-8-(2-methylpyrimidin-5-yl)-9H-purin-6-yl]amino}-L-prolinamide | Calc'd 436, found 436 |
| 15-11 | 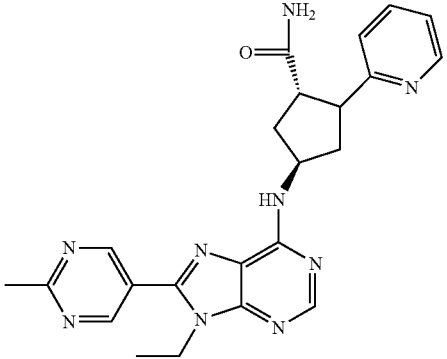 [SMILES: CCn1c(-c2cnc(C)nc2)nc2c(N[C@@H]3CC(c4ccccn4)[C@@H](C(N)=O)C3)ncnc21] | (4S)-4-{[9-ethyl-8-(2-methylpyrimidin-5-yl)-9H-purin-6-yl]amino}-1-pyridin-2-yl-D-prolinamide | Calc'd 445, found 445 |
| 15-12 | 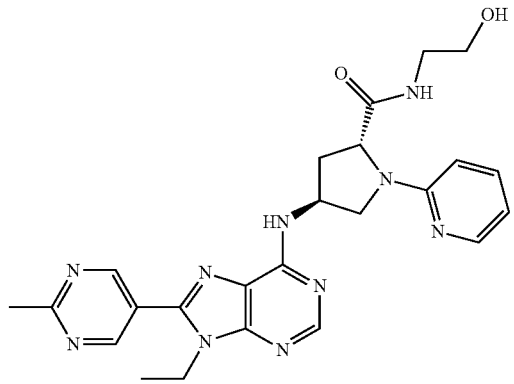 [SMILES: CCn1c(-c2cnc(C)nc2)nc2c(N[C@H]3C[C@H](C(=O)NCCO)N(c4ccccn4)C3)ncnc21] | (4S)-4-{[9-ethyl-8-(2-methylpyrimidin-5-yl)-9H-purin-6-yl]amino}-N-(2-hydroxyethyl)-1-pyridin-2-yl-D-prolinamide | Calc'd 489, found 489 |
| 15-13 | 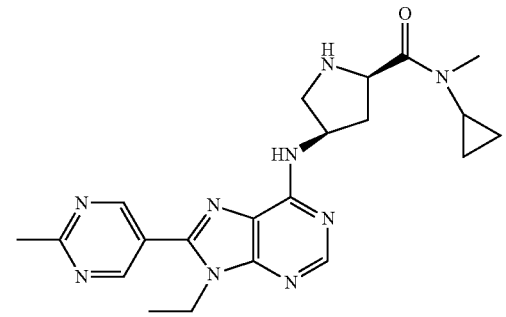 [SMILES: CCn1c(-c2cnc(C)nc2)nc2c(N[C@H]3CN[C@@H](C(=O)N(C)C4CC4)C3)ncnc21] | (4R)-N-cyclopropyl-4-{[9-ethyl-8-(2-methylpyrimidin-5-yl)-9H-purin-6-yl]amino}-N-methyl-D-prolinamide | Calc'd 422, found 422 |

TABLE 15-continued

| Compound | Structure | Compound Name | Exact Mass [M + H]+ |
|---|---|---|---|
| 15-14 | 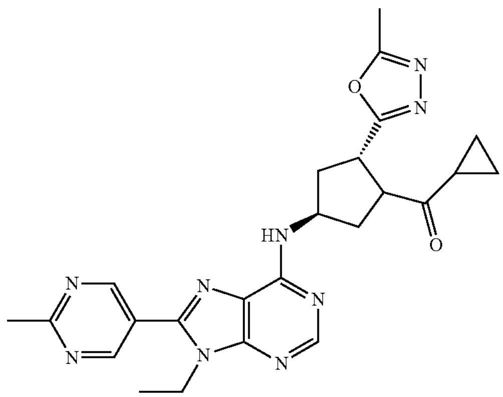 [SMILES: CCn1c(-c2cnc(C)nc2)nc2c(N[C@@H]3CC(C(=O)C4CC4)[C@@H](c4nnc(C)o4)C3)ncnc21] | N-[(3S,5R)-1-(cyclopropylcarbonyl)-5-(5-methyl-1,3,4-oxadiazol-2-yl)pyrrolidin-3-yl]-9-ethyl-8-(2-methylpyrimidin-5-yl)-9H-purin-6-amine | Calc'd 475, found 475 |

Compound Examples of Table 16

Example 31: Preparation of Compound 16-1

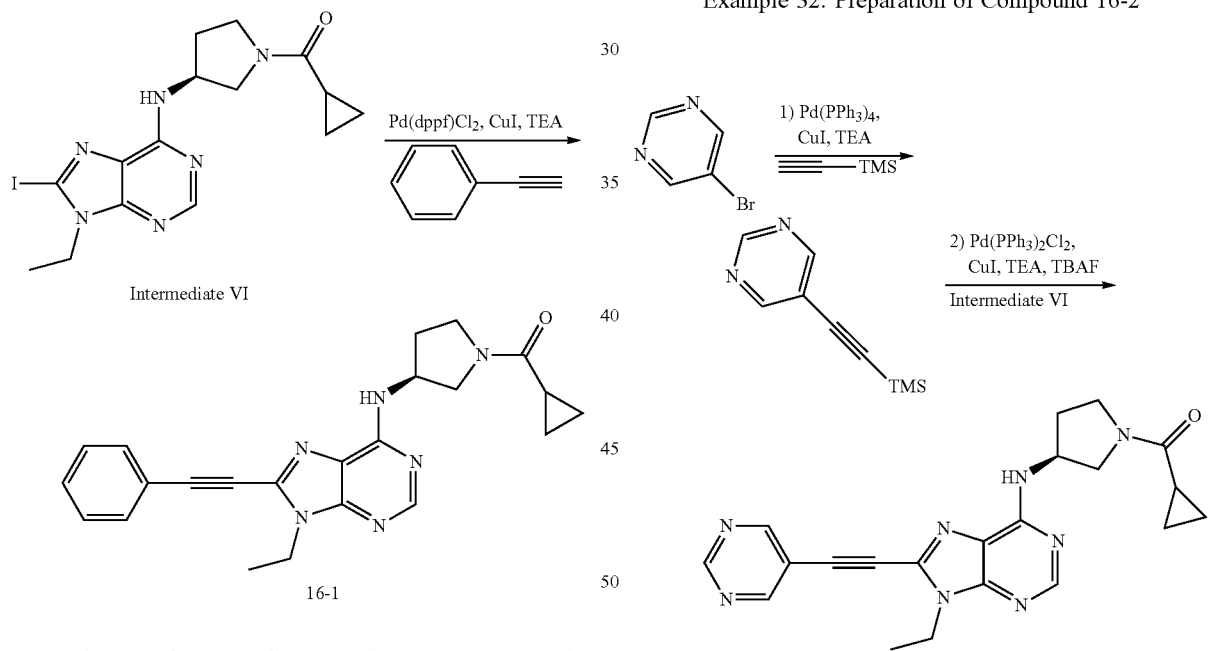

A mixture of Intermediate VI (50 mg, 0.12 mmol), ethynylbenzene (24 mg, 0.24 mmol, commercially available from Zibo Hanwang Trade Co. Ltd.), copper(I) iodide (4.5 mg, 0.02 mmol), triethylamine (23.7 mg, 0.24 mmol) and [1,1'-bis(diphenylphosphino)ferrocene]palladium(II) chloride (PdCl$_2$(dppf)-CH$_2$Cl$_2$) (8.6 mg, 0.01 mmol) in acetonitrile (3 mL) was stirred for 1 hour at 40° C. The mixture was then cooled and concentrated in vacuo. The residue obtained was purified by preparative HPLC [Column: Xbridge RP18, 5 μg, 19×150 mm; mobile phase: water (0.05% Ammonium bicarbonate+Carbon dioxide) and acetonitrile (10% acetonitrile up to 40% in 10 min, hold 100% for 2 min, down to 10% in 2 min)] to afford compound 16-1. $^1$H NMR (300 MHz, CD$_3$OD): δ8.25-8.20 (m, 1H), 7.59 (dd, J=7.5 and 1.5 Hz, 2H), 7.42-7.30 (m, 3H), 5.00-4.75 (m, 1H), 4.36 (q, J=7.2 Hz, 2H), 4.15-3.72 (m, 2H), 3.71-3.44 (m, 2H), 2.40-1.95 (m, 2H), 1.76-1.69 (m, 1H) 1.40 (t, J=7.2 Hz, 3H), 0.83-0.72 (m, 4H). MS (ESI) calc'd for (C$_{23}$H$_{25}$N$_6$O) [M+H]: 401. found, 401.

Example 32: Preparation of Compound 16-2

Step 1: Preparation of 5-((trimethylsilyl)ethynyl)pyrimidine

To a solution of 5-bromo-2-methylpyrimidine (2.0 g, 12.7 mmol, commercially available from Shanghai Bide Pharmatech Ltd) in triethylamine (50 mL) were added ethynyltrimethylsilane (2.0 g, 20.4 mmol), tetrakis(triphenylphosphine)palladium (Pd(PPh$_3$)$_4$) (2.2 g, 1.9 mmol) and copper (I) iodide (0.1 mg, 0.5 mmol). The reaction mixture was stirred at 80° C. for 12 h. The solution was then cooled and filtered, and the filtrate was concentrated in vacuo to give a residue which was purified by silica gel column chromatography eluting with 1%-2% ethyl acetate in petroleum ether to afford 5-((trimethylsilyl)ethynyl)pyrimidine. $^1$H NMR (300 MHz, CDCl$_3$) δ 9.13 (s, 1H), 8.79 (s, 2H), 0.28 (s, 9H). MS (ESI) calc'd for (C$_9$H$_{12}$N$_2$Si) [M+H]$^+$, 177.0. found, 177.0.

Step 2: Preparation of Compound 16-2

To a solution of 5-((trimethylsilyl)ethynyl)pyrimidine (124 mg, 0.69 mmol) in N,N-dimethylformamide (2 mL) were added Intermediate VI (100 mg, 0.23 mmol), bis(triphenylphosphine)palladium(II) chloride (Pd(PPh$_3$)$_2$Cl$_2$) (16.5 mg, 0.023 mmol), copper(I) iodide (13.4 mg, 0.07 mmol), triethylamine (71 mg, 0.39 mmol) and tetrabutylammonium fluoride (61.3 mg, 0.23 mmol). The reaction mixture was stirred at 65° C. for 15 min. The mixture was then cooled and quenched with water (2 mL). The solution was filtered and the filtrate was concentrated in vacuo to give a residue, which was purified by reverse phase preparative HPLC [Column: Sunfire C18 5 m OBD, 19×150 mm; Mobile phase: A: Water (10 mM NH$_4$HCO$_3$), B: acetonitrile; Flow rate: 20 mL/min; UV detection: 220/254 nm] to afford compound 16-2. $^1$H NMR (300 MHz, MeOD-d$_4$) δ 9.25 (s, 1H), 9.11 (s, 2H), 8.36 (m, 1H), 5.10-4.80 (m, 1H), 4.46 (q, J=7.2 Hz, 2H), 4.25-3.55 (m, 4H), 2.51-2.08 (m, 2H), 1.87-1.80 (m, 1H), 1.52 (t, J=7.2 Hz, 3H), 1.00-0.82 (m, 4H). MS (ESI) calc'd for (C$_{21}$H$_{23}$N$_8$O) [M+H]$^+$, 403. found, 403.

Compounds 16-3 and 16-4 were prepared in an analogous fashion to Example 31 using the corresponding acetylenes.

TABLE 16

| Compound | Structure | Compound Name | Exact Mass [M + H]+ |
|---|---|---|---|
| 16-1 | 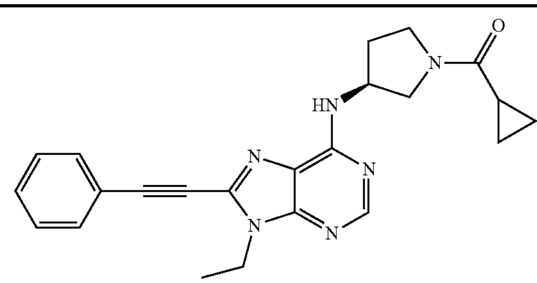 | N-[(3S)-1-(cyclopropylcarbonyl)pyrrolidin-3-yl]-9-ethyl-8-(phenylethynyl)-9H-purin-6-amine | Calc'd 401, found 401 |
| 16-2 | 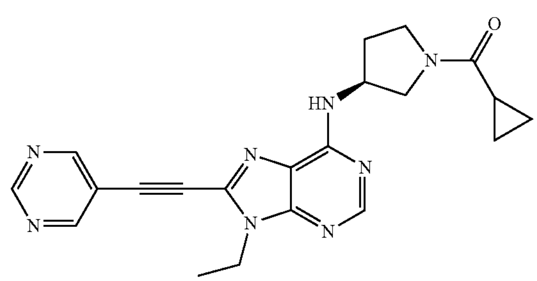 [SMILES: CCn1c(C#Cc2cncnc2)nc2c(N[C@H]3CCN(C(=O)C4CC4)C3)ncnc21] | N-[(3S)-1-(cyclopropylcarbonyl)pyrrolidin-3-yl]-9-ethyl-8-(pyrimidin-5-ylethynyl)-9H-purin-6-amine | Calc'd 403, found 403 |
| 16-3 | 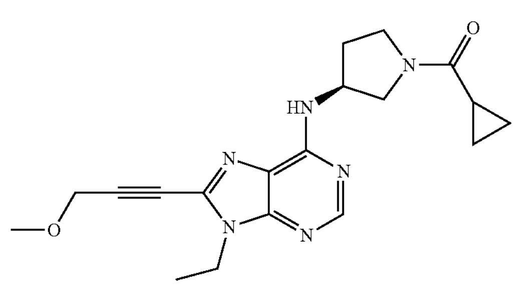 [SMILES: CCn1c(C#CCOC)nc2c(N[C@H]3CCN(C(=O)C4CC4)C3)ncnc21] | N-[(3S)-1-(cyclopropylcarbonyl)pyrrolidin-3-yl]-9-ethyl-8-(3-methoxyprop-1-yn-1-yl)-9H-purin-6-amine | Calc'd 369, found 369 |
| 16-4 | 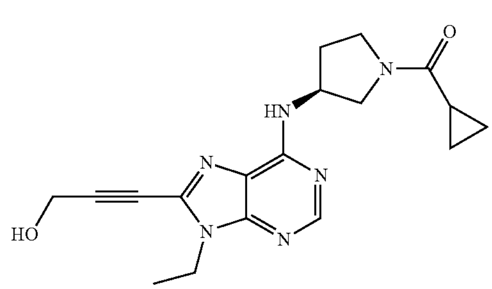 [SMILES: CCn1c(C#CCO)nc2c(N[C@H]3CCN(C(=O)C4CC4)C3)ncnc21] | 3-(6-{[(3S)-1-(cyclopropylcarbonyl)pyrrolidin-3-yl]amino}-9-ethyl-9H-purin-8-yl)prop-2-yn-1-ol | Calc'd 355, found 355 |

HTRF PI3K Biochemical Assay to Measure Intrinsic Potency of Compound Inhibitors

The PI3-Kinase biochemical assays were developed to measure the intrinsic potency and compound dependent inhibition of the alpha, beta, delta, and gamma PI3K isoform enzymes. This assay was developed and further optimized from a kit produced by Upstate (Millipore catalog #33-047) and has been configured for HTS and SAR screening. Briefly, this procedure exploits the exquisite specificity and high affinity binding of enzyme reaction substrate phosphatidyl(3,4,5)triphosphate (PIP3) to the GRP1 pleckstrin homology (PH) domain to generate the signal. In the absence of PIP3, an HTRF (Homogeneous Time-Resolved Fluorescence energy transfer) complex is formed consisting of europium (Eu)-labeled anti-GST, GSTtagged GRP1-PH domain, biotin-PIP3 and streptavidin conjugated APC. The native PIP3 produced by PI3-Kinase activity disrupts in a competitive manner the biotin-PIP3 from the PH domain, resulting in the loss of energy transfer (HTRF complex) and a decrease in the signal. The format of this assay is the same for all 4 isoforms of PI3K; the differences lie in the concentration of enzyme used to achieve robust assay window. The alpha, beta, and delta assays are run at 0.5, 1, and 0.3 nM enzymes and the gamma assay is run at 5 nM enzyme. The ATP concentration is 100 uM in the alpha, beta, and delta assays and 50 uM ATP in the gamma assay. All reactions are run at 5 uM PIP2.

Assay Protocol

Compounds are serially diluted (3-fold in 100% DMSO) across a 384-well polypropylene source plated from column 3 to column 12 and column 13 to column 22, to yield 10 concentration dose response for each test compound. Columns 1, 2, 23 and 24 contain either only DMSO or pharmacological known control inhibitor. Once titrations are made, 2.5 nL of the compounds on 384 well plates are reformatted and transferred by acoustic dispense in quadruplicates to a 1536 assay plate (Greiner) to assay across all four PI3K isoform enzymes.

The PI3-Kinase biochemical assay was optimized using the HTRF kit provided by Upstate (Millipore). The assay kit contains six reagents: 1) 4× Reaction Buffer; 2) native PIP2 (substrate); 3) Stop (EDTA); 4) Detection Mix A (Streptavidin-APC); 5) Detection Mix B (Eu-labeled Anti-GST plus GST-tagged PH-domain); 6) Detection Mix C. In addition, the following items were obtained or purchased; PI3Kinase (alpha 14-602, beta 14-603, gamma 14-558 and delta 14-604 from Upstate; Millipore), dithiothreitol (Sigma, D-5545), Adenosine-5' triphosphate (InVitrogen, Cat#AS001A), native PIP3 (PI(3,4,5)P3, diC8, H$^+$, CELLSIGNALS, INC. Cat #907) DMSO (Sigma, 472301).

PI3Kinase Reaction Buffer is prepared by dilution the stock 1:4 with de-ionized water. DTT, PIP2 and Biotin-PIP3 were added to 1536 assay plate at a final concentration of 5 mM, 5 mM and 25 nM on the day of use. Enzyme addition and compound pre-incubation are initiated by the addition of 1.25 ul of PI3K (at twice its final concentration) in the 1× reaction buffer to all wells using a BioRaptor. Plates are incubated at room temperature for 15 minutes. Reactions are initiated by addition of 1.25 ul of 2× substrate solution (PIP2 and ATP in 1× reaction buffer) using BioRaptor. Plates are incubated in humidified chamber at room temperature for one hour. Reactions are quenched by addition of 0.625 uL of stop solution to all wells using the BioRaptor. The quenched reactions are then processed to detect product formation by adding 0.625 uL of Detection Solution to all wells using the BioRaptor (Detection mix C, Detection Mix A, and Detection Mix B combined together in an 18:1:1 ratio prepared 2 hours prior to use). Following a one hour incubation in the dark, the HTRF signal is measured on the Envision plate reader set for 330 nm excitation and dual emission detection at 620 nM (Eu) and 665 nM (APC).

Data Analysis

The loss of the HTRF signal is due to the displacement of biotinylated-PIP3 from the PH domain by the PI3K-dependent conversion of PIP2 to PIP3. This loss of signal is nonlinear with respect to both increasing product and time. This non-linear detection will impact accuracy of $IC_{50}$ calculations; therefore, there is a need for a correction factor to obtain more accurate $IC_{50}$ values. This correction is derived from a PIP3 standard curve run in a separate assay plate. All data were calculated using the ratio of acceptor (APC) to donor (Europium) fluorescence in each well of the assay plate. The percent inhibition for each compound concentration was calculated as follows: % inhibition=100× (fluorescence ratio−CtrlB)/(CtrlA−CtrlB) where CtrlA=PI3Kinase reaction+known reference inhibitor and CtrlB=PI3K+DMSO. An $IC_{50}$ was then calculated fitting the % inhibition data to the equation: % inhibition=min+(Max−min)/1+([inhibitor]/$IC_{50}$)^n) where min is the % inhibition with inhibitor, max is the signal in DMSO control, and n is the Hill slope.

Biological Data

The following table tabulates the biological data disclosed for the instant invention. The biological data was collected using the methodology described above. For each compound, PI3Kdelta $IC_{50}$ values are listed along with the relative selectivity versus PI3Kalpha, as well as the physical form of the compound dosed in this assay.

The determination of relative selectivity for a given compound is defined as the relative ratio of the (PI3K-alpha$IC_{50}$ value/PI3K-delta $IC_{50}$ value).

| Compound Number | Form Screened | PI3Kdelta IC50 (nM) | Selectivity versus PI3Kalpha |
|---|---|---|---|
| 1-1 | neutral | 15 | >10 |
| 1-2 | neutral | 1.8 | >10 |
| 1-3 | TFA salt | 98 | >10 |
| 1-4 | TFA salt | 1.7 | >10 |
| 1-5 | TFA salt | <1.0 | >10 |
| 1-6 | TFA salt | <1.0 | 8 |
| 1-7 | TFA salt | 6.7 | >10 |
| 1-8 | TFA salt | 1.7 | >10 |
| 1-9 | TFA salt | <1.0 | >10 |
| 1-10 | neutral | 15 | >10 |
| 1-11 | neutral | 250 | >10 |
| 1-12 | neutral | 19 | >10 |
| 1-13 | neutral | <1.0 | >10 |
| 1-14 | TFA salt | 1.1 | >10 |
| 1-15 | neutral | 10 | >10 |
| 1-16 | neutral | 49 | >10 |
| 1-17 | TFA salt | 8.8 | >10 |
| 1-18 | TFA salt | 2.0 | >10 |
| 1-19 | TFA salt | 69 | >10 |
| 1-20 | TFA salt | 12 | >10 |
| 1-21 | neutral | 9.4 | >10 |
| 1-22 | TFA salt | <1.0 | >10 |
| 1-23 | TFA salt | <1.0 | >10 |
| 1-24 | TFA salt | 1.5 | >10 |
| 2-1 | TFA salt | 32 | >10 |
| 2-2 | TFA salt | 52 | |
| 2-3 | TFA salt | <1.0 | >10 |
| 2-4 | TFA salt | <1.0 | >10 |
| 2-5 | TFA salt | 1.5 | >10 |

-continued

| Compound Number | Form Screened | PI3Kdelta IC50 (nM) | Selectivity versus PI3Kalpha |
|---|---|---|---|
| 2-6 | TFA salt | 1.6 | >10 |
| 2-7 | TFA salt | 1.2 | >10 |
| 2-8 | TFA salt | 2.2 | >10 |
| 2-9 | TFA salt | <1.0 | >10 |
| 2-10 | TFA salt | <1.0 | >10 |
| 2-11 | TFA salt | 3.6 | >10 |
| 2-12 | TFA salt | 3.5 | >10 |
| 2-13 | TFA salt | 17 | >10 |
| 2-14 | TFA salt | 1.2 | >10 |
| 2-15 | TFA salt | <1.0 | >10 |
| 2-16 | TFA salt | 53 | >10 |
| 2-17 | TFA salt | 2.7 | >10 |
| 2-18 | TFA salt | 2.4 | >10 |
| 2-19 | TFA salt | 2.1 | >10 |
| 2-20 | TFA salt | 1.4 | >10 |
| 2-21 | TFA salt | <1.0 | >10 |
| 2-22 | TFA salt | 1.7 | >10 |
| 2-23 | TFA salt | 8.0 | >10 |
| 2-24 | TFA salt | 6.8 | >10 |
| 2-25 | neutral | 3.7 | >10 |
| 2-26 | neutral | 10 | >10 |
| 2-27 | neutral | 28 | >10 |
| 2-28 | neutral | 15 | >10 |
| 2-29 | neutral | 11 | >10 |
| 2-30 | TFA salt | 15 | >10 |
| 2-31 | TFA salt | 10 | >10 |
| 2-32 | neutral | 3.1 | >10 |
| 2-33 | neutral | 3.1 | >10 |
| 2-34 | TFA salt | 11 | >10 |
| 2-35 | TFA salt | <1.0 | >10 |
| 2-36 | neutral | 17 | >10 |
| 2-37 | neutral | <1.0 | >10 |
| 2-38 | neutral | 1.7 | >10 |
| 2-39 | neutral | <1.0 | >10 |
| 2-40 | neutral | 1.6 | >10 |
| 2-41 | neutral | 4.3 | >10 |
| 2-42 | TFA salt | 29 | >10 |
| 2-43 | TFA salt | 16 | >10 |
| 2-44 | neutral | 9.0 | >10 |
| 2-45 | neutral | 57 | >10 |
| 2-46 | neutral | 9.2 | >10 |
| 2-47 | TFA salt | 17 | >10 |
| 2-48 | neutral | 16 | >10 |
| 2-49 | TFA salt | 1.0 | >10 |
| 2-50 | TFA salt | <1.0 | >10 |
| 2-51 | TFA salt | <1.0 | >10 |
| 2-52 | TFA salt | 4.9 | >10 |
| 2-53 | TFA salt | 4.7 | >10 |
| 2-54 | TFA salt | 63 | >10 |
| 2-55 | TFA salt | 1.5 | >10 |
| 2-56 | TFA salt | 1.0 | >10 |
| 2-57 | TFA salt | 7.1 | >10 |
| 2-58 | TFA salt | 22 | >10 |
| 2-59 | TFA salt | <1.0 | >10 |
| 2-60 | TFA salt | 1.6 | >10 |
| 2-61 | TFA salt | 23 | >10 |
| 2-62 | TFA salt | 6.0 | >10 |
| 2-63 | TFA salt | <1.0 | >10 |
| 2-64 | TFA salt | 6.7 | >10 |
| 2-65 | TFA salt | 11 | >10 |
| 2-66 | TFA salt | 10 | >10 |
| 2-67 | TFA salt | 1.5 | >10 |
| 2-68 | TFA salt | 26 | >10 |
| 2-69 | TFA salt | 3.8 | >10 |
| 2-70 | TFA salt | 7.4 | >10 |
| 2-71 | TFA salt | 4.2 | >10 |
| 2-72 | TFA salt | 2.8 | >10 |
| 2-73 | TFA salt | 4.2 | >10 |
| 2-74 | TFA salt | 3.1 | >10 |
| 2-75 | TFA salt | 4.7 | >10 |
| 2-76 | TFA salt | 3.1 | >10 |
| 2-77 | TFA salt | 2.1 | >10 |
| 2-78 | TFA salt | 4.6 | >10 |
| 2-79 | TFA salt | 17 | >10 |
| 2-80 | TFA salt | 61 | >10 |
| 2-81 | TFA salt | 13 | >10 |
| 2-82 | TFA salt | 21 | >10 |
| 2-83 | TFA salt | 19 | >10 |
| 2-84 | TFA salt | 20 | >10 |
| 2-85 | TFA salt | 7.3 | >10 |
| 2-86 | TFA salt | 46 | >10 |
| 2-87 | TFA salt | 1.7 | >10 |
| 2-88 | TFA salt | <1.0 | >10 |
| 2-89 | TFA salt | 3.9 | >10 |
| 2-90 | neutral | 1.3 | >10 |
| 2-91 | neutral | 12 | >10 |
| 2-92 | neutral | <1.0 | >10 |
| 2-93 | neutral | 11.2 | >10 |
| 2-94 | neutral | <1.0 | >10 |
| 2-95 | neutral | 4.5 | >10 |
| 2-96 | neutral | 6.0 | >10 |
| 2-97 | neutral | 2.9 | >10 |
| 2-98 | neutral | 2.8 | >10 |
| 2-99 | neutral | 2.8 | >10 |
| 2-100 | neutral | 6.3 | >10 |
| 2-101 | neutral | <1.0 | >10 |
| 2-102 | neutral | <1.0 | >10 |
| 2-103 | neutral | 1.8 | >10 |
| 2-104 | neutral | 3.4 | >10 |
| 2-105 | neutral | <1.0 | >10 |
| 2-106 | neutral | 1.2 | >10 |
| 3-1 | neutral | 11 | >10 |
| 3-2 | neutral | <1.0 | >10 |
| 3-3 | neutral | 4.3 | >10 |
| 3-4 | neutral | 7.7 | >10 |
| 3-5 | neutral | 4.5 | >10 |
| 3-6 | neutral | 1.6 | >10 |
| 3-7 | neutral | 2.2 | >10 |
| 3-8 | neutral | 14 | >10 |
| 3-9 | neutral | 1.3 | >10 |
| 3-10 | neutral | 1.8 | >10 |
| 3-11 | neutral | <1.0 | >10 |
| 3-12 | neutral | 690 | >10 |
| 3-13 | neutral | 2.4 | >10 |
| 3-14 | neutral | 2.1 | >10 |
| 3-15 | neutral | 4.3 | >10 |
| 3-16 | neutral | 3.4 | >10 |
| 3-17 | neutral | <1.0 | >10 |
| 3-18 | neutral | 2.6 | >10 |
| 3-19 | neutral | 3.8 | >10 |
| 3-20 | neutral | 3.5 | >10 |
| 3-21 | neutral | 3.4 | >10 |
| 3-22 | neutral | 2.9 | >10 |
| 3-23 | neutral | 5.4 | >10 |
| 3-24 | neutral | <1.0 | >10 |
| 3-25 | neutral | <1.0 | >10 |
| 3-26 | neutral | 34 | >10 |
| 3-27 | neutral | 39 | >10 |
| 3-28 | neutral | 6.7 | >10 |
| 3-29 | neutral | 40 | >10 |
| 3-30 | TFA salt | 1.2 | >10 |
| 3-31 | neutral | 4.0 | >10 |
| 3-32 | neutral | 1.9 | >10 |
| 3-33 | TFA salt | 2.3 | >10 |
| 3-34 | TFA salt | 2.0 | >10 |
| 3-35 | neutral | <1.0 | >10 |
| 3-36 | neutral | 1.2 | >10 |
| 3-37 | neutral | 5.4 | >10 |
| 3-38 | neutral | 1.8 | >10 |
| 3-39 | neutral | 3.4 | >10 |
| 3A-1 | TFA salt | 1.0 | >10 |
| 3A-2 | TFA salt | <1.0 | >10 |
| 3A-3 | TFA salt | <1.0 | >10 |
| 3A-4 | TFA salt | <1.0 | >10 |
| 3A-5 | TFA salt | <1.0 | >10 |
| 3A-6 | TFA salt | <1.0 | >10 |
| 3A-7 | TFA salt | <1.0 | >10 |
| 3A-8 | TFA salt | <1.0 | >10 |
| 4-1 | neutral | <1.0 | >10 |

-continued

| Compound Number | Form Screened | PI3Kdelta IC50 (nM) | Selectivity versus PI3Kalpha |
|---|---|---|---|
| 4-2 | neutral | 6.9 | >10 |
| 4-3 | neutral | 3.7 | >10 |
| 4-4 | neutral | <1.0 | >10 |
| 4-5 | neutral | 9.6 | >10 |
| 4-6 | neutral | 4.7 | >10 |
| 4-7 | neutral | 1.4 | >10 |
| 4-8 | neutral | 2.3 | >10 |
| 4-9 | neutral | 6.6 | >10 |
| 4-10 | neutral | 13 | >10 |
| 4-11 | neutral | 12 | >10 |
| 4-12 | TFA salt | 8.2 | >10 |
| 4-13 | TFA salt | 14 | >10 |
| 5-1 | TFA salt | 13 | >10 |
| 5-2 | neutral | 35 | >10 |
| 5-3 | TFA salt | 32 | >10 |
| 5-4 | TFA salt | 5.3 | >10 |
| 5-5 | TFA salt | 3.7 | >10 |
| 5-6 | TFA salt | 11 | >10 |
| 5-7 | TFA salt | 120 | >10 |
| 5-8 | neutral | 12 | >10 |
| 6-1 | neutral | 20 | >10 |
| 6-2 | neutral | 85 | >10 |
| 6-3 | neutral | 6.7 | >10 |
| 6-4 | neutral | 140 | >10 |
| 6-5 | neutral | 800 | >10 |
| 6-6 | neutral | 62 | >10 |
| 6-7 | neutral | 19 | >10 |
| 6-8 | neutral | 72 | >10 |
| 6-9 | neutral | 3.3 | >10 |
| 6-10 | neutral | 16 | >10 |
| 6-11 | neutral | 73 | >10 |
| 6-12 | neutral | 25 | >10 |
| 6-13 | neutral | 12 | >10 |
| 6-14 | TFA salt | 17 | >10 |
| 6-15 | neutral | 230 | >10 |
| 6-16 | neutral | 20 | >10 |
| 6-17 | neutral | 14 | >10 |
| 6-18 | neutral | 15 | >10 |
| 6-19 | neutral | 31 | >10 |
| 6-20 | neutral | 23 | >10 |
| 6-21 | neutral | 17 | >10 |
| 7-1 | neutral | 47 | >10 |
| 7-2 | neutral | 51 | >10 |
| 7-3 | TFA salt | 140 | >10 |
| 7-4 | TFA salt | 500 | >10 |
| 7-5 | neutral | 130 | >10 |
| 7-6 | TFA salt | 110 | >10 |
| 7-7 | neutral | 770 | >10 |
| 7-8 | neutral | 190 | >10 |
| 7-9 | TFA salt | 98 | >10 |
| 7-10 | neutral | 120 | >10 |
| 7-11 | neutral | 14 | >10 |
| 7-12 | TFA salt | 39 | >10 |
| 7-13 | neutral | 32 | >10 |
| 7-14 | neutral | 22 | >10 |
| 7-15 | TFA salt | 7.6 | >10 |
| 7-16 | TFA salt | 120 | >10 |
| 7-17 | neutral | 74 | >10 |
| 7-18 | neutral | 11 | >10 |
| 7-19 | neutral | 380 | >10 |
| 7-20 | neutral | 710 | >10 |
| 7-21 | neutral | 2.4 | >10 |
| 7-22 | neutral | 230 | >10 |
| 7-23 | neutral | 120 | >10 |
| 7-24 | neutral | 150 | >10 |
| 7-25 | neutral | 100 | >10 |
| 7-26 | neutral | 28 | >10 |
| 7-27 | neutral | 5.2 | >10 |
| 7-28 | neutral | 3.2 | >10 |
| 8-1 | neutral | 510 | >10 |
| 8-2 | neutral | <1.0 | >10 |
| 8-3 | neutral | 11 | >10 |
| 8-4 | TFA salt | 100 | >10 |
| 8-5 | neutral | 23 | >10 |
| 8-6 | neutral | 8.2 | >10 |
| 8-7 | neutral | 35 | >10 |
| 8-8 | neutral | <1.0 | >10 |
| 9-1 | neutral | 20 | >10 |
| 9-2 | neutral | 36 | >10 |
| 9-3 | neutral | 67 | >10 |
| 9-4 | neutral | <1.0 | >10 |
| 9-5 | neutral | 580 | >10 |
| 10-1 | neutral | 42 | >10 |
| 10-2 | neutral | 41 | >10 |
| 10-3 | neutral | 96 | >10 |
| 11-1 | neutral | 7.4 | >10 |
| 12-1 | neutral | 30 | >10 |
| 12-2 | neutral | 8.9 | >10 |
| 12-3 | neutral | 1.6 | >10 |
| 12-4 | neutral | 4.5 | >10 |
| 12-5 | neutral | 1.2 | >10 |
| 12-6 | neutral | 1.7 | >10 |
| 12-7 | TFA salt | 6.4 | >10 |
| 12-8 | neutral | 9.7 | >10 |
| 12-9 | neutral | 1.4 | >10 |
| 12-10 | TFA salt | <1.0 | >10 |
| 12-11 | TFA salt | <1.0 | >10 |
| 12-12 | TFA salt | 2.9 | >10 |
| 12-13 | TFA salt | 1.7 | >10 |
| 12-14 | TFA salt | 1.6 | >10 |
| 12-15 | TFA salt | 8.2 | >10 |
| 12-16 | TFA salt | 16 | >10 |
| 12-17 | TFA salt | 13 | >10 |
| 12-18 | TFA salt | 13 | >10 |
| 12-19 | TFA salt | 13 | >10 |
| 12-20 | TFA salt | 9.4 | >10 |
| 12-21 | TFA salt | 7.0 | >10 |
| 12-22 | TFA salt | 5.3 | >10 |
| 12-23 | TFA salt | 3.5 | >10 |
| 12-24 | TFA salt | 1.9 | >10 |
| 12-25 | TFA salt | 1.4 | >10 |
| 12-26 | neutral | <1.0 | >10 |
| 12-27 | neutral | 5.1 | >10 |
| 13-1 | TFA salt | 21 | >10 |
| 13-2 | TFA salt | 9.2 | >10 |
| 13-3 | TFA salt | 8.7 | >10 |
| 13-4 | TFA salt | 8.2 | >10 |
| 13-5 | TFA salt | 6.2 | >10 |
| 13-6 | TFA salt | 4.6 | >10 |
| 13-7 | TFA salt | 4.1 | >10 |
| 13-8 | TFA salt | 3.9 | >10 |
| 13-9 | TFA salt | 3.5 | >10 |
| 13-10 | TFA salt | 2.0 | >10 |
| 13-11 | neutral | 4.3 | >10 |
| 14-1 | neutral | 11 | >10 |
| 14-2 | neutral | 10 | >10 |
| 14-3 | neutral | 5.4 | >10 |
| 14-4 | neutral | 24 | >10 |
| 14-5 | neutral | 21 | >10 |
| 14-6 | neutral | 4.3 | >10 |
| 14-7 | neutral | 13 | >10 |
| 15-1 | neutral | 2.5 | >10 |
| 15-2 | TFA salt | 14 | >10 |
| 15-3 | TFA salt | 12 | >10 |
| 15-4 | TFA salt | 15 | >10 |
| 15-5 | TFA salt | 3.0 | >10 |
| 15-6 | TFA salt | 20 | >10 |
| 15-7 | TFA salt | 5.8 | >10 |
| 15-8 | TFA salt | 8.8 | >10 |
| 15-9 | TFA salt | 46 | >10 |
| 15-10 | TFA salt | 60 | >10 |
| 15-11 | TFA salt | 7.7 | >10 |
| 15-12 | TFA salt | 4.6 | >10 |
| 15-13 | TFA salt | 29 | >10 |
| 15-14 | TFA salt | 39 | >10 |
| 16-1 | neutral | 1.9 | >10 |
| 16-2 | neutral | 20 | >10 |
| 16-3 | neutral | 63 | >10 |
| 16-4 | neutral | 48 | >10 |

The invention claimed is:
1. A compound of formula I or a pharmaceutically acceptable salt or stereoisomer thereof:

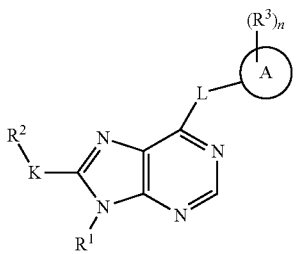

I

R¹ is selected from methyl, ethyl, propyl, cyclopropyl, cyclopropylmethyl, 2-2-difluoroethyl, and 2-2-2-trifluoroethyl;
R² is selected from pyrimidinyl, pyridinyl, pyrrolo[2,3-b]pyridinyl, pyrrolidinyl, oxetanyl, cyclohexyl, azetidinyl, phenyl, pyrazolyl, imidazolyl, indolyl, indazolyl, thiazolyl, hydrogen, 1H-pyrazolo[3,4-b]pyridinyl], benzimidazolyl, cyclopropyl, tert-butyl, ethyl, methyl, methylpropyl, 4,5,6,7-tetrahydro-1H-benzimidazolyl, and morpholinyl, wherein R² is substituted with 0, 1, 2, 3, or 4 independently selected R³ substituents;
n is 0, 1, 2, 3, or 4;
A is selected from pyrrolidinyl, piperidinyl, azetidinyl, azaspiro[2.4]hept-7-yl, and azepanyl;
L is selected from NH, and N($C_{1-10}$alkyl);
K is selected from a bond, NH, O, C(O), CH₂, N($C_{1-5}$) alkyl, —C(O)N(R$^b$)—(CH₂)$_m$—, N, S, SO₂, and $C_{2-10}$ alkynylene;
R$^b$ is H or $C_{1-10}$ alkyl,
m is 0, 1, 2, or 3;
R³ is independently selected from:
fluoro, chloro, methyl, ethyl, propyl, methoxy, methoxymethyl, methylethyl, 2-methylbuten-4-yl, 2-methylpropyl, 1,3,4-oxadiazolyl, pyridinyl, isoquinolinyl, cyclopropylmethyl, cyclopropylethyl, isopropyl, hydroxy, oxo, dimethylamino, tert-butyl, trifluoromethyl, trifluoroethyl, carboxy, tert-butylcarboxy, fluoroethylcarboxy, tetrahydrothiophenylcarboxy, methylpropylcarboxy, propylcarboxy, benzylcarboxy, 2,2-dimethylpropylcarboxy, methylcarboxy, ethylcarboxy, methylethylcarboxy, cyclopentylcarbonyl, cyclohexylcarboxy, cyclobutylcarbonyl, 2,2,2-trifluoroethylcarboxy, spiro[2.4]hept-1-ylcarbonyl, spiro[2.5]oct-1-ylcarbonyl, benzylcarbonyl, imidazolylcarbonyl, ethylcarbonyl, piperidinylcarbonyl, pyrrolidinylcarbonyl, cyclohexylcarbonyl, isopropylcarbonyl, tetrahydro-2H-pyran-4-ylcarbonyl, oxazolylcarbonyl, cyclopropylcarbonyl, azetidinylcarbonyl, cyclopropylaminocarbonyl, tetrahydrofuranylcarbonyl, isoxazolylcarbonyl, triazolylcarbonyl, thiadiazolylcarbonyl, cyclobutylaminocarbonyl, furanylmethylaminocarbonyl, aminocarbonyl, pyrazolylcarbonyl, hydroxymethyl, oxadiazolylcarbonyl, ethylsulfonyl, methylsulfonyl, (cyclopropylmethyl)aminocarbonyl, azabicyclo[3.1.0]hex-6-ylcarbonyl, trifluoroethylaminocarbonyl, (tetrahydrothiophenylmethyl)aminocarbonyl, cyclohexylaminocarbonyl, ethylaminocarbonyl, (1,1,3,3-tetramethylbutyl)aminocarbonyl, oxazolylcarbonylamino, dimethylpropylaminocarbonyl, methylcarbonylamino, bicyclo[1.1.1]pent-1-ylcarbonyl, methylaminocarbonyl, propylaminocarbonyl, isopropylaminocarbonyl, phenyl, pyrimidinyl, thieno[3,2-c]pyridinyl, morpholinylcarbonyl, butylaminocarbonyl,
2-methylprop-1-enyl, cyano, (methylamino)methylcarbonyl, amino, hydroxyisopropyl, 2-hydroxypropyl, hydroxycarbonyl, methoxycarbonyl, and isobutylcarbonyl; wherein R³ is each substituted with 0, 1, 2, 3, or 4 substituents, R⁴;
wherein R³ is each substituted with 0, 1, 2, 3, or 4 R⁴ substituents and each R⁴ is independently selected from:
halogen,
$C_{1-10}$ alkyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
aryl $C_{2-10}$ alkynyl(oxy)$_{0-1}$(carbonyl)$_{0-1}C_{0-10}$ alkyl,
$C_{3-12}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
($C_{3-12}$)heterocycloalkyl $C_{0-10}$ alkyl(oxy)$_{0-1}$(carbonyl)$_{0-1}C_{0-10}$ alkyl,
$C_{1-10}$ alkyl(carbonyl)$_{0-1}$oxy$C_{0-10}$ alkyl,
$C_{1-10}$ heteroalkyl(carbonyl)$_{0-1}$oxy$C_{0-10}$ alkyl,
aryl $C_{0-10}$ alkyl (carbonyl)$_{0-1}$oxy$C_{0-10}$ alkyl,
($C_{3-12}$)cycloalkyl $C_{0-10}$ alkyl(carbonyl)$_{0-1}$oxy$C_{0-10}$ alkyl,
heteroaryl$C_{0-10}$ alkyl(carbonyl)$_{0-1}$oxy$C_{0-10}$ alkyl,
($C_{3-12}$)heterocycloalkyl $C_{0-10}$ alkyl(carbonyl)$_{0-1}$oxy $C_{0-10}$ alkyl,
(($C_{0-10}$)alkyl)$_{1-2}$aminocarbonyloxy,
aryl ($C_{0-10}$)alkylaminocarbonyloxy,
($C_{3-12}$)cycloalkyl($C_{0-10}$)alkylaminocarbonyloxy,
heteroaryl($C_{0-10}$)alkylaminocarbonyloxy,
($C_{3-12}$)heterocycloalkyl($C_{0-10}$)alkylaminocarbonyloxy,
$C_{1-10}$ alkylaminocarbonyl$C_{0-10}$ alkyl,
$C_{3-12}$ cycloalkyl $C_{0-10}$ alkylaminocarbonyl$C_{0-10}$ alkyl,
aryl $C_{0-10}$ alkylaminocarbonyl$C_{0-10}$ alkyl,
heteroaryl $C_{0-10}$ alkylaminocarbonyl$C_{0-10}$ alkyl,
($C_{3-12}$)heterocycloalkyl $C_{0-10}$ alkylaminocarbonyl$C_{0-10}$ alkyl,
$C_{1-10}$ alkyl (oxy)$_{0-1}$(carbonyl)$_{0-1}$amino$C_{0-10}$ alkyl,
$C_{3-12}$ cycloalkyl $C_{0-10}$ alkyl (oxy)$_{0-1}$(carbonyl)$_{0-1}$amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino$C_{0-10}$ alkyl,
($C_{3-12}$)heterocycloalkyl $C_{0-10}$ alkyl(oxy)$_{0-1}$(carbonyl)$_{0-1}$amino$C_{0-10}$ alkyl,
—CO₂($C_{0-10}$ alkyl),
—($C_{0-10}$ alkyl)CO₂H,
Oxo (=O),
$C_{1-10}$ alkylS(O)$_{1-2}$,
$C_{1-10}$ heteroalkyl S(O)$_{1-2}$,
($C_{3-12}$)cycloalkyl S(O)$_{1-2}$,
($C_{3-12}$)cycloheteroalkylS(O)$_{1-2}$,
heteroarylS(O)$_{1-2}$,
aryl S(O)$_{1-2}$,
$C_{0-6}$ alkyl(amino)$_{0-1}$S(O)$_{1-2}$amino,
$C_{1-10}$ heteroalkyl(amino)$_{0-1}$S(O)$_{1-2}$amino,
($C_{3-12}$)cycloalkyl(amino)$_{0-1}$S(O)$_{1-2}$amino,
($C_{3-12}$)cycloheteroalkyl(amino)$_{0-1}$S(O)$_{1-2}$amino,
heteroaryl(amino)$_{0-1}$S(O)$_{1-2}$amino,
aryl(amino)$_{0-1}$S(O)$_{1-2}$amino,
—SO₂N($C_{1-6}$alkyl)$_{1-2}$,
—SO₂$C_{1-6}$alkyl,
—SO₂CF₃, —SO$_2$CF$_2$H,
amino,
(C$_{0-10}$ alkyl)$_{1-2}$ amino,
-(oxy)$_{0-1}$(carbonyl)$_{0-1}$N(C$_{0-10}$ alkyl)$_{1-2}$,
hydroxy,
(C$_{1-10}$ alkyl)OH,
C$_{1-10}$ alkoxy,
cyano, and
C$_{1-6}$haloalkyl;

R$^4$ is substituted with 0, 1, 2, or 3 R$^5$ substituents and each R$^5$ substituent is independently selected from hydroxy, (C$_{1-6}$)alkyl, (C$_{1-6}$)alkoxy, (C$_{1-10}$ alkyl)OH, halogen, CO$_2$H, —(C$_{0-6}$)alkylCN, —O(C=O)C$_1$-C$_6$ alkyl, —(C=O)OC$_1$-C$_6$ alkyl, NO$_2$, trifluoromethoxy, trifluoroethoxy, trifluoromethyl, trifluoroethyl, —N—C(O)O(C$_{0-6}$)alkyl, C$_{1-10}$ alkylsulfonyl, C$_{1-10}$ heteroalkyl, aryl, (C$_{3-12}$)cycloalkyl, heteroaryl, (C$_{3-12}$)heterocycloalkyl, C$_{1-10}$ heteroalkylsulfonyl, oxo (O=), (C$_{3-12}$)cycloalkylsulfonyl, (C$_{3-12}$)cycloheteroalkylsulfonyl, heteroarylsulfonyl, arylsulfonyl, aminosulfonyl, —SO$_2$N(C$_{1-6}$alkyl)$_{1-2}$, —SO$_2$C$_{1-6}$alkyl, —SO$_2$CF$_3$, —SO$_2$CF$_2$H, —C$_{1-10}$ alkylsulfinyl, —O$_{(0-1)}$(C$_{1-10}$)haloalkyl, amino(C$_{1-6}$alkyl)$_{0-2}$ and NH$_2$; and R$^5$ is substituted with 0, 1, or 2 R$^6$ substituents and each R$^6$ substituent is independently selected from hydroxy, (C$_{1-6}$)alkyl, (C$_{1-6}$)alkoxy, (C$_{1-10}$ alkyl)OH, halogen, CO$_2$H, —(C$_{0-6}$)alkylCN, —O(C=O)C$_1$-C$_6$ alkyl, —(C=O)OC$_1$-C$_6$ alkyl, NO$_2$, trifluoromethoxy, trifluoroethoxy, trifluoromethyl, trifluoroethyl, —N—C(O)O(C$_{0-6}$)alkyl, C$_{1-10}$ alkylsulfonyl, C$_{1-10}$ heteroalkylsulfonyl, oxo (O=), (C$_{3-12}$)cycloalkylsulfonyl, (C$_{3-12}$)cycloheteroalkylsulfonyl, heteroarylsulfonyl, arylsulfonyl, aminosulfonyl, —SO$_2$N(C$_{1-6}$alkyl)$_{1-2}$, —SO$_2$C$_{1-6}$alkyl, —SO$_2$CF$_3$, —SO$_2$CF$_2$H, —O$_{(0-1)}$(C$_{1-10}$)haloalkyl, amino(C$_{1-6}$alkyl)$_{0-2}$ and NH$_2$.

2. A compound or a pharmaceutically acceptable salt, or a stereoisomer thereof, wherein the compound is selected from:

tert-butyl-3-{[8-(1-ethyl-5-methyl-1H-pyrazol-4-yl)-9-methyl-9H-purin-6-yl]amino}pyrrolidine-1-carboxylate;
tert-butyl 3-((8-(1-ethyl-5-methyl-1H-pyrazol-4-yl)-9-methyl-9H-purin-6-yl)(methyl)amino)pyrrolidine-1-carboxylate;
tert-butyl 3-((9-ethyl-8-(6-methoxy-5-methylpyridin-3-yl)-9H-purin-6-yl)(methyl)amino)pyrrolidine-1-carboxylate;
tert-butyl 3-((9-ethyl-8-(6-methoxy-5-methylpyridin-3-yl)-9H-purin-6-yl)amino)pyrrolidine-1-carboxylate;
tert-butyl 3-((8-(2-(tert-butyl)thiazol-5-yl)-9-ethyl-9H-purin-6-yl)amino)pyrrolidine-1-carboxylate;
tert-butyl 3-((8-(2-(tert-butyl)thiazol-5-yl)-9-ethyl-9H-purin-6-yl)(methyl)amino)pyrrolidine-1-carboxylate;
tert-butyl 3-((8-(6-methoxy-5-methylpyridin-3-yl)-9-methyl-9H-purin-6-yl)amino)pyrrolidine-1-carboxylate;
tert-butyl 3-((8-(2-(tert-butyl)thiazol-5-yl)-9-methyl-9H-purin-6-yl)amino)pyrrolidine-1-carboxylate;
tert-butyl 3-((8-(1-ethyl-5-methyl-1H-pyrazol-4-yl)-9-methyl-9H-purin-6-yl)amino)azetidine-1-carboxylate;
tert-butyl 3-((8-(1-ethyl-5-methyl-1H-pyrazol-4-yl)-9-methyl-9H-purin-6-yl)amino)piperidine-1-carboxylate;
tert-butyl 3-((9-ethyl-8-(2-methylpyrimidin-5-yl)-9H-purin-6-yl)amino)pyrrolidine-1-carboxylate;
8-(1-ethyl-5-methyl-1H-pyrazol-4-yl)-9-methyl-N-[1-propanoylpyrrolidin-3-yl]-9H-purin-6-amine;
N-{1-[(2,5-dimethyl-1,3-oxazol-4-yl)carbonyl]pyrrolidin-3-yl}-8-(1-ethyl-5-methyl-1H-pyrazol-4-yl)-9-methyl-9H-purin-6-amine;
8-(1-ethyl-5-methyl-1H-pyrazol-4-yl)-9-methyl-N-[1-propanoylpyrrolidin-3-yl]-9H-purin-6-amine;
8-(1-ethyl-5-methyl-1H-pyrazol-4-yl)-9-methyl-N-[1-(tetrahydro-2H-pyran-4-ylcarbonyl)pyrrolidin-3-yl]-9H-purin-6-amine;
N-{1-[(2,5-dimethyl-1,3-oxazol-4-yl)carbonyl]pyrrolidin-3-yl}-8-(1-ethyl-5-methyl-1H-pyrazol-4-yl)-9-methyl-9H-purin-6-amine;
N-{1-[(2,2-dimethyltetrahydro-2H-pyran-4-yl)carbonyl]pyrrolidin-3-yl}-8-(1-ethyl-5-methyl-1H-pyrazol-4-yl)-9-methyl-9H-purin-6-amine;
N-[1-(cyclopropylcarbonyl)pyrrolidin-3-yl]-8-(1-ethyl-5-methyl-1H-pyrazol-4-yl)-9-methyl-9H-purin-6-amine;
1-(3-((9-ethyl-8-(6-methoxy-5-methylpyridin-3-yl)-9H-purin-6-yl)(methyl)amino)pyrrolidin-1-yl)propan-1-one;
1-(3-((9-ethyl-8-(6-methoxy-5-methylpyridin-3-yl)-9H-purin-6-yl)amino)pyrrolidin-1-yl)propan-1-one;
1-(3-((8-(2-(tert-butyl)thiazol-5-yl)-9-ethyl-9H-purin-6-yl)amino)pyrrolidin-1-yl)propan-1-one;
1-(3-((8-(2-(tert-butyl)thiazol-5-yl)-9-ethyl-9H-purin-6-yl)(methyl)amino)pyrrolidin-1-yl)propan-1-one;
1-(3-((8-(6-methoxy-5-methylpyridin-3-yl)-9-methyl-9H-purin-6-yl)amino)pyrrolidin-1-yl)propan-1-one;
1-(3-((8-(6-methoxy-5-methylpyridin-3-yl)-9-methyl-9H-purin-6-yl)(methyl)amino)pyrrolidin-1-yl)propan-1-one;
1-(3-((8-(2-(tert-butyl)thiazol-5-yl)-9-methyl-9H-purin-6-yl)amino)pyrrolidin-1-yl)propan-1-one;
1-(3-((9-ethyl-8-(1-ethyl-5-methyl-1H-pyrazol-4-yl)-9H-purin-6-yl)amino)pyrrolidin-1-yl)propan-1-one;
1-(3-((9-cyclopropyl-8-(1-ethyl-5-methyl-1H-pyrazol-4-yl)-9H-purin-6-yl)amino)pyrrolidin-1-yl)propan-1-one;
1-(3-((9-ethyl-8-(2-methylpyrimidin-5-yl)-9H-purin-6-yl)amino)pyrrolidin-1-yl)propan-1-one;
(3-((9-ethyl-8-(2-methylpyrimidin-5-yl)-9H-purin-6-yl)amino)pyrrolidin-1-yl)(tetrahydro-2H-pyran-4-yl)methanone;
(2,5-dimethyloxazol-4-yl)(3-((9-ethyl-8-(2-methylpyrimidin-5-yl)-9H-purin-6-yl)amino)pyrrolidin-1-yl)methanone;
(2,2-dimethyltetrahydro-2H-pyran-4-yl)(3-((9-ethyl-8-(2-methylpyrimidin-5-yl)-9H-purin-6-yl)amino)pyrrolidin-1-yl)methanone;
cyclopropyl(3-((9-ethyl-8-(2-methylpyrimidin-5-yl)-9H-purin-6-yl)amino)pyrrolidin-1-yl)methanone;
cyclobutyl(3-((9-ethyl-8-(2-methylpyrimidin-5-yl)-9H-purin-6-yl)amino)pyrrolidin-1-yl)methanone;
cyclopentyl(3-((9-ethyl-8-(2-methylpyrimidin-5-yl)-9H-purin-6-yl)amino)pyrrolidin-1-yl)methanone;
(3,3-difluorocyclobutyl)(3-((9-ethyl-8-(2-methylpyrimidin-5-yl)-9H-purin-6-yl)amino)pyrrolidin-1-yl)methanone;
1-(3-((9-methyl-8-(6-(trifluoromethyl)pyridin-3-yl)-9H-purin-6-yl)amino)pyrrolidin-1-yl)propan-1-one;
1-(3-((9-methyl-8-(1H-pyrrolo[2,3-b]pyridin-5-yl)-9H-purin-6-yl)amino)pyrrolidin-1-yl)propan-1-one;
1-(3-((8-(1H-indazol-5-yl)-9-methyl-9H-purin-6-yl)amino)pyrrolidin-1-yl)propan-1-one;
1-(3-((8-(1H-indol-6-yl)-9-methyl-9H-purin-6-yl)amino)pyrrolidin-1-yl)propan-1-one;
1-(3-((9-methyl-8-(6-methylpyridin-3-yl)-9H-purin-6-yl)amino)pyrrolidin-1-yl)propan-1-one;

1-(3-((8-(1H-indazol-6-yl)-9-methyl-9H-purin-6-yl)amino)pyrrolidin-1-yl)propan-1-one;
1-(3-((8-(6-methoxy-5-(trifluoromethyl)pyridin-3-yl)-9-methyl-9H-purin-6-yl)amino)pyrrolidin-1-yl)propan-1-one;
1-(3-((8-(1H-indol-5-yl)-9-methyl-9H-purin-6-yl)amino)pyrrolidin-1-yl)propan-1-one;
tert-butyl-3-{[9-ethyl-8-(1-ethyl-5-methyl-1H-pyrazol-4-yl)-9H-purin-6-yl]amino}pyrrolidine-1-carboxylate;
tert-butyl-3-{[9-ethyl-8-(2-methylpyrimidin-5-yl)-9H-purin-6-yl]amino}-4-hydroxypyrrolidine-1-carboxylate;
tert-butyl-3-{[9-ethyl-8-(2-methylpyrimidin-5-yl)-9H-purin-6-yl]amino}piperidine-1-carboxylate;
1-tert-butyl 2-methyl-4-{[9-ethyl-8-(2-methylpyrimidin-5-yl)-9H-purin-6-yl]amino}pyrrolidine-1,2-dicarboxylate;
1-(tert-butoxycarbonyl)-4-{[9-ethyl-8-(2-methylpyrimidin-5-yl)-9H-purin-6-yl]amino}-D-proline;
1-tert-butyl 2-methyl-4-{[9-ethyl-8-(2-methylpyrimidin-5-yl)-9H-purin-6-yl]amino}pyrrolidine-1,2-dicarboxylate;
tert-butyl-4-{[9-ethyl-8-(2-methylpyrimidin-5-yl)-9H-purin-6-yl]amino}-2-(hydroxymethyl)pyrrolidine-1-carboxylate;
tert-butyl4-{[9-ethyl-8-(2-methylpyrimidin-5-yl)-9H-purin-6-yl]amino}-3,3-difluoropyrrolidine-1-carboxylate;
tert-butyl-3-({9-ethyl-8-[6-(trifluoromethyl)pyridin-3-yl]-9H-purin-6-yl}amino)pyrrolidine-1-carboxylate;
tert-butyl-3-{[9-ethyl-8-(6-methoxypyridin-3-yl)-9H-purin-6-yl]amino}pyrrolidine-1-carboxylate;
tert-butyl-3-({9-ethyl-8-[4-(trifluoromethyl)phenyl]-9H-purin-6-yl}amino)pyrrolidine-1-carboxylate;
N-[1-(cyclopropylcarbonyl)-4,4-difluoropyrrolidin-3-yl]-9-ethyl-8-(2-methylpyrimidin-5-yl)-9H-purin-6-amine;
N-[-1-(cyclopropylcarbonyl)-4,4-difluoropyrrolidin-3-yl]-9-ethyl-8-(2-methylpyrimidin-5-yl)-9H-purin-6-amine;
9-ethyl-8-(2-methylpyrimidin-5-yl)-N-[-1-propanoylpiperidin-3-yl]-9H-purin-6-amine;
N-[-1-(cyclopropylcarbonyl)piperidin-3-yl]-9-ethyl-8-(2-methylpyrimidin-5-yl)-9H-purin-6-amine;
8-(1-ethyl-5-methyl-1H-pyrazol-4-yl)-9-methyl-N-[-1-(tetrahydro-2H-pyran-4-ylcarbonyl)piperidin-3-yl]-9H-purin-6-amine;
4-[-3-{[9-ethyl-8-(2-methylpyrimidin-5-yl)-9H-purin-6-yl]amino}pyrrolidin-1-yl]-2-methyl-4-oxobutan-2-ol;
N-{-1-[(dimethylamino)acetyl]pyrrolidin-3-yl}-9-ethyl-8-(2-methylpyrimidin-5-yl)-9H-purin-6-amine;
9-ethyl-8-(2-methylpyrimidin-5-yl)-N-[-1-(tetrahydrofuran-2-ylcarbonyl)pyrrolidin-3-yl]-9H-purin-6-amine;
9-ethyl-8-(2-methylpyrimidin-5-yl)-N-[(1-(spiro[2.4]hept-1-ylcarbonyl)pyrrolidin-3-yl]-9H-purin-6-amine;
9-ethyl-8-(2-methylpyrimidin-5-yl)-N-[-1-(phenylacetyl)pyrrolidin-3-yl]-9H-purin-6-amine;
3-((9-ethyl-8-(2-methylpyrimidin-5-yl)-9H-purin-6-yl)amino)pyrrolidin-1-yl)((-2-(fluoromethyl)cyclopropyl)methanone;
9-ethyl-N-{-1-[(trans-3-methoxycyclobutyl)carbonyl]pyrrolidin-3-yl}-8-(2-methylpyrimidin-5-yl)-9H-purin-6-amine;
9-ethyl-8-(2-methylpyrimidin-5-yl)-N-{(-1-[-tetrahydrofuran-3-ylcarbonyl]pyrrolidin-3-yl}-9H-purin-6-amine;
9-ethyl-N-[-1-(1-methyl-D-prolyl)pyrrolidin-3-yl]-8-(2-methylpyrimidin-5-yl)-9H-purin-6-amine;
9-ethyl-N-[-1-(2-methylpropanoyl)piperidin-3-yl]-8-(2-methylpyrimidin-5-yl)-9H-purin-6-amine;
8-(1-ethyl-5-methyl-1H-pyrazol-4-yl)-9-methyl-N-(1-propanoylazetidin-3-yl)-9H-purin-6-amine;
8-(1-ethyl-5-methyl-1H-pyrazol-4-yl)-9-methyl-N-[-1-propanoylpiperidin-3-yl]-9H-purin-6-amine;
9-ethyl-N-{-1-[(1-methylcyclopropyl)carbonyl]pyrrolidin-3-yl}-8-(2-methylpyrimidin-5-yl)-9H-purin-6-amine;
8-(1-ethyl-5-methyl-1H-pyrazol-4-yl)-9-methyl-N-[1-(tetrahydro-2H-pyran-4-ylcarbonyl)azetidin-3-yl]-9H-purin-6-amine;
N-[-1-(cyclopropylcarbonyl)pyrrolidin-3-yl]-9-ethyl-8-[6-(trifluoromethyl)pyridin-3-yl]-9H-purin-6-amine;
N-[-1-(cyclopropylcarbonyl)pyrrolidin-3-yl]-9-ethyl-8-(6-methoxypyridin-3-yl)-9H-purin-6-amine;
N-[1-{[-2,2-dimethylcyclopropyl]carbonyl}pyrrolidin-3-yl]-9-ethyl-8-[6-(trifluoromethyl)pyridin-3-yl]-9H-purin-6-amine;
[1-(cyclopropylcarbonyl)-4-{[9-ethyl-8-(2-methylpyrimidin-5-yl)-9H-purin-6-yl]amino}pyrrolidin-2-yl]methanol;
methyl-1-(cyclopropylcarbonyl)-4-{[9-ethyl-8-(2-methylpyrimidin-5-yl)-9H-purin-6-yl]amino}-D-prolinate;
N-{-1-[(-2,2-difluorocyclopropyl)carbonyl]pyrrolidin-3-yl}-9-ethyl-8-(2-methylpyrimidin-5-yl)-9H-purin-6-amine;
N-{-1-[(-2,2-dimethylcyclopropyl)carbonyl]pyrrolidin-3-yl}-9-ethyl-8-(2-methylpyrimidin-5-yl)-9H-purin-6-amine;
9-ethyl-N-[-1-{[1-(methoxymethyl)cyclobutyl]carbonyl}pyrrolidin-3-yl]-8-(2-methylpyrimidin-5-yl)-9H-purin-6-amine;
1-{[-3-{[9-ethyl-8-(2-methylpyrimidin-5-yl)-9H-purin-6-yl]amino}pyrrolidin-1-yl]carbonyl}cyclopentanol;
N-{-1-[(3,3-dimethylcyclobutyl)carbonyl]pyrrolidin-3-yl}-9-ethyl-8-(2-methylpyrimidin-5-yl)-9H-purin-6-amine;
9-ethyl-8-(2-methylpyrimidin-5-yl)-N-{-1-[(2,2,3,3-tetramethylcyclopropyl)carbonyl]pyrrolidin-3-yl}-9H-purin-6-amine;
9-ethyl-N-[-1-{[1-(methoxymethyl)cyclopropyl]carbonyl}pyrrolidin-3-yl]-8-(2-methylpyrimidin-5-yl)-9H-purin-6-amine;
1-{[-3-{[9-ethyl-8-(2-methylpyrimidin-5-yl)-9H-purin-6-yl]amino}pyrrolidin-1-yl]carbonyl}cyclopentanecarbonitrile;
3-{[-3-{[9-ethyl-8-(2-methylpyrimidin-5-yl)-9H-purin-6-yl]amino}pyrrolidin-1-yl]carbonyl}cyclobutanol;
5-{[-3-{[9-ethyl-8-(2-methylpyrimidin-5-yl)-9H-purin-6-yl]amino}pyrrolidin-1-yl]carbonyl}pyrrolidin-2-one;
1-{[-3-{[9-ethyl-8-(2-methylpyrimidin-5-yl)-9H-purin-6-yl]amino}pyrrolidin-1-yl]carbonyl}cyclopropanecarbonitrile;
1-{[-3-{[9-ethyl-8-(2-methylpyrimidin-5-yl)-9H-purin-6-yl]amino}pyrrolidin-1-yl]carbonyl}cyclopropanol;
4-{[-3-{[9-ethyl-8-(2-methylpyrimidin-5-yl)-9H-purin-6-yl]amino}pyrrolidin-1-yl]carbonyl}-3,3-dimethylazetidin-2-one;
9-ethyl-8-(2-methylpyrimidin-5-yl)-N-{-1-[(-2-methyltetrahydrofuran-2-yl)carbonyl]pyrrolidin-3-yl}-9H-purin-6-amine;
[3-{[9-ethyl-8-(2-methylpyrimidin-5-yl)-9H-purin-6-yl]amino}pyrrolidin-1-yl](1-methyl-1H-imidazol-5-yl)methanone;

9-ethyl-N-{1-[(5-methylisoxazol-3-yl)carbonyl]pyrrolidin-3-yl}-8-(2-methylpyrimidin-5-yl)-9H-purin-6-amine;
9-ethyl-8-(2-methylpyrimidin-5-yl)-N-{1-[(5-methyl-1,2,3-thiadiazol-4-yl)carbonyl]pyrrolidin-3-yl}-9H-purin-6-amine;
9-ethyl-8-(2-methylpyrimidin-5-yl)-N-[1-(1,3-oxazol-4-ylcarbonyl)pyrrolidin-3-yl]-9H-purin-6-amine;
9-ethyl-N-{1-[(1-methyl-1H-pyrazol-4-yl)carbonyl]pyrrolidin-3-yl}-8-(2-methylpyrimidin-5-yl)-9H-purin-6-amine;
9-ethyl-N-{1-[(4-methyl-1,3-oxazol-5-yl)carbonyl]pyrrolidin-3-yl}-8-(2-methylpyrimidin-5-yl)-9H-purin-6-amine;
9-ethyl-8-(2-methylpyrimidin-5-yl)-N-{1-[(1-methyl-1H-1,2,3-triazol-4-yl)carbonyl]pyrrolidin-3-yl}-9H-purin-6-amine;
9-ethyl-8-(2-methylpyrimidin-5-yl)-N-[1-(1,3-oxazol-5-ylcarbonyl)pyrrolidin-3-yl]-9H-purin-6-amine;
N-[1-(bicyclo[1.1.1]pent-1-ylcarbonyl)pyrrolidin-3-yl]-9-ethyl-8-(2-methylpyrimidin-5-yl)-9H-purin-6-amine;
9-ethyl-8-(2-methylpyrimidin-5-yl)-N-[1-(piperidin-4-ylcarbonyl)pyrrolidin-3-yl]-9H-purin-6-amine;
9-ethyl-N-[1-{[1-(1-methylethyl)azetidin-3-yl]carbonyl}pyrrolidin-3-yl]-8-(2-methylpyrimidin-5-yl)-9H-purin-6-amine;
N-[1-(2-amino-2-methylpropanoyl)pyrrolidin-3-yl]-9-ethyl-8-(2-methylpyrimidin-5-yl)-9H-purin-6-amine;
4-{[(3 S)-3-{[9-ethyl-8-(2-methylpyrimidin-5-yl)-9H-purin-6-yl]amino}pyrrolidin-1-yl]carbonyl}-1-(1-methylethyl)pyrrolidin-2-one;
9-ethyl-N-[1-{[1-(methylamino)cyclopropyl]carbonyl}pyrrolidin-3-yl]-8-(2-methylpyrimidin-5-yl)-9H-purin-6-amine;
9-ethyl-8-(2-methylpyrimidin-5-yl)-N-[1-(piperidin-2-ylcarbonyl)pyrrolidin-3-yl]-9H-purin-6-amine;
N-{1-[(1-aminocyclopropyl)carbonyl]pyrrolidin-3-yl}-9-ethyl-8-(2-methylpyrimidin-5-yl)-9H-purin-6-amine;
N-[(-1-2-azabicyclo[3.1.0]hex-6-ylcarbonyl)pyrrolidin-3-yl]-9-ethyl-8-(2-methylpyrimidin-5-yl)-9H-purin-6-amine;
9-ethyl-N-{1-[3-(methylamino)propanoyl]pyrrolidin-3-yl}-8-(2-methylpyrimidin-5-yl)-9H-purin-6-amine;
N-[-1-(cyclopropylcarbonyl)-4-methylpyrrolidin-3-yl]-9-ethyl-8-(2-methylpyrimidin-5-yl)-9H-purin-6-amine;
9-ethyl-8-(2-methylpyrimidin-5-yl)-N-[4-methyl-1-(-spiro[2.5]oct-1-ylcarbonyl)pyrrolidin-3-yl]-9H-purin-6-amine;
9-ethyl-N-[-{4-methyl-1-(1,3-oxazol-4-yl carbonyl)pyrrolidin-3-yl]-8-(2-methylpyrimidin-5-yl)-9H-purin-6-amine;
9-ethyl-N-[-1-{[-2-methylcyclopropyl]carbonyl}pyrrolidin-3-yl]-8-(2-methylpyrimidin-5-yl)-9H-purin-6-amine;
N-[-1-(cyclopropylcarbonyl)-2-methylpyrrolidin-3-yl]-9-ethyl-8-(2-methylpyrimidin-5-yl)-9H-purin-6-amine;
N-[1-(cyclopropylcarbonyl)-4,4-dimethylpyrrolidin-3-yl]-9-ethyl-8-(2-methylpyrimidin-5-yl)-9H-purin-6-amine;
1-(cyclopropylcarbonyl)-4-{-[9-ethyl-8-(2-methylpyrimidin-5-yl)-9H-purin-6-yl]amino}pyrrolidin-3-ol;
4-{[-3-{[9-ethyl-8-(2-methylpyrimidin-5-yl)-9H-purin-6-yl]amino}pyrrolidin-1-yl]carbonyl}cyclohexanol;
4-{[-3-{[9-ethyl-8-(2-methylpyrimidin-5-yl)-9H-purin-6-yl](methyl)amino}pyrrolidin-1-yl]carbonyl}cyclohexanol;
9-ethyl-N-{1-[-tetrahydrofuran-3-ylcarbonyl]pyrrolidin-3-yl}-8-[6-(trifluoromethyl)pyridin-3-yl]-9H-purin-6-amine;
9-ethyl-N-{1-[(3-methoxycyclobutyl)carbonyl]pyrrolidin-3-yl}-8-[6-(trifluoromethyl)pyridin-3-yl]-9H-purin-6-amine;
3-fluoro-5-(9-methyl-6-{[-1-propanoylpyrrolidin-3-yl]amino}-9H-purin-8-yl)phenol;
8-(3-fluoro-4-methoxyphenyl)-9-methyl-N-[-1-propanoylpyrrolidin-3-yl]-9H-purin-6-amine;
9-methyl-8-(5-methyl-1-phenyl-1H-pyrazol-4-yl)-N-[-1-propanoylpyrrolidin-3-yl]-9H-purin-6-amine;
8-(1-ethyl-5-methyl-1H-imidazol-4-yl)-9-methyl-N-[-1-propanoylpyrrolidin-3-yl]-9H-purin-6-amine;
8-(5-aminopyridin-3-yl)-9-methyl-N-[-1-propanoylpyrrolidin-3-yl]-9H-purin-6-amine;
8-(6-chloropyridin-3-yl)-9-methyl-N-[-1-propanoylpyrrolidin-3-yl]-9H-purin-6-amine;
9-methyl-8-(2-methylpyrimidin-5-yl)-N-[-1-propanoylpyrrolidin-3-yl]-9H-purin-6-amine;
N-[-1-(cyclopropylcarbonyl)-4-methylpyrrolidin-3-yl]-9-ethyl-8-(2-methylpyrimidin-5-yl)-9H-purin-6-amine;
N-[5-(cyclopropylcarbonyl)-5-azaspiro[2.4]hept-7-yl]-9-ethyl-8-(2-methylpyrimidin-5-yl)-9H-purin-6-amine;
N-[-1-(cyclopropylcarbonyl)-3-methylpyrrolidin-3-yl]-9-ethyl-8-(2-methylpyrimidin-5-yl)-9H-purin-6-amine;
N-[-1-(cyclopropylcarbonyl)-4-ethylpyrrolidin-3-yl]-9-ethyl-8-(2-methylpyrimidin-5-yl)-9H-purin-6-amine;
N-[-1-(cyclopropylcarbonyl)-4-fluoropyrrolidin-3-yl]-9-ethyl-8-(2-methylpyrimidin-5-yl)-9H-purin-6-amine;
N-[-1-(cyclopropylcarbonyl)-4-(trifluoromethyl)pyrrolidin-3-yl]-9-ethyl-8-(2-methylpyrimidin-5-yl)-9H-purin-6-amine;
N-[-1-(cyclopropylcarbonyl)pyrrolidin-3-yl]-9-methyl-8-(2-methylpyrimidin-5-yl)-9H-purin-6-amine;
N-[-1-(cyclopropylcarbonyl)pyrrolidin-3-yl]-9-ethyl-8-(1H-pyrrolo[2,3-b]pyridin-5-yl)-9H-purin-6-amine;
8-(5-chloro-6-methoxypyridin-3-yl)-N-[-1-(cyclopropylcarbonyl)pyrrolidin-3-yl]-9-ethyl-9H-purin-6-amine;
N-[-1-(cyclopropylcarbonyl)-4-fluoropyrrolidin-3-yl]-9-ethyl-8-(2-methylpyrimidin-5-yl)-9H-purin-6-amine;
9-methyl-8-[4-(methylsulfonyl)phenyl]-N-[-1-propanoylpyrrolidin-3-yl]-9H-purin-6-amine;
N-[-1-(cyclopropylcarbonyl)pyrrolidin-3-yl]-N,9-diethyl-8-(2-methylpyrimidin-5-yl)-9H-purin-6-amine;
N-[-1-(cyclopropylcarbonyl)pyrrolidin-3-yl]-9-ethyl-N-methyl-8-(2-methylpyrimidin-5-yl)-9H-purin-6-amine;
N-[-1-(cyclopropylcarbonyl)pyrrolidin-3-yl]-9-ethyl-8-[4-(trifluoromethyl)phenyl]-9H-purin-6-amine;
8-(6-methoxypyridin-3-yl)-9-methyl-N-[-1-propanoylpyrrolidin-3-yl]-9H-purin-6-amine;
8-(4-methoxy-3-methylphenyl)-9-methyl-N-[-1-propanoylpyrrolidin-3-yl]-9H-purin-6-amine;
2-methoxy-5-(9-methyl-6-{[-1-propanoylpyrrolidin-3-yl]amino}-9H-purin-8-yl)pyridine-3-carbonitrile;
2-[5-(9-methyl-6-{[-1-propanoylpyrrolidin-3-yl]amino}-9H-purin-8-yl)pyridin-3-yl]propan-2-ol;
N-[-1-(cyclopropylcarbonyl)pyrrolidin-3-yl]-9-ethyl-8-(1-methyl-1H-pyrazolo[3,4-b]pyridin-5-yl)-9H-purin-6-amine;
N-[-1-(cyclopropylcarbonyl)pyrrolidin-3-yl]-9-ethyl-8-[1-(2,2,2-trifluoroethyl)-1H-pyrazol-4-yl]-9H-purin-6-amine;

N-[-1-(cyclopropylcarbonyl)pyrrolidin-3-yl]-9-ethyl-8-(5-phenylpyridin-3-yl)-9H-purin-6-amine;
8-(5-chloropyridin-3-yl)-N-[-1-(cyclopropylcarbonyl)pyrrolidin-3-yl]-9-ethyl-9H-purin-6-amine;
[5-(6-{[-1-(cyclopropylcarbonyl)pyrrolidin-3-yl]amino)}-9-ethyl-9H-purin-8-yl)pyrimidin-2-yl]methanol;
9-ethyl-8-(2-methylpyrimidin-5-yl)-N-[-1-pyridin-2-ylpyrrolidin-3-yl]-9H-purin-6-amine;
9-ethyl-8-(2-methylpyrimidin-5-yl)-N-[-1-pyrimidin-2-ylpyrrolidin-3-yl]-9H-purin-6-amine;
9-ethyl-N-[-1-(5-methylpyridin-2-yl)pyrrolidin-3-yl]-8-(2-methylpyrimidin-5-yl)-9H-purin-6-amine;
9-ethyl-N-[-1-pyridin-2-ylpyrrolidin-3-yl]-8-[6-(trifluoromethyl)pyridin-3-yl]-9H-purin-6-amine;
9-ethyl-8-(2-methylpyrimidin-5-yl)-N-[-1-pyridin-2-ylpiperidin-3-yl]-9H-purin-6-amine;
9-ethyl-N-[-1-(4-ethylpyridin-2-yl)pyrrolidin-3-yl]-8-(2-methylpyrimidin-5-yl)-9H-purin-6-amine;
9-ethyl-N-[-1-(6-methoxypyridin-2-yl)pyrrolidin-3-yl]-8-(2-methylpyrimidin-5-yl)-9H-purin-6-amine;
9-ethyl-N-{-1-[6-(methylamino)pyridin-2-yl]pyrrolidin-3-yl}-8-(2-methylpyrimidin-5-yl)-9H-purin-6-amine;
9-ethyl-N-[-1-isoquinolin-1-ylpyrrolidin-3-yl]-8-(2-methylpyrimidin-5-yl)-9H-purin-6-amine;
9-ethyl-N-[-1-(3-methylpyridin-2-yl)pyrrolidin-3-yl]-8-(2-methylpyrimidin-5-yl)-9H-purin-6-amine;
6-[-3-{[9-ethyl-8-(2-methylpyrimidin-5-yl)-9H-purin-6-yl]amino}pyrrolidin-1-yl]pyridine-3-carbonitrile;
methyl-4-{[9-ethyl-8-(2-methylpyrimidin-5-yl)-9H-purin-6-yl]amino}-1-pyridin-2-yl-D-prolinate;
9-ethyl-8-(2-methylpyrimidin-5-yl)-N-[-1-thieno[3,2-c]pyridin-4-ylpyrrolidin-3-yl]-9H-purin-6-amine;
6-{[1-(cyclopropylcarbonyl)pyrrolidin-3-yl]amino}-N-(cyclopropylmethyl)-9-ethyl-9H-purine-8-carboxamide;
6-{[-1-(cyclopropylcarbonyl)pyrrolidin-3-yl]amino}-9-ethyl-N-(2-methoxyethyl)-9H-purine-8-carboxamide;
6-{[-1-(cyclopropylcarbonyl)pyrrolidin-3-yl]amino}-9-ethyl-N-(2,2,2-trifluoroethyl)-9H-purine-8-carboxamide;
N-[-1-(cyclopropylcarbonyl)pyrrolidin-3-yl]-9-ethyl-8-(morpholin-4-ylcarbonyl)-9H-purin-6-amine;
6-{[-1-(cyclopropylcarbonyl)pyrrolidin-3-yl]amino}-9-ethyl-N,N-dimethyl-9H-purine-8-carboxamide;
6-{[-1-(cyclopropylcarbonyl)pyrrolidin-3-yl]amino}-9-ethyl-N-oxetan-3-yl-9H-purine-8-carboxamide;
6-{[-1-(cyclopropylcarbonyl)pyrrolidin-3-yl]amino}-9-ethyl-N-(trans-4-hydroxycyclohexyl)-9H-purine-8-carboxamide;
N-[-1-(cyclopropylcarbonyl)pyrrolidin-3-yl]-9-ethyl-8-(pyrrolidin-1-ylcarbonyl)-9H-purin-6-amine;
6-{[-1-(cyclobutylcarbonyl)pyrrolidin-3-yl]amino}-9-ethyl-N-(2,2,2-trifluoroethyl)-9H-purine-8-carboxamide;
9-ethyl-6-{[-1-pyridin-2-ylpyrrolidin-3-yl]amino}-N-(2,2,2-trifluoroethyl)-9H-purine-8-carboxamide;
6-{[-1-(cyclopropylcarbonyl)pyrrolidin-3-yl]amino}-9-ethyl-9H-purine-8-carb oxamide;
6-{[-1-(cyclopropylcarbonyl)pyrrolidin-3-yl]amino}-N-[(1  S)-1-cyclopropylethyl]-9-ethyl-9H-purine-8-carb oxamide;
N-cyclohexyl-6-{[-1-(cyclopropylcarbonyl)pyrrolidin-3-yl]amino}-9-ethyl-9H-purine-8-carboxamide;
6-{[-1-(cyclopropylcarbonyl)pyrrolidin-3-yl]amino}-9-ethyl-N-methyl-N-(2,2,2-trifluoroethyl)-9H-purine-8-carboxamide;
N-tert-butyl-6-{[-1-(cyclopropylcarbonyl)pyrrolidin-3-yl]amino}-9-ethyl-9H-purine-8-carboxamide;
6-{[-1-(cyclopropylcarbonyl)pyrrolidin-3-yl]amino}-9-ethyl-N-(3,3,3-trifluoropropyl)-9H-purine-8-carboxamide;
6-{[-1-(cyclopropylcarbonyl)pyrrolidin-3-yl]amino}-9-ethyl-N-phenyl-9H-purine-8-carboxamide;
6-{[-1-(cyclopropylcarbonyl)pyrrolidin-3-yl]amino}-N,9-diethyl-9H-purine-8-carboxamide;
6-{[-1-(cyclopropylcarbonyl)pyrrolidin-3-yl]amino}-9-ethyl-N-pyridin-2-yl-9H-purine-8-carboxamide;
6-{[-1-(cyclopropylcarbonyl)pyrrolidin-3-yl]amino}-9-ethyl-N-pyridin-3-yl-9H-purine-8-carboxamide;
N-[-1-(cyclopropylcarbonyl)pyrrolidin-3-yl]-8-(cyclopropylmethyl)-9-ethyl-9H-purin-6-amine;
9-ethyl-8-(2-methylpropyl)-N-[-1-propanoylpyrrolidin-3-yl]-9H-purin-6-amine;
9-methyl-8-(2-methylpropyl)-N-[-1-propanoylpyrrolidin-3-yl]-9H-purin-6-amine;
9-ethyl-8-methyl-N-[-1-propanoylpyrrolidin-3-yl]-9H-purin-6-amine;
N-[-1-(cyclopropylcarbonyl)pyrrolidin-3-yl]-9-ethyl-8-(1-methylethyl)-9H-purin-6-amine;
3-(6-{[-1-(cyclopropylcarbonyl)pyrrolidin-3-yl]amino}-9-ethyl-9H-purin-8-yl)propan-1-ol;
N-[-1-(cyclopropylcarbonyl)pyrrolidin-3-yl]-9-ethyl-8-(2,2,2-trifluoroethyl)-9H-purin-6-amine;
N-[-1-(cyclopropylcarbonyl)pyrrolidin-3-yl]-9-ethyl-8-(methoxymethyl)-9H-purin-6-amine;
8-cyclopropyl-9-methyl-N-[-1-propanoylpyrrolidin-3-yl]-9H-purin-6-amine;
8-cyclopropyl-N-[-1-(cyclopropylcarbonyl)pyrrolidin-3-yl]-9-ethyl-9H-purin-6-amine;
9-ethyl-N-[-1-propanoylpyrrolidin-3-yl]-8-(trifluoromethyl)-9H-purin-6-amine;
8-(difluoromethyl)-9-ethyl-N-{-1-[(1-methyl-1H-pyrazol-3-yl)carbonyl]pyrrolidin-3-yl}-9H-purin-6-amine;
8-(difluoromethyl)-9-ethyl-N-[-1-propanoylpyrrolidin-3-yl]-9H-purin-6-amine;
N-[-1-(cyclopropylcarbonyl)pyrrolidin-3-yl]-8-(difluoromethyl)-9-ethyl-9H-purin-6-amine;
N-[-1-(cyclobutylcarbonyl)pyrrolidin-3-yl]-8-(difluoromethyl)-9-ethyl-9H-purin-6-amine;
8-(difluoromethyl)-9-ethyl-N-[-1-(1,3-oxazol-4-ylcarbonyl)pyrrolidin-3-yl]-9H-purin-6-amine;
8-(difluoromethyl)-9-ethyl-N-{-1-[(trans-3-methoxycyclobutyl)carbonyl]pyrrolidin-3-yl)}-9H-purin-6-amine;
8-(difluoromethyl)-9-ethyl-N-[-1-(1-methyl-D-prolyl)pyrrolidin-3-yl]-9H-purin-6-amine;
8-(difluoromethyl)-9-ethyl-N-[-1-(spiro[2.4]hept-1-ylcarbonyl)pyrrolidin-3-yl]-9H-purin-6-amine;
N-[-1-(cyclopropylcarbonyl)pyrrolidin-3-yl]-9-ethyl-8-(2-methoxyethyl)-9H-purin-6-amine;
N-[-1-(cyclopropylcarbonyl)pyrrolidin-3-yl]-8,9-diethyl-9H-purin-6-amine;
8-tert-butyl-N-[-1-(cyclopropylcarbonyl)pyrrolidin-3-yl]-9-ethyl-9H-purin-6-amine;
N-[-1-(cyclopropylcarbonyl)pyrrolidin-3-yl]-9-ethyl-8-{[1-(methyl sulfonyl)azetidin-3-yl]methyl}-9H-purin-6-amine;
8-(difluoromethyl)-9-ethyl-N-[-1-pyridin-2-ylpyrrolidin-3-yl]-9H-purin-6-amine;
N-[-1-(azetidin-1-ylcarbonyl)pyrrolidin-3-yl]-8-(difluoromethyl)-9-ethyl-9H-purin-6-amine;
8-(difluoromethyl)-9-ethyl-N-{-1-[(3-methoxyazetidin-1-yl)carbonyl]pyrrolidin-3-yl}-9H-purin-6-amine;

1-(6-{[-1-(cyclopropylcarbonyl)pyrrolidin-3-yl]amino}-9-ethyl-9H-purin-8-yl)pyrrolidin-3-ol;
8-(1H-benzimidazol-1-yl)-N-[-1-(cyclopropylcarbonyl)pyrrolidin-3-yl]-9-ethyl-9H-purin-6-amine;
N-[-1-(cyclopropylcarbonyl)pyrrolidin-3-yl]-9-ethyl-8-[4-(trifluoromethyl)-1H-imidazol-1-yl]-9H-purin-6-amine;
cyclopropyl[-3-({9-ethyl-8-[methyl(2-methylpropyl)amino]-9H-purin-6-yl}amino)pyrrolidin-1-yl]methanone;
N-[-1-(cyclopropylcarbonyl)pyrrolidin-3-yl]-9-ethyl-8-phenoxy-9H-purin-6-amine;
N-[-1-(cyclopropylcarbonyl)pyrrolidin-3-yl]-9-ethyl-8-(3-fluoro-4-methoxyphenoxy)-9H-purin-6-amine;
N-[-1-(cyclopropylcarbonyl)pyrrolidin-3-yl]-9-ethyl-8-(1-methylethoxy)-9H-purin-6-amine;
N-[-1-(cyclopropylcarbonyl)pyrrolidin-3-yl]-9-ethyl-8-(4, 5,6,7-tetrahydro-1H-benzimidazol-1-yl)-9H-purin-6-amine;
8-(1-ethyl-5-methyl-1H-pyrazol-4-yl)-N-[-1-propanoylpyrrolidin-3-yl]-9-propyl-9H-purin-6-amine;
8-(2-methylpyrimidin-5-yl)-N-[-1-propanoylpyrrolidin-3-yl]-9-propyl-9H-purin-6-amine;
9-(cyclopropylmethyl)-8-(1-ethyl-5-methyl-1H-pyrazol-4-yl)-N-[-1-propanoylpyrrolidin-3-yl]-9H-purin-6-amine;
9-(2,2-difluoroethyl)-8-(1-ethyl-5-methyl-1H-pyrazol-4-yl)-N-[-1-propanoylpyrrolidin-3-yl]-9H-purin-6-amine;
N-[-1-(cyclopropylcarbonyl)pyrrolidin-3-yl]-8-(2-methylpyrimidin-5-yl)-9-(2,2,2-trifluoroethyl)-9H-purin-6-amine;
8-(1-ethyl-5-methyl-1H-pyrazol-4-yl)-9-methyl-N-[-1-propylpyrrolidin-3-yl]-9H-purin-6-amine;
N-[5-(1-cyclopropylethyl)-5-azaspiro[2.4]hept-7-yl]-9-ethyl-8-(2-methylpyrimidin-5-yl)-9H-purin-6-amine;
9-ethyl-N-[5-(1-methylethyl)-5-azaspiro[2.4]hept-7-yl]-8-(2-methylpyrimidin-5-yl)-9H-purin-6-amine;
8-(1-ethyl-5-methyl-1H-pyrazol-4-yl)-N-[-1-(ethylsulfonyl)piperidin-3-yl]-9-methyl-9H-purin-6-amine;
N-ethyl-3-{[8-(1-ethyl-5-methyl-1H-pyrazol-4-yl)-9-methyl-9H-purin-6-yl]amino}piperidine-1-carboxamide;
3-{[9-ethyl-8-(2-methylpyrimidin-5-yl)-9H-purin-6-yl]amino}-N-(2-methoxyethyl)pyrrolidine-1-carboxamide;
9-ethyl-N-{-1-[(2-methylazetidin-1-yl)carbonyl]pyrrolidin-3-yl}-8-(2-methylpyrimidin-5-yl)-9H-purin-6-amine;
9-ethyl-8-(2-methylpyrimidin-5-yl)-N-[-1-(morpholin-4-ylcarbonyl)pyrrolidin-3-yl]-9H-purin-6-amine;
9-ethyl-8-(2-methylpyrimidin-5-yl)-N-[-1-(piperidin-1-ylcarbonyl)pyrrolidin-3-yl]-9H-purin-6-amine;
N-cyclopropyl-3-{[9-ethyl-8-(2-methylpyrimidin-5-yl)-9H-purin-6-yl]amino}pyrrolidine-1-carboxamide;
N-(cyclopropylmethyl)-3-{[9-ethyl-8-(2-methylpyrimidin-5-yl)-9H-purin-6-yl]amino}pyrrolidine-1-carboxamide;
3-{[9-ethyl-8-(2-methylpyrimidin-5-yl)-9H-purin-6-yl]amino}-N-(2,2,2-trifluoroethyl)pyrrolidine-1-carboxamide;
N-[-1-(azetidin-1-ylcarbonyl)pyrrolidin-3-yl]-9-ethyl-8-(2-methylpyrimidin-5-yl)-9H-purin-6-amine;
9-ethyl-N-{-1-[(3-methoxyazetidin-1-yl)carbonyl]pyrrolidin-3-yl}-8-(2-methylpyrimidin-5-yl)-9H-purin-6-amine;
N-{-1-[(3,3-dimethylpyrrolidin-1-yl)carbonyl]pyrrolidin-3-yl}-9-ethyl-8-(2-methylpyrimidin-5-yl)-9H-purin-6-amine;
9-ethyl-N-[-1-{[-3-fluoropyrrolidin-1-yl]carbonyl}pyrrolidin-3-yl]-8-(2-methylpyrimidin-5-yl)-9H-purin-6-amine;
9-ethyl-N-[-1-{[-3-methoxypyrrolidin-1-yl]carbonyl}pyrrolidin-3-yl]-8-(2-methylpyrimidin-5-yl)-9H-purin-6-amine;
N-cyclohexyl-3-{[9-ethyl-8-(2-methylpyrimidin-5-yl)-9H-purin-6-yl]amino}pyrrolidine-1-carboxamide;
ethyl N-{[-3-{[9-ethyl-8-(2-methylpyrimidin-5-yl)-9H-purin-6-yl]amino}pyrrolidin-1-yl]carbonyl})-beta-alaninate;
ethyl N-{[-3-{[9-ethyl-8-(2-methylpyrimidin-5-yl)-9H-purin-6-yl]amino}pyrrolidin-1-yl]carbonyl}(D and L)-alaninate;
3-{[9-ethyl-8-(2-methylpyrimidin-5-yl)-9H-purin-6-yl]amino}-N-(1-methyl ethyl)pyrrolidine-1-carboxamide;
N-[(-1,1-dioxidotetrahydrothiophen-3-yl)methyl]-3-{[9-ethyl-8-(2-methylpyrimidin-5-yl)-9H-purin-6-yl]amino}pyrrolidine-1-carboxamide;
3-{[9-ethyl-8-(2-methylpyrimidin-5-yl)-9H-purin-6-yl]amino}-N-(furan-2-ylmethyl)pyrrolidine-1-carboxamide;
N-cyclobutyl-3-{[9-ethyl-8-(2-methylpyrimidin-5-yl)-9H-purin-6-yl]amino}pyrrolidine-1-carboxamide;
N-butyl-3-{[9-ethyl-8-(2-methylpyrimidin-5-yl)-9H-purin-6-yl]amino}pyrrolidine-1-carboxamide;
methyl N-{[-3-{[9-ethyl-8-(2-methylpyrimidin-5-yl)-9H-purin-6-yl]amino}pyrrolidin-1-yl]carbonyl})-2-methylalaninate;
3-{[9-ethyl-8-(2-methylpyrimidin-5-yl)-9H-purin-6-yl]amino}-N-(1,1,3,3-tetramethylbutyl)pyrrolidine-1-carboxamide;
N-[-1-(azetidin-1-ylcarbonyl)pyrrolidin-3-yl]-9-ethyl-8-[6-(trifluoromethyl)pyridin-3-yl]-9H-purin-6-amine;
9-ethyl-6-({-1-[(3-methoxyazetidin-1-yl)carbonyl]pyrrolidin-3-yl}amino)-N-(2,2,2-trifluoroethyl)-9H-purine-8-carboxamide;
2,2,2-trifluoroethyl-3-{[9-ethyl-8-(2-methylpyrimidin-5-yl)-9H-purin-6-yl]amino}pyrrolidine-1-carboxylate;
methyl-3-{[9-ethyl-8-(2-methylpyrimidin-5-yl)-9H-purin-6-yl]amino}pyrrolidine-1-carboxylate;
2-fluoroethyl-3-{[9-ethyl-8-(2-methylpyrimidin-5-yl)-9H-purin-6-yl]amino}pyrrolidine-1-carboxylate;
2,2-dimethylpropyl-3-{[9-ethyl-8-(2-methylpyrimidin-5-yl)-9H-purin-6-yl]amino}pyrrolidine-1-carboxylate;
1-methylethyl-3-{[9-ethyl-8-(2-methylpyrimidin-5-yl)-9H-purin-6-yl]amino}pyrrolidine-1-carboxylate;
1,1-dioxidotetrahydrothiophen-3-yl-3-{[9-ethyl-8-(2-methylpyrimidin-5-yl)-9H-purin-6-yl]amino}pyrrolidine-1-carboxylate;
2-methoxyethyl-3-{[9-ethyl-8-(2-methylpyrimidin-5-yl)-9H-purin-6-yl]amino}pyrrolidine-1-carboxylate;
cyclohexyl-3-{[9-ethyl-8-(2-methylpyrimidin-5-yl)-9H-purin-6-yl]amino}pyrrolidine-1-carboxylate;
1-methylpropyl-3-{[9-ethyl-8-(2-methylpyrimidin-5-yl)-9H-purin-6-yl]amino}pyrrolidine-1-carboxylate;
benzyl-3-{[9-ethyl-8-(2-methylpyrimidin-5-yl)-9H-purin-6-yl]amino}pyrrolidine-1-carboxylate;
3-(dimethylamino)propyl-3-{[9-ethyl-8-(2-methylpyrimidin-5-yl)-9H-purin-6-yl]amino}pyrrolidine-1-carboxylate;
4-{[8-(1-ethyl-5-methyl-1H-pyrazol-4-yl)-9-methyl-9H-purin-6-yl]amino}-1-propylpyrrolidin-2-one;

4-{[8-(1-ethyl-5-methyl-1H-pyrazol-4-yl)-9-methyl-9H-purin-6-yl]amino}-1-(2-methylprop-2-en-1-yl)pyrrolidin-2-one;
4-{[8-(1-ethyl-5-methyl-1H-pyrazol-4-yl)-9-methyl-9H-purin-6-yl]amino}-1-(2-methylpropyl)pyrrolidin-2-one;
4-{[9-ethyl-8-(2-methylpyrimidin-5-yl)-9H-purin-6-yl]amino}-1-propylpyrrolidin-2-one;
5-{[9-ethyl-8-(2-methylpyrimidin-5-yl)-9H-purin-6-yl]amino}-1-propylpiperidin-2-one;
5-1-(cyclopropylmethyl)-5-{[9-ethyl-8-(2-methylpyrimidin-5-yl)-9H-purin-6-yl]amino}piperidin-2-one;
1-(cyclopropylmethyl)-6-{[9-ethyl-8-(2-methylpyrimidin-5-yl)-9H-purin-6-yl]amino}azepan-2-one;
1-(cyclopropylcarbonyl)-4-{[9-ethyl-8-(2-methylpyrimidin-5-yl)-9H-purin-6-yl]amino}-D-proline;
1-(cyclopropylcarbonyl)-4-{[9-ethyl-8-(2-methylpyrimidin-5-yl)-9H-purin-6-yl]amino}-N,N-dimethyl-D-prolinamide;
1-(cyclopropylcarbonyl)-4-{[9-ethyl-8-(2-methylpyrimidin-5-yl)-9H-purin-6-yl]amino}-N-methyl-D-prolinamide;
1-(cyclopropylcarbonyl)-4-{[9-ethyl-8-(2-methylpyrimidin-5-yl)-9H-purin-6-yl]amino}-N-(1-methylethyl)-D-prolinamide;
1-(cyclopropylcarbonyl)-4-{[9-ethyl-8-(2-methylpyrimidin-5-yl)-9H-purin-6-yl]amino}-D-prolinamide;
1-(cyclopropylcarbonyl)-N-[-1,2-dimethylpropyl]-4-{[9-ethyl-8-(2-methylpyrimidin-5-yl)-9H-purin-6-yl]amino}-D-prolinamide;
1-(cyclopropylcarbonyl)-4-{[9-ethyl-8-(2-methylpyrimidin-5-yl)-9H-purin-6-yl]amino}-N-(2-hydroxyethyl)-D-prolinamide;
1-(cyclopropylcarbonyl)-N-[2-(dimethylamino)ethyl]-4-{[9-ethyl-8-(2-methylpyrimidin-5-yl)-9H-purin-6-yl]amino}-D-prolinamide;
1-(cyclopropylcarbonyl)-4-{[9-ethyl-8-(2-methylpyrimidin-5-yl)-9H-purin-6-yl]amino}-N-methyl-L-prolinamide;
1-(cyclopropylcarbonyl)-4-{[9-ethyl-8-(2-methylpyrimidin-5-yl)-9H-purin-6-yl]amino}-L-prolinamide;
4-{[9-ethyl-8-(2-methylpyrimidin-5-yl)-9H-purin-6-yl]amino)}-1-pyridin-2-yl-D-prolinamide;
4-{[9-ethyl-8-(2-methylpyrimidin-5-yl)-9H-purin-6-yl]amino}-N-(2-hydroxyethyl)-1-pyridin-2-yl-D-prolinamide;
N-cyclopropyl-4-{[9-ethyl-8-(2-methylpyrimidin-5-yl)-9H-purin-6-yl]amino}-N-methyl-D-prolinamide;
N-[-1-(cyclopropylcarbonyl)-5-(5-methyl-1,3,4-oxadiazol-2-yl)pyrrolidin-3-yl]-9-ethyl-8-(2-methylpyrimidin-5-yl)-9H-purin-6-amine;
N-[-1-(cyclopropylcarbonyl)pyrrolidin-3-yl]-9-ethyl-8-(phenylethynyl)-9H-purin-6-amine;
N-[-1-(cyclopropylcarbonyl)pyrrolidin-3-yl]-9-ethyl-8-(pyrimidin-5-ylethynyl)-9H-purin-6-amine;
N-[-1-(cyclopropylcarbonyl)pyrrolidin-3-yl]-9-ethyl-8-(3-methoxyprop-1-yn-1-yl)-9H-purin-6-amine; and
3-(6-{[-1-(cyclopropylcarbonyl)pyrrolidin-3-yl]amino}-9-ethyl-9H-purin-8-yl)prop-2-yn-1-ol.

3. A compound according to claim 1, wherein K is a bond, —C(O)—NH—, —C(O)—, —C(O)—N(CH$_3$)—, —C(O)—N(CH$_3$)—CH$_2$—, —CH$_2$—, —O—, —C≡C—, or —C(O)—NH—CH$_2$—.

4. A compound according to claim 1, wherein K is a bond.

5. A compound according to claim 3, wherein L is selected from: —NH— and —N(C$_{1-6}$)alkyl.

6. A compound according to claim 1, wherein R$^4$ is independently selected from halogen, C$_{1-10}$ alkyl(oxy)$_{0-1}$ (carbonyl)$_{0-1}$C$_{0-10}$ alkyl, aryl C$_{0-10}$ alkyl(oxy)$_{0-1}$(carbonyl)$_{0-1}$C$_{0-10}$ alkyl, C$_{3-8}$ cycloalkyl C$_{0-10}$ alkyl(oxy)$_{0-1}$(carbonyl)$_{0-1}$C$_{0-10}$ alkyl, heteroaryl C$_{0-10}$ alkyl(oxy)$_{0-1}$ (carbonyl)$_{0-1}$C$_{0-10}$ alkyl, C$_{3-8}$heterocycloalkyl C$_{0-10}$ alkyl(oxy)$_{0-1}$ (carbonyl)$_{0-1}$C$_{0-10}$ alkyl, C$_{1-10}$ alkylaminocarbonylC$_{0-10}$ alkyl, Oxo (=O), (C$_{0-10}$ alkyl)$_{1-2}$ amino, hydroxy, (C$_{1-10}$ alkyl)OH, C$_{1-10}$ alkoxy, cyano, and C$_{1-6}$haloalkyl; wherein R$^4$ is substituted with 0, 1, 2, or 3 R$^5$.

7. A compound of claim 2 or a pharmaceutically acceptable salt thereof wherein the compound is selected from:

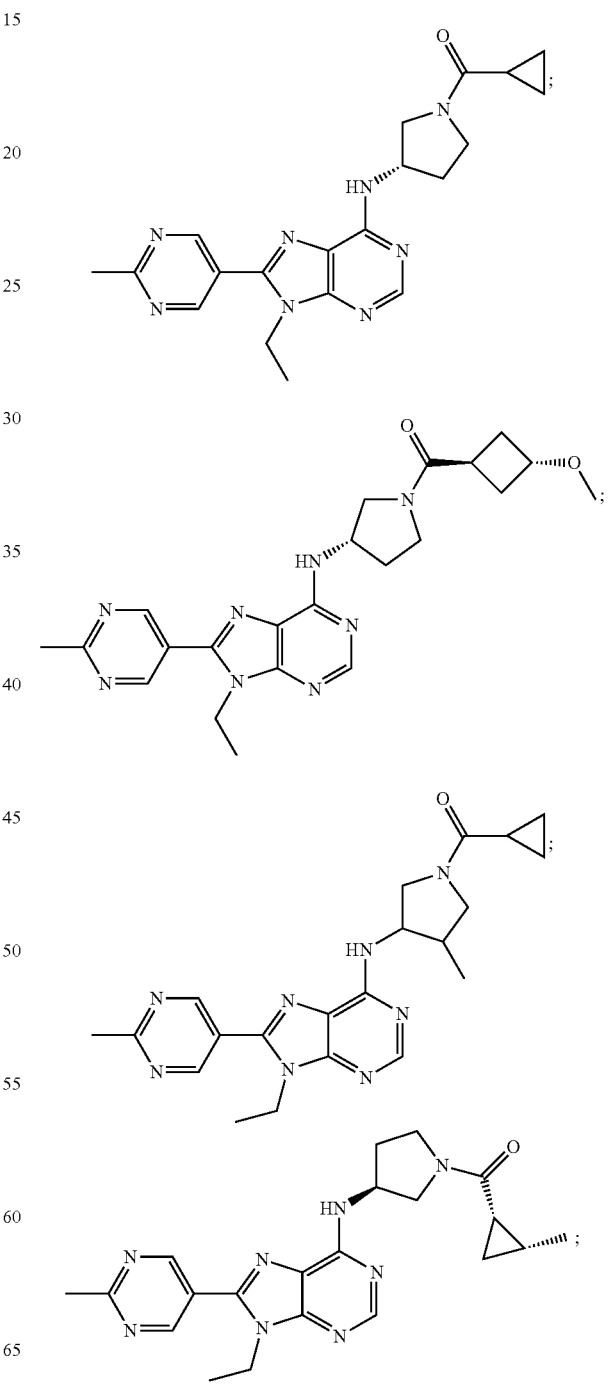

337
-continued
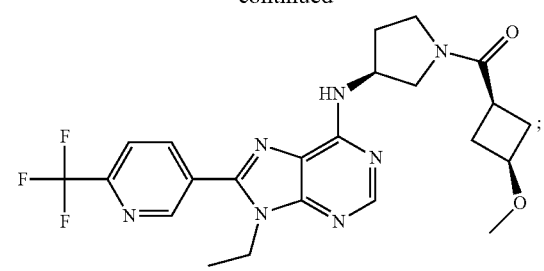
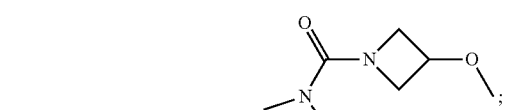
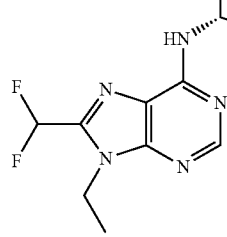
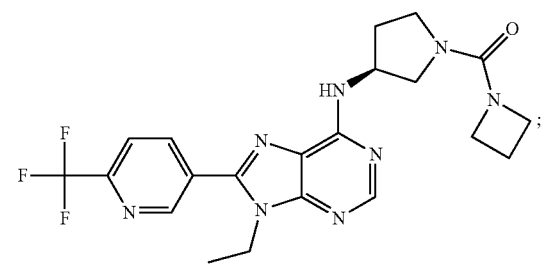
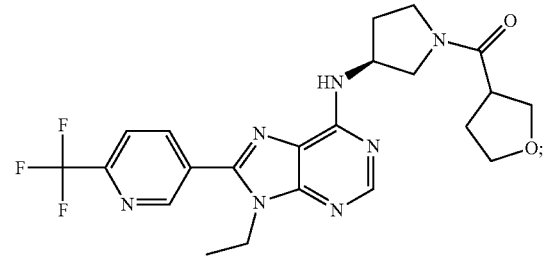
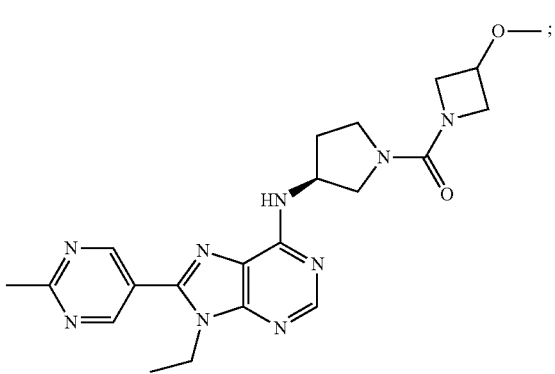
338
-continued
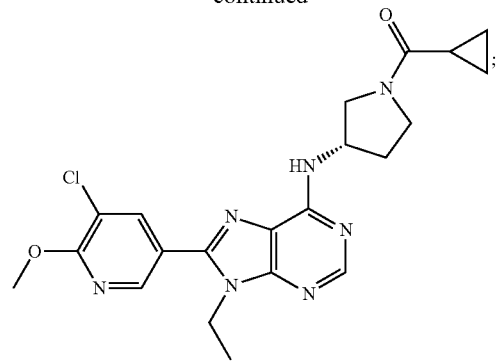
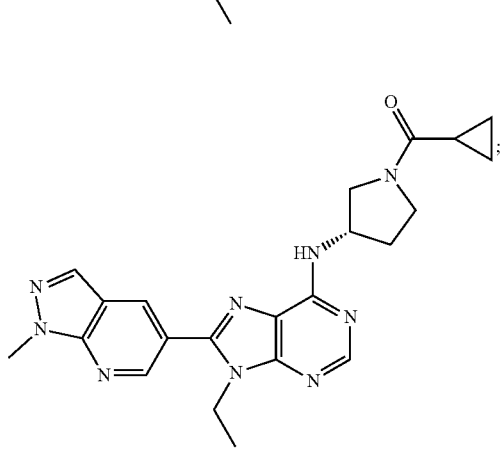
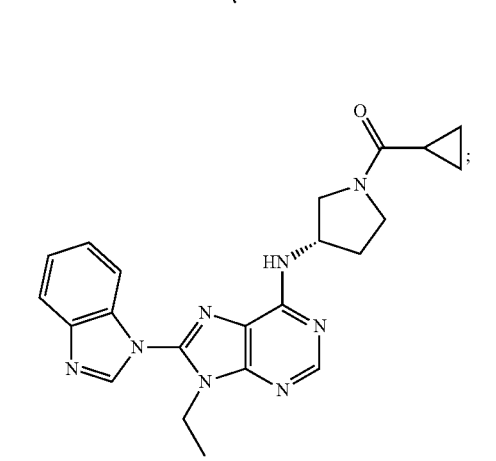
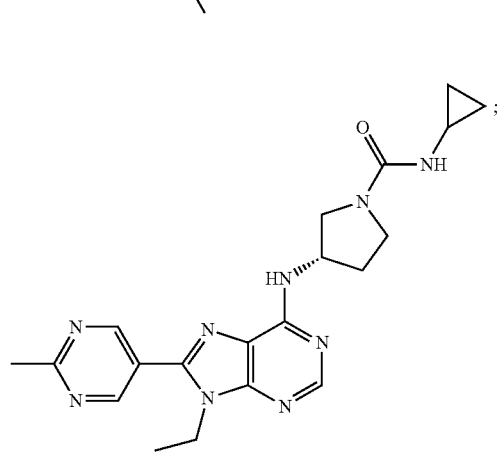
and

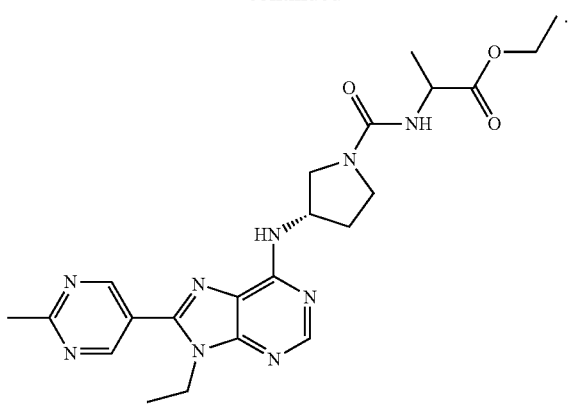 [SMILES: CCOC(=O)C(C)NC(=O)N1CC[C@H](Nc2ncnc3c2nc(-c2cnc(C)nc2)n3CC)C1]
8. A compound of claim 7 or a pharmaceutically acceptable salt thereof, wherein the compound is selected from:
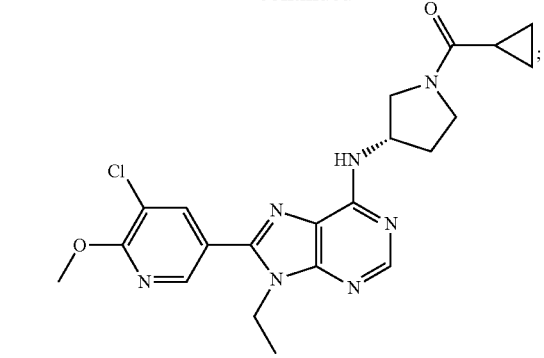
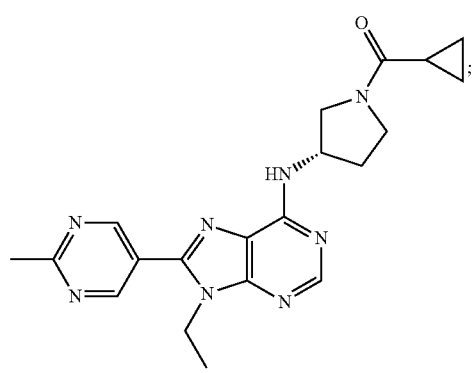
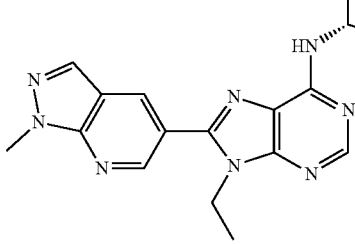
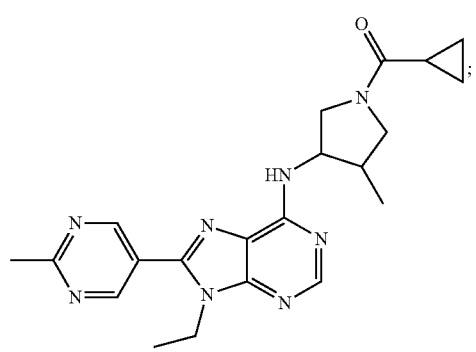 [SMILES: CCn1c(-c2cnc(C)nc2)nc2c(NC3CN(C(=O)C4CC4)CC3C)ncnc21]
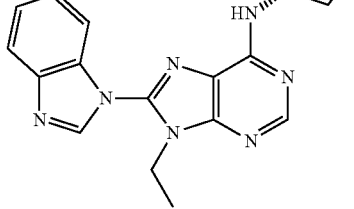
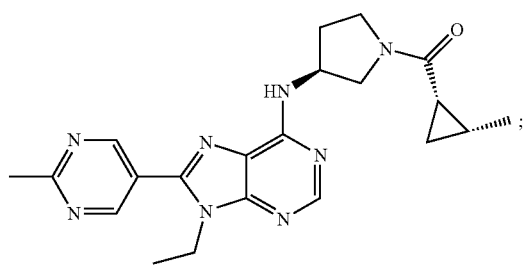
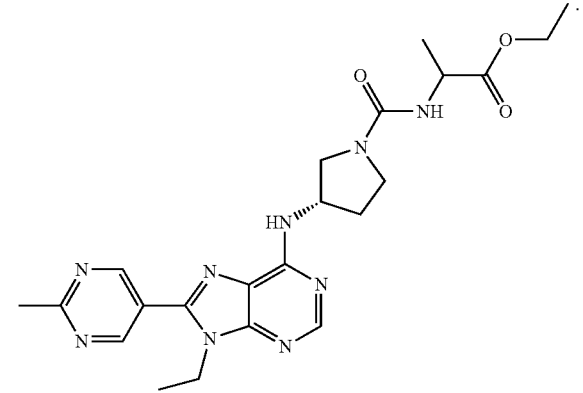
9. A compound of claim 8 or a pharmaceutically acceptable salt thereof, wherein the compound is selected from:

11. A compound of claim 1 or a pharmaceutically acceptable salt thereof, wherein the compound is:

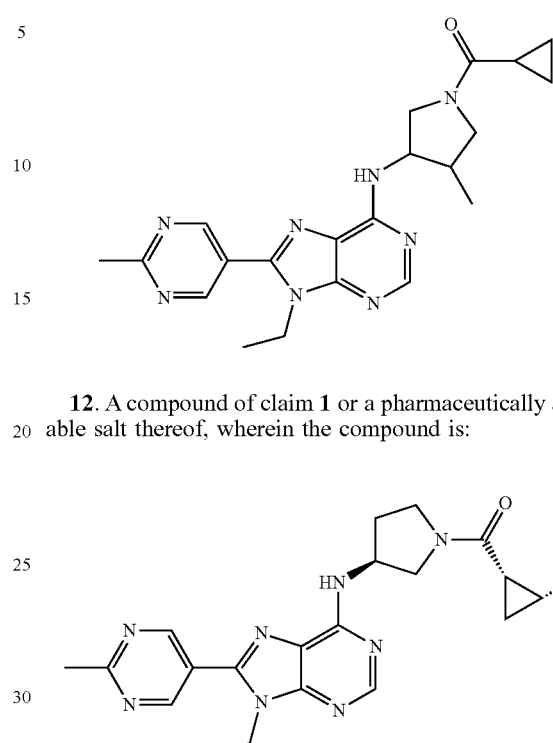

12. A compound of claim 1 or a pharmaceutically acceptable salt thereof, wherein the compound is:

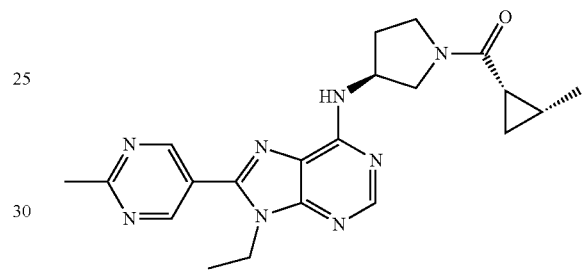

13. A pharmaceutical composition comprising a compound of claim 1 or a pharmaceutically acceptable salt or stereoisomer thereof and a pharmaceutically acceptable carrier.

14. A pharmaceutical composition according to claim 13, further comprising one or more other therapeutic agents.

15. A method for the treatment of a PI3K-delta-mediated disease comprising administering to a patient in need thereof a therapeutically effective amount of a compound of claim 1 or a pharmaceutically acceptable salt or a stereoisomer thereof, wherein the PI3K-delta-mediated disease is arthritis.

16. A method of treating a condition in a mammal that can be ameliorated by the selective inhibition of PI3K-delta which condition is arthritis comprising administering to the mammal in need of such treatment, a therapeutically effective amount of a compound according to claim 1 or a pharmaceutically acceptable salt or a stereoisomer thereof.

17. A method according to claim 16, wherein said condition is selected from rheumatoid arthritis, juvenile arthritis, and psoriatic arthritis.

18. A method of treating arthritis in a mammal in need thereof, comprising administering a therapeutically effective amount of a compound according to claim 1 or a pharmaceutically acceptable salt thereof.

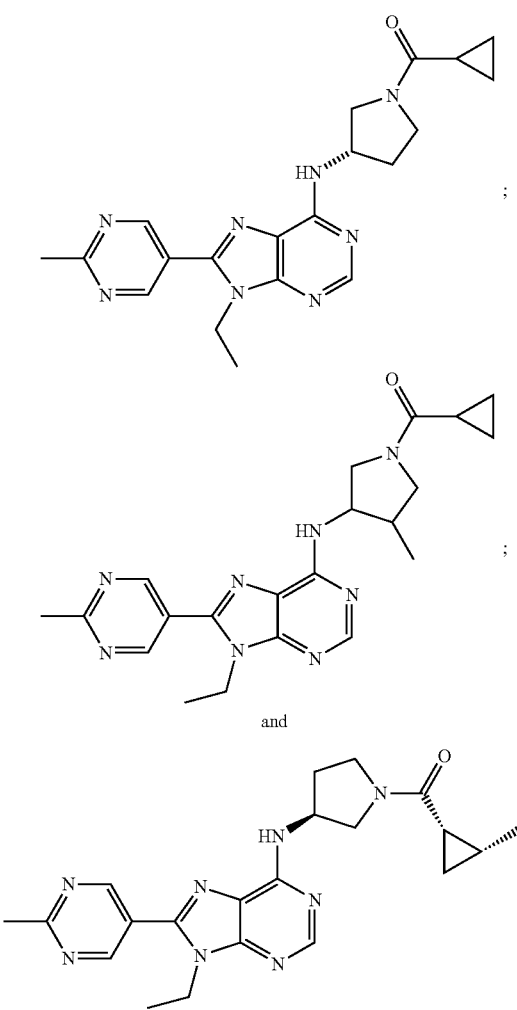

10. A compound of claim 1 or a pharmaceutically acceptable salt thereof, wherein the compound is:

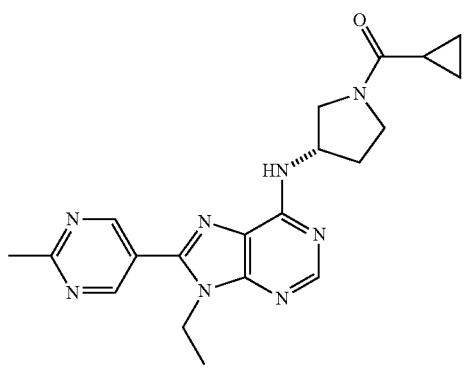

\* \* \* \* \*